US012584172B2

(12) United States Patent
Hunter et al.

(10) Patent No.: US 12,584,172 B2
(45) Date of Patent: Mar. 24, 2026

(54) CHROMOSOME BIOMARKER

(71) Applicant: Oxford BioDynamics PLC, Oxford (GB)

(72) Inventors: Ewan Hunter, Oxford (GB); Aroul Ramadass, Oxford (GB); Alexandre Akoulitchev, Oxford (GB)

(73) Assignee: Oxford BioDynamics PLC, Oxford (GB)

( * ) Notice: Subject to any disclaimer, the term of this patent is extended or adjusted under 35 U.S.C. 154(b) by 284 days.

(21) Appl. No.: 17/287,092

(22) PCT Filed: Oct. 21, 2019

(86) PCT No.: PCT/GB2019/052996
§ 371 (c)(1),
(2) Date: Apr. 20, 2021

(87) PCT Pub. No.: WO2020/084289
PCT Pub. Date: Apr. 30, 2020

(65) Prior Publication Data
US 2022/0282328 A1 Sep. 8, 2022

(30) Foreign Application Priority Data

Oct. 22, 2018 (GB) ....................................... 1817181
Mar. 25, 2019 (GB) ....................................... 1904066

(51) Int. Cl.
*C12Q 1/6876* (2018.01)
*C12Q 1/6806* (2018.01)
*G16H 20/30* (2018.01)

(52) U.S. Cl.
CPC ......... *C12Q 1/6876* (2013.01); *C12Q 1/6806* (2013.01); *G16H 20/30* (2018.01); *C12Q 2600/124* (2013.01)

(58) Field of Classification Search
CPC .............................. C12Q 1/6876; G16H 20/30
See application file for complete search history.

(56) References Cited

U.S. PATENT DOCUMENTS

| | | | |
|---|---|---|---|
| 7,998,744 | B2 | 8/2011 | Stevenson |
| 2015/0031061 | A1 | 1/2015 | Elenitoba-Johnson |
| 2017/0166981 | A1 | 6/2017 | Craig |

FOREIGN PATENT DOCUMENTS

WO WO-2016207661 A1 * 12/2016 ................ A61P 3/10

OTHER PUBLICATIONS

Wei et al. 3C-based methods to detect long-range chromatin interactions. Front Biol (Beijing). Feb. 2011;6(1):76-81. doi: 10.1007/s11515-011-0980-6. Epub Jan. 29, 2011. PMID: 39398263; PMCID: PMC11469636 (Year: 2011).*
Bouchard, C., 'Genomic scan for maximal oxygen uptake and its response to training in the Heritage Family Study'. Journal of Applied Physiology. Feb. 2000, vol. 88, pp. 551-559.
Oxford Biodynamics Press Release of Jan. 23, 2017.

(Continued)

*Primary Examiner* — Aaron A Priest
*Assistant Examiner* — Tian Yu
(74) *Attorney, Agent, or Firm* — FisherBroyles, LLP; Adam K. Whiting; Adelaide K. Leitzel

(57) ABSTRACT

A process for analysing chromosome regions and interactions relating to physical performance.

6 Claims, 18 Drawing Sheets

Specification includes a Sequence Listing.

(56)     References Cited

OTHER PUBLICATIONS

Guilherme, J., et al., "Genetics and sport performance: current challenges and directions to the future", Revista Brasileira de EDUCA00 Fisica e Esporte, vol. 28, No. 1, Mar. 1, 2014 (Mar. 1, 2014), pp. 177-193, XP055558473, DOI: 10.1590/S1807-55092014000100177.

Ostrander, E., et al., "Genetics of Athletic Performance", Annual Review of Genomics and Human Genetics, vol. 10, No. 1, Sep. 1, 2009 (Sep. 1, 2009), pp. 407-429, XP055558459, US ISSN: 1527-8204, DOI: 10.1146/annurev-genom-082908-150058.

Sharp, N.C. Craig, "The Human Genome and Sport, Including Epigenetics, Gene Doping, and Athleticogenomics", Endocrinology and Metabolism Clinics of North America., vol. 39, No. 1, Mar. 1, 2010 (Mar. 1, 2010), pp. 201-215, XP055558468, Philadelphia ISSN: 0889-8529, DOI: 10.1016/j.ec1.2009.10.010.

Yu, B., et al., "Genetics of Athletic Performance" In: "Encyclopedia of Life Sciences", Jun. 17, 2010 (Jun. 17, 2010), John Wiley & Sons, Ltd, Chichester, XP055558481, ISBN: 978-0-470-01590-2 DOI: 10.1002/9780470015902.a0022400.

* cited by examiner

Figure 3
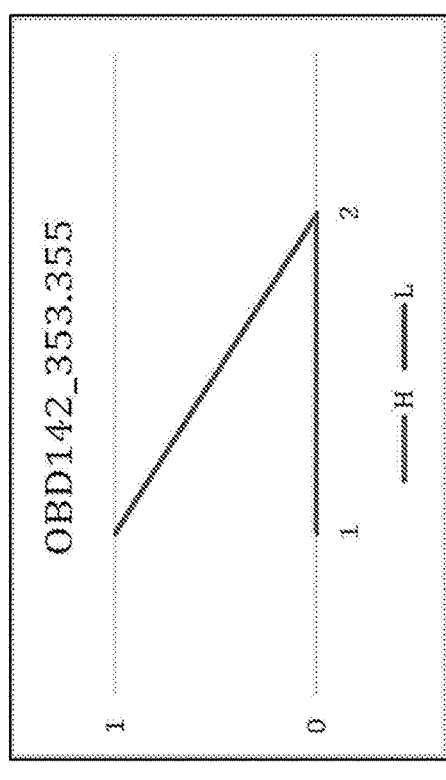
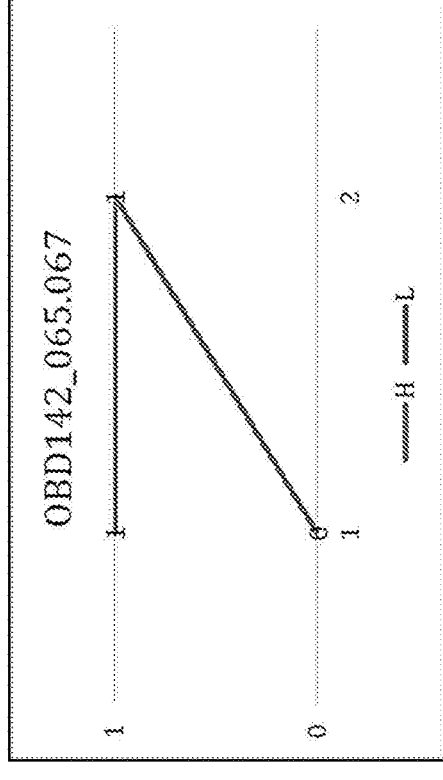
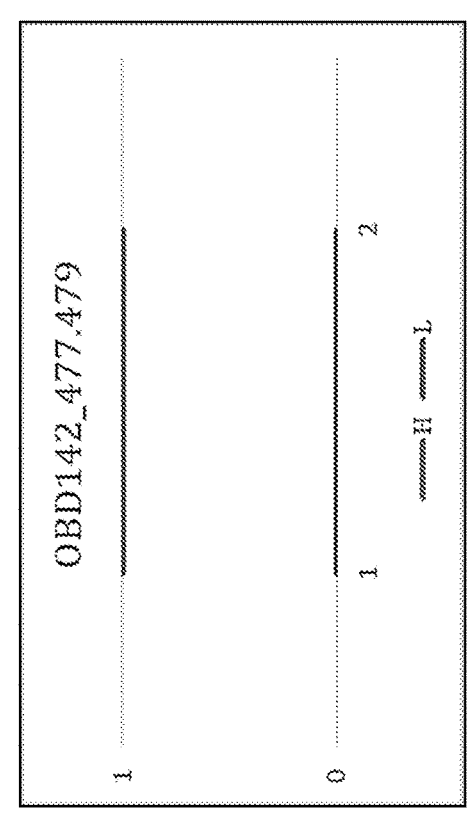

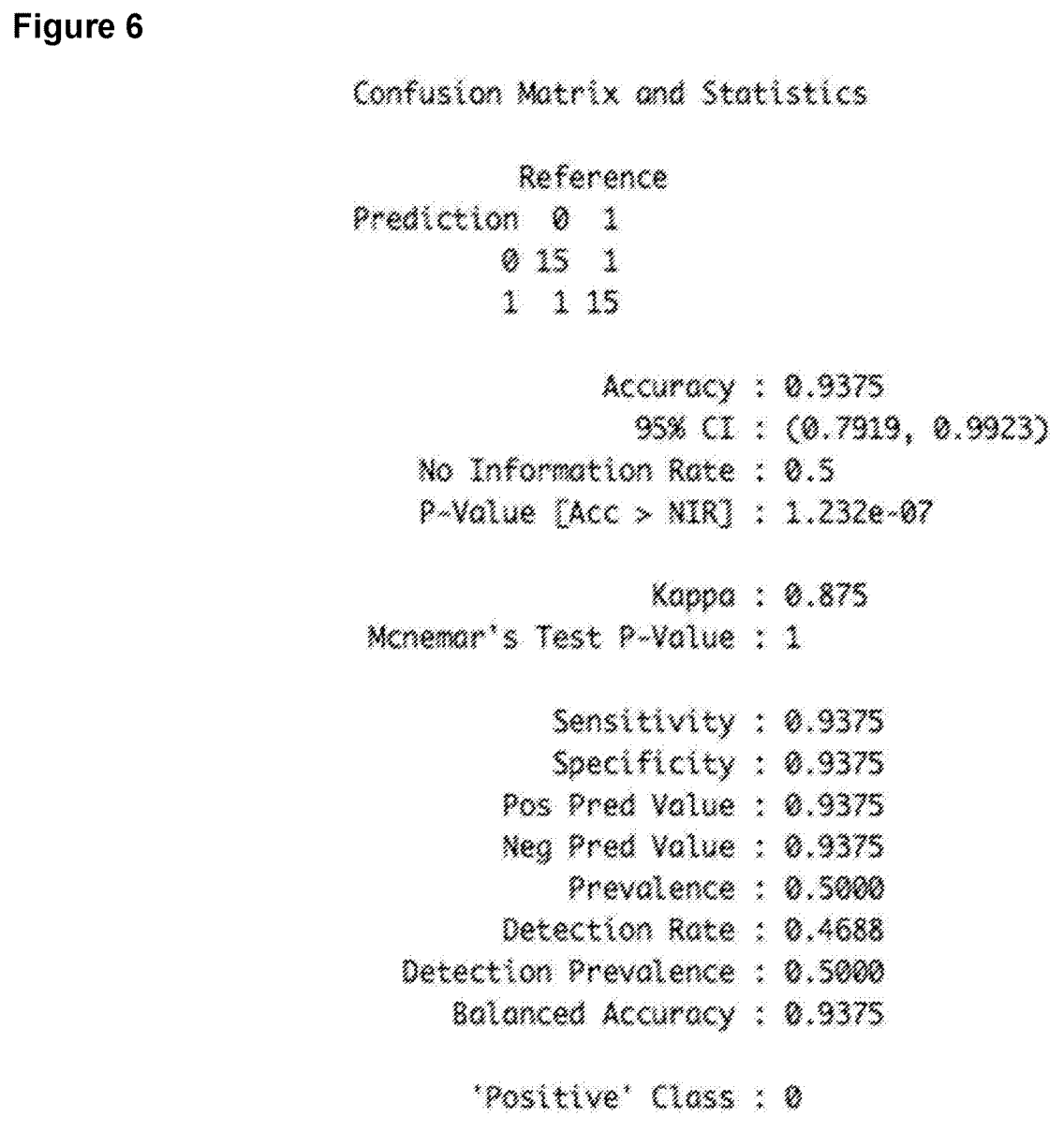

Confusion Matrix and Statistics

```
          Reference
Prediction  0  1
         0 15  1
         1  1 15

Accuracy : 0.9375
                 95% CI : (0.7919, 0.9923)
    No Information Rate : 0.5
    P-Value [Acc > NIR] : 1.232e-07

Kappa : 0.875
 Mcnemar's Test P-Value : 1

Sensitivity : 0.9375
            Specificity : 0.9375
         Pos Pred Value : 0.9375
         Neg Pred Value : 0.9375
             Prevalence : 0.5000
         Detection Rate : 0.4688
   Detection Prevalence : 0.5000
      Balanced Accuracy : 0.9375

'Positive' Class : 0
```

Figure 6

Distribution Curve for Aerobic Capacity in Epifit Study (n=85)

VENN diagram of the top 250 loops in sedentary subjects compared to the 2 athletic groups Strength_Ctrl 72
(22.4%)

175
(54.3%)

Endurance_Ctrl 75
23.3%

This shows that 175 CCSs are shared in the sedentary subjects compared to the 2 athlete groups. These are loops present in sedentary but absent in training. There are 75 unique CCSs in the comparison to Endurance and 72 to strength

Figure 12

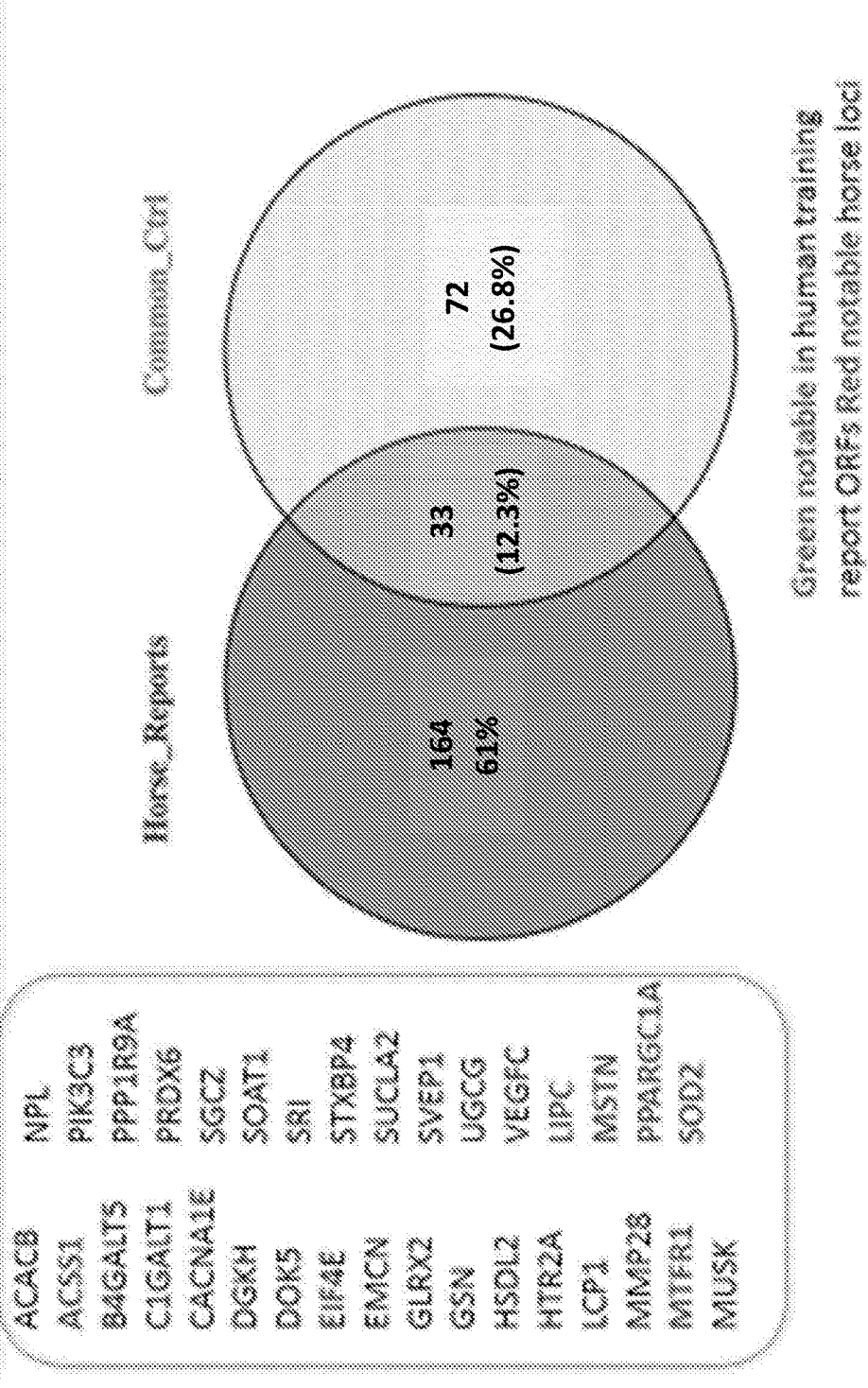

VENN comparison of Horse genetics and Report ORFs with ORFs with significant common CCSs in sedentary subjects Common_Ctrl Horse_Reports 72
(26.8%)

33
(12.3%)

164
61%

ACACB          NPL
ACSS1          PIK3C3
B4GALT5        PPP1R9A
C1GALT1        PROX6
CACNA1E        SGCZ
DGKH           SOAT1
DOK5           SRI
EIF4E          STXBP4
EMCN           SUCLA2
GLRX2          SVEP1
GSN            UGCG
HSDL2          VEGFC
HTR2A          LIPC
LCP2           MSTN
MMP28          PPARGC1A
MTFR1          SOD2
MUSK

Green notable in human training
report ORFs Red notable horse loci

| | A | B | C | D |
|---|---|---|---|---|
| 1 | Marker | Stats_CV | Stats_CS | Marker |
| 2 | OBO142_433.435 | 0.01290572 | 0.328290877 | OBO142_433.435 |
| 3 | OBO142_353.355 | 0.02356851 | 0.201245427 | OBO142_353.355 |
| 4 | OBO142_261.263 | 0.03096974 | 0.08554256 | OBO142_261.263 |
| 5 | OBO142_513.515 | 0.03583026 | 1 | OBO142_513.515 |
| 6 | OBO142_021.023 | 0.06817021 | 0.086853307 | OBO142_021.023 |
| 7 | OBO142_313.315 | 0.06915879 | 0.024329662 | OBO142_313.315 |
| 8 | OBO142_073.075 | 0.08839179 | 0.0147082786 | OBO142_073.075 |
| 9 | Group_s2 | 0.08839179 | 0.077405989 | Group_v2 |
| 10 | OBO142_205.207 | 0.09164972 | 1 | OBO142_205.207 |
| 11 | OBO142_461.463 | 0.09164972 | 0.01770556 | OBO142_461.463 |
| 12 | OBO142_497.499 | 0.09164972 | 0.247600428 | OBO142_497.499 |

Figure 16

| | A | B | C | D |
|---|---|---|---|---|
| 1 | Marker | Stats_CS | Stats_CV | Marker |
| 2 | OBO142_073.075 | 0.014782786 | 0.08839179 | OBO142_073.075 |
| 3 | OBO142_029.031 | 0.01770556 | 1 | OBO142_029.031 |
| 4 | OBO142_461.463 | 0.01770556 | 0.09164972 | OBO142_461.463 |
| 5 | OBO142_169.171 | 0.00169621 | 1 | OBO142_169.171 |
| 6 | OBO142_429.431 | 0.023549199 | 1 | OBO142_429.431 |
| 7 | OBO142_313.315 | 0.024329662 | 0.06915879 | OBO142_313.315 |
| 8 | OBO142_493.495 | 0.030273855 | 0.08608314 | OBO142_493.495 |
| 9 | OBO142_457.459 | 0.043391466 | 0.69003797 | OBO142_457.459 |
| 10 | OBO142_277.279 | 0.048135281 | 0.21510564 | OBO142_277.279 |
| 11 | OBO142_021.023 | 0.065754175 | 0.15236533 | OBO142_021.023 |
| 12 | OBO142_209.211 | 0.065754175 | 0.50892571 | OBO142_209.211 |
| 13 | OBO142_389.391 | 0.065754175 | 1 | OBO142_389.391 |
| 14 | OBO142_397.399 | 0.065754175 | 1 | OBO142_397.399 |
| 15 | Group_v2 | 0.077405989 | 0.08839179 | Group_s2 |
| 16 | OBO142_261.263 | 0.08554256 | 0.03096974 | OBO142_261.263 |
| 17 | OBO142_345.347 | 0.08554256 | 1 | OBO142_345.347 |
| 18 | OBO142_077.079 | 0.08653307 | 1 | OBO142_077.079 |
| 19 | OBO142_109.111 | 0.109796792 | 1 | OBO142_109.111 |
| 20 | OBO142_273.275 | 0.110314369 | 0.50892571 | OBO142_273.275 |
| 21 | OBO142_473.475 | 0.110314369 | 1 | OBO142_473.475 |

| | Probe | Chr | Horse_Genomic | | Human_Genomic | | Marker_Type |
|---|---|---|---|---|---|---|---|
| 1 | Probe | Chr | Horse_Genomic | | Human_Genomic | | Marker_Type |
| 2 | OBDIS4_013.015_1x | ORF37_7_82065043_82065799_82046828_80246039_FF | AMPP | ARNTL | DKK3 | | Sprinter |
| 3 | OBDIS4_041.043_14x | ORF24_7_26019921_26021160_26862320_26963327_RF | TAGLN | | CBL | MCAM | Stayer |
| 4 | OBDIS4_049.051_114x | ORF1_3_38982976_38984487_38897821_38902724_RR | MCIR | | NFKD1 | | Stayer |
| 5 | OBDIS4_073.075_1x | ORF12_28_42033251_42034809_42111316_42112829_FR | PPARA | | PPARA | | Stayer |
| 6 | OBDIS4_085.087_12x | ORF31_24_18025107_18025879_18088550_18090004_FR | SYNJ2BP | | RGS6 | | Sprinter |
| 7 | OBDIS4_093.095_12x | ORF28_19_27971050_27974189_28026396_28038610_FR | TFRC | DIO2 | IL1RAP | | Sprinter |
| 8 | OBDIS4_125.127_12x | ORF51_4_788561_790967_729450_731106_FR | CDC136 | MIR1248 | CD6 | | Sprinter |
| 9 | OBDIS4_157.159_12x | ORF86_19_45858761_45861211_45772880_45782396_RR | EEF1A1 | | PLCXD2 | PHLDB2 | Stayer |
| 10 | OBDIS4_229.231_1x | ORF73_16_84538528_84540820_84582113_84585716_FR | | | MBNL1 | | Sprinter |
| 11 | OBDIS4_245.247_1x | ORF88_3_100800337_100801373_100744664_100751637_FF_MIR218 | MIR218 | | PPARGC1A | | Sprinter |

```
                        SEQUENCE LISTING

<160> NUMBER OF SEQ ID NOS: 1631

<210> SEQ ID NO 1
<211> LENGTH: 14
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 1
ccgcgnggng gcag                                                       14

<210> SEQ ID NO 2
<211> LENGTH: 60
<212> TYPE: DNA
<213> ORGANISM: Homo sapiens

<400> SEQUENCE: 2
tttaaaacta agtctaaccg cctgaaagtc gagagggaag tgctacgcat cccgcgcaca    60

<210> SEQ ID NO 3
<211> LENGTH: 60
<212> TYPE: DNA
<213> ORGANISM: Homo sapiens

<400> SEQUENCE: 3
agaggctcaa aacttctgtc tggtaaattc gattttctcc tattgctcta catcactcgg    60

<210> SEQ ID NO 4
<211> LENGTH: 60
<212> TYPE: DNA
<213> ORGANISM: Homo sapiens

<400> SEQUENCE: 4
ccccatagga ggcttctggg aagcccagtc gagatgcatc catgttgtca tgggtataag    60

<210> SEQ ID NO 5
<211> LENGTH: 60
<212> TYPE: DNA
<213> ORGANISM: Homo sapiens

<400> SEQUENCE: 5
ttcctaccac ccaaattcta ttattctatc gagaggcacc aggatgctga gaggatgaga    60

<210> SEQ ID NO 6
<211> LENGTH: 60
<212> TYPE: DNA
<213> ORGANISM: Homo sapiens

<400> SEQUENCE: 6
tcgtgttagt taaatcggcc gatttgtctc gagaaaagag aaggactggg tcatggtggg    60

<210> SEQ ID NO 7
<211> LENGTH: 60
<212> TYPE: DNA
<213> ORGANISM: Homo sapiens
```

-continued

```
<400> SEQUENCE: 7
ccgcctcgcc acagctctcc agtgagattc gatcctttta aactttgtta ggcaagacca      60

<210> SEQ ID NO 8
<211> LENGTH: 60
<212> TYPE: DNA
<213> ORGANISM: Homo sapiens

<400> SEQUENCE: 8
ttgatctttt ttaaaatagg gatggggttc gagagaagga gaatgaagca gaaagcttgt      60

<210> SEQ ID NO 9
<211> LENGTH: 60
<212> TYPE: DNA
<213> ORGANISM: Homo sapiens

<400> SEQUENCE: 9
ctgtaaccag aggagcagag tctgcacatc gattcctctt actgcactgc aggtccaggg      60

<210> SEQ ID NO 10
<211> LENGTH: 60
<212> TYPE: DNA
<213> ORGANISM: Homo sapiens

<400> SEQUENCE: 10
acccaaaatt tacttgcaat cactttaatc gagctcttgg atgtctgggg attgttctgc      60

<210> SEQ ID NO 11
<211> LENGTH: 60
<212> TYPE: DNA
<213> ORGANISM: Homo sapiens

<400> SEQUENCE: 11
gatagaatta aacattgaag gcaaactttc gattagggtt ttagtttTct ttaagttttt      60

<210> SEQ ID NO 12
<211> LENGTH: 60
<212> TYPE: DNA
<213> ORGANISM: Homo sapiens

<400> SEQUENCE: 12
gagcacaggt gctggattca ggcttccttc gattcaaact tccctcacac tgacattttt      60

<210> SEQ ID NO 13
<211> LENGTH: 60
<212> TYPE: DNA
<213> ORGANISM: Homo sapiens

<400> SEQUENCE: 13
ggagaaaaag gggctttacg cagtccattc gatgcagtca ggagtcagga cagcatctcc      60

<210> SEQ ID NO 14
<211> LENGTH: 60
<212> TYPE: DNA
<213> ORGANISM: Homo sapiens

<400> SEQUENCE: 14
cacaatgcct tccctcttc caccccttTc gatcactgtc cttcgtacac tcaagatata      60

<210> SEQ ID NO 15
<211> LENGTH: 60
<212> TYPE: DNA
<213> ORGANISM: Homo sapiens
```

-continued

```
<400> SEQUENCE: 15
gtaaaaacca gcttccaggg accagatgtc gagatcagta ttgaaatgca ccatttcatt        60

<210> SEQ ID NO 16
<211> LENGTH: 60
<212> TYPE: DNA
<213> ORGANISM: Homo sapiens

<400> SEQUENCE: 16
cataagagat gactggcctt ttgctgtttc gatggcccgg cttcctcttt gggacttcag        60

<210> SEQ ID NO 17
<211> LENGTH: 60
<212> TYPE: DNA
<213> ORGANISM: Homo sapiens

<400> SEQUENCE: 17
taatgaaatt gtcttttgt gtcttcttc gaggatttct agactttctg tgcatcacta         60

<210> SEQ ID NO 18
<211> LENGTH: 60
<212> TYPE: DNA
<213> ORGANISM: Homo sapiens

<400> SEQUENCE: 18
aagcataaat tcgttttccc cttgactttc gagactccat aaagcacacg cacaaaggcc        60

<210> SEQ ID NO 19
<211> LENGTH: 60
<212> TYPE: DNA
<213> ORGANISM: Homo sapiens

<400> SEQUENCE: 19
gtaacatgct gaataacaac atttcagttc gagcgttgtg gcagagcttc cttgttactg        60

<210> SEQ ID NO 20
<211> LENGTH: 60
<212> TYPE: DNA
<213> ORGANISM: Homo sapiens

<400> SEQUENCE: 20
acagtgctgc ctcttctgtg cagatgcttc gaaacccatg taatttcata gctatgatgg        60

<210> SEQ ID NO 21
<211> LENGTH: 60
<212> TYPE: DNA
<213> ORGANISM: Homo sapiens

<400> SEQUENCE: 21
ttgcctccat tttaaaattg aagaaacttc gaataaaatt gaaacatcct accaccaaca        60

<210> SEQ ID NO 22
<211> LENGTH: 60
<212> TYPE: DNA
<213> ORGANISM: Homo sapiens

<400> SEQUENCE: 22
cagctggagc tcagccggat gcgcaacttc gagaagagat atttgcacat ccgtgttcgt        60

<210> SEQ ID NO 23
<211> LENGTH: 60
<212> TYPE: DNA
```

<213> ORGANISM: Homo sapiens

<400> SEQUENCE: 23
agtgggccac cactgcctaa gaactacttc gaggccaata ctactgtcgg ccgcatccgt          60

<210> SEQ ID NO 24
<211> LENGTH: 60
<212> TYPE: DNA
<213> ORGANISM: Homo sapiens

<400> SEQUENCE: 24
gccgtcggtg gagaaattta aaactatttc gagtcagtaa ctggactcag ttaaggaagg          60

<210> SEQ ID NO 25
<211> LENGTH: 60
<212> TYPE: DNA
<213> ORGANISM: Homo sapiens

<400> SEQUENCE: 25
cactgagctg cacgaagatg ctgccatcga ttctcaattg ggaaaagcac atgggatatg          60

<210> SEQ ID NO 26
<211> LENGTH: 60
<212> TYPE: DNA
<213> ORGANISM: Homo sapiens

<400> SEQUENCE: 26
ttaaaagtaa agtaagtaga ggtcagtctc gaagctttga agattagttt ttgaacagtg          60

<210> SEQ ID NO 27
<211> LENGTH: 60
<212> TYPE: DNA
<213> ORGANISM: Homo sapiens

<400> SEQUENCE: 27
caagaatcag ttctgagaaa tcaatgcctc gagaaccaac gaaacactgg gccgcctgca          60

<210> SEQ ID NO 28
<211> LENGTH: 60
<212> TYPE: DNA
<213> ORGANISM: Homo sapiens

<400> SEQUENCE: 28
tgaacattat ccaggagctc atactgcttc gatgaccaca gaggcgccag aaggccacag          60

<210> SEQ ID NO 29
<211> LENGTH: 60
<212> TYPE: DNA
<213> ORGANISM: Homo sapiens

<400> SEQUENCE: 29
caatgtacaa tctaccagga actgaagttc gagcagcact tggctttctt cctttttaga          60

<210> SEQ ID NO 30
<211> LENGTH: 60
<212> TYPE: DNA
<213> ORGANISM: Homo sapiens

<400> SEQUENCE: 30
gaaagctggg tatgggagtg tgcacacttc gagatctcag aaagggcata actgtatttt          60

<210> SEQ ID NO 31
<211> LENGTH: 60

<212> TYPE: DNA
<213> ORGANISM: Homo sapiens

<400> SEQUENCE: 31
attgcctcca ttttaaaatt gaagaaactc gatggagttt gggtttaagc actgcttttt      60

<210> SEQ ID NO 32
<211> LENGTH: 60
<212> TYPE: DNA
<213> ORGANISM: Homo sapiens

<400> SEQUENCE: 32
aggcctcgcc tatgaatagc ataccagctc gattattctt ctctcacaca atttctgaag      60

<210> SEQ ID NO 33
<211> LENGTH: 60
<212> TYPE: DNA
<213> ORGANISM: Homo sapiens

<400> SEQUENCE: 33
ctccgcccgc cagctctgca gcttcccttc gacgcttcct acttttctcc aggaaattat      60

<210> SEQ ID NO 34
<211> LENGTH: 60
<212> TYPE: DNA
<213> ORGANISM: Homo sapiens

<400> SEQUENCE: 34
tcactccagg acccccccag ccctgtgttc gaggttgttt tgccagtcgt ctgtttggca      60

<210> SEQ ID NO 35
<211> LENGTH: 60
<212> TYPE: DNA
<213> ORGANISM: Homo sapiens

<400> SEQUENCE: 35
ggaaacacaa agttcttggc aaagcttcga gtcttggagg tgttgttatt tgcccaaagc      60

<210> SEQ ID NO 36
<211> LENGTH: 60
<212> TYPE: DNA
<213> ORGANISM: Homo sapiens

<400> SEQUENCE: 36
gtggccttat tttgcaaagg ggcaaacttc gaaggtgatg aaacggaggc ccagagaggg      60

<210> SEQ ID NO 37
<211> LENGTH: 60
<212> TYPE: DNA
<213> ORGANISM: Homo sapiens

<400> SEQUENCE: 37
tacctccagt cttggttatt ctgagagttc gagtcaggat tcagacccaa gtctaactct      60

<210> SEQ ID NO 38
<211> LENGTH: 60
<212> TYPE: DNA
<213> ORGANISM: Homo sapiens

<400> SEQUENCE: 38
gggtccaaac ctgcaaatcc ccagctgttc gaaaatgtgt ctgctttttc atggacacca      60

<210> SEQ ID NO 39

-continued

```
<211> LENGTH: 60
<212> TYPE: DNA
<213> ORGANISM: Homo sapiens

<400> SEQUENCE: 39
ttcctaccac ccaaattcta ttattctatc gagaggctga gatgaacaag gcagacgcag      60

<210> SEQ ID NO 40
<211> LENGTH: 60
<212> TYPE: DNA
<213> ORGANISM: Homo sapiens

<400> SEQUENCE: 40
tacctccagt cttggttatt ctgagagttc gacaagtgcg ctagtgccgc ttgtcaagag      60

<210> SEQ ID NO 41
<211> LENGTH: 60
<212> TYPE: DNA
<213> ORGANISM: Homo sapiens

<400> SEQUENCE: 41
ataaattcct ttgtgaattt tgatctcttc gaagacttgt tctgttggag gcatgtccct      60

<210> SEQ ID NO 42
<211> LENGTH: 60
<212> TYPE: DNA
<213> ORGANISM: Homo sapiens

<400> SEQUENCE: 42
cttccccaag aattttggat tatatctctc gagaaagggt aaggaagagt caaagctgta      60

<210> SEQ ID NO 43
<211> LENGTH: 60
<212> TYPE: DNA
<213> ORGANISM: Homo sapiens

<400> SEQUENCE: 43
caatttctgg ggatacagta gtgaagagtc gatggcatgg gatctctgct atttatctct      60

<210> SEQ ID NO 44
<211> LENGTH: 26
<212> TYPE: DNA
<213> ORGANISM: Homo sapiens

<400> SEQUENCE: 44
ggtattggaa cttcagagag gtaggc                                           26

<210> SEQ ID NO 45
<211> LENGTH: 23
<212> TYPE: DNA
<213> ORGANISM: Homo sapiens

<400> SEQUENCE: 45
gaggagggag agtgctactt gcc                                              23

<210> SEQ ID NO 46
<211> LENGTH: 23
<212> TYPE: DNA
<213> ORGANISM: Homo sapiens

<400> SEQUENCE: 46
gccccattga gcatcacaga ggg                                              23
```

<210> SEQ ID NO 47
<211> LENGTH: 23
<212> TYPE: DNA
<213> ORGANISM: Homo sapiens

<400> SEQUENCE: 47
tccccacttc tcctccacaa ggc                                    23

<210> SEQ ID NO 48
<211> LENGTH: 23
<212> TYPE: DNA
<213> ORGANISM: Homo sapiens

<400> SEQUENCE: 48
ccccaggagt gatggctcag aat                                    23

<210> SEQ ID NO 49
<211> LENGTH: 23
<212> TYPE: DNA
<213> ORGANISM: Homo sapiens

<400> SEQUENCE: 49
gcctcccaaa ccattccctc gga                                    23

<210> SEQ ID NO 50
<211> LENGTH: 23
<212> TYPE: DNA
<213> ORGANISM: Homo sapiens

<400> SEQUENCE: 50
gccccataca ctgctcactg gct                                    23

<210> SEQ ID NO 51
<211> LENGTH: 23
<212> TYPE: DNA
<213> ORGANISM: Homo sapiens

<400> SEQUENCE: 51
cactcctgcc gctgagattc ctg                                    23

<210> SEQ ID NO 52
<211> LENGTH: 23
<212> TYPE: DNA
<213> ORGANISM: Homo sapiens

<400> SEQUENCE: 52
ccgccattgg gttgttttgc ccc                                    23

<210> SEQ ID NO 53
<211> LENGTH: 23
<212> TYPE: DNA
<213> ORGANISM: Homo sapiens

<400> SEQUENCE: 53
gccttgagca tacccactgt cag                                    23

<210> SEQ ID NO 54
<211> LENGTH: 26
<212> TYPE: DNA
<213> ORGANISM: Homo sapiens

<400> SEQUENCE: 54
accaagcaca gtggctgaca catctg                                 26

-continued

```
<210> SEQ ID NO 55
<211> LENGTH: 23
<212> TYPE: DNA
<213> ORGANISM: Homo sapiens

<400> SEQUENCE: 55
aagccctgga gtgggagatt gct                                              23

<210> SEQ ID NO 56
<211> LENGTH: 23
<212> TYPE: DNA
<213> ORGANISM: Homo sapiens

<400> SEQUENCE: 56
caacctggag tcctgaagac ccc                                              23

<210> SEQ ID NO 57
<211> LENGTH: 26
<212> TYPE: DNA
<213> ORGANISM: Homo sapiens

<400> SEQUENCE: 57
ccaccttggc aaatggcttc tctgct                                           26

<210> SEQ ID NO 58
<211> LENGTH: 23
<212> TYPE: DNA
<213> ORGANISM: Homo sapiens

<400> SEQUENCE: 58
ctccctgccc tccatttgcc ttt                                              23

<210> SEQ ID NO 59
<211> LENGTH: 26
<212> TYPE: DNA
<213> ORGANISM: Homo sapiens

<400> SEQUENCE: 59
gcactgagtt gtgggttttc aaaggt                                           26

<210> SEQ ID NO 60
<211> LENGTH: 26
<212> TYPE: DNA
<213> ORGANISM: Homo sapiens

<400> SEQUENCE: 60
gctatttgcg tggtggtgac aatgat                                           26

<210> SEQ ID NO 61
<211> LENGTH: 26
<212> TYPE: DNA
<213> ORGANISM: Homo sapiens

<400> SEQUENCE: 61
atcatcacct tagtatcccc acctct                                           26

<210> SEQ ID NO 62
<211> LENGTH: 23
<212> TYPE: DNA
<213> ORGANISM: Homo sapiens

<400> SEQUENCE: 62
aagtgtcagc ctctgcccgt agc                                              23
```

-continued

<210> SEQ ID NO 63
<211> LENGTH: 23
<212> TYPE: DNA
<213> ORGANISM: Homo sapiens

<400> SEQUENCE: 63
gggtgaggtt ctttccctgt agg                                        23

<210> SEQ ID NO 64
<211> LENGTH: 23
<212> TYPE: DNA
<213> ORGANISM: Homo sapiens

<400> SEQUENCE: 64
gtctcttctt ctctctggtc ggc                                        23

<210> SEQ ID NO 65
<211> LENGTH: 23
<212> TYPE: DNA
<213> ORGANISM: Homo sapiens

<400> SEQUENCE: 65
cccacacctc cagttgtccc aca                                        23

<210> SEQ ID NO 66
<211> LENGTH: 26
<212> TYPE: DNA
<213> ORGANISM: Homo sapiens

<400> SEQUENCE: 66
tactcttcaa aagcacagcc aacggg                                     26

<210> SEQ ID NO 67
<211> LENGTH: 23
<212> TYPE: DNA
<213> ORGANISM: Homo sapiens

<400> SEQUENCE: 67
ggtggaagtc gtctgccaag atg                                        23

<210> SEQ ID NO 68
<211> LENGTH: 26
<212> TYPE: DNA
<213> ORGANISM: Homo sapiens

<400> SEQUENCE: 68
tggctaactg tctcctcaaa atccta                                     26

<210> SEQ ID NO 69
<211> LENGTH: 26
<212> TYPE: DNA
<213> ORGANISM: Homo sapiens

<400> SEQUENCE: 69
cgtaacaccc gaatcagtgg aaggaa                                     26

<210> SEQ ID NO 70
<211> LENGTH: 23
<212> TYPE: DNA
<213> ORGANISM: Homo sapiens

<400> SEQUENCE: 70
gcctcctctc cctatctctg gat                                                          23

<210> SEQ ID NO 71
<211> LENGTH: 24
<212> TYPE: DNA
<213> ORGANISM: Homo sapiens

<400> SEQUENCE: 71
cagatgctgg gttttgccct cagg                                                         24

<210> SEQ ID NO 72
<211> LENGTH: 26
<212> TYPE: DNA
<213> ORGANISM: Homo sapiens

<400> SEQUENCE: 72
tgactctgct gtagatgtcc tggctc                                                       26

<210> SEQ ID NO 73
<211> LENGTH: 23
<212> TYPE: DNA
<213> ORGANISM: Homo sapiens

<400> SEQUENCE: 73
gggtgaggtt ctttccctgt agg                                                          23

<210> SEQ ID NO 74
<211> LENGTH: 26
<212> TYPE: DNA
<213> ORGANISM: Homo sapiens

<400> SEQUENCE: 74
ggtagaaagc gtttagccct gtattt                                                       26

<210> SEQ ID NO 75
<211> LENGTH: 26
<212> TYPE: DNA
<213> ORGANISM: Homo sapiens

<400> SEQUENCE: 75
caccttcatc cttcaccaag tcctgc                                                       26

<210> SEQ ID NO 76
<211> LENGTH: 26
<212> TYPE: DNA
<213> ORGANISM: Homo sapiens

<400> SEQUENCE: 76
ccctcaaccc atttccttca cttgcc                                                       26

<210> SEQ ID NO 77
<211> LENGTH: 26
<212> TYPE: DNA
<213> ORGANISM: Homo sapiens

<400> SEQUENCE: 77
tgaggatggt cagtgagact cgtaaa                                                       26

<210> SEQ ID NO 78
<211> LENGTH: 26
<212> TYPE: DNA
<213> ORGANISM: Homo sapiens

<400> SEQUENCE: 78

-continued

```
acagtagaca gacagcacag ggttta                                26

<210> SEQ ID NO 79
<211> LENGTH: 23
<212> TYPE: DNA
<213> ORGANISM: Homo sapiens

<400> SEQUENCE: 79
aaaggtggtg ggcaggactc cag                                   23

<210> SEQ ID NO 80
<211> LENGTH: 23
<212> TYPE: DNA
<213> ORGANISM: Homo sapiens

<400> SEQUENCE: 80
atgtagggca tcaccacagc gtg                                   23

<210> SEQ ID NO 81
<211> LENGTH: 23
<212> TYPE: DNA
<213> ORGANISM: Homo sapiens

<400> SEQUENCE: 81
tccccacttc tcctccacaa ggc                                   23

<210> SEQ ID NO 82
<211> LENGTH: 23
<212> TYPE: DNA
<213> ORGANISM: Homo sapiens

<400> SEQUENCE: 82
aaaggtggtg ggcaggactc cag                                   23

<210> SEQ ID NO 83
<211> LENGTH: 26
<212> TYPE: DNA
<213> ORGANISM: Homo sapiens

<400> SEQUENCE: 83
actcggctaa ccctctactt caaggt                                26

<210> SEQ ID NO 84
<211> LENGTH: 23
<212> TYPE: DNA
<213> ORGANISM: Homo sapiens

<400> SEQUENCE: 84
ggcggctgtg tgagttttgc caa                                   23

<210> SEQ ID NO 85
<211> LENGTH: 26
<212> TYPE: DNA
<213> ORGANISM: Homo sapiens

<400> SEQUENCE: 85
accattagtt ggctcatctc cttgcc                                26

<210> SEQ ID NO 86
<211> LENGTH: 26
<212> TYPE: DNA
<213> ORGANISM: Homo sapiens
```

-continued

<400> SEQUENCE: 86
ggaggcaagg ctgtgatgaa agtcaa                                        26

<210> SEQ ID NO 87
<211> LENGTH: 23
<212> TYPE: DNA
<213> ORGANISM: Homo sapiens

<400> SEQUENCE: 87
gtgagtgggt ttccctgctg aac                                          23

<210> SEQ ID NO 88
<211> LENGTH: 23
<212> TYPE: DNA
<213> ORGANISM: Homo sapiens

<400> SEQUENCE: 88
gctgctgtgg gtttctgcga cat                                          23

<210> SEQ ID NO 89
<211> LENGTH: 23
<212> TYPE: DNA
<213> ORGANISM: Homo sapiens

<400> SEQUENCE: 89
gcctggaaca gttgagcaaa cgc                                          23

<210> SEQ ID NO 90
<211> LENGTH: 23
<212> TYPE: DNA
<213> ORGANISM: Homo sapiens

<400> SEQUENCE: 90
ccagtgcctc tcttcagcat ccc                                          23

<210> SEQ ID NO 91
<211> LENGTH: 23
<212> TYPE: DNA
<213> ORGANISM: Homo sapiens

<400> SEQUENCE: 91
ctcacacaga gaggaggaga gga                                          23

<210> SEQ ID NO 92
<211> LENGTH: 23
<212> TYPE: DNA
<213> ORGANISM: Homo sapiens

<400> SEQUENCE: 92
ccccaggttt ggaagttctc agc                                          23

<210> SEQ ID NO 93
<211> LENGTH: 23
<212> TYPE: DNA
<213> ORGANISM: Homo sapiens

<400> SEQUENCE: 93
cggagcagaa cattcgccta agc                                          23

<210> SEQ ID NO 94
<211> LENGTH: 23
<212> TYPE: DNA
<213> ORGANISM: Homo sapiens -continued

```
<400> SEQUENCE: 94
gcagtgtgac aaggaagcag cag                                     23

<210> SEQ ID NO 95
<211> LENGTH: 23
<212> TYPE: DNA
<213> ORGANISM: Homo sapiens

<400> SEQUENCE: 95
accctcagaa atccctccca ggc                                     23

<210> SEQ ID NO 96
<211> LENGTH: 26
<212> TYPE: DNA
<213> ORGANISM: Homo sapiens

<400> SEQUENCE: 96
tcttcaccat tttcttgagc actgtg                                  26

<210> SEQ ID NO 97
<211> LENGTH: 23
<212> TYPE: DNA
<213> ORGANISM: Homo sapiens

<400> SEQUENCE: 97
gccagccact gtcccaagga gat                                     23

<210> SEQ ID NO 98
<211> LENGTH: 23
<212> TYPE: DNA
<213> ORGANISM: Homo sapiens

<400> SEQUENCE: 98
cgcagggcta atcttcctca acc                                     23

<210> SEQ ID NO 99
<211> LENGTH: 23
<212> TYPE: DNA
<213> ORGANISM: Homo sapiens

<400> SEQUENCE: 99
ttttgaggga gagtccgtga agc                                     23

<210> SEQ ID NO 100
<211> LENGTH: 23
<212> TYPE: DNA
<213> ORGANISM: Homo sapiens

<400> SEQUENCE: 100
atcacggaca ggcacctacg gct                                     23

<210> SEQ ID NO 101
<211> LENGTH: 26
<212> TYPE: DNA
<213> ORGANISM: Homo sapiens

<400> SEQUENCE: 101
atcaaactcc agcaatctga ctccag                                  26

<210> SEQ ID NO 102
<211> LENGTH: 26
<212> TYPE: DNA
```

-continued

<213> ORGANISM: Homo sapiens

<400> SEQUENCE: 102
gccaggctca ctcctttccc ttttag                                      26

<210> SEQ ID NO 103
<211> LENGTH: 26
<212> TYPE: DNA
<213> ORGANISM: Homo sapiens

<400> SEQUENCE: 103
gccctgagac aagcattttc ctcgtc                                      26

<210> SEQ ID NO 104
<211> LENGTH: 23
<212> TYPE: DNA
<213> ORGANISM: Homo sapiens

<400> SEQUENCE: 104
cggagtctcg tcccgacatt tac                                         23

<210> SEQ ID NO 105
<211> LENGTH: 23
<212> TYPE: DNA
<213> ORGANISM: Homo sapiens

<400> SEQUENCE: 105
actgtgtggg aggaaggtgg agg                                         23

<210> SEQ ID NO 106
<211> LENGTH: 23
<212> TYPE: DNA
<213> ORGANISM: Homo sapiens

<400> SEQUENCE: 106
cacccacctt tgttcacccg ctc                                         23

<210> SEQ ID NO 107
<211> LENGTH: 23
<212> TYPE: DNA
<213> ORGANISM: Homo sapiens

<400> SEQUENCE: 107
cccaggtagt cgtggaaacg gat                                         23

<210> SEQ ID NO 108
<211> LENGTH: 26
<212> TYPE: DNA
<213> ORGANISM: Homo sapiens

<400> SEQUENCE: 108
cccctggctt taggcttaga ttctct                                      26

<210> SEQ ID NO 109
<211> LENGTH: 23
<212> TYPE: DNA
<213> ORGANISM: Homo sapiens

<400> SEQUENCE: 109
ttctcgcctg cttcctgcct gtg                                         23

<210> SEQ ID NO 110
<211> LENGTH: 23

<212> TYPE: DNA
<213> ORGANISM: Homo sapiens

<400> SEQUENCE: 110
gccattcggt gacatcaggg tga                                                      23

<210> SEQ ID NO 111
<211> LENGTH: 26
<212> TYPE: DNA
<213> ORGANISM: Homo sapiens

<400> SEQUENCE: 111
agagtcacgg tttctgccta tcaaga                                                   26

<210> SEQ ID NO 112
<211> LENGTH: 23
<212> TYPE: DNA
<213> ORGANISM: Homo sapiens

<400> SEQUENCE: 112
cctctcgctg aagtccctgc cat                                                      23

<210> SEQ ID NO 113
<211> LENGTH: 23
<212> TYPE: DNA
<213> ORGANISM: Homo sapiens

<400> SEQUENCE: 113
cagggaaggg agaatagtca ggg                                                      23

<210> SEQ ID NO 114
<211> LENGTH: 26
<212> TYPE: DNA
<213> ORGANISM: Homo sapiens

<400> SEQUENCE: 114
ggagagaaga taggctggca atagat                                                   26

<210> SEQ ID NO 115
<211> LENGTH: 23
<212> TYPE: DNA
<213> ORGANISM: Homo sapiens

<400> SEQUENCE: 115
cacctcctcc ctcaacccct aag                                                      23

<210> SEQ ID NO 116
<211> LENGTH: 26
<212> TYPE: DNA
<213> ORGANISM: Homo sapiens

<400> SEQUENCE: 116
atttaggcac ttgggagagg agagcc                                                   26

<210> SEQ ID NO 117
<211> LENGTH: 26
<212> TYPE: DNA
<213> ORGANISM: Homo sapiens

<400> SEQUENCE: 117
ctgatgatag ttagggagag gtgagt                                                   26

<210> SEQ ID NO 118

-continued

```
<211> LENGTH: 26
<212> TYPE: DNA
<213> ORGANISM: Homo sapiens

<400> SEQUENCE: 118
aaggtttgtg gctcttgaac atacca                                       26

<210> SEQ ID NO 119
<211> LENGTH: 26
<212> TYPE: DNA
<213> ORGANISM: Homo sapiens

<400> SEQUENCE: 119
aatggcacat cctccaaccc caaacc                                       26

<210> SEQ ID NO 120
<211> LENGTH: 26
<212> TYPE: DNA
<213> ORGANISM: Homo sapiens

<400> SEQUENCE: 120
tgtgtgtcta ctgccaactc tgccct                                       26

<210> SEQ ID NO 121
<211> LENGTH: 23
<212> TYPE: DNA
<213> ORGANISM: Homo sapiens

<400> SEQUENCE: 121
cctcaggtca ggttttgtca cgg                                          23

<210> SEQ ID NO 122
<211> LENGTH: 23
<212> TYPE: DNA
<213> ORGANISM: Homo sapiens

<400> SEQUENCE: 122
ccgcccgcat tggcatccga ata                                          23

<210> SEQ ID NO 123
<211> LENGTH: 23
<212> TYPE: DNA
<213> ORGANISM: Homo sapiens

<400> SEQUENCE: 123
ccgagccttc tccctttct cca                                           23

<210> SEQ ID NO 124
<211> LENGTH: 23
<212> TYPE: DNA
<213> ORGANISM: Homo sapiens

<400> SEQUENCE: 124
cagaactcct caggctcaga cac                                          23

<210> SEQ ID NO 125
<211> LENGTH: 26
<212> TYPE: DNA
<213> ORGANISM: Homo sapiens

<400> SEQUENCE: 125
ctggctcaat aagagtgctt tccttg                                       26
```

-continued

```
<210> SEQ ID NO 126
<211> LENGTH: 23
<212> TYPE: DNA
<213> ORGANISM: Homo sapiens

<400> SEQUENCE: 126
tggcagggaa agactcggag gtc                                              23

<210> SEQ ID NO 127
<211> LENGTH: 26
<212> TYPE: DNA
<213> ORGANISM: Homo sapiens

<400> SEQUENCE: 127
cctcttccct aactgcgaaa caaaac                                           26

<210> SEQ ID NO 128
<211> LENGTH: 60
<212> TYPE: DNA
<213> ORGANISM: Homo sapiens

<400> SEQUENCE: 128
accgcctcac ctcagctctc cagtgagatc gatcctccca cctaagcttc ccaagttgct      60

<210> SEQ ID NO 129
<211> LENGTH: 60
<212> TYPE: DNA
<213> ORGANISM: Homo sapiens

<400> SEQUENCE: 129
gacacctcct ctcccttccc tcccttctc gagttatcaa aatattttga gagacagtat       60

<210> SEQ ID NO 130
<211> LENGTH: 60
<212> TYPE: DNA
<213> ORGANISM: Homo sapiens

<400> SEQUENCE: 130
gacacctcct ctcccttccc tcccttctc gatggccaca tgtggccagt ggctctcatg       60

<210> SEQ ID NO 131
<211> LENGTH: 60
<212> TYPE: DNA
<213> ORGANISM: Homo sapiens

<400> SEQUENCE: 131
tgcagaaagt actacaaaaa aagaagcttc gaaaatgttg gagatgagag tttcttcacc      60

<210> SEQ ID NO 132
<211> LENGTH: 60
<212> TYPE: DNA
<213> ORGANISM: Homo sapiens

<400> SEQUENCE: 132
ggcaggtgga tcatttgagg tcaagagctc gacagagcaa gacaccatct ccaaaaagaa      60

<210> SEQ ID NO 133
<211> LENGTH: 60
<212> TYPE: DNA
<213> ORGANISM: Homo sapiens

<400> SEQUENCE: 133
tgtcctttca aggaaggatt agcatccttc gaaagaccta tcaggatttc atttgtaatg      60
```

-continued

<210> SEQ ID NO 134
<211> LENGTH: 60
<212> TYPE: DNA
<213> ORGANISM: Homo sapiens

<400> SEQUENCE: 134
cctcgtcgtc ccctctcttc ctcgttcctc gaacatctcc aagtcagata atcataacaa          60

<210> SEQ ID NO 135
<211> LENGTH: 60
<212> TYPE: DNA
<213> ORGANISM: Homo sapiens

<400> SEQUENCE: 135
atctattata atgatgcaat attgttaatc gattcaaaga tcaaattaat tattaaagct          60

<210> SEQ ID NO 136
<211> LENGTH: 60
<212> TYPE: DNA
<213> ORGANISM: Homo sapiens

<400> SEQUENCE: 136
attttaaatg tggcatttta ggtttatttc gattttgcat aaattgaaaa agctggagat          60

<210> SEQ ID NO 137
<211> LENGTH: 60
<212> TYPE: DNA
<213> ORGANISM: Homo sapiens

<400> SEQUENCE: 137
tgctgaaaga aaacacaatt tatttaagtc gaaattttgg aaaagccctg atttaagtca          60

<210> SEQ ID NO 138
<211> LENGTH: 60
<212> TYPE: DNA
<213> ORGANISM: Homo sapiens

<400> SEQUENCE: 138
gacacctcct ctcccttccc tcccttctc gatcactttg caaagctttg ttggctaggc          60

<210> SEQ ID NO 139
<211> LENGTH: 60
<212> TYPE: DNA
<213> ORGANISM: Homo sapiens

<400> SEQUENCE: 139
taaataaaat tgtctttttt tgtcttctc gattacagag aactaagtac attttaaatc          60

<210> SEQ ID NO 140
<211> LENGTH: 60
<212> TYPE: DNA
<213> ORGANISM: Homo sapiens

<400> SEQUENCE: 140
cttaattttt tttctttgaa tgcctctatc gacagtcttc tctctacttt ctacagtgaa          60

<210> SEQ ID NO 141
<211> LENGTH: 60
<212> TYPE: DNA
<213> ORGANISM: Homo sapiens

<400> SEQUENCE: 141
acacctcacc cacccagctg ggctggcctc gatgccatta aatcatcccg tgaccttcct          60

-continued

<210> SEQ ID NO 142
<211> LENGTH: 60
<212> TYPE: DNA
<213> ORGANISM: Homo sapiens

<400> SEQUENCE: 142
ggcaggcgga tcatttcagg tcaggagttc gacctgaaat ttccatacta aatttaaata      60

<210> SEQ ID NO 143
<211> LENGTH: 60
<212> TYPE: DNA
<213> ORGANISM: Homo sapiens

<400> SEQUENCE: 143
cctcgtcgtc ccctctcttc ctcgttcctc gacaggaaag catacggaaa aagttaaaga      60

<210> SEQ ID NO 144
<211> LENGTH: 60
<212> TYPE: DNA
<213> ORGANISM: Homo sapiens

<400> SEQUENCE: 144
aatttcacat tgatacattg atagacattc gaaatcatac acagcatact ctcaaaccat      60

<210> SEQ ID NO 145
<211> LENGTH: 60
<212> TYPE: DNA
<213> ORGANISM: Homo sapiens

<400> SEQUENCE: 145
aaatgtataa gaacagaaga gaattatctc gacatgtctg aaaagtatta tcagccctct      60

<210> SEQ ID NO 146
<211> LENGTH: 60
<212> TYPE: DNA
<213> ORGANISM: Homo sapiens

<400> SEQUENCE: 146
aaaacaccct gaattggaag aaagaaactc gagggatgag tgtgtatcat caaagtcaaa      60

<210> SEQ ID NO 147
<211> LENGTH: 60
<212> TYPE: DNA
<213> ORGANISM: Homo sapiens

<400> SEQUENCE: 147
cgcggggcct tctgggccag gcgggccctc gaaaagcccc acgccccccc agagctgctg      60

<210> SEQ ID NO 148
<211> LENGTH: 60
<212> TYPE: DNA
<213> ORGANISM: Homo sapiens

<400> SEQUENCE: 148
aatacgtggt caatctaagg attatagttc gaaaagatta atgatgtatt gatgacactt      60

<210> SEQ ID NO 149
<211> LENGTH: 60
<212> TYPE: DNA
<213> ORGANISM: Homo sapiens

<400> SEQUENCE: 149

399                                                                                                                400

-continued cttgcctagt ctttaattta tttatttatc gacatttttt tcttatcaac gagacgatgt        60

<210> SEQ ID NO 150
<211> LENGTH: 60
<212> TYPE: DNA
<213> ORGANISM: Homo sapiens

<400> SEQUENCE: 150
aattagacaa cgactatatg actctgtctc gagattggtc ttaacacact attgattatt        60

<210> SEQ ID NO 151
<211> LENGTH: 60
<212> TYPE: DNA
<213> ORGANISM: Homo sapiens

<400> SEQUENCE: 151
aaaaagagaa aagcaggtta gcacattgtc gaccccgccc ccgggatggg ggaactggcc        60

<210> SEQ ID NO 152
<211> LENGTH: 60
<212> TYPE: DNA
<213> ORGANISM: Homo sapiens

<400> SEQUENCE: 152
aaattttcaa gtgtacgata tggtatcatc gaccccgccc ccgggatggg ggaactggcc        60

<210> SEQ ID NO 153
<211> LENGTH: 60
<212> TYPE: DNA
<213> ORGANISM: Homo sapiens

<400> SEQUENCE: 153
aaacttacga ttacatttag agatcacttc gaccccgccc ccgggatggg ggaactggcc        60

<210> SEQ ID NO 154
<211> LENGTH: 60
<212> TYPE: DNA
<213> ORGANISM: Homo sapiens

<400> SEQUENCE: 154
aagggctcgg gagctccctc ggcacacctc gaggagtgcc aggcatctac tgctctgtcc        60

<210> SEQ ID NO 155
<211> LENGTH: 60
<212> TYPE: DNA
<213> ORGANISM: Homo sapiens

<400> SEQUENCE: 155
cccctggctc acctacacaa aattgtgctc gactctactc ttagccctgc taaataagta        60

<210> SEQ ID NO 156
<211> LENGTH: 60
<212> TYPE: DNA
<213> ORGANISM: Homo sapiens

<400> SEQUENCE: 156
attatattag tgctgtaata aaattaagtc gacacatttg atactgctta ttgggttatt        60

<210> SEQ ID NO 157
<211> LENGTH: 60
<212> TYPE: DNA
<213> ORGANISM: Homo sapiens

<400> SEQUENCE: 157

-continued

```
taccttgaaa agctcttcag tatgattatc gagctttagc cattctagta attattaaaa      60

<210> SEQ ID NO 158
<211> LENGTH: 60
<212> TYPE: DNA
<213> ORGANISM: Homo sapiens

<400> SEQUENCE: 158
atgaattaat gtttcctaga aagttgtctc gaaagaagaa agtgtcaggg ttcaactgcc      60

<210> SEQ ID NO 159
<211> LENGTH: 60
<212> TYPE: DNA
<213> ORGANISM: Homo sapiens

<400> SEQUENCE: 159
cctcgtcgtc ccctctcttc ctcgttcctc gatgcgggac tgattgttac agaactgttt      60

<210> SEQ ID NO 160
<211> LENGTH: 60
<212> TYPE: DNA
<213> ORGANISM: Homo sapiens

<400> SEQUENCE: 160
ggggatgggg ccgaaatatg attgcacttc gagtttgttt agtttttatc ttccccattt      60

<210> SEQ ID NO 161
<211> LENGTH: 60
<212> TYPE: DNA
<213> ORGANISM: Homo sapiens

<400> SEQUENCE: 161
ggggatgggg ccgaaatatg attgcacttc gaacttcagc acctgacctt tgtcatcaac      60

<210> SEQ ID NO 162
<211> LENGTH: 60
<212> TYPE: DNA
<213> ORGANISM: Homo sapiens

<400> SEQUENCE: 162
agaggctgag gtgaaaagat tgtttgagtc gaagatcatt gtctcatttt tttacttgtt      60

<210> SEQ ID NO 163
<211> LENGTH: 60
<212> TYPE: DNA
<213> ORGANISM: Homo sapiens

<400> SEQUENCE: 163
agaggctgag gtgaaaagat tgtttgagtc gatacactga acaagtgcca gagcagaata      60

<210> SEQ ID NO 164
<211> LENGTH: 60
<212> TYPE: DNA
<213> ORGANISM: Homo sapiens

<400> SEQUENCE: 164
ggtgggagga tcacttgagg tcagaagttc gatctcctga cctcaagtga tcctctagct      60

<210> SEQ ID NO 165
<211> LENGTH: 60
<212> TYPE: DNA
<213> ORGANISM: Homo sapiens
```

-continued

```
<400> SEQUENCE: 165
tatcaagtta aacattcaga cgtctaggtc gacttgaagt tcacctaaag ttttccagtc          60

<210> SEQ ID NO 166
<211> LENGTH: 60
<212> TYPE: DNA
<213> ORGANISM: Homo sapiens

<400> SEQUENCE: 166
atagtataga atgacagcat gctggttatc gacaagagtt cttaaaaagc ctaaatgtca          60

<210> SEQ ID NO 167
<211> LENGTH: 60
<212> TYPE: DNA
<213> ORGANISM: Homo sapiens

<400> SEQUENCE: 167
attccacaaa tatttgtgag caccatcttc gagctcatta gttcaagacc agcctgggca          60

<210> SEQ ID NO 168
<211> LENGTH: 60
<212> TYPE: DNA
<213> ORGANISM: Homo sapiens

<400> SEQUENCE: 168
ctctcaactt tggatgtaag aatcatcttc gagattttga ctctccacct gccccacagg          60

<210> SEQ ID NO 169
<211> LENGTH: 60
<212> TYPE: DNA
<213> ORGANISM: Homo sapiens

<400> SEQUENCE: 169
cggtccctct gccccggtta cctacccgtc gacatgacac ttgggtgggg atacagggcc          60

<210> SEQ ID NO 170
<211> LENGTH: 60
<212> TYPE: DNA
<213> ORGANISM: Homo sapiens

<400> SEQUENCE: 170 tcccctctt cctctgcctc ccttcccctc gaaaactgat taaaaagaat attgctggct           60

<210> SEQ ID NO 171
<211> LENGTH: 60
<212> TYPE: DNA
<213> ORGANISM: Homo sapiens

<400> SEQUENCE: 171
tcacttttat ttatcttact cactttctc gaggaattct cagaattctc ctcaacccac          60

<210> SEQ ID NO 172
<211> LENGTH: 60
<212> TYPE: DNA
<213> ORGANISM: Homo sapiens

<400> SEQUENCE: 172
tttcttccaa ctgagagaat cttaaaaatc gaaattggat aaggaaaaaa gtgaaatgtg          60

<210> SEQ ID NO 173
<211> LENGTH: 60
<212> TYPE: DNA
<213> ORGANISM: Homo sapiens
```

-continued

```
<400> SEQUENCE: 173
ttttagtttt atttatttag ttatcatctc gaaaaacaaa caacaataac agcaaccctc        60

<210> SEQ ID NO 174
<211> LENGTH: 60
<212> TYPE: DNA
<213> ORGANISM: Homo sapiens

<400> SEQUENCE: 174
gcaagacttt gtctcaaaac aaaagtgttc gaaaaagtca tcgtttaaaa ggtaaaatgt        60

<210> SEQ ID NO 175
<211> LENGTH: 60
<212> TYPE: DNA
<213> ORGANISM: Homo sapiens

<400> SEQUENCE: 175
tccattagct ctgctttcaa atactatatc gatgtagctt atgtaaaata aatgtattaa        60

<210> SEQ ID NO 176
<211> LENGTH: 60
<212> TYPE: DNA
<213> ORGANISM: Homo sapiens

<400> SEQUENCE: 176
tcaaagttac agtttatata attagaaatc gatctaacct caattccagt cccacaaatg        60

<210> SEQ ID NO 177
<211> LENGTH: 60
<212> TYPE: DNA
<213> ORGANISM: Homo sapiens

<400> SEQUENCE: 177
tcaagaaaaa ataataataa ttttttttc gaacttatgg ctcaagcgat tctcttgctt        60

<210> SEQ ID NO 178
<211> LENGTH: 60
<212> TYPE: DNA
<213> ORGANISM: Homo sapiens

<400> SEQUENCE: 178
aagcaagaga atcgcttgag ccataagttc gatgctgctt tgggaactga aggttttct        60

<210> SEQ ID NO 179
<211> LENGTH: 60
<212> TYPE: DNA
<213> ORGANISM: Homo sapiens

<400> SEQUENCE: 179
cgtagaacta agatgtattc aaagtcagtc gaaaaagatt agaaaagttc aactctaaga        60

<210> SEQ ID NO 180
<211> LENGTH: 60
<212> TYPE: DNA
<213> ORGANISM: Homo sapiens

<400> SEQUENCE: 180
aggcaggcag atcaatgagg ttgggagatc gacaagttca gtaattctga ggtgagtttt        60

<210> SEQ ID NO 181
<211> LENGTH: 60
<212> TYPE: DNA
```

-continued

<213> ORGANISM: Homo sapiens

<400> SEQUENCE: 181
gttgttataa ctatatcatg agactaagtc gaaaaaaaaa aacaataatt tcagctgtat      60

<210> SEQ ID NO 182
<211> LENGTH: 60
<212> TYPE: DNA
<213> ORGANISM: Homo sapiens

<400> SEQUENCE: 182
tatattagaa acatgtctga aaaaagtatc gataaatgta tacgttgatg tacattgata      60

<210> SEQ ID NO 183
<211> LENGTH: 60
<212> TYPE: DNA
<213> ORGANISM: Homo sapiens

<400> SEQUENCE: 183
ggtattacct tgatggcctt aaagaagatc gagccagagg gcctctgttc atgtttgggc      60

<210> SEQ ID NO 184
<211> LENGTH: 60
<212> TYPE: DNA
<213> ORGANISM: Homo sapiens

<400> SEQUENCE: 184
tcaagaaaaa ataataataa ttttttttt gattcctgct acacattttg gcagaatact      60

<210> SEQ ID NO 185
<211> LENGTH: 60
<212> TYPE: DNA
<213> ORGANISM: Homo sapiens

<400> SEQUENCE: 185
catggtttat aatccttttt atacattgtc gacactgtat tttcacagat cactctggag      60

<210> SEQ ID NO 186
<211> LENGTH: 60
<212> TYPE: DNA
<213> ORGANISM: Homo sapiens

<400> SEQUENCE: 186
agaacttcct gatatatttt ttttcttttc gaaggtctta aaatgttttt aaacatgacc      60

<210> SEQ ID NO 187
<211> LENGTH: 60
<212> TYPE: DNA
<213> ORGANISM: Homo sapiens

<400> SEQUENCE: 187
gactcttaaa acaataatat caaacaactc gacttgtcat ttagttcttt gggaagcagt      60

<210> SEQ ID NO 188
<211> LENGTH: 60
<212> TYPE: DNA
<213> ORGANISM: Homo sapiens

<400> SEQUENCE: 188
aattagacaa cgactatatg actctgtctc gactttaaag caagtacttc ttgtatgctc      60

<210> SEQ ID NO 189
<211> LENGTH: 60

<212> TYPE: DNA
<213> ORGANISM: Homo sapiens

<400> SEQUENCE: 189
tctttgtttc ctgtttccac ttcttatttc gatatttatt gagtgctact atatatatgc          60

<210> SEQ ID NO 190
<211> LENGTH: 60
<212> TYPE: DNA
<213> ORGANISM: Homo sapiens

<400> SEQUENCE: 190
tatgaatccc taaatgtcac acatcaagtc gaattatata agataccctg aaatttaagg          60

<210> SEQ ID NO 191
<211> LENGTH: 60
<212> TYPE: DNA
<213> ORGANISM: Homo sapiens

<400> SEQUENCE: 191
atgactgtgg aaggttctga tgtctctgtc gatgaaatgg agagaggaga aagaaaagaa          60

<210> SEQ ID NO 192
<211> LENGTH: 60
<212> TYPE: DNA
<213> ORGANISM: Homo sapiens

<400> SEQUENCE: 192
atgactgtgg aaggttctga tgtctctgtc gacatcattt ttacaaataa gaccagatgt          60

<210> SEQ ID NO 193
<211> LENGTH: 60
<212> TYPE: DNA
<213> ORGANISM: Homo sapiens

<400> SEQUENCE: 193
aatattgcta ctggaaaatc tgaatctttc gaagaaagcc ctttgtaagt tgttttcaaa          60

<210> SEQ ID NO 194
<211> LENGTH: 60
<212> TYPE: DNA
<213> ORGANISM: Homo sapiens

<400> SEQUENCE: 194
aactatgtga cttttagcta tacgagtttc gactgggttc taaatagtta atgtcatagt          60

<210> SEQ ID NO 195
<211> LENGTH: 60
<212> TYPE: DNA
<213> ORGANISM: Homo sapiens

<400> SEQUENCE: 195
taaaactatt ttaaatgttt ttaaagtatc gatgtgtact ttgacatctg tgatgatgat          60

<210> SEQ ID NO 196
<211> LENGTH: 60
<212> TYPE: DNA
<213> ORGANISM: Homo sapiens

<400> SEQUENCE: 196
ttatggctta gaagtagaaa gtcataaatc gattcctaaa aattaatgag gtgaatagta          60

<210> SEQ ID NO 197

-continued

```
<211> LENGTH: 60
<212> TYPE: DNA
<213> ORGANISM: Homo sapiens

<400> SEQUENCE: 197
tttctatgaa gaatgttcaa gatgcaattc gagctacata ctattatata ttttcacagt        60

<210> SEQ ID NO 198
<211> LENGTH: 60
<212> TYPE: DNA
<213> ORGANISM: Homo sapiens

<400> SEQUENCE: 198
ctctataaat ttaccagaat ataaattctc gactaaaagt tcagttcttc attcccacta        60

<210> SEQ ID NO 199
<211> LENGTH: 60
<212> TYPE: DNA
<213> ORGANISM: Homo sapiens

<400> SEQUENCE: 199
atcttacaaa gaataattct aagaaaagtc gagcattgga gaaaatctcc cttttctttt        60

<210> SEQ ID NO 200
<211> LENGTH: 60
<212> TYPE: DNA
<213> ORGANISM: Homo sapiens

<400> SEQUENCE: 200
tgtttttatt ttcatgtttt aattttgttc gaactcttga cctcaggtaa accacccacc        60

<210> SEQ ID NO 201
<211> LENGTH: 60
<212> TYPE: DNA
<213> ORGANISM: Homo sapiens

<400> SEQUENCE: 201
agaactggtt attgatctat tcagggattc gaaataatag attatgaata aattattctg        60

<210> SEQ ID NO 202
<211> LENGTH: 60
<212> TYPE: DNA
<213> ORGANISM: Homo sapiens

<400> SEQUENCE: 202 cttttttgaag attataatct attagtgatc gaggcttttt tgctttttttt tttttgagat        60

<210> SEQ ID NO 203
<211> LENGTH: 60
<212> TYPE: DNA
<213> ORGANISM: Homo sapiens

<400> SEQUENCE: 203
ctatatgtaa gttacaatat gtaaggtatc gatagtcact gagactaatt taatgttata        60

<210> SEQ ID NO 204
<211> LENGTH: 60
<212> TYPE: DNA
<213> ORGANISM: Homo sapiens

<400> SEQUENCE: 204
tgtaggcaga ttacctgaag ttaggagttc gattaggaat aacctatcat tagagttgtt        60
```

-continued

```
<210> SEQ ID NO 205
<211> LENGTH: 26
<212> TYPE: DNA
<213> ORGANISM: Homo sapiens

<400> SEQUENCE: 205
actgaaggtt cccaagttcc cgagag                                        26

<210> SEQ ID NO 206
<211> LENGTH: 26
<212> TYPE: DNA
<213> ORGANISM: Homo sapiens

<400> SEQUENCE: 206
gctccacatt tcccaatcta acctgc                                        26

<210> SEQ ID NO 207
<211> LENGTH: 24
<212> TYPE: DNA
<213> ORGANISM: Homo sapiens

<400> SEQUENCE: 207
gtccctctgc cctctcttat tggc                                          24

<210> SEQ ID NO 208
<211> LENGTH: 26
<212> TYPE: DNA
<213> ORGANISM: Homo sapiens

<400> SEQUENCE: 208
aatctctgtc cccaactgta tctggc                                        26

<210> SEQ ID NO 209
<211> LENGTH: 23
<212> TYPE: DNA
<213> ORGANISM: Homo sapiens

<400> SEQUENCE: 209
cccagtctca ggctttgtca ctc                                           23

<210> SEQ ID NO 210
<211> LENGTH: 26
<212> TYPE: DNA
<213> ORGANISM: Homo sapiens

<400> SEQUENCE: 210
ggcaagtttc ctgacctctc tgacat                                        26

<210> SEQ ID NO 211
<211> LENGTH: 23
<212> TYPE: DNA
<213> ORGANISM: Homo sapiens

<400> SEQUENCE: 211
ttctccctcg gacgctcatc ctc                                           23

<210> SEQ ID NO 212
<211> LENGTH: 26
<212> TYPE: DNA
<213> ORGANISM: Homo sapiens

<400> SEQUENCE: 212
ctggaacttg tttaggcact gaagca                                        26
```

-continued

```
<210> SEQ ID NO 213
<211> LENGTH: 26
<212> TYPE: DNA
<213> ORGANISM: Homo sapiens

<400> SEQUENCE: 213
gctgtcattt tcagtgatag gcacac                                      26

<210> SEQ ID NO 214
<211> LENGTH: 24
<212> TYPE: DNA
<213> ORGANISM: Homo sapiens

<400> SEQUENCE: 214
gctggtttcc tgagaaggta actc                                        24

<210> SEQ ID NO 215
<211> LENGTH: 23
<212> TYPE: DNA
<213> ORGANISM: Homo sapiens

<400> SEQUENCE: 215
ttcttgccct gtccctctgc cct                                         23

<210> SEQ ID NO 216
<211> LENGTH: 25
<212> TYPE: DNA
<213> ORGANISM: Homo sapiens

<400> SEQUENCE: 216
agatgctggc agtctccctc ttgag                                       25

<210> SEQ ID NO 217
<211> LENGTH: 26
<212> TYPE: DNA
<213> ORGANISM: Homo sapiens

<400> SEQUENCE: 217
ctgaaatccc atagtgagat gccttc                                      26

<210> SEQ ID NO 218
<211> LENGTH: 23
<212> TYPE: DNA
<213> ORGANISM: Homo sapiens

<400> SEQUENCE: 218
gcccttctcc aaaaacacct cac                                         23

<210> SEQ ID NO 219
<211> LENGTH: 20
<212> TYPE: DNA
<213> ORGANISM: Homo sapiens

<400> SEQUENCE: 219
caggcggatc atttcaggtc                                             20

<210> SEQ ID NO 220
<211> LENGTH: 23
<212> TYPE: DNA
<213> ORGANISM: Homo sapiens

<400> SEQUENCE: 220
tcatcctcct ccacacccgc cta                                         23
```

<210> SEQ ID NO 221
<211> LENGTH: 20
<212> TYPE: DNA
<213> ORGANISM: Homo sapiens

<400> SEQUENCE: 221
caggcggatc atttcaggtc                                                                    20

<210> SEQ ID NO 222
<211> LENGTH: 26
<212> TYPE: DNA
<213> ORGANISM: Homo sapiens

<400> SEQUENCE: 222
cacctcaaaa gacaacccca gaccca                                                             26

<210> SEQ ID NO 223
<211> LENGTH: 26
<212> TYPE: DNA
<213> ORGANISM: Homo sapiens

<400> SEQUENCE: 223
ctgccccttt ctttattcct acttcc                                                             26

<210> SEQ ID NO 224
<211> LENGTH: 23
<212> TYPE: DNA
<213> ORGANISM: Homo sapiens

<400> SEQUENCE: 224
accccaccaa gagcaccttc tgc                                                                23

<210> SEQ ID NO 225
<211> LENGTH: 23
<212> TYPE: DNA
<213> ORGANISM: Homo sapiens

<400> SEQUENCE: 225
cagtctctgt ggcaactctc gtg                                                                23

<210> SEQ ID NO 226
<211> LENGTH: 23
<212> TYPE: DNA
<213> ORGANISM: Homo sapiens

<400> SEQUENCE: 226
ccccatcgct gctggaaacc att                                                                23

<210> SEQ ID NO 227
<211> LENGTH: 26
<212> TYPE: DNA
<213> ORGANISM: Homo sapiens

<400> SEQUENCE: 227
gagtatttac gatggtcagg tgctgc                                                             26

<210> SEQ ID NO 228
<211> LENGTH: 23
<212> TYPE: DNA
<213> ORGANISM: Homo sapiens

<400> SEQUENCE: 228

-continued gacctgtggt tctgactgtc cag                                              23

<210> SEQ ID NO 229
<211> LENGTH: 26
<212> TYPE: DNA
<213> ORGANISM: Homo sapiens

<400> SEQUENCE: 229
gggctggtta gtcagttatc cctttt                                           26

<210> SEQ ID NO 230
<211> LENGTH: 23
<212> TYPE: DNA
<213> ORGANISM: Homo sapiens

<400> SEQUENCE: 230
ccacttccct gccttttctg gct                                              23

<210> SEQ ID NO 231
<211> LENGTH: 23
<212> TYPE: DNA
<213> ORGANISM: Homo sapiens

<400> SEQUENCE: 231
gcggagcctc tttgaacaga agc                                              23

<210> SEQ ID NO 232
<211> LENGTH: 26
<212> TYPE: DNA
<213> ORGANISM: Homo sapiens

<400> SEQUENCE: 232
gcaacctggt ctcctacctg cttcta                                           26

<210> SEQ ID NO 233
<211> LENGTH: 24
<212> TYPE: DNA
<213> ORGANISM: Homo sapiens

<400> SEQUENCE: 233
tagcagacaa tcagagggtt ttgc                                             24

<210> SEQ ID NO 234
<211> LENGTH: 26
<212> TYPE: DNA
<213> ORGANISM: Homo sapiens

<400> SEQUENCE: 234
gctggtagtt ggcttttggg aagaac                                           26

<210> SEQ ID NO 235
<211> LENGTH: 26
<212> TYPE: DNA
<213> ORGANISM: Homo sapiens

<400> SEQUENCE: 235
caggaggtgt ggatttgact catact                                           26

<210> SEQ ID NO 236
<211> LENGTH: 23
<212> TYPE: DNA
<213> ORGANISM: Homo sapiens

<400> SEQUENCE: 236

-continued tcatcctcct ccacacccgc cta                                                23

<210> SEQ ID NO 237
<211> LENGTH: 23
<212> TYPE: DNA
<213> ORGANISM: Homo sapiens

<400> SEQUENCE: 237
gggagtaggg agcagaacca gga                                                23

<210> SEQ ID NO 238
<211> LENGTH: 26
<212> TYPE: DNA
<213> ORGANISM: Homo sapiens

<400> SEQUENCE: 238
caacaaggag ggagtgacca caagat                                             26

<210> SEQ ID NO 239
<211> LENGTH: 26
<212> TYPE: DNA
<213> ORGANISM: Homo sapiens

<400> SEQUENCE: 239
gcaaagggca ggtcatcatc attcaa                                             26

<210> SEQ ID NO 240
<211> LENGTH: 23
<212> TYPE: DNA
<213> ORGANISM: Homo sapiens

<400> SEQUENCE: 240
aagacatagg cactttgaga ggc                                                23

<210> SEQ ID NO 241
<211> LENGTH: 26
<212> TYPE: DNA
<213> ORGANISM: Homo sapiens

<400> SEQUENCE: 241
ggacagattt ggagacccat agaaag                                             26

<210> SEQ ID NO 242
<211> LENGTH: 26
<212> TYPE: DNA
<213> ORGANISM: Homo sapiens

<400> SEQUENCE: 242
gtaacacagg taggaaggag tggagc                                             26

<210> SEQ ID NO 243
<211> LENGTH: 26
<212> TYPE: DNA
<213> ORGANISM: Homo sapiens

<400> SEQUENCE: 243
gtgaggaagg tgtagaagaa cagact                                             26

<210> SEQ ID NO 244
<211> LENGTH: 23
<212> TYPE: DNA
<213> ORGANISM: Homo sapiens -continued

<400> SEQUENCE: 244
cttgtcgtag aggatgctca ggc                                                          23

<210> SEQ ID NO 245
<211> LENGTH: 23
<212> TYPE: DNA
<213> ORGANISM: Homo sapiens

<400> SEQUENCE: 245
cctggatgtt cattcccacc tgg                                                          23

<210> SEQ ID NO 246
<211> LENGTH: 23
<212> TYPE: DNA
<213> ORGANISM: Homo sapiens

<400> SEQUENCE: 246
tactcctcgt tccctttct ctc                                                           23

<210> SEQ ID NO 247
<211> LENGTH: 20
<212> TYPE: DNA
<213> ORGANISM: Homo sapiens

<400> SEQUENCE: 247
gcagattcca cagggcttac                                                              20

<210> SEQ ID NO 248
<211> LENGTH: 21
<212> TYPE: DNA
<213> ORGANISM: Homo sapiens

<400> SEQUENCE: 248
tttgtcatgt tgtccaggct g                                                            21

<210> SEQ ID NO 249
<211> LENGTH: 20
<212> TYPE: DNA
<213> ORGANISM: Homo sapiens

<400> SEQUENCE: 249
gctggtctca aagtcctggc                                                              20

<210> SEQ ID NO 250
<211> LENGTH: 20
<212> TYPE: DNA
<213> ORGANISM: Homo sapiens

<400> SEQUENCE: 250
gctggtctca aactcctggc                                                              20

<210> SEQ ID NO 251
<211> LENGTH: 20
<212> TYPE: DNA
<213> ORGANISM: Homo sapiens

<400> SEQUENCE: 251
agtatttgag gctgggcatg                                                              20

<210> SEQ ID NO 252
<211> LENGTH: 25
<212> TYPE: DNA
<213> ORGANISM: Homo sapiens -continued

```
<400> SEQUENCE: 252
ttctttgtct cccctctcta ctcct                                    25

<210> SEQ ID NO 253
<211> LENGTH: 26
<212> TYPE: DNA
<213> ORGANISM: Homo sapiens

<400> SEQUENCE: 253
acaggaaatc cagtatcttg gggaaa                                   26

<210> SEQ ID NO 254
<211> LENGTH: 25
<212> TYPE: DNA
<213> ORGANISM: Homo sapiens

<400> SEQUENCE: 254
acggttagaa gatttgccag aggat                                    25

<210> SEQ ID NO 255
<211> LENGTH: 25
<212> TYPE: DNA
<213> ORGANISM: Homo sapiens

<400> SEQUENCE: 255
gaatatcaaa gatgccaggg agctg                                    25

<210> SEQ ID NO 256
<211> LENGTH: 20
<212> TYPE: DNA
<213> ORGANISM: Homo sapiens

<400> SEQUENCE: 256
gacgtttcac catgttgccc                                          20

<210> SEQ ID NO 257
<211> LENGTH: 20
<212> TYPE: DNA
<213> ORGANISM: Homo sapiens

<400> SEQUENCE: 257
gaatgaaact ctgaggccgg                                          20

<210> SEQ ID NO 258
<211> LENGTH: 26
<212> TYPE: DNA
<213> ORGANISM: Homo sapiens

<400> SEQUENCE: 258
tgtgttatca ggataagatt ccaggt                                   26

<210> SEQ ID NO 259
<211> LENGTH: 23
<212> TYPE: DNA
<213> ORGANISM: Homo sapiens

<400> SEQUENCE: 259
aggatcttgc tgtttgtttc acg                                      23

<210> SEQ ID NO 260
<211> LENGTH: 26
<212> TYPE: DNA
```

-continued

```
<213> ORGANISM: Homo sapiens

<400> SEQUENCE: 260
ccctaaaccc agtaatcctg tgcttc                                    26

<210> SEQ ID NO 261
<211> LENGTH: 26
<212> TYPE: DNA
<213> ORGANISM: Homo sapiens

<400> SEQUENCE: 261
gcagaaacag gacctcaaac ggttag                                    26

<210> SEQ ID NO 262
<211> LENGTH: 26
<212> TYPE: DNA
<213> ORGANISM: Homo sapiens

<400> SEQUENCE: 262
agtttctctc tgttcccagt ttgctg                                    26

<210> SEQ ID NO 263
<211> LENGTH: 23
<212> TYPE: DNA
<213> ORGANISM: Homo sapiens

<400> SEQUENCE: 263
gttcctttgc cctcttcagt ggc                                       23

<210> SEQ ID NO 264
<211> LENGTH: 26
<212> TYPE: DNA
<213> ORGANISM: Homo sapiens

<400> SEQUENCE: 264
tagcatcctg ccttgactga gggtga                                    26

<210> SEQ ID NO 265
<211> LENGTH: 26
<212> TYPE: DNA
<213> ORGANISM: Homo sapiens

<400> SEQUENCE: 265
gagtatttac gatggtcagg tgctgc                                    26

<210> SEQ ID NO 266
<211> LENGTH: 26
<212> TYPE: DNA
<213> ORGANISM: Homo sapiens

<400> SEQUENCE: 266
ggctcacaca ggcttctgga taggaa                                    26

<210> SEQ ID NO 267
<211> LENGTH: 23
<212> TYPE: DNA
<213> ORGANISM: Homo sapiens

<400> SEQUENCE: 267
attactcagc ccctcggagc cat                                       23

<210> SEQ ID NO 268
<211> LENGTH: 23
```

-continued

```
<212> TYPE: DNA
<213> ORGANISM: Homo sapiens

<400> SEQUENCE: 268
gactcagggc tggcagtgaa cga                                           23

<210> SEQ ID NO 269
<211> LENGTH: 23
<212> TYPE: DNA
<213> ORGANISM: Homo sapiens

<400> SEQUENCE: 269
gactcagggc tggcagtgaa cga                                           23

<210> SEQ ID NO 270
<211> LENGTH: 26
<212> TYPE: DNA
<213> ORGANISM: Homo sapiens

<400> SEQUENCE: 270
ttatggagaa catcctcagt gtcctg                                        26

<210> SEQ ID NO 271
<211> LENGTH: 23
<212> TYPE: DNA
<213> ORGANISM: Homo sapiens

<400> SEQUENCE: 271
caagaactga ccccaagtcc ctg                                           23

<210> SEQ ID NO 272
<211> LENGTH: 26
<212> TYPE: DNA
<213> ORGANISM: Homo sapiens

<400> SEQUENCE: 272
ggcagccact tcatccatcc agaatc                                        26

<210> SEQ ID NO 273
<211> LENGTH: 25
<212> TYPE: DNA
<213> ORGANISM: Homo sapiens

<400> SEQUENCE: 273
tgtgttccca caaattggaa atgcc                                         25

<210> SEQ ID NO 274
<211> LENGTH: 25
<212> TYPE: DNA
<213> ORGANISM: Homo sapiens

<400> SEQUENCE: 274
ccatgctggc attcatctat ttggt                                         25

<210> SEQ ID NO 275
<211> LENGTH: 25
<212> TYPE: DNA
<213> ORGANISM: Homo sapiens

<400> SEQUENCE: 275
tagaagtcac tcactcccat cctct                                         25

<210> SEQ ID NO 276
```

-continued

```
<211> LENGTH: 25
<212> TYPE: DNA
<213> ORGANISM: Homo sapiens

<400> SEQUENCE: 276
acagtcagtg attggcacag agtaa                                          25

<210> SEQ ID NO 277
<211> LENGTH: 25
<212> TYPE: DNA
<213> ORGANISM: Homo sapiens

<400> SEQUENCE: 277
acactttaga cagagtgaca gggtc                                          25

<210> SEQ ID NO 278
<211> LENGTH: 25
<212> TYPE: DNA
<213> ORGANISM: Homo sapiens

<400> SEQUENCE: 278
aggaatggtt actgctcctc tttgt                                          25

<210> SEQ ID NO 279
<211> LENGTH: 20
<212> TYPE: DNA
<213> ORGANISM: Homo sapiens

<400> SEQUENCE: 279
agtccccaca actgccaatg                                                20

<210> SEQ ID NO 280
<211> LENGTH: 25
<212> TYPE: DNA
<213> ORGANISM: Homo sapiens

<400> SEQUENCE: 280
agtctaagag atggtcacac ccatt                                          25

<210> SEQ ID NO 281
<211> LENGTH: 20
<212> TYPE: DNA
<213> ORGANISM: Homo sapiens

<400> SEQUENCE: 281
gtttgggagg ccaatgtagg                                                20

<210> SEQ ID NO 282
<211> LENGTH: 26
<212> TYPE: DNA
<213> ORGANISM: Homo sapiens

<400> SEQUENCE: 282
ttagtctgta tggtagtgtg tgcctg                                         26

<210> SEQ ID NO 283
<211> LENGTH: 26
<212> TYPE: DNA
<213> ORGANISM: Homo sapiens

<400> SEQUENCE: 283
gtcagagttg ccgataggtc ttgcta                                         26
```

-continued

```
<210> SEQ ID NO 284
<211> LENGTH: 23
<212> TYPE: DNA
<213> ORGANISM: Homo sapiens

<400> SEQUENCE: 284
ggtgggtctg actgcctttc tca                                     23

<210> SEQ ID NO 285
<211> LENGTH: 26
<212> TYPE: DNA
<213> ORGANISM: Homo sapiens

<400> SEQUENCE: 285
acatctatct tgcccctcac tcaggt                                  26

<210> SEQ ID NO 286
<211> LENGTH: 23
<212> TYPE: DNA
<213> ORGANISM: Homo sapiens

<400> SEQUENCE: 286
gcctgaggga gcaagttcaa ccc                                     23

<210> SEQ ID NO 287
<211> LENGTH: 26
<212> TYPE: DNA
<213> ORGANISM: Homo sapiens

<400> SEQUENCE: 287
gaaggaggga ggtaggagag tcatta                                  26

<210> SEQ ID NO 288
<211> LENGTH: 23
<212> TYPE: DNA
<213> ORGANISM: Homo sapiens

<400> SEQUENCE: 288
gaggaggaga aactcagaag ccc                                     23

<210> SEQ ID NO 289
<211> LENGTH: 26
<212> TYPE: DNA
<213> ORGANISM: Homo sapiens

<400> SEQUENCE: 289
gcacaagacc tcacattctg atgggc                                  26

<210> SEQ ID NO 290
<211> LENGTH: 26
<212> TYPE: DNA
<213> ORGANISM: Homo sapiens

<400> SEQUENCE: 290
caaagagaaa gggctgagga tgaagc                                  26

<210> SEQ ID NO 291
<211> LENGTH: 26
<212> TYPE: DNA
<213> ORGANISM: Homo sapiens

<400> SEQUENCE: 291
cccctcatct cagtatgttt atgtcc                                  26
```

-continued

```
<210> SEQ ID NO 292
<211> LENGTH: 23
<212> TYPE: DNA
<213> ORGANISM: Homo sapiens

<400> SEQUENCE: 292
gcctggcaag gagtaagcat tcg                                          23

<210> SEQ ID NO 293
<211> LENGTH: 25
<212> TYPE: DNA
<213> ORGANISM: Homo sapiens

<400> SEQUENCE: 293
atgctccctc ccttatcttt tggta                                        25

<210> SEQ ID NO 294
<211> LENGTH: 26
<212> TYPE: DNA
<213> ORGANISM: Homo sapiens

<400> SEQUENCE: 294
ccccaaactc ccagacacat cagaga                                       26

<210> SEQ ID NO 295
<211> LENGTH: 25
<212> TYPE: DNA
<213> ORGANISM: Homo sapiens

<400> SEQUENCE: 295
tgctgtcaaa atggtgcctg aaaat                                        25

<210> SEQ ID NO 296
<211> LENGTH: 20
<212> TYPE: DNA
<213> ORGANISM: Homo sapiens

<400> SEQUENCE: 296
cttactgcag cctcacactc                                              20

<210> SEQ ID NO 297
<211> LENGTH: 23
<212> TYPE: DNA
<213> ORGANISM: Homo sapiens

<400> SEQUENCE: 297
gacagtaaac acacccactc ccc                                          23

<210> SEQ ID NO 298
<211> LENGTH: 20
<212> TYPE: DNA
<213> ORGANISM: Homo sapiens

<400> SEQUENCE: 298
cttactgcag cctcacactc                                              20

<210> SEQ ID NO 299
<211> LENGTH: 26
<212> TYPE: DNA
<213> ORGANISM: Homo sapiens

<400> SEQUENCE: 299
ccctcacttt ccttctactc ttcaag                                       26
```

-continued

```
<210> SEQ ID NO 300
<211> LENGTH: 26
<212> TYPE: DNA
<213> ORGANISM: Homo sapiens

<400> SEQUENCE: 300
tgttcccttt gttcaaccca ggctat                                      26

<210> SEQ ID NO 301
<211> LENGTH: 23
<212> TYPE: DNA
<213> ORGANISM: Homo sapiens

<400> SEQUENCE: 301
atgggtgagg atgctggcaa tgc                                         23

<210> SEQ ID NO 302
<211> LENGTH: 23
<212> TYPE: DNA
<213> ORGANISM: Homo sapiens

<400> SEQUENCE: 302
cctgaatctg ctgtggcttg ggc                                         23

<210> SEQ ID NO 303
<211> LENGTH: 23
<212> TYPE: DNA
<213> ORGANISM: Homo sapiens

<400> SEQUENCE: 303
ccagtaggag ggaagacacg gtc                                         23

<210> SEQ ID NO 304
<211> LENGTH: 26
<212> TYPE: DNA
<213> ORGANISM: Homo sapiens

<400> SEQUENCE: 304
gatttaggca ctacggagaa aagggc                                      26

<210> SEQ ID NO 305
<211> LENGTH: 23
<212> TYPE: DNA
<213> ORGANISM: Homo sapiens

<400> SEQUENCE: 305
tatcgtccag gaggcaaggg tcc                                         23

<210> SEQ ID NO 306
<211> LENGTH: 25
<212> TYPE: DNA
<213> ORGANISM: Homo sapiens

<400> SEQUENCE: 306
agaggagagc aggcacaggt atcgt                                       25

<210> SEQ ID NO 307
<211> LENGTH: 23
<212> TYPE: DNA
<213> ORGANISM: Homo sapiens

<400> SEQUENCE: 307
```

-continued

```
tatcgtccag gaggcaaggg tcc                                              23

<210> SEQ ID NO 308
<211> LENGTH: 23
<212> TYPE: DNA
<213> ORGANISM: Homo sapiens

<400> SEQUENCE: 308
gcctcttccc accagcctga ctt                                              23

<210> SEQ ID NO 309
<211> LENGTH: 26
<212> TYPE: DNA
<213> ORGANISM: Homo sapiens

<400> SEQUENCE: 309
gatgaggtaa ccaaagttca gggaga                                           26

<210> SEQ ID NO 310
<211> LENGTH: 26
<212> TYPE: DNA
<213> ORGANISM: Homo sapiens

<400> SEQUENCE: 310
ctctctcctc atcctccctc ctaata                                           26

<210> SEQ ID NO 311
<211> LENGTH: 26
<212> TYPE: DNA
<213> ORGANISM: Homo sapiens

<400> SEQUENCE: 311
gggagccaga aagatagcaa tgccta                                           26

<210> SEQ ID NO 312
<211> LENGTH: 26
<212> TYPE: DNA
<213> ORGANISM: Homo sapiens

<400> SEQUENCE: 312
tcactccctc tcttctcccc ttcact                                           26

<210> SEQ ID NO 313
<211> LENGTH: 23
<212> TYPE: DNA
<213> ORGANISM: Homo sapiens

<400> SEQUENCE: 313
ctctgtggca tccctaaatc ccg                                              23

<210> SEQ ID NO 314
<211> LENGTH: 23
<212> TYPE: DNA
<213> ORGANISM: Homo sapiens

<400> SEQUENCE: 314
actcctcaag cccagacaat ggc                                              23

<210> SEQ ID NO 315
<211> LENGTH: 26
<212> TYPE: DNA
<213> ORGANISM: Homo sapiens

<400> SEQUENCE: 315
```

```
gtcagttcag gtctggtttt gccaca                                    26

<210> SEQ ID NO 316
<211> LENGTH: 26
<212> TYPE: DNA
<213> ORGANISM: Homo sapiens

<400> SEQUENCE: 316
ctctccttta tccctaccc tgctca                                     26

<210> SEQ ID NO 317
<211> LENGTH: 24
<212> TYPE: DNA
<213> ORGANISM: Homo sapiens

<400> SEQUENCE: 317
gggacccttt cttcttgctc tgat                                      24

<210> SEQ ID NO 318
<211> LENGTH: 26
<212> TYPE: DNA
<213> ORGANISM: Homo sapiens

<400> SEQUENCE: 318
cattcttgac cctctcactc tgtgcc                                    26

<210> SEQ ID NO 319
<211> LENGTH: 26
<212> TYPE: DNA
<213> ORGANISM: Homo sapiens

<400> SEQUENCE: 319
caccataaaa tagggcaagg tcagca                                    26

<210> SEQ ID NO 320
<211> LENGTH: 25
<212> TYPE: DNA
<213> ORGANISM: Homo sapiens

<400> SEQUENCE: 320
ggatagaagg cacagtgacc ctcct                                     25

<210> SEQ ID NO 321
<211> LENGTH: 24
<212> TYPE: DNA
<213> ORGANISM: Homo sapiens

<400> SEQUENCE: 321
ggcacgcaat ctcaatctcg gctc                                      24

<210> SEQ ID NO 322
<211> LENGTH: 23
<212> TYPE: DNA
<213> ORGANISM: Homo sapiens

<400> SEQUENCE: 322
agagggaaag gcaggtcgtg agc                                       23

<210> SEQ ID NO 323
<211> LENGTH: 24
<212> TYPE: DNA
<213> ORGANISM: Homo sapiens
```

-continued

```
<400> SEQUENCE: 323
tgtgtgctag gctgatatgg tttg                                      24

<210> SEQ ID NO 324
<211> LENGTH: 21
<212> TYPE: DNA
<213> ORGANISM: Homo sapiens

<400> SEQUENCE: 324
agtctaaagc ccatgtgagc c                                         21

<210> SEQ ID NO 325
<211> LENGTH: 20
<212> TYPE: DNA
<213> ORGANISM: Homo sapiens

<400> SEQUENCE: 325
ctcagcacca gaactagggc                                           20

<210> SEQ ID NO 326
<211> LENGTH: 23
<212> TYPE: DNA
<213> ORGANISM: Homo sapiens

<400> SEQUENCE: 326
gctctaggtg ctgatgattc aac                                       23

<210> SEQ ID NO 327
<211> LENGTH: 22
<212> TYPE: DNA
<213> ORGANISM: Homo sapiens

<400> SEQUENCE: 327
ggtccccaca ttacattttg gc                                        22

<210> SEQ ID NO 328
<211> LENGTH: 21
<212> TYPE: DNA
<213> ORGANISM: Homo sapiens

<400> SEQUENCE: 328
agggtgttct aagaaggcag c                                         21

<210> SEQ ID NO 329
<211> LENGTH: 25
<212> TYPE: DNA
<213> ORGANISM: Homo sapiens

<400> SEQUENCE: 329
tttttattaa ctgcacggca cacct                                     25

<210> SEQ ID NO 330
<211> LENGTH: 25
<212> TYPE: DNA
<213> ORGANISM: Homo sapiens

<400> SEQUENCE: 330
actaagaatg gatggggcca attat                                     25

<210> SEQ ID NO 331
<211> LENGTH: 25
<212> TYPE: DNA
<213> ORGANISM: Homo sapiens
```

-continued

```
<400> SEQUENCE: 331
gaatatcaaa gatgccaggg agctg                                         25

<210> SEQ ID NO 332
<211> LENGTH: 25
<212> TYPE: DNA
<213> ORGANISM: Homo sapiens

<400> SEQUENCE: 332
ctgcacattt cctagtaggc tctct                                         25

<210> SEQ ID NO 333
<211> LENGTH: 20
<212> TYPE: DNA
<213> ORGANISM: Homo sapiens

<400> SEQUENCE: 333
gtcactcccc attccatccg                                               20

<210> SEQ ID NO 334
<211> LENGTH: 21
<212> TYPE: DNA
<213> ORGANISM: Homo sapiens

<400> SEQUENCE: 334
cccattcgtc tctctgagct g                                             21

<210> SEQ ID NO 335
<211> LENGTH: 25
<212> TYPE: DNA
<213> ORGANISM: Homo sapiens

<400> SEQUENCE: 335
ttggtgaaag gaagggagta gaagt                                         25

<210> SEQ ID NO 336
<211> LENGTH: 20
<212> TYPE: DNA
<213> ORGANISM: Homo sapiens

<400> SEQUENCE: 336
tgccatcaca cccatgcatg                                               20

<210> SEQ ID NO 337
<211> LENGTH: 24
<212> TYPE: DNA
<213> ORGANISM: Homo sapiens

<400> SEQUENCE: 337
attgctgtgg agggaatggt gtgc                                          24

<210> SEQ ID NO 338
<211> LENGTH: 23
<212> TYPE: DNA
<213> ORGANISM: Homo sapiens

<400> SEQUENCE: 338
ttttgtaaag ggcacccgaa ggg                                           23

<210> SEQ ID NO 339
<211> LENGTH: 26
<212> TYPE: DNA
```

-continued

<213> ORGANISM: Homo sapiens

<400> SEQUENCE: 339
agcatcacct tcgtatcttc cccaag                                  26

<210> SEQ ID NO 340
<211> LENGTH: 23
<212> TYPE: DNA
<213> ORGANISM: Homo sapiens

<400> SEQUENCE: 340
gcctgctctt ccctgtttct gcc                                     23

<210> SEQ ID NO 341
<211> LENGTH: 26
<212> TYPE: DNA
<213> ORGANISM: Homo sapiens

<400> SEQUENCE: 341
aaacaaagcc tcacaaactc cacagc                                  26

<210> SEQ ID NO 342
<211> LENGTH: 26
<212> TYPE: DNA
<213> ORGANISM: Homo sapiens

<400> SEQUENCE: 342
atccaaacac aggacgagaa taaagc                                  26

<210> SEQ ID NO 343
<211> LENGTH: 23
<212> TYPE: DNA
<213> ORGANISM: Homo sapiens

<400> SEQUENCE: 343
ttttgtccct cttcaggcag tgc                                     23

<210> SEQ ID NO 344
<211> LENGTH: 23
<212> TYPE: DNA
<213> ORGANISM: Homo sapiens

<400> SEQUENCE: 344
gcagaggagg tgggactttc agc                                     23

<210> SEQ ID NO 345
<211> LENGTH: 23
<212> TYPE: DNA
<213> ORGANISM: Homo sapiens

<400> SEQUENCE: 345
ctgcctcacc ctggcttctt tca                                     23

<210> SEQ ID NO 346
<211> LENGTH: 23
<212> TYPE: DNA
<213> ORGANISM: Homo sapiens

<400> SEQUENCE: 346
ccgccactca gccattgttt cca                                     23

<210> SEQ ID NO 347
<211> LENGTH: 26

-continued

```
<212> TYPE: DNA
<213> ORGANISM: Homo sapiens

<400> SEQUENCE: 347
gctacacaaa gagacttcca gtgatt                                          26

<210> SEQ ID NO 348
<211> LENGTH: 23
<212> TYPE: DNA
<213> ORGANISM: Homo sapiens

<400> SEQUENCE: 348
ggtggaggcg agggatactg cta                                             23

<210> SEQ ID NO 349
<211> LENGTH: 26
<212> TYPE: DNA
<213> ORGANISM: Homo sapiens

<400> SEQUENCE: 349
gcaaatgctt aggacccaaa cccttt                                          26

<210> SEQ ID NO 350
<211> LENGTH: 26
<212> TYPE: DNA
<213> ORGANISM: Homo sapiens

<400> SEQUENCE: 350
cacttgcacc cctaaagcta ttgaaa                                          26

<210> SEQ ID NO 351
<211> LENGTH: 25
<212> TYPE: DNA
<213> ORGANISM: Homo sapiens

<400> SEQUENCE: 351
aattttggtt ggcagctggt agaag                                           25

<210> SEQ ID NO 352
<211> LENGTH: 25
<212> TYPE: DNA
<213> ORGANISM: Homo sapiens

<400> SEQUENCE: 352
cttgaaatgc gaccagtggg aatta                                           25

<210> SEQ ID NO 353
<211> LENGTH: 25
<212> TYPE: DNA
<213> ORGANISM: Homo sapiens

<400> SEQUENCE: 353
aggaaatagc ccaaatgcaa ctgaa                                           25

<210> SEQ ID NO 354
<211> LENGTH: 25
<212> TYPE: DNA
<213> ORGANISM: Homo sapiens

<400> SEQUENCE: 354
ctcaacttca aaatcggttg gggaa                                           25

<210> SEQ ID NO 355
```

```
<211> LENGTH: 25
<212> TYPE: DNA
<213> ORGANISM: Homo sapiens

<400> SEQUENCE: 355
tttctgtctg caaatcctcc accta                                      25

<210> SEQ ID NO 356
<211> LENGTH: 20
<212> TYPE: DNA
<213> ORGANISM: Homo sapiens

<400> SEQUENCE: 356
cgagaagggt ggctcatgag                                            20

<210> SEQ ID NO 357
<211> LENGTH: 24
<212> TYPE: DNA
<213> ORGANISM: Homo sapiens

<400> SEQUENCE: 357
atggaaaccc aagtttgcaa ggaa                                       24

<210> SEQ ID NO 358
<211> LENGTH: 19
<212> TYPE: DNA
<213> ORGANISM: Homo sapiens

<400> SEQUENCE: 358
gccacaagag atctgggac                                             19

<210> SEQ ID NO 359
<211> LENGTH: 60
<212> TYPE: DNA
<213> ORGANISM: Homo sapiens

<400> SEQUENCE: 359
tcaagaaaaa ataataataa ttttttttttc gattcctgct acacattttg gcagaatact    60

<210> SEQ ID NO 360
<211> LENGTH: 60
<212> TYPE: DNA
<213> ORGANISM: Homo sapiens

<400> SEQUENCE: 360
atgcaatcac caaaaatgtt ttaatttctc gactcttggt gatccaggtt tcagaacttc    60

<210> SEQ ID NO 361
<211> LENGTH: 60
<212> TYPE: DNA
<213> ORGANISM: Homo sapiens

<400> SEQUENCE: 361
ggtcaccagc acagaatgat gatgaggatc gactcttggt gatccaggtt tcagaacttc    60

<210> SEQ ID NO 362
<211> LENGTH: 60
<212> TYPE: DNA
<213> ORGANISM: Homo sapiens

<400> SEQUENCE: 362
cggtccctct gccccggtta cctacccgtc gacattggaa tcactttcta atccgggaca    60
```

-continued

```
<210> SEQ ID NO 363
<211> LENGTH: 60
<212> TYPE: DNA
<213> ORGANISM: Homo sapiens

<400> SEQUENCE: 363
cggtccctct gccccggtta cctacccgtc gaggacattc cggctacccc ttcccatcac      60

<210> SEQ ID NO 364
<211> LENGTH: 60
<212> TYPE: DNA
<213> ORGANISM: Homo sapiens

<400> SEQUENCE: 364
attttaaatg tggcatttta ggtttatttc gattttgcat aaattgaaaa agctggagat      60

<210> SEQ ID NO 365
<211> LENGTH: 60
<212> TYPE: DNA
<213> ORGANISM: Homo sapiens

<400> SEQUENCE: 365
ccttgtctat gaagtaagag attaaatctc gaaataaacc taaaatgcca catttaaaat      60

<210> SEQ ID NO 366
<211> LENGTH: 60
<212> TYPE: DNA
<213> ORGANISM: Homo sapiens

<400> SEQUENCE: 366
gggggaaggg cccatgcgga caagtagctc gactggcctc ccacgcctcc tcctttcctg      60

<210> SEQ ID NO 367
<211> LENGTH: 60
<212> TYPE: DNA
<213> ORGANISM: Homo sapiens

<400> SEQUENCE: 367
atatttaaaa aaaattaaga tgtaattttc gactggcctc ccacgcctcc tcctttcctg      60

<210> SEQ ID NO 368
<211> LENGTH: 60
<212> TYPE: DNA
<213> ORGANISM: Homo sapiens

<400> SEQUENCE: 368
aaacatttct cctgcccctc cttttccttc gagcagcagc gaactgtgat tgctgtgagt      60

<210> SEQ ID NO 369
<211> LENGTH: 60
<212> TYPE: DNA
<213> ORGANISM: Homo sapiens

<400> SEQUENCE: 369
tttaaaaaag ctatgtttca gcataaaatc gattagatgc tctgcagctt cctgaagtgt      60

<210> SEQ ID NO 370
<211> LENGTH: 60
<212> TYPE: DNA
<213> ORGANISM: Homo sapiens

<400> SEQUENCE: 370
tttaaaaaag ctatgtttca gcataaaatc gagtgattgt tttaagtgct ctaggcaagt      60
```

-continued

<210> SEQ ID NO 371
<211> LENGTH: 60
<212> TYPE: DNA
<213> ORGANISM: Homo sapiens

<400> SEQUENCE: 371
ttatagtgag aatatatgac ttttgtaatc gagtttttatc tttattccct ccccattggt    60

<210> SEQ ID NO 372
<211> LENGTH: 60
<212> TYPE: DNA
<213> ORGANISM: Homo sapiens

<400> SEQUENCE: 372
aaatgtataa gaacagaaga gaattatctc gacatgtctg aaaagtatta tcagccctct    60

<210> SEQ ID NO 373
<211> LENGTH: 60
<212> TYPE: DNA
<213> ORGANISM: Homo sapiens

<400> SEQUENCE: 373
tataaaggtg gttagggaca gattttcatc gaatttcacc catggtggag atatttcact    60

<210> SEQ ID NO 374
<211> LENGTH: 60
<212> TYPE: DNA
<213> ORGANISM: Homo sapiens

<400> SEQUENCE: 374
ctaggaaaaa agaatgggaa ggaatagatc gatatagaat ctcagttatt cctcaggaaa    60

<210> SEQ ID NO 375
<211> LENGTH: 60
<212> TYPE: DNA
<213> ORGANISM: Homo sapiens

<400> SEQUENCE: 375
ttcaaggaat taaacctagc ccttactatc gattttaggg tatggatatt aggagccata    60

<210> SEQ ID NO 376
<211> LENGTH: 60
<212> TYPE: DNA
<213> ORGANISM: Homo sapiens

<400> SEQUENCE: 376
accgcctcac ctcagctctc cagtgagatc gatcctccca cctaagcttc ccaagttgct    60

<210> SEQ ID NO 377
<211> LENGTH: 60
<212> TYPE: DNA
<213> ORGANISM: Homo sapiens

<400> SEQUENCE: 377
tgctgaaaga aaacacaatt tatttaagtc gagacacaat taaggttgat acaaaaaaag    60

<210> SEQ ID NO 378
<211> LENGTH: 60
<212> TYPE: DNA
<213> ORGANISM: Homo sapiens

<400> SEQUENCE: 378
tgctgaaaga aaacacaatt tatttaagtc gaaattttgg aaaagccctg atttaagtca    60

<210> SEQ ID NO 379
<211> LENGTH: 60
<212> TYPE: DNA
<213> ORGANISM: Homo sapiens

<400> SEQUENCE: 379
ccacacatga ctgtatattt aaattaattc gatgcccaaa ggactgtcat aatcactcag      60

<210> SEQ ID NO 380
<211> LENGTH: 60
<212> TYPE: DNA
<213> ORGANISM: Homo sapiens

<400> SEQUENCE: 380
aaaacaccct gaattggaag aaagaaactc gagggatgag tgtgtatcat caaagtcaaa      60

<210> SEQ ID NO 381
<211> LENGTH: 60
<212> TYPE: DNA
<213> ORGANISM: Homo sapiens

<400> SEQUENCE: 381
catgttttga aaaactatg catggatttc gagggatgag tgtgtatcat caaagtcaaa      60

<210> SEQ ID NO 382
<211> LENGTH: 60
<212> TYPE: DNA
<213> ORGANISM: Homo sapiens

<400> SEQUENCE: 382
tttagataac caatgtatag tacgttaatc gatgtgaagt tcaagaactg acaaggctgt      60

<210> SEQ ID NO 383
<211> LENGTH: 60
<212> TYPE: DNA
<213> ORGANISM: Homo sapiens

<400> SEQUENCE: 383
cgcggggcct tctgggccag gcgggccctc gaaaagcccc acgccccccc agagctgctg      60

<210> SEQ ID NO 384
<211> LENGTH: 60
<212> TYPE: DNA
<213> ORGANISM: Homo sapiens

<400> SEQUENCE: 384
cccggtttcc tcatctgtcc ctgccccctc gagacttgac tggggacaa tccactttga      60

<210> SEQ ID NO 385
<211> LENGTH: 60
<212> TYPE: DNA
<213> ORGANISM: Homo sapiens

<400> SEQUENCE: 385
cccggtttcc tcatctgtcc ctgccccctc gagtctcaga tgtgagggct ggaacagatg      60

<210> SEQ ID NO 386
<211> LENGTH: 60
<212> TYPE: DNA
<213> ORGANISM: Homo sapiens

<400> SEQUENCE: 386

-continued cccggtttcc tcatctgtcc ctgcccctc gaacaatctt gagcatagag aaccagaccc          60

<210> SEQ ID NO 387
<211> LENGTH: 60
<212> TYPE: DNA
<213> ORGANISM: Homo sapiens

<400> SEQUENCE: 387
cccggtttcc tcatctgtcc ctgcccctc gaagtatgga ggtaaatgcc aaaggctcag          60

<210> SEQ ID NO 388
<211> LENGTH: 60
<212> TYPE: DNA
<213> ORGANISM: Homo sapiens

<400> SEQUENCE: 388
agaaaccaca aagctaggaa ttaaattttc gaatgttttt cttcctctta agtgagataa          60

<210> SEQ ID NO 389
<211> LENGTH: 60
<212> TYPE: DNA
<213> ORGANISM: Homo sapiens

<400> SEQUENCE: 389
aatacgtggt caatctaagg attatagttc gaaaagatta atgatgtatt gatgacactt          60

<210> SEQ ID NO 390
<211> LENGTH: 60
<212> TYPE: DNA
<213> ORGANISM: Homo sapiens

<400> SEQUENCE: 390
gacacctcct ctcccttccc tccccttctc gagttatcaa aatattttga gagacagtat          60

<210> SEQ ID NO 391
<211> LENGTH: 60
<212> TYPE: DNA
<213> ORGANISM: Homo sapiens

<400> SEQUENCE: 391
gacacctcct ctcccttccc tccccttctc gatcactttg caaagctttg ttggctaggc          60

<210> SEQ ID NO 392
<211> LENGTH: 60
<212> TYPE: DNA
<213> ORGANISM: Homo sapiens

<400> SEQUENCE: 392
gacacctcct ctcccttccc tccccttctc gaaggaaaag ccctggggcc agctgtagag          60

<210> SEQ ID NO 393
<211> LENGTH: 60
<212> TYPE: DNA
<213> ORGANISM: Homo sapiens

<400> SEQUENCE: 393
gacacctcct ctcccttccc tccccttctc gatggccaca tgtggccagt ggctctcatg          60

<210> SEQ ID NO 394
<211> LENGTH: 60
<212> TYPE: DNA
<213> ORGANISM: Homo sapiens

<400> SEQUENCE: 394

-continued

```
ccgctctgct atggaccccg gctcgctctc gacttggccc ccagcatgtc ctcagccacc      60

<210> SEQ ID NO 395
<211> LENGTH: 60
<212> TYPE: DNA
<213> ORGANISM: Homo sapiens

<400> SEQUENCE: 395
ttataattgt tactattggg aagaggattc gacacagaaa ctaagttttc aaaataaaaa      60

<210> SEQ ID NO 396
<211> LENGTH: 60
<212> TYPE: DNA
<213> ORGANISM: Homo sapiens

<400> SEQUENCE: 396
gccaagaggg gaaaggactc atgttctctc gactgcctcc tctcccacct ctgctcggat      60

<210> SEQ ID NO 397
<211> LENGTH: 60
<212> TYPE: DNA
<213> ORGANISM: Homo sapiens

<400> SEQUENCE: 397
ccacccctgc tgctctggac ctggtggatc gacttttgtt tcctgtcatt caagctgcgt      60

<210> SEQ ID NO 398
<211> LENGTH: 60
<212> TYPE: DNA
<213> ORGANISM: Homo sapiens

<400> SEQUENCE: 398
tttggtgatg aaatgaaaat aatttatttc gaagagctcc ttattccagt agaaacacaa      60

<210> SEQ ID NO 399
<211> LENGTH: 60
<212> TYPE: DNA
<213> ORGANISM: Homo sapiens

<400> SEQUENCE: 399
accatcagaa agctccattt tcttttgttc gacatgattt tatgactgat tggtcatagg      60

<210> SEQ ID NO 400
<211> LENGTH: 60
<212> TYPE: DNA
<213> ORGANISM: Homo sapiens

<400> SEQUENCE: 400
tgtcctttca aggaaggatt agcatccttc gaaagaccta tcaggatttc atttgtaatg      60

<210> SEQ ID NO 401
<211> LENGTH: 60
<212> TYPE: DNA
<213> ORGANISM: Homo sapiens

<400> SEQUENCE: 401
cttgcctagt ctttaattta tttatttatc gacatttttt tcttatcaac gagacgatgt      60

<210> SEQ ID NO 402
<211> LENGTH: 60
<212> TYPE: DNA
<213> ORGANISM: Homo sapiens
```

-continued

```
<400> SEQUENCE: 402
tgcagaaagt actacaaaaa aagaagcttc gaaaatgttg gagatgagag tttcttcacc      60

<210> SEQ ID NO 403
<211> LENGTH: 60
<212> TYPE: DNA
<213> ORGANISM: Homo sapiens

<400> SEQUENCE: 403
catggtttat aatccttttt atacattgtc gacactgtat tttcacagat cactctggag      60

<210> SEQ ID NO 404
<211> LENGTH: 60
<212> TYPE: DNA
<213> ORGANISM: Homo sapiens

<400> SEQUENCE: 404
agaacttcct gatatatttt ttttcttttc gaaggtctta aaatgttttt aaacatgacc      60

<210> SEQ ID NO 405
<211> LENGTH: 60
<212> TYPE: DNA
<213> ORGANISM: Homo sapiens

<400> SEQUENCE: 405
gactcttaaa acaataatat caaacaactc gacttgtcat ttagttcttt gggaagcagt      60

<210> SEQ ID NO 406
<211> LENGTH: 60
<212> TYPE: DNA
<213> ORGANISM: Homo sapiens

<400> SEQUENCE: 406
acaacagaat agaacatatt caattaaatc gacataggaa taggtttcag atcctagtct      60

<210> SEQ ID NO 407
<211> LENGTH: 60
<212> TYPE: DNA
<213> ORGANISM: Homo sapiens

<400> SEQUENCE: 407
taataatttt atataataga attttgactc gaagttgatg tcaagattta tggcttacat      60

<210> SEQ ID NO 408
<211> LENGTH: 60
<212> TYPE: DNA
<213> ORGANISM: Homo sapiens

<400> SEQUENCE: 408
aattagacaa cgactatatg actctgtctc gactttaaag caagtacttc ttgtatgctc      60

<210> SEQ ID NO 409
<211> LENGTH: 60
<212> TYPE: DNA
<213> ORGANISM: Homo sapiens

<400> SEQUENCE: 409
aattagacaa cgactatatg actctgtctc gagattggtc ttaacacact attgattatt      60

<210> SEQ ID NO 410
<211> LENGTH: 60
<212> TYPE: DNA
<213> ORGANISM: Homo sapiens
```

-continued

<400> SEQUENCE: 410
gcaaattttg gagcctaacc tccaaaattc gagcacaaaa ctttgtccac atttctgatt          60

<210> SEQ ID NO 411
<211> LENGTH: 60
<212> TYPE: DNA
<213> ORGANISM: Homo sapiens

<400> SEQUENCE: 411
aaaaagagaa aagcaggtta gcacattgtc gaccccgccc ccgggatggg ggaactggcc          60

<210> SEQ ID NO 412
<211> LENGTH: 60
<212> TYPE: DNA
<213> ORGANISM: Homo sapiens

<400> SEQUENCE: 412
ctctataaat ttaccagaat ataaattctc gaagtgatct ctaaatgtaa tcgtaagttt          60

<210> SEQ ID NO 413
<211> LENGTH: 60
<212> TYPE: DNA
<213> ORGANISM: Homo sapiens

<400> SEQUENCE: 413
aaattttcaa gtgtacgata tggtatcatc gaccccgccc ccgggatggg ggaactggcc          60

<210> SEQ ID NO 414
<211> LENGTH: 60
<212> TYPE: DNA
<213> ORGANISM: Homo sapiens

<400> SEQUENCE: 414
aaacttacga ttacatttag agatcacttc gaccccgccc ccgggatggg ggaactggcc          60

<210> SEQ ID NO 415
<211> LENGTH: 60
<212> TYPE: DNA
<213> ORGANISM: Homo sapiens

<400> SEQUENCE: 415
gagagatgcc cactcatacc atataacttc gaccccgccc ccgggatggg ggaactggcc          60

<210> SEQ ID NO 416
<211> LENGTH: 60
<212> TYPE: DNA
<213> ORGANISM: Homo sapiens

<400> SEQUENCE: 416
ccacataaaa ccttgggttc ttaatttatc gaagttgagt tacgtgttta aaaaagaaa          60

<210> SEQ ID NO 417
<211> LENGTH: 60
<212> TYPE: DNA
<213> ORGANISM: Homo sapiens

<400> SEQUENCE: 417
tcatataaat gccccacaga gtgcagcatc gaacctcgcc ccctgcacga cccacacaaa          60

<210> SEQ ID NO 418
<211> LENGTH: 60
<212> TYPE: DNA

-continued

```
<213> ORGANISM: Homo sapiens

<400> SEQUENCE: 418
atgaaagaat atgatttttt tttttactc gagtgtaaaa gggctttac tggtgcacac        60

<210> SEQ ID NO 419
<211> LENGTH: 60
<212> TYPE: DNA
<213> ORGANISM: Homo sapiens

<400> SEQUENCE: 419
taaataaaat tgtctttttt tgtctttctc gagattttga aacaccttca gtttgaagac      60

<210> SEQ ID NO 420
<211> LENGTH: 60
<212> TYPE: DNA
<213> ORGANISM: Homo sapiens

<400> SEQUENCE: 420
taaataaaat tgtctttttt tgtctttctc gattacagag aactaagtac attttaaatc      60

<210> SEQ ID NO 421
<211> LENGTH: 60
<212> TYPE: DNA
<213> ORGANISM: Homo sapiens

<400> SEQUENCE: 421
ggcaggtgga tcatttgagg tcaagagctc gacagagcaa gacaccatct ccaaaaagaa      60

<210> SEQ ID NO 422
<211> LENGTH: 60
<212> TYPE: DNA
<213> ORGANISM: Homo sapiens

<400> SEQUENCE: 422
tctaaggtat agttttgggt ataaaccatc gaacattacc cccgattgtt ttggaaatta      60

<210> SEQ ID NO 423
<211> LENGTH: 60
<212> TYPE: DNA
<213> ORGANISM: Homo sapiens

<400> SEQUENCE: 423
ttatttgtta atatccagta gtatttaatc gattgccgtt ggctcaaagt aatatttgaa      60

<210> SEQ ID NO 424
<211> LENGTH: 60
<212> TYPE: DNA
<213> ORGANISM: Homo sapiens

<400> SEQUENCE: 424
aagggctcgg gagctccctc ggcacacctc gaggagtgcc aggcatctac tgctctgtcc      60

<210> SEQ ID NO 425
<211> LENGTH: 60
<212> TYPE: DNA
<213> ORGANISM: Homo sapiens

<400> SEQUENCE: 425
aggaatccat tttcagatca caccccagtc gaaagaaaac catttggatg accgtggaag      60

<210> SEQ ID NO 426
<211> LENGTH: 60
```

-continued

```
<212> TYPE: DNA
<213> ORGANISM: Homo sapiens

<400> SEQUENCE: 426
cccctggctc acctacacaa aattgtgctc gactctactc ttagccctgc taaataagta      60

<210> SEQ ID NO 427
<211> LENGTH: 60
<212> TYPE: DNA
<213> ORGANISM: Homo sapiens

<400> SEQUENCE: 427
cccctggctc acctacacaa aattgtgctc gaatgtctga acaagtgaat gaacaaatga      60

<210> SEQ ID NO 428
<211> LENGTH: 60
<212> TYPE: DNA
<213> ORGANISM: Homo sapiens

<400> SEQUENCE: 428
attatattag tgctgtaata aaattaagtc gacacatttg atactgctta ttgggttatt      60

<210> SEQ ID NO 429
<211> LENGTH: 60
<212> TYPE: DNA
<213> ORGANISM: Homo sapiens

<400> SEQUENCE: 429
taccttgaaa agctcttcag tatgattatc gaaagattca ttttcatgtt ccgttttatc      60

<210> SEQ ID NO 430
<211> LENGTH: 60
<212> TYPE: DNA
<213> ORGANISM: Homo sapiens

<400> SEQUENCE: 430
taccttgaaa agctcttcag tatgattatc gagctttagc cattctagta attattaaaa      60

<210> SEQ ID NO 431
<211> LENGTH: 60
<212> TYPE: DNA
<213> ORGANISM: Homo sapiens

<400> SEQUENCE: 431
agatctcaca tgtaaattag aatagcagtc gactaaatat aaagactcaa taaccaccat      60

<210> SEQ ID NO 432
<211> LENGTH: 60
<212> TYPE: DNA
<213> ORGANISM: Homo sapiens

<400> SEQUENCE: 432
ttttctccca aagtttatat cctaatattc gaggaaggtt atatttttgg ctatgcatct      60

<210> SEQ ID NO 433
<211> LENGTH: 60
<212> TYPE: DNA
<213> ORGANISM: Homo sapiens

<400> SEQUENCE: 433
tgtctgttcc agagtggccc gcagctcctc gaggagctgg cactcttata cacctctggg      60

<210> SEQ ID NO 434
```

```
<211> LENGTH: 60
<212> TYPE: DNA
<213> ORGANISM: Homo sapiens

<400> SEQUENCE: 434
tgagttactg tttttccttc cttttgattc gagaagaaac caagaattag agggatttaa      60

<210> SEQ ID NO 435
<211> LENGTH: 60
<212> TYPE: DNA
<213> ORGANISM: Homo sapiens

<400> SEQUENCE: 435
atgaattaat gtttcctaga aagttgtctc gaaagaagaa agtgtcaggg ttcaactgcc      60

<210> SEQ ID NO 436
<211> LENGTH: 60
<212> TYPE: DNA
<213> ORGANISM: Homo sapiens

<400> SEQUENCE: 436
ggtcaggtct gtgctatgga aagagctctc gacctccagt ctttcctctc gcataaatgg      60

<210> SEQ ID NO 437
<211> LENGTH: 60
<212> TYPE: DNA
<213> ORGANISM: Homo sapiens

<400> SEQUENCE: 437
tctttatggt gtctctttat atatttactc gagaaagaag taacacacta ttgctaattc      60

<210> SEQ ID NO 438
<211> LENGTH: 60
<212> TYPE: DNA
<213> ORGANISM: Homo sapiens

<400> SEQUENCE: 438
gaattagcaa tagtgtgtta cttctttctc gatattttac atggaatctt tcccttttta      60

<210> SEQ ID NO 439
<211> LENGTH: 60
<212> TYPE: DNA
<213> ORGANISM: Homo sapiens

<400> SEQUENCE: 439
tacctttcca tttgtctcct tcccttcatc gatattttac atggaatctt tcccttttta      60

<210> SEQ ID NO 440
<211> LENGTH: 60
<212> TYPE: DNA
<213> ORGANISM: Homo sapiens

<400> SEQUENCE: 440
atctggcttc acattcctcg gcccttcctc gactctccct ctgtaggcct ccaccatgga      60

<210> SEQ ID NO 441
<211> LENGTH: 60
<212> TYPE: DNA
<213> ORGANISM: Homo sapiens

<400> SEQUENCE: 441
attcatttat ctgtattctt agtatgcttc gaaggtaata taaccttgaa aatgtaacaa      60
```

-continued

```
<210> SEQ ID NO 442
<211> LENGTH: 60
<212> TYPE: DNA
<213> ORGANISM: Homo sapiens

<400> SEQUENCE: 442
ctcttcaggg gtgtgtggag taaatagctc gagtttgtcc acagccctca cagcccttgg      60

<210> SEQ ID NO 443
<211> LENGTH: 60
<212> TYPE: DNA
<213> ORGANISM: Homo sapiens

<400> SEQUENCE: 443
taaaaagaaa catatgaaac ttattttatc gaccctatag attttttcaat atatgtttat     60

<210> SEQ ID NO 444
<211> LENGTH: 60
<212> TYPE: DNA
<213> ORGANISM: Homo sapiens

<400> SEQUENCE: 444
tcagataagt aacttcctga taattaactc gaagtccagg attcattata aacactgata      60

<210> SEQ ID NO 445
<211> LENGTH: 60
<212> TYPE: DNA
<213> ORGANISM: Homo sapiens

<400> SEQUENCE: 445
tcagataagt aacttcctga taattaactc gagaaacatt tattggttgt ccaattgttt      60

<210> SEQ ID NO 446
<211> LENGTH: 60
<212> TYPE: DNA
<213> ORGANISM: Homo sapiens

<400> SEQUENCE: 446
cctcgtcgtc ccctctcttc ctcgttcctc gacaggaaag catacggaaa aagttaaaga      60

<210> SEQ ID NO 447
<211> LENGTH: 60
<212> TYPE: DNA
<213> ORGANISM: Homo sapiens

<400> SEQUENCE: 447
cctcgtcgtc ccctctcttc ctcgttcctc gatgcgggac tgattgttac agaactgttt      60

<210> SEQ ID NO 448
<211> LENGTH: 60
<212> TYPE: DNA
<213> ORGANISM: Homo sapiens

<400> SEQUENCE: 448
cctcgtcgtc ccctctcttc ctcgttcctc gaacatctcc aagtcagata atcataacaa      60

<210> SEQ ID NO 449
<211> LENGTH: 60
<212> TYPE: DNA
<213> ORGANISM: Homo sapiens

<400> SEQUENCE: 449
cctcgtcgtc ccctctcttc ctcgttcctc gagcctctgt cccaatgtca cctcttcaga      60
```

-continued

```
<210> SEQ ID NO 450
<211> LENGTH: 60
<212> TYPE: DNA
<213> ORGANISM: Homo sapiens

<400> SEQUENCE: 450
ggggatgggg ccgaaatatg attgcacttc gagtttgttt agttttttatc ttccccattt      60

<210> SEQ ID NO 451
<211> LENGTH: 60
<212> TYPE: DNA
<213> ORGANISM: Homo sapiens

<400> SEQUENCE: 451
ggggatgggg ccgaaatatg attgcacttc gaacttcagc acctgacctt tgtcatcaac      60

<210> SEQ ID NO 452
<211> LENGTH: 60
<212> TYPE: DNA
<213> ORGANISM: Homo sapiens

<400> SEQUENCE: 452
aaataatata caagtagtcc aactattttc gagtatttta gaaattacat gaaacatgaa      60

<210> SEQ ID NO 453
<211> LENGTH: 60
<212> TYPE: DNA
<213> ORGANISM: Homo sapiens

<400> SEQUENCE: 453
tcaggcttgc aggctcatgc ctgcaatgtc gagtatttta gaaattacat gaaacatgaa      60

<210> SEQ ID NO 454
<211> LENGTH: 60
<212> TYPE: DNA
<213> ORGANISM: Homo sapiens

<400> SEQUENCE: 454
atctattata atgatgcaat attgttaatc gagttttcct tcttaaagaa caaactcacc      60

<210> SEQ ID NO 455
<211> LENGTH: 60
<212> TYPE: DNA
<213> ORGANISM: Homo sapiens

<400> SEQUENCE: 455
atctattata atgatgcaat attgttaatc gattcaaaga tcaaattaat tattaaagct      60

<210> SEQ ID NO 456
<211> LENGTH: 60
<212> TYPE: DNA
<213> ORGANISM: Homo sapiens

<400> SEQUENCE: 456
ctgagtcttc attaccaaaa aaaaaagttc gaacatgcac tggggtttta ctaaaactat      60

<210> SEQ ID NO 457
<211> LENGTH: 60
<212> TYPE: DNA
<213> ORGANISM: Homo sapiens

<400> SEQUENCE: 457
cgttgcaaat tgtacatctt ctgctatttc gaatgcgaag ttgagaaatt ttacttattt      60
```

-continued

```
<210> SEQ ID NO 458
<211> LENGTH: 60
<212> TYPE: DNA
<213> ORGANISM: Homo sapiens

<400> SEQUENCE: 458 tactttttc atatggatat acagttattc gaggaggaat agtcacataa ataaattatt        60

<210> SEQ ID NO 459
<211> LENGTH: 60
<212> TYPE: DNA
<213> ORGANISM: Homo sapiens

<400> SEQUENCE: 459
tacatgaata tacagtcttg tattgttttc gatctataga atggaaggat agcattagct        60

<210> SEQ ID NO 460
<211> LENGTH: 60
<212> TYPE: DNA
<213> ORGANISM: Homo sapiens

<400> SEQUENCE: 460
tctttgtttc ctgtttccac ttcttatttc gatatttatt gagtgctact atatatatgc        60

<210> SEQ ID NO 461
<211> LENGTH: 60
<212> TYPE: DNA
<213> ORGANISM: Homo sapiens

<400> SEQUENCE: 461
actgtatctt ttgcttattt tctatacttc gaggcataga acctttcctt aaacttattt        60

<210> SEQ ID NO 462
<211> LENGTH: 60
<212> TYPE: DNA
<213> ORGANISM: Homo sapiens

<400> SEQUENCE: 462
actgtatctt ttgcttattt tctatacttc gatccctcct ggcctccccg cctccggcgt        60

<210> SEQ ID NO 463
<211> LENGTH: 60
<212> TYPE: DNA
<213> ORGANISM: Homo sapiens

<400> SEQUENCE: 463
taatgctgga gcaagacaaa gatagacttc gatccctcct ggcctccccg cctccggcgt        60

<210> SEQ ID NO 464
<211> LENGTH: 60
<212> TYPE: DNA
<213> ORGANISM: Homo sapiens

<400> SEQUENCE: 464
ttccacctgt aatactgtgc ctgtattctc gactcttctc gccctcttct ccagctctct        60

<210> SEQ ID NO 465
<211> LENGTH: 60
<212> TYPE: DNA
<213> ORGANISM: Homo sapiens

<400> SEQUENCE: 465
```

-continued agaggctgag gtgaaaagat tgtttgagtc gaagatcatt gtctcatttt tttacttgtt          60

<210> SEQ ID NO 466
<211> LENGTH: 60
<212> TYPE: DNA
<213> ORGANISM: Homo sapiens

<400> SEQUENCE: 466
agaggctgag gtgaaaagat tgtttgagtc gacaaatgtt atacatggct tgtaacactg          60

<210> SEQ ID NO 467
<211> LENGTH: 60
<212> TYPE: DNA
<213> ORGANISM: Homo sapiens

<400> SEQUENCE: 467
agaggctgag gtgaaaagat tgtttgagtc gacaacccaa ttttgttatt tgagtttctt          60

<210> SEQ ID NO 468
<211> LENGTH: 60
<212> TYPE: DNA
<213> ORGANISM: Homo sapiens

<400> SEQUENCE: 468
agaggctgag gtgaaaagat tgtttgagtc gaattcaatt ttactgcaaa cctcagcatc          60

<210> SEQ ID NO 469
<211> LENGTH: 60
<212> TYPE: DNA
<213> ORGANISM: Homo sapiens

<400> SEQUENCE: 469
agaggctgag gtgaaaagat tgtttgagtc gatacactga acaagtgcca gagcagaata          60

<210> SEQ ID NO 470
<211> LENGTH: 60
<212> TYPE: DNA
<213> ORGANISM: Homo sapiens

<400> SEQUENCE: 470
agaggctgag gtgaaaagat tgtttgagtc gagtcacatg atcaagcgct catttctgtt          60

<210> SEQ ID NO 471
<211> LENGTH: 60
<212> TYPE: DNA
<213> ORGANISM: Homo sapiens

<400> SEQUENCE: 471
gaggagagaa agaagacaaa gaagacactc gatctgccct gcggccccac ctgagtgatt          60

<210> SEQ ID NO 472
<211> LENGTH: 60
<212> TYPE: DNA
<213> ORGANISM: Homo sapiens

<400> SEQUENCE: 472
aatggcattc tccatttatt cgtatttatc gagactttct atgaaagctt ttttgatgtt          60

<210> SEQ ID NO 473
<211> LENGTH: 60
<212> TYPE: DNA
<213> ORGANISM: Homo sapiens

<400> SEQUENCE: 473

-continued ggctgaagaa tggaattgaa gtagaaaatc gatgattatc aagtatatac caaacattat        60

<210> SEQ ID NO 474
<211> LENGTH: 60
<212> TYPE: DNA
<213> ORGANISM: Homo sapiens

<400> SEQUENCE: 474
cttaattttt tttctttgaa tgcctctatc gacagtcttc tctctacttt ctacagtgaa        60

<210> SEQ ID NO 475
<211> LENGTH: 60
<212> TYPE: DNA
<213> ORGANISM: Homo sapiens

<400> SEQUENCE: 475
ggtgggagga tcacttgagg tcagaagttc gatctcctga cctcaagtga tcctctagct        60

<210> SEQ ID NO 476
<211> LENGTH: 60
<212> TYPE: DNA
<213> ORGANISM: Homo sapiens

<400> SEQUENCE: 476
atgaaagaaa taccaatatt tgtttaattc gaatctccaa cacgttattt accactggga        60

<210> SEQ ID NO 477
<211> LENGTH: 60
<212> TYPE: DNA
<213> ORGANISM: Homo sapiens

<400> SEQUENCE: 477
tggtggctga gtcctggcac agccactgtc gaagctgggc cccgcacccc ccacacaaac        60

<210> SEQ ID NO 478
<211> LENGTH: 60
<212> TYPE: DNA
<213> ORGANISM: Homo sapiens

<400> SEQUENCE: 478
taaattttta cttgtatttt tttgcatttc gagtactgtt tccttattgg tcttctatat        60

<210> SEQ ID NO 479
<211> LENGTH: 60
<212> TYPE: DNA
<213> ORGANISM: Homo sapiens

<400> SEQUENCE: 479
tatgaatccc taaatgtcac acatcaagtc gaattatata agataccctg aaatttaagg        60

<210> SEQ ID NO 480
<211> LENGTH: 60
<212> TYPE: DNA
<213> ORGANISM: Homo sapiens

<400> SEQUENCE: 480
cttgttatga ttttagtatg agatagtttc gagacagaat ttatttgtaa ttttatcaat        60

<210> SEQ ID NO 481
<211> LENGTH: 60
<212> TYPE: DNA
<213> ORGANISM: Homo sapiens -continued

```
<400> SEQUENCE: 481
tctgcgcaag ttttaatttt ctctaaggtc gatttcccca ccttcccaac ctccaagggt        60

<210> SEQ ID NO 482
<211> LENGTH: 60
<212> TYPE: DNA
<213> ORGANISM: Homo sapiens

<400> SEQUENCE: 482
taaaatataa atgaaagaag tacctcgttc gatttcccca ccttcccaac ctccaagggt        60

<210> SEQ ID NO 483
<211> LENGTH: 60
<212> TYPE: DNA
<213> ORGANISM: Homo sapiens

<400> SEQUENCE: 483
tttcatttag ttaaaaccag atacataatc gagagcacaa aggggaatcc caacagactc        60

<210> SEQ ID NO 484
<211> LENGTH: 60
<212> TYPE: DNA
<213> ORGANISM: Homo sapiens

<400> SEQUENCE: 484
cctctcccgc tctccactca cctcgtggtc gaagtgttgt ccctggactg gcagcatctg        60

<210> SEQ ID NO 485
<211> LENGTH: 60
<212> TYPE: DNA
<213> ORGANISM: Homo sapiens

<400> SEQUENCE: 485
aaattatgtt tcatggaatg atcaggaatc gaaactctct ccaatgaaac aattctttga        60

<210> SEQ ID NO 486
<211> LENGTH: 60
<212> TYPE: DNA
<213> ORGANISM: Homo sapiens

<400> SEQUENCE: 486
atgactgtgg aaggttctga tgtctctgtc gatgaaatgg agagaggaga aagaaaagaa        60

<210> SEQ ID NO 487
<211> LENGTH: 60
<212> TYPE: DNA
<213> ORGANISM: Homo sapiens

<400> SEQUENCE: 487
ttttactgtt tttgtaagag atatgttttc gagagttgca agtacctgcc taaatcactg        60

<210> SEQ ID NO 488
<211> LENGTH: 60
<212> TYPE: DNA
<213> ORGANISM: Homo sapiens

<400> SEQUENCE: 488
atgactgtgg aaggttctga tgtctctgtc gagagttgca agtacctgcc taaatcactg        60

<210> SEQ ID NO 489
<211> LENGTH: 60
<212> TYPE: DNA
<213> ORGANISM: Homo sapiens
```

-continued

<400> SEQUENCE: 489
atgactgtgg aaggttctga tgtctctgtc gacatcattt ttacaaataa gaccagatgt          60

<210> SEQ ID NO 490
<211> LENGTH: 60
<212> TYPE: DNA
<213> ORGANISM: Homo sapiens

<400> SEQUENCE: 490
gagagagcgc ctgacatata gtagaccttc gaggagagag aagggggctca aggcgcccga         60

<210> SEQ ID NO 491
<211> LENGTH: 60
<212> TYPE: DNA
<213> ORGANISM: Homo sapiens

<400> SEQUENCE: 491
aatattgcta ctggaaaatc tgaatctttc gaagaaagcc ctttgtaagt tgttttcaaa          60

<210> SEQ ID NO 492
<211> LENGTH: 60
<212> TYPE: DNA
<213> ORGANISM: Homo sapiens

<400> SEQUENCE: 492
ttaattttca aaaattcatt tccaacattc gacctcagtt gcattagata cagtaggatg          60

<210> SEQ ID NO 493
<211> LENGTH: 60
<212> TYPE: DNA
<213> ORGANISM: Homo sapiens

<400> SEQUENCE: 493
aactatgtga cttttagcta tacgagtttc gataaatcat gatcatggta ataataatta          60

<210> SEQ ID NO 494
<211> LENGTH: 60
<212> TYPE: DNA
<213> ORGANISM: Homo sapiens

<400> SEQUENCE: 494
aactatgtga cttttagcta tacgagtttc gactgggttc taaatagtta atgtcatagt          60

<210> SEQ ID NO 495
<211> LENGTH: 60
<212> TYPE: DNA
<213> ORGANISM: Homo sapiens

<400> SEQUENCE: 495 tttcccttttc ctttagacca tctctctttc gataactaag aagaagctac agaatctctc         60

<210> SEQ ID NO 496
<211> LENGTH: 60
<212> TYPE: DNA
<213> ORGANISM: Homo sapiens

<400> SEQUENCE: 496
gtttgtcctt ctcccaccct accccaactc gaatcattga cctagaattt tagaactgga          60

<210> SEQ ID NO 497
<211> LENGTH: 60
<212> TYPE: DNA

-continued

<213> ORGANISM: Homo sapiens

<400> SEQUENCE: 497
gtttgtcctt ctcccaccct accccaactc gatctctcaa agaaaagaag ttgggatgcc          60

<210> SEQ ID NO 498
<211> LENGTH: 60
<212> TYPE: DNA
<213> ORGANISM: Homo sapiens

<400> SEQUENCE: 498
tatcaagtta aacattcaga cgtctaggtc gagtagtatt tagctttctt cctttctaac          60

<210> SEQ ID NO 499
<211> LENGTH: 60
<212> TYPE: DNA
<213> ORGANISM: Homo sapiens

<400> SEQUENCE: 499
tatcaagtta aacattcaga cgtctaggtc gacttgaagt tcacctaaag ttttccagtc          60

<210> SEQ ID NO 500
<211> LENGTH: 60
<212> TYPE: DNA
<213> ORGANISM: Homo sapiens

<400> SEQUENCE: 500
taaaactatt ttaaatgttt ttaaagtatc gatgtgtact ttgacatctg tgatgatgat          60

<210> SEQ ID NO 501
<211> LENGTH: 60
<212> TYPE: DNA
<213> ORGANISM: Homo sapiens

<400> SEQUENCE: 501
gcaccccacc ctggatccct tgaaagcctc gacaatgtta ttctttgttt ctcttaccaa          60

<210> SEQ ID NO 502
<211> LENGTH: 60
<212> TYPE: DNA
<213> ORGANISM: Homo sapiens

<400> SEQUENCE: 502
ttggaattat caagaaagat aactaaattc gaaaaagatg tatttgtttt tgtttaatag          60

<210> SEQ ID NO 503
<211> LENGTH: 60
<212> TYPE: DNA
<213> ORGANISM: Homo sapiens

<400> SEQUENCE: 503
atagtataga atgacagcat gctggttatc gacaagagtt cttaaaaagc ctaaatgtca          60

<210> SEQ ID NO 504
<211> LENGTH: 60
<212> TYPE: DNA
<213> ORGANISM: Homo sapiens

<400> SEQUENCE: 504
gccattatta aaataaaaac caaacaattc gataaatgtg tattgaagtt ttttcccttt          60

<210> SEQ ID NO 505
<211> LENGTH: 60

```
<212> TYPE: DNA
<213> ORGANISM: Homo sapiens

<400> SEQUENCE: 505
gtgttctaga tgaggggaac agtggtgatc gaagtatact aactgaagga gaataaaaaa      60

<210> SEQ ID NO 506
<211> LENGTH: 60
<212> TYPE: DNA
<213> ORGANISM: Homo sapiens

<400> SEQUENCE: 506
attccacaaa tatttgtgag caccatcttc gagctcatta gttcaagacc agcctgggca      60

<210> SEQ ID NO 507
<211> LENGTH: 60
<212> TYPE: DNA
<213> ORGANISM: Homo sapiens

<400> SEQUENCE: 507
gtgttctaga tgaggggaac agtggtgatc gaaaatgcat ttaatatact taacctatca      60

<210> SEQ ID NO 508
<211> LENGTH: 60
<212> TYPE: DNA
<213> ORGANISM: Homo sapiens

<400> SEQUENCE: 508
gtgttctaga tgaggggaac agtggtgatc gactgtgagg atgaactaaa agcaaaccat      60

<210> SEQ ID NO 509
<211> LENGTH: 60
<212> TYPE: DNA
<213> ORGANISM: Homo sapiens

<400> SEQUENCE: 509
ctctcaactt tggatgtaag aatcatcttc gagattttga ctctccacct gccccacagg      60

<210> SEQ ID NO 510
<211> LENGTH: 60
<212> TYPE: DNA
<213> ORGANISM: Homo sapiens

<400> SEQUENCE: 510
cggtccctct gccccggtta cctacccgtc gacatgacac ttgggtgggg atacagggcc      60

<210> SEQ ID NO 511
<211> LENGTH: 60
<212> TYPE: DNA
<213> ORGANISM: Homo sapiens

<400> SEQUENCE: 511
cggtccctct gccccggtta cctacccgtc gaagtggaat gaaggagctt ctaagtcata      60

<210> SEQ ID NO 512
<211> LENGTH: 60
<212> TYPE: DNA
<213> ORGANISM: Homo sapiens

<400> SEQUENCE: 512 tcccctctt cctctgcctc ccttcccctc gatttgtaaa atgggctcat tagggaaaag      60

<210> SEQ ID NO 513
```

<211> LENGTH: 60
<212> TYPE: DNA
<213> ORGANISM: Homo sapiens

<400> SEQUENCE: 513 tcccctctt cctctgcctc ccttccctc gaaaactgat taaaaagaat attgctggct        60

<210> SEQ ID NO 514
<211> LENGTH: 60
<212> TYPE: DNA
<213> ORGANISM: Homo sapiens

<400> SEQUENCE: 514
aattactaag aaaaaagtgg ttacaatgtc gaagaacata aatattatgt ggagacttat        60

<210> SEQ ID NO 515
<211> LENGTH: 60
<212> TYPE: DNA
<213> ORGANISM: Homo sapiens

<400> SEQUENCE: 515
tcacttttat ttatcttact cactttctc gaggaattct cagaattctc ctcaacccac        60

<210> SEQ ID NO 516
<211> LENGTH: 60
<212> TYPE: DNA
<213> ORGANISM: Homo sapiens

<400> SEQUENCE: 516
acacctcacc cacccagctg ggctggcctc gatgccatta aatcatcccg tgaccttcct        60

<210> SEQ ID NO 517
<211> LENGTH: 60
<212> TYPE: DNA
<213> ORGANISM: Homo sapiens

<400> SEQUENCE: 517
tttcttccaa ctgagagaat cttaaaaatc gaaattggat aaggaaaaaa gtgaaatgtg        60

<210> SEQ ID NO 518
<211> LENGTH: 60
<212> TYPE: DNA
<213> ORGANISM: Homo sapiens

<400> SEQUENCE: 518
ttatggctta gaagtagaaa gtcataaatc gattcctaaa aattaatgag gtgaatagta        60

<210> SEQ ID NO 519
<211> LENGTH: 60
<212> TYPE: DNA
<213> ORGANISM: Homo sapiens

<400> SEQUENCE: 519
gttatcaatt ttacttataa gacctatttc gaggtattaa gggttggaat gaaaaataca        60

<210> SEQ ID NO 520
<211> LENGTH: 60
<212> TYPE: DNA
<213> ORGANISM: Homo sapiens

<400> SEQUENCE: 520
gttatcaatt ttacttataa gacctatttc gatgcaaaag acaacaaagt aggattttca        60

```
<210> SEQ ID NO 521
<211> LENGTH: 60
<212> TYPE: DNA
<213> ORGANISM: Homo sapiens

<400> SEQUENCE: 521
ttttagtttt atttatttag ttatcatctc gaaaaacaaa caacaataac agcaaccctc        60

<210> SEQ ID NO 522
<211> LENGTH: 60
<212> TYPE: DNA
<213> ORGANISM: Homo sapiens

<400> SEQUENCE: 522
tgaaatcaat agttttatat tagtcgtatc gagcattcta gaatcaaacc ttggggtatt        60

<210> SEQ ID NO 523
<211> LENGTH: 60
<212> TYPE: DNA
<213> ORGANISM: Homo sapiens

<400> SEQUENCE: 523
taccttccaa caggaagtgc aaactaattc gatcctaccc taccctaccc tggagtttcc        60

<210> SEQ ID NO 524
<211> LENGTH: 60
<212> TYPE: DNA
<213> ORGANISM: Homo sapiens

<400> SEQUENCE: 524
taccttccaa caggaagtgc aaactaattc gaataagaac ctcgttattc atgttcctct        60

<210> SEQ ID NO 525
<211> LENGTH: 60
<212> TYPE: DNA
<213> ORGANISM: Homo sapiens

<400> SEQUENCE: 525
tttctatgaa gaatgttcaa gatgcaattc gagctacata ctattatata ttttcacagt        60

<210> SEQ ID NO 526
<211> LENGTH: 60
<212> TYPE: DNA
<213> ORGANISM: Homo sapiens

<400> SEQUENCE: 526
aaataataac aaatatgaca gatattgatc gatgtcttaa cttgccacag agatattttc        60

<210> SEQ ID NO 527
<211> LENGTH: 60
<212> TYPE: DNA
<213> ORGANISM: Homo sapiens

<400> SEQUENCE: 527
gcaagacttt gtctcaaaac aaaagtgttc gaaaaagtca tcgtttaaaa ggtaaaatgt        60

<210> SEQ ID NO 528
<211> LENGTH: 60
<212> TYPE: DNA
<213> ORGANISM: Homo sapiens

<400> SEQUENCE: 528
aatttcacat tgatacattg atagacattc gaaatcatac acagcatact ctcaaaccat        60
```

<210> SEQ ID NO 529
<211> LENGTH: 60
<212> TYPE: DNA
<213> ORGANISM: Homo sapiens

<400> SEQUENCE: 529
tccattagct ctgctttcaa atactatatc gatgtagctt atgtaaaata aatgtattaa      60

<210> SEQ ID NO 530
<211> LENGTH: 60
<212> TYPE: DNA
<213> ORGANISM: Homo sapiens

<400> SEQUENCE: 530
tcaaagttac agtttatata attagaaatc gatctaacct caattccagt cccacaaatg      60

<210> SEQ ID NO 531
<211> LENGTH: 60
<212> TYPE: DNA
<213> ORGANISM: Homo sapiens

<400> SEQUENCE: 531
tagaattata atacattcca agctcttttc gaaaaattcg cattccttgg tcaagaaaac      60

<210> SEQ ID NO 532
<211> LENGTH: 60
<212> TYPE: DNA
<213> ORGANISM: Homo sapiens

<400> SEQUENCE: 532
tcaagaaaaa ataataataa tttttttttc gaacttatgg ctcaagcgat tctcttgctt      60

<210> SEQ ID NO 533
<211> LENGTH: 60
<212> TYPE: DNA
<213> ORGANISM: Homo sapiens

<400> SEQUENCE: 533
aagcaagaga atcgcttgag ccataagttc gatgctgctt tgggaactga aggtttttct      60

<210> SEQ ID NO 534
<211> LENGTH: 60
<212> TYPE: DNA
<213> ORGANISM: Homo sapiens

<400> SEQUENCE: 534
aacatacttt cctaaatttt accttttttc gagaaaacat ggacataaag atggcaacaa      60

<210> SEQ ID NO 535
<211> LENGTH: 60
<212> TYPE: DNA
<213> ORGANISM: Homo sapiens

<400> SEQUENCE: 535
ggcaggcaga tcactttagg tcaggagttc gaactcctga cttcaagtga ttcgcccacc      60

<210> SEQ ID NO 536
<211> LENGTH: 60
<212> TYPE: DNA
<213> ORGANISM: Homo sapiens

<400> SEQUENCE: 536
atctttctac atcagtaaac acaaactgtc gagaccatcc tggctaagac agtgaaaccc      60

-continued

<210> SEQ ID NO 537
<211> LENGTH: 60
<212> TYPE: DNA
<213> ORGANISM: Homo sapiens

<400> SEQUENCE: 537
ctctataaat ttaccagaat ataaattctc gactaaaagt tcagttcttc attcccacta      60

<210> SEQ ID NO 538
<211> LENGTH: 60
<212> TYPE: DNA
<213> ORGANISM: Homo sapiens

<400> SEQUENCE: 538
ccaaaagtaa tggcaacaaa agtcaaaatc gattcttggg aatttcccaa aatactgaaa      60

<210> SEQ ID NO 539
<211> LENGTH: 60
<212> TYPE: DNA
<213> ORGANISM: Homo sapiens

<400> SEQUENCE: 539
ggcaggcgga tctcctgagg tcaggagatc gattttgact tttgttgcca ttacttttgg      60

<210> SEQ ID NO 540
<211> LENGTH: 60
<212> TYPE: DNA
<213> ORGANISM: Homo sapiens

<400> SEQUENCE: 540
cgtagaacta agatgtattc aaagtcagtc gaaaaagatt agaaaagttc aactctaaga      60

<210> SEQ ID NO 541
<211> LENGTH: 60
<212> TYPE: DNA
<213> ORGANISM: Homo sapiens

<400> SEQUENCE: 541
atcttacaaa gaataattct aagaaaagtc gagcattgga gaaaatctcc cttttctttt      60

<210> SEQ ID NO 542
<211> LENGTH: 60
<212> TYPE: DNA
<213> ORGANISM: Homo sapiens

<400> SEQUENCE: 542
caaaacaatg tgttaacttt ttttttttttc gattgatgaa ggaagattct gcagaatgga      60

<210> SEQ ID NO 543
<211> LENGTH: 60
<212> TYPE: DNA
<213> ORGANISM: Homo sapiens

<400> SEQUENCE: 543 tgttttatt ttcatgtttt aattttgttc gaactcttga cctcaggtaa accacccacc      60

<210> SEQ ID NO 544
<211> LENGTH: 60
<212> TYPE: DNA
<213> ORGANISM: Homo sapiens

<400> SEQUENCE: 544

-continued

```
agaactggtt attgatctat tcagggattc gaaataatag attatgaata aattattctg       60

<210> SEQ ID NO 545
<211> LENGTH: 60
<212> TYPE: DNA
<213> ORGANISM: Homo sapiens

<400> SEQUENCE: 545
agaactggtt attgatctat tcagggattc gaatgaatga atgaaaataa agagccatgg       60

<210> SEQ ID NO 546
<211> LENGTH: 60
<212> TYPE: DNA
<213> ORGANISM: Homo sapiens

<400> SEQUENCE: 546
agaactggtt attgatctat tcagggattc gaagggtaaa tacttaagtc tttaaataaa       60

<210> SEQ ID NO 547
<211> LENGTH: 60
<212> TYPE: DNA
<213> ORGANISM: Homo sapiens

<400> SEQUENCE: 547
ttaaaagcct ttgattttta caaagtgatc gagtcagttt ccttttggta taaggatatc       60

<210> SEQ ID NO 548
<211> LENGTH: 60
<212> TYPE: DNA
<213> ORGANISM: Homo sapiens

<400> SEQUENCE: 548
ggcaggcgga tcatttcagg tcaggagttc gacctgaaat ttccatacta aatttaaata       60

<210> SEQ ID NO 549
<211> LENGTH: 60
<212> TYPE: DNA
<213> ORGANISM: Homo sapiens

<400> SEQUENCE: 549
aaataagaag aagaaaggaa aaaaatcttc gaaagagcgt aagatagaga ataattattt       60

<210> SEQ ID NO 550
<211> LENGTH: 60
<212> TYPE: DNA
<213> ORGANISM: Homo sapiens

<400> SEQUENCE: 550
ttgtttgtaa attgtttttc taaaatcttc gagagctggt tgaaaatttt gctctcaatt       60

<210> SEQ ID NO 551
<211> LENGTH: 60
<212> TYPE: DNA
<213> ORGANISM: Homo sapiens

<400> SEQUENCE: 551
ggtattacct tgatggcctt aaagaagatc gagccagagg gcctctgttc atgtttgggc       60

<210> SEQ ID NO 552
<211> LENGTH: 60
<212> TYPE: DNA
<213> ORGANISM: Homo sapiens

<400> SEQUENCE: 552
```

-continued

```
agaagactca ccaaaatttt atcctgtttc gaaccttata atggtgataa atcattaatg        60

<210> SEQ ID NO 553
<211> LENGTH: 60
<212> TYPE: DNA
<213> ORGANISM: Homo sapiens

<400> SEQUENCE: 553
ttccaaatac ttcctctgca aaatgccatc gaactcctgg cctcaagtca tccatccgcc        60

<210> SEQ ID NO 554
<211> LENGTH: 60
<212> TYPE: DNA
<213> ORGANISM: Homo sapiens

<400> SEQUENCE: 554
ctttttgaag attataatct attagtgatc gaggcttttt tgcttttttt tttttgagat        60

<210> SEQ ID NO 555
<211> LENGTH: 60
<212> TYPE: DNA
<213> ORGANISM: Homo sapiens

<400> SEQUENCE: 555
ctatatgtaa gttacaatat gtaaggtatc gatagtcact gagactaatt taatgttata        60

<210> SEQ ID NO 556
<211> LENGTH: 60
<212> TYPE: DNA
<213> ORGANISM: Homo sapiens

<400> SEQUENCE: 556
tatttaaatt tagtatggaa atttcaggtc gaaggcactg aatgtcagag ccaagctgta        60

<210> SEQ ID NO 557
<211> LENGTH: 60
<212> TYPE: DNA
<213> ORGANISM: Homo sapiens

<400> SEQUENCE: 557
aggcaggcag atcaatgagg ttgggagatc gacaagttca gtaattctga ggtgagtttt        60

<210> SEQ ID NO 558
<211> LENGTH: 60
<212> TYPE: DNA
<213> ORGANISM: Homo sapiens

<400> SEQUENCE: 558
tgtaggcaga ttacctgaag ttaggagttc gattaggaat aacctatcat tagagttgtt        60

<210> SEQ ID NO 559
<211> LENGTH: 60
<212> TYPE: DNA
<213> ORGANISM: Homo sapiens

<400> SEQUENCE: 559
gttgttataa ctatatcatg agactaagtc gaaaaaaaaa aacaataatt tcagctgtat        60

<210> SEQ ID NO 560
<211> LENGTH: 60
<212> TYPE: DNA
<213> ORGANISM: Homo sapiens
```

<400> SEQUENCE: 560
tatattagaa acatgtctga aaaaagtatc gataaatgta tacgttgatg tacattgata        60

<210> SEQ ID NO 561
<211> LENGTH: 60
<212> TYPE: DNA
<213> ORGANISM: Homo sapiens

<400> SEQUENCE: 561
aaatgtataa gaacagaaga gaattatctc gacatgtctg aaaagtatta tcagccctct        60

<210> SEQ ID NO 562
<211> LENGTH: 60
<212> TYPE: DNA
<213> ORGANISM: Homo sapiens

<400> SEQUENCE: 562
gacacctcct ctcccttccc tcccttctc gagttatcaa aatattttga gagacagtat        60

<210> SEQ ID NO 563
<211> LENGTH: 60
<212> TYPE: DNA
<213> ORGANISM: Homo sapiens

<400> SEQUENCE: 563
tgcagaaagt actacaaaaa aagaagcttc gaaaatgttg gagatgagag tttcttcacc        60

<210> SEQ ID NO 564
<211> LENGTH: 60
<212> TYPE: DNA
<213> ORGANISM: Homo sapiens

<400> SEQUENCE: 564
aattagacaa cgactatatg actctgtctc gactttaaag caagtacttc ttgtatgctc        60

<210> SEQ ID NO 565
<211> LENGTH: 60
<212> TYPE: DNA
<213> ORGANISM: Homo sapiens

<400> SEQUENCE: 565
aaaaagagaa aagcaggtta gcacattgtc gaccccgccc ccgggatggg ggaactggcc        60

<210> SEQ ID NO 566
<211> LENGTH: 60
<212> TYPE: DNA
<213> ORGANISM: Homo sapiens

<400> SEQUENCE: 566
cccctggctc acctacacaa aattgtgctc gactctactc ttagccctgc taaataagta        60

<210> SEQ ID NO 567
<211> LENGTH: 60
<212> TYPE: DNA
<213> ORGANISM: Homo sapiens

<400> SEQUENCE: 567
attatattag tgctgtaata aaattaagtc gacacatttg atactgctta ttgggttatt        60

<210> SEQ ID NO 568
<211> LENGTH: 60
<212> TYPE: DNA
<213> ORGANISM: Homo sapiens -continued

```
<400> SEQUENCE: 568
taccttgaaa agctcttcag tatgattatc gagctttagc cattctagta attattaaaa      60

<210> SEQ ID NO 569
<211> LENGTH: 60
<212> TYPE: DNA
<213> ORGANISM: Homo sapiens

<400> SEQUENCE: 569
cctcgtcgtc ccctctcttc ctcgttcctc gaacatctcc aagtcagata atcataacaa      60

<210> SEQ ID NO 570
<211> LENGTH: 60
<212> TYPE: DNA
<213> ORGANISM: Homo sapiens

<400> SEQUENCE: 570
atctattata atgatgcaat attgttaatc gattcaaaga tcaaattaat tattaaagct      60

<210> SEQ ID NO 571
<211> LENGTH: 60
<212> TYPE: DNA
<213> ORGANISM: Homo sapiens

<400> SEQUENCE: 571
agaggctgag gtgaaaagat tgtttgagtc gaagatcatt gtctcatttt tttacttgtt      60

<210> SEQ ID NO 572
<211> LENGTH: 60
<212> TYPE: DNA
<213> ORGANISM: Homo sapiens

<400> SEQUENCE: 572
aatggcattc tccatttatt cgtatttatc gagactttct atgaaagctt ttttgatgtt      60

<210> SEQ ID NO 573
<211> LENGTH: 60
<212> TYPE: DNA
<213> ORGANISM: Homo sapiens

<400> SEQUENCE: 573
cttaattttt tttctttgaa tgcctctatc gacagtcttc tctctacttt ctacagtgaa      60

<210> SEQ ID NO 574
<211> LENGTH: 60
<212> TYPE: DNA
<213> ORGANISM: Homo sapiens

<400> SEQUENCE: 574
ctctcaactt tggatgtaag aatcatcttc gagattttga ctctccacct gccccacagg      60

<210> SEQ ID NO 575
<211> LENGTH: 60
<212> TYPE: DNA
<213> ORGANISM: Homo sapiens

<400> SEQUENCE: 575
caaaacaatg tgttaacttt ttttttttttc gattgatgaa ggaagattct gcagaatgga      60

<210> SEQ ID NO 576
<211> LENGTH: 60
<212> TYPE: DNA
```

-continued

<213> ORGANISM: Homo sapiens

<400> SEQUENCE: 576
tccccctctt cctctgcctc ccttcccctc gaaaactgat taaaaagaat attgctggct          60

<210> SEQ ID NO 577
<211> LENGTH: 60
<212> TYPE: DNA
<213> ORGANISM: Homo sapiens

<400> SEQUENCE: 577
aatttcacat tgatacattg atagacattc gaaatcatac acagcatact ctcaaaccat          60

<210> SEQ ID NO 578
<211> LENGTH: 60
<212> TYPE: DNA
<213> ORGANISM: Homo sapiens

<400> SEQUENCE: 578
tgtaggcaga ttacctgaag ttaggagttc gattaggaat aacctatcat tagagttgtt          60

<210> SEQ ID NO 579
<211> LENGTH: 26
<212> TYPE: DNA
<213> ORGANISM: Homo sapiens

<400> SEQUENCE: 579
cacctcaaaa gacaaccccca gaccca                                              26

<210> SEQ ID NO 580
<211> LENGTH: 26
<212> TYPE: DNA
<213> ORGANISM: Homo sapiens

<400> SEQUENCE: 580
gctccacatt tcccaatcta acctgc                                               26

<210> SEQ ID NO 581
<211> LENGTH: 26
<212> TYPE: DNA
<213> ORGANISM: Homo sapiens

<400> SEQUENCE: 581
aatctctgtc cccaactgta tctggc                                               26

<210> SEQ ID NO 582
<211> LENGTH: 26
<212> TYPE: DNA
<213> ORGANISM: Homo sapiens

<400> SEQUENCE: 582
gagtatttac gatggtcagg tgctgc                                               26

<210> SEQ ID NO 583
<211> LENGTH: 23
<212> TYPE: DNA
<213> ORGANISM: Homo sapiens

<400> SEQUENCE: 583
gacctgtggt tctgactgtc cag                                                  23

<210> SEQ ID NO 584
<211> LENGTH: 26

-continued

```
<212> TYPE: DNA
<213> ORGANISM: Homo sapiens

<400> SEQUENCE: 584
gcaacctggt ctcctacctg cttcta                                      26

<210> SEQ ID NO 585
<211> LENGTH: 24
<212> TYPE: DNA
<213> ORGANISM: Homo sapiens

<400> SEQUENCE: 585
tagcagacaa tcagagggtt ttgc                                        24

<210> SEQ ID NO 586
<211> LENGTH: 26
<212> TYPE: DNA
<213> ORGANISM: Homo sapiens

<400> SEQUENCE: 586
gctggtagtt ggcttttggg aagaac                                      26

<210> SEQ ID NO 587
<211> LENGTH: 23
<212> TYPE: DNA
<213> ORGANISM: Homo sapiens

<400> SEQUENCE: 587
ttctccctcg gacgctcatc ctc                                         23

<210> SEQ ID NO 588
<211> LENGTH: 26
<212> TYPE: DNA
<213> ORGANISM: Homo sapiens

<400> SEQUENCE: 588
ctggaacttg tttaggcact gaagca                                      26

<210> SEQ ID NO 589
<211> LENGTH: 26
<212> TYPE: DNA
<213> ORGANISM: Homo sapiens

<400> SEQUENCE: 589
gcaaagggca ggtcatcatc attcaa                                      26

<210> SEQ ID NO 590
<211> LENGTH: 24
<212> TYPE: DNA
<213> ORGANISM: Homo sapiens

<400> SEQUENCE: 590
ccccgatgaa tgttaccctg tccc                                        24

<210> SEQ ID NO 591
<211> LENGTH: 26
<212> TYPE: DNA
<213> ORGANISM: Homo sapiens

<400> SEQUENCE: 591
ctgaaatccc atagtgagat gccttc                                      26

<210> SEQ ID NO 592
```

-continued

```
<211> LENGTH: 23
<212> TYPE: DNA
<213> ORGANISM: Homo sapiens

<400> SEQUENCE: 592
cctggatgtt cattcccacc tgg                                            23

<210> SEQ ID NO 593
<211> LENGTH: 20
<212> TYPE: DNA
<213> ORGANISM: Homo sapiens

<400> SEQUENCE: 593
gcagattcca cagggcttac                                                20

<210> SEQ ID NO 594
<211> LENGTH: 24
<212> TYPE: DNA
<213> ORGANISM: Homo sapiens

<400> SEQUENCE: 594
acccaaccct gctatacaat tcca                                           24

<210> SEQ ID NO 595
<211> LENGTH: 25
<212> TYPE: DNA
<213> ORGANISM: Homo sapiens

<400> SEQUENCE: 595
acagtcagtg attggcacag agtaa                                          25

<210> SEQ ID NO 596
<211> LENGTH: 20
<212> TYPE: DNA
<213> ORGANISM: Homo sapiens

<400> SEQUENCE: 596
gaatgaaact ctgaggccgg                                                20

<210> SEQ ID NO 597
<211> LENGTH: 26
<212> TYPE: DNA
<213> ORGANISM: Homo sapiens

<400> SEQUENCE: 597
ccctcacttt ccttctactc ttcaag                                         26

<210> SEQ ID NO 598
<211> LENGTH: 26
<212> TYPE: DNA
<213> ORGANISM: Homo sapiens

<400> SEQUENCE: 598
gtcagagttg ccgataggtc ttgcta                                         26

<210> SEQ ID NO 599
<211> LENGTH: 26
<212> TYPE: DNA
<213> ORGANISM: Homo sapiens

<400> SEQUENCE: 599
acatctatct tgcccctcac tcaggt                                         26
```

-continued

```
<210> SEQ ID NO 600
<211> LENGTH: 26
<212> TYPE: DNA
<213> ORGANISM: Homo sapiens

<400> SEQUENCE: 600
atccaaacac aggacgagaa taaagc                                          26

<210> SEQ ID NO 601
<211> LENGTH: 23
<212> TYPE: DNA
<213> ORGANISM: Homo sapiens

<400> SEQUENCE: 601
tatcgtccag gaggcaaggg tcc                                             23

<210> SEQ ID NO 602
<211> LENGTH: 26
<212> TYPE: DNA
<213> ORGANISM: Homo sapiens

<400> SEQUENCE: 602
gatgaggtaa ccaaagttca gggaga                                          26

<210> SEQ ID NO 603
<211> LENGTH: 26
<212> TYPE: DNA
<213> ORGANISM: Homo sapiens

<400> SEQUENCE: 603
ctctctcctc atcctccctc ctaata                                          26

<210> SEQ ID NO 604
<211> LENGTH: 26
<212> TYPE: DNA
<213> ORGANISM: Homo sapiens

<400> SEQUENCE: 604
gggagccaga aagatagcaa tgccta                                          26

<210> SEQ ID NO 605
<211> LENGTH: 23
<212> TYPE: DNA
<213> ORGANISM: Homo sapiens

<400> SEQUENCE: 605
gaggaggaga aactcagaag ccc                                             23

<210> SEQ ID NO 606
<211> LENGTH: 26
<212> TYPE: DNA
<213> ORGANISM: Homo sapiens

<400> SEQUENCE: 606
gcacaagacc tcacattctg atgggc                                          26

<210> SEQ ID NO 607
<211> LENGTH: 26
<212> TYPE: DNA
<213> ORGANISM: Homo sapiens

<400> SEQUENCE: 607 ctctcctta tccctaccc tgctca                                            26
```

-continued

```
<210> SEQ ID NO 608
<211> LENGTH: 23
<212> TYPE: DNA
<213> ORGANISM: Homo sapiens

<400> SEQUENCE: 608
cagagaaagg gagtttggag ggc                                              23

<210> SEQ ID NO 609
<211> LENGTH: 26
<212> TYPE: DNA
<213> ORGANISM: Homo sapiens

<400> SEQUENCE: 609
ccccaaactc ccagacacat cagaga                                           26

<210> SEQ ID NO 610
<211> LENGTH: 23
<212> TYPE: DNA
<213> ORGANISM: Homo sapiens

<400> SEQUENCE: 610
agagggaaag gcaggtcgtg agc                                              23

<210> SEQ ID NO 611
<211> LENGTH: 20
<212> TYPE: DNA
<213> ORGANISM: Homo sapiens

<400> SEQUENCE: 611
gctggtctca aactcctggg                                                  20

<210> SEQ ID NO 612
<211> LENGTH: 25
<212> TYPE: DNA
<213> ORGANISM: Homo sapiens

<400> SEQUENCE: 612
gggcatcttt cctcttattc aaggt                                            25

<210> SEQ ID NO 613
<211> LENGTH: 25
<212> TYPE: DNA
<213> ORGANISM: Homo sapiens

<400> SEQUENCE: 613
aggaaatagc ccaaatgcaa ctgaa                                            25

<210> SEQ ID NO 614
<211> LENGTH: 21
<212> TYPE: DNA
<213> ORGANISM: Homo sapiens

<400> SEQUENCE: 614
cccattcgtc tctctgagct g                                                21

<210> SEQ ID NO 615
<211> LENGTH: 60
<212> TYPE: DNA
<213> ORGANISM: Homo sapiens

<400> SEQUENCE: 615
tatcaagtta aacattcaga cgtctaggtc gacttgaagt tcacctaaag ttttccagtc      60
```

-continued

<210> SEQ ID NO 616
<211> LENGTH: 60
<212> TYPE: DNA
<213> ORGANISM: Homo sapiens

<400> SEQUENCE: 616
cgtagaacta agatgtattc aaagtcagtc gaaaaagatt agaaaagttc aactctaaga        60

<210> SEQ ID NO 617
<211> LENGTH: 60
<212> TYPE: DNA
<213> ORGANISM: Homo sapiens

<400> SEQUENCE: 617
gacacctcct ctcccttccc tcccttctc gagttatcaa aatattttga gagacagtat        60

<210> SEQ ID NO 618
<211> LENGTH: 60
<212> TYPE: DNA
<213> ORGANISM: Homo sapiens

<400> SEQUENCE: 618
accgcctcac ctcagctctc cagtgagatc gatcctccca cctaagcttc ccaagttgct        60

<210> SEQ ID NO 619
<211> LENGTH: 60
<212> TYPE: DNA
<213> ORGANISM: Homo sapiens

<400> SEQUENCE: 619
tgtcctttca aggaaggatt agcatccttc gaaagaccta tcaggatttc atttgtaatg        60

<210> SEQ ID NO 620
<211> LENGTH: 60
<212> TYPE: DNA
<213> ORGANISM: Homo sapiens

<400> SEQUENCE: 620
aagcaagaga atcgcttgag ccataagttc gatgctgctt tgggaactga aggttttct        60

<210> SEQ ID NO 621
<211> LENGTH: 60
<212> TYPE: DNA
<213> ORGANISM: Homo sapiens

<400> SEQUENCE: 621
agaggctgag gtgaaaagat tgtttgagtc gaagatcatt gtctcatttt tttacttgtt        60

<210> SEQ ID NO 622
<211> LENGTH: 26
<212> TYPE: DNA
<213> ORGANISM: Homo sapiens

<400> SEQUENCE: 622
gtaacacagg taggaaggag tggagc                                             26

<210> SEQ ID NO 623
<211> LENGTH: 23
<212> TYPE: DNA
<213> ORGANISM: Homo sapiens

<400> SEQUENCE: 623

-continued

```
tactcctcgt tccctttct ctc                                               23

<210> SEQ ID NO 624
<211> LENGTH: 26
<212> TYPE: DNA
<213> ORGANISM: Homo sapiens

<400> SEQUENCE: 624
gctccacatt tcccaatcta acctgc                                           26

<210> SEQ ID NO 625
<211> LENGTH: 26
<212> TYPE: DNA
<213> ORGANISM: Homo sapiens

<400> SEQUENCE: 625
actgaaggtt cccaagttcc cgagag                                           26

<210> SEQ ID NO 626
<211> LENGTH: 26
<212> TYPE: DNA
<213> ORGANISM: Homo sapiens

<400> SEQUENCE: 626
ggcaagtttc ctgacctctc tgacat                                           26

<210> SEQ ID NO 627
<211> LENGTH: 25
<212> TYPE: DNA
<213> ORGANISM: Homo sapiens

<400> SEQUENCE: 627
aggaatggtt actgctcctc tttgt                                            25

<210> SEQ ID NO 628
<211> LENGTH: 26
<212> TYPE: DNA
<213> ORGANISM: Homo sapiens

<400> SEQUENCE: 628
gcaaagggca ggtcatcatc attcaa                                           26

<210> SEQ ID NO 629
<211> LENGTH: 26
<212> TYPE: DNA
<213> ORGANISM: Homo sapiens

<400> SEQUENCE: 629
caccataaaa tagggcaagg tcagca                                           26

<210> SEQ ID NO 630
<211> LENGTH: 24
<212> TYPE: DNA
<213> ORGANISM: Homo sapiens

<400> SEQUENCE: 630
tgtgtgctag gctgatatgg tttg                                             24

<210> SEQ ID NO 631
<211> LENGTH: 26
<212> TYPE: DNA
<213> ORGANISM: Homo sapiens

<400> SEQUENCE: 631
```

-continued

```
gtcagagttg ccgataggtc ttgcta                                    26

<210> SEQ ID NO 632
<211> LENGTH: 26
<212> TYPE: DNA
<213> ORGANISM: Homo sapiens

<400> SEQUENCE: 632
ttagtctgta tggtagtgtg tgcctg                                    26

<210> SEQ ID NO 633
<211> LENGTH: 26
<212> TYPE: DNA
<213> ORGANISM: Homo sapiens

<400> SEQUENCE: 633
gaaggaggga ggtaggagag tcatta                                    26

<210> SEQ ID NO 634
<211> LENGTH: 25
<212> TYPE: DNA
<213> ORGANISM: Homo sapiens

<400> SEQUENCE: 634
attgaattct ctctgtggcc tttgc                                     25

<210> SEQ ID NO 635
<211> LENGTH: 26
<212> TYPE: DNA
<213> ORGANISM: Homo sapiens

<400> SEQUENCE: 635
ctctccttta tccctaccc tgctca                                     26

<210> SEQ ID NO 636
<211> LENGTH: 60
<212> TYPE: DNA
<213> ORGANISM: Homo sapiens

<400> SEQUENCE: 636
aaaaagaaag agggaagaag gaaagaagtc gatgaaacat gcagtcaact tgggaggccc    60

<210> SEQ ID NO 637
<211> LENGTH: 60
<212> TYPE: DNA
<213> ORGANISM: Homo sapiens

<400> SEQUENCE: 637
atgaaggtaa tagtacctta cctcgtagtc gaaaaaaaaa ttcctcccca taaagagacc    60

<210> SEQ ID NO 638
<211> LENGTH: 60
<212> TYPE: DNA
<213> ORGANISM: Homo sapiens

<400> SEQUENCE: 638
atgaaggtaa tagtacctta cctcgtagtc gattatcagc ctttttcttg aagaacctcc    60

<210> SEQ ID NO 639
<211> LENGTH: 60
<212> TYPE: DNA
<213> ORGANISM: Homo sapiens
```

-continued

```
<400> SEQUENCE: 639
aacacagatg atcatcataa gacgtaggtc gactacgagg taaggtacta ttaccttcat     60

<210> SEQ ID NO 640
<211> LENGTH: 60
<212> TYPE: DNA
<213> ORGANISM: Homo sapiens

<400> SEQUENCE: 640
gatgcaagta cttcctaatt tctctaagtc gaatcaaact ttaattttta gaaattcaaa     60

<210> SEQ ID NO 641
<211> LENGTH: 60
<212> TYPE: DNA
<213> ORGANISM: Homo sapiens

<400> SEQUENCE: 641
attttcatag ctattgcatt taactctttc gaaattgatt ttttttaaat agataagcaa     60

<210> SEQ ID NO 642
<211> LENGTH: 60
<212> TYPE: DNA
<213> ORGANISM: Homo sapiens

<400> SEQUENCE: 642
accagcaata tttgtgagag taccagtttc gaacttgatt cacactgtac tgtgagccag     60

<210> SEQ ID NO 643
<211> LENGTH: 60
<212> TYPE: DNA
<213> ORGANISM: Homo sapiens

<400> SEQUENCE: 643
accagcaata tttgtgagag taccagtttc gattttctag agatgtccaa gtgtacactt     60

<210> SEQ ID NO 644
<211> LENGTH: 60
<212> TYPE: DNA
<213> ORGANISM: Homo sapiens

<400> SEQUENCE: 644
accagcaata tttgtgagag taccagtttc gagagagcta ttgtttgatg ctgtgtattc     60

<210> SEQ ID NO 645
<211> LENGTH: 60
<212> TYPE: DNA
<213> ORGANISM: Homo sapiens

<400> SEQUENCE: 645
ttgcagtttg aagagatcag cattgaaatc gacccagctc agaagtactt cctgctgccc     60

<210> SEQ ID NO 646
<211> LENGTH: 60
<212> TYPE: DNA
<213> ORGANISM: Homo sapiens

<400> SEQUENCE: 646
tggtatacta attttacaga taaagaaatc gacccagctc agaagtactt cctgctgccc     60

<210> SEQ ID NO 647
<211> LENGTH: 60
<212> TYPE: DNA
<213> ORGANISM: Homo sapiens
```

```
<400> SEQUENCE: 647
ccccaaaatc ttttatttct gtagaaaatc gacaaatgta ggtaataaaa aaacatatga          60

<210> SEQ ID NO 648
<211> LENGTH: 60
<212> TYPE: DNA
<213> ORGANISM: Homo sapiens

<400> SEQUENCE: 648
tgcaagtaga ggattagtag cagttaaatc gacaaatgta ggtaataaaa aaacatatga          60

<210> SEQ ID NO 649
<211> LENGTH: 60
<212> TYPE: DNA
<213> ORGANISM: Homo sapiens

<400> SEQUENCE: 649
acagctctag gtttcttcaa tacgtttgtc gaaggcattc tttgcaaaga cattttatg           60

<210> SEQ ID NO 650
<211> LENGTH: 60
<212> TYPE: DNA
<213> ORGANISM: Homo sapiens

<400> SEQUENCE: 650
acagctctag gtttcttcaa tacgtttgtc gaaccctaga aattaagcaa attatagata          60

<210> SEQ ID NO 651
<211> LENGTH: 60
<212> TYPE: DNA
<213> ORGANISM: Homo sapiens

<400> SEQUENCE: 651
tgatgttggt atagagaggg cccagctctc gacttcaaga cccaccgaaa gactgggact          60

<210> SEQ ID NO 652
<211> LENGTH: 60
<212> TYPE: DNA
<213> ORGANISM: Homo sapiens

<400> SEQUENCE: 652
agtcccagtc tttcggtggg tcttgaagtc gactaccact aagctctcac tactaagctg          60

<210> SEQ ID NO 653
<211> LENGTH: 60
<212> TYPE: DNA
<213> ORGANISM: Homo sapiens

<400> SEQUENCE: 653
tgatgttggt atagagaggg cccagctctc gagggggaatg aaaaattaaa ggaactgacc         60

<210> SEQ ID NO 654
<211> LENGTH: 60
<212> TYPE: DNA
<213> ORGANISM: Homo sapiens

<400> SEQUENCE: 654
atctggtcta tgtccaggta ctctcggatc gaggttaaga gcatagactt tggagtttca          60

<210> SEQ ID NO 655
<211> LENGTH: 60
<212> TYPE: DNA
```

-continued

<213> ORGANISM: Homo sapiens

<400> SEQUENCE: 655
tgagatcaga gaacaaattg tccgggagtc gaggttaaga gcatagactt tggagtttca        60

<210> SEQ ID NO 656
<211> LENGTH: 60
<212> TYPE: DNA
<213> ORGANISM: Homo sapiens

<400> SEQUENCE: 656
atctggtcta tgtccaggta ctctcggatc gagtgcaggt atgtggaaac atgtttagtg        60

<210> SEQ ID NO 657
<211> LENGTH: 60
<212> TYPE: DNA
<213> ORGANISM: Homo sapiens

<400> SEQUENCE: 657
acctgaagtc agagtatgtg tgacagtttc gaccacggga ggaaaaaagc ggtccaagta        60

<210> SEQ ID NO 658
<211> LENGTH: 60
<212> TYPE: DNA
<213> ORGANISM: Homo sapiens

<400> SEQUENCE: 658
tagaatatgt agagatgtct cctttctatc gatgtgagta tcaagcagta acctgaaaaa        60

<210> SEQ ID NO 659
<211> LENGTH: 60
<212> TYPE: DNA
<213> ORGANISM: Homo sapiens

<400> SEQUENCE: 659
taggcagata aggacatatc tgtaattctc gaaacaacac ctgtttattt gtttacagtt        60

<210> SEQ ID NO 660
<211> LENGTH: 60
<212> TYPE: DNA
<213> ORGANISM: Homo sapiens

<400> SEQUENCE: 660
aactgtaaac aaataaacag gtgttgtttc gacagaagca gcactatgat ctctcactga        60

<210> SEQ ID NO 661
<211> LENGTH: 60
<212> TYPE: DNA
<213> ORGANISM: Homo sapiens

<400> SEQUENCE: 661
ggtatcaatt atagccgtct accttgtgtc gaaacaacac ctgtttattt gtttacagtt        60

<210> SEQ ID NO 662
<211> LENGTH: 60
<212> TYPE: DNA
<213> ORGANISM: Homo sapiens

<400> SEQUENCE: 662
tagaatatgt agagatgtct cctttctatc gacaacacta ggttatggtg tgataaggac        60

<210> SEQ ID NO 663
<211> LENGTH: 60

-continued

```
<212> TYPE: DNA
<213> ORGANISM: Homo sapiens

<400> SEQUENCE: 663
tcagtgagag atcatagtgc tgcttctgtc gagtcagact atagcgctac aggcaacatg        60

<210> SEQ ID NO 664
<211> LENGTH: 60
<212> TYPE: DNA
<213> ORGANISM: Homo sapiens

<400> SEQUENCE: 664
atccagacac tcaaggactt ccagtacatc gaatggccaa ataatatccc attgtatgaa        60

<210> SEQ ID NO 665
<211> LENGTH: 60
<212> TYPE: DNA
<213> ORGANISM: Homo sapiens

<400> SEQUENCE: 665
tcctccttca ctagctcttg gtggtacctc gaatggccaa ataatatccc attgtatgaa        60

<210> SEQ ID NO 666
<211> LENGTH: 60
<212> TYPE: DNA
<213> ORGANISM: Homo sapiens

<400> SEQUENCE: 666
tccctcacac acaagtcatg cagttttttc gattcagcca ggcttagctt ttccagggaa        60

<210> SEQ ID NO 667
<211> LENGTH: 60
<212> TYPE: DNA
<213> ORGANISM: Homo sapiens

<400> SEQUENCE: 667
tccctcacac acaagtcatg cagttttttc gaagtcaggg ctcaatgggc cttggggggg        60

<210> SEQ ID NO 668
<211> LENGTH: 60
<212> TYPE: DNA
<213> ORGANISM: Homo sapiens

<400> SEQUENCE: 668
tccctcacac acaagtcatg cagttttttc gaaattgtcg tttaattgcc taacctgcac        60

<210> SEQ ID NO 669
<211> LENGTH: 60
<212> TYPE: DNA
<213> ORGANISM: Homo sapiens

<400> SEQUENCE: 669
tccctcacac acaagtcatg cagttttttc gacttgggtc ttaattagga tcttttatgc        60

<210> SEQ ID NO 670
<211> LENGTH: 60
<212> TYPE: DNA
<213> ORGANISM: Homo sapiens

<400> SEQUENCE: 670
tccctcacac acaagtcatg cagttttttc gaatctctaa gactaaaatg aaatcctgga        60

<210> SEQ ID NO 671
```

-continued

```
<211> LENGTH: 60
<212> TYPE: DNA
<213> ORGANISM: Homo sapiens

<400> SEQUENCE: 671
tccctcacac acaagtcatg cagttttttc gatttattta cgttggtggc cacttggact      60

<210> SEQ ID NO 672
<211> LENGTH: 60
<212> TYPE: DNA
<213> ORGANISM: Homo sapiens

<400> SEQUENCE: 672
tccctcacac acaagtcatg cagttttttc gaccccaaca aaaatggaat aaaacccacc      60

<210> SEQ ID NO 673
<211> LENGTH: 60
<212> TYPE: DNA
<213> ORGANISM: Homo sapiens

<400> SEQUENCE: 673
tccctcacac acaagtcatg cagttttttc gaagcttgtt aagatccagt ttctggcctc      60

<210> SEQ ID NO 674
<211> LENGTH: 60
<212> TYPE: DNA
<213> ORGANISM: Homo sapiens

<400> SEQUENCE: 674
tccctcacac acaagtcatg cagttttttc gagtaaacta cattttacag tgtgaaaaat      60

<210> SEQ ID NO 675
<211> LENGTH: 60
<212> TYPE: DNA
<213> ORGANISM: Homo sapiens

<400> SEQUENCE: 675
tccctcacac acaagtcatg cagttttttc gaatgtccct tactatttat tcccccaaat      60

<210> SEQ ID NO 676
<211> LENGTH: 60
<212> TYPE: DNA
<213> ORGANISM: Homo sapiens

<400> SEQUENCE: 676
tccctcacac acaagtcatg cagttttttc gaatctgact ccatcacttg atcttgggca      60

<210> SEQ ID NO 677
<211> LENGTH: 60
<212> TYPE: DNA
<213> ORGANISM: Homo sapiens

<400> SEQUENCE: 677
tccctcacac acaagtcatg cagttttttc gacaaacgtc acctctgatg gagaatgctg      60

<210> SEQ ID NO 678
<211> LENGTH: 60
<212> TYPE: DNA
<213> ORGANISM: Homo sapiens

<400> SEQUENCE: 678
tccctcacac acaagtcatg cagttttttc gattgaagag ttaatgaaat aaccataatt      60
```

-continued

```
<210> SEQ ID NO 679
<211> LENGTH: 60
<212> TYPE: DNA
<213> ORGANISM: Homo sapiens

<400> SEQUENCE: 679
tccctcacac acaagtcatg cagttttttc gaaaaggctg catactatat gattccgatt      60

<210> SEQ ID NO 680
<211> LENGTH: 60
<212> TYPE: DNA
<213> ORGANISM: Homo sapiens

<400> SEQUENCE: 680
tgctatagag gcagctgtaa atataaattc gaaagtgtag attcagagat atcacatggt      60

<210> SEQ ID NO 681
<211> LENGTH: 60
<212> TYPE: DNA
<213> ORGANISM: Homo sapiens

<400> SEQUENCE: 681
gaaggcaacc agcttgcctt ctgaaggatc gagggtacat aagaggagtc tacactatga      60

<210> SEQ ID NO 682
<211> LENGTH: 60
<212> TYPE: DNA
<213> ORGANISM: Homo sapiens

<400> SEQUENCE: 682
tcatagtgta gactcctctt atgtaccctc gatgaggtgg gtagaatctt cattttaatc      60

<210> SEQ ID NO 683
<211> LENGTH: 60
<212> TYPE: DNA
<213> ORGANISM: Homo sapiens

<400> SEQUENCE: 683 tttttaaaa ttaaaatcat tttttgactc gagggtacat aagaggagtc tacactatga      60

<210> SEQ ID NO 684
<211> LENGTH: 60
<212> TYPE: DNA
<213> ORGANISM: Homo sapiens

<400> SEQUENCE: 684
tcatagtgta gactcctctt atgtaccctc gacctagagc tgttctctgg attctcagaa      60

<210> SEQ ID NO 685
<211> LENGTH: 60
<212> TYPE: DNA
<213> ORGANISM: Homo sapiens

<400> SEQUENCE: 685
taaggaaatg taaatgtaaa aagatgattc gattccctga tgttgacact tcaatttcca      60

<210> SEQ ID NO 686
<211> LENGTH: 60
<212> TYPE: DNA
<213> ORGANISM: Homo sapiens

<400> SEQUENCE: 686 ctgtaccccca tttcttccca cgtattcctc gaggaaggtt agccctgagc taacatctgc      60
```

-continued

```
<210> SEQ ID NO 687
<211> LENGTH: 60
<212> TYPE: DNA
<213> ORGANISM: Homo sapiens

<400> SEQUENCE: 687 ctgtaccccca tttcttccca cgtattcctc gaaactagga aattaacatt agtatagtac     60

<210> SEQ ID NO 688
<211> LENGTH: 60
<212> TYPE: DNA
<213> ORGANISM: Homo sapiens

<400> SEQUENCE: 688 ctgtaccccca tttcttccca cgtattcctc gagcccaacg ttttttattg acaagtaatt     60

<210> SEQ ID NO 689
<211> LENGTH: 60
<212> TYPE: DNA
<213> ORGANISM: Homo sapiens

<400> SEQUENCE: 689 ctgtaccccca tttcttccca cgtattcctc gatggtcaga gagttctgag catgtttgca     60

<210> SEQ ID NO 690
<211> LENGTH: 60
<212> TYPE: DNA
<213> ORGANISM: Homo sapiens

<400> SEQUENCE: 690
gatggccaat aaacacttga aaaggtactc gatttgccaa tattttgctg aggatttttc     60

<210> SEQ ID NO 691
<211> LENGTH: 60
<212> TYPE: DNA
<213> ORGANISM: Homo sapiens

<400> SEQUENCE: 691
tctttatatt gaggttctag cttgtgattc gagaaggaga ccttggttat ttattcttac     60

<210> SEQ ID NO 692
<211> LENGTH: 60
<212> TYPE: DNA
<213> ORGANISM: Homo sapiens

<400> SEQUENCE: 692
tggtacttac tcatttgata tctgcccgtc gaatgcaaac tatgccattc tccactacaa     60

<210> SEQ ID NO 693
<211> LENGTH: 60
<212> TYPE: DNA
<213> ORGANISM: Homo sapiens

<400> SEQUENCE: 693
tggtacttac tcatttgata tctgcccgtc gaagacatgg atatataaat atatgttttc     60

<210> SEQ ID NO 694
<211> LENGTH: 60
<212> TYPE: DNA
<213> ORGANISM: Homo sapiens

<400> SEQUENCE: 694
atgcaaaaat tctcaaaatt ttggcaactc gacgggcaga tatcaaatga gtaagtacca     60
```

-continued

```
<210> SEQ ID NO 695
<211> LENGTH: 60
<212> TYPE: DNA
<213> ORGANISM: Homo sapiens

<400> SEQUENCE: 695
tggtacttac tcatttgata tctgcccgtc gatctaagca gaaaacacga agaaacataa      60

<210> SEQ ID NO 696
<211> LENGTH: 60
<212> TYPE: DNA
<213> ORGANISM: Homo sapiens

<400> SEQUENCE: 696
atattaacag caaaccctta gtgggtactc gaagctccct aagattagga accttgtctt      60

<210> SEQ ID NO 697
<211> LENGTH: 60
<212> TYPE: DNA
<213> ORGANISM: Homo sapiens

<400> SEQUENCE: 697
atattaacag caaaccctta gtgggtactc gagggtactg agttgcagac aggttaatgg      60

<210> SEQ ID NO 698
<211> LENGTH: 60
<212> TYPE: DNA
<213> ORGANISM: Homo sapiens

<400> SEQUENCE: 698
atattaacag caaaccctta gtgggtactc gaagaaagta aaacaaatgg agagaagtgt      60

<210> SEQ ID NO 699
<211> LENGTH: 60
<212> TYPE: DNA
<213> ORGANISM: Homo sapiens

<400> SEQUENCE: 699
tcaaagtccc gttcaactgt acatttcttc gagttatatc agccactaac taacaaaaat      60

<210> SEQ ID NO 700
<211> LENGTH: 26
<212> TYPE: DNA
<213> ORGANISM: Homo sapiens

<400> SEQUENCE: 700
ctgggaatac ttatgatttg gcgacc                                          26

<210> SEQ ID NO 701
<211> LENGTH: 26
<212> TYPE: DNA
<213> ORGANISM: Homo sapiens

<400> SEQUENCE: 701
gcagattaga aaggagtcat cagaaa                                          26

<210> SEQ ID NO 702
<211> LENGTH: 26
<212> TYPE: DNA
<213> ORGANISM: Homo sapiens

<400> SEQUENCE: 702
```

-continued

```
ccaactctgt cgcttgttac acttag                                     26

<210> SEQ ID NO 703
<211> LENGTH: 26
<212> TYPE: DNA
<213> ORGANISM: Homo sapiens

<400> SEQUENCE: 703
cagttcacgg aaatgtcccc agagca                                     26

<210> SEQ ID NO 704
<211> LENGTH: 26
<212> TYPE: DNA
<213> ORGANISM: Homo sapiens

<400> SEQUENCE: 704
ccaactctgt cgcttgttac acttag                                     26

<210> SEQ ID NO 705
<211> LENGTH: 23
<212> TYPE: DNA
<213> ORGANISM: Homo sapiens

<400> SEQUENCE: 705
ggagagccac cctggataca cag                                        23

<210> SEQ ID NO 706
<211> LENGTH: 26
<212> TYPE: DNA
<213> ORGANISM: Homo sapiens

<400> SEQUENCE: 706
cggattttag agttgataag cacacc                                     26

<210> SEQ ID NO 707
<211> LENGTH: 26
<212> TYPE: DNA
<213> ORGANISM: Homo sapiens

<400> SEQUENCE: 707
cggattttag agttgataag cacacc                                     26

<210> SEQ ID NO 708
<211> LENGTH: 26
<212> TYPE: DNA
<213> ORGANISM: Homo sapiens

<400> SEQUENCE: 708
cggattttag agttgataag cacacc                                     26

<210> SEQ ID NO 709
<211> LENGTH: 25
<212> TYPE: DNA
<213> ORGANISM: Homo sapiens

<400> SEQUENCE: 709
gcagcagagt atcattcttg ccctc                                      25

<210> SEQ ID NO 710
<211> LENGTH: 24
<212> TYPE: DNA
<213> ORGANISM: Homo sapiens

<400> SEQUENCE: 710
```

-continued cgtctgagga aagtgccagg aaag                                                    24

<210> SEQ ID NO 711
<211> LENGTH: 26
<212> TYPE: DNA
<213> ORGANISM: Homo sapiens

<400> SEQUENCE: 711
tgctaaacaa ccactggacc actggg                                                  26

<210> SEQ ID NO 712
<211> LENGTH: 26
<212> TYPE: DNA
<213> ORGANISM: Homo sapiens

<400> SEQUENCE: 712
cgggcaaagg tctaacagaa gcagga                                                  26

<210> SEQ ID NO 713
<211> LENGTH: 26
<212> TYPE: DNA
<213> ORGANISM: Homo sapiens

<400> SEQUENCE: 713
ctcctctgga ctcctatttc tgggca                                                  26

<210> SEQ ID NO 714
<211> LENGTH: 26
<212> TYPE: DNA
<213> ORGANISM: Homo sapiens

<400> SEQUENCE: 714
ctcctctgga ctcctatttc tgggca                                                  26

<210> SEQ ID NO 715
<211> LENGTH: 26
<212> TYPE: DNA
<213> ORGANISM: Homo sapiens

<400> SEQUENCE: 715
cacttccttc agaaagcggg tgctca                                                  26

<210> SEQ ID NO 716
<211> LENGTH: 23
<212> TYPE: DNA
<213> ORGANISM: Homo sapiens

<400> SEQUENCE: 716
tgggaggaac caggtgggta acg                                                     23

<210> SEQ ID NO 717
<211> LENGTH: 23
<212> TYPE: DNA
<213> ORGANISM: Homo sapiens

<400> SEQUENCE: 717
tgggaggaac caggtgggta acg                                                     23

<210> SEQ ID NO 718
<211> LENGTH: 23
<212> TYPE: DNA
<213> ORGANISM: Homo sapiens -continued

```
<400> SEQUENCE: 718
gtcgccaggt tccgttcttg gtg                                    23

<210> SEQ ID NO 719
<211> LENGTH: 26
<212> TYPE: DNA
<213> ORGANISM: Homo sapiens

<400> SEQUENCE: 719
tgtgggcttg ttcttacttc ctgaat                                 26

<210> SEQ ID NO 720
<211> LENGTH: 23
<212> TYPE: DNA
<213> ORGANISM: Homo sapiens

<400> SEQUENCE: 720
aagcaacagt ggtggaggag acc                                    23

<210> SEQ ID NO 721
<211> LENGTH: 23
<212> TYPE: DNA
<213> ORGANISM: Homo sapiens

<400> SEQUENCE: 721
ggttagggag tgctatgagg gag                                    23

<210> SEQ ID NO 722
<211> LENGTH: 26
<212> TYPE: DNA
<213> ORGANISM: Homo sapiens

<400> SEQUENCE: 722
tacactttgg gagtttgtct ttgaag                                 26

<210> SEQ ID NO 723
<211> LENGTH: 24
<212> TYPE: DNA
<213> ORGANISM: Homo sapiens

<400> SEQUENCE: 723
cactatggaa aacagtatgg agat                                   24

<210> SEQ ID NO 724
<211> LENGTH: 26
<212> TYPE: DNA
<213> ORGANISM: Homo sapiens

<400> SEQUENCE: 724
tacactttgg gagtttgtct ttgaag                                 26

<210> SEQ ID NO 725
<211> LENGTH: 25
<212> TYPE: DNA
<213> ORGANISM: Homo sapiens

<400> SEQUENCE: 725
tctgataggg cttgtgattt tattt                                  25

<210> SEQ ID NO 726
<211> LENGTH: 25
<212> TYPE: DNA
<213> ORGANISM: Homo sapiens
```

-continued

<400> SEQUENCE: 726
gtctttccct atgtcaacct tgtgt                                          25

<210> SEQ ID NO 727
<211> LENGTH: 26
<212> TYPE: DNA
<213> ORGANISM: Homo sapiens

<400> SEQUENCE: 727
tcttcacctt agtctcctta tctcta                                         26

<210> SEQ ID NO 728
<211> LENGTH: 23
<212> TYPE: DNA
<213> ORGANISM: Homo sapiens

<400> SEQUENCE: 728
ccaccagtgc cacgagaacc tct                                            23

<210> SEQ ID NO 729
<211> LENGTH: 23
<212> TYPE: DNA
<213> ORGANISM: Homo sapiens

<400> SEQUENCE: 729
cagggctgct tgaatggaaa ggg                                            23

<210> SEQ ID NO 730
<211> LENGTH: 23
<212> TYPE: DNA
<213> ORGANISM: Homo sapiens

<400> SEQUENCE: 730
gggcagccag aaagcacaca gtt                                            23

<210> SEQ ID NO 731
<211> LENGTH: 23
<212> TYPE: DNA
<213> ORGANISM: Homo sapiens

<400> SEQUENCE: 731
aacccaatcc aggcaagcca ccc                                            23

<210> SEQ ID NO 732
<211> LENGTH: 23
<212> TYPE: DNA
<213> ORGANISM: Homo sapiens

<400> SEQUENCE: 732
gggcagccag aaagcacaca gtt                                            23

<210> SEQ ID NO 733
<211> LENGTH: 23
<212> TYPE: DNA
<213> ORGANISM: Homo sapiens

<400> SEQUENCE: 733
gggcagccag aaagcacaca gtt                                            23

<210> SEQ ID NO 734
<211> LENGTH: 23
<212> TYPE: DNA

<213> ORGANISM: Homo sapiens

<400> SEQUENCE: 734
gggcagccag aaagcacaca gtt                                          23

<210> SEQ ID NO 735
<211> LENGTH: 23
<212> TYPE: DNA
<213> ORGANISM: Homo sapiens

<400> SEQUENCE: 735
gggcagccag aaagcacaca gtt                                          23

<210> SEQ ID NO 736
<211> LENGTH: 26
<212> TYPE: DNA
<213> ORGANISM: Homo sapiens

<400> SEQUENCE: 736
tccattttcc ccatctctca ccctcc                                       26

<210> SEQ ID NO 737
<211> LENGTH: 26
<212> TYPE: DNA
<213> ORGANISM: Homo sapiens

<400> SEQUENCE: 737
tccattttcc ccatctctca ccctcc                                       26

<210> SEQ ID NO 738
<211> LENGTH: 23
<212> TYPE: DNA
<213> ORGANISM: Homo sapiens

<400> SEQUENCE: 738
gggcagccag aaagcacaca gtt                                          23

<210> SEQ ID NO 739
<211> LENGTH: 23
<212> TYPE: DNA
<213> ORGANISM: Homo sapiens

<400> SEQUENCE: 739
gggcagccag aaagcacaca gtt                                          23

<210> SEQ ID NO 740
<211> LENGTH: 23
<212> TYPE: DNA
<213> ORGANISM: Homo sapiens

<400> SEQUENCE: 740
aacccaatcc aggcaagcca ccc                                          23

<210> SEQ ID NO 741
<211> LENGTH: 23
<212> TYPE: DNA
<213> ORGANISM: Homo sapiens

<400> SEQUENCE: 741
gggcagccag aaagcacaca gtt                                          23

<210> SEQ ID NO 742
<211> LENGTH: 26

<212> TYPE: DNA
<213> ORGANISM: Homo sapiens

<400> SEQUENCE: 742
atccattttc cccatctctc accctc                                    26

<210> SEQ ID NO 743
<211> LENGTH: 24
<212> TYPE: DNA
<213> ORGANISM: Homo sapiens

<400> SEQUENCE: 743
gttgggcagc cagaaagcac acag                                      24

<210> SEQ ID NO 744
<211> LENGTH: 26
<212> TYPE: DNA
<213> ORGANISM: Homo sapiens

<400> SEQUENCE: 744
gagcaaagta gtcagccagc cagaat                                    26

<210> SEQ ID NO 745
<211> LENGTH: 24
<212> TYPE: DNA
<213> ORGANISM: Homo sapiens

<400> SEQUENCE: 745
aaacctgtgc gggctgtctg acca                                      24

<210> SEQ ID NO 746
<211> LENGTH: 23
<212> TYPE: DNA
<213> ORGANISM: Homo sapiens

<400> SEQUENCE: 746
tcccgctccc tgttttccac cat                                       23

<210> SEQ ID NO 747
<211> LENGTH: 26
<212> TYPE: DNA
<213> ORGANISM: Homo sapiens

<400> SEQUENCE: 747
gcctgaaccc acttagataa tgtgtg                                    26

<210> SEQ ID NO 748
<211> LENGTH: 23
<212> TYPE: DNA
<213> ORGANISM: Homo sapiens

<400> SEQUENCE: 748
cctgggtaga tgagcctgta gcc                                       23

<210> SEQ ID NO 749
<211> LENGTH: 23
<212> TYPE: DNA
<213> ORGANISM: Homo sapiens

<400> SEQUENCE: 749
ccctcgcctc ctattcctat ggc                                       23

<210> SEQ ID NO 750

<211> LENGTH: 23
<212> TYPE: DNA
<213> ORGANISM: Homo sapiens

<400> SEQUENCE: 750
ccacgccatt taggactcgg gtc                                               23

<210> SEQ ID NO 751
<211> LENGTH: 24
<212> TYPE: DNA
<213> ORGANISM: Homo sapiens

<400> SEQUENCE: 751
tatgggattt ctttggtagg gacg                                             24

<210> SEQ ID NO 752
<211> LENGTH: 23
<212> TYPE: DNA
<213> ORGANISM: Homo sapiens

<400> SEQUENCE: 752
gcccaacctc tgtgttccca ttc                                              23

<210> SEQ ID NO 753
<211> LENGTH: 23
<212> TYPE: DNA
<213> ORGANISM: Homo sapiens

<400> SEQUENCE: 753
gcccaacctc tgtgttccca ttc                                              23

<210> SEQ ID NO 754
<211> LENGTH: 26
<212> TYPE: DNA
<213> ORGANISM: Homo sapiens

<400> SEQUENCE: 754
gaacaggtgg ctcacaaagg aggata                                           26

<210> SEQ ID NO 755
<211> LENGTH: 23
<212> TYPE: DNA
<213> ORGANISM: Homo sapiens

<400> SEQUENCE: 755
gctccagttt gctgaaccaa ccc                                              23

<210> SEQ ID NO 756
<211> LENGTH: 23
<212> TYPE: DNA
<213> ORGANISM: Homo sapiens

<400> SEQUENCE: 756
ggcacccctt atcagagacc agc                                              23

<210> SEQ ID NO 757
<211> LENGTH: 23
<212> TYPE: DNA
<213> ORGANISM: Homo sapiens

<400> SEQUENCE: 757
ggcacccctt atcagagacc agc                                              23

```
<210> SEQ ID NO 758
<211> LENGTH: 23
<212> TYPE: DNA
<213> ORGANISM: Homo sapiens

<400> SEQUENCE: 758
ccaaaacctg acaagcacag cat                                            23

<210> SEQ ID NO 759
<211> LENGTH: 23
<212> TYPE: DNA
<213> ORGANISM: Homo sapiens

<400> SEQUENCE: 759
ggcacccctt atcagagacc agc                                            23

<210> SEQ ID NO 760
<211> LENGTH: 23
<212> TYPE: DNA
<213> ORGANISM: Homo sapiens

<400> SEQUENCE: 760
gaccttcatc cgagcctccg ttt                                            23

<210> SEQ ID NO 761
<211> LENGTH: 23
<212> TYPE: DNA
<213> ORGANISM: Homo sapiens

<400> SEQUENCE: 761
gagaccttca tccgagcctc cgt                                            23

<210> SEQ ID NO 762
<211> LENGTH: 23
<212> TYPE: DNA
<213> ORGANISM: Homo sapiens

<400> SEQUENCE: 762
gaccttcatc cgagcctccg ttt                                            23

<210> SEQ ID NO 763
<211> LENGTH: 24
<212> TYPE: DNA
<213> ORGANISM: Homo sapiens

<400> SEQUENCE: 763
atccaaacca ttgaaaccct gggc                                           24

<210> SEQ ID NO 764
<211> LENGTH: 26
<212> TYPE: DNA
<213> ORGANISM: Homo sapiens

<400> SEQUENCE: 764
tccttgtgac ctattggact gagggc                                         26

<210> SEQ ID NO 765
<211> LENGTH: 26
<212> TYPE: DNA
<213> ORGANISM: Homo sapiens

<400> SEQUENCE: 765
cctgattcta aacagcattc tgggag                                         26
```

<210> SEQ ID NO 766
<211> LENGTH: 26
<212> TYPE: DNA
<213> ORGANISM: Homo sapiens

<400> SEQUENCE: 766
actctttacc ctgtggtgtg gacggt                                    26

<210> SEQ ID NO 767
<211> LENGTH: 26
<212> TYPE: DNA
<213> ORGANISM: Homo sapiens

<400> SEQUENCE: 767
ccaactctgt cgcttgttac acttag                                    26

<210> SEQ ID NO 768
<211> LENGTH: 26
<212> TYPE: DNA
<213> ORGANISM: Homo sapiens

<400> SEQUENCE: 768
gcacaacaat ggagtgaccc acagca                                    26

<210> SEQ ID NO 769
<211> LENGTH: 23
<212> TYPE: DNA
<213> ORGANISM: Homo sapiens

<400> SEQUENCE: 769
ccgacaaagg gcagaggtga gat                                       23

<210> SEQ ID NO 770
<211> LENGTH: 26
<212> TYPE: DNA
<213> ORGANISM: Homo sapiens

<400> SEQUENCE: 770
caccaggttt tccccttcag tgtgac                                    26

<210> SEQ ID NO 771
<211> LENGTH: 26
<212> TYPE: DNA
<213> ORGANISM: Homo sapiens

<400> SEQUENCE: 771
gaccgatttg aggtgcttac ggatgg                                    26

<210> SEQ ID NO 772
<211> LENGTH: 24
<212> TYPE: DNA
<213> ORGANISM: Homo sapiens

<400> SEQUENCE: 772
gctgggtcac cacgcatagg atga                                      24

<210> SEQ ID NO 773
<211> LENGTH: 23
<212> TYPE: DNA
<213> ORGANISM: Homo sapiens

<400> SEQUENCE: 773
agggcagagg gctatgggtg ctt                                       23

<210> SEQ ID NO 774
<211> LENGTH: 23
<212> TYPE: DNA
<213> ORGANISM: Homo sapiens

<400> SEQUENCE: 774
agggcagagg gctatgggtg ctt                                              23

<210> SEQ ID NO 775
<211> LENGTH: 26
<212> TYPE: DNA
<213> ORGANISM: Homo sapiens

<400> SEQUENCE: 775
atggatggct ctgtcaactt cttcag                                           26

<210> SEQ ID NO 776
<211> LENGTH: 26
<212> TYPE: DNA
<213> ORGANISM: Homo sapiens

<400> SEQUENCE: 776
atggatggct ctgtcaactt cttcag                                           26

<210> SEQ ID NO 777
<211> LENGTH: 26
<212> TYPE: DNA
<213> ORGANISM: Homo sapiens

<400> SEQUENCE: 777
cacttggagc ggttttgttc acactt                                           26

<210> SEQ ID NO 778
<211> LENGTH: 26
<212> TYPE: DNA
<213> ORGANISM: Homo sapiens

<400> SEQUENCE: 778
gatggcagca tagtaacagt tctaca                                           26

<210> SEQ ID NO 779
<211> LENGTH: 26
<212> TYPE: DNA
<213> ORGANISM: Homo sapiens

<400> SEQUENCE: 779
gaacaactgc tccaacacaa acaagc                                           26

<210> SEQ ID NO 780
<211> LENGTH: 23
<212> TYPE: DNA
<213> ORGANISM: Homo sapiens

<400> SEQUENCE: 780
ttcccctcct ctccattggg tca                                              23

<210> SEQ ID NO 781
<211> LENGTH: 23
<212> TYPE: DNA
<213> ORGANISM: Homo sapiens

<400> SEQUENCE: 781

-continued

```
cttccttcag aaagcgggtg ctc                                          23

<210> SEQ ID NO 782
<211> LENGTH: 23
<212> TYPE: DNA
<213> ORGANISM: Homo sapiens

<400> SEQUENCE: 782
gactgagcat tatggaggca gcc                                          23

<210> SEQ ID NO 783
<211> LENGTH: 26
<212> TYPE: DNA
<213> ORGANISM: Homo sapiens

<400> SEQUENCE: 783
tccatcttgg gtcccttctc catcct                                       26

<210> SEQ ID NO 784
<211> LENGTH: 23
<212> TYPE: DNA
<213> ORGANISM: Homo sapiens

<400> SEQUENCE: 784
ttgggtccct tctccatcct gcc                                          23

<210> SEQ ID NO 785
<211> LENGTH: 23
<212> TYPE: DNA
<213> ORGANISM: Homo sapiens

<400> SEQUENCE: 785
gccctcggtg tagtccttgc tgt                                          23

<210> SEQ ID NO 786
<211> LENGTH: 26
<212> TYPE: DNA
<213> ORGANISM: Homo sapiens

<400> SEQUENCE: 786
acttgaagac agaactgctt tgacaa                                       26

<210> SEQ ID NO 787
<211> LENGTH: 25
<212> TYPE: DNA
<213> ORGANISM: Homo sapiens

<400> SEQUENCE: 787
tctgagatgt ccttcttgat tcata                                        25

<210> SEQ ID NO 788
<211> LENGTH: 26
<212> TYPE: DNA
<213> ORGANISM: Homo sapiens

<400> SEQUENCE: 788
cacctgcgta gatttgtgta accacg                                       26

<210> SEQ ID NO 789
<211> LENGTH: 25
<212> TYPE: DNA
<213> ORGANISM: Homo sapiens

<400> SEQUENCE: 789
```

-continued

```
actatggaaa acagtatgga gattt                                    25

<210> SEQ ID NO 790
<211> LENGTH: 26
<212> TYPE: DNA
<213> ORGANISM: Homo sapiens

<400> SEQUENCE: 790
gccactatgg aaaacagtat ggagat                                   26

<210> SEQ ID NO 791
<211> LENGTH: 26
<212> TYPE: DNA
<213> ORGANISM: Homo sapiens

<400> SEQUENCE: 791
ggactcaggg ctcatctctc atttgt                                   26

<210> SEQ ID NO 792
<211> LENGTH: 23
<212> TYPE: DNA
<213> ORGANISM: Homo sapiens

<400> SEQUENCE: 792
cccaaaggtc cagagcggag aaa                                      23

<210> SEQ ID NO 793
<211> LENGTH: 23
<212> TYPE: DNA
<213> ORGANISM: Homo sapiens

<400> SEQUENCE: 793
caacccaaag gtccagagcg gag                                      23

<210> SEQ ID NO 794
<211> LENGTH: 23
<212> TYPE: DNA
<213> ORGANISM: Homo sapiens

<400> SEQUENCE: 794
cccttgtgac ctcctactct gcc                                      23

<210> SEQ ID NO 795
<211> LENGTH: 23
<212> TYPE: DNA
<213> ORGANISM: Homo sapiens

<400> SEQUENCE: 795
gctgaagttg accttgtctc cgc                                      23

<210> SEQ ID NO 796
<211> LENGTH: 23
<212> TYPE: DNA
<213> ORGANISM: Homo sapiens

<400> SEQUENCE: 796
attcggtggg tctggagaga ggc                                      23

<210> SEQ ID NO 797
<211> LENGTH: 23
<212> TYPE: DNA
<213> ORGANISM: Homo sapiens
```

-continued

```
<400> SEQUENCE: 797
gggaggagaa gcagagcaca cag                                           23

<210> SEQ ID NO 798
<211> LENGTH: 23
<212> TYPE: DNA
<213> ORGANISM: Homo sapiens

<400> SEQUENCE: 798
ggaggctgat gtctgtcctt ggg                                           23

<210> SEQ ID NO 799
<211> LENGTH: 23
<212> TYPE: DNA
<213> ORGANISM: Homo sapiens

<400> SEQUENCE: 799
cccgctgctc tcaacagaca ctg                                           23

<210> SEQ ID NO 800
<211> LENGTH: 26
<212> TYPE: DNA
<213> ORGANISM: Homo sapiens

<400> SEQUENCE: 800
atgagaacca aggtcaggga ggtaaa                                        26

<210> SEQ ID NO 801
<211> LENGTH: 26
<212> TYPE: DNA
<213> ORGANISM: Homo sapiens

<400> SEQUENCE: 801
cccactctct ttgaaggaaa tcacat                                        26

<210> SEQ ID NO 802
<211> LENGTH: 23
<212> TYPE: DNA
<213> ORGANISM: Homo sapiens

<400> SEQUENCE: 802
cctccaccat tctcctccag tcc                                           23

<210> SEQ ID NO 803
<211> LENGTH: 23
<212> TYPE: DNA
<213> ORGANISM: Homo sapiens

<400> SEQUENCE: 803
ggcagggtca ttgtgatggt ccg                                           23

<210> SEQ ID NO 804
<211> LENGTH: 23
<212> TYPE: DNA
<213> ORGANISM: Homo sapiens

<400> SEQUENCE: 804
cctcctatca tctctctccc cac                                           23

<210> SEQ ID NO 805
<211> LENGTH: 23
<212> TYPE: DNA
<213> ORGANISM: Homo sapiens
```

-continued

<400> SEQUENCE: 805 agtctccccct cccactgttg gca                                      23

<210> SEQ ID NO 806
<211> LENGTH: 26
<212> TYPE: DNA
<213> ORGANISM: Homo sapiens

<400> SEQUENCE: 806
cttagactcc agtggctgaa tgtcca                                    26

<210> SEQ ID NO 807
<211> LENGTH: 23
<212> TYPE: DNA
<213> ORGANISM: Homo sapiens

<400> SEQUENCE: 807
gaacttctcg tgggacaccc tca                                       23

<210> SEQ ID NO 808
<211> LENGTH: 26
<212> TYPE: DNA
<213> ORGANISM: Homo sapiens

<400> SEQUENCE: 808 gttctttttcc tggtaggtca tcctgt                                   26

<210> SEQ ID NO 809
<211> LENGTH: 26
<212> TYPE: DNA
<213> ORGANISM: Homo sapiens

<400> SEQUENCE: 809
gcctgaaccc acttagataa tgtgtg                                    26

<210> SEQ ID NO 810
<211> LENGTH: 23
<212> TYPE: DNA
<213> ORGANISM: Homo sapiens

<400> SEQUENCE: 810
cactgtggca ctgggaggaa acg                                       23

<210> SEQ ID NO 811
<211> LENGTH: 26
<212> TYPE: DNA
<213> ORGANISM: Homo sapiens

<400> SEQUENCE: 811
gttcctgtgg ttggttggtt gggatg                                    26

<210> SEQ ID NO 812
<211> LENGTH: 23
<212> TYPE: DNA
<213> ORGANISM: Homo sapiens

<400> SEQUENCE: 812
tcccgctccc tgttttccac cat                                       23

<210> SEQ ID NO 813
<211> LENGTH: 23
<212> TYPE: DNA

```
<213> ORGANISM: Homo sapiens

<400> SEQUENCE: 813
cccatccctt tcagcctcac tca                                         23

<210> SEQ ID NO 814
<211> LENGTH: 23
<212> TYPE: DNA
<213> ORGANISM: Homo sapiens

<400> SEQUENCE: 814
gggtcagtct ccgcagcac aaa                                          23

<210> SEQ ID NO 815
<211> LENGTH: 25
<212> TYPE: DNA
<213> ORGANISM: Homo sapiens

<400> SEQUENCE: 815
tcagtcaata catacagttc atact                                       25

<210> SEQ ID NO 816
<211> LENGTH: 23
<212> TYPE: DNA
<213> ORGANISM: Homo sapiens

<400> SEQUENCE: 816
tccacggttc aggcatccac tgg                                         23

<210> SEQ ID NO 817
<211> LENGTH: 23
<212> TYPE: DNA
<213> ORGANISM: Homo sapiens

<400> SEQUENCE: 817
ccccgaaggc aggctatgga gaa                                         23

<210> SEQ ID NO 818
<211> LENGTH: 26
<212> TYPE: DNA
<213> ORGANISM: Homo sapiens

<400> SEQUENCE: 818
gacaaggaca acacaaagaa ggaaaa                                      26

<210> SEQ ID NO 819
<211> LENGTH: 23
<212> TYPE: DNA
<213> ORGANISM: Homo sapiens

<400> SEQUENCE: 819
agagcgtccc tggaaagtgg cag                                         23

<210> SEQ ID NO 820
<211> LENGTH: 23
<212> TYPE: DNA
<213> ORGANISM: Homo sapiens

<400> SEQUENCE: 820
ttgggcagag gagaagagtg tgc                                         23

<210> SEQ ID NO 821
<211> LENGTH: 23
```

-continued

```
<212> TYPE: DNA
<213> ORGANISM: Homo sapiens

<400> SEQUENCE: 821
ggcatctcct cttctgctca cac                                           23

<210> SEQ ID NO 822
<211> LENGTH: 23
<212> TYPE: DNA
<213> ORGANISM: Homo sapiens

<400> SEQUENCE: 822
gagacaggtg gatggcgatg gta                                           23

<210> SEQ ID NO 823
<211> LENGTH: 23
<212> TYPE: DNA
<213> ORGANISM: Homo sapiens

<400> SEQUENCE: 823
cctccatctc tgccactcag gaa                                           23

<210> SEQ ID NO 824
<211> LENGTH: 23
<212> TYPE: DNA
<213> ORGANISM: Homo sapiens

<400> SEQUENCE: 824
tgcctctcct gcctctgtct cac                                           23

<210> SEQ ID NO 825
<211> LENGTH: 23
<212> TYPE: DNA
<213> ORGANISM: Homo sapiens

<400> SEQUENCE: 825
gggcgaacag caagagacaa gca                                           23

<210> SEQ ID NO 826
<211> LENGTH: 23
<212> TYPE: DNA
<213> ORGANISM: Homo sapiens

<400> SEQUENCE: 826
ccctggatgt gtgaccttcg gca                                           23

<210> SEQ ID NO 827
<211> LENGTH: 24
<212> TYPE: DNA
<213> ORGANISM: Homo sapiens

<400> SEQUENCE: 827
gattgagact tgcgttttga gggc                                          24

<210> SEQ ID NO 828
<211> LENGTH: 60
<212> TYPE: DNA
<213> ORGANISM: Homo sapiens

<400> SEQUENCE: 828
attgaaataa aaaagtcagt agaaaagatc gacaataaag actatcaagt attgtactaa   60

<210> SEQ ID NO 829
```

-continued

```
<211> LENGTH: 60
<212> TYPE: DNA
<213> ORGANISM: Homo sapiens

<400> SEQUENCE: 829
gctggggcca tgtacatcct gggcaccatc gataagaaaa caaaatgcct caaaagaagt        60

<210> SEQ ID NO 830
<211> LENGTH: 60
<212> TYPE: DNA
<213> ORGANISM: Homo sapiens

<400> SEQUENCE: 830
gcctttctca aaacccactg tacacagctc gattttaatg gctgcttaat ctgagtggct        60

<210> SEQ ID NO 831
<211> LENGTH: 60
<212> TYPE: DNA
<213> ORGANISM: Homo sapiens

<400> SEQUENCE: 831
gcctttctca aaacccactg tacacagctc gagccaccag ctcataaagc ccctgtgatc        60

<210> SEQ ID NO 832
<211> LENGTH: 60
<212> TYPE: DNA
<213> ORGANISM: Homo sapiens

<400> SEQUENCE: 832
tgaacagtca agactggtga ggaagaattc gaagcctatg ctgccttcct gaagcctcct        60

<210> SEQ ID NO 833
<211> LENGTH: 60
<212> TYPE: DNA
<213> ORGANISM: Homo sapiens

<400> SEQUENCE: 833
cgtgtacctc acagggttct tctaaagatc gatgagaact tttaagatct actctcttag        60

<210> SEQ ID NO 834
<211> LENGTH: 60
<212> TYPE: DNA
<213> ORGANISM: Homo sapiens

<400> SEQUENCE: 834
atttcttgac agcgtgaatt ctttaccctc gagctaaaaa tttcacaaat aaactcataa        60

<210> SEQ ID NO 835
<211> LENGTH: 60
<212> TYPE: DNA
<213> ORGANISM: Homo sapiens

<400> SEQUENCE: 835
atttcttgac agcgtgaatt ctttaccctc gattatctac ttgcagataa cctttttcc         60

<210> SEQ ID NO 836
<211> LENGTH: 60
<212> TYPE: DNA
<213> ORGANISM: Homo sapiens

<400> SEQUENCE: 836
atttcttgac agcgtgaatt ctttaccctc gaggtacata gaagtactaa aatacacaaa        60
```

```
<210> SEQ ID NO 837
<211> LENGTH: 60
<212> TYPE: DNA
<213> ORGANISM: Homo sapiens

<400> SEQUENCE: 837
atttcttgac agcgtgaatt ctttaccctc gagagaagtc agaagaatct ctggttactt      60

<210> SEQ ID NO 838
<211> LENGTH: 60
<212> TYPE: DNA
<213> ORGANISM: Homo sapiens

<400> SEQUENCE: 838
atttcttgac agcgtgaatt ctttaccctc gatgatattt atctgtgtca tttttaatag      60

<210> SEQ ID NO 839
<211> LENGTH: 60
<212> TYPE: DNA
<213> ORGANISM: Homo sapiens

<400> SEQUENCE: 839
attcaaaaac acacaagtac tattaaattc gaatccttgc aaaaatttct cttttgttta      60

<210> SEQ ID NO 840
<211> LENGTH: 60
<212> TYPE: DNA
<213> ORGANISM: Homo sapiens

<400> SEQUENCE: 840
aaaaaaatct gttcagctaa tttctaactc gacaaagctc tgtattcttt ttttaattg      60

<210> SEQ ID NO 841
<211> LENGTH: 60
<212> TYPE: DNA
<213> ORGANISM: Homo sapiens

<400> SEQUENCE: 841
aaaaaaatct gttcagctaa tttctaactc gaataaagga tggttggaaa aaaataaat      60

<210> SEQ ID NO 842
<211> LENGTH: 60
<212> TYPE: DNA
<213> ORGANISM: Homo sapiens

<400> SEQUENCE: 842
tacagctcag atcaaattgt tctcagaatc gattgtatcc tgttggtcta tacttctgtc      60

<210> SEQ ID NO 843
<211> LENGTH: 60
<212> TYPE: DNA
<213> ORGANISM: Homo sapiens

<400> SEQUENCE: 843
tacagctcag atcaaattgt tctcagaatc gaaatgcacc aagaaaaaga ctgctatgta      60

<210> SEQ ID NO 844
<211> LENGTH: 60
<212> TYPE: DNA
<213> ORGANISM: Homo sapiens

<400> SEQUENCE: 844
ttaagcactt aatttttttt tcttgtgttc gattgtatcc tgttggtcta tacttctgtc      60
```

<210> SEQ ID NO 845
<211> LENGTH: 60
<212> TYPE: DNA
<213> ORGANISM: Homo sapiens

<400> SEQUENCE: 845
tctctctaga gctccacgga gttcgcagtc gactaataaa gtagcatcaa aatatataag        60

<210> SEQ ID NO 846
<211> LENGTH: 60
<212> TYPE: DNA
<213> ORGANISM: Homo sapiens

<400> SEQUENCE: 846
ctgtgcgtat gtacaattgt tttaatcctc gacagacgcg gtacccgacc aggttgtcac        60

<210> SEQ ID NO 847
<211> LENGTH: 60
<212> TYPE: DNA
<213> ORGANISM: Homo sapiens

<400> SEQUENCE: 847
agttattgac tcaacaaaca ttattgactc gatgtacact ctggctagac cagggcagga        60

<210> SEQ ID NO 848
<211> LENGTH: 60
<212> TYPE: DNA
<213> ORGANISM: Homo sapiens

<400> SEQUENCE: 848
gagatatata cagcattttt tcagaaaatc gagagcaaag agacactggt tgaaatgaga        60

<210> SEQ ID NO 849
<211> LENGTH: 60
<212> TYPE: DNA
<213> ORGANISM: Homo sapiens

<400> SEQUENCE: 849
taaagaaacg tctatgaaaa ttcaaaactc gaaacacaat aatatttgta tttggctgtt        60

<210> SEQ ID NO 850
<211> LENGTH: 60
<212> TYPE: DNA
<213> ORGANISM: Homo sapiens

<400> SEQUENCE: 850
taaagaaacg tctatgaaaa ttcaaaactc gaagatataa ttccactact tttggcttct        60

<210> SEQ ID NO 851
<211> LENGTH: 60
<212> TYPE: DNA
<213> ORGANISM: Homo sapiens

<400> SEQUENCE: 851
taaagaaacg tctatgaaaa ttcaaaactc gacagcgcta acagcaacaa aaacagtcaa        60

<210> SEQ ID NO 852
<211> LENGTH: 60
<212> TYPE: DNA
<213> ORGANISM: Homo sapiens

<400> SEQUENCE: 852
taaagaaacg tctatgaaaa ttcaaaactc gagttgagtt tgatgttaat ttcgtaaaat        60

-continued

```
<210> SEQ ID NO 853
<211> LENGTH: 60
<212> TYPE: DNA
<213> ORGANISM: Homo sapiens

<400> SEQUENCE: 853
taaagaaacg tctatgaaaa ttcaaaactc gattctgtaa aatgaaaagc tttttcagag          60

<210> SEQ ID NO 854
<211> LENGTH: 60
<212> TYPE: DNA
<213> ORGANISM: Homo sapiens

<400> SEQUENCE: 854
taaagaaacg tctatgaaaa ttcaaaactc gacagttatg taaatcaaag tatgaagaca          60

<210> SEQ ID NO 855
<211> LENGTH: 60
<212> TYPE: DNA
<213> ORGANISM: Homo sapiens

<400> SEQUENCE: 855
taaagaaacg tctatgaaaa ttcaaaactc gagtcttgag ttttaatgta gattaagcca          60

<210> SEQ ID NO 856
<211> LENGTH: 60
<212> TYPE: DNA
<213> ORGANISM: Homo sapiens

<400> SEQUENCE: 856
cgggcaaaaa ctagctattt aatatctctc gagaggggca gaataaatga tcgctaatgc          60

<210> SEQ ID NO 857
<211> LENGTH: 60
<212> TYPE: DNA
<213> ORGANISM: Homo sapiens

<400> SEQUENCE: 857
gcattagcga tcatttattc tgcccctctc gaagactctg atggtttctg gtttgttgaa          60

<210> SEQ ID NO 858
<211> LENGTH: 60
<212> TYPE: DNA
<213> ORGANISM: Homo sapiens

<400> SEQUENCE: 858
gcattagcga tcatttattc tgcccctctc gaggtggggt ttttcttgcg cttgcactgt          60

<210> SEQ ID NO 859
<211> LENGTH: 60
<212> TYPE: DNA
<213> ORGANISM: Homo sapiens

<400> SEQUENCE: 859
ctccactcat atgtggaaat aaacatgtc gattcagttt tgatggacga ggttcagaga          60

<210> SEQ ID NO 860
<211> LENGTH: 60
<212> TYPE: DNA
<213> ORGANISM: Homo sapiens

<400> SEQUENCE: 860
```
tgtcttcaat aaattgtgtt gggaaaattc gagtccctcc tacaactcca cttaatgggg      60

<210> SEQ ID NO 861
<211> LENGTH: 60
<212> TYPE: DNA
<213> ORGANISM: Homo sapiens

<400> SEQUENCE: 861
tgtcttcaat aaattgtgtt gggaaaattc gaaatgaggg tttcaatagt tcaaaatttt      60

<210> SEQ ID NO 862
<211> LENGTH: 60
<212> TYPE: DNA
<213> ORGANISM: Homo sapiens

<400> SEQUENCE: 862
gaacgtgatg atgtagtcta tacagaagtc gaagtgagac ttcttcaaaa aaagttcacg      60

<210> SEQ ID NO 863
<211> LENGTH: 60
<212> TYPE: DNA
<213> ORGANISM: Homo sapiens

<400> SEQUENCE: 863
gaacgtgatg atgtagtcta tacagaagtc gaagtttcac acaatattct attaactcac      60

<210> SEQ ID NO 864
<211> LENGTH: 60
<212> TYPE: DNA
<213> ORGANISM: Homo sapiens

<400> SEQUENCE: 864
gaacgtgatg atgtagtcta tacagaagtc gactgaacac cacaatccaa cggaagttcc      60

<210> SEQ ID NO 865
<211> LENGTH: 60
<212> TYPE: DNA
<213> ORGANISM: Homo sapiens

<400> SEQUENCE: 865
caacggcatg ttggatgtac aaatgggttc gaatagttac catctgtagt cttgatctct      60

<210> SEQ ID NO 866
<211> LENGTH: 60
<212> TYPE: DNA
<213> ORGANISM: Homo sapiens

<400> SEQUENCE: 866
agaattggta ggtattgtag tgatgtattc gaagattgtt cattatatca aaccatgaca      60

<210> SEQ ID NO 867
<211> LENGTH: 60
<212> TYPE: DNA
<213> ORGANISM: Homo sapiens

<400> SEQUENCE: 867
actggagact aggcagagga aaaacctttc gagacaattt atgatcagga aaaatggacc      60

<210> SEQ ID NO 868
<211> LENGTH: 60
<212> TYPE: DNA
<213> ORGANISM: Homo sapiens

<400> SEQUENCE: 868

-continued

```
aatatagtac aggaacatct tagattcctc gagttcacac agccaagaat gatccgattt      60

<210> SEQ ID NO 869
<211> LENGTH: 60
<212> TYPE: DNA
<213> ORGANISM: Homo sapiens

<400> SEQUENCE: 869
gctgcaggaa gtgatgtcaa aaggagggtc gaaaactacc acatttccat ttcagtttaa      60

<210> SEQ ID NO 870
<211> LENGTH: 60
<212> TYPE: DNA
<213> ORGANISM: Homo sapiens

<400> SEQUENCE: 870
gctgcaggaa gtgatgtcaa aaggagggtc gatcagtggt caacccttgt aagttcatca      60

<210> SEQ ID NO 871
<211> LENGTH: 60
<212> TYPE: DNA
<213> ORGANISM: Homo sapiens

<400> SEQUENCE: 871
ttccttctct gtacacaaag aagtgaactc gactgcatta attttcctt ttgaaacagt      60

<210> SEQ ID NO 872
<211> LENGTH: 60
<212> TYPE: DNA
<213> ORGANISM: Homo sapiens

<400> SEQUENCE: 872
ggggccaaga gtaatgcttc gtatatagtc gaatttccac aagtaatttt gaatttcagg      60

<210> SEQ ID NO 873
<211> LENGTH: 60
<212> TYPE: DNA
<213> ORGANISM: Homo sapiens

<400> SEQUENCE: 873
ggttaagagc agagccttta aaatcagatc gagagccgcg agttatgagc tctccgcctt      60

<210> SEQ ID NO 874
<211> LENGTH: 60
<212> TYPE: DNA
<213> ORGANISM: Homo sapiens

<400> SEQUENCE: 874
agagtttgga gaaggaagtt ggtctccttc gagagccgcg agttatgagc tctccgcctt      60

<210> SEQ ID NO 875
<211> LENGTH: 60
<212> TYPE: DNA
<213> ORGANISM: Homo sapiens

<400> SEQUENCE: 875
atgtatttaa aaacatttct tgaaggcctc gagagccgcg agttatgagc tctccgcctt      60

<210> SEQ ID NO 876
<211> LENGTH: 60
<212> TYPE: DNA
<213> ORGANISM: Homo sapiens
```

-continued

```
<400> SEQUENCE: 876 actttttcata gtttctcctt ctaaactctc gagagccgcg agttatgagc tctccgcctt        60

<210> SEQ ID NO 877
<211> LENGTH: 60
<212> TYPE: DNA
<213> ORGANISM: Homo sapiens

<400> SEQUENCE: 877
tttaagctct gagttagtct attttctatc gagagccgcg agttatgagc tctccgcctt        60

<210> SEQ ID NO 878
<211> LENGTH: 60
<212> TYPE: DNA
<213> ORGANISM: Homo sapiens

<400> SEQUENCE: 878
aaaagaaatt atagagttaa ttacctcatc gatttctgtt tgggatgtga cgtacaattc        60

<210> SEQ ID NO 879
<211> LENGTH: 60
<212> TYPE: DNA
<213> ORGANISM: Homo sapiens

<400> SEQUENCE: 879
ttgtatcatt aattagggct ttgaatggtc gatttctgtt tgggatgtga cgtacaattc        60

<210> SEQ ID NO 880
<211> LENGTH: 60
<212> TYPE: DNA
<213> ORGANISM: Homo sapiens

<400> SEQUENCE: 880
tcattcatgg gtgagttggt acttttctc gatgctcaaa cagtgtttgc caagtggatg        60

<210> SEQ ID NO 881
<211> LENGTH: 60
<212> TYPE: DNA
<213> ORGANISM: Homo sapiens

<400> SEQUENCE: 881
tcattcatgg gtgagttggt acttttctc gaccacctgt atagctgtga ggccactggt        60

<210> SEQ ID NO 882
<211> LENGTH: 60
<212> TYPE: DNA
<213> ORGANISM: Homo sapiens

<400> SEQUENCE: 882
atacccacat tctgaccccc gagtcagctc gaccacctgt atagctgtga ggccactggt        60

<210> SEQ ID NO 883
<211> LENGTH: 60
<212> TYPE: DNA
<213> ORGANISM: Homo sapiens

<400> SEQUENCE: 883
acatcattag tcattgtgga aatacaaatc gaagtgtttt attttcaaga gcaaaggtta        60

<210> SEQ ID NO 884
<211> LENGTH: 60
<212> TYPE: DNA
<213> ORGANISM: Homo sapiens
```

-continued

<400> SEQUENCE: 884
tgggagtaca gagaaaattc tataagattc gaacatccag ggaatccata ttttctttta      60

<210> SEQ ID NO 885
<211> LENGTH: 60
<212> TYPE: DNA
<213> ORGANISM: Homo sapiens

<400> SEQUENCE: 885
ttccgtgact cagagctgtt ggtacctttc gagtgcattg aatgagatgt aagtcatcac      60

<210> SEQ ID NO 886
<211> LENGTH: 60
<212> TYPE: DNA
<213> ORGANISM: Homo sapiens

<400> SEQUENCE: 886
tggcctcata atttttcaat atgctcaatc gataatttgc tggaacagct cagagaactc      60

<210> SEQ ID NO 887
<211> LENGTH: 60
<212> TYPE: DNA
<213> ORGANISM: Homo sapiens

<400> SEQUENCE: 887
cacaatgaaa atttgaaaat attttgagtc gaaaacaaaa tattggtttc acctaagata      60

<210> SEQ ID NO 888
<211> LENGTH: 60
<212> TYPE: DNA
<213> ORGANISM: Homo sapiens

<400> SEQUENCE: 888
ccgttcacgg aagaagcgca agccctattc gatcagctct ggcgccgtgg ggagtggagc      60

<210> SEQ ID NO 889
<211> LENGTH: 60
<212> TYPE: DNA
<213> ORGANISM: Homo sapiens

<400> SEQUENCE: 889
atgagagact cccattaaaa atcgtgtctc gatgatttac aggaaggcat caactaaaaa      60

<210> SEQ ID NO 890
<211> LENGTH: 60
<212> TYPE: DNA
<213> ORGANISM: Homo sapiens

<400> SEQUENCE: 890
atgagagact cccattaaaa atcgtgtctc gatgcagagc agtgaataat atgtgtgcag      60

<210> SEQ ID NO 891
<211> LENGTH: 60
<212> TYPE: DNA
<213> ORGANISM: Homo sapiens

<400> SEQUENCE: 891
atgagagact cccattaaaa atcgtgtctc gacaccaaga actgaacatc tatactcttc      60

<210> SEQ ID NO 892
<211> LENGTH: 24
<212> TYPE: DNA

<213> ORGANISM: Homo sapiens

<400> SEQUENCE: 892
gtcaatggaa ggagggaaat aata                                          24

<210> SEQ ID NO 893
<211> LENGTH: 23
<212> TYPE: DNA
<213> ORGANISM: Homo sapiens

<400> SEQUENCE: 893
cctcggacct ctctcgctga tac                                           23

<210> SEQ ID NO 894
<211> LENGTH: 23
<212> TYPE: DNA
<213> ORGANISM: Homo sapiens

<400> SEQUENCE: 894
agaactgctg gcaagggaga cag                                           23

<210> SEQ ID NO 895
<211> LENGTH: 23
<212> TYPE: DNA
<213> ORGANISM: Homo sapiens

<400> SEQUENCE: 895
aactgctggc aagggagaca ggg                                           23

<210> SEQ ID NO 896
<211> LENGTH: 23
<212> TYPE: DNA
<213> ORGANISM: Homo sapiens

<400> SEQUENCE: 896
agcctgaagt gggaaccaac ccc                                           23

<210> SEQ ID NO 897
<211> LENGTH: 24
<212> TYPE: DNA
<213> ORGANISM: Homo sapiens

<400> SEQUENCE: 897
actgtaaacc tgggaacaac acca                                          24

<210> SEQ ID NO 898
<211> LENGTH: 26
<212> TYPE: DNA
<213> ORGANISM: Homo sapiens

<400> SEQUENCE: 898
ggatgaccct aacatttcag caaaca                                        26

<210> SEQ ID NO 899
<211> LENGTH: 26
<212> TYPE: DNA
<213> ORGANISM: Homo sapiens

<400> SEQUENCE: 899
ctttgctctt agacctcct tccaca                                         26

<210> SEQ ID NO 900
<211> LENGTH: 26

-continued

```
<212> TYPE: DNA
<213> ORGANISM: Homo sapiens

<400> SEQUENCE: 900
ctttgctctt agaccctcct tccaca                                              26

<210> SEQ ID NO 901
<211> LENGTH: 26
<212> TYPE: DNA
<213> ORGANISM: Homo sapiens

<400> SEQUENCE: 901
tgaccctaac atttcagcaa acattg                                             26

<210> SEQ ID NO 902
<211> LENGTH: 24
<212> TYPE: DNA
<213> ORGANISM: Homo sapiens

<400> SEQUENCE: 902
tgaaggcagg ctttgttcta tttt                                               24

<210> SEQ ID NO 903
<211> LENGTH: 26
<212> TYPE: DNA
<213> ORGANISM: Homo sapiens

<400> SEQUENCE: 903
tttgctctta gaccctcctt ccacat                                             26

<210> SEQ ID NO 904
<211> LENGTH: 26
<212> TYPE: DNA
<213> ORGANISM: Homo sapiens

<400> SEQUENCE: 904
ctgtaggttc aacttcttat cagtgc                                             26

<210> SEQ ID NO 905
<211> LENGTH: 26
<212> TYPE: DNA
<213> ORGANISM: Homo sapiens

<400> SEQUENCE: 905
cccctgtagg ttcaacttct tatcag                                             26

<210> SEQ ID NO 906
<211> LENGTH: 26
<212> TYPE: DNA
<213> ORGANISM: Homo sapiens

<400> SEQUENCE: 906
gtgagcacag agtgagagaa tcatct                                             26

<210> SEQ ID NO 907
<211> LENGTH: 26
<212> TYPE: DNA
<213> ORGANISM: Homo sapiens

<400> SEQUENCE: 907
gtgagcacag agtgagagaa tcatct                                             26

<210> SEQ ID NO 908
```

-continued

```
<211> LENGTH: 23
<212> TYPE: DNA
<213> ORGANISM: Homo sapiens

<400> SEQUENCE: 908
agggaggctc acgctggcag taa                                                23

<210> SEQ ID NO 909
<211> LENGTH: 24
<212> TYPE: DNA
<213> ORGANISM: Homo sapiens

<400> SEQUENCE: 909
gtcagcaacc atcattattt ccta                                               24

<210> SEQ ID NO 910
<211> LENGTH: 23
<212> TYPE: DNA
<213> ORGANISM: Homo sapiens

<400> SEQUENCE: 910
gactccgctg gctcatctcc ttc                                                23

<210> SEQ ID NO 911
<211> LENGTH: 23
<212> TYPE: DNA
<213> ORGANISM: Homo sapiens

<400> SEQUENCE: 911
ggcatactgt cgtgtctcag gag                                                23

<210> SEQ ID NO 912
<211> LENGTH: 26
<212> TYPE: DNA
<213> ORGANISM: Homo sapiens

<400> SEQUENCE: 912
cactcgtggc attgaaacca aagtct                                             26

<210> SEQ ID NO 913
<211> LENGTH: 23
<212> TYPE: DNA
<213> ORGANISM: Homo sapiens

<400> SEQUENCE: 913
ctgacctgct ccccagtgaa act                                                23

<210> SEQ ID NO 914
<211> LENGTH: 23
<212> TYPE: DNA
<213> ORGANISM: Homo sapiens

<400> SEQUENCE: 914
ctgacctgct ccccagtgaa act                                                23

<210> SEQ ID NO 915
<211> LENGTH: 23
<212> TYPE: DNA
<213> ORGANISM: Homo sapiens

<400> SEQUENCE: 915
ctgacctgct ccccagtgaa act                                                23
```

-continued

```
<210> SEQ ID NO 916
<211> LENGTH: 23
<212> TYPE: DNA
<213> ORGANISM: Homo sapiens

<400> SEQUENCE: 916
ctgacctgct ccccagtgaa act                                          23

<210> SEQ ID NO 917
<211> LENGTH: 23
<212> TYPE: DNA
<213> ORGANISM: Homo sapiens

<400> SEQUENCE: 917
ctgacctgct ccccagtgaa act                                          23

<210> SEQ ID NO 918
<211> LENGTH: 23
<212> TYPE: DNA
<213> ORGANISM: Homo sapiens

<400> SEQUENCE: 918
atgctgacct gctccccagt gaa                                          23

<210> SEQ ID NO 919
<211> LENGTH: 23
<212> TYPE: DNA
<213> ORGANISM: Homo sapiens

<400> SEQUENCE: 919
ctgacctgct ccccagtgaa act                                          23

<210> SEQ ID NO 920
<211> LENGTH: 26
<212> TYPE: DNA
<213> ORGANISM: Homo sapiens

<400> SEQUENCE: 920
ggagaaagca accaatgaac ggaaga                                       26

<210> SEQ ID NO 921
<211> LENGTH: 23
<212> TYPE: DNA
<213> ORGANISM: Homo sapiens

<400> SEQUENCE: 921
ttccctctgt cctgcctcaa tgc                                          23

<210> SEQ ID NO 922
<211> LENGTH: 26
<212> TYPE: DNA
<213> ORGANISM: Homo sapiens

<400> SEQUENCE: 922
gtgcggtcac aagaatctct aatacg                                       26

<210> SEQ ID NO 923
<211> LENGTH: 26
<212> TYPE: DNA
<213> ORGANISM: Homo sapiens

<400> SEQUENCE: 923
gtgaaataag ccagatagag aaagac                                       26
```

-continued

```
<210> SEQ ID NO 924
<211> LENGTH: 24
<212> TYPE: DNA
<213> ORGANISM: Homo sapiens

<400> SEQUENCE: 924
tagagagccc agaaataaat ccat                                          24

<210> SEQ ID NO 925
<211> LENGTH: 26
<212> TYPE: DNA
<213> ORGANISM: Homo sapiens

<400> SEQUENCE: 925
gaatagagag cccagaaata aatcca                                        26

<210> SEQ ID NO 926
<211> LENGTH: 23
<212> TYPE: DNA
<213> ORGANISM: Homo sapiens

<400> SEQUENCE: 926
gcgacacctc ctctgttgcc aag                                           23

<210> SEQ ID NO 927
<211> LENGTH: 24
<212> TYPE: DNA
<213> ORGANISM: Homo sapiens

<400> SEQUENCE: 927
tacagagaac agattggtgg tcac                                          24

<210> SEQ ID NO 928
<211> LENGTH: 24
<212> TYPE: DNA
<213> ORGANISM: Homo sapiens

<400> SEQUENCE: 928
tacagagaac agattggtgg tcac                                          24

<210> SEQ ID NO 929
<211> LENGTH: 24
<212> TYPE: DNA
<213> ORGANISM: Homo sapiens

<400> SEQUENCE: 929
tacagagaac agattggtgg tcac                                          24

<210> SEQ ID NO 930
<211> LENGTH: 23
<212> TYPE: DNA
<213> ORGANISM: Homo sapiens

<400> SEQUENCE: 930
cactgccaca aaagccgctc tgg                                           23

<210> SEQ ID NO 931
<211> LENGTH: 26
<212> TYPE: DNA
<213> ORGANISM: Homo sapiens

<400> SEQUENCE: 931
gaaagatgcc cagtctgtgt cggaga                                        26
```

```
<210> SEQ ID NO 932
<211> LENGTH: 23
<212> TYPE: DNA
<213> ORGANISM: Homo sapiens

<400> SEQUENCE: 932
tggagtaaga cgccgaaaac act                                           23

<210> SEQ ID NO 933
<211> LENGTH: 23
<212> TYPE: DNA
<213> ORGANISM: Homo sapiens

<400> SEQUENCE: 933
aggagtccct gccctcggaa tct                                           23

<210> SEQ ID NO 934
<211> LENGTH: 23
<212> TYPE: DNA
<213> ORGANISM: Homo sapiens

<400> SEQUENCE: 934
aggagtccct gccctcggaa tct                                           23

<210> SEQ ID NO 935
<211> LENGTH: 26
<212> TYPE: DNA
<213> ORGANISM: Homo sapiens

<400> SEQUENCE: 935
gcagggagtc agtcattttg tttctc                                        26

<210> SEQ ID NO 936
<211> LENGTH: 26
<212> TYPE: DNA
<213> ORGANISM: Homo sapiens

<400> SEQUENCE: 936
ttatcttctt tacctacatt ccaggg                                        26

<210> SEQ ID NO 937
<211> LENGTH: 24
<212> TYPE: DNA
<213> ORGANISM: Homo sapiens

<400> SEQUENCE: 937
acttacaaac ccaatcacta cata                                          24

<210> SEQ ID NO 938
<211> LENGTH: 23
<212> TYPE: DNA
<213> ORGANISM: Homo sapiens

<400> SEQUENCE: 938
aatctattcc cactcacctc tgg                                           23

<210> SEQ ID NO 939
<211> LENGTH: 24
<212> TYPE: DNA
<213> ORGANISM: Homo sapiens

<400> SEQUENCE: 939
```
gaataggtcc ttttgttttg tttt                                    24

<210> SEQ ID NO 940
<211> LENGTH: 23
<212> TYPE: DNA
<213> ORGANISM: Homo sapiens

<400> SEQUENCE: 940
acggaagcag aatggagagt ggg                                    23

<210> SEQ ID NO 941
<211> LENGTH: 23
<212> TYPE: DNA
<213> ORGANISM: Homo sapiens

<400> SEQUENCE: 941
cccaagtgct gcttctattt cct                                    23

<210> SEQ ID NO 942
<211> LENGTH: 26
<212> TYPE: DNA
<213> ORGANISM: Homo sapiens

<400> SEQUENCE: 942
tcccagattc tacccttgac cctcat                                    26

<210> SEQ ID NO 943
<211> LENGTH: 24
<212> TYPE: DNA
<213> ORGANISM: Homo sapiens

<400> SEQUENCE: 943
ggatgagttc taaatgaata atga                                    24

<210> SEQ ID NO 944
<211> LENGTH: 23
<212> TYPE: DNA
<213> ORGANISM: Homo sapiens

<400> SEQUENCE: 944
attgagtggc tggcggtcac ggt                                    23

<210> SEQ ID NO 945
<211> LENGTH: 23
<212> TYPE: DNA
<213> ORGANISM: Homo sapiens

<400> SEQUENCE: 945
ttattgagtg gctggcggtc acg                                    23

<210> SEQ ID NO 946
<211> LENGTH: 26
<212> TYPE: DNA
<213> ORGANISM: Homo sapiens

<400> SEQUENCE: 946
ggtggcaaaa gccccaagag aatgag                                    26

<210> SEQ ID NO 947
<211> LENGTH: 24
<212> TYPE: DNA
<213> ORGANISM: Homo sapiens

<400> SEQUENCE: 947

-continued ggcaaaggac ttgaaaagac attt                                    24

<210> SEQ ID NO 948
<211> LENGTH: 23
<212> TYPE: DNA
<213> ORGANISM: Homo sapiens

<400> SEQUENCE: 948
gaggattggc agcagatgtt agc                                     23

<210> SEQ ID NO 949
<211> LENGTH: 23
<212> TYPE: DNA
<213> ORGANISM: Homo sapiens

<400> SEQUENCE: 949
ccctaccagg ctcagatggg att                                     23

<210> SEQ ID NO 950
<211> LENGTH: 23
<212> TYPE: DNA
<213> ORGANISM: Homo sapiens

<400> SEQUENCE: 950
cccaggaccc aggttttctt acc                                     23

<210> SEQ ID NO 951
<211> LENGTH: 24
<212> TYPE: DNA
<213> ORGANISM: Homo sapiens

<400> SEQUENCE: 951
tgtgcccatc ttcctctact ttat                                    24

<210> SEQ ID NO 952
<211> LENGTH: 23
<212> TYPE: DNA
<213> ORGANISM: Homo sapiens

<400> SEQUENCE: 952
ccctactggt tcatctccac cca                                     23

<210> SEQ ID NO 953
<211> LENGTH: 26
<212> TYPE: DNA
<213> ORGANISM: Homo sapiens

<400> SEQUENCE: 953
cccctctcca gcagttttga gtaata                                  26

<210> SEQ ID NO 954
<211> LENGTH: 26
<212> TYPE: DNA
<213> ORGANISM: Homo sapiens

<400> SEQUENCE: 954
gcccctctcc agcagttttg agtaat                                  26

<210> SEQ ID NO 955
<211> LENGTH: 23
<212> TYPE: DNA
<213> ORGANISM: Homo sapiens -continued

```
<400> SEQUENCE: 955
ccctctccag cagttttgag taa                                          23

<210> SEQ ID NO 956
<211> LENGTH: 24
<212> TYPE: DNA
<213> ORGANISM: Homo sapiens

<400> SEQUENCE: 956
tctcaacaga ggagtaagat gtat                                         24

<210> SEQ ID NO 957
<211> LENGTH: 23
<212> TYPE: DNA
<213> ORGANISM: Homo sapiens

<400> SEQUENCE: 957
gccgtcagta ttgtttggct ggc                                          23

<210> SEQ ID NO 958
<211> LENGTH: 23
<212> TYPE: DNA
<213> ORGANISM: Homo sapiens

<400> SEQUENCE: 958
acacagagag agcccctcag agc                                          23

<210> SEQ ID NO 959
<211> LENGTH: 23
<212> TYPE: DNA
<213> ORGANISM: Homo sapiens

<400> SEQUENCE: 959
gacaagggaa ggaccgaaaa gcc                                          23

<210> SEQ ID NO 960
<211> LENGTH: 23
<212> TYPE: DNA
<213> ORGANISM: Homo sapiens

<400> SEQUENCE: 960
gacaaggtgg aaaggtaggc acg                                          23

<210> SEQ ID NO 961
<211> LENGTH: 24
<212> TYPE: DNA
<213> ORGANISM: Homo sapiens

<400> SEQUENCE: 961
aataagtcct cgggatgtaa tgta                                         24

<210> SEQ ID NO 962
<211> LENGTH: 26
<212> TYPE: DNA
<213> ORGANISM: Homo sapiens

<400> SEQUENCE: 962
cctacaatca ccacaggacc tctcca                                       26

<210> SEQ ID NO 963
<211> LENGTH: 26
<212> TYPE: DNA
<213> ORGANISM: Homo sapiens
```

-continued

<400> SEQUENCE: 963
ggataggaac aaagcaagaa tgatgt                                                          26

<210> SEQ ID NO 964
<211> LENGTH: 26
<212> TYPE: DNA
<213> ORGANISM: Homo sapiens

<400> SEQUENCE: 964
gaagatagtg gaatgctttt ggtgac                                                          26

<210> SEQ ID NO 965
<211> LENGTH: 26
<212> TYPE: DNA
<213> ORGANISM: Homo sapiens

<400> SEQUENCE: 965
cactaacaga gcattttctt caagga                                                          26

<210> SEQ ID NO 966
<211> LENGTH: 24
<212> TYPE: DNA
<213> ORGANISM: Homo sapiens

<400> SEQUENCE: 966
tgaagaataa aacccagacc aaaa                                                            24

<210> SEQ ID NO 967
<211> LENGTH: 26
<212> TYPE: DNA
<213> ORGANISM: Homo sapiens

<400> SEQUENCE: 967
gccgaccttc tgagatacta acggtg                                                          26

<210> SEQ ID NO 968
<211> LENGTH: 23
<212> TYPE: DNA
<213> ORGANISM: Homo sapiens

<400> SEQUENCE: 968
cagttgttag cccaggtgcc aat                                                             23

<210> SEQ ID NO 969
<211> LENGTH: 26
<212> TYPE: DNA
<213> ORGANISM: Homo sapiens

<400> SEQUENCE: 969
ccgtttccta ccagtgtgac taccag                                                          26

<210> SEQ ID NO 970
<211> LENGTH: 23
<212> TYPE: DNA
<213> ORGANISM: Homo sapiens

<400> SEQUENCE: 970
gcagtcccta tgagaaaccc agc                                                             23

<210> SEQ ID NO 971
<211> LENGTH: 26
<212> TYPE: DNA

-continued

<213> ORGANISM: Homo sapiens

<400> SEQUENCE: 971
caaatctggt gataaatccg catcca                                    26

<210> SEQ ID NO 972
<211> LENGTH: 23
<212> TYPE: DNA
<213> ORGANISM: Homo sapiens

<400> SEQUENCE: 972
gcagtcccta tgagaaaccc agc                                       23

<210> SEQ ID NO 973
<211> LENGTH: 24
<212> TYPE: DNA
<213> ORGANISM: Homo sapiens

<400> SEQUENCE: 973
tgttactccg atactgcttt ctta                                      24

<210> SEQ ID NO 974
<211> LENGTH: 23
<212> TYPE: DNA
<213> ORGANISM: Homo sapiens

<400> SEQUENCE: 974
ggacttgccc tcggtgtttt gtg                                       23

<210> SEQ ID NO 975
<211> LENGTH: 23
<212> TYPE: DNA
<213> ORGANISM: Homo sapiens

<400> SEQUENCE: 975
cctcctctcc cttctgccat cag                                       23

<210> SEQ ID NO 976
<211> LENGTH: 23
<212> TYPE: DNA
<213> ORGANISM: Homo sapiens

<400> SEQUENCE: 976
agtctgtctt cactaacgat ggc                                       23

<210> SEQ ID NO 977
<211> LENGTH: 23
<212> TYPE: DNA
<213> ORGANISM: Homo sapiens

<400> SEQUENCE: 977
tcccttttcc tgcctccctc ccc                                       23

<210> SEQ ID NO 978
<211> LENGTH: 23
<212> TYPE: DNA
<213> ORGANISM: Homo sapiens

<400> SEQUENCE: 978
gacagtggtc tccttcttac ctg                                       23

<210> SEQ ID NO 979
<211> LENGTH: 26

<212> TYPE: DNA
<213> ORGANISM: Homo sapiens

<400> SEQUENCE: 979
cagggacaat cacttctaaa cactaa                                              26

<210> SEQ ID NO 980
<211> LENGTH: 26
<212> TYPE: DNA
<213> ORGANISM: Homo sapiens

<400> SEQUENCE: 980
gttttgttga cttctcacca gcaaga                                             26

<210> SEQ ID NO 981
<211> LENGTH: 23
<212> TYPE: DNA
<213> ORGANISM: Homo sapiens

<400> SEQUENCE: 981
atccacacag aagttagggc tgc                                                23

<210> SEQ ID NO 982
<211> LENGTH: 23
<212> TYPE: DNA
<213> ORGANISM: Homo sapiens

<400> SEQUENCE: 982
aggaagagca gcaccaggca cct                                                23

<210> SEQ ID NO 983
<211> LENGTH: 24
<212> TYPE: DNA
<213> ORGANISM: Homo sapiens

<400> SEQUENCE: 983
ccacatttct cacttcaggt aagc                                               24

<210> SEQ ID NO 984
<211> LENGTH: 26
<212> TYPE: DNA
<213> ORGANISM: Homo sapiens

<400> SEQUENCE: 984
gatttccctc tgtcctgcct caatgc                                             26

<210> SEQ ID NO 985
<211> LENGTH: 23
<212> TYPE: DNA
<213> ORGANISM: Homo sapiens

<400> SEQUENCE: 985
caagcggaga gagacgacac tgc                                                23

<210> SEQ ID NO 986
<211> LENGTH: 26
<212> TYPE: DNA
<213> ORGANISM: Homo sapiens

<400> SEQUENCE: 986
ctttccgcac cctctgaact tttggg                                             26

<210> SEQ ID NO 987

-continued

```
<211> LENGTH: 26
<212> TYPE: DNA
<213> ORGANISM: Homo sapiens

<400> SEQUENCE: 987
gagcgaaaga acggatgaag catttt                                          26

<210> SEQ ID NO 988
<211> LENGTH: 24
<212> TYPE: DNA
<213> ORGANISM: Homo sapiens

<400> SEQUENCE: 988
caggaccatc aagataaatg aata                                            24

<210> SEQ ID NO 989
<211> LENGTH: 23
<212> TYPE: DNA
<213> ORGANISM: Homo sapiens

<400> SEQUENCE: 989
tggaggaagg gagccaggac ccc                                             23

<210> SEQ ID NO 990
<211> LENGTH: 23
<212> TYPE: DNA
<213> ORGANISM: Homo sapiens

<400> SEQUENCE: 990
gcaccactgg cagagtttac ggt                                             23

<210> SEQ ID NO 991
<211> LENGTH: 24
<212> TYPE: DNA
<213> ORGANISM: Homo sapiens

<400> SEQUENCE: 991
ctggagaaaa ggagtatgga gaat                                            24

<210> SEQ ID NO 992
<211> LENGTH: 24
<212> TYPE: DNA
<213> ORGANISM: Homo sapiens

<400> SEQUENCE: 992
aaggctttta tgtgaacaga gata                                            24

<210> SEQ ID NO 993
<211> LENGTH: 25
<212> TYPE: DNA
<213> ORGANISM: Homo sapiens

<400> SEQUENCE: 993
gaaataaagt caatcttcct gaaaa                                           25

<210> SEQ ID NO 994
<211> LENGTH: 23
<212> TYPE: DNA
<213> ORGANISM: Homo sapiens

<400> SEQUENCE: 994
cactgactac acggaagatg gcg                                             23
```

-continued

```
<210> SEQ ID NO 995
<211> LENGTH: 26
<212> TYPE: DNA
<213> ORGANISM: Homo sapiens

<400> SEQUENCE: 995
ttttgaccag cagatagtgt cgtgtc                                        26

<210> SEQ ID NO 996
<211> LENGTH: 23
<212> TYPE: DNA
<213> ORGANISM: Homo sapiens

<400> SEQUENCE: 996
gggcactctg gattgagaca gta                                           23

<210> SEQ ID NO 997
<211> LENGTH: 23
<212> TYPE: DNA
<213> ORGANISM: Homo sapiens

<400> SEQUENCE: 997
gcttcccaga acccaaatct ccc                                           23

<210> SEQ ID NO 998
<211> LENGTH: 23
<212> TYPE: DNA
<213> ORGANISM: Homo sapiens

<400> SEQUENCE: 998
cttccgatgg acgaatctca ggc                                           23

<210> SEQ ID NO 999
<211> LENGTH: 26
<212> TYPE: DNA
<213> ORGANISM: Homo sapiens

<400> SEQUENCE: 999
ccctccaatg aaagtagtct gcctgc                                        26

<210> SEQ ID NO 1000
<211> LENGTH: 23
<212> TYPE: DNA
<213> ORGANISM: Homo sapiens

<400> SEQUENCE: 1000
tgggcacaaa gggtgaagtg gtg                                           23

<210> SEQ ID NO 1001
<211> LENGTH: 24
<212> TYPE: DNA
<213> ORGANISM: Homo sapiens

<400> SEQUENCE: 1001
ggaagaccag agaacagaac tgat                                          24

<210> SEQ ID NO 1002
<211> LENGTH: 24
<212> TYPE: DNA
<213> ORGANISM: Homo sapiens

<400> SEQUENCE: 1002
ggaagaccag agaacagaac tgat                                          24
```

-continued

```
<210> SEQ ID NO 1003
<211> LENGTH: 24
<212> TYPE: DNA
<213> ORGANISM: Homo sapiens

<400> SEQUENCE: 1003
ggaagaccag agaacagaac tgat                                          24

<210> SEQ ID NO 1004
<211> LENGTH: 24
<212> TYPE: DNA
<213> ORGANISM: Homo sapiens

<400> SEQUENCE: 1004
ggaagaccag agaacagaac tgat                                          24

<210> SEQ ID NO 1005
<211> LENGTH: 24
<212> TYPE: DNA
<213> ORGANISM: Homo sapiens

<400> SEQUENCE: 1005
ggaagaccag agaacagaac tgat                                          24

<210> SEQ ID NO 1006
<211> LENGTH: 26
<212> TYPE: DNA
<213> ORGANISM: Homo sapiens

<400> SEQUENCE: 1006
gacctcaaca gaaagtcctc aacagg                                        26

<210> SEQ ID NO 1007
<211> LENGTH: 24
<212> TYPE: DNA
<213> ORGANISM: Homo sapiens

<400> SEQUENCE: 1007
cctcaacaga aagtcctcaa cagg                                          24

<210> SEQ ID NO 1008
<211> LENGTH: 23
<212> TYPE: DNA
<213> ORGANISM: Homo sapiens

<400> SEQUENCE: 1008
ggtcctgctc tatctttccc ctc                                           23

<210> SEQ ID NO 1009
<211> LENGTH: 23
<212> TYPE: DNA
<213> ORGANISM: Homo sapiens

<400> SEQUENCE: 1009
agggcttcag caggcagagg gat                                           23

<210> SEQ ID NO 1010
<211> LENGTH: 26
<212> TYPE: DNA
<213> ORGANISM: Homo sapiens

<400> SEQUENCE: 1010
ggtaacttga ataagccac agaggg                                         26
```

-continued

<210> SEQ ID NO 1011
<211> LENGTH: 24
<212> TYPE: DNA
<213> ORGANISM: Homo sapiens

<400> SEQUENCE: 1011
ttgaagttta ccaggagagg aaaa                                          24

<210> SEQ ID NO 1012
<211> LENGTH: 26
<212> TYPE: DNA
<213> ORGANISM: Homo sapiens

<400> SEQUENCE: 1012
ggagatgaaa gacaatggat gagata                                        26

<210> SEQ ID NO 1013
<211> LENGTH: 23
<212> TYPE: DNA
<213> ORGANISM: Homo sapiens

<400> SEQUENCE: 1013
cctgcctccc ctcacaacac aca                                           23

<210> SEQ ID NO 1014
<211> LENGTH: 23
<212> TYPE: DNA
<213> ORGANISM: Homo sapiens

<400> SEQUENCE: 1014
ctcgccctgt gtagcacctc tct                                           23

<210> SEQ ID NO 1015
<211> LENGTH: 24
<212> TYPE: DNA
<213> ORGANISM: Homo sapiens

<400> SEQUENCE: 1015
tccaacattg ctttactctt atga                                          24

<210> SEQ ID NO 1016
<211> LENGTH: 23
<212> TYPE: DNA
<213> ORGANISM: Homo sapiens

<400> SEQUENCE: 1016
gccgcttcca cccaggacag taa                                           23

<210> SEQ ID NO 1017
<211> LENGTH: 26
<212> TYPE: DNA
<213> ORGANISM: Homo sapiens

<400> SEQUENCE: 1017
ctgacactga gcacagggtt tggaag                                        26

<210> SEQ ID NO 1018
<211> LENGTH: 26
<212> TYPE: DNA
<213> ORGANISM: Homo sapiens

<400> SEQUENCE: 1018

-continued

```
gagagaagcc accaagataa gtccac                                          26

<210> SEQ ID NO 1019
<211> LENGTH: 26
<212> TYPE: DNA
<213> ORGANISM: Homo sapiens

<400> SEQUENCE: 1019
ctttgtttac ctggcatctt gagtca                                         26

<210> SEQ ID NO 1020
<211> LENGTH: 60
<212> TYPE: DNA
<213> ORGANISM: Homo sapiens

<400> SEQUENCE: 1020
ttccttcatc atttgttatt tcctctgttc gaatagggct gaaccaatgg ccatacacac    60

<210> SEQ ID NO 1021
<211> LENGTH: 60
<212> TYPE: DNA
<213> ORGANISM: Homo sapiens

<400> SEQUENCE: 1021
gaggcccatt gcaggtactt gggctgcatc gattatccca ctacacagga tttatataag    60

<210> SEQ ID NO 1022
<211> LENGTH: 60
<212> TYPE: DNA
<213> ORGANISM: Homo sapiens

<400> SEQUENCE: 1022
ccagactgaa ttttgtacag agtacacctc gaagtaatct gactttaaaa tggttctttt    60

<210> SEQ ID NO 1023
<211> LENGTH: 60
<212> TYPE: DNA
<213> ORGANISM: Homo sapiens

<400> SEQUENCE: 1023
tggtaagtgt attatataag aaaaaaactc gatcctctaa tcctgaatac caggttgggc    60

<210> SEQ ID NO 1024
<211> LENGTH: 60
<212> TYPE: DNA
<213> ORGANISM: Homo sapiens

<400> SEQUENCE: 1024
ttgcattcat tcttttgcag aaacatactc gatcctctaa tcctgaatac caggttgggc    60

<210> SEQ ID NO 1025
<211> LENGTH: 60
<212> TYPE: DNA
<213> ORGANISM: Homo sapiens

<400> SEQUENCE: 1025
gcccaacctg gtattcagga ttagaggatc gagaagccag gcatgaattc tggtgtttgc    60

<210> SEQ ID NO 1026
<211> LENGTH: 60
<212> TYPE: DNA
<213> ORGANISM: Homo sapiens

<400> SEQUENCE: 1026
```

-continued

--- ctcgtcagta ctctcagtgt ttcctcattc gatcactttg gacatttttaa cagcactaag        60

<210> SEQ ID NO 1027
<211> LENGTH: 60
<212> TYPE: DNA
<213> ORGANISM: Homo sapiens

<400> SEQUENCE: 1027
tcttgcccga aggcagagag ctcagaactc gaagtgagca ggatttattg aataacagaa        60

<210> SEQ ID NO 1028
<211> LENGTH: 60
<212> TYPE: DNA
<213> ORGANISM: Homo sapiens

<400> SEQUENCE: 1028
tcttgcccga aggcagagag ctcagaactc gaacactctt gttctgcttc ctcatcactt        60

<210> SEQ ID NO 1029
<211> LENGTH: 60
<212> TYPE: DNA
<213> ORGANISM: Homo sapiens

<400> SEQUENCE: 1029
ttgcttgggt ttatgatttt gtgcggggtc gagttctgag ctctctgcct tcgggcaaga        60

<210> SEQ ID NO 1030
<211> LENGTH: 60
<212> TYPE: DNA
<213> ORGANISM: Homo sapiens

<400> SEQUENCE: 1030
tcttgcccga aggcagagag ctcagaactc gagctgctgc agtcattttg tcaccataca        60

<210> SEQ ID NO 1031
<211> LENGTH: 60
<212> TYPE: DNA
<213> ORGANISM: Homo sapiens

<400> SEQUENCE: 1031
ctgtctagta tcttaaaatt gacatggatc gagttctgag ctctctgcct tcgggcaaga        60

<210> SEQ ID NO 1032
<211> LENGTH: 60
<212> TYPE: DNA
<213> ORGANISM: Homo sapiens

<400> SEQUENCE: 1032
agtctatcca attacagtaa tttaagcttc gagagcctgt ggtctaagaa agagtgagag        60

<210> SEQ ID NO 1033
<211> LENGTH: 60
<212> TYPE: DNA
<213> ORGANISM: Homo sapiens

<400> SEQUENCE: 1033
ccttagtacc tgcttagtac ccgctttgtc gaagcaaaag caattaccac ccccagcttt        60

<210> SEQ ID NO 1034
<211> LENGTH: 60
<212> TYPE: DNA
<213> ORGANISM: Homo sapiens -continued

```
<400> SEQUENCE: 1034
taaaaacaca tttacagtgc cactgtactc gaagcaaaag caattaccac ccccagcttt        60

<210> SEQ ID NO 1035
<211> LENGTH: 60
<212> TYPE: DNA
<213> ORGANISM: Homo sapiens

<400> SEQUENCE: 1035
gacctccctt acagtacctg cagacttgtc gatgaactcc cactccagtg gtgagaaacc        60

<210> SEQ ID NO 1036
<211> LENGTH: 60
<212> TYPE: DNA
<213> ORGANISM: Homo sapiens

<400> SEQUENCE: 1036
gacctccctt acagtacctg cagacttgtc gagttcccat atgggcagta tgtagggcac        60

<210> SEQ ID NO 1037
<211> LENGTH: 60
<212> TYPE: DNA
<213> ORGANISM: Homo sapiens

<400> SEQUENCE: 1037
taattctctg tagtgaatcc cttcctgatc gagggggcat cacagagtca aaggcagcga        60

<210> SEQ ID NO 1038
<211> LENGTH: 60
<212> TYPE: DNA
<213> ORGANISM: Homo sapiens

<400> SEQUENCE: 1038
ggaatataat ctaacaccgt gtaaccattc gactccaaat aaactgaata cagaaagttt        60

<210> SEQ ID NO 1039
<211> LENGTH: 60
<212> TYPE: DNA
<213> ORGANISM: Homo sapiens

<400> SEQUENCE: 1039
ggaatataat ctaacaccgt gtaaccattc gaaaattttg aaacaattcc tctgccattt        60

<210> SEQ ID NO 1040
<211> LENGTH: 60
<212> TYPE: DNA
<213> ORGANISM: Homo sapiens

<400> SEQUENCE: 1040
ggtactagat gacgtagtcc gataagattc gatttcccca tctgtaaaat gttttctttg        60

<210> SEQ ID NO 1041
<211> LENGTH: 60
<212> TYPE: DNA
<213> ORGANISM: Homo sapiens

<400> SEQUENCE: 1041
ggtactagat gacgtagtcc gataagattc gacacaaatc cccctgctac tgtttaattc        60

<210> SEQ ID NO 1042
<211> LENGTH: 60
<212> TYPE: DNA
<213> ORGANISM: Homo sapiens
```

<400> SEQUENCE: 1042
ggtactagat gacgtagtcc gataagattc gaaaagttct gccagtcctc cacttacagc     60

<210> SEQ ID NO 1043
<211> LENGTH: 60
<212> TYPE: DNA
<213> ORGANISM: Homo sapiens

<400> SEQUENCE: 1043
ggtactagat gacgtagtcc gataagattc gaaacccgaa ataaaattct taccctggct     60

<210> SEQ ID NO 1044
<211> LENGTH: 60
<212> TYPE: DNA
<213> ORGANISM: Homo sapiens

<400> SEQUENCE: 1044
ggtactagat gacgtagtcc gataagattc gagttccaat tccttagcct ggtaaccaag     60

<210> SEQ ID NO 1045
<211> LENGTH: 60
<212> TYPE: DNA
<213> ORGANISM: Homo sapiens

<400> SEQUENCE: 1045
ggtactagat gacgtagtcc gataagattc gacaacattc tggtgtgact gtgaatgagc     60

<210> SEQ ID NO 1046
<211> LENGTH: 60
<212> TYPE: DNA
<213> ORGANISM: Homo sapiens

<400> SEQUENCE: 1046
ggtactagat gacgtagtcc gataagattc gactctgcag agttctcact actccgcttg     60

<210> SEQ ID NO 1047
<211> LENGTH: 60
<212> TYPE: DNA
<213> ORGANISM: Homo sapiens

<400> SEQUENCE: 1047
ggtactagat gacgtagtcc gataagattc gattggtttg gctgttcttg atccgtttac     60

<210> SEQ ID NO 1048
<211> LENGTH: 60
<212> TYPE: DNA
<213> ORGANISM: Homo sapiens

<400> SEQUENCE: 1048
aaactgcctc ataggtttct tgtgaggatc gaaaaagatg cttgatatga tttcactctt     60

<210> SEQ ID NO 1049
<211> LENGTH: 60
<212> TYPE: DNA
<213> ORGANISM: Homo sapiens

<400> SEQUENCE: 1049
aaactgcctc ataggtttct tgtgaggatc gatgatgtta gtggttgtag tggctctttg     60

<210> SEQ ID NO 1050
<211> LENGTH: 60
<212> TYPE: DNA

-continued

<213> ORGANISM: Homo sapiens

<400> SEQUENCE: 1050
gcaatgtgct atactgcaga ttctaaactc gatgatgtta gtggttgtag tggctctttg      60

<210> SEQ ID NO 1051
<211> LENGTH: 60
<212> TYPE: DNA
<213> ORGANISM: Homo sapiens

<400> SEQUENCE: 1051
ctagagctct ggaggccctg ctgacggctc gatgatgtta gtggttgtag tggctctttg      60

<210> SEQ ID NO 1052
<211> LENGTH: 60
<212> TYPE: DNA
<213> ORGANISM: Homo sapiens

<400> SEQUENCE: 1052
aagactaatt ctgggctgtg ccaattggtc gatgatgtta gtggttgtag tggctctttg      60

<210> SEQ ID NO 1053
<211> LENGTH: 60
<212> TYPE: DNA
<213> ORGANISM: Homo sapiens

<400> SEQUENCE: 1053
caaagagcca ctacaaccac taacatcatc gaatttttgg aaggcttgtt atttggaaga      60

<210> SEQ ID NO 1054
<211> LENGTH: 60
<212> TYPE: DNA
<213> ORGANISM: Homo sapiens

<400> SEQUENCE: 1054
caaagagcca ctacaaccac taacatcatc gaaaagttgc aatcatgctt aatacataat      60

<210> SEQ ID NO 1055
<211> LENGTH: 60
<212> TYPE: DNA
<213> ORGANISM: Homo sapiens

<400> SEQUENCE: 1055
caagagaaga caacatttat ctgttatgtc gatgatgtta gtggttgtag tggctctttg      60

<210> SEQ ID NO 1056
<211> LENGTH: 60
<212> TYPE: DNA
<213> ORGANISM: Homo sapiens

<400> SEQUENCE: 1056
caaagagcca ctacaaccac taacatcatc gagagaagca ttttcctttg tttctatctc      60

<210> SEQ ID NO 1057
<211> LENGTH: 60
<212> TYPE: DNA
<213> ORGANISM: Homo sapiens

<400> SEQUENCE: 1057
caaagagcca ctacaaccac taacatcatc gatgcttctg tgggataaaa agtgtagttc      60

<210> SEQ ID NO 1058
<211> LENGTH: 60

```
<212> TYPE: DNA
<213> ORGANISM: Homo sapiens

<400> SEQUENCE: 1058
caaagagcca ctacaaccac taacatcatc gataggaggc aactattaag aaagggcttt        60

<210> SEQ ID NO 1059
<211> LENGTH: 60
<212> TYPE: DNA
<213> ORGANISM: Homo sapiens

<400> SEQUENCE: 1059
tgatacttta aaaattttt ttaaatgatc gatgatgtta gtggttgtag tggctctttg        60

<210> SEQ ID NO 1060
<211> LENGTH: 60
<212> TYPE: DNA
<213> ORGANISM: Homo sapiens

<400> SEQUENCE: 1060
caaagagcca ctacaaccac taacatcatc gaagtgttta gtgagagaat cttttttctt        60

<210> SEQ ID NO 1061
<211> LENGTH: 60
<212> TYPE: DNA
<213> ORGANISM: Homo sapiens

<400> SEQUENCE: 1061
caaagagcca ctacaaccac taacatcatc gatgtggaga atagcccatc ttgctcattt        60

<210> SEQ ID NO 1062
<211> LENGTH: 60
<212> TYPE: DNA
<213> ORGANISM: Homo sapiens

<400> SEQUENCE: 1062
caaagagcca ctacaaccac taacatcatc gaaggtagag agagaatgct ctggggatga        60

<210> SEQ ID NO 1063
<211> LENGTH: 60
<212> TYPE: DNA
<213> ORGANISM: Homo sapiens

<400> SEQUENCE: 1063
ttttagagcc tgccctctgt actccaaatc gatgatgtta gtggttgtag tggctctttg        60

<210> SEQ ID NO 1064
<211> LENGTH: 60
<212> TYPE: DNA
<213> ORGANISM: Homo sapiens

<400> SEQUENCE: 1064
caaagagcca ctacaaccac taacatcatc gacaaaaga aaaatcagcc tcataatgca        60

<210> SEQ ID NO 1065
<211> LENGTH: 60
<212> TYPE: DNA
<213> ORGANISM: Homo sapiens

<400> SEQUENCE: 1065
tgcatttgtc aaaattaaga aattaacatc gatgatgtta gtggttgtag tggctctttg        60

<210> SEQ ID NO 1066
```

-continued

```
<211> LENGTH: 60
<212> TYPE: DNA
<213> ORGANISM: Homo sapiens

<400> SEQUENCE: 1066
caaagagcca ctacaaccac taacatcatc gaatgccccc atttgaaaag agttataata       60

<210> SEQ ID NO 1067
<211> LENGTH: 60
<212> TYPE: DNA
<213> ORGANISM: Homo sapiens

<400> SEQUENCE: 1067
ttaactatcc caaattccat tctctttctc gatgatgtta gtggttgtag tggctctttg       60

<210> SEQ ID NO 1068
<211> LENGTH: 60
<212> TYPE: DNA
<213> ORGANISM: Homo sapiens

<400> SEQUENCE: 1068
caaagagcca ctacaaccac taacatcatc gatttcaaag cacttgtcat acactctttc       60

<210> SEQ ID NO 1069
<211> LENGTH: 60
<212> TYPE: DNA
<213> ORGANISM: Homo sapiens

<400> SEQUENCE: 1069
caaagagcca ctacaaccac taacatcatc gaggaaatga gtatcctcaa gagtctacac       60

<210> SEQ ID NO 1070
<211> LENGTH: 60
<212> TYPE: DNA
<213> ORGANISM: Homo sapiens

<400> SEQUENCE: 1070
gctccaagac aggacatgga ggtgttcatc gatgatgtta gtggttgtag tggctctttg       60

<210> SEQ ID NO 1071
<211> LENGTH: 60
<212> TYPE: DNA
<213> ORGANISM: Homo sapiens

<400> SEQUENCE: 1071
caaagagcca ctacaaccac taacatcatc gaaaatttcc gagacttcgt tggctttgtt       60

<210> SEQ ID NO 1072
<211> LENGTH: 60
<212> TYPE: DNA
<213> ORGANISM: Homo sapiens

<400> SEQUENCE: 1072
caaagagcca ctacaaccac taacatcatc gataaatctg ttaaaaatga gcaaagatca       60

<210> SEQ ID NO 1073
<211> LENGTH: 60
<212> TYPE: DNA
<213> ORGANISM: Homo sapiens

<400> SEQUENCE: 1073
cttgacaagt tcaatctaaa caaatatatc gatgatgtta gtggttgtag tggctctttg       60
```

```
<210> SEQ ID NO 1074
<211> LENGTH: 60
<212> TYPE: DNA
<213> ORGANISM: Homo sapiens

<400> SEQUENCE: 1074
caaagagcca ctacaaccac taacatcatc gattttaaag agaaacatgg tatttcaccc       60

<210> SEQ ID NO 1075
<211> LENGTH: 60
<212> TYPE: DNA
<213> ORGANISM: Homo sapiens

<400> SEQUENCE: 1075
caaagagcca ctacaaccac taacatcatc gaatcagagc ctttgccaga atctgacaga       60

<210> SEQ ID NO 1076
<211> LENGTH: 60
<212> TYPE: DNA
<213> ORGANISM: Homo sapiens

<400> SEQUENCE: 1076
gtcttcacat tgcttccaac agtagtcgtc gatgatgtta gtggttgtag tggctctttg       60

<210> SEQ ID NO 1077
<211> LENGTH: 60
<212> TYPE: DNA
<213> ORGANISM: Homo sapiens

<400> SEQUENCE: 1077
caaagagcca ctacaaccac taacatcatc gaccccacaa ggcttagcag ggacaaggtt       60

<210> SEQ ID NO 1078
<211> LENGTH: 60
<212> TYPE: DNA
<213> ORGANISM: Homo sapiens

<400> SEQUENCE: 1078
cccctctttg aactcttcgt tggaagtttc gatgatgtta gtggttgtag tggctctttg       60

<210> SEQ ID NO 1079
<211> LENGTH: 60
<212> TYPE: DNA
<213> ORGANISM: Homo sapiens

<400> SEQUENCE: 1079
agagaatagt gtgagaaatg gtcatctttc gaggaatgag atggtcggta catgagaaca       60

<210> SEQ ID NO 1080
<211> LENGTH: 60
<212> TYPE: DNA
<213> ORGANISM: Homo sapiens

<400> SEQUENCE: 1080
tgttctcatg taccgaccat ctcattcctc gagtgaggct gttttatttg cttggtgcac       60

<210> SEQ ID NO 1081
<211> LENGTH: 60
<212> TYPE: DNA
<213> ORGANISM: Homo sapiens

<400> SEQUENCE: 1081
gcgccatgtt aaccgtcaaa cgggtacctc gatgctggta gataggggaa tggttcctgg       60
```

-continued

<210> SEQ ID NO 1082
<211> LENGTH: 60
<212> TYPE: DNA
<213> ORGANISM: Homo sapiens

<400> SEQUENCE: 1082
ctatgtaatc acagcttgat gttccaattc gatgctggta gatagggggaa tggttcctgg     60

<210> SEQ ID NO 1083
<211> LENGTH: 60
<212> TYPE: DNA
<213> ORGANISM: Homo sapiens

<400> SEQUENCE: 1083
aactacatta attaagaact tctgttcatc gatttcagtt ttgaaactgt aagagtaatt     60

<210> SEQ ID NO 1084
<211> LENGTH: 24
<212> TYPE: DNA
<213> ORGANISM: Homo sapiens

<400> SEQUENCE: 1084
acttgtaggt gagaaagaaa tagc                                           24

<210> SEQ ID NO 1085
<211> LENGTH: 26
<212> TYPE: DNA
<213> ORGANISM: Homo sapiens

<400> SEQUENCE: 1085
cctgtctcac catcttcttt tgcctg                                         26

<210> SEQ ID NO 1086
<211> LENGTH: 26
<212> TYPE: DNA
<213> ORGANISM: Homo sapiens

<400> SEQUENCE: 1086
ccaactgaac aagtgaacgc tgccag                                         26

<210> SEQ ID NO 1087
<211> LENGTH: 24
<212> TYPE: DNA
<213> ORGANISM: Homo sapiens

<400> SEQUENCE: 1087
aaatcggtga agaaatgtag aaaa                                           24

<210> SEQ ID NO 1088
<211> LENGTH: 23
<212> TYPE: DNA
<213> ORGANISM: Homo sapiens

<400> SEQUENCE: 1088
atttcccctt gtaggctggt ggc                                            23

<210> SEQ ID NO 1089
<211> LENGTH: 23
<212> TYPE: DNA
<213> ORGANISM: Homo sapiens

<400> SEQUENCE: 1089
tatgccaggg aggtagagca gcc                                            23

-continued

```
<210> SEQ ID NO 1090
<211> LENGTH: 26
<212> TYPE: DNA
<213> ORGANISM: Homo sapiens

<400> SEQUENCE: 1090
gaccttgttt tgttcccgtg acagca                                          26

<210> SEQ ID NO 1091
<211> LENGTH: 26
<212> TYPE: DNA
<213> ORGANISM: Homo sapiens

<400> SEQUENCE: 1091
gcaaagagca atgagatgtc tatgat                                          26

<210> SEQ ID NO 1092
<211> LENGTH: 23
<212> TYPE: DNA
<213> ORGANISM: Homo sapiens

<400> SEQUENCE: 1092
agcctctccc tcccagcaaa gcg                                             23

<210> SEQ ID NO 1093
<211> LENGTH: 23
<212> TYPE: DNA
<213> ORGANISM: Homo sapiens

<400> SEQUENCE: 1093
agcctctccc tcccagcaaa gcg                                             23

<210> SEQ ID NO 1094
<211> LENGTH: 23
<212> TYPE: DNA
<213> ORGANISM: Homo sapiens

<400> SEQUENCE: 1094
agcctctccc tcccagcaaa gcg                                             23

<210> SEQ ID NO 1095
<211> LENGTH: 24
<212> TYPE: DNA
<213> ORGANISM: Homo sapiens

<400> SEQUENCE: 1095
tatcagtcag caactcagag gaac                                            24

<210> SEQ ID NO 1096
<211> LENGTH: 23
<212> TYPE: DNA
<213> ORGANISM: Homo sapiens

<400> SEQUENCE: 1096
agccagagcc ttgctgtagt cag                                             23

<210> SEQ ID NO 1097
<211> LENGTH: 23
<212> TYPE: DNA
<213> ORGANISM: Homo sapiens

<400> SEQUENCE: 1097
```

-continued

```
tgtcctccectt ttgcccctcc cct                                    23

<210> SEQ ID NO 1098
<211> LENGTH: 23
<212> TYPE: DNA
<213> ORGANISM: Homo sapiens

<400> SEQUENCE: 1098
gccctctgct tagtaacccc tcc                                      23

<210> SEQ ID NO 1099
<211> LENGTH: 23
<212> TYPE: DNA
<213> ORGANISM: Homo sapiens

<400> SEQUENCE: 1099
ccaaaacccc acccacgctg agc                                      23

<210> SEQ ID NO 1100
<211> LENGTH: 23
<212> TYPE: DNA
<213> ORGANISM: Homo sapiens

<400> SEQUENCE: 1100
tccaaaaccc cacccacgct gag                                      23

<210> SEQ ID NO 1101
<211> LENGTH: 23
<212> TYPE: DNA
<213> ORGANISM: Homo sapiens

<400> SEQUENCE: 1101
gaggtcacag ttcccttgtt ggc                                      23

<210> SEQ ID NO 1102
<211> LENGTH: 24
<212> TYPE: DNA
<213> ORGANISM: Homo sapiens

<400> SEQUENCE: 1102
ggaggagtaa atgaatgttt gttt                                     24

<210> SEQ ID NO 1103
<211> LENGTH: 26
<212> TYPE: DNA
<213> ORGANISM: Homo sapiens

<400> SEQUENCE: 1103
cgtaatgaag cagactttg gtcagg                                    26

<210> SEQ ID NO 1104
<211> LENGTH: 26
<212> TYPE: DNA
<213> ORGANISM: Homo sapiens

<400> SEQUENCE: 1104
ccagcagatg acagcagcaa taaggg                                   26

<210> SEQ ID NO 1105
<211> LENGTH: 23
<212> TYPE: DNA
<213> ORGANISM: Homo sapiens

<400> SEQUENCE: 1105
```

```
cgccagcaga tgacagcagc aat                                           23

<210> SEQ ID NO 1106
<211> LENGTH: 23
<212> TYPE: DNA
<213> ORGANISM: Homo sapiens

<400> SEQUENCE: 1106
cgccagcaga tgacagcagc aat                                           23

<210> SEQ ID NO 1107
<211> LENGTH: 23
<212> TYPE: DNA
<213> ORGANISM: Homo sapiens

<400> SEQUENCE: 1107
cgccagcaga tgacagcagc aat                                           23

<210> SEQ ID NO 1108
<211> LENGTH: 23
<212> TYPE: DNA
<213> ORGANISM: Homo sapiens

<400> SEQUENCE: 1108
cgccagcaga tgacagcagc aat                                           23

<210> SEQ ID NO 1109
<211> LENGTH: 23
<212> TYPE: DNA
<213> ORGANISM: Homo sapiens

<400> SEQUENCE: 1109
gcacctgaca gcagcacaga ctg                                           23

<210> SEQ ID NO 1110
<211> LENGTH: 23
<212> TYPE: DNA
<213> ORGANISM: Homo sapiens

<400> SEQUENCE: 1110
cgccagcaga tgacagcagc aat                                           23

<210> SEQ ID NO 1111
<211> LENGTH: 23
<212> TYPE: DNA
<213> ORGANISM: Homo sapiens

<400> SEQUENCE: 1111
gcacctgaca gcagcacaga ctg                                           23

<210> SEQ ID NO 1112
<211> LENGTH: 23
<212> TYPE: DNA
<213> ORGANISM: Homo sapiens

<400> SEQUENCE: 1112
ggatgttcca gcctgagttc ctc                                           23

<210> SEQ ID NO 1113
<211> LENGTH: 23
<212> TYPE: DNA
<213> ORGANISM: Homo sapiens
```

-continued

<400> SEQUENCE: 1113
gctcgccgta gcattcctca cac                                                        23

<210> SEQ ID NO 1114
<211> LENGTH: 26
<212> TYPE: DNA
<213> ORGANISM: Homo sapiens

<400> SEQUENCE: 1114
caacctattg ccgatgccct caaact                                                     26

<210> SEQ ID NO 1115
<211> LENGTH: 26
<212> TYPE: DNA
<213> ORGANISM: Homo sapiens

<400> SEQUENCE: 1115
cctactacaa cctattgccg atgccc                                                     26

<210> SEQ ID NO 1116
<211> LENGTH: 26
<212> TYPE: DNA
<213> ORGANISM: Homo sapiens

<400> SEQUENCE: 1116
gccgatgccc tcaaactatt tatcaa                                                     26

<210> SEQ ID NO 1117
<211> LENGTH: 23
<212> TYPE: DNA
<213> ORGANISM: Homo sapiens

<400> SEQUENCE: 1117
gcaaaggacc caacatcgta ggc                                                        23

<210> SEQ ID NO 1118
<211> LENGTH: 23
<212> TYPE: DNA
<213> ORGANISM: Homo sapiens

<400> SEQUENCE: 1118
gcaaaggacc caacatcgta ggc                                                        23

<210> SEQ ID NO 1119
<211> LENGTH: 23
<212> TYPE: DNA
<213> ORGANISM: Homo sapiens

<400> SEQUENCE: 1119
gctcgccgta gcattcctca cac                                                        23

<210> SEQ ID NO 1120
<211> LENGTH: 26
<212> TYPE: DNA
<213> ORGANISM: Homo sapiens

<400> SEQUENCE: 1120
tgtgattgat aggactgctt tgaggc                                                     26

<210> SEQ ID NO 1121
<211> LENGTH: 26
<212> TYPE: DNA
<213> ORGANISM: Homo sapiens -continued

```
<400> SEQUENCE: 1121
ttgtgtttga gtctggcttg tctaat                                          26

<210> SEQ ID NO 1122
<211> LENGTH: 23
<212> TYPE: DNA
<213> ORGANISM: Homo sapiens

<400> SEQUENCE: 1122
gcaaaggacc caacatcgta ggc                                             23

<210> SEQ ID NO 1123
<211> LENGTH: 26
<212> TYPE: DNA
<213> ORGANISM: Homo sapiens

<400> SEQUENCE: 1123
caacctattg ccgatgccct caaact                                          26

<210> SEQ ID NO 1124
<211> LENGTH: 24
<212> TYPE: DNA
<213> ORGANISM: Homo sapiens

<400> SEQUENCE: 1124
ctacaaccta ttgccgatgc cctc                                            24

<210> SEQ ID NO 1125
<211> LENGTH: 23
<212> TYPE: DNA
<213> ORGANISM: Homo sapiens

<400> SEQUENCE: 1125
ggcttagggc attggttagg agc                                             23

<210> SEQ ID NO 1126
<211> LENGTH: 25
<212> TYPE: DNA
<213> ORGANISM: Homo sapiens

<400> SEQUENCE: 1126
tctctctgtt tctcagttct atcgc                                           25

<210> SEQ ID NO 1127
<211> LENGTH: 24
<212> TYPE: DNA
<213> ORGANISM: Homo sapiens

<400> SEQUENCE: 1127
atcattgaag ttagaaaagg tctt                                            24

<210> SEQ ID NO 1128
<211> LENGTH: 23
<212> TYPE: DNA
<213> ORGANISM: Homo sapiens

<400> SEQUENCE: 1128
gcaaaggaat gccaactgcc agc                                             23

<210> SEQ ID NO 1129
<211> LENGTH: 23
<212> TYPE: DNA
```

<213> ORGANISM: Homo sapiens

<400> SEQUENCE: 1129
cctttaccca actcccactg agg                                          23

<210> SEQ ID NO 1130
<211> LENGTH: 26
<212> TYPE: DNA
<213> ORGANISM: Homo sapiens

<400> SEQUENCE: 1130
cctactacaa cctattgccg atgccc                                       26

<210> SEQ ID NO 1131
<211> LENGTH: 23
<212> TYPE: DNA
<213> ORGANISM: Homo sapiens

<400> SEQUENCE: 1131
gcaaaggacc caacatcgta ggc                                          23

<210> SEQ ID NO 1132
<211> LENGTH: 26
<212> TYPE: DNA
<213> ORGANISM: Homo sapiens

<400> SEQUENCE: 1132
ctgatttgtg ggcatcgtct acagtt                                       26

<210> SEQ ID NO 1133
<211> LENGTH: 23
<212> TYPE: DNA
<213> ORGANISM: Homo sapiens

<400> SEQUENCE: 1133
gcaaaggacc caacatcgta ggc                                          23

<210> SEQ ID NO 1134
<211> LENGTH: 23
<212> TYPE: DNA
<213> ORGANISM: Homo sapiens

<400> SEQUENCE: 1134
cgagggagag agtaaagcca acc                                          23

<210> SEQ ID NO 1135
<211> LENGTH: 26
<212> TYPE: DNA
<213> ORGANISM: Homo sapiens

<400> SEQUENCE: 1135
cctactacaa cctattgccg atgccc                                       26

<210> SEQ ID NO 1136
<211> LENGTH: 26
<212> TYPE: DNA
<213> ORGANISM: Homo sapiens

<400> SEQUENCE: 1136
tcaggtagca ctcttatctt tccaga                                       26

<210> SEQ ID NO 1137
<211> LENGTH: 24

-continued

```
<212> TYPE: DNA
<213> ORGANISM: Homo sapiens

<400> SEQUENCE: 1137
tagggagttg gcactggcac tttt                                        24

<210> SEQ ID NO 1138
<211> LENGTH: 23
<212> TYPE: DNA
<213> ORGANISM: Homo sapiens

<400> SEQUENCE: 1138
gctcgccgta gcattcctca cac                                         23

<210> SEQ ID NO 1139
<211> LENGTH: 26
<212> TYPE: DNA
<213> ORGANISM: Homo sapiens

<400> SEQUENCE: 1139
caggaagact ttattatgga atgcgt                                      26

<210> SEQ ID NO 1140
<211> LENGTH: 26
<212> TYPE: DNA
<213> ORGANISM: Homo sapiens

<400> SEQUENCE: 1140
cctactacaa cctattgccg atgccc                                      26

<210> SEQ ID NO 1141
<211> LENGTH: 25
<212> TYPE: DNA
<213> ORGANISM: Homo sapiens

<400> SEQUENCE: 1141
cttgaaacct gacaaagata ccagc                                       25

<210> SEQ ID NO 1142
<211> LENGTH: 24
<212> TYPE: DNA
<213> ORGANISM: Homo sapiens

<400> SEQUENCE: 1142
ttccattcca agattgatga aaat                                        24

<210> SEQ ID NO 1143
<211> LENGTH: 26
<212> TYPE: DNA
<213> ORGANISM: Homo sapiens

<400> SEQUENCE: 1143
gcagacacaa gcaagtaaat agacaa                                      26

<210> SEQ ID NO 1144
<211> LENGTH: 26
<212> TYPE: DNA
<213> ORGANISM: Homo sapiens

<400> SEQUENCE: 1144
cctactacaa cctattgccg atgccc                                      26

<210> SEQ ID NO 1145
```

-continued

```
<211> LENGTH: 28
<212> TYPE: DNA
<213> ORGANISM: Homo sapiens

<400> SEQUENCE: 1145
cacagaatag tctcccaaat agtttatg                                    28

<210> SEQ ID NO 1146
<211> LENGTH: 24
<212> TYPE: DNA
<213> ORGANISM: Homo sapiens

<400> SEQUENCE: 1146
agtgaaggag gagagtcatc tgct                                        24

<210> SEQ ID NO 1147
<211> LENGTH: 26
<212> TYPE: DNA
<213> ORGANISM: Homo sapiens

<400> SEQUENCE: 1147
gagccaaacc ataaagagaa agactg                                      26

<210> SEQ ID NO 1148
<211> LENGTH: 24
<212> TYPE: DNA
<213> ORGANISM: Homo sapiens

<400> SEQUENCE: 1148
tccataaaca ggtgaggaag acac                                        24

<210> SEQ ID NO 1149
<211> LENGTH: 26
<212> TYPE: DNA
<213> ORGANISM: Homo sapiens

<400> SEQUENCE: 1149
ttagtctctt tcttcagatg gctatc                                      26

<210> SEQ ID NO 1150
<211> LENGTH: 26
<212> TYPE: DNA
<213> ORGANISM: Homo sapiens

<400> SEQUENCE: 1150
acaacgagga ctcagatttc tcagag                                      26

<210> SEQ ID NO 1151
<211> LENGTH: 24
<212> TYPE: DNA
<213> ORGANISM: Homo sapiens

<400> SEQUENCE: 1151
gcaagttagt ggttgagatt ggat                                        24

<210> SEQ ID NO 1152
<211> LENGTH: 23
<212> TYPE: DNA
<213> ORGANISM: Homo sapiens

<400> SEQUENCE: 1152
tatgccaggg aggtagagca gcc                                         23
```

-continued

```
<210> SEQ ID NO 1153
<211> LENGTH: 23
<212> TYPE: DNA
<213> ORGANISM: Homo sapiens

<400> SEQUENCE: 1153
gcttgacttg ctctgggagg aga                                          23

<210> SEQ ID NO 1154
<211> LENGTH: 26
<212> TYPE: DNA
<213> ORGANISM: Homo sapiens

<400> SEQUENCE: 1154
ctaataaact cagcgaggca gcagga                                       26

<210> SEQ ID NO 1155
<211> LENGTH: 23
<212> TYPE: DNA
<213> ORGANISM: Homo sapiens

<400> SEQUENCE: 1155
agcctctccc tcccagcaaa gcg                                          23

<210> SEQ ID NO 1156
<211> LENGTH: 26
<212> TYPE: DNA
<213> ORGANISM: Homo sapiens

<400> SEQUENCE: 1156
gcctcagaaa gagttgtagt tattgt                                       26

<210> SEQ ID NO 1157
<211> LENGTH: 26
<212> TYPE: DNA
<213> ORGANISM: Homo sapiens

<400> SEQUENCE: 1157
cagttttgta gagcacctga ttagaa                                       26

<210> SEQ ID NO 1158
<211> LENGTH: 23
<212> TYPE: DNA
<213> ORGANISM: Homo sapiens

<400> SEQUENCE: 1158
gggctctact cagtgattgc ctg                                          23

<210> SEQ ID NO 1159
<211> LENGTH: 23
<212> TYPE: DNA
<213> ORGANISM: Homo sapiens

<400> SEQUENCE: 1159
agcctctccc tcccagcaaa gcg                                          23

<210> SEQ ID NO 1160
<211> LENGTH: 23
<212> TYPE: DNA
<213> ORGANISM: Homo sapiens

<400> SEQUENCE: 1160
gccatcagtg accaaggcac ctc                                          23
```

-continued

<210> SEQ ID NO 1161
<211> LENGTH: 23
<212> TYPE: DNA
<213> ORGANISM: Homo sapiens

<400> SEQUENCE: 1161
atcagagggt ggttatgtcg ggc                                        23

<210> SEQ ID NO 1162
<211> LENGTH: 23
<212> TYPE: DNA
<213> ORGANISM: Homo sapiens

<400> SEQUENCE: 1162
atcagagggt ggttatgtcg ggc                                        23

<210> SEQ ID NO 1163
<211> LENGTH: 23
<212> TYPE: DNA
<213> ORGANISM: Homo sapiens

<400> SEQUENCE: 1163
gggtcaggtt ggtgagagaa ggg                                        23

<210> SEQ ID NO 1164
<211> LENGTH: 23
<212> TYPE: DNA
<213> ORGANISM: Homo sapiens

<400> SEQUENCE: 1164
atggatggtg gatggtggga acc                                        23

<210> SEQ ID NO 1165
<211> LENGTH: 23
<212> TYPE: DNA
<213> ORGANISM: Homo sapiens

<400> SEQUENCE: 1165
ttccaccccg tccccatctt cac                                        23

<210> SEQ ID NO 1166
<211> LENGTH: 24
<212> TYPE: DNA
<213> ORGANISM: Homo sapiens

<400> SEQUENCE: 1166
aagagtaatc tgcttggtaa atag                                       24

<210> SEQ ID NO 1167
<211> LENGTH: 26
<212> TYPE: DNA
<213> ORGANISM: Homo sapiens

<400> SEQUENCE: 1167
ctacttgaag aaataagcct tgctgc                                     26

<210> SEQ ID NO 1168
<211> LENGTH: 26
<212> TYPE: DNA
<213> ORGANISM: Homo sapiens

<400> SEQUENCE: 1168
ccactttatg aagcaaatgg acaagc                                     26

<210> SEQ ID NO 1169
<211> LENGTH: 23
<212> TYPE: DNA
<213> ORGANISM: Homo sapiens

<400> SEQUENCE: 1169
cccttctctc tgttgctgcc gtg                                                                           23

<210> SEQ ID NO 1170
<211> LENGTH: 23
<212> TYPE: DNA
<213> ORGANISM: Homo sapiens

<400> SEQUENCE: 1170
gctcgcaggt gctgggaata cag                                                                           23

<210> SEQ ID NO 1171
<211> LENGTH: 23
<212> TYPE: DNA
<213> ORGANISM: Homo sapiens

<400> SEQUENCE: 1171
tggtgtctca ggcttggcag cag                                                                           23

<210> SEQ ID NO 1172
<211> LENGTH: 23
<212> TYPE: DNA
<213> ORGANISM: Homo sapiens

<400> SEQUENCE: 1172
gagagagccc aggttagaca gcg                                                                           23

<210> SEQ ID NO 1173
<211> LENGTH: 23
<212> TYPE: DNA
<213> ORGANISM: Homo sapiens

<400> SEQUENCE: 1173
aaacaaagcc agggaggagg acg                                                                           23

<210> SEQ ID NO 1174
<211> LENGTH: 23
<212> TYPE: DNA
<213> ORGANISM: Homo sapiens

<400> SEQUENCE: 1174
gccagaaagg aaggtgggag cct                                                                           23

<210> SEQ ID NO 1175
<211> LENGTH: 23
<212> TYPE: DNA
<213> ORGANISM: Homo sapiens

<400> SEQUENCE: 1175
ccactactct catagggagg gag                                                                           23

<210> SEQ ID NO 1176
<211> LENGTH: 23
<212> TYPE: DNA
<213> ORGANISM: Homo sapiens

<400> SEQUENCE: 1176

-continued

```
gctcgccgta gcattcctca cac                                         23

<210> SEQ ID NO 1177
<211> LENGTH: 23
<212> TYPE: DNA
<213> ORGANISM: Homo sapiens

<400> SEQUENCE: 1177
ggcttcaacc gtctccaagg ctt                                         23

<210> SEQ ID NO 1178
<211> LENGTH: 26
<212> TYPE: DNA
<213> ORGANISM: Homo sapiens

<400> SEQUENCE: 1178
ttctgtagag cctcaccaac actgtg                                      26

<210> SEQ ID NO 1179
<211> LENGTH: 26
<212> TYPE: DNA
<213> ORGANISM: Homo sapiens

<400> SEQUENCE: 1179
cgacttctcg gttgtttagc atcaca                                      26

<210> SEQ ID NO 1180
<211> LENGTH: 25
<212> TYPE: DNA
<213> ORGANISM: Homo sapiens

<400> SEQUENCE: 1180
cgtgacagca gttttattgt ttggg                                       25

<210> SEQ ID NO 1181
<211> LENGTH: 23
<212> TYPE: DNA
<213> ORGANISM: Homo sapiens

<400> SEQUENCE: 1181
ggacccgagc accactcttg aga                                         23

<210> SEQ ID NO 1182
<211> LENGTH: 23
<212> TYPE: DNA
<213> ORGANISM: Homo sapiens

<400> SEQUENCE: 1182
tcccagaaca gccagcacag cag                                         23

<210> SEQ ID NO 1183
<211> LENGTH: 23
<212> TYPE: DNA
<213> ORGANISM: Homo sapiens

<400> SEQUENCE: 1183
gtgactgcca ggtttgccac caa                                         23

<210> SEQ ID NO 1184
<211> LENGTH: 26
<212> TYPE: DNA
<213> ORGANISM: Homo sapiens

<400> SEQUENCE: 1184
```

-continued

```
cctactacaa cctattgccg atgccc                                    26

<210> SEQ ID NO 1185
<211> LENGTH: 26
<212> TYPE: DNA
<213> ORGANISM: Homo sapiens

<400> SEQUENCE: 1185
cgatgccctc aaactattta tcaaag                                    26

<210> SEQ ID NO 1186
<211> LENGTH: 23
<212> TYPE: DNA
<213> ORGANISM: Homo sapiens

<400> SEQUENCE: 1186
gaccacacac caggaggctg atg                                       23

<210> SEQ ID NO 1187
<211> LENGTH: 26
<212> TYPE: DNA
<213> ORGANISM: Homo sapiens

<400> SEQUENCE: 1187
ccactatttc cacaccacac agtctg                                    26

<210> SEQ ID NO 1188
<211> LENGTH: 23
<212> TYPE: DNA
<213> ORGANISM: Homo sapiens

<400> SEQUENCE: 1188
tggcactcct cctcgtcatc agg                                       23

<210> SEQ ID NO 1189
<211> LENGTH: 23
<212> TYPE: DNA
<213> ORGANISM: Homo sapiens

<400> SEQUENCE: 1189
gctcgccgta gcattcctca cac                                       23

<210> SEQ ID NO 1190
<211> LENGTH: 24
<212> TYPE: DNA
<213> ORGANISM: Homo sapiens

<400> SEQUENCE: 1190
acataaagaa cactctatcc aaaa                                      24

<210> SEQ ID NO 1191
<211> LENGTH: 24
<212> TYPE: DNA
<213> ORGANISM: Homo sapiens

<400> SEQUENCE: 1191
ttcgcaaagg acccaacatc gtag                                      24

<210> SEQ ID NO 1192
<211> LENGTH: 23
<212> TYPE: DNA
<213> ORGANISM: Homo sapiens
```

-continued

<400> SEQUENCE: 1192
gctcgccgta gcattcctca cac                                          23

<210> SEQ ID NO 1193
<211> LENGTH: 23
<212> TYPE: DNA
<213> ORGANISM: Homo sapiens

<400> SEQUENCE: 1193
gctcgccgta gcattcctca cac                                          23

<210> SEQ ID NO 1194
<211> LENGTH: 26
<212> TYPE: DNA
<213> ORGANISM: Homo sapiens

<400> SEQUENCE: 1194
tcgctgagga gcatccaact tgatta                                       26

<210> SEQ ID NO 1195
<211> LENGTH: 24
<212> TYPE: DNA
<213> ORGANISM: Homo sapiens

<400> SEQUENCE: 1195
ctgtcaacgg gatgtgaggt cagc                                         24

<210> SEQ ID NO 1196
<211> LENGTH: 26
<212> TYPE: DNA
<213> ORGANISM: Homo sapiens

<400> SEQUENCE: 1196
cctactacaa cctattgccg atgccc                                       26

<210> SEQ ID NO 1197
<211> LENGTH: 23
<212> TYPE: DNA
<213> ORGANISM: Homo sapiens

<400> SEQUENCE: 1197
ctcagcagga aatcgccctc cag                                          23

<210> SEQ ID NO 1198
<211> LENGTH: 23
<212> TYPE: DNA
<213> ORGANISM: Homo sapiens

<400> SEQUENCE: 1198
gctcgccgta gcattcctca cac                                          23

<210> SEQ ID NO 1199
<211> LENGTH: 26
<212> TYPE: DNA
<213> ORGANISM: Homo sapiens

<400> SEQUENCE: 1199
gctccaacac aacccagtta tttctg                                       26

<210> SEQ ID NO 1200
<211> LENGTH: 26
<212> TYPE: DNA
<213> ORGANISM: Homo sapiens -continued

```
<400> SEQUENCE: 1200
cctactacaa cctattgccg atgccc                                        26

<210> SEQ ID NO 1201
<211> LENGTH: 26
<212> TYPE: DNA
<213> ORGANISM: Homo sapiens

<400> SEQUENCE: 1201
cctactacaa cctattgccg atgccc                                        26

<210> SEQ ID NO 1202
<211> LENGTH: 23
<212> TYPE: DNA
<213> ORGANISM: Homo sapiens

<400> SEQUENCE: 1202
gacccaaagc agagaggcaa ctg                                           23

<210> SEQ ID NO 1203
<211> LENGTH: 26
<212> TYPE: DNA
<213> ORGANISM: Homo sapiens

<400> SEQUENCE: 1203
caacctattg ccgatgccct caaact                                        26

<210> SEQ ID NO 1204
<211> LENGTH: 26
<212> TYPE: DNA
<213> ORGANISM: Homo sapiens

<400> SEQUENCE: 1204
tagggaaccg actgaatctg atacag                                        26

<210> SEQ ID NO 1205
<211> LENGTH: 26
<212> TYPE: DNA
<213> ORGANISM: Homo sapiens

<400> SEQUENCE: 1205
caatacttta gagtcacatc tcgtgc                                        26

<210> SEQ ID NO 1206
<211> LENGTH: 25
<212> TYPE: DNA
<213> ORGANISM: Homo sapiens

<400> SEQUENCE: 1206
gtgtgtaagt tctaagtgtt tatta                                         25

<210> SEQ ID NO 1207
<211> LENGTH: 26
<212> TYPE: DNA
<213> ORGANISM: Homo sapiens

<400> SEQUENCE: 1207
caacctattg ccgatgccct caaact                                        26

<210> SEQ ID NO 1208
<211> LENGTH: 26
<212> TYPE: DNA
```

-continued

<213> ORGANISM: Homo sapiens

<400> SEQUENCE: 1208
caacccaaag caatccagca aagcat                                        26

<210> SEQ ID NO 1209
<211> LENGTH: 28
<212> TYPE: DNA
<213> ORGANISM: Homo sapiens

<400> SEQUENCE: 1209
gatgtttctt attttgagtt ttcccagg                                      28

<210> SEQ ID NO 1210
<211> LENGTH: 24
<212> TYPE: DNA
<213> ORGANISM: Homo sapiens

<400> SEQUENCE: 1210
gtcatcattt atgtggaagg aata                                          24

<210> SEQ ID NO 1211
<211> LENGTH: 26
<212> TYPE: DNA
<213> ORGANISM: Homo sapiens

<400> SEQUENCE: 1211
aaccctgtca taagttgaag aagagc                                        26

<210> SEQ ID NO 1212
<211> LENGTH: 60
<212> TYPE: DNA
<213> ORGANISM: Homo sapiens

<400> SEQUENCE: 1212
aatatttctt taagactaat tgttctactc gaggcattaa atactttccc tctagccagc   60

<210> SEQ ID NO 1213
<211> LENGTH: 60
<212> TYPE: DNA
<213> ORGANISM: Homo sapiens

<400> SEQUENCE: 1213
cagaatctct ctgcttaatg ggcccatatc gacagcttaa cggattttca cagagtacac   60

<210> SEQ ID NO 1214
<211> LENGTH: 60
<212> TYPE: DNA
<213> ORGANISM: Homo sapiens

<400> SEQUENCE: 1214
cattggagtg gaatagagag cttataaatc gacagcttaa cggattttca cagagtacac   60

<210> SEQ ID NO 1215
<211> LENGTH: 60
<212> TYPE: DNA
<213> ORGANISM: Homo sapiens

<400> SEQUENCE: 1215
gaccctatgc tcctttcctg gaacatcatc gagatgtatg acaacaaatg ccagtattta   60

<210> SEQ ID NO 1216
<211> LENGTH: 60

-continued

```
<212> TYPE: DNA
<213> ORGANISM: Homo sapiens

<400> SEQUENCE: 1216
taaccaaacc atagtgtgaa aacagctttc gatatgtaat tttattaaga atattatttt      60

<210> SEQ ID NO 1217
<211> LENGTH: 60
<212> TYPE: DNA
<213> ORGANISM: Homo sapiens

<400> SEQUENCE: 1217
gaatgggtac tctgctggaa agttgatttc gaggtgaaag ccgagggaag tgagtagcca      60

<210> SEQ ID NO 1218
<211> LENGTH: 60
<212> TYPE: DNA
<213> ORGANISM: Homo sapiens

<400> SEQUENCE: 1218
ttgggtacta gaacccttac agctcctttc gataagaatg ccaggatctt ttgctgggga      60

<210> SEQ ID NO 1219
<211> LENGTH: 60
<212> TYPE: DNA
<213> ORGANISM: Homo sapiens

<400> SEQUENCE: 1219
ttgggtacta gaacccttac agctcctttc gacaaatcta tgatatcaag aataactaac      60

<210> SEQ ID NO 1220
<211> LENGTH: 60
<212> TYPE: DNA
<213> ORGANISM: Homo sapiens

<400> SEQUENCE: 1220
taacatgctc agtaaatgct acctgtggtc gagcttttct tatccatgct tcaggggtga      60

<210> SEQ ID NO 1221
<211> LENGTH: 60
<212> TYPE: DNA
<213> ORGANISM: Homo sapiens

<400> SEQUENCE: 1221
atccctgtac tcctgtgacc agggcacgtc gagctttcaa ctgaaactta ggattttgga      60

<210> SEQ ID NO 1222
<211> LENGTH: 60
<212> TYPE: DNA
<213> ORGANISM: Homo sapiens

<400> SEQUENCE: 1222
atccctgtac tcctgtgacc agggcacgtc gattaatata atacatcaca ttaacagaat      60

<210> SEQ ID NO 1223
<211> LENGTH: 60
<212> TYPE: DNA
<213> ORGANISM: Homo sapiens

<400> SEQUENCE: 1223
caaaaaatgc actctttcaa agaatctctc gaaaagcaag atccttcttt taatggaatt      60

<210> SEQ ID NO 1224
```

-continued

```
<211> LENGTH: 60
<212> TYPE: DNA
<213> ORGANISM: Homo sapiens

<400> SEQUENCE: 1224
caaaaaatgc actctttcaa agaatctctc gattcagtgt gattggaatc atggaaggag          60

<210> SEQ ID NO 1225
<211> LENGTH: 60
<212> TYPE: DNA
<213> ORGANISM: Homo sapiens

<400> SEQUENCE: 1225
ttaaacaaca aaacccaaca gaggaaattc gacacttacc acaatgaggt ggatgccttc          60

<210> SEQ ID NO 1226
<211> LENGTH: 60
<212> TYPE: DNA
<213> ORGANISM: Homo sapiens

<400> SEQUENCE: 1226
gtcactgcct tcaaacctta tggtacgatc gagaagctaa aacaagtata aatatatatg          60

<210> SEQ ID NO 1227
<211> LENGTH: 60
<212> TYPE: DNA
<213> ORGANISM: Homo sapiens

<400> SEQUENCE: 1227
ctgctgttta ctcaatatca tgacaatttc gactggtaaa tatggtaacc ccaaagcaat          60

<210> SEQ ID NO 1228
<211> LENGTH: 60
<212> TYPE: DNA
<213> ORGANISM: Homo sapiens

<400> SEQUENCE: 1228
ttgtcacagt gtagtgagga gataaatatc gaagaggata aactggtccc tgcacagtct          60

<210> SEQ ID NO 1229
<211> LENGTH: 60
<212> TYPE: DNA
<213> ORGANISM: Homo sapiens

<400> SEQUENCE: 1229
gttacaaccc ctgacatgaa aaaggtactc gatgctgggt ttgagtaacg ctggagctgc          60

<210> SEQ ID NO 1230
<211> LENGTH: 60
<212> TYPE: DNA
<213> ORGANISM: Homo sapiens

<400> SEQUENCE: 1230
gttacaaccc ctgacatgaa aaaggtactc gaagaggata aactggtccc tgcacagtct          60

<210> SEQ ID NO 1231
<211> LENGTH: 60
<212> TYPE: DNA
<213> ORGANISM: Homo sapiens

<400> SEQUENCE: 1231
acagtaaagg tgttttggac ttattggctc gatgttaaag aatagttcta ttctactttg          60
```

-continued

```
<210> SEQ ID NO 1232
<211> LENGTH: 60
<212> TYPE: DNA
<213> ORGANISM: Homo sapiens

<400> SEQUENCE: 1232
acagtaaagg tgttttggac ttattggctc gaaatatatt atgatgtacc tctgaaaaaa       60

<210> SEQ ID NO 1233
<211> LENGTH: 60
<212> TYPE: DNA
<213> ORGANISM: Homo sapiens

<400> SEQUENCE: 1233
tgtgttttac ttttaatgga gttgctgttc gagagtggtg tgttagctct ccgccttggg       60

<210> SEQ ID NO 1234
<211> LENGTH: 60
<212> TYPE: DNA
<213> ORGANISM: Homo sapiens

<400> SEQUENCE: 1234
taagtctctt ctgaaaaaaa atagcaggtc gaatccaatc acatttgcga atgcccttca       60

<210> SEQ ID NO 1235
<211> LENGTH: 60
<212> TYPE: DNA
<213> ORGANISM: Homo sapiens

<400> SEQUENCE: 1235
attgtgcgca aaggaaatta ttctaagatc gaacactgtt cagctctttt gtctggtgat       60

<210> SEQ ID NO 1236
<211> LENGTH: 60
<212> TYPE: DNA
<213> ORGANISM: Homo sapiens

<400> SEQUENCE: 1236
aaccagactg atgttaacat cgccacgttc gagtacctgt gctcagcaac aagatggctt       60

<210> SEQ ID NO 1237
<211> LENGTH: 60
<212> TYPE: DNA
<213> ORGANISM: Homo sapiens

<400> SEQUENCE: 1237
aagccatctt gttgctgagc acaggtactc gaacactgtt cagctctttt gtctggtgat       60

<210> SEQ ID NO 1238
<211> LENGTH: 60
<212> TYPE: DNA
<213> ORGANISM: Homo sapiens

<400> SEQUENCE: 1238
aaatcagaga gacactctct ggatggtctc gaacactaga tctttgagtc tagtctcttt       60

<210> SEQ ID NO 1239
<211> LENGTH: 60
<212> TYPE: DNA
<213> ORGANISM: Homo sapiens

<400> SEQUENCE: 1239
gagtctctag gtacctgtcc gcttcaggtc gagcatctgg actaatttgt cccgagctgc       60
```

-continued

<210> SEQ ID NO 1240
<211> LENGTH: 60
<212> TYPE: DNA
<213> ORGANISM: Homo sapiens

<400> SEQUENCE: 1240
gagtctctag gtacctgtcc gcttcaggtc gatagaaatg aagagctcag ctgggtggct      60

<210> SEQ ID NO 1241
<211> LENGTH: 60
<212> TYPE: DNA
<213> ORGANISM: Homo sapiens

<400> SEQUENCE: 1241
gagtctctag gtacctgtcc gcttcaggtc gatttggaga tggttgtaca atgctataaa      60

<210> SEQ ID NO 1242
<211> LENGTH: 60
<212> TYPE: DNA
<213> ORGANISM: Homo sapiens

<400> SEQUENCE: 1242
aggaaatgaa catctaaatt caagaagctc gacagtacta gaaaccaacc ccttctcccc      60

<210> SEQ ID NO 1243
<211> LENGTH: 60
<212> TYPE: DNA
<213> ORGANISM: Homo sapiens

<400> SEQUENCE: 1243
ctatttcatg ctacgccctt gggctttatc gagagtctgc tgaatttgtc tgccacctct      60

<210> SEQ ID NO 1244
<211> LENGTH: 60
<212> TYPE: DNA
<213> ORGANISM: Homo sapiens

<400> SEQUENCE: 1244
taattaaaat ttgataataa aggcctactc gatgccctcc ttcttgtact cctcctgctc      60

<210> SEQ ID NO 1245
<211> LENGTH: 60
<212> TYPE: DNA
<213> ORGANISM: Homo sapiens

<400> SEQUENCE: 1245
cctccaggaa ttctgttaag atgtattttc gagttagaaa attccctct atttgtagtt      60

<210> SEQ ID NO 1246
<211> LENGTH: 60
<212> TYPE: DNA
<213> ORGANISM: Homo sapiens

<400> SEQUENCE: 1246
ataaaaagca aataagtgct agtgttactc gaaaagttgg caggtcttaa tctactggat      60

<210> SEQ ID NO 1247
<211> LENGTH: 60
<212> TYPE: DNA
<213> ORGANISM: Homo sapiens

<400> SEQUENCE: 1247
ataaaaagca aataagtgct agtgttactc gaggcttaca tttcatctgg gaagtttttc      60

<210> SEQ ID NO 1248
<211> LENGTH: 60
<212> TYPE: DNA
<213> ORGANISM: Homo sapiens

<400> SEQUENCE: 1248
ataaaaagca aataagtgct agtgttactc gaataccacg tttactcaga caagagaaac        60

<210> SEQ ID NO 1249
<211> LENGTH: 60
<212> TYPE: DNA
<213> ORGANISM: Homo sapiens

<400> SEQUENCE: 1249
ataaaaagca aataagtgct agtgttactc gagcctgttg ggcgtgagat aatcaccttc        60

<210> SEQ ID NO 1250
<211> LENGTH: 60
<212> TYPE: DNA
<213> ORGANISM: Homo sapiens

<400> SEQUENCE: 1250
ataaaaagca aataagtgct agtgttactc gagcctccag aactctgagg aataaatgtc        60

<210> SEQ ID NO 1251
<211> LENGTH: 60
<212> TYPE: DNA
<213> ORGANISM: Homo sapiens

<400> SEQUENCE: 1251
ataaaaagca aataagtgct agtgttactc gaatttcgtt tctgctagtg ctttagcaca        60

<210> SEQ ID NO 1252
<211> LENGTH: 60
<212> TYPE: DNA
<213> ORGANISM: Homo sapiens

<400> SEQUENCE: 1252
atgtccagag aatggaaaca aacctgactc gaggaatacg tgggaagaaa tggggtacag        60

<210> SEQ ID NO 1253
<211> LENGTH: 60
<212> TYPE: DNA
<213> ORGANISM: Homo sapiens

<400> SEQUENCE: 1253
aataaccaac ataactagaa aattctcctc gaggaatacg tgggaagaaa tggggtacag        60

<210> SEQ ID NO 1254
<211> LENGTH: 60
<212> TYPE: DNA
<213> ORGANISM: Homo sapiens

<400> SEQUENCE: 1254 ctgtaccccca tttcttccca cgtattcctc gagagctata tcaaaaagat tttggtattt        60

<210> SEQ ID NO 1255
<211> LENGTH: 60
<212> TYPE: DNA
<213> ORGANISM: Homo sapiens

<400> SEQUENCE: 1255

-continued

```
gacaggggtc tagaatcata gatttccctc gatcttgagg ttgacagtta ccacaattat      60

<210> SEQ ID NO 1256
<211> LENGTH: 60
<212> TYPE: DNA
<213> ORGANISM: Homo sapiens

<400> SEQUENCE: 1256
gacaggggtc tagaatcata gatttccctc gaatatgtag ttgagtcaga tctgggattt      60

<210> SEQ ID NO 1257
<211> LENGTH: 60
<212> TYPE: DNA
<213> ORGANISM: Homo sapiens

<400> SEQUENCE: 1257
gacaggggtc tagaatcata gatttccctc gataccccag ttttcttttt gatcccttca      60

<210> SEQ ID NO 1258
<211> LENGTH: 60
<212> TYPE: DNA
<213> ORGANISM: Homo sapiens

<400> SEQUENCE: 1258
gcttccagaa atgagagcag acttcaagtc gatattttga ataaggctta cagcaagggt      60

<210> SEQ ID NO 1259
<211> LENGTH: 60
<212> TYPE: DNA
<213> ORGANISM: Homo sapiens

<400> SEQUENCE: 1259
ggtgtgtagg cacaggggtt ggatctcttc gatttttatg ggtatctcac tctacaattt      60

<210> SEQ ID NO 1260
<211> LENGTH: 60
<212> TYPE: DNA
<213> ORGANISM: Homo sapiens

<400> SEQUENCE: 1260
acatgctcag aaataaaaac attaattttc gacaaatact gtaggatttc aagggaagaa      60

<210> SEQ ID NO 1261
<211> LENGTH: 60
<212> TYPE: DNA
<213> ORGANISM: Homo sapiens

<400> SEQUENCE: 1261
ttaaagctat agtgaatgaa gcaatatatc gagttgtctt ctaaaagaca gtctaataat      60

<210> SEQ ID NO 1262
<211> LENGTH: 60
<212> TYPE: DNA
<213> ORGANISM: Homo sapiens

<400> SEQUENCE: 1262
gagtctctag gtacctgtcc gcttcaggtc gagctgtcaa ggggcaaaaa aaaaaaaaaa      60

<210> SEQ ID NO 1263
<211> LENGTH: 60
<212> TYPE: DNA
<213> ORGANISM: Homo sapiens

<400> SEQUENCE: 1263
```

-continued

```
agggcactgc ccttgatcag gtaaatgttc gacctgaagc ggacaggtac ctagagactc      60

<210> SEQ ID NO 1264
<211> LENGTH: 60
<212> TYPE: DNA
<213> ORGANISM: Homo sapiens

<400> SEQUENCE: 1264
gagtctctag gtacctgtcc gcttcaggtc gatggtcggc acattttcgt agccaccctg      60

<210> SEQ ID NO 1265
<211> LENGTH: 60
<212> TYPE: DNA
<213> ORGANISM: Homo sapiens

<400> SEQUENCE: 1265
gagtctctag gtacctgtcc gcttcaggtc gaaattaaca gacacatctg tgtctgctct      60

<210> SEQ ID NO 1266
<211> LENGTH: 60
<212> TYPE: DNA
<213> ORGANISM: Homo sapiens

<400> SEQUENCE: 1266
gcgaggtcat gaatgtacaa gtataatgtc gagtataagt taaacgtgat taaatgtaag      60

<210> SEQ ID NO 1267
<211> LENGTH: 60
<212> TYPE: DNA
<213> ORGANISM: Homo sapiens

<400> SEQUENCE: 1267
gcgaggtcat gaatgtacaa gtataatgtc gattaaaata ttttactttt ccttaattac      60

<210> SEQ ID NO 1268
<211> LENGTH: 60
<212> TYPE: DNA
<213> ORGANISM: Homo sapiens

<400> SEQUENCE: 1268
atgggtattg ctttatgcct gctgtgtttc gaattgaatg gagacgcctt ttggtaggat      60

<210> SEQ ID NO 1269
<211> LENGTH: 60
<212> TYPE: DNA
<213> ORGANISM: Homo sapiens

<400> SEQUENCE: 1269
cttacattta atcacgttta acttatactc gaggtgctca tcccgaggta cttagcgcct      60

<210> SEQ ID NO 1270
<211> LENGTH: 60
<212> TYPE: DNA
<213> ORGANISM: Homo sapiens

<400> SEQUENCE: 1270
atcctaccaa aaggcgtctc cattcaattc gattaaaata ttttactttt ccttaattac      60

<210> SEQ ID NO 1271
<211> LENGTH: 60
<212> TYPE: DNA
<213> ORGANISM: Homo sapiens
```

-continued

```
<400> SEQUENCE: 1271
caacgacaca aaggtgtaca cacaaacatc gatttttgct aagatggttg caaatgatag        60

<210> SEQ ID NO 1272
<211> LENGTH: 60
<212> TYPE: DNA
<213> ORGANISM: Homo sapiens

<400> SEQUENCE: 1272
caacgacaca aaggtgtaca cacaaacatc gaaagaaaga tttctttaga ctcttaagat        60

<210> SEQ ID NO 1273
<211> LENGTH: 60
<212> TYPE: DNA
<213> ORGANISM: Homo sapiens

<400> SEQUENCE: 1273
cagctgtaca tttttagttg tgcgcacttc gacgagtcaa aaccgacgga agtcaggcag        60

<210> SEQ ID NO 1274
<211> LENGTH: 60
<212> TYPE: DNA
<213> ORGANISM: Homo sapiens

<400> SEQUENCE: 1274
aatctcacta gaaggtacag gtgtcaagtc gacgagtcaa aaccgacgga agtcaggcag        60

<210> SEQ ID NO 1275
<211> LENGTH: 60
<212> TYPE: DNA
<213> ORGANISM: Homo sapiens

<400> SEQUENCE: 1275
ctcaggttaa gtcccctgt acctgctgtc gagacagacg tgtgccttct tgaaaaagcc        60

<210> SEQ ID NO 1276
<211> LENGTH: 26
<212> TYPE: DNA
<213> ORGANISM: Homo sapiens

<400> SEQUENCE: 1276
ttttgtgtcc taatggaagg ctgtgc                                           26

<210> SEQ ID NO 1277
<211> LENGTH: 23
<212> TYPE: DNA
<213> ORGANISM: Homo sapiens

<400> SEQUENCE: 1277
ggcacttctg gtgtttcagc ctc                                              23

<210> SEQ ID NO 1278
<211> LENGTH: 23
<212> TYPE: DNA
<213> ORGANISM: Homo sapiens

<400> SEQUENCE: 1278
cagtgcggta tcggtgaagg gaa                                              23

<210> SEQ ID NO 1279
<211> LENGTH: 23
<212> TYPE: DNA
<213> ORGANISM: Homo sapiens
```

```
<400> SEQUENCE: 1279
cctgccacat ccgctcttgg ttg                                          23

<210> SEQ ID NO 1280
<211> LENGTH: 26
<212> TYPE: DNA
<213> ORGANISM: Homo sapiens

<400> SEQUENCE: 1280
cgtctcccca ttgtaaggta aactcc                                       26

<210> SEQ ID NO 1281
<211> LENGTH: 26
<212> TYPE: DNA
<213> ORGANISM: Homo sapiens

<400> SEQUENCE: 1281
gttgtgtgga aacctcttct gcccca                                       26

<210> SEQ ID NO 1282
<211> LENGTH: 26
<212> TYPE: DNA
<213> ORGANISM: Homo sapiens

<400> SEQUENCE: 1282
tggtgttgtg tggaaacctc ttctgc                                       26

<210> SEQ ID NO 1283
<211> LENGTH: 23
<212> TYPE: DNA
<213> ORGANISM: Homo sapiens

<400> SEQUENCE: 1283 ccctttttcat caatgttcgg gtg                                         23

<210> SEQ ID NO 1284
<211> LENGTH: 23
<212> TYPE: DNA
<213> ORGANISM: Homo sapiens

<400> SEQUENCE: 1284
ccgtgccttg gttctctctt ctg                                          23

<210> SEQ ID NO 1285
<211> LENGTH: 24
<212> TYPE: DNA
<213> ORGANISM: Homo sapiens

<400> SEQUENCE: 1285
ggctgactga agatactttg gcat                                         24

<210> SEQ ID NO 1286
<211> LENGTH: 26
<212> TYPE: DNA
<213> ORGANISM: Homo sapiens

<400> SEQUENCE: 1286
cctggctgac tgaagatact ttggca                                       26

<210> SEQ ID NO 1287
<211> LENGTH: 26
<212> TYPE: DNA
```

-continued

```
<213> ORGANISM: Homo sapiens

<400> SEQUENCE: 1287
tacccataaa tgtgtttgct gttcac                                        26

<210> SEQ ID NO 1288
<211> LENGTH: 26
<212> TYPE: DNA
<213> ORGANISM: Homo sapiens

<400> SEQUENCE: 1288
tacccataaa tgtgtttgct gttcac                                        26

<210> SEQ ID NO 1289
<211> LENGTH: 23
<212> TYPE: DNA
<213> ORGANISM: Homo sapiens

<400> SEQUENCE: 1289
gacacttgga gcctgttgtt tct                                           23

<210> SEQ ID NO 1290
<211> LENGTH: 23
<212> TYPE: DNA
<213> ORGANISM: Homo sapiens

<400> SEQUENCE: 1290
gagttgtagt cccctgccca cct                                           23

<210> SEQ ID NO 1291
<211> LENGTH: 23
<212> TYPE: DNA
<213> ORGANISM: Homo sapiens

<400> SEQUENCE: 1291
caccacgcag cagcccgaaa cat                                           23

<210> SEQ ID NO 1292
<211> LENGTH: 23
<212> TYPE: DNA
<213> ORGANISM: Homo sapiens

<400> SEQUENCE: 1292
gggaactaac cccacgacaa gac                                           23

<210> SEQ ID NO 1293
<211> LENGTH: 23
<212> TYPE: DNA
<213> ORGANISM: Homo sapiens

<400> SEQUENCE: 1293
gactcccacg gataagatgc tcc                                           23

<210> SEQ ID NO 1294
<211> LENGTH: 23
<212> TYPE: DNA
<213> ORGANISM: Homo sapiens

<400> SEQUENCE: 1294
gggaactaac cccacgacaa gac                                           23

<210> SEQ ID NO 1295
<211> LENGTH: 26
```

-continued

```
<212> TYPE: DNA
<213> ORGANISM: Homo sapiens

<400> SEQUENCE: 1295
ggatttccta tggcagcctc cttgga                                      26

<210> SEQ ID NO 1296
<211> LENGTH: 26
<212> TYPE: DNA
<213> ORGANISM: Homo sapiens

<400> SEQUENCE: 1296
ggatttccta tggcagcctc cttgga                                      26

<210> SEQ ID NO 1297
<211> LENGTH: 24
<212> TYPE: DNA
<213> ORGANISM: Homo sapiens

<400> SEQUENCE: 1297
gctttcccta tttgatttca gaag                                        24

<210> SEQ ID NO 1298
<211> LENGTH: 26
<212> TYPE: DNA
<213> ORGANISM: Homo sapiens

<400> SEQUENCE: 1298
gggctgtaac tgaccagaat ctttga                                      26

<210> SEQ ID NO 1299
<211> LENGTH: 23
<212> TYPE: DNA
<213> ORGANISM: Homo sapiens

<400> SEQUENCE: 1299
caagggtggt gtgacaggaa gtc                                         23

<210> SEQ ID NO 1300
<211> LENGTH: 23
<212> TYPE: DNA
<213> ORGANISM: Homo sapiens

<400> SEQUENCE: 1300
tcaagtcagt gccagtcaag ggc                                         23

<210> SEQ ID NO 1301
<211> LENGTH: 23
<212> TYPE: DNA
<213> ORGANISM: Homo sapiens

<400> SEQUENCE: 1301
ctttgtggtt catcctcagc ccc                                         23

<210> SEQ ID NO 1302
<211> LENGTH: 26
<212> TYPE: DNA
<213> ORGANISM: Homo sapiens

<400> SEQUENCE: 1302
ggatagtctg tggcaggctg gctttt                                      26

<210> SEQ ID NO 1303
```

-continued

```
<211> LENGTH: 23
<212> TYPE: DNA
<213> ORGANISM: Homo sapiens

<400> SEQUENCE: 1303
tggctacggc tgtgagagat gga                                          23

<210> SEQ ID NO 1304
<211> LENGTH: 26
<212> TYPE: DNA
<213> ORGANISM: Homo sapiens

<400> SEQUENCE: 1304
tcacccaaac cgtagagaca ggagtg                                       26

<210> SEQ ID NO 1305
<211> LENGTH: 23
<212> TYPE: DNA
<213> ORGANISM: Homo sapiens

<400> SEQUENCE: 1305
gtggctacgg ctgtgagaga tgg                                          23

<210> SEQ ID NO 1306
<211> LENGTH: 26
<212> TYPE: DNA
<213> ORGANISM: Homo sapiens

<400> SEQUENCE: 1306
ggaacaccaa taagtgggct aataca                                       26

<210> SEQ ID NO 1307
<211> LENGTH: 23
<212> TYPE: DNA
<213> ORGANISM: Homo sapiens

<400> SEQUENCE: 1307
gggcagagaa aagagtcact gtg                                          23

<210> SEQ ID NO 1308
<211> LENGTH: 24
<212> TYPE: DNA
<213> ORGANISM: Homo sapiens

<400> SEQUENCE: 1308
cagggactcc agaataactg accc                                         24

<210> SEQ ID NO 1309
<211> LENGTH: 23
<212> TYPE: DNA
<213> ORGANISM: Homo sapiens

<400> SEQUENCE: 1309
ctcaaacact cccagcgttg gca                                          23

<210> SEQ ID NO 1310
<211> LENGTH: 24
<212> TYPE: DNA
<213> ORGANISM: Homo sapiens

<400> SEQUENCE: 1310
gactgtaaag atgaaagaag attc                                         24
```

```
<210> SEQ ID NO 1311
<211> LENGTH: 26
<212> TYPE: DNA
<213> ORGANISM: Homo sapiens

<400> SEQUENCE: 1311
caaaagtctg ccaagttatt cctggg                                       26

<210> SEQ ID NO 1312
<211> LENGTH: 24
<212> TYPE: DNA
<213> ORGANISM: Homo sapiens

<400> SEQUENCE: 1312
gactgtaaag atgaaagaag attc                                         24

<210> SEQ ID NO 1313
<211> LENGTH: 26
<212> TYPE: DNA
<213> ORGANISM: Homo sapiens

<400> SEQUENCE: 1313
caaaagtctg ccaagttatt cctggg                                       26

<210> SEQ ID NO 1314
<211> LENGTH: 26
<212> TYPE: DNA
<213> ORGANISM: Homo sapiens

<400> SEQUENCE: 1314
caaaagtctg ccaagttatt cctggg                                       26

<210> SEQ ID NO 1315
<211> LENGTH: 24
<212> TYPE: DNA
<213> ORGANISM: Homo sapiens

<400> SEQUENCE: 1315
gactgtaaag atgaaagaag attc                                         24

<210> SEQ ID NO 1316
<211> LENGTH: 26
<212> TYPE: DNA
<213> ORGANISM: Homo sapiens

<400> SEQUENCE: 1316
gctattgtaa agaggctatg ccaact                                       26

<210> SEQ ID NO 1317
<211> LENGTH: 25
<212> TYPE: DNA
<213> ORGANISM: Homo sapiens

<400> SEQUENCE: 1317
ccattcaaca taccctcctc ctcgc                                        25

<210> SEQ ID NO 1318
<211> LENGTH: 23
<212> TYPE: DNA
<213> ORGANISM: Homo sapiens

<400> SEQUENCE: 1318
cataaagtag aggaggactg gtc                                          23
```

-continued

```
<210> SEQ ID NO 1319
<211> LENGTH: 23
<212> TYPE: DNA
<213> ORGANISM: Homo sapiens

<400> SEQUENCE: 1319
gccctcttgg gactgaactc tct                                        23

<210> SEQ ID NO 1320
<211> LENGTH: 26
<212> TYPE: DNA
<213> ORGANISM: Homo sapiens

<400> SEQUENCE: 1320
cagccctctt gggactgaac tctcta                                     26

<210> SEQ ID NO 1321
<211> LENGTH: 26
<212> TYPE: DNA
<213> ORGANISM: Homo sapiens

<400> SEQUENCE: 1321
cagccctctt gggactgaac tctcta                                     26

<210> SEQ ID NO 1322
<211> LENGTH: 26
<212> TYPE: DNA
<213> ORGANISM: Homo sapiens

<400> SEQUENCE: 1322
tcataggcaa tagatttcct gggagc                                     26

<210> SEQ ID NO 1323
<211> LENGTH: 23
<212> TYPE: DNA
<213> ORGANISM: Homo sapiens

<400> SEQUENCE: 1323
gacagccaga ctgatgggtg agg                                        23

<210> SEQ ID NO 1324
<211> LENGTH: 23
<212> TYPE: DNA
<213> ORGANISM: Homo sapiens

<400> SEQUENCE: 1324
cactcggcag atggcgtggc ata                                        23

<210> SEQ ID NO 1325
<211> LENGTH: 26
<212> TYPE: DNA
<213> ORGANISM: Homo sapiens

<400> SEQUENCE: 1325
atgtaactgc ctacgaaccc tccagg                                     26

<210> SEQ ID NO 1326
<211> LENGTH: 23
<212> TYPE: DNA
<213> ORGANISM: Homo sapiens

<400> SEQUENCE: 1326
gtggctacgg ctgtgagaga tgg                                        23
```

-continued

<210> SEQ ID NO 1327
<211> LENGTH: 23
<212> TYPE: DNA
<213> ORGANISM: Homo sapiens

<400> SEQUENCE: 1327
tggctacggc tgtgagagat gga                                           23

<210> SEQ ID NO 1328
<211> LENGTH: 23
<212> TYPE: DNA
<213> ORGANISM: Homo sapiens

<400> SEQUENCE: 1328
gaccaccccg cccaggctga cct                                           23

<210> SEQ ID NO 1329
<211> LENGTH: 23
<212> TYPE: DNA
<213> ORGANISM: Homo sapiens

<400> SEQUENCE: 1329
tggctacggc tgtgagagat gga                                           23

<210> SEQ ID NO 1330
<211> LENGTH: 24
<212> TYPE: DNA
<213> ORGANISM: Homo sapiens

<400> SEQUENCE: 1330
gaggaagatt ggcaacagat gcta                                          24

<210> SEQ ID NO 1331
<211> LENGTH: 23
<212> TYPE: DNA
<213> ORGANISM: Homo sapiens

<400> SEQUENCE: 1331
cccacacacc acaccactca tca                                           23

<210> SEQ ID NO 1332
<211> LENGTH: 26
<212> TYPE: DNA
<213> ORGANISM: Homo sapiens

<400> SEQUENCE: 1332
ggcttctggc acttactgaa tggctt                                        26

<210> SEQ ID NO 1333
<211> LENGTH: 25
<212> TYPE: DNA
<213> ORGANISM: Homo sapiens

<400> SEQUENCE: 1333
gaaagagaaa tacactcaac agaga                                         25

<210> SEQ ID NO 1334
<211> LENGTH: 26
<212> TYPE: DNA
<213> ORGANISM: Homo sapiens

<400> SEQUENCE: 1334

-continued tccagagggc tgaagacttg agaaag                                          26

<210> SEQ ID NO 1335
<211> LENGTH: 23
<212> TYPE: DNA
<213> ORGANISM: Homo sapiens

<400> SEQUENCE: 1335
taggtccttg gcatacgcat tga                                            23

<210> SEQ ID NO 1336
<211> LENGTH: 24
<212> TYPE: DNA
<213> ORGANISM: Homo sapiens

<400> SEQUENCE: 1336
gagtctacgc tacagataca aggg                                           24

<210> SEQ ID NO 1337
<211> LENGTH: 23
<212> TYPE: DNA
<213> ORGANISM: Homo sapiens

<400> SEQUENCE: 1337
atggtctgtg cccctggtgc cta                                            23

<210> SEQ ID NO 1338
<211> LENGTH: 26
<212> TYPE: DNA
<213> ORGANISM: Homo sapiens

<400> SEQUENCE: 1338
cacctcacat tctaacatct cagtct                                         26

<210> SEQ ID NO 1339
<211> LENGTH: 26
<212> TYPE: DNA
<213> ORGANISM: Homo sapiens

<400> SEQUENCE: 1339
ccagacagga ggagagaaca gatttc                                         26

<210> SEQ ID NO 1340
<211> LENGTH: 24
<212> TYPE: DNA
<213> ORGANISM: Homo sapiens

<400> SEQUENCE: 1340
cccgagtgct cagattcttg ctgg                                           24

<210> SEQ ID NO 1341
<211> LENGTH: 23
<212> TYPE: DNA
<213> ORGANISM: Homo sapiens

<400> SEQUENCE: 1341
cggacgctgg ttccatagtc gtg                                            23

<210> SEQ ID NO 1342
<211> LENGTH: 23
<212> TYPE: DNA
<213> ORGANISM: Homo sapiens

<400> SEQUENCE: 1342

-continued cggacgctgg ttccatagtc gtg                                                                    23

<210> SEQ ID NO 1343
<211> LENGTH: 23
<212> TYPE: DNA
<213> ORGANISM: Homo sapiens

<400> SEQUENCE: 1343
acgagcattt attgggcacg ggc                                                                    23

<210> SEQ ID NO 1344
<211> LENGTH: 26
<212> TYPE: DNA
<213> ORGANISM: Homo sapiens

<400> SEQUENCE: 1344
tgaaagcaaa gcacttggaa agcata                                                                 26

<210> SEQ ID NO 1345
<211> LENGTH: 26
<212> TYPE: DNA
<213> ORGANISM: Homo sapiens

<400> SEQUENCE: 1345
gtagattttg gacctcgtgt ctcaga                                                                 26

<210> SEQ ID NO 1346
<211> LENGTH: 26
<212> TYPE: DNA
<213> ORGANISM: Homo sapiens

<400> SEQUENCE: 1346
atgtggctat ccaactatcc cagcac                                                                 26

<210> SEQ ID NO 1347
<211> LENGTH: 23
<212> TYPE: DNA
<213> ORGANISM: Homo sapiens

<400> SEQUENCE: 1347
cctgggcgtc ctcagactgt ccg                                                                    23

<210> SEQ ID NO 1348
<211> LENGTH: 23
<212> TYPE: DNA
<213> ORGANISM: Homo sapiens

<400> SEQUENCE: 1348
gcggtgttgt gggcatcaag gtg                                                                    23

<210> SEQ ID NO 1349
<211> LENGTH: 24
<212> TYPE: DNA
<213> ORGANISM: Homo sapiens

<400> SEQUENCE: 1349
ttttatcctt gaagcgtatt gaat                                                                   24

<210> SEQ ID NO 1350
<211> LENGTH: 23
<212> TYPE: DNA
<213> ORGANISM: Homo sapiens -continued

```
<400> SEQUENCE: 1350
taagagttgg gaagtggtca agc                                          23

<210> SEQ ID NO 1351
<211> LENGTH: 26
<212> TYPE: DNA
<213> ORGANISM: Homo sapiens

<400> SEQUENCE: 1351
cggcaaggga gtaaacatca gagcaa                                       26

<210> SEQ ID NO 1352
<211> LENGTH: 26
<212> TYPE: DNA
<213> ORGANISM: Homo sapiens

<400> SEQUENCE: 1352
ccctttgtct cctgagcatc tggttt                                       26

<210> SEQ ID NO 1353
<211> LENGTH: 23
<212> TYPE: DNA
<213> ORGANISM: Homo sapiens

<400> SEQUENCE: 1353
actcacatca gtcagcagga agg                                          23

<210> SEQ ID NO 1354
<211> LENGTH: 25
<212> TYPE: DNA
<213> ORGANISM: Homo sapiens

<400> SEQUENCE: 1354
cgtgtattct gctgtttcca ggtgg                                        25

<210> SEQ ID NO 1355
<211> LENGTH: 23
<212> TYPE: DNA
<213> ORGANISM: Homo sapiens

<400> SEQUENCE: 1355
gggcaaggaa acagagccgt gta                                          23

<210> SEQ ID NO 1356
<211> LENGTH: 23
<212> TYPE: DNA
<213> ORGANISM: Homo sapiens

<400> SEQUENCE: 1356
gagtctccca gtctcagccc atc                                          23

<210> SEQ ID NO 1357
<211> LENGTH: 23
<212> TYPE: DNA
<213> ORGANISM: Homo sapiens

<400> SEQUENCE: 1357
gagtctccca gtctcagccc atc                                          23

<210> SEQ ID NO 1358
<211> LENGTH: 23
<212> TYPE: DNA
<213> ORGANISM: Homo sapiens
```

-continued

```
<400> SEQUENCE: 1358
ggctcagggt taggtcagga gtc                                        23

<210> SEQ ID NO 1359
<211> LENGTH: 26
<212> TYPE: DNA
<213> ORGANISM: Homo sapiens

<400> SEQUENCE: 1359
cccttctaac cacacacaag tccttt                                     26

<210> SEQ ID NO 1360
<211> LENGTH: 23
<212> TYPE: DNA
<213> ORGANISM: Homo sapiens

<400> SEQUENCE: 1360
tacattcagg aggactggag acg                                        23

<210> SEQ ID NO 1361
<211> LENGTH: 24
<212> TYPE: DNA
<213> ORGANISM: Homo sapiens

<400> SEQUENCE: 1361
taggcaggaa cactgtctac taca                                       24

<210> SEQ ID NO 1362
<211> LENGTH: 26
<212> TYPE: DNA
<213> ORGANISM: Homo sapiens

<400> SEQUENCE: 1362
ttacaccctt cggaggcact ggaaca                                     26

<210> SEQ ID NO 1363
<211> LENGTH: 23
<212> TYPE: DNA
<213> ORGANISM: Homo sapiens

<400> SEQUENCE: 1363
gcgagccatc gggaaagagc atc                                        23

<210> SEQ ID NO 1364
<211> LENGTH: 23
<212> TYPE: DNA
<213> ORGANISM: Homo sapiens

<400> SEQUENCE: 1364
ctccccaccc aagccaaaca ggt                                        23

<210> SEQ ID NO 1365
<211> LENGTH: 23
<212> TYPE: DNA
<213> ORGANISM: Homo sapiens

<400> SEQUENCE: 1365
ctccccaccc aagccaaaca ggt                                        23

<210> SEQ ID NO 1366
<211> LENGTH: 26
<212> TYPE: DNA
```

-continued

<213> ORGANISM: Homo sapiens

<400> SEQUENCE: 1366
ttctctgctc cttcctttcc aaactg                                          26

<210> SEQ ID NO 1367
<211> LENGTH: 23
<212> TYPE: DNA
<213> ORGANISM: Homo sapiens

<400> SEQUENCE: 1367
agaggaggaa atggcaggca gcc                                             23

<210> SEQ ID NO 1368
<211> LENGTH: 26
<212> TYPE: DNA
<213> ORGANISM: Homo sapiens

<400> SEQUENCE: 1368
tatccctaaa tgtccctttt cacagc                                          26

<210> SEQ ID NO 1369
<211> LENGTH: 23
<212> TYPE: DNA
<213> ORGANISM: Homo sapiens

<400> SEQUENCE: 1369
cctgcgtttc tccaaggatg gtc                                             23

<210> SEQ ID NO 1370
<211> LENGTH: 26
<212> TYPE: DNA
<213> ORGANISM: Homo sapiens

<400> SEQUENCE: 1370
ccctgtggca agtgatggca gtagaa                                          26

<210> SEQ ID NO 1371
<211> LENGTH: 23
<212> TYPE: DNA
<213> ORGANISM: Homo sapiens

<400> SEQUENCE: 1371
ttctgtggtc cctccgcctc cgc                                             23

<210> SEQ ID NO 1372
<211> LENGTH: 23
<212> TYPE: DNA
<213> ORGANISM: Homo sapiens

<400> SEQUENCE: 1372
gcagttcaac agcctggagc agc                                             23

<210> SEQ ID NO 1373
<211> LENGTH: 23
<212> TYPE: DNA
<213> ORGANISM: Homo sapiens

<400> SEQUENCE: 1373
gccctaacct ctccccttca cca                                             23

<210> SEQ ID NO 1374
<211> LENGTH: 24

-continued

```
<212> TYPE: DNA
<213> ORGANISM: Homo sapiens

<400> SEQUENCE: 1374
agaagagact tactgtgcta tttt                                          24

<210> SEQ ID NO 1375
<211> LENGTH: 26
<212> TYPE: DNA
<213> ORGANISM: Homo sapiens

<400> SEQUENCE: 1375
tcagactcta acccacctgt tcttgg                                        26

<210> SEQ ID NO 1376
<211> LENGTH: 24
<212> TYPE: DNA
<213> ORGANISM: Homo sapiens

<400> SEQUENCE: 1376
cttggtttcc tttgccttcc agaa                                          24

<210> SEQ ID NO 1377
<211> LENGTH: 26
<212> TYPE: DNA
<213> ORGANISM: Homo sapiens

<400> SEQUENCE: 1377
ggctctcact ctttctcctc agcaga                                        26

<210> SEQ ID NO 1378
<211> LENGTH: 26
<212> TYPE: DNA
<213> ORGANISM: Homo sapiens

<400> SEQUENCE: 1378
ggcaggatgg cattccacct tatgtc                                        26

<210> SEQ ID NO 1379
<211> LENGTH: 24
<212> TYPE: DNA
<213> ORGANISM: Homo sapiens

<400> SEQUENCE: 1379
ggttgctgtg acaaaatgcc atag                                          24

<210> SEQ ID NO 1380
<211> LENGTH: 26
<212> TYPE: DNA
<213> ORGANISM: Homo sapiens

<400> SEQUENCE: 1380
cattcaacat accctcctcc tcgctg                                        26

<210> SEQ ID NO 1381
<211> LENGTH: 25
<212> TYPE: DNA
<213> ORGANISM: Homo sapiens

<400> SEQUENCE: 1381
ggacattatt ctccaggaaa gacct                                         25

<210> SEQ ID NO 1382
```

-continued

```
<211> LENGTH: 23
<212> TYPE: DNA
<213> ORGANISM: Homo sapiens

<400> SEQUENCE: 1382
tcccattcaa cataccctcc tcc                                                23

<210> SEQ ID NO 1383
<211> LENGTH: 23
<212> TYPE: DNA
<213> ORGANISM: Homo sapiens

<400> SEQUENCE: 1383
cgccccaacc ttgctggaca ttg                                                23

<210> SEQ ID NO 1384
<211> LENGTH: 26
<212> TYPE: DNA
<213> ORGANISM: Homo sapiens

<400> SEQUENCE: 1384
cagaagaact cctgaaacgc caagaa                                             26

<210> SEQ ID NO 1385
<211> LENGTH: 26
<212> TYPE: DNA
<213> ORGANISM: Homo sapiens

<400> SEQUENCE: 1385
gccaacactg tggaactgaa tctaag                                             26

<210> SEQ ID NO 1386
<211> LENGTH: 26
<212> TYPE: DNA
<213> ORGANISM: Homo sapiens

<400> SEQUENCE: 1386
cagccgacag tagcccttag attgct                                             26

<210> SEQ ID NO 1387
<211> LENGTH: 23
<212> TYPE: DNA
<213> ORGANISM: Homo sapiens

<400> SEQUENCE: 1387
ccactccctt cccattcctc ctt                                                23

<210> SEQ ID NO 1388
<211> LENGTH: 23
<212> TYPE: DNA
<213> ORGANISM: Homo sapiens

<400> SEQUENCE: 1388
tctctgcccg tgactttgct cct                                                23

<210> SEQ ID NO 1389
<211> LENGTH: 26
<212> TYPE: DNA
<213> ORGANISM: Homo sapiens

<400> SEQUENCE: 1389
agattagggt tgctgagtgg gtcaat                                             26
```

-continued

```
<210> SEQ ID NO 1390
<211> LENGTH: 23
<212> TYPE: DNA
<213> ORGANISM: Homo sapiens

<400> SEQUENCE: 1390
caggaacctc taatccacgc cct                                            23

<210> SEQ ID NO 1391
<211> LENGTH: 23
<212> TYPE: DNA
<213> ORGANISM: Homo sapiens

<400> SEQUENCE: 1391
ttccaggaca accgcatcca ggg                                            23

<210> SEQ ID NO 1392
<211> LENGTH: 23
<212> TYPE: DNA
<213> ORGANISM: Homo sapiens

<400> SEQUENCE: 1392
acggctgtga gagatggaga gtc                                            23

<210> SEQ ID NO 1393
<211> LENGTH: 23
<212> TYPE: DNA
<213> ORGANISM: Homo sapiens

<400> SEQUENCE: 1393
aggtggcttc ctgtgggctg aga                                            23

<210> SEQ ID NO 1394
<211> LENGTH: 24
<212> TYPE: DNA
<213> ORGANISM: Homo sapiens

<400> SEQUENCE: 1394
cctctatgtt ttctcgttct ttta                                           24

<210> SEQ ID NO 1395
<211> LENGTH: 23
<212> TYPE: DNA
<213> ORGANISM: Homo sapiens

<400> SEQUENCE: 1395
aggcagtcca caaagccagc gtg                                            23

<210> SEQ ID NO 1396
<211> LENGTH: 26
<212> TYPE: DNA
<213> ORGANISM: Homo sapiens

<400> SEQUENCE: 1396
aggtggaaat gtaaggctga gtaggc                                         26

<210> SEQ ID NO 1397
<211> LENGTH: 25
<212> TYPE: DNA
<213> ORGANISM: Homo sapiens

<400> SEQUENCE: 1397
tcctctatgt tttctcgttc tttta                                          25
```

-continued

```
<210> SEQ ID NO 1398
<211> LENGTH: 23
<212> TYPE: DNA
<213> ORGANISM: Homo sapiens

<400> SEQUENCE: 1398
gggactcata gggagacaca tta                                              23

<210> SEQ ID NO 1399
<211> LENGTH: 26
<212> TYPE: DNA
<213> ORGANISM: Homo sapiens

<400> SEQUENCE: 1399
ctaaataaaa gagcactact gccaga                                           26

<210> SEQ ID NO 1400
<211> LENGTH: 24
<212> TYPE: DNA
<213> ORGANISM: Homo sapiens

<400> SEQUENCE: 1400
agaatccaca aatccatact gata                                             24

<210> SEQ ID NO 1401
<211> LENGTH: 23
<212> TYPE: DNA
<213> ORGANISM: Homo sapiens

<400> SEQUENCE: 1401
attgggcagg aggtgaggaa ctg                                              23

<210> SEQ ID NO 1402
<211> LENGTH: 26
<212> TYPE: DNA
<213> ORGANISM: Homo sapiens

<400> SEQUENCE: 1402
ttgatgctct ggattgggca ggaggt                                           26

<210> SEQ ID NO 1403
<211> LENGTH: 26
<212> TYPE: DNA
<213> ORGANISM: Homo sapiens

<400> SEQUENCE: 1403
gttttgttcc caagtgcctc tgacag                                           26

<210> SEQ ID NO 1404
<211> LENGTH: 60
<212> TYPE: DNA
<213> ORGANISM: Homo sapiens

<400> SEQUENCE: 1404
agtatttgta tttattctgg gagtttcatc gaactggctt catgccagat gctggaattg      60

<210> SEQ ID NO 1405
<211> LENGTH: 60
<212> TYPE: DNA
<213> ORGANISM: Homo sapiens

<400> SEQUENCE: 1405
aagttagtac tgcattgtta gtcaagtgtc gaaattgcta tgtataccaa agattaaggc      60
```

-continued

<210> SEQ ID NO 1406
<211> LENGTH: 60
<212> TYPE: DNA
<213> ORGANISM: Homo sapiens

<400> SEQUENCE: 1406
gccttaatct ttggtataca tagcaatttc gacccacaca gctcaagaag ctaatgcgca          60

<210> SEQ ID NO 1407
<211> LENGTH: 60
<212> TYPE: DNA
<213> ORGANISM: Homo sapiens

<400> SEQUENCE: 1407
gtacaatata gagacatcat tctcgttatc gattggcgca caagtgccag ggacacctgc          60

<210> SEQ ID NO 1408
<211> LENGTH: 60
<212> TYPE: DNA
<213> ORGANISM: Homo sapiens

<400> SEQUENCE: 1408
ggaagaggaa aagagaactt aaagaagatc gagagaaaag aaggacagac gaggcttcca          60

<210> SEQ ID NO 1409
<211> LENGTH: 60
<212> TYPE: DNA
<213> ORGANISM: Homo sapiens

<400> SEQUENCE: 1409
ggaagaggaa aagagaactt aaagaagatc gacggcagca tagcctctga gctggacagg          60

<210> SEQ ID NO 1410
<211> LENGTH: 60
<212> TYPE: DNA
<213> ORGANISM: Homo sapiens

<400> SEQUENCE: 1410
tacaggtgcc gtgtaccact ttgataagtc gaacatttgt tatttttttgt cttggtaatt          60

<210> SEQ ID NO 1411
<211> LENGTH: 60
<212> TYPE: DNA
<213> ORGANISM: Homo sapiens

<400> SEQUENCE: 1411
aaaactttca tcgcaaatgt actagctgtc gaaaacagca cagctttttg agccagaaaa          60

<210> SEQ ID NO 1412
<211> LENGTH: 60
<212> TYPE: DNA
<213> ORGANISM: Homo sapiens

<400> SEQUENCE: 1412
gtgcttcttt aagataccag ataattgatc gatacgacag aacctagaaa aagttccgag          60

<210> SEQ ID NO 1413
<211> LENGTH: 60
<212> TYPE: DNA
<213> ORGANISM: Homo sapiens

<400> SEQUENCE: 1413

-continued

```
ctcggaactt tttctaggtt ctgtcgtatc gattcaattc gtatatctcc ctctttctca        60

<210> SEQ ID NO 1414
<211> LENGTH: 60
<212> TYPE: DNA
<213> ORGANISM: Homo sapiens

<400> SEQUENCE: 1414
ggtctacccg tgcgtgttaa cgccggggtc gatacgacag aacctagaaa aagttccgag        60

<210> SEQ ID NO 1415
<211> LENGTH: 60
<212> TYPE: DNA
<213> ORGANISM: Homo sapiens

<400> SEQUENCE: 1415
cggcagagct cactgcagtc aattggaatc gaacactatg ataattcttt cccagattca        60

<210> SEQ ID NO 1416
<211> LENGTH: 60
<212> TYPE: DNA
<213> ORGANISM: Homo sapiens

<400> SEQUENCE: 1416
cggcagagct cactgcagtc aattggaatc gagtttatgc ctatcatagg acttgaacag        60

<210> SEQ ID NO 1417
<211> LENGTH: 60
<212> TYPE: DNA
<213> ORGANISM: Homo sapiens

<400> SEQUENCE: 1417
tcttcattta tttagtgctc acaaaaactc gaacactatg ataattcttt cccagattca        60

<210> SEQ ID NO 1418
<211> LENGTH: 60
<212> TYPE: DNA
<213> ORGANISM: Homo sapiens

<400> SEQUENCE: 1418
gggcgtattg ctatggttat gccccagctc gattgtctta tttttattta tttctatcac        60

<210> SEQ ID NO 1419
<211> LENGTH: 60
<212> TYPE: DNA
<213> ORGANISM: Homo sapiens

<400> SEQUENCE: 1419 ctttttttaca aatcctaaag gatgcccctc gattgtctta tttttattta tttctatcac       60

<210> SEQ ID NO 1420
<211> LENGTH: 60
<212> TYPE: DNA
<213> ORGANISM: Homo sapiens

<400> SEQUENCE: 1420
accagtgtca tcagtaccct agagggcttc gatgttgtct gccttttttaa tttttaacca      60

<210> SEQ ID NO 1421
<211> LENGTH: 60
<212> TYPE: DNA
<213> ORGANISM: Homo sapiens

<400> SEQUENCE: 1421
```

-continued

```
cctttgagtc tctggtcaag attctggctc gatgttgtct gccttttaa tttttaacca       60

<210> SEQ ID NO 1422
<211> LENGTH: 60
<212> TYPE: DNA
<213> ORGANISM: Homo sapiens

<400> SEQUENCE: 1422
cctttgagtc tctggtcaag attctggctc gaagattaga aatatttgga tatatttcta       60

<210> SEQ ID NO 1423
<211> LENGTH: 60
<212> TYPE: DNA
<213> ORGANISM: Homo sapiens

<400> SEQUENCE: 1423
gtgcgctgcg cagcttaaac agcagaattc gatgattctt gcccgagtca tatttcacta       60

<210> SEQ ID NO 1424
<211> LENGTH: 60
<212> TYPE: DNA
<213> ORGANISM: Homo sapiens

<400> SEQUENCE: 1424
gtgcgctgcg cagcttaaac agcagaattc gatcttaaat ttattgtatt ttgtttgcat       60

<210> SEQ ID NO 1425
<211> LENGTH: 60
<212> TYPE: DNA
<213> ORGANISM: Homo sapiens

<400> SEQUENCE: 1425
gtgcgctgcg cagcttaaac agcagaattc gacaaggatc agatatcatt aagtcaagtt       60

<210> SEQ ID NO 1426
<211> LENGTH: 60
<212> TYPE: DNA
<213> ORGANISM: Homo sapiens

<400> SEQUENCE: 1426
accagtgtca tcagtaccct agagggcttc gaatgttgaa acatactctc cagtgtgatg       60

<210> SEQ ID NO 1427
<211> LENGTH: 60
<212> TYPE: DNA
<213> ORGANISM: Homo sapiens

<400> SEQUENCE: 1427
accagtgtca tcagtaccct agagggcttc gaaacaaatg ctttatatac ttacatcatc       60

<210> SEQ ID NO 1428
<211> LENGTH: 60
<212> TYPE: DNA
<213> ORGANISM: Homo sapiens

<400> SEQUENCE: 1428
agtattggga aggagtcacg gtcagtaatc gagagcagca tgttagctct ccgccttcgg       60

<210> SEQ ID NO 1429
<211> LENGTH: 60
<212> TYPE: DNA
<213> ORGANISM: Homo sapiens
```

-continued

```
<400> SEQUENCE: 1429
cccctgcctt actcccaggg gccgccattc gatgggggca ccgggcaagt cactcaccct      60

<210> SEQ ID NO 1430
<211> LENGTH: 60
<212> TYPE: DNA
<213> ORGANISM: Homo sapiens

<400> SEQUENCE: 1430
aaggggaaaa aataaaaata gaagaccatc gaatccggta ctttctggcc ttccaaaaag      60

<210> SEQ ID NO 1431
<211> LENGTH: 60
<212> TYPE: DNA
<213> ORGANISM: Homo sapiens

<400> SEQUENCE: 1431
ctttttggaa ggccagaaag taccggattc gaccgtggtg tataatcctt ttaatatact      60

<210> SEQ ID NO 1432
<211> LENGTH: 60
<212> TYPE: DNA
<213> ORGANISM: Homo sapiens

<400> SEQUENCE: 1432
ataagtttgt tctgtaaccg taattaagtc gaaggatgtt ggtcctagac ccatccaaac      60

<210> SEQ ID NO 1433
<211> LENGTH: 60
<212> TYPE: DNA
<213> ORGANISM: Homo sapiens

<400> SEQUENCE: 1433
ataagtttgt tctgtaaccg taattaagtc gaatagccca cgttcaagtg gagaggaatt      60

<210> SEQ ID NO 1434
<211> LENGTH: 60
<212> TYPE: DNA
<213> ORGANISM: Homo sapiens

<400> SEQUENCE: 1434
ataagtttgt tctgtaaccg taattaagtc gacaaattct atcaactgat gaatttataa      60

<210> SEQ ID NO 1435
<211> LENGTH: 60
<212> TYPE: DNA
<213> ORGANISM: Homo sapiens

<400> SEQUENCE: 1435
ataagtttgt tctgtaaccg taattaagtc gaagctaaaa atatgcttta gtttaaaatt      60

<210> SEQ ID NO 1436
<211> LENGTH: 60
<212> TYPE: DNA
<213> ORGANISM: Homo sapiens

<400> SEQUENCE: 1436
gcaaagaaat atcttttatt tgcaaaattc gagatctggg ggtactgggt ggactctggg      60

<210> SEQ ID NO 1437
<211> LENGTH: 60
<212> TYPE: DNA
<213> ORGANISM: Homo sapiens
```

-continued

<400> SEQUENCE: 1437
acaaagattc tgtggttcct taccttcttc gagatctggg ggtactgggt ggactctggg     60

<210> SEQ ID NO 1438
<211> LENGTH: 60
<212> TYPE: DNA
<213> ORGANISM: Homo sapiens

<400> SEQUENCE: 1438
gtttgaagtt ttgattattg catgtaattc gactctagaa aagtctttga aagataaaag     60

<210> SEQ ID NO 1439
<211> LENGTH: 60
<212> TYPE: DNA
<213> ORGANISM: Homo sapiens

<400> SEQUENCE: 1439
tcagttatgg acatgtcttg aagttaaatc gactctagaa aagtctttga aagataaaag     60

<210> SEQ ID NO 1440
<211> LENGTH: 60
<212> TYPE: DNA
<213> ORGANISM: Homo sapiens

<400> SEQUENCE: 1440
gtttgaagtt ttgattattg catgtaattc gatcaaacat tattctggat gtttaagtga     60

<210> SEQ ID NO 1441
<211> LENGTH: 60
<212> TYPE: DNA
<213> ORGANISM: Homo sapiens

<400> SEQUENCE: 1441
tcagttatgg acatgtcttg aagttaaatc gatcaaacat tattctggat gtttaagtga     60

<210> SEQ ID NO 1442
<211> LENGTH: 60
<212> TYPE: DNA
<213> ORGANISM: Homo sapiens

<400> SEQUENCE: 1442
tcagttatgg acatgtcttg aagttaaatc gaatacacag ggtgtgagat taagagaaga     60

<210> SEQ ID NO 1443
<211> LENGTH: 60
<212> TYPE: DNA
<213> ORGANISM: Homo sapiens

<400> SEQUENCE: 1443
tcagttatgg acatgtcttg aagttaaatc gagaaatgtg acgcaataaa tttccgttgt     60

<210> SEQ ID NO 1444
<211> LENGTH: 60
<212> TYPE: DNA
<213> ORGANISM: Homo sapiens

<400> SEQUENCE: 1444
gtttgaagtt ttgattattg catgtaattc gaaagcccag gttgtcactg ggcttctgac     60

<210> SEQ ID NO 1445
<211> LENGTH: 60
<212> TYPE: DNA

-continued

<213> ORGANISM: Homo sapiens

<400> SEQUENCE: 1445
tcagttatgg acatgtcttg aagttaaatc gaatattacc taaattttat ctatatagaa        60

<210> SEQ ID NO 1446
<211> LENGTH: 60
<212> TYPE: DNA
<213> ORGANISM: Homo sapiens

<400> SEQUENCE: 1446
gggagctaaa agtacaattt ttaaagagtc gatccgtcac gtagcaatat cagctgtgcg        60

<210> SEQ ID NO 1447
<211> LENGTH: 60
<212> TYPE: DNA
<213> ORGANISM: Homo sapiens

<400> SEQUENCE: 1447
tgccagtgta cccaataggt acggcccgtc gagtcacccc agttctgagt caccccactt        60

<210> SEQ ID NO 1448
<211> LENGTH: 60
<212> TYPE: DNA
<213> ORGANISM: Homo sapiens

<400> SEQUENCE: 1448
aaaacccaag taaatgtcct tgattatttc gagggttttt ttttttttta attggtttta        60

<210> SEQ ID NO 1449
<211> LENGTH: 60
<212> TYPE: DNA
<213> ORGANISM: Homo sapiens

<400> SEQUENCE: 1449
taaaacccaa agacttcagc tttccctctc gagggttttt ttttttttta attggtttta        60

<210> SEQ ID NO 1450
<211> LENGTH: 60
<212> TYPE: DNA
<213> ORGANISM: Homo sapiens

<400> SEQUENCE: 1450
taaaaccaat taaaaaaaaa aaaaccctc gagtctctta accaattaca tgtgtgttgg        60

<210> SEQ ID NO 1451
<211> LENGTH: 60
<212> TYPE: DNA
<213> ORGANISM: Homo sapiens

<400> SEQUENCE: 1451
atggcccaat ggaatcagct gcagcagctc gatgacctgc actaggtacc gcaatgacct        60

<210> SEQ ID NO 1452
<211> LENGTH: 60
<212> TYPE: DNA
<213> ORGANISM: Homo sapiens

<400> SEQUENCE: 1452
aggtcattgc ggtacctagt gcaggtcatc gagcctgatt gtaatttata gactgaacag        60

<210> SEQ ID NO 1453
<211> LENGTH: 60

-continued

```
<212> TYPE: DNA
<213> ORGANISM: Homo sapiens

<400> SEQUENCE: 1453
aggtcattgc ggtacctagt gcaggtcatc gagcatgcgc tgcttgagcg tccgcggcag        60

<210> SEQ ID NO 1454
<211> LENGTH: 60
<212> TYPE: DNA
<213> ORGANISM: Homo sapiens

<400> SEQUENCE: 1454
attgcttaaa agtaaaagtg ccattgagtc gaaaaacttt tgaggcatcc actgaaaagc        60

<210> SEQ ID NO 1455
<211> LENGTH: 60
<212> TYPE: DNA
<213> ORGANISM: Homo sapiens

<400> SEQUENCE: 1455
attgcttaaa agtaaaagtg ccattgagtc gaatattaat gttttccaac aacagattta        60

<210> SEQ ID NO 1456
<211> LENGTH: 60
<212> TYPE: DNA
<213> ORGANISM: Homo sapiens

<400> SEQUENCE: 1456
agctgatttt actcttggat ttatttcatc gactgcgaac tccgtggagc tctagagaga        60

<210> SEQ ID NO 1457
<211> LENGTH: 60
<212> TYPE: DNA
<213> ORGANISM: Homo sapiens

<400> SEQUENCE: 1457
agctgatttt actcttggat ttatttcatc gactaataaa gtagcatcaa aatatataag        60

<210> SEQ ID NO 1458
<211> LENGTH: 60
<212> TYPE: DNA
<213> ORGANISM: Homo sapiens

<400> SEQUENCE: 1458
ggttcacaat gtagctattt ccaagcgatc gattcagttc cacctaagtt cttactgata        60

<210> SEQ ID NO 1459
<211> LENGTH: 60
<212> TYPE: DNA
<213> ORGANISM: Homo sapiens

<400> SEQUENCE: 1459
tcatccatgg aatgtaatga ctatgagatc gaattaatac cttttgaaaa aaacttagca        60

<210> SEQ ID NO 1460
<211> LENGTH: 60
<212> TYPE: DNA
<213> ORGANISM: Homo sapiens

<400> SEQUENCE: 1460
tcatccatgg aatgtaatga ctatgagatc gactctatgc tccagtcatt taaaaatagt        60

<210> SEQ ID NO 1461
```

-continued

```
<211> LENGTH: 60
<212> TYPE: DNA
<213> ORGANISM: Homo sapiens

<400> SEQUENCE: 1461
tagtgacttt ccccaaaata aagtacattc gatatttggc cagatttcct ggctaaagtt     60

<210> SEQ ID NO 1462
<211> LENGTH: 60
<212> TYPE: DNA
<213> ORGANISM: Homo sapiens

<400> SEQUENCE: 1462
tagtgacttt ccccaaaata aagtacattc gagattttcc tgacaaggta ccacccaagc     60

<210> SEQ ID NO 1463
<211> LENGTH: 60
<212> TYPE: DNA
<213> ORGANISM: Homo sapiens

<400> SEQUENCE: 1463
atatttgtac tggcaaactg ttctttactc gatacagtca gctccctgta cactcaggaa     60

<210> SEQ ID NO 1464
<211> LENGTH: 60
<212> TYPE: DNA
<213> ORGANISM: Homo sapiens

<400> SEQUENCE: 1464
atggagtacc tgagaaggtg atgttagctc gaaaaaatat ctgccaagag tgtggtactt     60

<210> SEQ ID NO 1465
<211> LENGTH: 60
<212> TYPE: DNA
<213> ORGANISM: Homo sapiens

<400> SEQUENCE: 1465
gctcaatgaa agggttccaa atcattgatc gatcactgac actgctcact gtgatctctt     60

<210> SEQ ID NO 1466
<211> LENGTH: 60
<212> TYPE: DNA
<213> ORGANISM: Homo sapiens

<400> SEQUENCE: 1466
gctcaatgaa agggttccaa atcattgatc gatttggacc ttgagtgcgc agtgtctgtg     60

<210> SEQ ID NO 1467
<211> LENGTH: 60
<212> TYPE: DNA
<213> ORGANISM: Homo sapiens

<400> SEQUENCE: 1467
attatgattg tggcaatgct tcggaaggtc gaaaccaccc tttaaaaaaa cattttttta     60

<210> SEQ ID NO 1468
<211> LENGTH: 23
<212> TYPE: DNA
<213> ORGANISM: Homo sapiens

<400> SEQUENCE: 1468
aagccacatc cttcccaccc agc                                            23
```

-continued

```
<210> SEQ ID NO 1469
<211> LENGTH: 23
<212> TYPE: DNA
<213> ORGANISM: Homo sapiens

<400> SEQUENCE: 1469
ggaagagtcc tgacgacatc ctg                                        23

<210> SEQ ID NO 1470
<211> LENGTH: 23
<212> TYPE: DNA
<213> ORGANISM: Homo sapiens

<400> SEQUENCE: 1470
gggctgcgga tgctgttcct tga                                        23

<210> SEQ ID NO 1471
<211> LENGTH: 23
<212> TYPE: DNA
<213> ORGANISM: Homo sapiens

<400> SEQUENCE: 1471
gtcaacattt cactccgtcg ggc                                        23

<210> SEQ ID NO 1472
<211> LENGTH: 23
<212> TYPE: DNA
<213> ORGANISM: Homo sapiens

<400> SEQUENCE: 1472
cgcctcagcg acacagagaa caa                                        23

<210> SEQ ID NO 1473
<211> LENGTH: 23
<212> TYPE: DNA
<213> ORGANISM: Homo sapiens

<400> SEQUENCE: 1473
cgcctcagcg acacagagaa caa                                        23

<210> SEQ ID NO 1474
<211> LENGTH: 24
<212> TYPE: DNA
<213> ORGANISM: Homo sapiens

<400> SEQUENCE: 1474
aatgcccttc cctaactctg aacg                                       24

<210> SEQ ID NO 1475
<211> LENGTH: 24
<212> TYPE: DNA
<213> ORGANISM: Homo sapiens

<400> SEQUENCE: 1475
ccaaactttt ctgtggaata cacg                                       24

<210> SEQ ID NO 1476
<211> LENGTH: 23
<212> TYPE: DNA
<213> ORGANISM: Homo sapiens

<400> SEQUENCE: 1476
cctgagcgag gtcacactgt tca                                        23
```

-continued

```
<210> SEQ ID NO 1477
<211> LENGTH: 23
<212> TYPE: DNA
<213> ORGANISM: Homo sapiens

<400> SEQUENCE: 1477
tgagagccgc tggtgtagat acg                                            23

<210> SEQ ID NO 1478
<211> LENGTH: 26
<212> TYPE: DNA
<213> ORGANISM: Homo sapiens

<400> SEQUENCE: 1478
ggtggtggct accctgaaac tcattg                                         26

<210> SEQ ID NO 1479
<211> LENGTH: 23
<212> TYPE: DNA
<213> ORGANISM: Homo sapiens

<400> SEQUENCE: 1479
tcccctctct ggtgctcctg aca                                            23

<210> SEQ ID NO 1480
<211> LENGTH: 23
<212> TYPE: DNA
<213> ORGANISM: Homo sapiens

<400> SEQUENCE: 1480
tcccctctct ggtgctcctg aca                                            23

<210> SEQ ID NO 1481
<211> LENGTH: 23
<212> TYPE: DNA
<213> ORGANISM: Homo sapiens

<400> SEQUENCE: 1481
accttctgag cacctcccac agc                                            23

<210> SEQ ID NO 1482
<211> LENGTH: 25
<212> TYPE: DNA
<213> ORGANISM: Homo sapiens

<400> SEQUENCE: 1482
ctctgagttg cttactgcct cctgc                                          25

<210> SEQ ID NO 1483
<211> LENGTH: 26
<212> TYPE: DNA
<213> ORGANISM: Homo sapiens

<400> SEQUENCE: 1483
gacaacatac acctctcaga cgatgc                                         26

<210> SEQ ID NO 1484
<211> LENGTH: 25
<212> TYPE: DNA
<213> ORGANISM: Homo sapiens

<400> SEQUENCE: 1484
tagttttagg gctgggcaca cagga                                          25
```

-continued

<210> SEQ ID NO 1485
<211> LENGTH: 26
<212> TYPE: DNA
<213> ORGANISM: Homo sapiens

<400> SEQUENCE: 1485
aaggtggagg gttcagatgg gctcat                                             26

<210> SEQ ID NO 1486
<211> LENGTH: 24
<212> TYPE: DNA
<213> ORGANISM: Homo sapiens

<400> SEQUENCE: 1486
tcaacaatgc taaatcacca aggg                                               24

<210> SEQ ID NO 1487
<211> LENGTH: 23
<212> TYPE: DNA
<213> ORGANISM: Homo sapiens

<400> SEQUENCE: 1487
taagacacaa cccctgccac ggg                                                23

<210> SEQ ID NO 1488
<211> LENGTH: 23
<212> TYPE: DNA
<213> ORGANISM: Homo sapiens

<400> SEQUENCE: 1488
taagacacaa cccctgccac ggg                                                23

<210> SEQ ID NO 1489
<211> LENGTH: 26
<212> TYPE: DNA
<213> ORGANISM: Homo sapiens

<400> SEQUENCE: 1489
agaagagtaa gacacaaccc ctgcca                                             26

<210> SEQ ID NO 1490
<211> LENGTH: 26
<212> TYPE: DNA
<213> ORGANISM: Homo sapiens

<400> SEQUENCE: 1490
tagttttagg gctgggcaca caggag                                             26

<210> SEQ ID NO 1491
<211> LENGTH: 23
<212> TYPE: DNA
<213> ORGANISM: Homo sapiens

<400> SEQUENCE: 1491
atgagaaggg caggacaggg ctg                                                23

<210> SEQ ID NO 1492
<211> LENGTH: 26
<212> TYPE: DNA
<213> ORGANISM: Homo sapiens

<400> SEQUENCE: 1492

-continued

```
gtgataagat ggaagccaag acaaaa                                        26

<210> SEQ ID NO 1493
<211> LENGTH: 23
<212> TYPE: DNA
<213> ORGANISM: Homo sapiens

<400> SEQUENCE: 1493
ttcctcttac cgtctcttgc gat                                          23

<210> SEQ ID NO 1494
<211> LENGTH: 23
<212> TYPE: DNA
<213> ORGANISM: Homo sapiens

<400> SEQUENCE: 1494
gcaaggttag tgagtggcga ggt                                          23

<210> SEQ ID NO 1495
<211> LENGTH: 23
<212> TYPE: DNA
<213> ORGANISM: Homo sapiens

<400> SEQUENCE: 1495
tggctggacc tgcctctcct ttc                                          23

<210> SEQ ID NO 1496
<211> LENGTH: 26
<212> TYPE: DNA
<213> ORGANISM: Homo sapiens

<400> SEQUENCE: 1496
gcaaaatggg caggaaggac atacaa                                       26

<210> SEQ ID NO 1497
<211> LENGTH: 26
<212> TYPE: DNA
<213> ORGANISM: Homo sapiens

<400> SEQUENCE: 1497
aatgggcagg aaggacatac aaaata                                       26

<210> SEQ ID NO 1498
<211> LENGTH: 26
<212> TYPE: DNA
<213> ORGANISM: Homo sapiens

<400> SEQUENCE: 1498
gcaaaatggg caggaaggac atacaa                                       26

<210> SEQ ID NO 1499
<211> LENGTH: 24
<212> TYPE: DNA
<213> ORGANISM: Homo sapiens

<400> SEQUENCE: 1499
tgggcaggaa ggacatacaa aata                                         24

<210> SEQ ID NO 1500
<211> LENGTH: 23
<212> TYPE: DNA
<213> ORGANISM: Homo sapiens

<400> SEQUENCE: 1500
```

-continued

___ tgtggaaaca ggaagggcac gac                                                      23

<210> SEQ ID NO 1501
<211> LENGTH: 24
<212> TYPE: DNA
<213> ORGANISM: Homo sapiens

<400> SEQUENCE: 1501
cagaagcaac acttaggcac ccag                                                     24

<210> SEQ ID NO 1502
<211> LENGTH: 26
<212> TYPE: DNA
<213> ORGANISM: Homo sapiens

<400> SEQUENCE: 1502
cgctttcctg acctcctacc catcaa                                                   26

<210> SEQ ID NO 1503
<211> LENGTH: 24
<212> TYPE: DNA
<213> ORGANISM: Homo sapiens

<400> SEQUENCE: 1503
gacagcccat aggttaggga cacc                                                     24

<210> SEQ ID NO 1504
<211> LENGTH: 26
<212> TYPE: DNA
<213> ORGANISM: Homo sapiens

<400> SEQUENCE: 1504
gacagcccat aggttaggga caccaa                                                   26

<210> SEQ ID NO 1505
<211> LENGTH: 23
<212> TYPE: DNA
<213> ORGANISM: Homo sapiens

<400> SEQUENCE: 1505
ccgctttcct gacctcctac cca                                                      23

<210> SEQ ID NO 1506
<211> LENGTH: 24
<212> TYPE: DNA
<213> ORGANISM: Homo sapiens

<400> SEQUENCE: 1506
gacagcccat aggttaggga cacc                                                     24

<210> SEQ ID NO 1507
<211> LENGTH: 24
<212> TYPE: DNA
<213> ORGANISM: Homo sapiens

<400> SEQUENCE: 1507
gttagggaca ccaaatagta tgct                                                     24

<210> SEQ ID NO 1508
<211> LENGTH: 24
<212> TYPE: DNA
<213> ORGANISM: Homo sapiens -continued

<400> SEQUENCE: 1508
gacagcccat aggttaggga cacc                                                    24

<210> SEQ ID NO 1509
<211> LENGTH: 23
<212> TYPE: DNA
<213> ORGANISM: Homo sapiens

<400> SEQUENCE: 1509
gctttcctga cctcctaccc atc                                                     23

<210> SEQ ID NO 1510
<211> LENGTH: 24
<212> TYPE: DNA
<213> ORGANISM: Homo sapiens

<400> SEQUENCE: 1510
atcatccatc ctcacttggg caca                                                    24

<210> SEQ ID NO 1511
<211> LENGTH: 23
<212> TYPE: DNA
<213> ORGANISM: Homo sapiens

<400> SEQUENCE: 1511
tcaaagccca gaatctccag cat                                                     23

<210> SEQ ID NO 1512
<211> LENGTH: 26
<212> TYPE: DNA
<213> ORGANISM: Homo sapiens

<400> SEQUENCE: 1512
gcactaagaa tcaaagtcgc cttcca                                                  26

<210> SEQ ID NO 1513
<211> LENGTH: 26
<212> TYPE: DNA
<213> ORGANISM: Homo sapiens

<400> SEQUENCE: 1513
aaggcttctg accaacacct ctgaga                                                  26

<210> SEQ ID NO 1514
<211> LENGTH: 23
<212> TYPE: DNA
<213> ORGANISM: Homo sapiens

<400> SEQUENCE: 1514
aggctgctga agtccccgta ggg                                                     23

<210> SEQ ID NO 1515
<211> LENGTH: 23
<212> TYPE: DNA
<213> ORGANISM: Homo sapiens

<400> SEQUENCE: 1515
ccaaggtgag tgcccatcct ctg                                                     23

<210> SEQ ID NO 1516
<211> LENGTH: 23
<212> TYPE: DNA
<213> ORGANISM: Homo sapiens

```
<400> SEQUENCE: 1516
tacagttggg acccctgatt ccg                                          23

<210> SEQ ID NO 1517
<211> LENGTH: 23
<212> TYPE: DNA
<213> ORGANISM: Homo sapiens

<400> SEQUENCE: 1517
ccaaggtgag tgcccatcct ctg                                          23

<210> SEQ ID NO 1518
<211> LENGTH: 26
<212> TYPE: DNA
<213> ORGANISM: Homo sapiens

<400> SEQUENCE: 1518
gactgaccta tgttgggaaa agcaaa                                       26

<210> SEQ ID NO 1519
<211> LENGTH: 24
<212> TYPE: DNA
<213> ORGANISM: Homo sapiens

<400> SEQUENCE: 1519
atgtatgttt atgtatgact tcct                                         24

<210> SEQ ID NO 1520
<211> LENGTH: 25
<212> TYPE: DNA
<213> ORGANISM: Homo sapiens

<400> SEQUENCE: 1520
ttttgcttgg cttgcttcct ttgga                                        25

<210> SEQ ID NO 1521
<211> LENGTH: 26
<212> TYPE: DNA
<213> ORGANISM: Homo sapiens

<400> SEQUENCE: 1521
ggttttcagc agattcttcc ttgagg                                       26

<210> SEQ ID NO 1522
<211> LENGTH: 26
<212> TYPE: DNA
<213> ORGANISM: Homo sapiens

<400> SEQUENCE: 1522
gaactgccta ctgctatgtg aggatg                                       26

<210> SEQ ID NO 1523
<211> LENGTH: 23
<212> TYPE: DNA
<213> ORGANISM: Homo sapiens

<400> SEQUENCE: 1523
gggtgaggaa gggacacagg cat                                          23

<210> SEQ ID NO 1524
<211> LENGTH: 23
<212> TYPE: DNA
```

-continued

<213> ORGANISM: Homo sapiens

<400> SEQUENCE: 1524
gggtgaggaa gggacacagg cat                                    23

<210> SEQ ID NO 1525
<211> LENGTH: 24
<212> TYPE: DNA
<213> ORGANISM: Homo sapiens

<400> SEQUENCE: 1525
gaagttagtc ctcactctcc tccc                                   24

<210> SEQ ID NO 1526
<211> LENGTH: 24
<212> TYPE: DNA
<213> ORGANISM: Homo sapiens

<400> SEQUENCE: 1526
aagttagtcc tcactctcct ccca                                   24

<210> SEQ ID NO 1527
<211> LENGTH: 26
<212> TYPE: DNA
<213> ORGANISM: Homo sapiens

<400> SEQUENCE: 1527
ctgccaatgg agcaagaact tcaaaa                                 26

<210> SEQ ID NO 1528
<211> LENGTH: 23
<212> TYPE: DNA
<213> ORGANISM: Homo sapiens

<400> SEQUENCE: 1528
gcacctattg cctgtcaagc ctc                                    23

<210> SEQ ID NO 1529
<211> LENGTH: 23
<212> TYPE: DNA
<213> ORGANISM: Homo sapiens

<400> SEQUENCE: 1529
cggctatgtc actcactacc tgg                                    23

<210> SEQ ID NO 1530
<211> LENGTH: 24
<212> TYPE: DNA
<213> ORGANISM: Homo sapiens

<400> SEQUENCE: 1530
cacctacggt ctgatggtat gtta                                   24

<210> SEQ ID NO 1531
<211> LENGTH: 26
<212> TYPE: DNA
<213> ORGANISM: Homo sapiens

<400> SEQUENCE: 1531
gacacaaata ccaaggagag aaaggc                                 26

<210> SEQ ID NO 1532
<211> LENGTH: 23

-continued

```
<212> TYPE: DNA
<213> ORGANISM: Homo sapiens

<400> SEQUENCE: 1532
ggagagcaag gtcctgggag tta                                          23

<210> SEQ ID NO 1533
<211> LENGTH: 23
<212> TYPE: DNA
<213> ORGANISM: Homo sapiens

<400> SEQUENCE: 1533
gaagaaatgg tagtgcccgc ccc                                          23

<210> SEQ ID NO 1534
<211> LENGTH: 23
<212> TYPE: DNA
<213> ORGANISM: Homo sapiens

<400> SEQUENCE: 1534
ggaagagtcc tgacgacatc ctg                                          23

<210> SEQ ID NO 1535
<211> LENGTH: 23
<212> TYPE: DNA
<213> ORGANISM: Homo sapiens

<400> SEQUENCE: 1535
ggcgaggctc tctcatctct ctc                                          23

<210> SEQ ID NO 1536
<211> LENGTH: 23
<212> TYPE: DNA
<213> ORGANISM: Homo sapiens

<400> SEQUENCE: 1536
ccgtcatagt tcccgtcctg agg                                          23

<210> SEQ ID NO 1537
<211> LENGTH: 23
<212> TYPE: DNA
<213> ORGANISM: Homo sapiens

<400> SEQUENCE: 1537
ctggagacac gctgaggatt ggc                                          23

<210> SEQ ID NO 1538
<211> LENGTH: 24
<212> TYPE: DNA
<213> ORGANISM: Homo sapiens

<400> SEQUENCE: 1538
aaactacaat gagataacca ccct                                         24

<210> SEQ ID NO 1539
<211> LENGTH: 25
<212> TYPE: DNA
<213> ORGANISM: Homo sapiens

<400> SEQUENCE: 1539
cataatgaga ctaaataact tgtcc                                        25

<210> SEQ ID NO 1540
```

<211> LENGTH: 23
<212> TYPE: DNA
<213> ORGANISM: Homo sapiens

<400> SEQUENCE: 1540
tccagagtgc ttcctgcccc aag                                          23

<210> SEQ ID NO 1541
<211> LENGTH: 23
<212> TYPE: DNA
<213> ORGANISM: Homo sapiens

<400> SEQUENCE: 1541
tccagagtgc ttcctgcccc aag                                          23

<210> SEQ ID NO 1542
<211> LENGTH: 26
<212> TYPE: DNA
<213> ORGANISM: Homo sapiens

<400> SEQUENCE: 1542
taacaggtgt gtgtgtaaga gaggga                                       26

<210> SEQ ID NO 1543
<211> LENGTH: 23
<212> TYPE: DNA
<213> ORGANISM: Homo sapiens

<400> SEQUENCE: 1543
accccaggtt cacgaaagtc agg                                          23

<210> SEQ ID NO 1544
<211> LENGTH: 23
<212> TYPE: DNA
<213> ORGANISM: Homo sapiens

<400> SEQUENCE: 1544
aaggcaggga gagccagaga aga                                          23

<210> SEQ ID NO 1545
<211> LENGTH: 25
<212> TYPE: DNA
<213> ORGANISM: Homo sapiens

<400> SEQUENCE: 1545
gtttatgtct tgtttctcct ggacg                                        25

<210> SEQ ID NO 1546
<211> LENGTH: 25
<212> TYPE: DNA
<213> ORGANISM: Homo sapiens

<400> SEQUENCE: 1546
ccattctgga aacaatctgg cagta                                        25

<210> SEQ ID NO 1547
<211> LENGTH: 25
<212> TYPE: DNA
<213> ORGANISM: Homo sapiens

<400> SEQUENCE: 1547
ccattctgga aacaatctgg cagta                                        25

-continued

```
<210> SEQ ID NO 1548
<211> LENGTH: 26
<212> TYPE: DNA
<213> ORGANISM: Homo sapiens

<400> SEQUENCE: 1548
aaagacagta gacacttcac caatga                                    26

<210> SEQ ID NO 1549
<211> LENGTH: 26
<212> TYPE: DNA
<213> ORGANISM: Homo sapiens

<400> SEQUENCE: 1549
agactggcag gaaataaacc aagttg                                    26

<210> SEQ ID NO 1550
<211> LENGTH: 24
<212> TYPE: DNA
<213> ORGANISM: Homo sapiens

<400> SEQUENCE: 1550
agacagtaga cacttcacca atga                                      24

<210> SEQ ID NO 1551
<211> LENGTH: 23
<212> TYPE: DNA
<213> ORGANISM: Homo sapiens

<400> SEQUENCE: 1551
ccaggtaaca ggatggctca agg                                       23

<210> SEQ ID NO 1552
<211> LENGTH: 23
<212> TYPE: DNA
<213> ORGANISM: Homo sapiens

<400> SEQUENCE: 1552
ctctgtggtg tcattgcccc ttc                                       23

<210> SEQ ID NO 1553
<211> LENGTH: 26
<212> TYPE: DNA
<213> ORGANISM: Homo sapiens

<400> SEQUENCE: 1553
tggtcctgag acgactacct tgaagt                                    26

<210> SEQ ID NO 1554
<211> LENGTH: 26
<212> TYPE: DNA
<213> ORGANISM: Homo sapiens

<400> SEQUENCE: 1554
ctttagagca tacagtaagc caatgg                                    26

<210> SEQ ID NO 1555
<211> LENGTH: 23
<212> TYPE: DNA
<213> ORGANISM: Homo sapiens

<400> SEQUENCE: 1555
ccacctttcc gcagtatcct cac                                       23
```

-continued

```
<210> SEQ ID NO 1556
<211> LENGTH: 23
<212> TYPE: DNA
<213> ORGANISM: Homo sapiens

<400> SEQUENCE: 1556
ggacgcagcc atcttgcccc gaa                                          23

<210> SEQ ID NO 1557
<211> LENGTH: 24
<212> TYPE: DNA
<213> ORGANISM: Homo sapiens

<400> SEQUENCE: 1557
gtagaagtgg gttttagaga gggt                                         24

<210> SEQ ID NO 1558
<211> LENGTH: 23
<212> TYPE: DNA
<213> ORGANISM: Homo sapiens

<400> SEQUENCE: 1558
tggctggacc tgcctctcct ttc                                          23

<210> SEQ ID NO 1559
<211> LENGTH: 23
<212> TYPE: DNA
<213> ORGANISM: Homo sapiens

<400> SEQUENCE: 1559
cagaccagca gcccttatgg aca                                          23

<210> SEQ ID NO 1560
<211> LENGTH: 26
<212> TYPE: DNA
<213> ORGANISM: Homo sapiens

<400> SEQUENCE: 1560
ggtttagagg tcctgatttg ttctcc                                       26

<210> SEQ ID NO 1561
<211> LENGTH: 23
<212> TYPE: DNA
<213> ORGANISM: Homo sapiens

<400> SEQUENCE: 1561
tgacacttct cccatcaaga ggg                                          23

<210> SEQ ID NO 1562
<211> LENGTH: 26
<212> TYPE: DNA
<213> ORGANISM: Homo sapiens

<400> SEQUENCE: 1562
cttgcccttg tggatagaga gtaggc                                       26

<210> SEQ ID NO 1563
<211> LENGTH: 24
<212> TYPE: DNA
<213> ORGANISM: Homo sapiens

<400> SEQUENCE: 1563
gggagattgg caacagatgt aagc                                         24
```

-continued

<210> SEQ ID NO 1564
<211> LENGTH: 23
<212> TYPE: DNA
<213> ORGANISM: Homo sapiens

<400> SEQUENCE: 1564
tccaccgcat cagcaccttc cca                                            23

<210> SEQ ID NO 1565
<211> LENGTH: 23
<212> TYPE: DNA
<213> ORGANISM: Homo sapiens

<400> SEQUENCE: 1565
tccaccgcat cagcaccttc cca                                            23

<210> SEQ ID NO 1566
<211> LENGTH: 26
<212> TYPE: DNA
<213> ORGANISM: Homo sapiens

<400> SEQUENCE: 1566
ttttcatact ttcctctcct tgcccc                                        26

<210> SEQ ID NO 1567
<211> LENGTH: 23
<212> TYPE: DNA
<213> ORGANISM: Homo sapiens

<400> SEQUENCE: 1567
gcttccgcct ccaaatggca tct                                           23

<210> SEQ ID NO 1568
<211> LENGTH: 26
<212> TYPE: DNA
<213> ORGANISM: Homo sapiens

<400> SEQUENCE: 1568
ttttcatact ttcctctcct tgcccc                                        26

<210> SEQ ID NO 1569
<211> LENGTH: 23
<212> TYPE: DNA
<213> ORGANISM: Homo sapiens

<400> SEQUENCE: 1569
gagttccttc ttgctcacgg gtg                                           23

<210> SEQ ID NO 1570
<211> LENGTH: 23
<212> TYPE: DNA
<213> ORGANISM: Homo sapiens

<400> SEQUENCE: 1570
gagttccttc ttgctcacgg gtg                                           23

<210> SEQ ID NO 1571
<211> LENGTH: 24
<212> TYPE: DNA
<213> ORGANISM: Homo sapiens

<400> SEQUENCE: 1571

-continued

```
ttgaaagaaa tgccaacaaa tgat                                    24

<210> SEQ ID NO 1572
<211> LENGTH: 23
<212> TYPE: DNA
<213> ORGANISM: Homo sapiens

<400> SEQUENCE: 1572
gggcagaagt tgaagccatc ctg                                     23

<210> SEQ ID NO 1573
<211> LENGTH: 23
<212> TYPE: DNA
<213> ORGANISM: Homo sapiens

<400> SEQUENCE: 1573
ccctctcaca tcccttgccc tgt                                     23

<210> SEQ ID NO 1574
<211> LENGTH: 25
<212> TYPE: DNA
<213> ORGANISM: Homo sapiens

<400> SEQUENCE: 1574
cttttgttag acagaagtta tcaat                                   25

<210> SEQ ID NO 1575
<211> LENGTH: 23
<212> TYPE: DNA
<213> ORGANISM: Homo sapiens

<400> SEQUENCE: 1575
tacgggatga agtctggagg cat                                     23

<210> SEQ ID NO 1576
<211> LENGTH: 26
<212> TYPE: DNA
<213> ORGANISM: Homo sapiens

<400> SEQUENCE: 1576
cccaaaaggc ttctgaccaa cacctc                                  26

<210> SEQ ID NO 1577
<211> LENGTH: 26
<212> TYPE: DNA
<213> ORGANISM: Homo sapiens

<400> SEQUENCE: 1577
gagaataaat aggtgatgtg ggaggc                                  26

<210> SEQ ID NO 1578
<211> LENGTH: 26
<212> TYPE: DNA
<213> ORGANISM: Homo sapiens

<400> SEQUENCE: 1578
caaactcaag acctcacatt gtcagg                                  26

<210> SEQ ID NO 1579
<211> LENGTH: 23
<212> TYPE: DNA
<213> ORGANISM: Homo sapiens

<400> SEQUENCE: 1579
```

```
ggtttggtga cttgctgaag ggc                                        23

<210> SEQ ID NO 1580
<211> LENGTH: 23
<212> TYPE: DNA
<213> ORGANISM: Homo sapiens

<400> SEQUENCE: 1580
ccaaggtgag tgcccatcct ctg                                        23

<210> SEQ ID NO 1581
<211> LENGTH: 23
<212> TYPE: DNA
<213> ORGANISM: Homo sapiens

<400> SEQUENCE: 1581
aggacctcaa ggacttcatc cgc                                        23

<210> SEQ ID NO 1582
<211> LENGTH: 26
<212> TYPE: DNA
<213> ORGANISM: Homo sapiens

<400> SEQUENCE: 1582
ctaaacagca taatactact tgcctc                                     26

<210> SEQ ID NO 1583
<211> LENGTH: 24
<212> TYPE: DNA
<213> ORGANISM: Homo sapiens

<400> SEQUENCE: 1583
gaataaagta atgtaacagg aaga                                       24

<210> SEQ ID NO 1584
<211> LENGTH: 24
<212> TYPE: DNA
<213> ORGANISM: Homo sapiens

<400> SEQUENCE: 1584
atgttactcc gatactgctt tctt                                       24

<210> SEQ ID NO 1585
<211> LENGTH: 26
<212> TYPE: DNA
<213> ORGANISM: Homo sapiens

<400> SEQUENCE: 1585
agcggaagtg cccctgcttt ggttta                                     26

<210> SEQ ID NO 1586
<211> LENGTH: 26
<212> TYPE: DNA
<213> ORGANISM: Homo sapiens

<400> SEQUENCE: 1586
ggatgtgtcc ataactggt ggctgt                                      26

<210> SEQ ID NO 1587
<211> LENGTH: 23
<212> TYPE: DNA
<213> ORGANISM: Homo sapiens
```

-continued

```
<400> SEQUENCE: 1587
gagagggaag gaggaaacga agc                                           23

<210> SEQ ID NO 1588
<211> LENGTH: 23
<212> TYPE: DNA
<213> ORGANISM: Homo sapiens

<400> SEQUENCE: 1588
ctatgtgctg tgccagagat ggg                                           23

<210> SEQ ID NO 1589
<211> LENGTH: 23
<212> TYPE: DNA
<213> ORGANISM: Homo sapiens

<400> SEQUENCE: 1589
tctccgcctt gccaacccca tca                                           23

<210> SEQ ID NO 1590
<211> LENGTH: 24
<212> TYPE: DNA
<213> ORGANISM: Homo sapiens

<400> SEQUENCE: 1590
aaagtgagac attttagtgc tccg                                          24

<210> SEQ ID NO 1591
<211> LENGTH: 26
<212> TYPE: DNA
<213> ORGANISM: Homo sapiens

<400> SEQUENCE: 1591
acagaacccg aacagtcaga cgctct                                        26

<210> SEQ ID NO 1592
<211> LENGTH: 23
<212> TYPE: DNA
<213> ORGANISM: Homo sapiens

<400> SEQUENCE: 1592
tggcaccaca tcactcctgc tgc                                           23

<210> SEQ ID NO 1593
<211> LENGTH: 23
<212> TYPE: DNA
<213> ORGANISM: Homo sapiens

<400> SEQUENCE: 1593
cactccaccc tggcgtgttt tcc                                           23

<210> SEQ ID NO 1594
<211> LENGTH: 24
<212> TYPE: DNA
<213> ORGANISM: Homo sapiens

<400> SEQUENCE: 1594
tttcagggca gaataaagat acat                                          24

<210> SEQ ID NO 1595
<211> LENGTH: 26
<212> TYPE: DNA
<213> ORGANISM: Homo sapiens
```

-continued

```
<400> SEQUENCE: 1595
cagaacctga ctatgtaggc acgctg                                        26

<210> SEQ ID NO 1596
<211> LENGTH: 26
<212> TYPE: DNA
<213> ORGANISM: Homo sapiens

<400> SEQUENCE: 1596
cacctcaaaa gacaacccca gaccca                                        26

<210> SEQ ID NO 1597
<211> LENGTH: 26
<212> TYPE: DNA
<213> ORGANISM: Homo sapiens

<400> SEQUENCE: 1597
gctccacatt tcccaatcta acctgc                                        26

<210> SEQ ID NO 1598
<211> LENGTH: 26
<212> TYPE: DNA
<213> ORGANISM: Homo sapiens

<400> SEQUENCE: 1598
aatctctgtc cccaactgta tctggc                                        26

<210> SEQ ID NO 1599
<211> LENGTH: 26
<212> TYPE: DNA
<213> ORGANISM: Homo sapiens

<400> SEQUENCE: 1599
gagtatttac gatggtcagg tgctgc                                        26

<210> SEQ ID NO 1600
<211> LENGTH: 23
<212> TYPE: DNA
<213> ORGANISM: Homo sapiens

<400> SEQUENCE: 1600
gacctgtggt tctgactgtc cag                                           23

<210> SEQ ID NO 1601
<211> LENGTH: 26
<212> TYPE: DNA
<213> ORGANISM: Homo sapiens

<400> SEQUENCE: 1601
gcaacctggt ctcctacctg cttcta                                        26

<210> SEQ ID NO 1602
<211> LENGTH: 24
<212> TYPE: DNA
<213> ORGANISM: Homo sapiens

<400> SEQUENCE: 1602
tagcagacaa tcagagggtt ttgc                                          24

<210> SEQ ID NO 1603
<211> LENGTH: 26
<212> TYPE: DNA
```

-continued

<213> ORGANISM: Homo sapiens

<400> SEQUENCE: 1603
gctggtagtt ggcttttggg aagaac                                    26

<210> SEQ ID NO 1604
<211> LENGTH: 23
<212> TYPE: DNA
<213> ORGANISM: Homo sapiens

<400> SEQUENCE: 1604
ttctccctcg dacgctcatc ctc                                       23

<210> SEQ ID NO 1605
<211> LENGTH: 26
<212> TYPE: DNA
<213> ORGANISM: Homo sapiens

<400> SEQUENCE: 1605
ctggaacttg tttaggcact gaagca                                    26

<210> SEQ ID NO 1606
<211> LENGTH: 26
<212> TYPE: DNA
<213> ORGANISM: Homo sapiens

<400> SEQUENCE: 1606
gcaaagggca ggtcatcatc attcaa                                    26

<210> SEQ ID NO 1607
<211> LENGTH: 24
<212> TYPE: DNA
<213> ORGANISM: Homo sapiens

<400> SEQUENCE: 1607
ccccgatgaa tgttaccctg tccc                                      24

<210> SEQ ID NO 1608
<211> LENGTH: 26
<212> TYPE: DNA
<213> ORGANISM: Homo sapiens

<400> SEQUENCE: 1608
ctgaaatccc atagtgagat gccttc                                    26

<210> SEQ ID NO 1609
<211> LENGTH: 23
<212> TYPE: DNA
<213> ORGANISM: Homo sapiens

<400> SEQUENCE: 1609
cctggatgtt cattcccacc tgg                                       23

<210> SEQ ID NO 1610
<211> LENGTH: 20
<212> TYPE: DNA
<213> ORGANISM: Homo sapiens

<400> SEQUENCE: 1610
gcagattcca cagggcttac                                           20

<210> SEQ ID NO 1611
<211> LENGTH: 24

-continued

```
<212> TYPE: DNA
<213> ORGANISM: Homo sapiens

<400> SEQUENCE: 1611
acccaaccct gctatacaat tcca                                      24

<210> SEQ ID NO 1612
<211> LENGTH: 25
<212> TYPE: DNA
<213> ORGANISM: Homo sapiens

<400> SEQUENCE: 1612
acagtcagtg attggcacag agtaa                                     25

<210> SEQ ID NO 1613
<211> LENGTH: 20
<212> TYPE: DNA
<213> ORGANISM: Homo sapiens

<400> SEQUENCE: 1613
gaatgaaact ctgaggccgg                                           20

<210> SEQ ID NO 1614
<211> LENGTH: 26
<212> TYPE: DNA
<213> ORGANISM: Homo sapiens

<400> SEQUENCE: 1614
ccctcacttt ccttctactc ttcaag                                    26

<210> SEQ ID NO 1615
<211> LENGTH: 26
<212> TYPE: DNA
<213> ORGANISM: Homo sapiens

<400> SEQUENCE: 1615
gtcagagttg ccgataggtc ttgcta                                    26

<210> SEQ ID NO 1616
<211> LENGTH: 26
<212> TYPE: DNA
<213> ORGANISM: Homo sapiens

<400> SEQUENCE: 1616
acatctatct tgcccctcac tcaggt                                    26

<210> SEQ ID NO 1617
<211> LENGTH: 26
<212> TYPE: DNA
<213> ORGANISM: Homo sapiens

<400> SEQUENCE: 1617
atccaaacac aggacgagaa taaagc                                    26

<210> SEQ ID NO 1618
<211> LENGTH: 23
<212> TYPE: DNA
<213> ORGANISM: Homo sapiens

<400> SEQUENCE: 1618
tatcgtccag gaggcaaggg tcc                                       23

<210> SEQ ID NO 1619
```

```
<211> LENGTH: 26
<212> TYPE: DNA
<213> ORGANISM: Homo sapiens

<400> SEQUENCE: 1619
gatgaggtaa ccaaagttca gggaga                                        26

<210> SEQ ID NO 1620
<211> LENGTH: 26
<212> TYPE: DNA
<213> ORGANISM: Homo sapiens

<400> SEQUENCE: 1620
ctctctcctc atcctccctc ctaata                                        26

<210> SEQ ID NO 1621
<211> LENGTH: 26
<212> TYPE: DNA
<213> ORGANISM: Homo sapiens

<400> SEQUENCE: 1621
gggagccaga aagatagcaa tgccta                                        26

<210> SEQ ID NO 1622
<211> LENGTH: 23
<212> TYPE: DNA
<213> ORGANISM: Homo sapiens

<400> SEQUENCE: 1622
gaggaggaga aactcagaag ccc                                           23

<210> SEQ ID NO 1623
<211> LENGTH: 26
<212> TYPE: DNA
<213> ORGANISM: Homo sapiens

<400> SEQUENCE: 1623
gcacaagacc tcacattctg atgggc                                        26

<210> SEQ ID NO 1624
<211> LENGTH: 26
<212> TYPE: DNA
<213> ORGANISM: Homo sapiens

<400> SEQUENCE: 1624
ctctccttta tccctaccc tgctca                                         26

<210> SEQ ID NO 1625
<211> LENGTH: 23
<212> TYPE: DNA
<213> ORGANISM: Homo sapiens

<400> SEQUENCE: 1625
cagagaaagg gagtttggag ggc                                           23
```

-continued

```
<210> SEQ ID NO 1626
<211> LENGTH: 26
<212> TYPE: DNA
<213> ORGANISM: Homo sapiens

<400> SEQUENCE: 1626
ccccaaactc ccagacacat cagaga                                  26

<210> SEQ ID NO 1627
<211> LENGTH: 23
<212> TYPE: DNA
<213> ORGANISM: Homo sapiens

<400> SEQUENCE: 1627
agagggaaag gcaggtcgtg agc                                     23

<210> SEQ ID NO 1628
<211> LENGTH: 20
<212> TYPE: DNA
<213> ORGANISM: Homo sapiens

<400> SEQUENCE: 1628
gctggtctca aactcctggg                                         20

<210> SEQ ID NO 1629
<211> LENGTH: 25
<212> TYPE: DNA
<213> ORGANISM: Homo sapiens

<400> SEQUENCE: 1629
gggcatcttt cctcttattc aaggt                                   25

<210> SEQ ID NO 1630
<211> LENGTH: 25
<212> TYPE: DNA
<213> ORGANISM: Homo sapiens

<400> SEQUENCE: 1630
aggaaatagc ccaaatgcaa ctgaa                                   25

<210> SEQ ID NO 1631
<211> LENGTH: 21
<212> TYPE: DNA
<213> ORGANISM: Homo sapiens

<400> SEQUENCE: 1631
cccattcgtc tctctgagct g                                       21
```

CHROMOSOME BIOMARKER

CROSS-REFERENCE

This application is the National Phase application of International Application No. PCT/GB2019/052996, filed Oct. 21, 2019, claiming benefit of United Kingdom Application No. 1817181.9, filed Oct. 22, 2018 and United Kingdom Application No. 1904066.6, filed Mar. 25, 2019. These applications, in their entirety, are incorporated herein by reference.

FIELD OF THE INVENTION

The invention relates to detecting chromosome interactions.

BACKGROUND OF THE INVENTION

Physical performance is complex and cannot be predicted using available methods. It is clear coordination, flexibility, precision, power, speed, endurance, balance, awareness efficiency, and timing are relevant to performance.

SUMMARY OF THE INVENTION

The inventors have identified chromosomal interactions relevant to physical performance using an approach which analyses subgroups in a population. The inventors' work allows physical performance to be typed and modulated in an entirely new way which is more sensitive and personalised than genomic or protein typing, and which reflects the individual history of the individual. This has applications in fitness and physical training regimes, as well as in sports medicine.

Accordingly, the invention provides a process for detecting a chromosome state which represents a subgroup in a population comprising determining whether a chromosome interaction relating to that chromosome state is present or absent within a defined region of the genome, wherein said subgroup relates to physical performance in an individual; and wherein said chromosome interaction has optionally been identified by a method of determining which chromosomal interactions are relevant to a chromosome state corresponding to a physical performance subgroup of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to a physical performance subgroup; and wherein the chromosome interaction either:

(i) corresponds to any one of the chromosome interactions shown in any of Tables 3, 7, 8, 9, 25 and 30; and/or (ii) corresponds to any one of the chromosome interactions shown in any of Tables 13, 14, 18, 22, 23 and 24; and/or (iii) corresponds to any one of the chromosome interactions shown in Table 31 or 32; and/or (iv) is present in a 4,000 base region which comprises or which flanks (i), (ii) or (iii); and/or (v) is present in any one of the regions or genes listed in Table 21, 24, 25, 30, 31 or 32.

In a preferred embodiment, the invention provides a process for detecting a chromosome state which represents a subgroup in a population comprising determining whether a chromosome interaction relating to that chromosome state is present or absent within a defined region of the genome, wherein said subgroup relates to physical performance in an individual; and wherein the chromosome interaction either:

(a) corresponds to any one of the chromosome interactions shown in any of Tables 33, 34, 35, 36, 37, 38, 39, 40 or 41, or in any of FIG. 16, 17 or 18; and/or (b) is present in a 4,000 base region which comprises or which flanks (a).

DETAILED DESCRIPTION OF THE INVENTION

Aspects of the Invention

The inventions concerns a panel of epigenetic markers which relate to the regulation and stratification of physical performance, in particular strength and endurance. The markers are preferably stable and may allow detection of a predisposition in physiology to a specific stimulus, such as physical training.

The invention also includes monitoring of physical performance or responsiveness of physical performance to a specific stimulus, such as a specific training regimen. The invention therefore provides in one aspect a 'live' ongoing readout of physical performance status allowing a personalised stimulus to be given to the individual which reflects the individual's needs.

The inventions provided a method of selecting an individual for a given physical task, such as racing or specific training. The invention also provides a method of selecting or designing a training or fitness regime, for example for a specific individual.

The invention also provides methods of predicting physical performance, including whether an individual would have high strength or endurance or both, for example as measured in any specific way described herein.

The invention allows categorisation of individuals into 'fit', 'strong', or 'sedentary'. The invention allows stratification of 'baseline' individuals entering training programmes for better predisposition for either strength, or endurance-de facto predictive biomarkers for response. The invention also allows stratification of early biomarker evidence of response to training in individuals-de facto early response biomarkers for monitoring training progress.

Any marker disclosed herein may be used in the method of the invention, including any marker disclosed in any table or Figure. Preferred markers are shown in:

Tables 3, 7, 8, 9, 25 and 30; and

Tables 13, 14, 18, 22, 23 and 24; and

Table 31 or 32; and

Tables 33 to 41; and

FIGS. 16 to 18.

Physical Performance

The invention relates to determining physical performance. The process of the invention may detect responsiveness to a stimulus relating to physical performance, for example to training, such as strength or endurance training. The training typically comprises subjecting the individual to physical exertion, for example in terms of the applying force, moving physically, running or carrying out a specific physical activity (for example as disclosed herein) over a certain time period. The process of the invention may be used to detect a high or low response to the stimulus, such as a high or low response to any specific training or physical activity disclosed herein. Preferably the invention detects the response to strength or endurance training.

The invention can be used to select an individual suitable for a physical activity, such as a sport. Preferred sports including strength or endurance sports. A preferred endurance sport is racing or running. Thus the invention may be used to select an individual that is suited to any particular activity mentioned herein, such as training.

The Process of the Invention

The process of the invention comprises a typing system for detecting chromosome interactions relevant to physical performance. This typing may be performed using the EpiSwitch™ system mentioned herein which is based on cross-linking regions of chromosome which have come together in the chromosome interaction, subjecting the chromosomal DNA to cleavage and then ligating the nucleic acids present in the cross-linked entity to derive a ligated nucleic acid with sequence from both the regions which formed the chromosomal interaction. Detection of this ligated nucleic acid allows determination of the presence or absence of a particular chromosome interaction.

The chromosomal interactions may be identified using the above described method in which populations of first and second nucleic acids are used. These nucleic acids can also be generated using EpiSwitch™ technology.

The Epigenetic Interactions Relevant to the Invention

As used herein, the term 'epigenetic' and 'chromosome' interactions typically refer to interactions between distal regions of a chromosome, said interactions being dynamic and altering, forming or breaking depending upon the status of the region of the chromosome.

In particular processes of the invention chromosome interactions are typically detected by first generating a ligated nucleic acid that comprises sequence from both regions of the chromosomes that are part of the interactions. In such processes the regions can be cross-linked by any suitable means. In a preferred embodiment, the interactions are cross-linked using formaldehyde, but may also be cross-linked by any aldehyde, or D-Biotinoyl-e-aminocaproic acid-N-hydroxysuccinimide ester or Digoxigenin-3-O-methylcarbonyl-e-aminocaproic acid-N-hydroxysuccinimide ester. Para-formaldehyde can cross link DNA chains which are 4 Angstroms apart. Preferably the chromosome interactions are on the same chromosome and optionally 2 to 10 Angstroms apart.

The chromosome interaction may reflect the status of the region of the chromosome, for example, if it is being transcribed or repressed. Chromosome interactions which are specific to subgroups as defined herein have been found to be stable, thus providing a reliable means of measuring the differences between the two subgroups.

In addition, chromosome interactions specific to a characteristic (such as physical performance) will normally occur early in a biological process, for example compared to other epigenetic markers such as methylation or changes to binding of histone proteins, and are also capable of providing a 'live' readout of the status of the individual. Thus the process of the invention is able to detect early stages of a biological process as well as allowing continuous monitoring. Chromosome interactions also reflect the current state of the individual and therefore can be used to assess changes to physical performance. Furthermore there is little variation in the relevant chromosome interactions between individuals within the same subgroup. Detecting chromosome interactions is highly informative with up to 50 different possible interactions per gene, and so processes of the invention can interrogate 500,000 different interactions.

Preferred Marker Sets

Herein the term 'marker' or 'biomarker' refers to a specific chromosome interaction which can be detected (typed) in the invention. Specific markers are disclosed herein, any of which may be used in the invention or any of which may be used in any combination with other specific markers or combinations disclosed herein. Preferably sets of markers may be used, for example in the combinations or numbers disclosed herein. The specific markers disclosed in the tables herein are preferred as well as markers presents in genes and regions mentioned in the tables herein are preferred. These may be typed by any suitable method, for example the PCR or probe based methods disclosed herein, including a qPCR method. The markers are defined herein by location or by probe and/or primer sequences.

Location and Causes of Epigenetic Interactions

Epigenetic chromosomal interactions may overlap and include the regions of chromosomes shown to encode relevant or undescribed genes, but equally may be in intergenic regions. The chromosome interactions which are detected in the invention could be caused by changes to the underlying DNA sequence, by environmental factors, DNA methylation, non-coding antisense RNA transcripts, non-mutagenic carcinogens, histone modifications, chromatin remodelling and specific local DNA interactions. The changes which lead to the chromosome interactions may be caused by changes to the underlying nucleic acid sequence, which themselves do not directly affect a gene product or the mode of gene expression. Such changes may be for example, SNPs within and/or outside of the genes, gene fusions and/or deletions of intergenic DNA, microRNA, and non-coding RNA. For example, it is known that roughly 20% of SNPs are in non-coding regions, and therefore the process as described is also informative in non-coding situation. In one embodiment the regions of the chromosome which come together to form the interaction are less than 5 kb, 3 kb, 1 kb, 500 base pairs or 200 base pairs apart on the same chromosome.

The chromosome interaction which is detected is preferably within any of the genes mentioned in Table 21. However it may also be upstream, for example up to 50,000, up to 30,000, up to 20,000, up to 10,000 or up to 5000 bases upstream from the gene. It may be downstream, for example up to 50,000, up to 30,000, up to 20,000, up to 10,000 or up to 5000 bases downstream from the gene. It may be upstream or downstream from coding sequences, for example by any of these specific numbers of bases.

Subgroups, Time Points and Personalisation

One aim of the present invention is to determine a characteristic relevant to physical performance. This may be at one or more defined time points for the same individual, for example at at least 1, 2, 5, 8 or 10 different time points. The durations between the time points may be at least 20, 50, 80 or 100 days. Typically testing of the individual (by the process of the invention) may occur before a physical stimulus is applied, or during or after. The testing may determine the predisposition to certain types of response, or the actual response to the stimulus.

As used herein, a "subgroup" preferably refers to a population subgroup (a subgroup in a population), more preferably a subgroup in the population of a human or horse population. The invention includes detecting and applying a physical stimulus to particular subgroups in a population. The inventors have discovered that chromosome interactions differ between subsets (for example at least two subsets) in a given population. Identifying these differences will allow categorisation of individuals and this allows personalised stimuli to be given, such a personalised training, or allows selection of the individual for particular physical activities.

Generating Ligated Nucleic Acids

Certain embodiments of the invention utilise ligated nucleic acids, in particular ligated DNA. These comprise sequences from both of the regions that come together in a chromosome interaction and therefore provide information about the interaction. The EpiSwitch™ method described herein uses generation of such ligated nucleic acids to detect chromosome interactions.

Thus a process of the invention may comprise a step of generating ligated nucleic acids (e.g. DNA) by the following steps (including a method comprising these steps):

(i) cross-linking of epigenetic chromosomal interactions present at the chromosomal locus, preferably in vitro;

(ii) optionally isolating the cross-linked DNA from said chromosomal locus;

(iii) subjecting said cross-linked DNA to cutting, for example by restriction digestion with an enzyme that cuts it at least once (in particular an enzyme that cuts at least once within said chromosomal locus);

(iv) ligating said cross-linked cleaved DNA ends (in particular to form DNA loops); and (v) optionally identifying the presence of said ligated DNA and/or said DNA loops, in particular using techniques such as PCR (polymerase chain reaction), to identify the presence of a specific chromosomal interaction.

These steps may be carried out to detect the chromosome interactions for any embodiment mentioned herein. The steps may also be carried out to generate the first and/or second set of nucleic acids mentioned herein.

PCR (polymerase chain reaction) may be used to detect or identify the ligated nucleic acid, for example the size of the PCR product produced may be indicative of the specific chromosome interaction which is present, and may therefore be used to identify the status of the locus. In preferred embodiments at least 1, 2 or 3 primers or primer pairs as shown in Table 24, 25 or 30 are used in the PCR reaction. In other preferred embodiments at least 1, 2 or 3 primers or primer pairs as shown in Table 31 or 32 are used in the PCR reaction. The skilled person will be aware of numerous restriction enzymes which can be used to cut the DNA within the chromosomal locus of interest. It will be apparent that the particular enzyme used will depend upon the locus studied and the sequence of the DNA located therein. A non-limiting example of a restriction enzyme which can be used to cut the DNA as described in the present invention is Taql.

Embodiments such as EpiSwitch™ Technology

The EpiSwitch™ Technology also relates to the use of microarray EpiSwitch™ marker data in the detection of epigenetic chromosome conformation signatures specific for phenotypes. Embodiments such as EpiSwitch™ which utilise ligated nucleic acids in the manner described herein have several advantages. They have a low level of stochastic noise, for example because the nucleic acid sequences from the first set of nucleic acids of the present invention either hybridise or fail to hybridise with the second set of nucleic acids. This provides a binary result permitting a relatively simple way to measure a complex mechanism at the epigenetic level. EpiSwitch™ technology also has fast processing time and low cost. In one embodiment the processing time is 3 hours to 6 hours.

Samples and Sample Treatment

The process of the invention will normally be carried out on a sample. The sample may be obtained at a defined time point, for example at any time point defined herein. The sample will normally contain DNA from the individual. It will normally contain cells. In one embodiment a sample is obtained by minimally invasive means and may for example be a blood sample. DNA may be extracted and cut up with a standard restriction enzyme. This can pre-determine which chromosome conformations are retained and will be detected with the EpiSwitch™ platforms. Due to the synchronisation of chromosome interactions between tissues and blood, including horizontal transfer, a blood sample can be used to detect the chromosome interactions in tissues.

Properties of Nucleic Acids of the Invention

The invention relates to certain nucleic acids, such as the ligated nucleic acids which are described herein as being used or generated in the process of the invention. These may be the same as, or have any of the properties of, the first and second nucleic acids mentioned herein. The nucleic acids of the invention typically comprise two portions each comprising sequence from one of the two regions of the chromosome which come together in the chromosome interaction. Typically each portion is at least 8, 10, 15, 20, 30 or 40 nucleotides in length, for example 10 to 40 nucleotides in length. Preferred nucleic acids comprise sequence from any of the genes mentioned in any of the tables, including Table 21. Typically preferred nucleic acids comprise the specific probe sequences mentioned in Table 24, 25 or 30; or fragments and/or homologues of such sequences. Preferred nucleic acids also comprise the specific probe sequences mentioned in Table 31 or 32; or fragments and/or homologues of such sequences. Preferably the nucleic acids are DNA. It is understood that where a specific sequence is provided the invention may use the complementary sequence as required in the particular embodiment.

The primers shown in Table 24, 25 or 30 may also be used in the invention as mentioned herein. In one embodiment primers are used which comprise any of: the sequences shown in Table 24, 25 or 30; or fragments and/or homologues of any sequence shown in Table 24, 25 or 30.

The primers shown in Table 31 or 32 may also be used in the invention as mentioned herein. In one embodiment primers are used which comprise any of: the sequences shown in Table 31 or 32; or fragments and/or homologues of any sequence shown in Table 31 or 32.

The Second Set of Nucleic Acids—the 'Index' Sequences

The second set of nucleic acid sequences has the function of being a set of index sequences, and is essentially a set of nucleic acid sequences which are suitable for identifying subgroup specific sequence. They can represents the 'background' chromosomal interactions and might be selected in some way or be unselected. They are in general a subset of all possible chromosomal interactions.

The second set of nucleic acids may be derived by any suitable process. They can be derived computationally or they may be based on chromosome interaction in individuals. They typically represent a larger population group than the first set of nucleic acids. In one particular embodiment, the second set of nucleic acids represents all possible epigenetic chromosomal interactions in a specific set of genes. In another particular embodiment, the second set of nucleic acids represents a large proportion of all possible epigenetic chromosomal interactions present in a population described herein. In one particular embodiment, the second set of nucleic acids represents at least 50% or at least 80% of epigenetic chromosomal interactions in at least 20, 50, 100 or 500 genes, for example in 20 to 100 or 50 to 500 genes.

The second set of nucleic acids typically represents at least 100 possible epigenetic chromosome interactions which modify, regulate or in any way mediate a phenotype in population. The second set of nucleic acids may represent chromosome interactions that affect a physical characteristic. The second set of nucleic acids typically comprises sequences representing epigenetic interactions both relevant and not relevant to a physical performance subgroup.

In one particular embodiment the second set of nucleic acids derive at least partially from naturally occurring sequences in a population, and are typically obtained by in silico processes. Said nucleic acids may further comprise single or multiple mutations in comparison to a corresponding portion of nucleic acids present in the naturally occurring nucleic acids. Mutations include deletions, substitutions and/or additions of one or more nucleotide base pairs. In one particular embodiment, the second set of nucleic acids may comprise sequence representing a homologue and/or ortho-logue with at least 70% sequence identity to the corresponding portion of nucleic acids present in the naturally occurring species. In another particular embodiment, at least 80% sequence identity or at least 90% sequence identity to the corresponding portion of nucleic acids present in the naturally occurring species is provided.

Properties of the Second Set of Nucleic Acids

In one particular embodiment, there are at least 100 different nucleic acid sequences in the second set of nucleic acids, preferably at least 1000, 2000 or 5000 different nucleic acids sequences, with up to 100,000, 1,000,000 or 10,000,000 different nucleic acid sequences. A typical number would be 100 to 1,000,000, such as 1,000 to 100,000 different nucleic acids sequences. All or at least 90% or at least 50% or these would correspond to different chromosomal interactions.

In one particular embodiment, the second set of nucleic acids represent chromosome interactions in at least 20 different loci or genes, preferably at least 40 different loci or genes, and more preferably at least 100, at least 500, at least 1000 or at least 5000 different loci or genes, such as 100 to 10,000 different loci or genes. The lengths of the second set of nucleic acids are suitable for them to specifically hybri-dise according to Watson Crick base pairing to the first set of nucleic acids to allow identification of chromosome interactions specific to subgroups. Typically the second set of nucleic acids will comprise two portions corresponding in sequence to the two chromosome regions which come together in the chromosome interaction. The second set of nucleic acids typically comprise nucleic acid sequences which are at least 10, preferably 20, and preferably still 30 bases (nucleotides) in length. In another embodiment, the nucleic acid sequences may be at the most 500, preferably at most 100, and preferably still at most 50 base pairs in length. In a preferred embodiment, the second set of nucleic acids comprises nucleic acid sequences of between 17 and 25 base pairs. In one embodiment at least 100, 80% or 50% of the second set of nucleic acid sequences have lengths as described above. Preferably the different nucleic acids do not have any overlapping sequences, for example at least 100%, 90%, 80% or 50% of the nucleic acids do not have the same sequence over at least 5 contiguous nucleotides.

Given that the second set of nucleic acids acts as an 'index' then the same set of second nucleic acids may be used with different sets of first nucleic acids which represent subgroups for different characteristics, i.e. the second set of nucleic acids may represent a 'universal' collection of nucleic acids which can be used to identify chromosome interactions relevant to different characteristics.

The First Set of Nucleic Acids

The first set of nucleic acids are typically from subgroups relevant to physical performance. The first nucleic acids may have any of the characteristics and properties of the second set of nucleic acids mentioned herein. The first set of nucleic acids is normally derived from samples from the individuals which have undergone treatment and processing as described herein, particularly the EpiSwitch™ cross-linking and cleaving steps. Typically the first set of nucleic acids represents all or at least 80% or 50% of the chromosome interactions present in the samples taken from the individu-als.

Typically, the first set of nucleic acids represents a smaller population of chromosome interactions across the loci or genes represented by the second set of nucleic acids in comparison to the chromosome interactions represented by second set of nucleic acids, i.e. the second set of nucleic acids is representing a background or index set of interac-tions in a defined set of loci or genes.

Library of Nucleic Acids

Any of the types of nucleic acid populations mentioned herein may be present in the form of a library comprising at least 200, at least 500, at least 1000, at least 5000 or at least 10000 different nucleic acids of that type, such as 'first' or 'second' nucleic acids. Such a library may be in the form of being bound to an array. A library may for example comprise all of the nucleic acids disclosed in any table disclosed herein, or all of the probe sequences disclosed in any table herein.

Hybridisation

The invention requires a means for allowing wholly or partially complementary nucleic acid sequences from the first set of nucleic acids and the second set of nucleic acids to hybridise. In one embodiment all of the first set of nucleic acids is contacted with all of the second set of nucleic acids in a single assay, i.e. in a single hybridisation step. However any suitable assay can be used.

Labelled Nucleic Acids and Pattern of Hybridisation

The nucleic acids mentioned herein may be labelled, preferably using an independent label such as a fluorophore (fluorescent molecule) or radioactive label which assists detection of successful hybridisation. Certain labels can be detected under UV light. The pattern of hybridisation, for example on an array described herein, represents differences in epigenetic chromosome interactions between the two subgroups, and thus provides a process of comparing epi-genetic chromosome interactions and determination of which epigenetic chromosome interactions are specific to a subgroup in the population of the present invention.

The term 'pattern of hybridisation' broadly covers the presence and absence of hybridisation between the first and second set of nucleic acids, i.e. which specific nucleic acids from the first set hybridise to which specific nucleic acids from the second set, and so it not limited to any particular assay or technique, or the need to have a surface or array on which a 'pattern' can be detected.

Selecting a Subgroup with Particular Characteristics

The invention provides a process which comprises detect-ing the presence or absence of chromosome interactions, typically 5 to 20 or 5 to 500 such interactions, preferably 20 to 300 or 50 to 100 interactions, in order to determine the presence or absence of a characteristic relating to physical performance in an individual. Preferably the chromosome interactions are those in any of the genes mentioned herein or in any Table herein. In one embodiment the chromosome interactions which are typed are those represented in any of Tables 3, 7, 8, 9, 25 and 30. In another embodiment the chromosome interactions are those represented in any of Tables 13, 14, 18, 22, 23 and 24. In a preferred embodiment the chromosome interactions which are typed are those represented in Table 31 or 32. In one embodiment the chromosome interactions which are typed are those from any of Tables 33, 34, 35, 36, 37, 38, 39 or 40 or in any of FIG. 16, 17 or 18. The relevant chromosome interaction may be present or absent for a given characteristic, and therefore either presence or absence of the interaction will indicate the presence of the characteristic.

The Individual that is Tested

The individual that is tested is preferably a human or horse. The human be an athlete or sportsman. The human is typically 30 years old or less. The horse may be any type of horse mentioned herein, such as a Thoroughbred. The horse may be racing horse. The horse may be one which is not a racing horse, but which optionally is being considered for selection as a race horse. The horse may be less than 500 days old, such as less than 200 or less than 100 days old.

Preferred Gene Regions, Loci, Genes and Chromosome Interactions

For all aspects of the invention preferred gene regions, loci, genes and chromosome interactions are mentioned in the tables, for example in any of Tables 3, 7, 8, 9, 25 and 30 (preferably for typing humans) or in any of Tables 13, 14, 18, 22, 23 and 24 (preferably for typing horses), or in Table 31 or 32 (preferably for typing humans). Typically in the processes of the invention chromosome interactions are detected from at least 1, 2, 10, 30 or 50 genes listed in Table 21. The chromosome interaction may be upstream or downstream of any of the genes mentioned herein, for example 50 kb upstream or 20 kb downstream, for example from the coding sequence.

In one embodiment at least 5, 10 or all of the chromosome interactions of Table 3 are typed. In one embodiment at least the interactions with the top 5 or 10 highest odds ratio of Table 3 are typed.

In one embodiment at least 5, 10, 15 or all of the chromosome interactions in Table 7 are typed. In one embodiment at least the interactions with the smallest 5, 10 or 15 mean p values of Table 7 are typed.

In one embodiment at least 5, 10, 15, 20 or all of the chromosome interactions in Table 8 are typed. In one embodiment at least the interactions with the smallest 5, 10, 15 or 20 mean p values of Table 8 are typed.

In one embodiment at least 5, 10, 15, 20 or all of the chromosome interactions in Table 9 are typed. In one embodiment at least the interactions with the smallest 5, 10, 15 or 20 mean p values of Table 9 are typed.

In one embodiment at least 5, 10, 15 or all of the chromosome interactions in Table 13 are typed. In one embodiment at least the interactions with the smallest 5 or 10 Exact Boschloo p value of Table 13 are typed.

In one embodiment at least 5, 10, 15 or all of the chromosome interactions in Table 14 are typed.

In one embodiment at least 5, 10, 20, 30 or all of the chromosome interactions in Table 18 are typed. In one embodiment at least the interactions with the smallest 5, 10, 20 or 30 Exact Boschloo p value of Table 18 are typed.

In one embodiment at least 5, 10 or all of the chromosome interactions of Table 22 are typed. In one embodiment at least the interactions with the top 5 or 10 highest odds ratio of Table 22 are typed.

In one embodiment at least 5, 10, 15 or all of the chromosome interactions of Table 23 are typed.

In one embodiment at least 5, 10, 20, 30 or all of the chromosome interactions of Table 24 are typed. In one embodiment at least the interactions with the top 5, 10, 20, 30 GLMNET values of Table 24 are typed.

In one embodiment at least 5, 10, 20, 30, 40, 50 or all of the chromosome interactions of Table 25 are typed. In one embodiment at least the interactions with the smallest 5, 10, 20, 30, 40, 50 adjusted p values of Table 25 are typed. In one embodiment at least the markers numbered 1 to 30 in Table 25 are typed. In another at least the markers numbers 31 to 77 in Table 25 are typed.

In one embodiment at least 5, 10, 20, 30, 40, 50, 150, 180 or all of the chromosome interactions of Table 30 are typed. In one embodiment at least the interactions with the smallest 5, 10, 20, 30, 40, 50, 150, or 180 adjusted p values of Table 30 are typed. In one embodiment at least the markers numbered 1 to 50 in Table 30 are typed. In another embodiment at least the markers numbered 51 to 100 in Table 30 are typed. In another embodiment at least the markers numbered 101 to 150 in Table 30 are typed. In one embodiment at least the markers numbered 151 to 202 in Table 30 are typed.

In one embodiment at least 5, 10 or all of the chromosome interactions of Table 31 are typed.

In one embodiment at least 5 or all of the chromosome interactions of Table 32 are typed.

In one embodiment at least 5, 10, 20, 30, 40, 50, 150, 180, 200, 250 or all of the chromosome interactions of Table 33 are typed. In one embodiment at least the interactions with the smallest 5, 10, 20, 30, 40, 50, 150, 180 or 250 adjusted p values of Table 33 are typed. In one embodiment at least the markers numbered 1 to 50 in Table 33 are typed. In another embodiment at least the markers numbered 51 to 100 in Table 33 are typed. In another embodiment at least the markers numbered 101 to 150 in Table 33 are typed. In one embodiment at least the markers numbered 151 to 202 in Table 33 are typed. In one embodiment at least the markers numbered 202 to 320 in Table 33 are typed.

In one embodiment at least 5, 10, 20, 30, 40, 50 or all of the chromosome interactions of Table 34 are typed.

In one embodiment at least 5, 10, 20, 30 or all of the chromosome interactions of Table 35 are typed.

In one embodiment at least 5, 10, 15 or all of the chromosome interactions of Table 36 are typed.

In one embodiment at least 5, 10, 20, 30, 40, 50, 150, 180 or all of the chromosome interactions of Table 37 are typed. In one embodiment at least the interactions with the smallest 5, 10, 20, 30, 40, 50, 150, or 180 adjusted p values of Table 37 are typed. In one embodiment at least the markers numbered 1 to 50 in Table 37 are typed. In another embodiment at least the markers numbered 51 to 100 in Table 37 are typed. In another embodiment at least the markers numbered 101 to 150 in Table 37 are typed. In one embodiment at least the markers numbered 151 to 202 in Table 37 are typed.

In one embodiment at least 5, 10 or all of the chromosome interactions of Table 38 are typed.

In one embodiment at least 5 or all of the chromosome interactions of Table 39 are typed.

In one embodiment at least 5, 10 or all of the chromosome interactions of Table 40 are typed. In one embodiment at least the 3 'shared' chromosome interactions of Table 40 are typed. In one embodiment at least the 7 'strength' chromosome interactions of Table 40 are typed.

In one embodiment at least 5, 10, 20, 30, 40, 50 or all of the chromosome interactions of Table 41 are typed. In one embodiment at least the interactions with the smallest 5, 10, 20, 30, 40, 50 adjusted p values of Table 41 are typed. In one embodiment at least the markers numbered 1 to 30 in Table 41 are typed. In another at least the markers numbers 31 to 77 in Table 41 are typed. [Table 41 is shown in abbreviated form to avoid duplicating information from Table 25 which relates to the same marker set. It is understood that smallest p values mentioned here can be obtained from Table 25]

In one embodiment at least 5, 8 or all of the chromosome interactions of FIG. 16 are typed.

In one embodiment at least 5, 10 or all of the chromosome interactions of FIG. 17 are typed.

In one embodiment at least 5, 8 or all of the chromosome interactions of FIG. 18 are typed.

Typically at least 5, 10, 15, 20, 30, 40 or 70 chromosome interactions are typed from any of genes or regions disclosed the tables herein, or parts of tables disclosed herein. Typically the chromosome interactions which are typed are present in at least 20, 50 or all of the genes mentioned in Table 21.

For all aspects of the invention preferred gene regions, loci, genes and chromosome interactions are mentioned in Tables 24 and 30.

In one embodiment the locus (including the gene and/or place where the chromosome interaction is detected) may comprise a CTCF binding site. This is any sequence capable of binding transcription repressor CTCF. That sequence may consist of or comprise the sequence CCCTC which may be present in 1, 2 or 3 copies at the locus. The CTCF binding site sequence may comprise the sequence CCGCGNGG-NGGCAG (SEQ ID NO:1) (in IUPAC notation). The CTCF binding site may be within at least 100, 500, 1000 or 4000 bases of the chromosome interaction or within any of the chromosome regions shown Table 24 or 30.

Thus typically sequence from both regions of the probe (i.e. from both sites of the chromosome interaction) could be detected. In preferred embodiments probes are used in the process which comprise or consist of the same or complementary sequence to a probe shown in any table. In some embodiments probes are used which comprise sequence which is homologous to any of the probe sequences shown in the tables.

Tables Provided Herein

The tables show probe (Episwitch™ marker) data and gene data representing chromosome interactions relevant to physical performance. The probe sequences show sequence which can be used to detect a ligated product generated from both sites of gene regions that have come together in chromosome interactions, i.e. the probe will comprise sequence which is complementary to sequence in the ligated product. The first two sets of Start-End positions show probe positions, and the second two sets of Start-End positions show the relevant 4 kb region. The following information is provided in the probe data table:

HyperG_Stats: p-value for the probability of finding that number of significant EpiSwitch™ markers in the locus based on the parameters of hypergeometric enrichment Probe Count Total: Total number of EpiSwitch™ Conformations tested at the locus Probe Count Sig: Number of EpiSwitch™ Conformations found to be statistically significant at the locus FDR HyperG: Multi-test (Fimmunoresposivenesse Discovery Rate) corrected hypergeometric p-value Percent Sig: Percentage of significant EpiSwitch™ markers relative the number of markers tested at the locus logFC: logarithm base 2 of Epigenetic Ratio (FC)

AveExpr: average log 2-expression for the probe over all arrays and channels

T: moderated t-statistic p-value: raw p-value adj. p-value: adjusted p-value or q-value B-B-statistic (lods or B) is the log-odds that that gene is differentially expressed.

FC-non-log Fold Change

FC_1-non-log Fold Change centred around zero

LS-Binary value this relates to FC_1 values. FC_1 value below-1.1 it is set to −1 and if the FC_1 value is above 1.1 it is set to 1. Between those values the value is 0

The tables also shows genes where a relevant chromosome interaction has been found to occur. The p-value in the loci table is the same as the HyperG_Stats (p-value for the probability of finding that number of significant EpiSwitch™ markers in the locus based on the parameters of hypergeometric enrichment).

The probes are designed to be 30 bp away from the Taq1 site. In case of PCR, PCR primers are typically designed to detect ligated product but their locations from the Taq1 site vary.

Probe locations:

Start 1-30 bases upstream of Taql site on fragment 1

End 1-Taql restriction site on fragment 1

Start 2-Taql restriction site on fragment 2

End 2-30 bases downstream of Taql site on fragment 2

4 kb Sequence Location:

Start 1-4000 bases upstream of Taql site on fragment 1

End 1-Taql restriction site on fragment 1

Start 2-Taql restriction site on fragment 2

End 2-4000 bases downstream of Taql site on fragment 2

GLMNET values related to procedures for fitting the entire lasso or elastic-net regularization (Lambda set to 0.5 (elastic-net)).

Preferred Embodiments for Sample Preparation and Chromosome Interaction Detection Methods of preparing samples and detecting chromosome conformations are described herein. Optimised (non-conventional) versions of these methods can be used, for example as described in this section.

Typically the sample will contain at least $2 \times 10^5$ cells. The sample may contain up to $5 \times 10^5$ cells. In one embodiment, the sample will contain $2 \times 10^5$ to $5.5 \times 10^5$ cells Crosslinking of epigenetic chromosomal interactions present at the chromosomal locus is described herein. This may be performed before cell lysis takes place. Cell lysis may be performed for 3 to 7 minutes, such as 4 to 6 or about 5 minutes. In some embodiments, cell lysis is performed for at least 5 minutes and for less than 10 minutes.

Digesting DNA with a restriction enzyme is described herein. Typically, DNA restriction is performed at about 55° C. to about 70° C., such as for about 65° C., for a period of about 10 to 30 minutes, such as about 20 minutes.

Preferably a frequent cutter restriction enzyme is used which results in fragments of ligated DNA with an average fragment size up to 4000 base pair. Optionally the restriction enzyme results in fragments of ligated DNA have an average fragment size of about 200 to 300 base pairs, such as about 256 base pairs.

In one embodiment, the typical fragment size is from 200 base pairs to 4,000 base pairs, such as 400 to 2,000 or 500 to 1,000 base pairs.

In one embodiment of the EpiSwitch method a DNA precipitation step is not performed between the DNA restriction digest step and the DNA ligation step.

DNA ligation is described herein. Typically the DNA ligation is performed for 5 to 30 minutes, such as about 10 minutes.

The protein in the sample may be digested enzymatically, for example using a proteinase, optionally Proteinase K. The protein may be enzymatically digested for a period of about 30 minutes to 1 hour, for example for about 45 minutes. In one embodiment after digestion of the protein, for example Proteinase K digestion, there is no cross-link reversal or phenol DNA extraction step. In one embodiment PCR detection is capable of detecting a single copy of the ligated nucleic acid, preferably with a binary read-out for presence/absence of the ligated nucleic acid.

FIG. 14 shows a preferred method of detecting chromosome interactions.

PROCESSES AND USES OF THE INVENTION

The process of the invention can be described in different ways. It can be described as a method of making a ligated nucleic acid comprising (i) in vitro cross-linking of chromosome regions which have come together in a chromosome interaction; (ii) subjecting said cross-linked DNA to cutting or restriction digestion cleavage; and (iii) ligating said cross-linked cleaved DNA ends to form a ligated nucleic acid, wherein detection of the ligated nucleic acid may be used to determine the chromosome state at a locus, and wherein preferably:

the locus may be any of the loci, regions or genes mentioned in any table, and/or wherein the chromosomal interaction may be any of the chromosome interactions mentioned herein or corresponding to any of the probes disclosed in any table, and/or wherein the ligated product may have or comprise (i) sequence which is the same as or homologous to any of the probe sequences disclosed in any table herein; or (ii) sequence which is complementary to (ii).

The process of the invention can be described as a process for detecting chromosome states which represent different subgroups in a population comprising determining whether a chromosome interaction is present or absent within a defined epigenetically active region of the genome, wherein preferably:

the subgroup is defined by presence or absence of physical performance, and/or the chromosome state may be at any locus, region or gene mentioned in any table; and/or the chromosome interaction may be any of those mentioned in any table or corresponding to any of the probes disclosed in that table.

The process of the invention can be described as a method of making a ligated nucleic acid comprising (i) in vitro cross-linking of chromosome regions which have come together in a chromosome interaction; (ii) subjecting said cross-linked DNA to cutting or restriction digestion cleavage; and (iii) ligating said cross-linked cleaved DNA ends to form a ligated nucleic acid, wherein detection of the ligated nucleic acid may be used to determine the chromosome state at a locus, and wherein preferably:

the locus may be any of the loci, regions or genes mentioned in any table, and/or wherein the chromosomal interaction may be any of the chromosome interactions mentioned herein or corresponding to any of the probes disclosed in any table, and/or wherein the ligated product may have or comprise (i) sequence which is the same as or homologous to any of the probe sequences disclosed in any table; or (ii) sequence which is complementary to (ii).

The process of the invention can be described as a process for detecting chromosome states which represent different subgroups in a population comprising determining whether a chromosome interaction is present or absent within a defined epigenetically active region of the genome, wherein preferably:

the subgroup is defined by presence or absence of physical performance, and/or the chromosome state may be at any locus, region or gene mentioned in any table; and/or the chromosome interaction may be any of those mentioned in any table or corresponding to any of the probes disclosed in that table.

The invention includes detecting chromosome interactions at any locus, gene or regions mentioned in any table, such as Table 24 or 30. The invention includes use of the nucleic acids and probes mentioned herein to detect chromosome interactions, for example use of at least 1, 5, 10, 50, 100 such nucleic acids or probes to detect chromosome interactions, preferably in at least 1, 5, 10, 50, 100 different loci or genes.

The invention includes detection of chromosome interactions using any of the primers or primer pairs listed in Table 24 or 30 or using variants of these primers as described herein (sequences comprising the primer sequences or comprising fragments and/or homologues of the primer sequences).

The invention includes detecting chromosome interactions at any locus, gene or regions mentioned Table 24 or 30. The invention includes use of the nucleic acids and probes mentioned herein to detect chromosome interactions, for example use of at least 1, 5, 10, 50, 100, 200, 250, 300 such nucleic acids or probes to detect chromosome interactions, preferably in at least 1, 5, 10, 50, 100, 200, 250, 300 different loci or genes. The invention includes detection of chromosome interactions using any of the primers or primer pairs listed in Table 24 or 30 or using variants of these primers as described herein (sequences comprising the primer sequences or comprising fragments and/or homologues of the primer sequences).

When analysing whether a chromosome interaction occurs 'within' a defined gene, region or location, either both the parts of the chromosome which have together in the interaction are within the defined gene, region or location or in some embodiments only one part of the chromosome is within the defined, gene, region or location.

Use of the Method of the Invention to Identify New Training or Fitness Regimens

Knowledge of chromosome interactions can be used to identify new fitness or training regimens. The invention provides methods and uses of chromosomes interactions defined herein to identify or design new agents.

Homologues

Homologues of polynucleotide/nucleic acid (e.g. DNA) sequences are referred to herein. Such homologues typically have at least 70% homology, preferably at least 80%, at least 85%, at least 90%, at least 95%, at least 97%, at least 98% or at least 99% homology, for example over a region of at least 10, 15, 20, 30, 100 or more contiguous nucleotides, or across the portion of the nucleic acid which is from the region of the chromosome involved in the chromosome interaction. The homology may be calculated on the basis of nucleotide identity (sometimes referred to as "hard homology").

Therefore, in a particular embodiment, homologues of polynucleotide/nucleic acid (e.g. DNA) sequences are referred to herein by reference to percentage sequence identity. Typically such homologues have at least 70% sequence identity, preferably at least 80%, at least 85%, at least 90%, at least 95%, at least 97%, at least 98% or at least 99% sequence identity, for example over a region of at least 10, 15, 20, 30, 100 or more contiguous nucleotides, or across the portion of the nucleic acid which is from the region of the chromosome involved in the chromosome interaction.

For example the UWGCG Package provides the BEST-FIT program which can be used to calculate homology and/or % sequence identity (for example used on its default settings) (Devereux et al (1984) Nucleic Acids Research 12, p 387-395). The PILEUP and BLAST algorithms can be used to calculate homology and/or % sequence identity and/or line up sequences (such as identifying equivalent or corresponding sequences (typically on their default settings)), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W5 T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, $M=5$, $N=4$, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P (N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by 1, 2, 3, 4 or more bases, such as less than 10, 15 or 20 bases (which may be substitutions, deletions or insertions of nucleotides).

These changes may be measured across any of the regions mentioned above in relation to calculating homology and/or % sequence identity.

Homology of a 'pair of primers' can be calculated, for example, by considering the two sequences as a single sequence (as if the two sequences are joined together) for the purpose of then comparing against the another primer pair which again is considered as a single sequence.

Arrays

The second set of nucleic acids may be bound to an array, and in one embodiment there are at least 15,000, 45,000, 100,000 or 250,000 different second nucleic acids bound to the array, which preferably represent at least 300, 900, 2000 or 5000 loci. In one embodiment one, or more, or all of the different populations of second nucleic acids are bound to more than one distinct region of the array, in effect repeated on the array allowing for error detection. The array may be based on an Agilent SurePrint G3 Custom CGH microarray platform. Detection of binding of first nucleic acids to the array may be performed by a dual colour system.

Forms of the Substance Mentioned Herein

Any of the substances, such as nucleic acids or therapeutic agents, mentioned herein may be in purified or isolated form. They may be in a form which is different from that found in nature, for example they may be present in combination with other substance with which they do not occur in nature. The nucleic acids (including portions of sequences defined herein) may have sequences which are different to those found in nature, for example having at least 1, 2, 3, 4 or more nucleotide changes in the sequence as described in the section on homology. The nucleic acids may have heterologous sequence at the 5' or 3' end. The nucleic acids may be chemically different from those found in nature, for example they may be modified in some way, but preferably are still capable of Watson-Crick base pairing. Where appropriate the nucleic acids will be provided in double stranded or single stranded form. The invention provides all of the specific nucleic acid sequences mentioned herein in single or double stranded form, and thus includes the complementary strand to any sequence which is disclosed.

The invention provides a kit for carrying out any process of the invention, including detection of a chromosomal interaction relating to physical performance. Such a kit can include a specific binding agent capable of detecting the relevant chromosomal interaction, such as agents capable of detecting a ligated nucleic acid generated by processes of the invention. Preferred agents present in the kit include probes capable of hybridising to the ligated nucleic acid or primer pairs, for example as described herein, capable of amplifying the ligated nucleic acid in a PCR reaction.

The invention provides a device that is capable of detecting the relevant chromosome interactions. The device preferably comprises any specific binding agents, probe or primer pair capable of detecting the chromosome interaction, such as any such agent, probe or primer pair described herein.

Detection Methods

In one embodiment quantitative detection of the ligated sequence which is relevant to a chromosome interaction is carried out using a probe which is detectable upon activation during a PCR reaction, wherein said ligated sequence comprises sequences from two chromosome regions that come together in an epigenetic chromosome interaction, wherein said method comprises contacting the ligated sequence with the probe during a PCR reaction, and detecting the extent of activation of the probe, and wherein said probe binds the ligation site. The method typically allows particular interactions to be detected in a MIQE compliant manner using a dual labelled fluorescent hydrolysis probe.

The probe is generally labelled with a detectable label which has an inactive and active state, so that it is only detected when activated. The extent of activation will be related to the extent of template (ligation product) present in the PCR reaction. Detection may be carried out during all or some of the PCR, for example for at least 50% or 80% of the cycles of the PCR.

The probe can comprise a fluorophore covalently attached to one end of the oligonucleotide, and a quencher attached to the other end of the nucleotide, so that the fluorescence of the fluorophore is quenched by the quencher. In one embodiment the fluorophore is attached to the 5'end of the oligonucleotide, and the quencher is covalently attached to the 3' end of the oligonucleotide. Fluorophores that can be used in the methods of the invention include FAM, TET, JOE, Yakima Yellow, HEX, Cyanine3, ATTO 550, TAMRA, ROX, Texas Red, Cyanine 3.5, LC610, LC 640, ATTO 647N, Cyanine 5, Cyanine 5.5 and ATTO 680. Quenchers that can be used with the appropriate fluorophore include TAM, BHQ1, DAB, Eclip, BHQ2 and BBQ650, optionally wherein said fluorophore is selected from HEX, Texas Red and FAM. Preferred combinations of fluorophore and quencher include FAM with BHQ1 and Texas Red with BHQ2.

Use of the Probe in a qPCR Assay

Hydrolysis probes of the invention are typically temperature gradient optimised with concentration matched negative controls. Preferably single-step PCR reactions are optimized. More preferably a standard curve is calculated. An advantage of using a specific probe that binds across the junction of the ligated sequence is that specificity for the ligated sequence can be achieved without using a nested PCR approach. The methods described herein allow accurate and precise quantification of low copy number targets. The target ligated sequence can be purified, for example gel-purified, prior to temperature gradient optimization. The target ligated sequence can be sequenced. Preferably PCR reactions are performed using about 10 ng, or 5 to 15 ng, or 10 to 20 ng, or 10 to 50 ng, or 10 to 200 ng template DNA.

Forward and reverse primers are designed such that one primer binds to the sequence of one of the chromosome regions represented in the ligated DNA sequence, and the other primer binds to other chromosome region represented in the ligated DNA sequence, for example, by being complementary to the sequence.

Choice of Ligated DNA Target

The invention includes selecting primers and a probe for use in a PCR method as defined herein comprising selecting primers based on their ability to bind and amplify the ligated sequence and selecting the probe sequence based properties of the target sequence to which it will bind, in particular the curvature of the target sequence.

Probes are typically designed/chosen to bind to ligated sequences which are juxtaposed restriction fragments spanning the restriction site. In one embodiment of the invention, the predicted curvature of possible ligated sequences relevant to a particular chromosome interaction is calculated, for example using a specific algorithm referenced herein. The curvature can be expressed as degrees per helical turn, e.g. 10.5° per helical turn. Ligated sequences are selected for targeting where the ligated sequence has a curvature propensity peak score of at least 5° per helical turn, typically at least 10°, 15° or 20° per helical turn, for example 5° to 20° per helical turn. Preferably the curvature propensity score per helical turn is calculated for at least 20, 50, 100, 200 or 400 bases, such as for 20 to 400 bases upstream and/or downstream of the ligation site. Thus in one embodiment the target sequence in the ligated product has any of these levels of curvature. Target sequences can also be chosen based on lowest thermodynamic structure free energy.

Particular Embodiments

In one embodiment only intrachromosomal interactions are typed/detected, and no extrachromosomal interactions (between different chromosomes) are typed/detected.

In particular embodiments certain chromosome interactions are not typed, for example any specific interaction mentioned herein (for example as defined by any probe or primer pair mentioned herein). In some embodiments chromosome interactions are not typed in any of the genes mentioned here, for example in any gene mentioned in Table 21.

PUBLICATIONS

The contents of all publications mentioned herein are incorporated by reference into the present specification and may be used to further define the features relevant to the invention.

Tables

Table 1 shows patient sample for the human study.

Table 2 shows the classification of responders in the human study.

Tables 3 and 4 show markers from the human study which are preferably used for typing humans.

Table 5 illustrates for the human study predispositions present in subjects.

Table 6 shows markers from the human study, which are preferably used for typing humans.

Table 7 shows predictive markers for strength training response, which are preferably used for typing humans.

Table 8 shows predictive markers for endurance training response, which are preferably used for typing humans.

Table 9 shows predictive markers for either strength or endurance training response, which are preferably used for typing humans.

Table 10 shows the samples for the equine study.

Table 11 defines the 'sex' description used in Table 10.

Table 12 shows the sex distribution in the equine study.

Table 13 shows the top markers for Stayer versus Sprinter phenotype (n=32, 16 Stayer, 16 Sprinter), which are preferably used to type horses.

Table 14 shows markers discovered in humans that applicable to horses, and the closest genomic loci, which can be used to type horses.

Table 15 shows classifier calls for Sprinters and Stayers

Table 16 shows probability scores for the equine study.

Table 17 shows classifier calls of naïve samples from young Thoroughbreds.

Table 18 shows the informative markers from the equine study, which are preferably used to type horses.

Tables 19 and 20 show the subjects for the human study.

Table 21 shows preferred genes for carrying out the invention.

Table 22 and 23 shows preferred markers from the equine study and the traits they relate to, which are preferably used to type horses.

Table 24 shows markers identified in the equine study, which are preferably used to type horses.

Table 25 shows markers identified in the human study, which are preferably used to type humans.

Table 26 shows another set of preferred genes for carrying out the invention.

Table 27 shows pathway analysis for genes locations for 171 chromosome interactions shared between the strength and endurance groups.

Table 28 shows pathway analysis for genes locations for the top 79 chromosome interactions which are unique to the endurance group.

Table 29 shows pathway analysis for genes locations for the top 79 chromosome interactions which are unique to the strength group.

Tables 30 to 32 show markers identified in the human study, which are preferably used to type humans. To clarify the nomenclature used in the tables, including Table 30:

E_Trn refers to presence in Endurance Training

Str_Trn refers to presence in Strength Training

E_Ctrl refers to presence in Endurance Control (i.e. absence in Endurance Training)

Str_Ctrl refers to presence in Strength Control (i.e. absence in Strength Training)

Table 33 shows markers from an equine study, which are preferably used to type horses. In LS column: 1 means present in Sprinters, while (−1) means present in Stayers. The 'Loop detection' column is de facto decoding what +1 and −1 means in terms of detection.

Table 34 shows markers from a human study, which are preferably used to type humans.

Table 35 shows preferred markers from a horse study, which are preferably used to type horses.

Table 36 shows preferred markers from a human study, which are preferably used to type humans.

Table 37 shows an updated version of Table 30. The same markers are typed in this study in humans, preferably used to type humans.

Table 38 shows an updated version of Table 31. The same markers are typed in a human study and preferably used to type humans.

Table 39 shows an updated version of Table 32. The same markers are typed in a human study and preferably used to type humans.

Table 40 shows markers corresponding to those shown in FIG. 15, which are preferably used to type humans.

Table 41 shows updated results for Table 25, where the markers are from a human study and are preferably used to type human.

FIGS. 16 and 17 shows markers from a human study, which preferably can be used to type humans.

FIG. 18 shows markers from a horse study, which preferably can be used to type horses.

Preferred Methods

Figure 1:
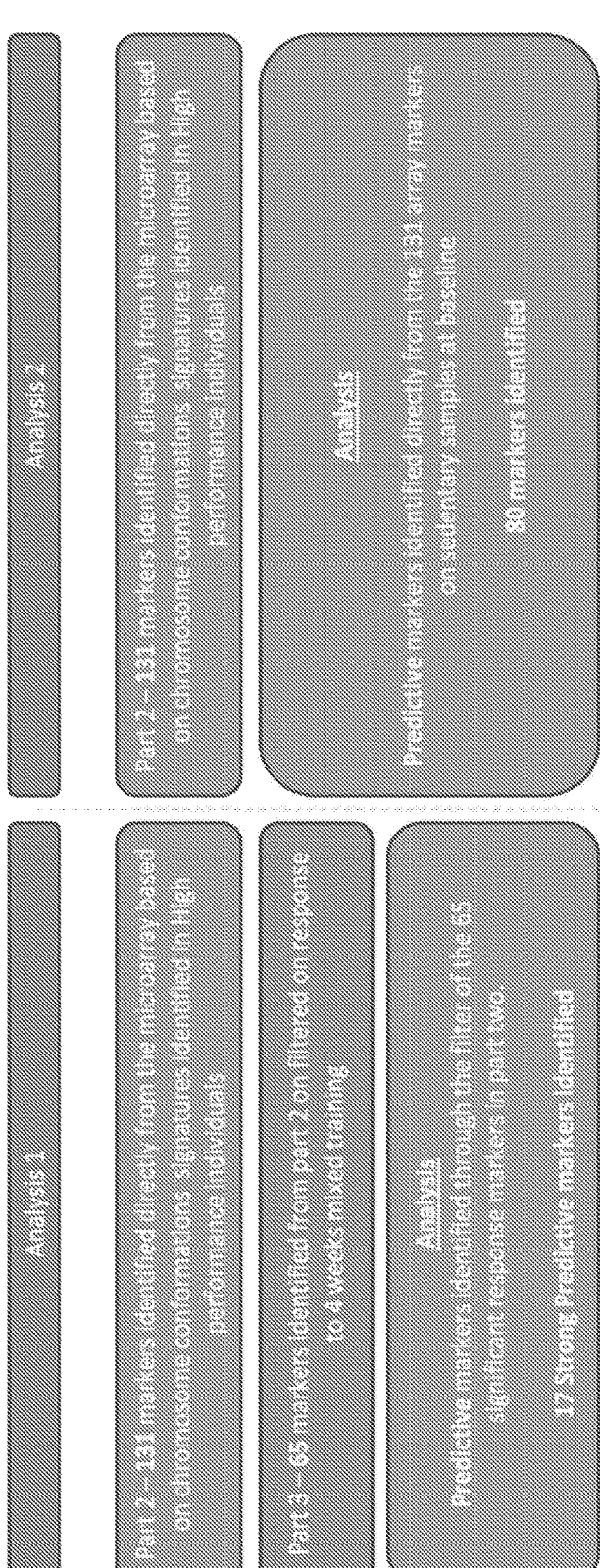

The following numbered paragraphs define preferred methods:

1. A process for detecting a chromosome state which represents a subgroup in a population comprising determining whether a chromosome interaction relating to that chromosome state is present or absent within a defined region of the genome, wherein said subgroup relates to physical performance in an individual; and wherein said chromosome interaction has optionally been identified by a method of determining which chromosomal interactions are relevant to a chromosome state corresponding to a physical performance subgroup of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to a physical performance subgroup; and wherein the chromosome interaction either:

(i) corresponds to any one of the chromosome interactions shown in any of Tables 3, 7, 8, 9, 25 and 30; and/or (ii) corresponds to any one of the chromosome interactions shown in any of Tables 13, 14, 18, 22, 23 and 24; and/or (iii) is present in a 4,000 base region which comprises or which flanks (i) or (ii); and/or (iv) is present in any one of the regions or genes listed in Table 21, 24, 25 or 30.

2. A process according to paragraph 1 wherein:

the individual is a human and the subgroup is a human subgroup the individual is a horse and the subgroup is a horse subgroup, and wherein optionally:

(i) the process is carried out to determining physical performance ability, and/or (ii) the process is carried out to detect responsiveness to a stimulus relating to physical performance, which is preferably physical training, and optionally strength or endurance training; and/or (iii) the process is carried out to select an individual suitable for a physical activity, which is preferably a sport; and/or (iv) the process is carried out to select a stimulus relating to physical performance to give to the individual, wherein said stimulus is a type of physical training.

3. A process according to paragraph 1 or 2 wherein a specific combination of chromosome interactions are typed:

(i) comprising all of the chromosome interactions represented in any of Tables 3, 7, 8, 9, 25 and 30 or any of Tables 13, 14, 18, 22, 23; and/or (ii) comprising at least 10%, 20%, 50%, or 80% of the chromosome interactions in any of Tables 3, 7, 8, 9, 25 and 30 or any of Tables 13, 14, 18, 22, 23; and/or (iii) which together are present in at least 10, 50 or 100 of the regions or genes listed in any of Tables 21, 24, 25 or 30; and/or (iv) wherein at least 10, 50, 100, 150, 200 or 300 chromosome interactions are typed which are present in a 4,000 base region which comprises or which flanks the chromosome interactions represented in any of Tables 3, 7, 8, 9, 25 and 30 or any of Tables 13, 14, 18, 22, 23.

4. A process according to any one of the preceding paragraphs in which the chromosome interactions are typed:

in a sample from an individual, and/or by detecting the presence or absence of a DNA loop at the site of the chromosome interactions, and/or detecting the presence or absence of distal regions of a chromosome being brought together in a chromosome conformation, and/or by detecting the presence of a ligated nucleic acid which is generated during said typing and whose sequence comprises two regions each corresponding to the regions of the chromosome which come together in the chromosome interaction, wherein detection of the ligated nucleic acid is preferably by using either:

(i) a probe that has at least 70% identity to any of the specific probe sequences mentioned in Table 24, 25 or 30, and/or (ii) by a primer pair which has at least 70% identity to any primer pair in Table 24, 25 or 30.

5. A process according to any one of the preceding paragraphs, wherein:

the second set of nucleic acids is from a larger group of individuals than the first set of nucleic acids; and/or the first set of nucleic acids is from at least 8 individuals; and/or the first set of nucleic acids is from at least 4 individuals from a first subgroup and at least 4 individuals from a second subgroup which is preferably non-overlapping with the first subgroup.

6. A process according to any one of the preceding paragraphs wherein:

the second set of nucleic acids represents an unselected group; and/or wherein the second set of nucleic acids is bound to an array at defined locations; and/or wherein the second set of nucleic acids represents chromosome interactions in least 100 different genes; and/or wherein the second set of nucleic acids comprises at least 1,000 different nucleic acids representing at least 1,000 different chromosome interactions; and/or wherein the first set of nucleic acids and the second set of nucleic acids comprise at least 100 nucleic acids with length 10 to 100 nucleotide bases.

7. A process according to any one of the preceding paragraphs, wherein the first set of nucleic acids is obtainable in a process comprising the steps of:

(i) cross-linking of chromosome regions which have come together in a chromosome interaction;

(ii) subjecting said cross-linked regions to cleavage, optionally by restriction digestion cleavage with an enzyme; and (iii) ligating said cross-linked cleaved DNA ends to form the first set of nucleic acids (in particular comprising ligated DNA).

8. A process according to any one of the preceding paragraphs:

wherein at least 10 to 50 different chromosome interactions are typed, preferably in 10 to 50 different regions or genes optionally as defined in Table 21, 24, 25 or 30; and/or which is:

(i) carried out on a human or horse athlete; and/or (ii) carried out as part of a training regime, preferably after the start of the training regime; and/or (iii) carried out on a Thoroughbred horse, preferably a racing horse; or (iv) carried out on a human individual of who is less than 20 years old or is carried out on a horse that is less than 18 months old, and/or (v) which is carried out at multiple time points to assess physical performance characteristics at specific time points, wherein the process is optionally carried out at at least 3 time points, which are preferably at least 30 days apart from each other.

9. A process according to any one of the preceding paragraphs wherein said defined region of the genome:

(i) comprises a single nucleotide polymorphism (SNP); and/or (ii) expresses a microRNA (miRNA); and/or (iii) expresses a non-coding RNA (ncRNA); and/or (iv) expresses a nucleic acid sequence encoding at least 10 contiguous amino acid residues; and/or (v) expresses a regulating element; and/or (vii) comprises a CTCF binding site.

10. A process according to any one of the preceding paragraphs:

which is carried out to identify an individual that is suited to endurance training, and preferably the identified individual is then subject to endurance training, which optionally occurs on at least 100 days out of the next 365 days after the identification; or which is carried out to identify an individual that is suited to strength training, and preferably the identified individual is then subject to strength training, which optionally occurs on at least 100 days out of the next 365 days after the identification.

11. A process according to any one of the preceding paragraphs which is carried out to select the individual for racing.

12. A process according to any one of the preceding paragraphs which is carried out to identify or design a an agent that affects physical performance, wherein said process is used to detect whether a candidate agent is able to cause a change to a chromosome state which is associated with a different physical performance state; wherein the chromosomal interaction is any specific interaction or combination of interactions defined in any paragraph and/or is present in any one of the regions or genes listed in Table 21, 24, 25 or 30; and/or the change in chromosomal interaction is monitored using (i) a probe that has at least 70% identity to any of the specific probe sequences mentioned in Table 24, 25 or 30, and/or (ii) by a primer pair which has at least 70% identity to any primer pair in Table 24, 25 or 30.

13. A process according to paragraph 12 which comprises selecting a target based on detection of chromosome interactions, and preferably screening for a modulator of the target to identify an agent which affects physical performance, wherein said target is optionally a protein.

14. A process according to any one of the preceding paragraphs, wherein the typing or detecting comprises specific detection of the ligated product by quantitative PCR (qPCR) which uses primers capable of amplifying the ligated product and a probe which binds the ligation site during the PCR reaction, wherein said probe comprises sequence which is complementary to sequence from each of the chromosome regions that have come together in the chromosome interaction, wherein preferably said probe comprises:

an oligonucleotide which specifically binds to said ligated product, and/or a fluorophore covalently attached to the 5' end of the oligonucleotide, and/or a quencher covalently attached to the 3' end of the oligonucleotide, and optionally said fluorophore is selected from HEX, Texas Red and FAM; and/or said probe comprises a nucleic acid sequence of length 10 to 40 nucleotide bases, preferably a length of 20 to 30 nucleotide bases.

15. A process according to any one of the proceeding paragraphs which further comprises:

producing a report on the physical performance characteristics of the individual based on the results of the process, or inputting the results of the process into a database, or assigning a specific fitness or training regime to the individual based on the results of the process, or designing a specific fitness or training regime for the individual based on the results of the process.

Specific Embodiments

The EpiSwitch™ platform technology detects epigenetic regulatory signatures of regulatory changes between normal and abnormal conditions at loci. The EpiSwitch™ platform identifies and monitors the fundamental epigenetic level of gene regulation associated with regulatory high order structures of human chromosomes also known as chromosome conformation signatures. Chromosome signatures are a distinct primary step in a cascade of gene deregulation. They are high order biomarkers with a unique set of advantages against biomarker platforms that utilize late epigenetic and gene expression biomarkers, such as DNA methylation and RNA profiling.

EpiSwitch™ Array Assay

The custom EpiSwitch™ array-screening platforms come in 4 densities of, 15K, 45K, 100K, and 250K unique chromosome conformations, each chimeric fragment is repeated on the arrays 4 times, making the effective densities 60K, 180K, 400K and 1 Million respectively.

Custom Designed EpiSwitch™ Arrays

The 15K EpiSwitch™ array can screen the whole genome including around 300 loci interrogated with the EpiSwitch™ Biomarker discovery technology. The EpiSwitch™ array is built on the Agilent SurePrint G3 Custom CGH microarray platform; this technology offers 4 densities, 60K, 180K, 400K and 1 Million probes. The density per array is reduced to 15K, 45K, 100K and 250K as each EpiSwitch™ probe is presented as a quadruplicate, thus allowing for statistical evaluation of the reproducibility. The average number of potential EpiSwitch™ markers interrogated per genetic loci is 50; as such the numbers of loci that can be investigated are 300, 900, 2000, and 5000.

EpiSwitch™ Custom Array Pipeline

The EpiSwitch™ array is a dual colour system with one set of samples, after EpiSwitch™ library generation, labelled in Cy5 and the other of sample (controls) to be compared/analyzed labelled in Cy3. The arrays are scanned using the Agilent SureScan Scanner and the resultant features extracted using the Agilent Feature Extraction software. The data is then processed using the EpiSwitch™ array processing scripts in R. The arrays are processed using standard dual colour packages in Bioconductor in R: Limma*. The normalisation of the arrays is done using the normalisedWithinArrays function in Limma * and this is done to the on chip Agilent positive controls and EpiSwitch™ positive controls. The data is filtered based on the Agilent Flag calls, the Agilent control probes are removed and the technical replicate probes are averaged, in order for them to be analysed using Limma*. The probes are modelled based on their difference between the 2 scenarios being compared and then corrected by using False Discovery Rate. Probes with Coefficient of Variation (CV)<=30% that are <=−1.1 or =>1.1 and pass the p<=0.1 FDR p-value are used for further screening. To reduce the probe set further Multiple Factor Analysis is performed using the FactorMineR package in R.

\* Note: LIMMA is Linear Models and Empirical Bayes Processes for Assessing Differential Expression in Microarray Experiments. Limma is an R package for the analysis of gene expression data arising from microarray or RNA-Seq.

The pool of probes is initially selected based on adjusted p-value, FC and CV<30% (arbitrary cut off point) parameters for final picking. Further analyses and the final list are drawn based only on the first two parameters (adj. p-value; FC).

Statistical Pipeline

EpiSwitch™ screening arrays are processed using the EpiSwitch™ Analytical Package in R in order to select high value EpiSwitch™ markers for translation on to the EpiSwitch™ PCR platform.

Step 1

Probes are selected based on their corrected p-value (False Discovery Rate, FDR), which is the product of a modified linear regression model. Probes below p-value <=0.1 are selected and then further reduced by their Epigenetic ratio (ER), probes ER have to be <=−1.1 or =>1.1 in order to be selected for further analysis. The last filter is a coefficient of variation (CV), probes have to be below <=0.3.

Step 2

The top 40 markers from the statistical lists are selected based on their ER for selection as markers for PCR translation. The top 20 markers with the highest negative ER load and the top 20 markers with the highest positive ER load form the list.

Step 3

The resultant markers from step 1, the statistically significant probes form the bases of enrichment analysis using hypergeometric enrichment (HE). This analysis enables marker reduction from the significant probe list, and along with the markers from step 2 forms the list of probes translated on to the EpiSwitch™ PCR platform.

The statistical probes are processed by HE to determine which genetic locations have an enrichment of statistically significant probes, indicating which genetic locations are hubs of epigenetic difference.

The most significant enriched loci based on a corrected p-value are selected for probe list generation. Genetic locations below p-value of 0.3 or 0.2 are selected. The statistical probes mapping to these genetic locations, with the markers from step 2, form the high value markers for EpiSwitch™ PCR translation.

Array Design and Processing

Array Design

1. Genetic loci are processed using the SII software (currently v3.2) to:
   a. Pull out the sequence of the genome at these specific genetic loci (gene sequence with 50 kb upstream and 20 kb downstream)
   b. Define the probability that a sequence within this region is involved in CCs
   c. Cut the sequence using a specific RE
   d. Determine which restriction fragments are likely to interact in a certain orientation
   e. Rank the likelihood of different CCs interacting together.
2. Determine array size and therefore number of probe positions available (x)
3. Pull out x/4 interactions.
4. For each interaction define sequence of 30 bp to restriction site from part 1 and 30 bp to restriction site of part 2. Check those regions aren't repeats, if so exclude and take next interaction down on the list. Join both 30 bp to define probe.
5. Create list of x/4 probes plus defined control probes and replicate 4 times to create list to be created on array
6. Upload list of probes onto Agilent Sure design website for custom CGH array.
7. Use probe group to design Agilent custom CGH array.

Array Processing

1. Process samples using EpiSwitch™ Standard Operating Procedure (SOP) for template production.
2. Clean up with ethanol precipitation by array processing laboratory.
3. Process samples as per Agilent SureTag complete DNA labelling kit-Agilent Oligonucleotide Array-based CGH for Genomic DNA Analysis Enzymatic labelling for Blood, Cells or Tissues
4. Scan using Agilent C Scanner using Agilent feature extraction software.

EpiSwitch™

EpiSwitch™ biomarker signatures demonstrate high robustness, sensitivity and specificity in the stratification of complex disease phenotypes. This technology takes advantage of the latest breakthroughs in the science of epigenetics, monitoring and evaluation of chromosome conformation signatures as a highly informative class of epigenetic biomarkers. Current research methodologies deployed in academic environment require from 3 to 7 days for biochemical processing of cellular material in order to detect CCSs. Those procedures have limited sensitivity, and reproducibility; and furthermore, do not have the benefit of the targeted insight provided by the EpiSwitch™ Analytical Package at the design stage.

EpiSwitch™ Array in Silico Marker Identification

CCS sites across the genome are directly evaluated by the EpiSwitch™ Array on clinical samples from testing cohorts for identification of all relevant stratifying lead biomarkers. The EpiSwitch™ Array platform is used for marker identification due to its high-throughput capacity, and its ability to screen large numbers of loci rapidly. The array used was the Agilent custom-CGH array, which allows markers identified through the in silico software to be interrogated.

EpiSwitch™ PCR

Potential markers identified by EpiSwitch™ Array are then validated either by EpiSwitch™ PCR or DNA sequencers (i.e. Roche 454, Nanopore MinION, etc.). The top PCR markers which are statistically significant and display the best reproducibility are selected for further reduction into the final EpiSwitch™ Signature Set, and validated on an independent cohort of samples. EpiSwitch™ PCR can be performed by a trained technician following a standardised operating procedure protocol established. All protocols and manufacture of reagents are performed under ISO 13485 and 9001 accreditation to ensure the quality of the work and the ability to transfer the protocols. EpiSwitch™ PCR and EpiSwitch™ Array biomarker platforms are compatible with analysis of both whole blood and cell lines. The tests are sensitive enough to detect abnormalities in very low copy numbers using small volumes of blood.

Example 1

This work concerns human epigenetic biomarkers which monitor physiological differences and predispositions associated with physical fitness training programs. Defined biomarkers have been discovered and evaluated to assist in the determination of epigenetic predisposition for either strength or endurance training, with monitoring after 4 weeks of mixed training and 8 weeks of specialized training.

Participant Recruitment:

Participants were recruited using posted fly paper, electronic newsletter, local print and radio media, targeted recruitment at local athletics clubs and word of mouth. To be eligible for enrolment to the study, participants were required to meet the following 'performance' criteria.

Group 1: strength athlete: Participant should be a regular weight-lifter. Example provided: 100 kg body mass and have a current accumulated total of 550 kg across; bench-press+squat+deadlift exercise.

Group 2: fitness athlete: Participant should be a regular fitness athlete. Example provided: current 10 km run time: <40 mins; or current 5 km run time <19 mins.

Group 3: sedentary non-athlete: has not been participating in sport or any form of structured exercise that causes physical exertion for >3 years.

Study Enrolment

Requisite criteria for potential enrolment were subjective (participant) reporting of athletic ability in order to meet one of three distinct phenotypes; 1) strength athlete 2) fitness athlete 3) sedentary non-athlete. Subsequently, eighty five (n=85) male participants aged 18-54 years, provided written informed consent prior to enrolling to the study. To confirm the meeting of enrolment criteria, comprehensive medical and athletic history were obtained before familiarisation protocol, blood sampling and performance tests were performed.

Familiarisation Protocol

Prior to physiological assessment, participants were acquainted with study procedures, personnel and provided with triaxial accelerometers (ActiGraph GT3X+, ActiGraph Corp), which were worn for 7-days in order to objectively determine participant physical activity, prior to physiological assessment.

Blood Sampling

Following overnight fast, morning blood samples were drawn from an antecubital vein by venepuncture, using 22 gauge needle into a 6 ml EDTA (BD Vacutainer®) blood tube. The blood tubes underwent 12 gentle inversions and immediately frozen at −80° C.

Anthropometrics

Height was determined using a portable stadiometer (Seca, Birmingham, U.K.). Body mass was measured to the nearest 0.1 kg by commercially available scales (body composition analyser TBF-300, Tanita, Tokyo, Japan). Total body fat percentage was calculated using bioelectrical impedance analysis (BIA) using a commercially available analyser (body composition analyser TBF-300, Tanita, Tokyo, Japan).

Strength Tests

For the 1RM tests, each subject attempted a weight that he believed could be lifted only once using maximum effort. The subject then added weight in increments of 2.2-4.5 kg until the heaviest load that could be successfully lifted once was determined. The subjects rested for approximately 3-5 minutes between attempts. The criterion for participant maximum strength was the combined 1RM max lifts (kg) for Squat+Bench Press+Deadlift exercises. Participant relative strength ratio was calculated as [Maximum Strength: Body Mass (kg:kg)]

Squat Exercise, 1 Rep Maximum (SQ 1RM)

During the SQ 1RM test, each lifter assumed an upright position, with the top of the bar not more than 3.0 cm below the top of the anterior deltoids. With both hands grasping the bar, the bar was removed from the rack, and the lifter moved back to assume a ready position, with knees extended, looking forward at the chief referee. On command, the lifter bent the knees and lowered the body in one smooth descent, until the top surface of the legs at the hip joint were lower than the top of the knees. The lifter then raised himself from the deepest point of the SQ to a standing position, with the knees extended. On command, the lifter replaced the weight back onto the rack with the aid of a spotter.

Bench Press, 1 Rep Maximum (BP 1RM)

The participant placed himself in a supine position, keeping his head, shoulders, and buttocks in constant contact with the weightlifting bench. The lifter's feet remained flat and motionless on the floor during the attempt. The participant received the bar at full arm's length from a spotter located behind the head of the bench. The bar was then lowered to the chest at a point 1-2 cm below the nipple line along the chest. When the bar became motionless on the chest, "press" command was issued and the participant extended his arms, returning the weight back to its starting position. Once the arms were completely extended, the chief referee gave a rack command, and the spotter aided the participant in returning the weight back to the racks on the bench.

Dead-lift, 1 Rep Maximum (DL 1RM)

For the DL 1RM, the participants feet and hands were spaced evenly from the centre of the bar and were allowed to be placed close to its centre (power style), or farther from the centre (sumo style). The participant lifted the bar vertically from the floor with one smooth motion until the knees and back extended the body to an erect position. When the knees became fully extended, upon command, and the participant lowered the bar to the floor.

Peak Aerobic Capacity

Peak aerobic capacity ($\dot{V}O_2$peak) was obtained indirect calorimetery on an electronically braked cycle ergometer (Velotron, RacerMate, Seattle, WA, USA). Gas exchange was collected throughout the test using a metabolic cart (Moxus, AEI Technologies, Pittsburgh, PA, USA). The test consisted unloaded pedalling for 1 min, followed by a step-wise increase to 50 W for 2 min. Subsequently, work rate was increased by 30 W min[31][1] until the participant reached volitional fatigue (determined by the inability to maintain a minimum cadence above 60 rpm, blood lactate $>7$ mmol.l$^{-1}$, respiratory exchange ratio $>1.15$; reaching $>90\%$ of age predicted heart rate maximum). $\dot{V}O_2$peak values were confirmed as the highest value during the final stage of the ramp protocol. Work rate (WR) was collected continuously throughout the test and peak aerobic power was calculated using the average WR from the last 30 s of the test.

Phenotype Confirmation

Group 1: Participants were required to meet at least the 90th percentile for strength STRENGTH PHENOTYPE: Relative Strength Ratio* (RSR)>4.5 kg:kg $$RSR=[(SQ1RM\ kg+BP1RM\ kg+DL1RM\ kg)+Body\ Mass(kg)]$$

Group 2: Participants were required to meet at least the 90th percentile for aerobic capacity FITNESS PHENOTYPE: $\dot{V}O_2$peak $>51.4$ ml·kg$^{-1}$ Group 3: Participants were required to be on or below the 50th percentile for strength and aerobic capacity Strength: Relative Strength Ratio*(RSR)<3 kg:kg Fitness: 50th Percentile: VO$_2$peak <40.8 ml·kg$^{-1}$ Samples and Processing The samples used in the study are shown in Table 1. The EpiSwitch™ template was prepared for each of the samples using the EpiSwitch™ extraction procedure. The 3C template library was quantified and the amount standardised to 1 ng/µl. A serial dilution was created and Nested PCR performed according to the EpiSwitch™ protocols.

Nested PCR was performed using the created serial dilutions for each sample for all 65 markers identified in part 2. For each marker the appropriate controls were included, these consisted of a no template control (NTC, all other reagents minus any DNA template) to monitor for any potential contamination of PCR reagents and a genomic control (negative control) to ensure the PCR products being detected are specific 3C products. The Nested PCR was analysed using high throughput capillary gel electrophoresis (LabChip GX Touch HT, Perkin Elmer) to identify and size the PCR products.

Training Response Annotations

The Nested PCR data was analysed using the retrospective annotation of end-point outcome for high and low response to exercise. To generate the annotations for each training group the individuals increase in physiological measurements due to undertaking the specified training regime, was ranked. The top 5 individuals in the ranking system were classed as High Responders for that training regime, the bottom 5 individuals were classed as Low responders (see table 2).

Results Overview

The analysis for part three of the project has been performed in two separate ways. The first is a direct analysis for predictive capability of 65 markers identified through the response analysis in part two and now screened in the third part of the project. The second is a parallel analysis of all the top 131 markers originally translated from EpiSwitch™ array of the high achieving Endurance and Strength Athletes. In this analysis the markers were evaluated strictly for their predictive potential using their baseline readouts and retrospective annotations of end-point outcome as High and Low response to specialized training by the end of 8 weeks of training. FIG. 1 provides a graphical representation and overview of the analysis.

Figure 2:
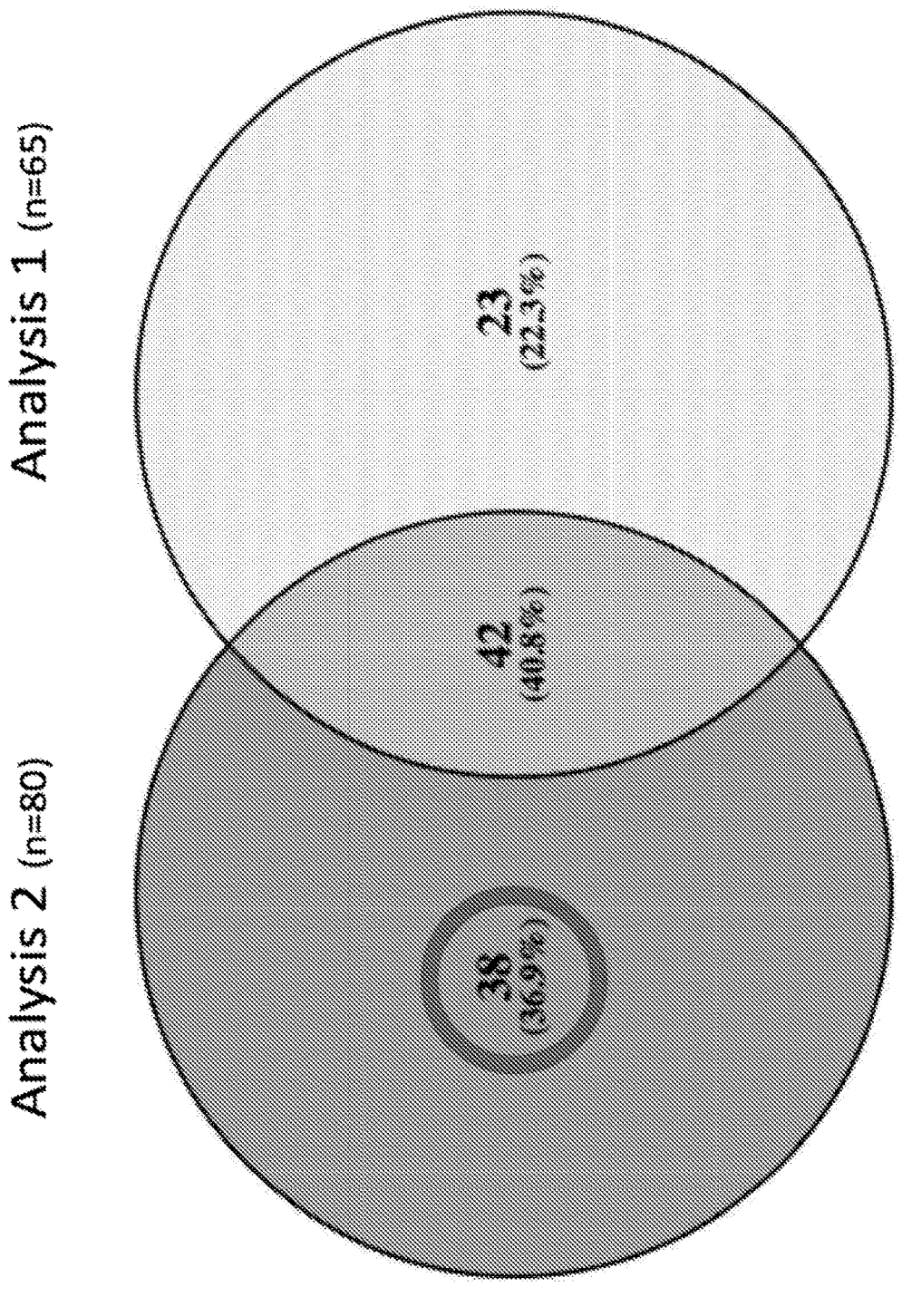

When compared, the two analysis streams have an overlap of 40.8%. The second analysis identifies 38 additional markers from the 131 original markers at the start of part 2 that are prime candidates to be predictive markers for training response. The overlap is shown in FIG. 2, with a circle marking the markers identified in the section 2 analysis stream that have not been processed. [FIG. 2 shows a Venn diagram of 80 potential markers identified in Analysis 2 compared to the 65 markers identified in part 2 and screened in part 3 based on exercise response]

Analysis 1

Analysis 1 was based on 3 comparisons. These three questions were designed to identify the markers from the 65 that were originally filtered on their responsiveness to mixed exercise and were predictive of an individual's outcome to specific training regimes or training in general. To that end the nested PCR data was analysed in three stratification groups:

1. High versus Low response (H/L) for Strength Training—to identify markers that were predictive at baseline to the end-point outcome of high or low response to Strength training.

2. High versus Low response (H/L) for Cardiovascular Endurance Training—to identify markers that are predicative at baseline to the end-point outcome of high or low response to Strength training at baseline.

3. High versus Low (H/L) response independent of training, grouping Strength and Endurance together—to identify markers that are predictive at baseline to the end-point outcome of a response to any/a training program at baseline.

The annotations of the outcome response to the training regimes at 8 weeks (after 4 weeks of specific cardio or strength training) were used to identify markers that are statistically significant for exercise response for the individual training regimes the third group looked at markers that were significant in both training programs.

To ensure the markers were predictive of training response H/L outcome and not just response markers, the binary nature of the marker at baseline and 8 weeks was investigated. Only markers that showed concordance between the two time points were selected. Filtering chromosome conformations that are stably detected before and after training that also show statistical significance between low and high response to the training programs selects for high quality markers that represent an inherent stable regulation framework in individuals that pre-disposes them to physiologically advance well or poorly to the final outcome of physical training of particular type.

Out of the 65 markers filtered through exercise response to 4-week of mixed training, 17 were found to be statistically significant. These are detailed in Table 3 and 4. These 17 markers represent a pool of high quality markers for the predisposition of training response in individuals at baseline (naïve) before training commences. The odds ratio shown in Table 3 is the measure of how strongly the absence and detection of the individual marker is associated with High/Low predicted outcome response to training in the sample population. An odds ratio of 1 indicates there is no difference between the two subpopulations (High and low response). The data strongly suggest that 17 discovered predictive markers are strongly associated with the successful outcome of training in the sample population with odds ratios of between 2 and 12. Each marker was also individually assessed using Welch's t-test. This is a statistical test used to compare two sample populations and ascertain if the populations have equal means. An equal mean demonstrating that the two populations are not significant different. The p values shown in Table 5 are a measure of confidence that the inequality in the population means is due to actual differences and not be chance sampling.

A p value cut off of 0.3 is used to determine if the difference in detection of chromosome conformations are statistically significant. As will be seen in other literature this differs from the normally used 0.05 values. The 0.3 limit was experimentally derived to assure capturing markers that provide useful information gain, for example in the machine learning classifiers, strengthening the classifier performance.

The significant p values for each marker show the statistical significance of the odds ratios (OR) between training types in Table 3. The data in Tables 3 and 4 demonstrate quality and robustness of the 17 predictive markers identified.

Binary data from the marker OBD142_081.083_1.4x, as shown in Table 5 gives a useful example of both the higher detection rates between High and Low responders to exercise, in this case cardio endurance training and the predisposition already present at baseline before training commences. The data also represents a documented phenomenon of interference by mixed training causing disruption to the regulation before the chromatin regulation is reprogrammed back to its original predisposition state.

We identified the regulatory frame work for predictive advantage and predisposition of High response outcome in individuals being present at onset. The regulatory frame work in the low responders either preprogrammes to match that of the high responders, which they inherently possess already or fails to change at all. The markers represented in FIG. 3 are all marker for high response in strength training. FIG. 6. showing changes in detection for specific markers from baseline and after 8 weeks of training (4 weeks mixed, 4 weeks strength training), Y axis detection state 0=no detection, 1=detection, X axis 1=baseline, 2=8 weeks. FIG. 3A shows High responders is fixed with Low responders reprogramming causing the marker to become detectable due to the training programme. FIG. 3B shows High responders is fixed with Low responders reprogramming causing the marker to become undetectable due to the training programme. FIG. 3C shows High responders is fixed with Low responders also fixed, showing no modification of the chromatin landscape for this particular interaction.

Three of the 17 markers identified are anchored in the 3' UTR of the DKK3 genetic locus (Table 6). It is evident that the DKK3 3'UTR is a hub of epigenetic control for this specific genetic locus with differential genomic architecture changing the regulation and accessibility creating predisposition for training response.

Analysis 2

The rationale for the second analysis was to look at the 131 markers screened at baseline in part 2 against retrospective annotations of end-point outcome of High or Low response to specialised training after 8 weeks. Many potential predictive markers may have been excluded in Analysis 1 as they were largely insensitive to the 4 weeks of mixed training. In contrast to analysis 1, which identified predictive markers with additional feature of responsiveness to mixed exercise, Analysis 2 was designed only to identify markers that were predictive of an individual's response to specific training programs.

Analysis 2 was based on the same three comparisons.

1. High versus Low response for Strength Training—to identify markers that were predictive at baseline to the end-point outcome of high or low response to Strength training at baseline.
2. High versus Low response for Cardiovascular Endurance Training—to identify markers that are predicative at baseline to the end-point outcome of high or low response to Strength training at baseline.
3. High versus Low response independent of training, grouping Strength and Endurance together—to identify markers that are predictive at baseline to the end-point outcome of a response to any/a training program at baseline.

Welch's t-test was used to investigate the three comparisons. The test was cross validated by performing 1000 repeats with randomised sample selection. This gives 1000 different sample populations to test for the same 131 markers. Resampling and cross validation are used to ensure that the markers can generalise to an independent data set. The analysis output statistics for the predictive markers are shown in tables 7, 8 and 9. When duplications between the comparisons were removed the analysis identified 80 potential predictive markers. These 80 contained all 17 good predictive markers identified in Analysis 1.

Figure 4:
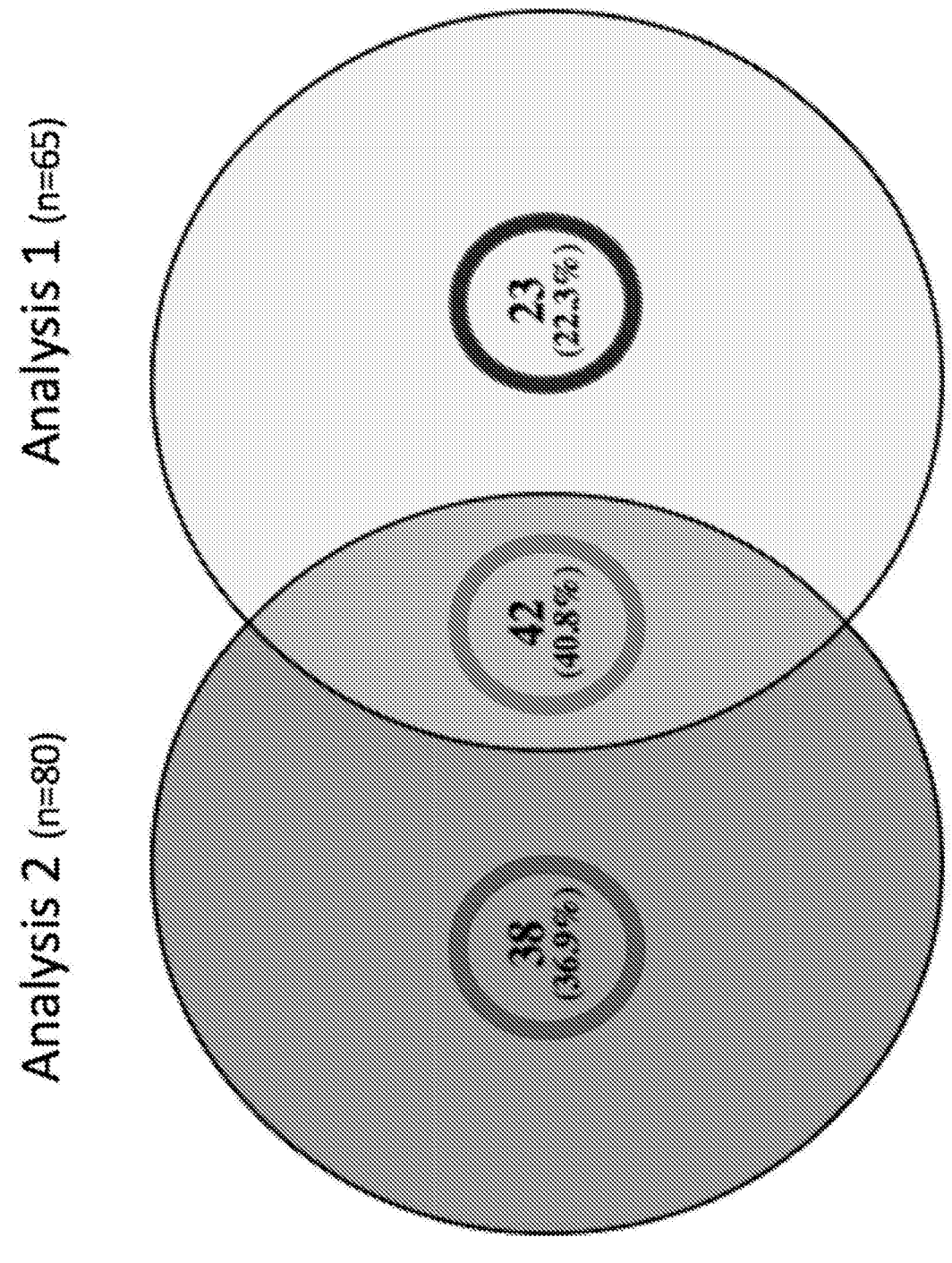
Figure 5:
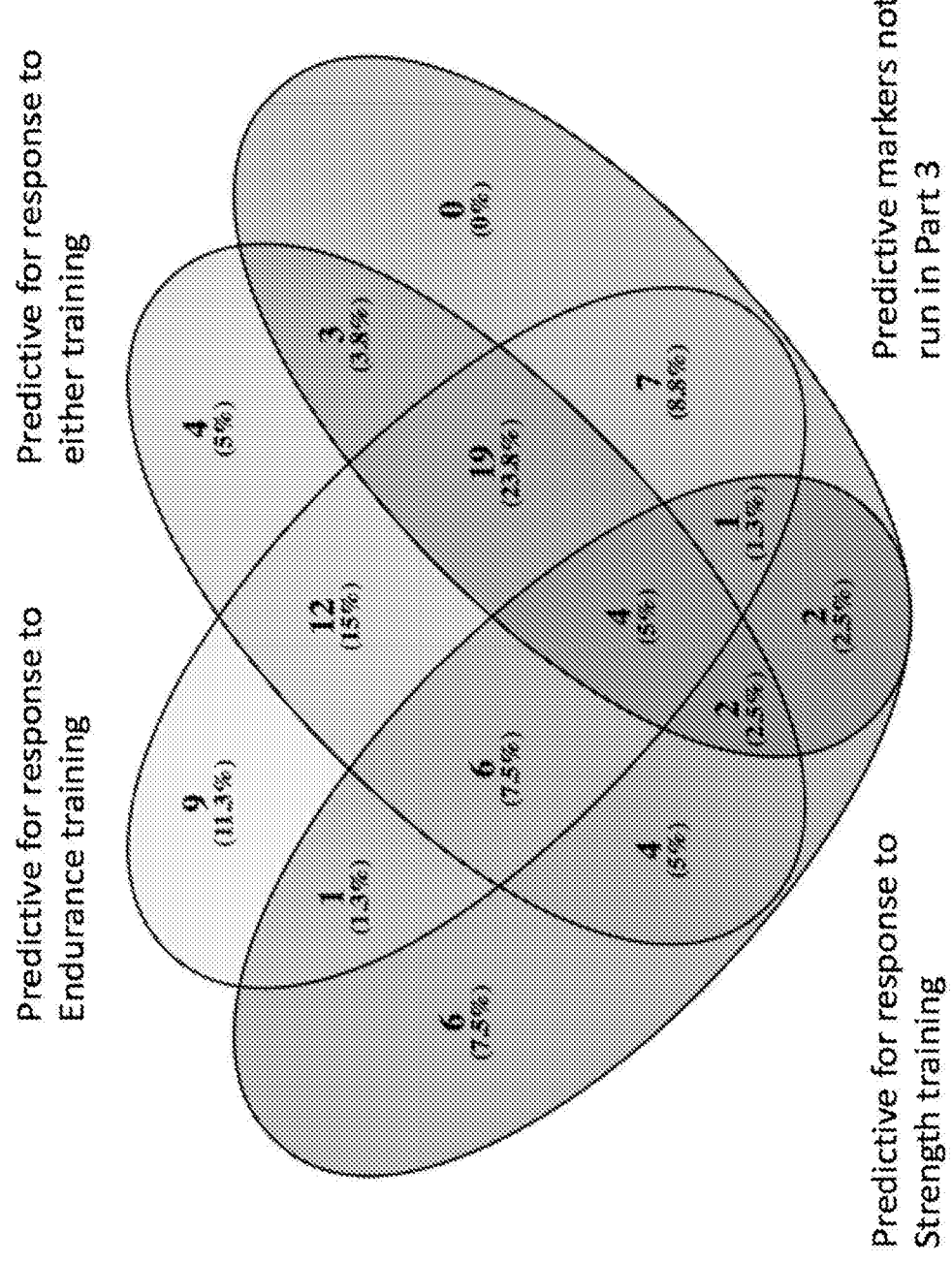

FIG. 4 shows the analysis overlap. The circle on the left represents 38 additional predictive markers from Analysis 2. The circle in the middle shows the 42 overlapping predictive markers that have been investigated in part 2 and 3. These include the 17 markers detailed in Analysis 1. The circle on the right shows 23 markers investigated in part 2 and 3 that are Responsive markers to training. The composition of the 80 markers identified in Analysis two is shown in the Venn diagram in FIG. 5.

It is important to mention, that as an independent validation of the methodology in general and individual markers in particular, top significant markers with predictive powers for strength or endurance training outcome have been successfully translated into markers in an equine study. Based on the evolutionary conservation of genetic and epigenetic regulatory mechanisms underlying those markers, equine study of stayers and sprinters achieved 93,75% accuracy in classification of the development cohort of 32 (FIG. 6 which shows confusion matrix results).

CONCLUSIONS

1. Existing chromosome conformation signatures can be predictive of later response outcome to training phenotypes. This is consistent with a number of validated studies for development of the predictive biomarkers to response to various treatments.
2. Statistically significant disseminating EpiSwitch™ markers identified and evaluated in strength/endurance training for human participants have been successfully translated into statistically significant equine markers for stratification of verified Sprinters and Stayers.
3. The 10 discovered markers classify between Sprinter and Stayer phenotypes with an accuracy of 93.75% on the available set of 32 validated samples.

Analysis 2 has identified 80 strong predictive markers, these include all the 17 predictive/response markers earlier reported in analysis 1 and an additional 38 markers that are predictive for H/L outcome to training response phenotypes when measured at baseline.

SUMMARY

We have successfully identified and evaluated significant predictive biomarkers for H/L outcome of the strength/endurance training. These results achieve the objective of the project.

17 high quality robust predictive stable markers, with sensitivity to mixed training, have been developed for use in baseline prediction of an individual's response outcome to specialized training regimes.

A further 38 strictly predictive markers, independent of response to mixed training, have been identified and evaluated at baseline, for use in baseline prediction of an individual's response outcome to specialized training regimes.

Example 2

Identification of validated signatures contain binary CCSs which are either present, or absent as conditional biomarkers of epigenetic regulation in equine individuals in strength or endurance training.

We identified CCSs biomarkers to successfully distinguish between Thoroughbreds, trained as either sprinters or a stayers. These markers can be used to determine predisposition and monitoring of young unraced Thoroughbreds as they are selected and undergo the training programs for sprinters and stayers. The markers are relevant to training potential, physiological monitoring and epigenetic reprogramming through training.

Project Approach

The top 50 EpiSwitch™ markers, identified from the work in human was translated into EpiSwitch™ designed Equine nested PCR assays and tested by the EpiSwitch™ PCR platform using Thoroughbreds with a defined phenotype: 1) sprinting 2) long-distance (Stayers) for evaluation of best disseminating markers for Sprinters and Stayers.

Samples

A total of 48 Samples were used as shown in Table 10:

16 Untrained young Thoroughbreds.

16 Trained Thoroughbreds classed as Sprinters.

16 Trained Thoroughbreds classed as Stayers.

The sex distribution between the sprinter and stayer sample types is balanced. The untrained male samples are skewed towards Colts against their castrated peers (Gelding), table 4. This skew will be accounted for in the biostatistical analysis.

Genome Conversion

The 131 markers identified on the Human array and translated to Nested PCR were translated from the GRCh38 Human Genome assembly to the EquCab2.0 Equine genome assembly using LiftOver (USSC). In total 114 of these were successfully translated. OBD's internal primer design application was used to design Nested primer sets for PCR, 65 of the 114 markers met the strict criteria for the successful primer design according to EpiSwitch™ operational procedures and methodology. The top 50 markers were selected for EpiSwitch™ equine nested PCR interrogation.

Nested PCR Screening

The EpiSwitch™ template was prepared for each of the samples using the EpiSwitch™ extraction standard operation procedure. The 3C template library was quantified and the amount standardised to 1 ng/μl. A serial dilution was created and Nested PCR performed according to the EpiSwitch™ protocols Nested PCR was performed using the created serial dilutions for each sample for all 50 markers selected. The Nested PCR was analysed using high throughput capillary gel electrophoresis (LabChip GX Touch HT, Perkin Elmer) to identify and size the PCR products. The data for the 16 Sprinters and 16 stayers was analysed using Boschloos' Test with resampling. The top 17 markers are shown in table 13.

In total, 17 of the 50 markers investigated were found to be statistically significant using a Boschloo p value cut off of 0.2. Importantly, this selection is produced using dilution individual titres, so each marker is produced by p-values based on the specific titres. Resampling of the data set was performed 100 times with a 66.7% partition, from the dataset of 32, 22 samples were selected at random and the statistical tests performed. This was repeated 100 times with the median result of this documented in table 13. These 17 markers represent interactions spaced around 16 genomic loci. The markers OBD154_045/047 and OBD154_049/051 are unique interactions that are across the same genomic location, see Table 4. The data show that a number of translated markers, discovered originally in a human cohort, are also applicable to horses.

MTFR1 (mitochondrial fission regulator 1) is notable from amongst identified loci as this was indicated in the most significant region from the Horse genetics for selection in thoroughbred Horses. Mitochondrial function and the management of reactive oxygen species are important for favorable exercise responses and therefore MTFR1 may impose strong selection pressure in Thoroughbreds by protection of mitochondria-rich tissue against oxidative stress. As such it is an excellent region for racing performance and endurance.

Classification

Figure 7:
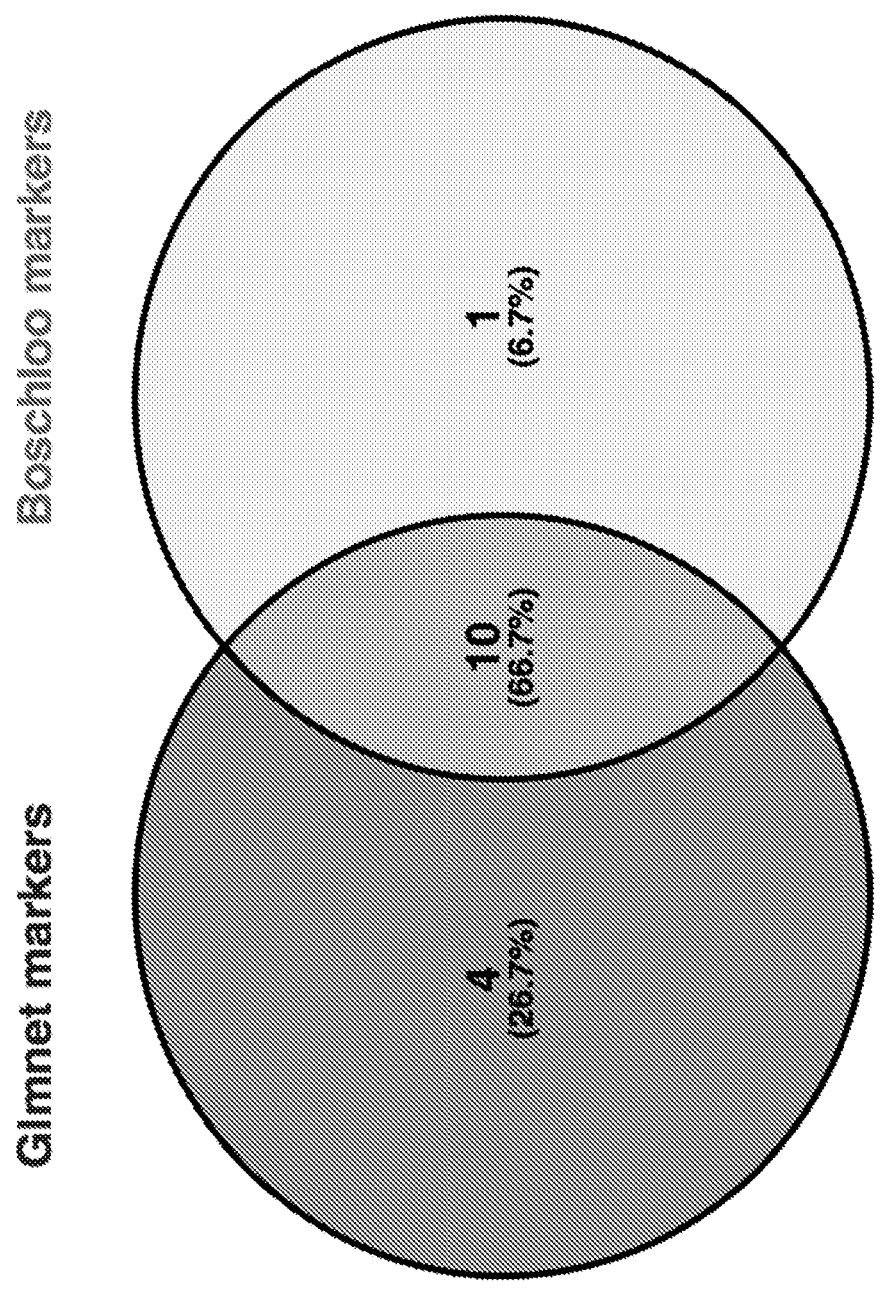
Figure 8:
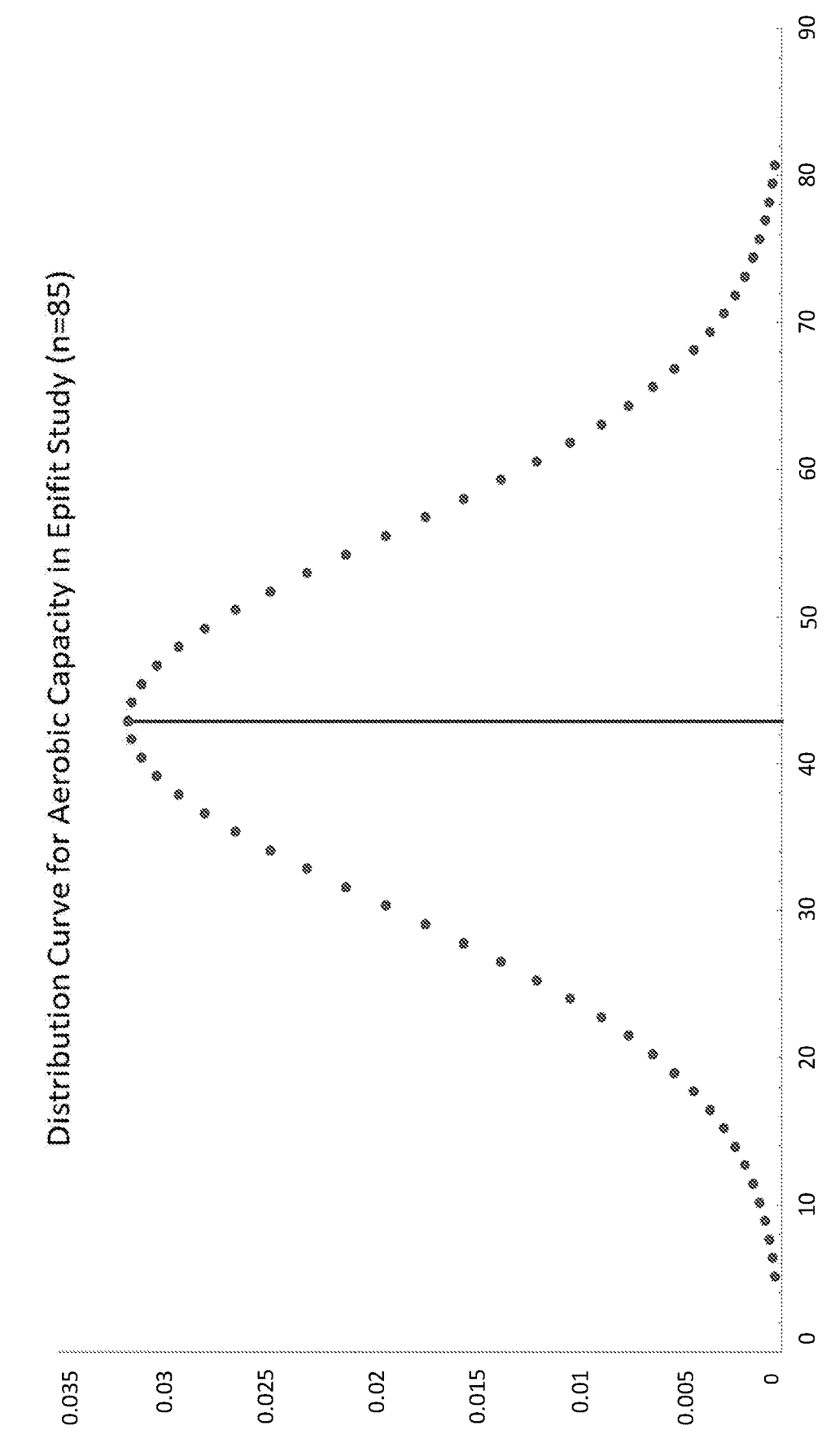
Figure 9:
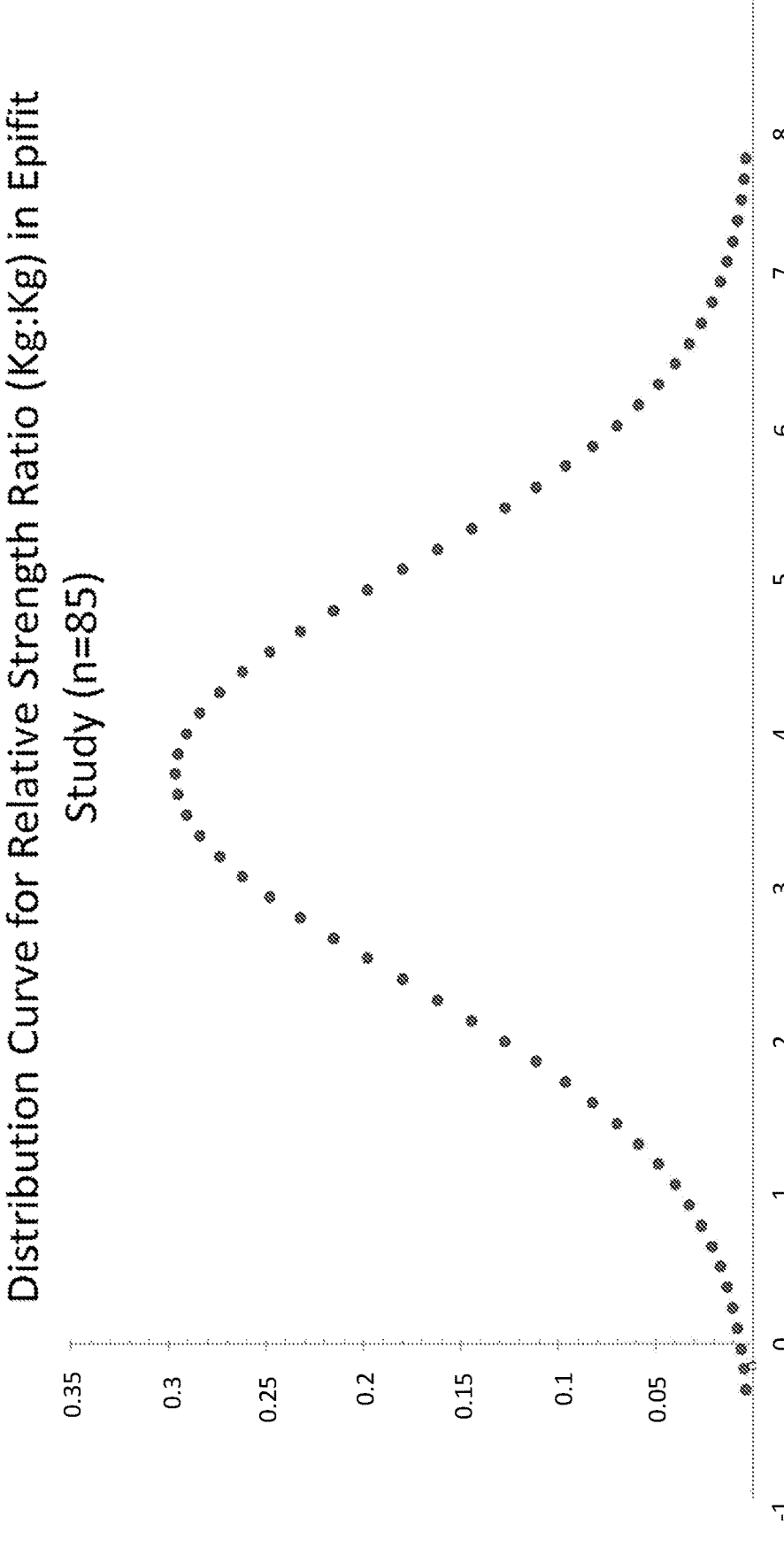
Figure 10:
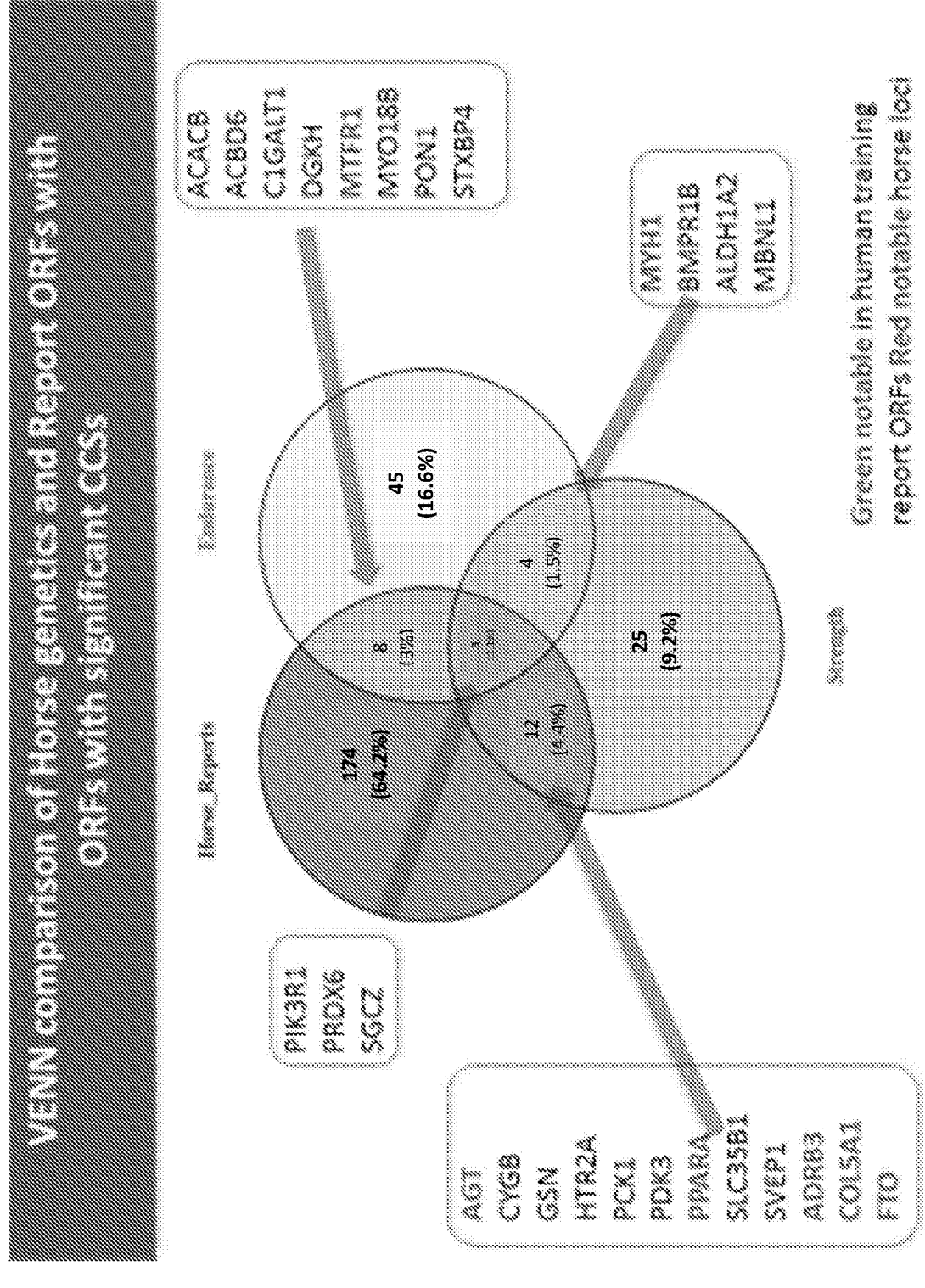
Figure 11:
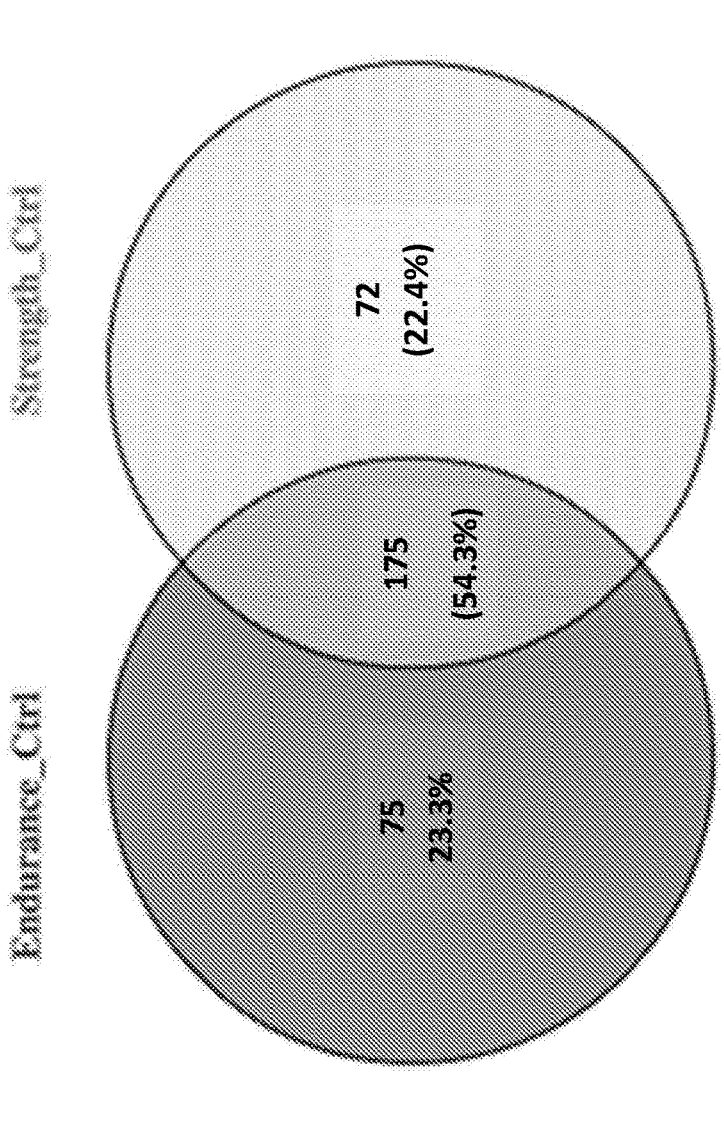
Figure 13:
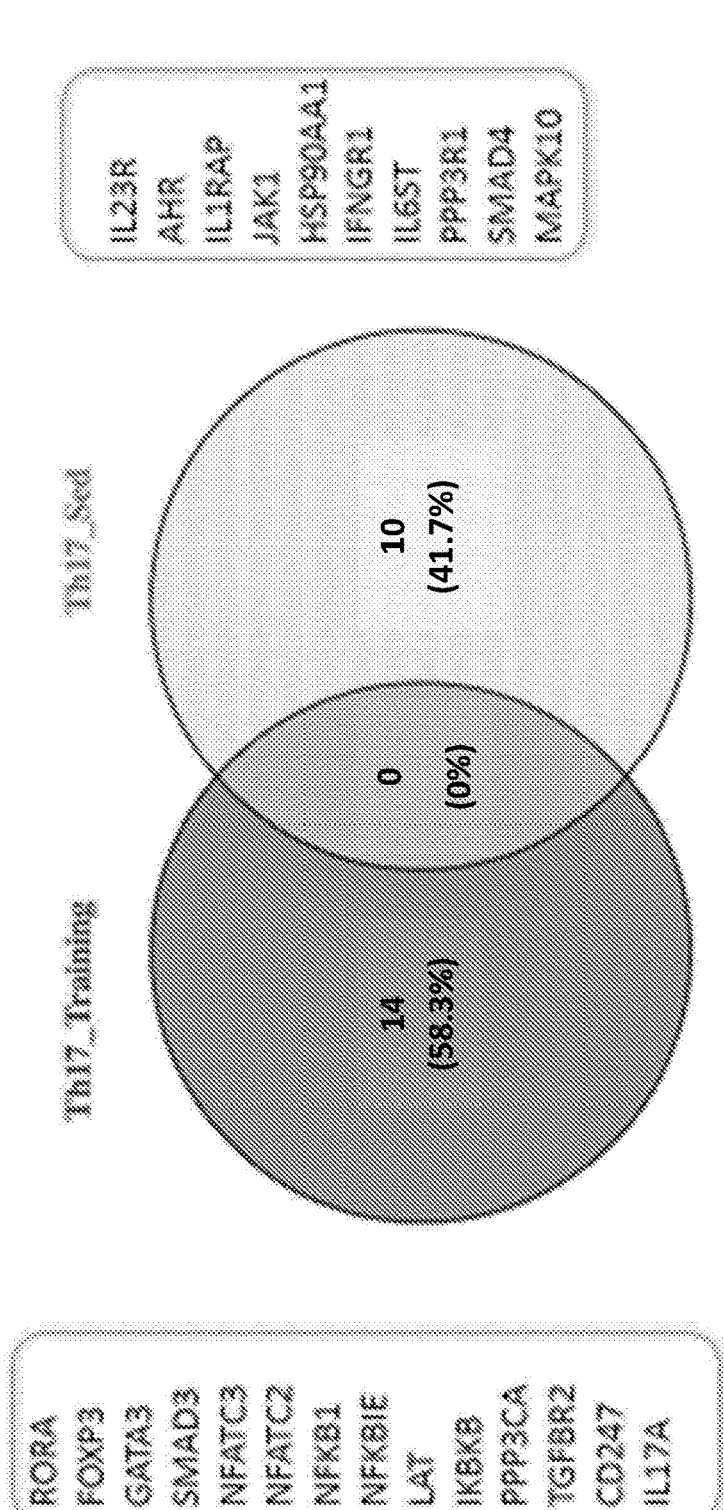
Figure 14:
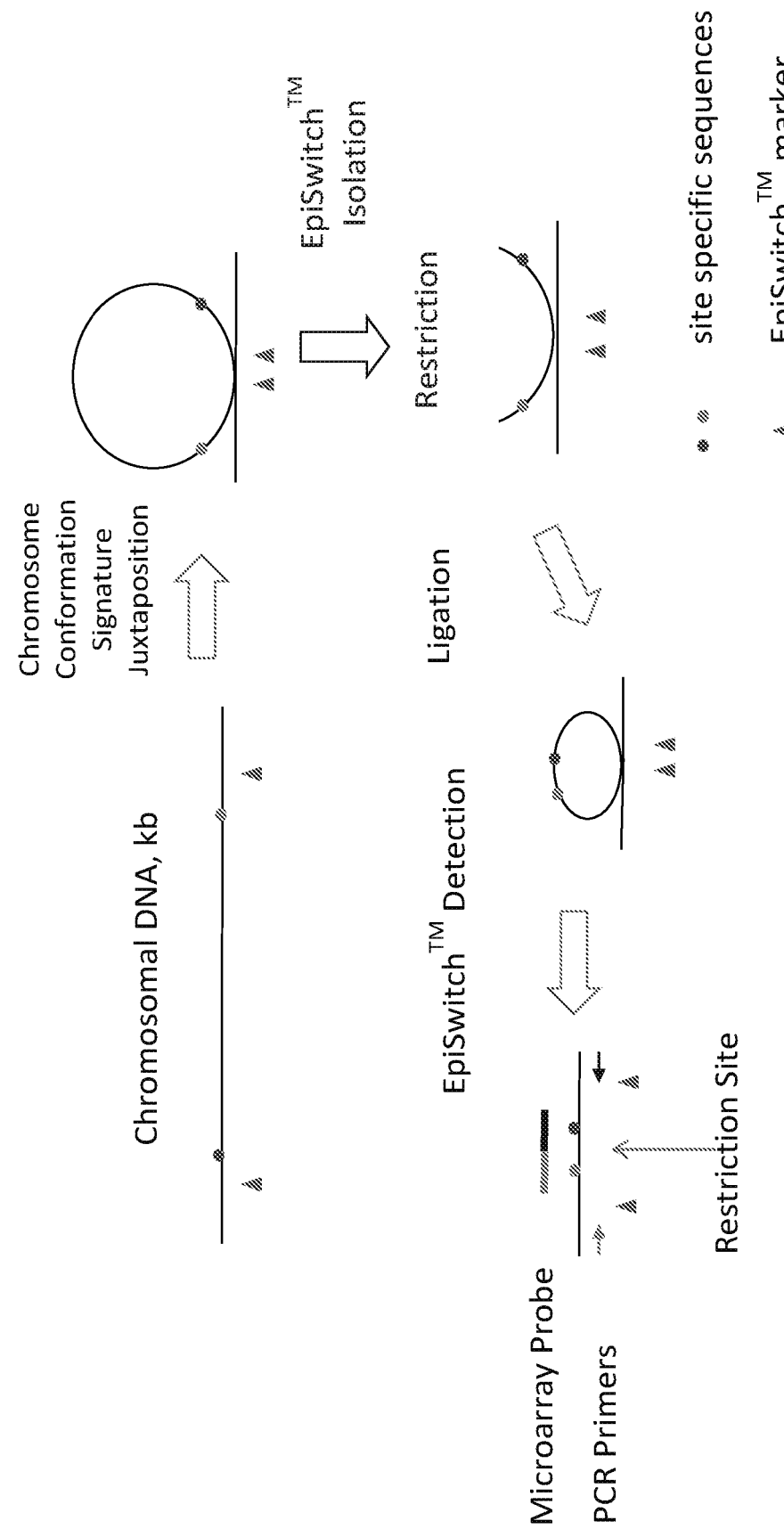

A classifier based on the Sprinter vs Stayer markers identified on the trained samples was developed to enable the classification of the untrained samples. Glmnet (Lasso and Elastic-Net Regularized Generalized Linear Models) was used to rank the markers in their ability to classify between sample types. The top 14 markers identified in Glmnet were then compared to the top 11 markers based on Boschloos' p value (Table 13). As shown in FIG. 7, 10 of the markers showed concordance and were shared between the two statistical analyses. The 10 concordant markers were selected to develop the classifier. XGBoost was used to model the markers and build a classifier.

The XGBoost model is an ensemble-based classifier that uses a series of weak classifying models to produce one overall strong model. In this gradient boosting methodology an initial model is created from the training data, a second model is then created that attempts to correct any errors in classification from the first model. This process is repeated n number of times to produce a final model that will classify the training set. A process of early stopping, ending the classifier build chain earlier then the initially set n value, is used to prevent the model over fitting the training set. A classification of the training set based on Sprinters and Stayers is shown in FIG. 6. Based on the 10 markers, the EpiSwitch™ test classifies well between Sprinters and Stayers, with an accuracy of 93.75%.

The probability calls of the 10 markers classifier are shown in Table 15. By default, a probability score >0.5 by the classifier is considered a call for a Sprinter, while <0.5 is considered a call for Stayer. On the basis of the results of classification in Table 15, the original probability scores (>0.5 for Sprinter, <0.5 for Stayer) were adjusted for quality classification calls on naïve samples from young Thoroughbreds. The established cut offs for the classifier calls are shown in Table 16.

The classifier was applied to the data for the naïve samples from young Thoroughbreds with the call results in Table 17. For 4 of the samples the classifier was unable to call the phenotype with high enough certainty and they fell into the unclassified limits. The remaining 12 samples were successfully called with a prediction of epigenetic profile conducive for the potential good Sprinter or Stayer. The 10 discovered markers classify between Sprinter and Stayer phenotypes with an accuracy of 93.75% on the available set of 32 validated samples.

Example 3

Further Work on the Human Study

A multinomial Glmnet regression analysis was performed based on three annotation groups, High responder, Medium responder and Low responder to each training type. Each CCS identified as predictive at baseline relative to training response outcomes was then compared across the time points for the sedentary controls to remove any CCS that showed variation due to effects other than the training under investigation. In total 18 CCS were identified as predictive for response to Strength training and 7 for response to Endurance training. Two of the CCS are shared between the training types (Mixed). Results are shown in tables 31 and 32.

Loop detected, or EpiSwitch marker present, are strict categories of predictive and stable markers for strength or endurance training. 'High-responder' markers are parts of epigenetic profile that conducive to very good physiological response to training program (using $VO_2$ maximum and one-repetition maximum strength tests), i.e responders in our use of term. 'Low-responders' is the data analysis term that marks the stable predictive markers for individuals who will not change much their physiological performance after the training program ('non-responders').

Considering that 'high response' is the physiological data analysis term for 'responder' biomarker, and 'low-response' for 'non-responders', the majority of predictive response biomarkers are strength or endurance specific. However, several biomarkers reflect a dual function and provide information for good response in both endurance and strength.

The loop detected refers to array data, however Table 31 refers to strength and Table 32 refers to endurance based on PCR data. In regards to marker definitions and marker categories used by data analysis on array data:

Strength control: these are is just reference controls on the untrained side-readouts on the group of sedentary individuals before training at baseline. This is a physiological baseline control group.

Endurance control: same as above, but for endurance.

Strength training: these are reference controls, retrospective and ultimate positive controls, on high achievers in strength read out on the group of strength trained individuals after successful training. This is a physiological, positive control group.

Endurance training: same as before but for endurance.

This group of markers should be evaluated based on the following rules: the high responder markers as predictive and stable (from baseline onwards) responder markers, while low responder are the opposite side-predictive and stable markers of non-response to training. Generally predictive markers are specific for either strength or endurance as they were developed separately on either strength or endurance programmes and control groups. However there is some overlap, probably reflecting physiological overlap of the relevant regulatory networks-several markers are good predictive marker for good response in both strength or endurance training.

Overall Review of the Work

The original pool of genetic sites on the screening array was comprised of 1) inflammatory genes, 2) loci associated with micro-satellite differences in Thoroughbred horses and translated into humans. Thoroughbreds are highly inbred and the input of genetic component into phenotypical differences is highly limited in those subjects—this was considered the right model to search for any associations with epigenetic control sites, in terms of chromosome conformations. The fact that statistically significant sites are associated broadly with some of the well-known genes functionally linked to strength and endurance is the consequence of an independent selection. Importantly, screening of the potential candidates for chromosome conformation markers was driven by proprietary EpiSwitch annotations within non-coding parts of the genome within 100 kb windows of the referenced loci: upstream, downstream or encompassing the whole genes within the chromatin domain. At any part of the selection of CCS marker leads, no comparative assessment for any gene expression of any genes in the vicinity were made to assist the selection, thus excluding any link or correlation to gene expression changes of any of the genes and their known functional link to physical training outcomes.

Tables 34 to 36 show preferred powerful markers. The odds ratio shown in Table 36 is the measure of how strongly the absence and detection of the individual marker is associated with High/Low predicted outcome response to training in the sample population. An odds ratio of 1 indicates there is no difference between the two subpopulations (High and low response). The data strongly suggest that 17 discovered predictive markers are strongly associated with the successful outcome of training in the sample population with odds ratios of between 2 and 12.

Each marker was also individually assessed using Welch's t-test. This is a statistical test used to compare two sample populations and ascertain if the populations have equal means. An equal mean demonstrating that the two populations are not significant different. The p values shown are a measure of confidence that the inequality in the population means is due to actual differences and not be chance sampling.

We used a p value cut off of 0.3 to determine if the difference in detection of chromosome conformations are statistically significant. As will be seen in other literature this differs from the normally used 0.05 values. Through our previous projects, assay type and know-how the 0.3 limit was experimentally derived to assure capturing markers that provide useful information gain in the machine learning classifiers, strengthening the classifier performance. The significant p values for each marker show the statistical significance of the odds ratios (OR) between training types in this table. The data in this table demonstrates quality and robustness of the 17 predictive markers identified.

Figure 15:
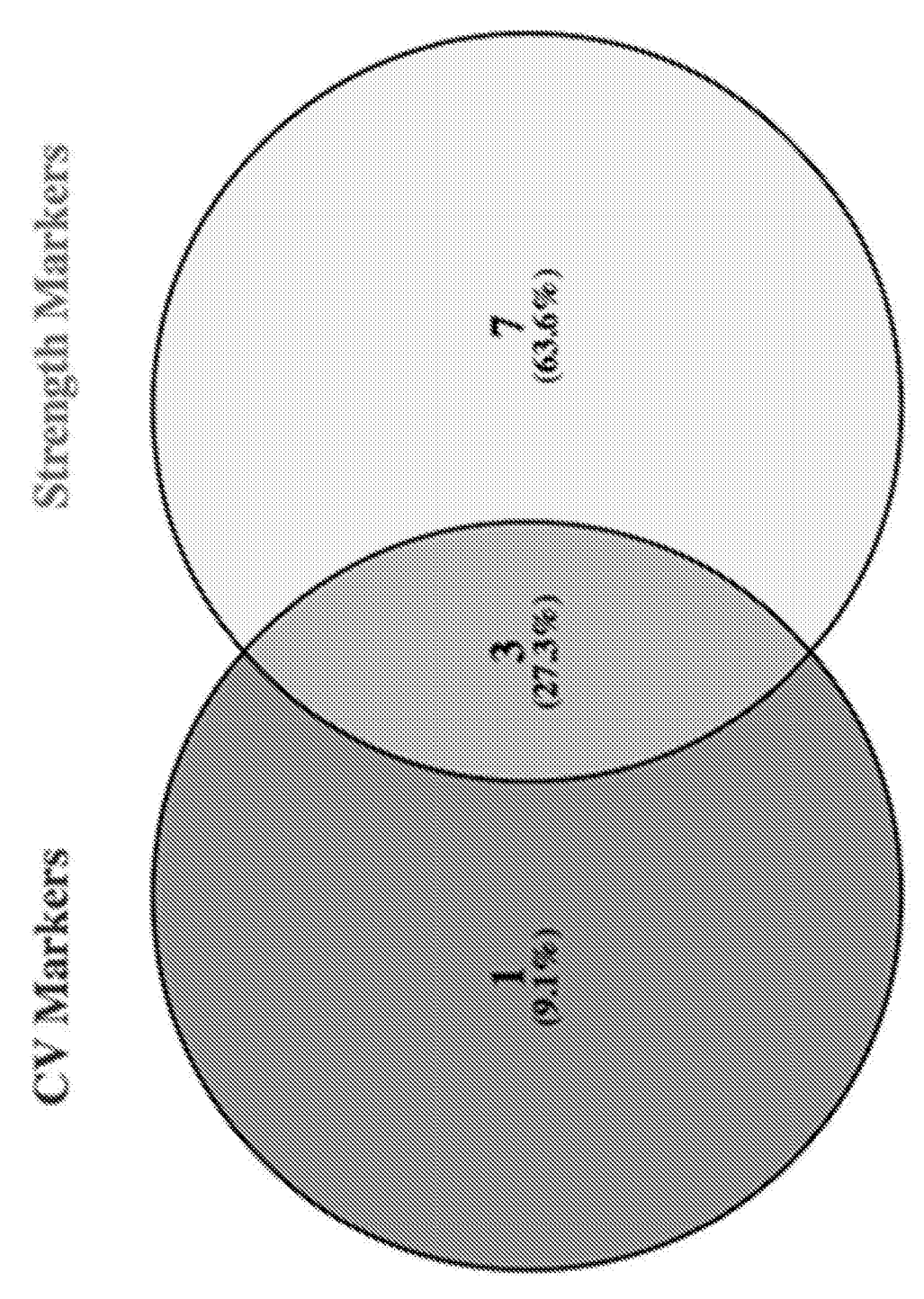

FIG. 15 is a VENN Diagram of Significant Markers for CV and Strength Baseline and 8 weeks. These markers are show in Table 40.

FIG. 16 shows baseline CV markers based on High and Low CV groups Exact P-values for association. These are the top 10 significant markers for the subjects at baseline based on the CV ranges. The range for Strength is a significant at baseline also. This indicates the close association between CV and strength ranges in these markers.

FIG. 17 shows baseline Strength markers based on high and Low Strength group Exact P-values for association. These are the top 20 significant markers for the subjects at baseline based on the Strength ranges. The range for CV is a significant at baseline also. This indicates the close association between CV and strength ranges in these markers.

FIG. 18 shows 10 Episwitch horse markers Identified from a UK cohort. The figure shows the genomic location in horses and the homologous region in the Human genome and the type of the marker: Sprinter or Stayer. The same 10 markers were used to classify the Singaporean Horses.

TABLE 1

| Patient Sample ID | Phenotype | Response |
|---|---|---|
| B16.3 | Control | — |
| B17.3 | Strength | — |
| B26.3 | Cardio | High |
| B33.3 | Cardio | — |
| B34.3 | Cardio | High |
| B37.3 | Strength | High |
| B38.3 | Cardio | Low |
| B39.3 | Strength | High |
| B40.3 | Cardio | High |
| B43.3 | Cardio | Low |
| B44.3 | Cardio | High |
| B45.3 | Strength | Low |
| B46.3 | Strength | High |
| B51.3 | Strength | — |
| B52.3 | Control | — |
| B61.3 | Cardio | High |
| B62.3 | Strength | Low |
| B63.3 | Excluded | — |
| B64.3 | Strength | Low |
| B68.3 | Cardio | — |
| B70.3 | Strength | High |
| B71.3 | Cardio | Low |
| B72.3 | Strength | High |
| B73.3 | Cardio | Low |
| B74.3 | Strength | — |
| B76.3 | Strength | Low |
| B77.3 | Cardio | Low |
| B78.3 | Strength | — |
| B79.3 | Excluded | — |
| B80.3 | Cardio | — |

TABLE 1-continued

| Patient Sample ID | Phenotype | Response |
|---|---|---|
| B83.3 | Strength | Low |
| B85.3 | Cardio | — |

TABLE 2

| Individual | Rank | Label |
|---|---|---|
| A | 1 | High response |
| B | 2 | High response |
| C | 3 | High response |
| D | 4 | High response |
| E | 5 | High response |
| F | 6 | — |
| G | 7 | — |
| H | 8 | — |
| I | 9 | — |
| J | 10 | Low response |
| K | 11 | Low response |
| L | 12 | Low response |
| M | 13 | Low response |
| N | 14 | Low response |

TABLE 3

| Marker | Training | Odds Ratio |
|---|---|---|
| OBD142_029.031_1x | Presence in Endurance and Strength | 7.2 |
| OBD142_061.063_1.8x | Presence in Endurance and Strength | 8.2 |
| OBD142_069.071_1.2x | Presence in Endurance and Strength | 8 |
| OBD142_089.091_1x | Presence in Endurance and Strength | 2.9 |
| OBD142_137.139_1.2x | Presence in Endurance and Strength | 8 |
| OBD142_081.083_1.4x | Presence in Endurance | 6 |
| OBD142_189.191_1x | Presence in Endurance | 4.5 |
| OBD142_213.215_1.4x | Presence in Endurance | 2.25 |
| OBD142_017.019_1.2x | Presence in Strength | 4 |
| OBD142_037.039_1x | Presence in Strength | 12 |
| OBD142_065.067_1x | Presence in Strength | 5 |
| OBD142_133.135_1x | Presence in Strength | 4 |
| OBD142_253.255_1.2x | Presence in Strength | 12 |
| OBD142_353.355_1x | Presence in Strength | 9 |
| OBD142_477.479_1x | Presence in Strength | 9 |
| OBD142_181.183_1.4x | Presence in Strength | 2 |
| OBD142_397.399_1x | Presence in Strength | 2 |

TABLE 4

| | Training type | | |
|---|---|---|---|
| Marker | Combined | Cardio | Strength |
| OBD142_029.031_1x | 0.01668097 | 0.066688 | 0.01613009 |
| OBD142_061.063_1.8x | 0.01851064 | 0.11741215 | 0.10680154 |
| OBD142_069.071_1.2x | 0.00255609 | 0.066688 | 0.05766889 |
| OBD142_089.091_1x | 0.12375267 | 0.40122897 | 0.18059725 |
| OBD142_137.139_1.2x | 0.06270144 | 0.11741215 | 0.18262433 |
| OBD142_081.083_1.4x | 0.13923948 | 0.070484 | 0.7999889 |
| OBD142_189.191_1x | 0.11969458 | 0.11741215 | 0.84528948 |
| OBD142_213.215_1.4x | 1 | 0.69409048 | 0.13523206 |
| OBD142_017.019_1.2x | 0.72495046 | 0.54542431 | 0.28124028 |
| OBD142_037.039_1x | 0.15251771 | 1 | 0.02525659 |
| OBD142_065.067_1x | 0.13191103 | 0.54542431 | 0.05766889 |
| OBD142_133.135_1x | 0.46156086 | 1 | 0.01613009 |
| OBD142_253.255_1.2x | 0.44960749 | 0.61010368 | 0.02421162 |
| OBD142_353.355_1x | 0.11969458 | 1 | 0.01615402 |
| OBD142_477.479_1x | 0.42751765 | 1 | 0.02525659 |
| OBD142_181.183_1.4x | 0.75595814 | 0.74070856 | 0.17780781 |
| OBD142_397.399_1x | 0.15163712 | 0.66842823 | 0.09667637 |

TABLE 5

| Trainee | Base line | 4 weeks | 8 weeks | Response to training |
|---|---|---|---|---|
| B26 | 1 | 0 | 1 | High |
| B34 | 1 | 0 | 1 | High |
| B40 | 1 | 0 | 1 | High |
| B44 | 0 | 0 | 0 | High |
| B61 | 0 | 0 | 0 | High |
| B38 | 0 | 0 | 0 | Low |
| B43 | 0 | 0 | 0 | Low |
| B71 | 0 | 0 | 0 | Low |

TABLE 5-continued

| Trainee | Base line | 4 weeks | 8 weeks | Response to training |
|---|---|---|---|---|
| B73 | 0 | 1 | 0 | Low |
| B77 | 0 | 1 | 0 | Low |

TABLE 6

| Marker | High or low response | Training type |
|---|---|---|
| OBD142_061.063_1.8x | High | Both |
| OBD142_069.071_1.2x | High | Both |
| OBD142_065.067_1x | High | Strength |

| Marker with Dilution | Marker | Freq | Rank Sum | Rank Mean | Rank Median | Mean p value | Median p value |
|---|---|---|---|---|---|---|---|
| OBD142_437.439_1.2x | OBD142_437.439 | 1000 | 198 | 1.98 | 2 | 0.01576 | 0.01562 |
| OBD142_025.027_1x | OBD142_025.027 | 1000 | 1224.5 | 12.245 | 8.5 | 0.08678 | 0.09375 |
| OBD142_417.419_1x | OBD142_417.419 | 1000 | 1369 | 13.69 | 13 | 0.09328 | 0.12500 |
| OBD142_517.519_1.2x | OBD142_517.519 | 1000 | 1251.5 | 12.515 | 13 | 0.09312 | 0.12500 |
| OBD142_065.067_1x | OBD142_065.067 | 971 | 3903 | 39.03 | 35.5 | 0.20758 | 0.13696 |
| OBD142_513.515_1.2x | OBD142_513.515 | 971 | 3903 | 39.03 | 35.5 | 0.20758 | 0.13696 |
| OBD142_017.019_1x | OBD142_017.019 | 977 | 4446 | 44.46 | 40 | 0.23382 | 0.28125 |
| OBD142_029.031_1x | OBD142_029.031 | 972 | 4681.5 | 46.815 | 40.5 | 0.23992 | 0.28125 |
| OBD142_069.071_1.2x | OBD142_069.071 | 972 | 5103.5 | 51.035 | 40 | 0.26566 | 0.28125 |
| OBD142_085.087_1.2x | OBD142_085.087 | 972 | 4667 | 46.67 | 41 | 0.24252 | 0.28125 |
| OBD142_093.095_1x | OBD142_093.095 | 1000 | 3945 | 39.45 | 40 | 0.22246 | 0.28125 |
| OBD142_117.119_1.2x | OBD142_117.119 | 1000 | 4206.5 | 42.065 | 38.5 | 0.23621 | 0.28125 |
| OBD142_125.127_1.2x | OBD142_125.127 | 977 | 4446 | 44.46 | 40 | 0.23382 | 0.28125 |
| OBD142_157.159_1.4x | OBD142_157.159 | 1000 | 3707.5 | 37.075 | 38 | 0.22324 | 0.28125 |
| OBD142_233.235_1.4x | OBD142_233.235 | 1000 | 3707.5 | 37.075 | 38 | 0.22324 | 0.28125 |
| OBD142_285.287_1.4x | OBD142_285.287 | 975 | 4749 | 47.49 | 37.75 | 0.24953 | 0.28125 |
| OBD142_325.327_1.4x | OBD142_325.327 | 1000 | 4206.5 | 42.065 | 38.5 | 0.23621 | 0.28125 |
| OBD142_449.451_1x | OBD142_449.451 | 1000 | 3738 | 37.38 | 38.25 | 0.21652 | 0.28125 |
| OBD142_461.463_1.4x | OBD142_461.463 | 972 | 4667 | 46.67 | 41 | 0.24252 | 0.28125 |
| OBD142_469.471_1x | OBD142_469.471 | 975 | 4749 | 47.49 | 37.75 | 0.24953 | 0.28125 |
| OBD142_133.135_1x | OBD142_133.135 | 504 | 14009 | 140.09 | 86.5 | 0.60112 | 0.34375 |
| OBD142_181.183_1.4x | OBD142_181.183 | 504 | 14009 | 140.09 | 86.5 | 0.60112 | 0.34375 |
| OBD142_397.399_1x | OBD142_397.399 | 504 | 14009 | 140.09 | 86.5 | 0.60112 | 0.34375 |
| OBD142_253.255_1.2x | OBD142_253.255 | 867 | 7643 | 76.43 | 109.25 | 0.62216 | 0.34375 |
| OBD142_181.183_1.4x | OBD142_181.183 | 504 | 14009 | 140.09 | 86.5 | 0.60112 | 0.34375 |
| OBD142_037.039_1x | OBD142_037.039 | 779 | 8626.5 | 86.265 | 113 | 0.35984 | 0.45312 |
| OBD142_353.355_1x | OBD142_353.355 | 699 | 8585.5 | 85.855 | 113 | 0.35078 | 0.45312 |

Table 7 shows predictive markers for strength training response, which are preferably used for typing humans. (Present in strength training in humans)

| Marker with Dilution | Marker | Freq | Rank Sum | Rank Mean | Rank Median | Mean p value | Median p value |
|---|---|---|---|---|---|---|---|
| OBD142_005.007_1x | OBD142_005.007 | 527 | 12594.5 | 125.945 | 76.5 | 0.57000 | 0.28906 |
| OBD142_009.011_1.4x | OBD142_009.011 | 737 | 9784 | 97.84 | 44.5 | 0.44750 | 0.18750 |
| OBD142_025.027_1.2x | OBD142_025.027 | 1000 | 11604 | 116.04 | 42 | 0.53687 | 0.18750 |
| OBD142_029.031_1.4x | OBD142_029.031 | 1000 | 2760.5 | 27.605 | 38 | 0.13594 | 0.18750 |
| OBD142_041.043_1.2x | OBD142_041.043 | 737 | 9784 | 97.84 | 44.5 | 0.44750 | 0.18750 |
| OBD142_045.047_1x | OBD142_045.047 | 525 | 13251.5 | 132.515 | 77.5 | 0.60297 | 0.28906 |
| OBD142_057.059_1.8x | OBD142_057.059 | 715 | 11959.5 | 119.595 | 51.5 | 0.55312 | 0.18750 |
| OBD142_061.063_1.4x | OBD142_061.063 | 814 | 10698.5 | 106.985 | 44.5 | 0.49625 | 0.18750 |
| OBD142_065.067_1.2x | OBD142_065.067 | 1000 | 859.5 | 8.595 | 9.5 | 0.05469 | 0.07031 |
| OBD142_069.071_1.2x | OBD142_069.071 | 967 | 10625.5 | 106.255 | 43 | 0.48812 | 0.18750 |
| OBD142_081.083_1.4x | OBD142_081.083 | 1000 | 2686 | 26.86 | 34 | 0.13008 | 0.18750 |
| OBD142_097.099_1.8x | OBD142_097.099 | 1000 | 11838 | 118.38 | 51.5 | 0.54500 | 0.18750 |
| OBD142_101.103_1x | OBD142_101.103 | 1000 | 5050 | 50.5 | 70 | 0.21125 | 0.28906 |
| OBD142_109.111_1.2x | OBD142_109.111 | 1000 | 11604 | 116.04 | 42 | 0.53687 | 0.18750 |
| OBD142_121.123_1.8x | OBD142_121.123 | 814 | 10698.5 | 106.985 | 44.5 | 0.49625 | 0.18750 |
| OBD142_133.135_1.8x | OBD142_133.135 | 737 | 9784 | 97.84 | 44.5 | 0.44750 | 0.18750 |
| OBD142_137.139_1.2x | OBD142_137.139 | 1000 | 3052 | 30.52 | 39 | 0.14414 | 0.18750 |
| OBD142_141.143_1.4x | OBD142_141.143 | 737 | 9784 | 97.84 | 44.5 | 0.44750 | 0.18750 |

-continued

| Marker with Dilution | Marker | Freq | Rank Sum | Rank Mean | Rank Median | Mean p value | Median p value |
|---|---|---|---|---|---|---|---|
| OBD142__145.147__1.4x | OBD142__145.147 | 523 | 12431.5 | 124.315 | 81.5 | 0.56711 | 0.28906 |
| OBD142__153.155__1.4x | OBD142__153.155 | 1000 | 914 | 9.14 | 10 | 0.05781 | 0.07031 |
| OBD142__157.159__1.4x | OBD142__157.159 | 514 | 13293.5 | 132.935 | 83.5 | 0.60250 | 0.28906 |
| OBD142__165.167__1x | OBD142__165.167 | 1000 | 4818.5 | 48.185 | 69.5 | 0.20031 | 0.28906 |
| OBD142__185.187__1.4x | OBD142__185.187 | 1000 | 3161 | 31.61 | 39 | 0.15117 | 0.18750 |
| OBD142__189.191__1x | OBD142__189.191 | 1000 | 2760.5 | 27.605 | 38 | 0.13594 | 0.18750 |
| OBD142__197.199__1.4x | OBD142__197.199 | 1000 | 2795 | 27.95 | 38 | 0.13711 | 0.18750 |
| OBD142__201.203__1.4x | OBD142__201.203 | 1000 | 2903.5 | 29.035 | 38.5 | 0.14180 | 0.18750 |
| OBD142__213.215__1.4x | OBD142__213.215 | 151 | 19515.5 | 195.155 | 212 | 0.90047 | 1.00000 |
| OBD142__233.235__1.2x | OBD142__233.235 | 505 | 12737 | 127.37 | 81.5 | 0.57758 | 0.28906 |
| OBD142__241.243__1x | OBD142__241.243 | 1000 | 2820.5 | 28.205 | 38 | 0.13828 | 0.18750 |
| OBD142__253.255__1.2x | OBD142__253.255 | 1000 | 5334.5 | 53.345 | 70 | 0.22125 | 0.28906 |
| OBD142__257.259__1.2x | OBD142__257.259 | 1000 | 11995.5 | 119.955 | 51.5 | 0.55312 | 0.18750 |
| OBD142__261.263__1x | OBD142__261.263 | 1000 | 5144 | 51.44 | 69.5 | 0.21031 | 0.28906 |
| OBD142__265.267__1.4x | OBD142__265.267 | 967 | 9975.5 | 99.755 | 41.5 | 0.46375 | 0.18750 |
| OBD142__273.275__1.4x | OBD142__273.275 | 962 | 12527 | 125.27 | 51.5 | 0.58562 | 0.18750 |
| OBD142__277.279__1.2x | OBD142__277.279 | 1000 | 3060 | 30.6 | 38.5 | 0.14766 | 0.18750 |
| OBD142__297.299__1.2x | OBD142__297.299 | 1000 | 847.5 | 8.475 | 9.5 | 0.05531 | 0.07031 |
| OBD142__309.311__1.4x | OBD142__309.311 | 806 | 9550 | 95.5 | 42 | 0.43937 | 0.18750 |
| OBD142__313.315__1x | OBD142__313.315 | 1000 | 2760.5 | 27.605 | 38 | 0.13594 | 0.18750 |
| OBD142__321.323__1.2x | OBD142__321.323 | 1000 | 11995.5 | 119.955 | 51.5 | 0.55312 | 0.18750 |
| OBD142__325.327__1.2x | OBD142__325.327 | 1000 | 4958.5 | 49.585 | 69.5 | 0.20344 | 0.28906 |
| OBD142__329.331__1.4x | OBD142__329.331 | 1000 | 2795 | 27.95 | 38 | 0.13711 | 0.18750 |
| OBD142__337.339__1x | OBD142__337.339 | 817 | 10759.5 | 107.595 | 43 | 0.49625 | 0.18750 |
| OBD142__357.359__1.4x | OBD142__357.359 | 962 | 12527 | 125.27 | 51.5 | 0.58562 | 0.18750 |
| OBD142__361.363__1.2x | OBD142__361.363 | 932 | 11406.5 | 114.065 | 43 | 0.52875 | 0.18750 |
| OBD142__373.375__1x | OBD142__373.375 | 1000 | 2903.5 | 29.035 | 38.5 | 0.14180 | 0.18750 |
| OBD142__393.395__1.2x | OBD142__393.395 | 1000 | 921.5 | 9.215 | 10.5 | 0.05781 | 0.07031 |
| OBD142__401.403__1x | OBD142__401.403 | 1000 | 2820.5 | 28.205 | 38 | 0.13828 | 0.18750 |
| OBD142__405.407__1x | OBD142__405.407 | 537 | 11739.5 | 117.395 | 73.5 | 0.52570 | 0.28906 |
| OBD142__413.415__1.2x | OBD142__413.415 | 638 | 10473 | 104.73 | 45.5 | 0.48812 | 0.18750 |
| OBD142__433.435__1x | OBD142__433.435 | 1000 | 2969.5 | 29.695 | 39 | 0.14297 | 0.18750 |
| OBD142__437.439__1x | OBD142__437.439 | 1000 | 5144 | 51.44 | 69.5 | 0.21031 | 0.28906 |
| OBD142__445.447__1.2x | OBD142__445.447 | 752 | 10351.5 | 103.515 | 45 | 0.48000 | 0.18750 |
| OBD142__457.459__1x | OBD142__457.459 | 1000 | 3016 | 30.16 | 38.5 | 0.14414 | 0.18750 |
| OBD142__469.471__1.2x | OBD142__469.471 | 1000 | 2829 | 28.29 | 38.5 | 0.13594 | 0.18750 |
| OBD142__477.479__1.2x | OBD142__477.479 | 752 | 10351.5 | 103.515 | 45 | 0.48000 | 0.18750 |
| OBD142__489.491__1x | OBD142__489.491 | 937 | 9975.5 | 99.755 | 41.5 | 0.46375 | 0.18750 |
| OBD142__501.503__1x | OBD142__501.503 | 537 | 11739.5 | 117.395 | 73.5 | 0.52570 | 0.28906 |
| OBD142__509.511__1.8x | OBD142__509.511 | 970 | 11725.5 | 117.255 | 43.25 | 0.54500 | 0.18750 |
| OBD142__517.519__1x | OBD142__517.519 | 1000 | 914 | 9.14 | 10 | 0.05781 | 0.07031 |

Table 8 shows predictive markers for endurance training response, which are preferably used for typing humans. (Present in endurance training in humans).

| Marker with Dilution | Marker | Freq | Rank Sum | Rank Mean | Rank Median | Mean p value | Median p value |
|---|---|---|---|---|---|---|---|
| OBD142__005.007__1x | OBD142__005.007 | 731 | 10275.5 | 102.755 | 71.5 | 0.33252 | 0.23486 |
| OBD142__017.019__1x | OBD142__017.019 | 657 | 8644 | 86.44 | 57.5 | 0.28238 | 0.23486 |
| OBD142__025.027__1.2x | OBD142__025.027 | 1000 | 1075 | 10.75 | 6.25 | 0.04110 | 0.03613 |
| OBD142__029.031__1x | OBD142__029.031 | 971 | 4960.5 | 49.605 | 39.5 | 0.17457 | 0.13770 |
| OBD142__041.043__1.4x | OBD142__041.043 | 837 | 9882.5 | 98.825 | 83.75 | 0.33162 | 0.28271 |
| OBD142__045.047__1.2x | OBD142__045.047 | 817 | 7944 | 79.44 | 52 | 0.25580 | 0.19141 |
| OBD142__057.059__1.4x | OBD142__057.059 | 707 | 8843 | 88.43 | 56.25 | 0.28852 | 0.19141 |
| OBD142__061.063__1.8x | OBD142__061.063 | 906 | 5038 | 50.38 | 28.5 | 0.16971 | 0.09229 |
| OBD142__065.067__1x | OBD142__065.067 | 992 | 2771.5 | 27.715 | 18.25 | 0.10043 | 0.05800 |
| OBD142__069.071__1.2x | OBD142__069.071 | 998 | 2877.5 | 28.775 | 16.25 | 0.10248 | 0.05800 |
| OBD142__085.087__1.4x | OBD142__085.087 | 783 | 13339.5 | 133.395 | 88.75 | 0.44247 | 0.28271 |
| OBD142__089.091__1x | OBD142__089.091 | 214 | 21704.5 | 217.045 | 221.25 | 0.70459 | 0.58105 |
| OBD142__097.099__1.8x | OBD142__097.099 | 986 | 4753 | 47.53 | 36.75 | 0.16534 | 0.13770 |
| OBD142__101.103__1x | OBD142__101.103 | 692 | 10572.5 | 105.725 | 74.75 | 0.34013 | 0.26685 |
| OBD142__113.115__1.2x | OBD142__113.115 | 633 | 11276 | 112.76 | 76.75 | 0.36933 | 0.26685 |
| OBD142__117.119__1.2x | OBD142__117.119 | 586 | 11545 | 115.45 | 80.75 | 0.36613 | 0.26685 |
| OBD142__121.123__1.8x | OBD142__121.123 | 785 | 12882.5 | 128.825 | 91.75 | 0.42484 | 0.28271 |
| OBD142__137.139__1.2x | OBD142__137.139 | 811 | 8486.5 | 84.865 | 55 | 0.28375 | 0.19751 |
| OBD142__145.147__1.2x | OBD142__145.147 | 779 | 9565.5 | 95.655 | 67 | 0.31244 | 0.23486 |
| OBD142__153.155__1.2x | OBD142__153.155 | 996 | 2110.5 | 21.105 | 13.5 | 0.08214 | 0.07031 |
| OBD142__157.159__1.4x | OBD142__157.159 | 901 | 4935 | 49.35 | 24 | 0.16512 | 0.09229 |
| OBD142__181.183__1.2x | OBD142__181.183 | 726 | 13631.5 | 136.315 | 88.5 | 0.44859 | 0.28271 |
| OBD142__185.187__1.4x | OBD142__185.187 | 800 | 7477.5 | 74.775 | 54.5 | 0.24398 | 0.19141 |
| OBD142__189.191__1.2x | OBD142__189.191 | 990 | 2092.5 | 20.925 | 13.75 | 0.08116 | 0.07031 |

-continued

| Marker with Dilution | Marker | Freq | Rank Sum | Rank Mean | Rank Median | Mean p value | Median p value |
|---|---|---|---|---|---|---|---|
| OBD142__197.199__1.4x | OBD142__197.199 | 806 | 10234 | 102.34 | 88 | 0.34598 | 0.28271 |
| OBD142__201.203__1.4x | OBD142__201.203 | 752 | 10967 | 109.67 | 93 | 0.36080 | 0.28271 |
| OBD142__225.227__1.2x | OBD142__225.227 | 910 | 9781 | 97.81 | 83.75 | 0.32891 | 0.28271 |
| OBD142__233.235__1.2x | OBD142__233.235 | 886 | 6386 | 63.86 | 29.75 | 0.21925 | 0.09229 |
| OBD142__241.243__1x | OBD142__241.243 | 883 | 4360.5 | 43.605 | 30.5 | 0.15074 | 0.11284 |
| OBD142__253.255__1.2x | OBD142__253.255 | 986 | 2287.5 | 22.875 | 18 | 0.08839 | 0.09229 |
| OBD142__257.259__1.2x | OBD142__257.259 | 961 | 6557.5 | 65.575 | 39.75 | 0.22005 | 0.13770 |
| OBD142__261.263__1x | OBD142__261.263 | 894 | 5356.5 | 53.565 | 26.25 | 0.17615 | 0.09229 |
| OBD142__273.275__1.4x | OBD142__273.275 | 864 | 10216.5 | 102.165 | 88 | 0.34298 | 0.28271 |
| OBD142__309.311__1.2x | OBD142__309.311 | 762 | 10278 | 102.78 | 64 | 0.33810 | 0.23486 |
| OBD142__321.323__1x | OBD142__321.323 | 958 | 5677.5 | 56.775 | 42.25 | 0.18968 | 0.13770 |
| OBD142__325.327__1.4x | OBD142__325.327 | 958 | 4037 | 40.37 | 20.75 | 0.13814 | 0.09229 |
| OBD142__329.331__1x | OBD142__329.331 | 943 | 6060.5 | 60.605 | 45 | 0.19830 | 0.13770 |
| OBD142__349.351__1x | OBD142__349.351 | 689 | 10674 | 106.74 | 74.75 | 0.35113 | 0.24731 |
| OBD142__353.355__1x | OBD142__353.355 | 743 | 9010.5 | 90.105 | 65.5 | 0.29709 | 0.23486 |
| OBD142__361.363__1.2x | OBD142__361.363 | 741 | 9202 | 92.02 | 59.5 | 0.30628 | 0.23486 |
| OBD142__373.375__1x | OBD142__373.375 | 952 | 5814 | 58.14 | 41.75 | 0.19707 | 0.13770 |
| OBD142__389.391__1x | OBD142__389.391 | 855 | 10445 | 104.45 | 84.75 | 0.35071 | 0.28271 |
| OBD142__393.395__1.2x | OBD142__393.395 | 961 | 5026 | 50.26 | 30.75 | 0.16382 | 0.10229 |
| OBD142__405.407__1x | OBD142__405.407 | 661 | 9730.5 | 97.305 | 74.25 | 0.32788 | 0.26685 |
| OBD142__433.435__1x | OBD142__433.435 | 663 | 10280.5 | 102.805 | 69 | 0.33826 | 0.23486 |
| OBD142__437.439__1.2x | OBD142__437.439 | 679 | 11065 | 110.65 | 77.25 | 0.36270 | 0.25977 |
| OBD142__445.447__1.2x | OBD142__445.447 | 959 | 5236.5 | 52.365 | 39 | 0.18092 | 0.13770 |
| OBD142__461.463__1.4x | OBD142__461.463 | 946 | 6240 | 62.4 | 36.5 | 0.21435 | 0.13770 |
| OBD142__469.471__1.2x | OBD142__469.471 | 832 | 8858.5 | 88.585 | 56.75 | 0.29436 | 0.19917 |
| OBD142__477.479__1x | OBD142__477.479 | 629 | 12148 | 121.48 | 74.75 | 0.40365 | 0.25977 |
| OBD142__489.491__1.2x | OBD142__489.491 | 748 | 7759.5 | 77.595 | 58.5 | 0.24931 | 0.20083 |
| OBD142__497.499__1.2x | OBD142__497.499 | 675 | 10138.5 | 101.385 | 77.25 | 0.33286 | 0.26331 |
| OBD142__509.511__1.8x | OBD142__509.511 | 988 | 4712 | 47.12 | 33 | 0.16110 | 0.10229 |
| OBD142__521.523__1.4x | OBD142__521.523 | 747 | 13280 | 132.8 | 93.5 | 0.44187 | 0.28271 |

Table 9 shows predictive markers for either strength or endurance training response, which are preferably used for typing humans. (Present in strength and endurance training in humans).

TABLE 10

| Patient Sample ID | Basic Annotation | Sex |
|---|---|---|
| Brigand | Horse - Sprinter | Gelding |
| Brigand | Horse - Sprinter | Gelding |
| Headway | Horse - Sprinter | Colt |
| Headway | Horse - Sprinter | Colt |
| Barton Mills | Horse - Sprinter | Colt |
| Barton Mills | Horse - Sprinter | Colt |
| Muthmir | Horse - Sprinter | Gelding |
| Muthmir | Horse - Sprinter | Gelding |
| One Master | Horse - Sprinter | Filly |
| One Master | Horse - Sprinter | Filly |
| Move Swiftly | Horse - Sprinter | Filly |
| Move Swiftly | Horse - Sprinter | Filly |
| Island of life | Horse - Sprinter | Filly |
| Island of life | Horse - Sprinter | Filly |
| Juthoor | Horse - Sprinter | Colt |
| Juthoor | Horse - Sprinter | Colt |
| Pretty Baby | Horse - Sprinter | Filly |
| Pretty Baby | Horse - Sprinter | Filly |
| Robin Weathers | Horse - Sprinter | Colt |
| Robin Weathers | Horse - Sprinter | Colt |
| Beshaayir | Horse - Sprinter | Filly |
| Beshaayir | Horse - Sprinter | Filly |
| Mashaheer | Horse - Sprinter | Gelding |
| Mashaheer | Horse - Sprinter | Gelding |
| Mubtasim | Horse - Sprinter | Gelding |
| Mubtasim | Horse - Sprinter | Gelding |
| Tasleet | Horse - Sprinter | Colt |
| Tasleet | Horse - Sprinter | Colt |
| Important Mission | Horse - Sprinter | Gelding |
| Important Mission | Horse - Sprinter | Gelding |
| Algaffaal | Horse - Sprinter | Colt |
| Algaffaal | Horse - Sprinter | Colt |
| Carpio | Horse - Untrained | Colt |

TABLE 10-continued

| Patient Sample ID | Basic Annotation | Sex |
|---|---|---|
| Carpio | Horse - Untrained | Colt |
| ex Donnellys Hollow | Horse - Untrained | Filly |
| ex Donnellys Hollow | Horse - Untrained | Filly |
| ex Marika | Horse - Untrained | Colt |
| ex Marika | Horse - Untrained | Colt |
| Narina | Horse - Untrained | Filly |
| Narina | Horse - Untrained | Filly |
| Setenta | Horse - Untrained | Colt |
| Setenta | Horse - Untrained | Colt |
| To Be Wild | Horse - Untrained | Colt |
| To Be Wild | Horse - Untrained | Colt |
| Starkers | Horse - Untrained | Filly |
| Starkers | Horse - Untrained | Filly |
| Soloist | Horse - Untrained | Filly |
| Soloist | Horse - Untrained | Filly |
| Field Gun | Horse - Untrained | Gelding |
| Field Gun | Horse - Untrained | Gelding |
| ex No Song | Horse - Untrained | Colt |
| ex No Song | Horse - Untrained | Colt |
| ex Celtic Lynn | Horse - Untrained | Colt |
| ex Celtic Lynn | Horse - Untrained | Colt |
| flare of firelight | Horse - Untrained | Colt |
| flare of firelight | Horse - Untrained | Colt |
| Second Thought | Horse - Untrained | Colt |
| Second Thought | Horse - Untrained | Colt |
| Dance Pearl | Horse - Untrained | Filly |
| Dance Pearl | Horse - Untrained | Filly |
| ex Yosoldina | Horse - Untrained | Filly |
| ex Yosoldina | Horse - Untrained | Filly |
| Queen of Mean | Horse - Untrained | Colt |
| Queen of Mean | Horse - Untrained | Colt |
| Al Muffrih | Horse - Stayer | Stayer |
| Al Muffrih | Horse - Stayer | Stayer |
| Dal Harraild | Horse - Stayer | Gelding |

TABLE 10-continued

| Patient Sample ID | Basic Annotation | Sex |
|---|---|---|
| Dal Harraild | Horse - Stayer | Gelding |
| Humble Hera | Horse - Stayer | Colt |
| Humble Hera | Horse - Stayer | Colt |
| Istanbul Sultan | Horse - Stayer | Gelding |
| Istanbul Sultan | Horse - Stayer | Gelding |

TABLE 12

| | Untrained | Sprinter | Stayer |
|---|---|---|---|
| Colt | 9 | 6 | 7 |
| Gelding | 1 | 5 | 4 |
| Filly | 6 | 5 | 5 |

| N | Marker | Exact_Boschloo_p.value | Median_Boshloo | Dilution | Type |
|---|---|---|---|---|---|
| 1 | OBD154_125/OBD154_127 | 0.00631 | 0.037817955 | OBD154_125/OBD154_127_1:2x | Present in Sprinter |
| 2 | OBD154_085/OBD154_087 | 0.03886 | 0.088156223 | OBD154_085/OBD154_087_1:2x | Present in Sprinter |
| 3 | OBD154_157/OBD154_159 | 0.03886 | 0.088156223 | OBD154_157/OBD154_159_1:2x | Present in Stayer |
| 4 | OBD154_013/OBD154_015 | 0.05011 | 0.13798237 | OBD154_013/OBD154_015_1x | Present in Sprinter |
| 5 | OBD154_245/OBD154_247 | 0.05011 | 0.13798237 | OBD154_245/OBD154_247_1x | Present in Sprinter |
| 6 | OBD154_229/OBD154_231 | 0.05419 | 0.239017755 | OBD154_229/OBD154_231_1x | Present in Sprinter |
| 7 | OBD154_093/OBD154_095 | 0.07514 | 0.239017755 | OBD154_093/OBD154_095_1:2x | Present in Sprinter |
| 8 | OBD154_049/OBD154_051 | 0.11993 | 0.243710751 | OBD154_049/OBD154_051_1:4x | Present in Sprinter |
| 9 | OBD154_201/OBD154_203 | 0.11993 | 0.243710751 | OBD154_201/OBD154_203_1:2x | Present in Stayer |
| 10 | OBD154_041/OBD154_043 | 0.12508 | 0.239017755 | OBD154_041/OBD154_043_1:4x | Present in Stayer |
| 11 | OBD154_073/OBD154_075 | 0.12508 | 0.239017755 | OBD154_073/OBD154_075_1x | Present in Stayer |
| 12 | OBD154_205/OBD154_207 | 0.12508 | 0.239017755 | OBD154_205/OBD154_207_1:2x | Present in Sprinter |
| 13 | OBD154_009/OBD154_011 | 0.18007 | 0.239017755 | OBD154_009/OBD154_011_1:2x | Present in Sprinter |
| 14 | OBD154_045/OBD154_047 | 0.18007 | 0.287077538 | OBD154_045/OBD154_047_1x | Present in Stayer |
| 15 | OBD154_141/OBD154_143 | 0.18007 | 0.287077538 | OBD154_141/OBD154_143_1x | Present in Sprinter |
| 16 | OBD154_165/OBD154_167 | 0.18007 | 0.287077538 | OBD154_165/OBD154_167_1x | Present in Sprinter |
| 17 | OBD154_213/OBD154_215 | 0.18007 | 0.265394144 | OBD154_213/OBD154_215_1:2x | Present in Stayer |

TABLE 10-continued

| Patient Sample ID | Basic Annotation | Sex |
|---|---|---|
| Young Rascal | Horse - Stayer | Colt |
| Young Rascal | Horse - Stayer | Colt |
| Give & Take | Horse - Stayer | Filly |
| Give & Take | Horse - Stayer | Filly |
| Alexana | Horse - Stayer | Filly |
| Alexana | Horse - Stayer | Filly |
| Call To Mind | Horse - Stayer | Colt |
| Call To Mind | Horse - Stayer | Colt |
| Cristal Spirit | Horse - Stayer | Gelding |
| Cristal Spirit | Horse - Stayer | Gelding |
| Heart of Grace | Horse - Stayer | Filly |
| Heart of Grace | Horse - Stayer | Filly |
| Mam'Selle | Horse - Stayer | Filly |
| Mam'Selle | Horse - Stayer | Filly |
| Smashed | Horse - Stayer | Colt |
| Smashed | Horse - Stayer | Colt |
| Dramatic Queen | Horse - Stayer | Filly |
| Dramatic Queen | Horse - Stayer | Filly |
| Nicklaus | Horse - Stayer | Colt |
| Nicklaus | Horse - Stayer | Colt |
| Reverend Jacobs | Horse - Stayer | Gelding |
| Reverend Jacobs | Horse - Stayer | Gelding |
| The Grand Visir | Horse - Stayer | Colt |
| The Grand Visir | Horse - Stayer | Colt |

TABLE 11

| Sex | Description |
|---|---|
| Colt | Male horse less than three years old |
| Gelding | Castrated Male horse less than three years old |
| Filly | Female horse less than three years old |

Table 13 shows the top markers for Stayer versus Sprinter phenotype (n=32, 16 Stayer, 16 Sprinter), which are preferably used to type horses.

| Marker | Nearest Gene/loci | Type |
|---|---|---|
| OBD154_045/OBD154_047 | MC1R/ NM_001081945 | Present in Stayer |
| OBD154_073/OBD154_075 | MIRLET7A-2/ PPARA | Present in Stayer |
| OBD154_009/OBD154_011 | MIR1898 | Present in Sprinter |
| OBD154_041/OBD154_043 | TAGLN/ MIR125B | Present in Stayer |
| OBD154_093/OBD154_095 | MIR1248/TFRC | Present in Sprinter |
| OBD154_085/OBD154_087 | SYNJ2BP | Present in Sprinter |
| OBD154_013/OBD154_015 | AMPP/ARNTL | Present in Sprinter |
| OBD154_049/OBD154_051 | MC1R/ NM_001081945 | Present in Sprinter |
| OBD154_125/OBD154_127 | CCDC146 | Present in Sprinter |
| OBD154_165/OBD154_167 | MIR17 | Present in Sprinter |
| OBD154_201/OBD154_203 | GSN | Present in Stayer |
| OBD154_229/OBD154_231 | ALPHA4GNT | Present in Sprinter |
| OBD154_213/OBD154_215 | BMP7 | Present in Stayer |
| OBD154_205/OBD154_207 | S100G/NROB1 | Present in Sprinter |
| OBD154_157/OBD154_159 | EEF1A1 | Present in Stayer |
| OBD154_245/OBD154_247 | MIR218 | Present in Sprinter |
| OBD154_141/OBD154_143 | NME1/SRSF1 | Present in Sprinter |

Table 14 shows markers discovered in humans that applicable to horses, and the closest genomic loci, which can be used to type horses.

TABLE 15

| Sample ID | Horse Name | Phenotype | Probability | Comments |
|---|---|---|---|---|
| Holo009 | One Master | Sprinter | 0.887 | Correct |
| Holo013 | Island of life | Sprinter | 0.962 | Correct |

TABLE 15-continued

| Sample ID | Horse Name | Phenotype | Probability | Comments |
|---|---|---|---|---|
| Holo019 | Robin Weathers | Sprinter | 0.321 | Misclassified |
| Holo017 | Pretty Baby | Sprinter | 0.872 | Correct |
| Holo015 | Juthoor | Sprinter | 0.974 | Correct |
| Holo023 | Masha heer | Sprinter | 0.960 | Correct |
| Holo003 | Headway | Sprinter | 0.852 | Correct |
| Holo011 | Move Swiftly | Sprinter | 0.993 | Correct |
| Holo007 | Muthmir | Sprinter | 0.732 | Correct |
| Holo031 | Algaffaal | Sprinter | 0.958 | Correct |
| Holo005 | Barton Mills | Sprinter | 0.974 | Correct |
| Holo021 | Beshaayir | Sprinter | 0.961 | Correct |
| Holo001 | Brigand | Sprinter | 0.991 | Correct |
| Holo025 | Mubtasim | Sprinter | 0.835 | Correct |
| Holo027 | Tasleet | Sprinter | 0.958 | Correct |
| Holo029 | Important Mission | Sprinter | 0.670 | Correct |
| Holo065 | Al Muffrih | Stayer | 0.150 | Correct |
| Holo077 | Alexana | Stayer | 0.014 | Correct |
| Holo069 | Humble Hero | Stayer | 0.550 | Misclassified |
| Holo091 | Nicklaus | Stayer | 0.086 | Correct |
| Holo071 | Istanbul Sultan | Stayer | 0.265 | Correct |
| Holo075 | Give & Take | Stayer | 0.271 | Correct |
| Holo083 | Heart of Grace | Stayer | 0.032 | Correct |
| Holo067 | Dal Harraild | Stayer | 0.298 | Correct |
| Holo089 | Dramatic Queen | Stayer | 0.027 | Correct |
| Holo079 | Call To Mind | Stayer | 0.032 | Correct |
| Holo095 | The Grand Visir | Stayer | 0.283 | Correct |
| Holo081 | Cristal Spirit | Stayer | 0.032 | Correct |
| Holo093 | Reverend Jacobs | Stayer | 0.095 | Correct |
| Holo087 | Smashed | Stayer | 0.167 | Correct |
| Holo073 | Young Rascal | Stayer | 0.166 | Correct |
| Holo085 | Mam'Selle | Stayer | 0.014 | Correct |

TABLE 16

| Probability Score | Classifier Call |
|---|---|
| <0.3 | Stayer |
| 0.31-0.69 | Unclassified |
| >0.7 | Sprinter |

TABLE 17

| Sample | Horse Name | Probability | Call |
|---|---|---|---|
| Holo053 | ex Celtic Lynn | 0.383045197 | Unclassified |
| Holo045 | Starkers | 0.165671632 | Stayer |
| Holo035 | ex Donnellys Hollow | 0.549999774 | Unclassified |
| Holo051 | ex No Song | 0.973659277 | Sprinter |
| Holo057 | Second Thought | 0.271233022 | Stayer |
| Holo059 | Dance Pearl | 0.549999774 | Unclassified |
| Holo039 | Narina | 0.871761441 | Sprinter |
| Holo043 | To Be Wild | 0.092756219 | Stayer |
| Holo061 | ex Yosoldina | 0.031833708 | Stayer |
| Holo055 | Flare of Firelight | 0.889145136 | Sprinter |
| Holo063 | Queen of Mean | 0.004074222 | Stayer |
| Holo047 | Soloist | 0.025709741 | Stayer |
| Holo033 | Carpio | 0.0436165 | Stayer |
| Holo041 | Setenta | 0.549999774 | Unclassified |
| Holo049 | Field Gun | 0.094702385 | Stayer |
| Holo037 | ex Marika | 0.882559121 | Sprinter |

| Marker | Exact_Boschloo_p.value | Type |
|---|---|---|
| OBD154_001/OBD154_003_1:2x | 0.597203758 | Present in Sprinter |
| OBD154_009/OBD154_011_1:2x | 0.180069259 | Present in Sprinter |
| OBD154_013/OBD154_015_1x | 0.050106528 | Present in Sprinter |
| OBD154_033/OBD154_035_1:4x | 0.283703806 | Present in Sprinter |
| OBD154_037/OBD154_039_1:8x | 0.523402567 | Present in Sprinter |
| OBD154_041/OBD154_043_1x | 0.64299739 | Present in Sprinter |
| OBD154_045/OBD154_047_1x | 0.180069259 | Present in stayer |
| OBD154_049/OBD154_051_1:4x | 0.11992508 | Present in Sprinter |
| OBD154_053/OBD154_055_1:2x | 0.597203758 | Present in Sprinter |
| OBD154_057/OBD154_059_1:2x | 0.663949317 | Present in Sprinter |
| OBD154_061/OBD154_063_1x | 0.663949317 | Present in stayer |
| OBD154_069/OBD154_071_1x | 0.23718116 | Present in Sprinter |
| OBD154_073/OBD154_075_1x | 0.125083174 | Present in stayer |
| OBD154_077/OBD154_079_1x | 0.422463565 | Present in Sprinter |
| OBD154_085/OBD154_087_1:2x | 0.038860637 | Present in Sprinter |
| OBD154_093/OBD154_095_1:2x | 0.075142123 | Present in Sprinter |
| OBD154_097/OBD154_099_1x | 0.523402567 | Present in Sprinter |
| OBD154_105/OBD154_107_1:2x | 0.210490032 | Present in Sprinter |
| OBD154_109/OBD154_lll_1:2x | 0.387940572 | Present in stayer |
| OBD154_113/OBD154_115_1:4x | 0.523402567 | Present in stayer |
| OBD154_117/OBD154_119_1x | 0.659282164 | Present in Sprinter |
| OBD154_121/OBD154_123_1x | 0.659282164 | Present in stayer |
| OBD154_125/OBD154_127_1:2x | 0.006313179 | Present in Sprinter |
| OBD154_133/OBD154_135_1:2x | 0.32961205 | Present in Sprinter |
| OBD154_137/OBD154_139_1x | 0.663949317 | Present in stayer |
| OBD154_141/OBD154_143_1x | 0.180069259 | Present in Sprinter |
| OBD154_149/OBD154_151_1:2x | 0.678620772 | Present in stayer |
| OBD154_153/OBD154_155_1:8x | 0.523402567 | Present in Sprinter |
| OBD154_157/OBD154_159_1:2x | 0.038860637 | Present in stayer |
| OBD154_161/OBD154_163_1:2x | 0.422463565 | Present in stayer |
| OBD154_165/OBD154_167_1x | 0.180069259 | Present in Sprinter |
| OBD154_169/OBD154_171_1:4x | 0.283703806 | Present in Sprinter |
| OBD154_177/OBD154_179_1x | 0.23718116 | Present in Sprinter |
| OBD154_185/OBD154_187_1x | 0.64299739 | Present in stayer |
| OBD154_201/OBD154_203_1x | 0.11992508 | Present in stayer |
| OBD154_205/OBD154_207_1:2x | 0.125083174 | Present in Sprinter |
| OBD154_209/OBD154_211_1:2x | 0.253032887 | Present in Sprinter |
| OBD154_213/OBD154_215_1:2x | 0.180069259 | Present in stayer |
| OBD154_217/OBD154_219_1x | 0.387940572 | Present in Sprinter |
| OBD154_229/OBD154_231_1x | 0.054191604 | Present in stayer |

-continued

| Marker | Exact__Boschloo__p.value | Type |
|---|---|---|
| OBD154__237/OBD154__239__1x | 0.23718116 | Present in Sprinter |
| OBD154__245/OBD154__247__1x | 0.050106528 | Present in stayer |

Table 18 shows the informative markers from the equine study, which are preferably used to type horses.

TABLE 19

| RANKING (*Elite Athlete) | Code | Age | Height (cm) | T. Body Mass (kg) | VO2max/kg | COMBINED 3 Lifts (kg) | Relative Strength (kg/kg) |
|---|---|---|---|---|---|---|---|
| *1 | C29 | 27 | 186.5 | 67 | 74.5 | 210 | 3.13 |
| *2 | C49 | 29 | 172.4 | 60 | 73.8 | 255 | 4.25 |
| *3 | C6 | 27 | 182 | 70.5 | 71.7 | 245 | 3.48 |
| *4 | C10 | 30 | 185.5 | 75 | 65.5 | 240 | 3.20 |
| *5 | C66 | 21 | 190.7 | 76 | 64.6 | 335 | 4.41 |
| *6 | C69 | 44 | 171 | 66 | 63.3 | 280 | 4.24 |
| *7 | C27 | 28 | 176 | 57 | 62.4 | 250 | 4.39 |
| 8 | C8 | 21 | 183.3 | 75 | 61.3 | 325 | 4.33 |
| 9 | C23 | 43 | 189.5 | 77 | 60.2 | 240 | 3.12 |
| 10 | C28 | 33 | 193 | 72.5 | 60.2 | 225 | 3.10 |
| 11 | C15 | 25 | 183 | 77 | 59.6 | 350 | 4.55 |
| 12 | C67 | 43 | 179.3 | 74 | 58.4 | 240 | 3.24 |
| 13 | B86 | 33 | 181 | 77.5 | 57.65 | 325 | 4.19 |
| 14 | C32 | 47 | 166.6 | 67 | 57.5 | 170 | 2.54 |
| 15 | C24 | 18 | 183 | 81 | 56.2 | 335 | 4.14 |
| 16 | C25 | 51 | 184 | 75 | 56.1 | 210 | 2.80 |
| 17 | C4 | 21 | 174 | 73 | 55.4 | 245 | 3.36 |
| 18 | C9 | 24 | 185.5 | 70.5 | 55.1 | 260 | 3.69 |
| 19 | C14 | 40 | 179.5 | 70 | 54.7 | 280 | 4.00 |
| 20 | A50 | 24 | 173.1 | 65 | 54.6 | 355 | 5.46 |
| 21 | C60 | 24 | 180 | 77.5 | 54.6 | 335 | 4.32 |
| 22 | C19 | 29 | 188 | 88 | 53.7 | 260 | 2.95 |
| 23 | C35 | 43 | 173.3 | 68 | 51 | 200 | 2.94 |
| 24 | A57 | 28 | 171.6 | 60 | 49.7 | 355 | 5.92 |
| 25 | C12 | 48 | 175 | 92 | 49.5 | 295 | 3.21 |
| 26 | B48 | 21 | 170.5 | 55 | 49.4 | 195 | 3.55 |
| 27 | A21 | 30 | 188.5 | 80 | 48.9 | 415 | 5.19 |
| 28 | B52 | 45 | 181.9 | 68.5 | 48.7 | 155 | 2.26 |
| 29 | A20 | 37 | 168 | 69 | 48.4 | 465 | 6.74 |
| 30 | A54 | 18 | 163 | 69 | 47.8 | 425 | 6.16 |
| 31 | A31 | 25 | 181.2 | 78 | 47.1 | 465 | 5.96 |
| 32 | A56 | 25 | 176.6 | 82.5 | 46.4 | 380 | 4.61 |
| 33 | A55 | 18 | 163 | 67.5 | 45.7 | 435 | 6.44 |
| 34 | A3 | 28 | 174 | 70 | 44.6 | 390 | 5.57 |
| 35 | B70 | 28 | 172.4 | 63.5 | 44.4 | 200 | 3.15 |
| 36 | A13 | 28 | 172 | 75 | 44 | 300 | 4.00 |
| 37 | B63 | 49 | 181.6 | 90 | 42.9 | 170 | 1.89 |
| 38 | A2 | 26 | 181 | 92.5 | 42.3 | 475 | 5.14 |
| 38 | A36 | 20 | 189.2 | 92 | 42.1 | 540 | 5.87 |
| 40 | A5 | 42 | 176 | 88 | 42 | 487.5 | 5.54 |
| 41 | A41 | 27 | 175.3 | 79.5 | 41.8 | 475 | 5.97 |
| 42 | A22 | 28 | 176 | 85 | 41 | 530 | 6.24 |
| 43 | A59 | 27 | 184.8 | 80 | 39.3 | 400 | 5.00 |
| 44 | A11 | 29 | 158 | 65.5 | 39.1 | 385 | 5.88 |
| 45 | B46 | 44 | 180.6 | 75 | 39 | 270 | 3.60 |
| 46 | B43 | 42 | 187.4 | 73 | 38.85 | 125 | 1.71 |
| 47 | A30 | 24 | 183.5 | 81 | 37 | 530 | 6.54 |
| 48 | B74 | 34 | 178.4 | 77.5 | 37 | 320 | 4.13 |
| 48 | B44 | 44 | 170.9 | 77 | 36.9 | 190 | 2.47 |
| 50 | A53 | 23 | 173 | 68 | 36.8 | 350 | 5.15 |
| 51 | B78 | 27 | 188.2 | 98 | 36.5 | 250 | 2.55 |
| 52 | A7 | 22 | 178 | 85 | 36 | 490 | 5.76 |
| 53 | B77 | 45 | 169.1 | 88.5 | 35.9 | 300 | 3.39 |
| 54 | B45 | 41 | 175.4 | 88.5 | 35.7 | 230 | 2.60 |
| 55 | B68 | 42 | 176.5 | 88 | 35.5 | 275 | 3.13 |
| 56 | B85 | 39 | 184.9 | 106 | 35.3 | 330 | 3.11 |
| 57 | A58 | 23 | 175 | 70 | 35.1 | 350 | 5.00 |
| 58 | B37 | 31 | 192.5 | 123 | 34.7 | 310 | 2.52 |
| 59 | B62 | 33 | 199.6 | 109.5 | 34.5 | 280 | 2.56 |
| 60 | B33 | 44 | 177.4 | 88.5 | 33.3 | 255 | 2.88 |
| 61 | B75 | 22 | 178.5 | 99 | 33.2 | 330 | 3.33 |
| 62 | B42 | 45 | 168.1 | 79 | 32.9 | 250 | 3.16 |
| 63 | B79 | 54 | 179 | 71 | 32.6 | 140 | 1.97 |
| 64 | B73 | 46 | 175.1 | 106.5 | 32.1 | 270 | 2.54 |

TABLE 19-continued

| RANKING (*Elite Athlete) | Code | Age | Height (cm) | T. Body Mass (kg) | VO2max/kg | COMBINED 3 Lifts (kg) | Relative Strength (kg/kg) |
|---|---|---|---|---|---|---|---|
| 65 | B64 | 36 | 181.5 | 89.5 | 32.1 | 285 | 3.18 |
| 66 | B18 | 25 | 172.5 | 82 | 32 | 165 | 2.01 |
| 67 | B82 | 35 | 170.3 | 88 | 32 | 315 | 3.58 |
| 68 | B71 | 42 | 184 | 95 | 31.8 | 260 | 2.74 |
| 69 | B16 | 41 | 174.5 | 79 | 31.1 | 260 | 3.29 |
| 70 | B61 | 29 | 180.9 | 97.5 | 31 | 190 | 1.95 |
| 71 | B65 | 33 | 181 | 65.5 | 31 | 145 | 2.21 |
| 72 | B38 | 21 | 194.2 | 73.5 | 30.5 | 130 | 1.77 |
| 73 | B83 | 43 | 186.7 | 94 | 30 | 290 | 3.09 |
| 74 | B81 | 43 | 174.8 | 86.5 | 29.9 | 280 | 3.24 |
| 75 | B80 | 47 | 185.6 | 85 | 29.9 | 170 | 2.00 |
| 76 | B17 | 31 | 171.5 | 89.5 | 29.1 | 345 | 3.85 |
| 77 | A1 | 29 | 176.5 | 89.5 | 28.1 | 467 | 5.22 |
| 78 | B39 | 26 | 185 | 97 | 28 | 200 | 2.06 |
| 79 | B87 | 34 | 187.1 | 101 | 27.9 | 235 | 2.33 |
| 80 | B72 | 33 | 183.5 | 134.5 | 27.8 | 280 | 2.08 |
| 81 | B26 | 30 | 197.5 | 131.5 | 27.1 | 275 | 2.09 |
| 82 | B51 | 33 | 175.4 | 99 | 27 | 270 | 2.73 |
| 83 | B34 | 25 | 175.5 | 92.5 | 25.9 | 300 | 3.24 |
| 84 | B76 | 24 | 196.7 | 74 | 24.5 | 144.5 | 1.95 |
| 85 | B40 | 34 | 169.8 | 78.5 | 24.3 | 170 | 2.17 |

KEY:
RELATIVE STRENGTH (STRONG GROUP) = BLUE
RELATIVE FITNESS (CARDIO GROUP) = ORANGE
SEDENTARY (UNTRAINED GROUP) = GREEN
*DIDN"T MEET CRITERIA (PERFORMANCE) = RED)
GENETIC DISORDER = BLACK

TABLE 20

| RANKING | Code | Age | Height (cm) | T. Body Mass (kg) | VO2max/kg | COMBINED 3 Lifts (kg) | Relative Strength (kg/kg) |
|---|---|---|---|---|---|---|---|
| 1 | A20 | 37 | 168 | 69 | 48.4 | 465 | 6.74 |
| 2 | A30 | 24 | 183.5 | 81 | 37 | 530 | 6.54 |
| 3 | A55 | 18 | 163 | 67.5 | 45.7 | 435 | 6.44 |
| 4 | A22 | 28 | 176 | 85 | 41 | 530 | 6.24 |
| 5 | A54 | 18 | 163 | 69 | 47.8 | 425 | 6.16 |
| 6 | A41 | 27 | 175.3 | 79.5 | 41.8 | 475 | 5.97 |
| 7 | A31 | 25 | 181.2 | 78 | 47.1 | 465 | 5.96 |
| 8 | A57 | 28 | 171.6 | 60 | 49.7 | 355 | 5.92 |
| *9 | A11 | 29 | 158 | 65.5 | 39.1 | 385 | 5.88 |
| 10 | A36 | 20 | 189.2 | 92 | 42.1 | 540 | 5.87 |
| 11 | A7 | 22 | 178 | 85 | 36 | 490 | 5.76 |
| 12 | A3 | 28 | 174 | 70 | 44.6 | 390 | 5.57 |
| 13 | A5 | 42 | 176 | 88 | 42 | 487.5 | 5.54 |
| 14 | A50 | 24 | 173.1 | 65 | 54.6 | 355 | 5.46 |
| 15 | A1 | 29 | 176.5 | 89.5 | 28.1 | 467 | 5.22 |
| 16 | A21 | 30 | 188.5 | 80 | 48.9 | 415 | 5.19 |
| 17 | A53 | 23 | 173 | 68 | 36.8 | 350 | 5.15 |
| 18 | A2 | 26 | 181 | 92.5 | 42.3 | 475 | 5.14 |
| 19 | A58 | 23 | 175 | 70 | 35.1 | 350 | 5.00 |
| 20 | A59 | 27 | 184.8 | 80 | 39.3 | 400 | 5.00 |
| 21 | A56 | 25 | 176.6 | 82.5 | 46.4 | 380 | 4.61 |
| 22 | C15 | 25 | 183 | 77 | 59.6 | 350 | 4.55 |
| 23 | C66 | 21 | 190.7 | 76 | 64.6 | 335 | 4.41 |
| 24 | C27 | 28 | 176 | 57 | 62.4 | 250 | 4.39 |
| 25 | C8 | 21 | 183.3 | 75 | 61.3 | 325 | 4.33 |
| 26 | C60 | 24 | 180 | 77.5 | 54.6 | 335 | 4.32 |
| 27 | C49 | 29 | 172.4 | 60 | 73.8 | 255 | 4.25 |
| 28 | C69 | 44 | 171 | 66 | 63.3 | 280 | 4.24 |
| 29 | B86 | 33 | 181 | 77.5 | 57.65 | 325 | 4.19 |
| 30 | C24 | 18 | 183 | 81 | 56.2 | 335 | 4.14 |
| 31 | B74 | 34 | 178.4 | 77.5 | 37 | 320 | 4.13 |
| 32 | A13 | 28 | 172 | 75 | 44 | 300 | 4.00 |
| 33 | C14 | 40 | 179.5 | 70 | 54.7 | 280 | 4.00 |
| 34 | B17 | 31 | 171.5 | 89.5 | 29.1 | 345 | 3.85 |
| 35 | C9 | 24 | 185.5 | 70.5 | 55.1 | 260 | 3.69 |
| 36 | B46 | 44 | 180.6 | 75 | 39 | 270 | 3.60 |
| 37 | B82 | 35 | 170.3 | 88 | 32 | 315 | 3.58 |
| 38 | B48 | 21 | 170.5 | 55 | 49.4 | 195 | 3.55 |
| 38 | C6 | 27 | 182 | 70.5 | 71.7 | 245 | 3.48 |

TABLE 20-continued

| RANKING | Code | Age | Height (cm) | T. Body Mass (kg) | VO2max/kg | COMBINED 3 Lifts (kg) | Relative Strength (kg/kg) |
|---|---|---|---|---|---|---|---|
| 40 | B77 | 45 | 169.1 | 88.5 | 35.9 | 300 | 3.39 |
| 41 | C4 | 21 | 174 | 73 | 55.4 | 245 | 3.36 |
| 42 | B75 | 22 | 178.5 | 99 | 33.2 | 330 | 3.33 |
| 43 | B16 | 41 | 174.5 | 79 | 31.1 | 260 | 3.29 |
| 44 | C67 | 43 | 179.3 | 74 | 58.4 | 240 | 3.24 |
| 45 | B34 | 25 | 175.5 | 92.5 | 25.9 | 300 | 3.24 |
| 46 | B81 | 43 | 174.8 | 86.5 | 29.9 | 280 | 3.24 |
| 47 | C12 | 48 | 175 | 92 | 49.5 | 295 | 3.21 |
| 48 | C10 | 30 | 185.5 | 75 | 65.5 | 240 | 3.20 |
| 48 | B64 | 36 | 181.5 | 89.5 | 32.1 | 285 | 3.18 |
| 50 | B42 | 45 | 168.1 | 79 | 32.9 | 250 | 3.16 |
| 51 | B70 | 28 | 172.4 | 63.5 | 44.4 | 200 | 3.15 |
| 52 | C29 | 27 | 186.5 | 67 | 74.5 | 210 | 3.13 |
| 53 | B68 | 42 | 176.5 | 88 | 35.5 | 275 | 3.13 |
| 54 | C23 | 43 | 189.5 | 77 | 60.2 | 240 | 3.12 |
| 55 | B85 | 39 | 184.9 | 106 | 35.3 | 330 | 3.11 |
| 56 | C28 | 33 | 193 | 72.5 | 60.2 | 225 | 3.10 |
| 57 | B83 | 43 | 186.7 | 94 | 30 | 290 | 3.09 |
| 58 | C19 | 29 | 188 | 88 | 53.7 | 260 | 2.95 |
| 59 | C35 | 43 | 173.3 | 68 | 51 | 200 | 2.94 |
| 60 | B33 | 44 | 177.4 | 88.5 | 33.3 | 255 | 2.88 |
| 61 | C25 | 51 | 184 | 75 | 56.1 | 210 | 2.80 |
| 62 | B71 | 42 | 184 | 95 | 31.8 | 260 | 2.74 |
| 63 | B51 | 33 | 175.4 | 99 | 27 | 270 | 2.73 |
| 64 | B45 | 41 | 175.4 | 88.5 | 35.7 | 230 | 2.60 |
| 65 | B62 | 33 | 199.6 | 109.5 | 34.5 | 280 | 2.56 |
| 66 | B78 | 27 | 188.2 | 98 | 36.5 | 250 | 2.55 |
| 67 | C32 | 47 | 166.6 | 67 | 57.5 | 170 | 2.54 |
| 68 | B73 | 46 | 175.1 | 106.5 | 32.1 | 270 | 2.54 |
| 69 | B37 | 31 | 192.5 | 123 | 34.7 | 310 | 2.52 |
| 70 | B44 | 44 | 170.9 | 77 | 36.9 | 190 | 2.47 |
| 71 | B87 | 34 | 187.1 | 101 | 27.9 | 235 | 2.33 |
| 72 | B52 | 45 | 181.9 | 68.5 | 48.7 | 155 | 2.26 |
| 73 | B65 | 33 | 181 | 65.5 | 31 | 145 | 2.21 |
| 74 | B40 | 34 | 169.8 | 78.5 | 24.3 | 170 | 2.17 |
| 75 | B26 | 30 | 197.5 | 131.5 | 27.1 | 275 | 2.09 |
| 76 | B72 | 33 | 183.5 | 134.5 | 27.8 | 280 | 2.08 |
| 77 | B39 | 26 | 185 | 97 | 28 | 200 | 2.06 |
| 78 | B18 | 25 | 172.5 | 82 | 32 | 165 | 2.01 |
| 79 | B80 | 47 | 185.6 | 85 | 29.9 | 170 | 2.00 |
| 80 | B79 | 54 | 179 | 71 | 32.6 | 140 | 1.97 |
| 81 | B76 | 24 | 196.7 | 74 | 24.5 | 144.5 | 1.95 |
| 82 | B61 | 29 | 180.9 | 97.5 | 31 | 190 | 1.95 |
| 83 | B63 | 49 | 181.6 | 90 | 42.9 | 170 | 1.89 |
| 84 | B38 | 21 | 194.2 | 73.5 | 30.5 | 130 | 1.77 |
| 85 | B43 | 42 | 187.4 | 73 | 38.85 | 125 | 1.71 |

*REMOVE - HALLMANS SYNDROME
KEY:
RELATIVE STRENGTH (STRONG GROUP) = BLUE
RELATIVE FITNESS (CARDIO GROUP) = ORANGE
SEDENTARY (UNTRAINED GROUP) = GREEN
DIDN'T MEET CRITERIA (PERFORMANCE) = RED)
GENETIC DISORDER = BLACK

TABLE 21.a

| Gene | Gene Name | Function |
|---|---|---|
| ACACB | Acetyl-CoA Carboxylase Beta | Protein Coding gene. Biotin Deficiency. Diabetes Mellitus. Noninsulin-Dependent. Associated with Metformin pathways. Pharmacodynamics and Regulation of cholestrol biosynthesis by SREBP. |
| ACBD6 | Acyl-CoA Binding Domain Containing 6 | Protein Coding gene. Related to Fatty-Acyl-CoA Biosynthesis and Metabolism. |
| ADRB3 | Adrenoceptor Beta 3 | Protein Coding gene. Body Mass Index Quantitative Trait Locus 11. Low Compliance Bladder. Related to Monoamine GPCRs and Peptide ligand-binding receptors pathways. |
| ALDH1A2 | Aldehyde Dehydrogenase 1 Family Member A2 | Protein Coding Gene. Associated with Diaphragm Disease and Neural Tube Defects. |
| ANO2 | Anoctamin 2 | Protein Coding Gene. Associated with Von Willebrand disease and Scrotal Carcinoma. Related to Olfactory Signaling Pathway and Ion channel transport. |

TABLE 21.a-continued

| Gene | Gene Name | Function |
|---|---|---|
| B3GAT1 | Beta-1,3-Glucuronyltransferase 1 | Protein Coding Gene. Associated with Renal Adenoma and Malignant Glandular Tumor Of Peripheral Nerve Sheath. Related to Glycosaminoglycan metabolism and Metabolism pathways. |
| B3GAT2 | Beta-1,3-Glucuronyltransferase 2 | Protein Coding gene. Diseases associated with B3GAT2 include Colonic Benign Neoplasm. Among its related pathways are Glycosaminoglycan metabolism and Metabolism. Involved in the biosynthesis of L2/HNK-1 carbohydrate epitope on both glycolipids and glycoproteins. |
| BMP7 | Bone Morphogenetic Protein 7 | Protein Coding gene. Diseases associated with BMP7 include Spondylolisthesis and Renal Fibrosis. Among its related pathways are Apoptotic Pathways in Synovial Fibroblasts and PEDF Induced Signaling. Induces cartilage and bone formation. May be the osteoinductive factor responsible for the phenomenon of epithelial osteogenesis. Plays a role in calcium regulation and bone homeostasis. |
| C1GALT1 | Core 1 Synthase, Glycoprotein-N-Acetylgalactosamine | Protein Coding gene. Diseases associated with C1GALT1 include Iga Glomerulonephritis and Hypersensitivity Vasculitis. Among its related pathways are Ectoderm Differentiation and Metabolism of proteins. |
| CALCR | Calcitonin Receptor | Protein Coding gene. Diseases associated with CALCR include Osteoporosis and Bone Mineral Density Quantitative Trait Locus 15. Among its related pathways are RANK Signaling in Osteoclasts and Osteoclast differentiation. |
| CARD11 | Caspase Recruitment Domain Family Member 11 | Protein Coding gene. Diseases associated with CARD11 include B-Cell Expansion With Nfkb And T-Cell Anergy and Immunodeficiency 11. Involved in the costimulatory signal essential for T-cell receptor (TCR)-mediated T-cell activation. |
| CASP9 | Caspase 9 | Protein Coding gene. Diseases associated with CASP9 include Brain Meningioma and Inflammatory Bowel Disease 7. Among its related pathways are Constitutive Signaling by AKT1 E17K in Cancer and Apoptotic Pathways in Synovial Fibroblasts. |
| CBL | Cbl Proto-Oncogene | Protein Coding gene. Diseases associated with CBL include Noonan Syndrome-Like Disorder With Or Without Juvenile Myelomonocytic Leukemia and Juvenile Myelomonocytic Leukemia. Among its related pathways are Negative regulation of FGFR3 signaling and RANK Signaling in Osteoclasts. |
| CD36 | CD36 Molecule | Protein Coding gene. Diseases associated with CD36 include Platelet Glycoprotein Iv Deficiency and Malaria. Among its related pathways are Cytokine Signaling in Immune system and Aryl Hydrocarbon Receptor. |
| COL13A1 | Collagen Type XIII Alpha 1 Chain | Protein Coding gene. Diseases associated with COL13A1 include Myasthenic Syndrome, Congenital, 19and Postsynaptic Congenital Myasthenic Syndromes. Among its related pathways are Integrin Pathway and ERK Signaling. |
| COL25A1 | Collagen Type XXV Alpha 1 Chain | Protein Coding gene. Diseases associated with COL25A1 include Fibrosis Of Extraocular Muscles, Congenital, 5 and Congenital Ptosis. Among its related pathways are Integrin Pathway and ERK Signaling. |
| COL4A2 | Collagen Type IV Alpha 2 Chain | Protein Coding gene. Diseases associated with COL4A2 include Porencephaly 2 and Hemorrhage, Intracerebral. Among its related pathways are Integrin Pathway and ERK Signaling. |
| COL5A1 | Collagen Type V Alpha 1 Chain | Protein Coding gene. Diseases associated with COL5A1 include Ehlers-Danlos Syndrome, Classic Type, 1and Ehlers-Danlos Syndrome Type 2. Among its related pathways are Integrin Pathway and ERK Signaling. |
| CYGB | Cytoglobin | Protein Coding gene. Diseases associated with CYGB include Ancylostomiasis. Among its related pathways are Metabolism and eNOS activation and regulation. |
| DGKH | Diacylglycerol Kinase Eta | Protein Coding gene. Diseases associated with DGKH include Adrenal Medulla Cancer and Extra-Adrenal Pheochromocytoma. Among its related pathways are Response to elevated platelet cytosolic Ca2+ and Signaling by GPCR. |
| DIAPH3 | Diaphanous Related Formin 3 | Protein Coding gene. Diseases associated with DIAPH3 include Auditory Neuropathy, Autosomal Dominant, 1and Autosomal Dominant Non-Syndromic Sensorineural Deafness Type Dfna. Among its related pathways are Actin Nucleation by ARP-WASP Complex and G-protein signaling RhoB regulation pathway. |
| DKK3 | Dickkopf WNT Signaling Pathway Inhibitor 3 | Protein Coding gene. Diseases associated with DKK3 include Oral Submucous Fibrosis. Among its related pathways are CDK-mediated phosphorylation and removal of Cdc6 and Regulation of Wnt/B-catenin Signaling by Small Molecule Compounds. |
| DLK1 | Delta Like Non-Canonical Notch Ligand 1 | Protein Coding gene. Diseases associated with DLK1 include Temple Syndrome and Idiopathic Central Precocious Puberty. Among its related pathways are Signaling by NOTCH1 and NOTCH2 Activation and Transmission of Signal to the Nucleus. |
| DOK5 | Docking Protein 5 | Protein Coding gene. Among its related pathways are Developmental Biology and Brain-Derived Neurotrophic Factor (BDNF) signaling pathway. |
| EGR3 | Early Growth Response 3 | Protein Coding gene. Diseases associated with EGR3 include Patella, Chondromalacia Of and Ancylostomiasis. Among its related pathways are Circadian rythm related genes and Viral carcinogenesis. |
| EHD1 | EH Domain Containing 1 | Protein Coding gene. Diseases associated with EHD1 include Venous Hemangioma and Photoallergic Dermatitis. Among its related pathways are Response to elevated platelet cytosolic Ca2+ and Angiopoietin Like Protein 8 Regulatory Pathway. |

TABLE 21.a-continued

| Gene | Gene Name | Function |
|---|---|---|
| EMCN | Endomucin | Protein Coding gene. mucin-like sialoglycoprotein that interferes with the assembly of focal adhesion complexes and inhibits interaction between cells and the extracellular matrix. |
| ETS1 | ETS Proto-Oncogene 1, Transcription Factor | Protein Coding gene. Diseases associated with ETS1 include Jacobsen Syndrome and Bone Ewing's Sarcoma. Among its related pathways are Neural Crest Differentiation and ErbB signaling pathway. |
| EYA1 | EYA Transcriptional Coactivator And Phosphatase 1 | Protein Coding gene. Diseases associated with EYA1 include Otofaciocervical Syndrome 1and Branchiootorenal Syndrome 1. Among its related pathways are DNA Double-Strand Break Repair and DNA Double Strand Break Response. |

TABLE 21.b

| Gene | Gene Name | Function |
|---|---|---|
| FBLN2 | Fibdin 2 | Protein Coding gene. Diseases associated with FBLN2 include Familial Osteochondritis Dissecans and Osteochondritis Dissecans. Among its related pathways are Cell adhesion_Cell-matrix glycoconjugates and Elastic fibre formation. |
| FBXO32 | F-Box Protein 32 | Protein Coding gene. Diseases associated with FBXO32 include Muscle Hypertrophy and Muscle Tissue Disease. Among its related pathways are Innate Immune System and FoxO family signaling. |
| FOXO1 | Forkhead Box O1 | Protein Coding gene. Diseases associated with FOXO1 include Rhabdomyosarcoma 2 and Rhabdomyosarcoma. Among its related pathways are Constitutive Signaling by AKT1 E17K in Cancer and Cytokine Signaling in Immune system. |
| FOXO3 | Forkhead Box O3 | Protein Coding gene. Diseases associated with FOXO3 include Chromosome 6Q Deletion and Rhabdomyosarcoma. Among its related pathways are Constitutive Signaling by AKT1 E17K in Cancer and NFAT and Cardiac Hypertrophy. |
| FTO | FTO, Alpha-Ketoglutarate Dependent Dioxygenase | Protein Coding gene. Diseases associated with FTO include Growth Retardation, Developmental Delay, And Facial Dysmorphism and Body Mass Index Quantitative Trait Locus 14. Among its related pathways are DNA Damage Reversaland FTO Obesity Variant Mechanism. |
| GPC5 | Glypican 5 | Protein Coding gene. Diseases associated with GPC5 include Simpson-Golabi-Behmel Syndrome and Tetralogy Of Fallot. Among its related pathways are Glycosaminoglycan metabolism and CDK-mediated phosphorylation and removal of Cdc6. |
| GPC6 | Glypican 6 | Protein Coding gene. Diseases associated with GPC6 include Omodysplasia 1 and Omodysplasia. Among its related pathways are Apoptotic Pathways in Synovial Fibroblasts and PAK Pathway. |
| GRB10 | Growth Factor Receptor Bound Protein 10 | Protein Coding gene. Diseases associated with GRB10 include Silver-Russell Syndrome and Albright's Hereditary Osteodystrophy. Among its related pathways are Beta-Adrenergic Signaling and RET signaling. |
| GSN | Gelsolin | Protein Coding gene. Diseases associated with GSN include Amyloidosis, Finnish Type and Lattice Corneal Dystrophy Type Ii. Among its related pathways are N-cadherin signaling events and Apoptosis and survival Caspase cascade. |
| HDAC9 | Histone Deacetylase 9 | Protein Coding gene. Diseases associated with HDAC9 include Gastrointestinal Neuroendocrine Tumor and Cutaneous T Cell Lymphoma. Among its related pathways are PEDF Induced Signaling and Signaling by NOTCH1. |
| HOXC6 | Homeobox C6 | Protein Coding gene. Gene Ontology (GO) annotations related to this gene include DNA binding transcription factor activity and transcription corepressor activity. |
| IGF1R | Insulin Like Growth Factor 1 Receptor | Protein Coding gene. Diseases associated with IGF1R include Insulin-Like Growth Factor I and Ring Chromosome 15. Among its related pathways are Apoptotic Pathways in Synovial Fibroblasts and NFAT and Cardiac Hypertrophy. |
| IL1RAP | Interleukin 1 Receptor Accessory Protein | Protein Coding gene. Diseases associated with IL1RAP include Stromal Keratitis and Chromosome Xp21 Deletion Syndrome. Among its related pathways are Bacterial infections in CF airways and IL-1 signaling pathway. |
| KDM1A | Lysine Demethylase 1A | Protein Coding gene. Diseases associated with KDM1A include Cleft Palate, Psychomotor Retardation, And Distinctive Facial Features and Kbg Syndrome. Among its related pathways are Response to elevated platelet cytosolic Ca2+ and Activated PKN1 stimulates transcription of AR (androgen receptor) regulated genes KLK2 and KLK3. |
| LAMA2 | Laminin Subunit Alpha 2 | Protein Coding gene. Diseases associated with LAMA2 include Muscular Dystrophy, Congenital Merosin-Deficient, 1Aand Congenital Muscular Dystrophy Type 1A. Among its related pathways are MET promotes cell motility and Integrin Pathway. |
| LCK | LCK Proto-Oncogene, Src Family Tyrosine Kinase | Protein Coding gene. Diseases associated with LCK include Immunodeficiency 22 and Cd45 Deficiency. Among its related pathways are G-protein signaling N-RAS regulation pathway and Cytokine Signaling in Immune system. |

TABLE 21.b-continued

| Gene | Gene Name | Function |
|------|-----------|----------|
| LDB2 | UM Domain Binding 2 | Protein Coding gene. Diseases associated with LDB2 include Retinal Detachment. Among its related pathways are Ectoderm Differentiation. |
| LMO4 | LIM Domain Only 4 | Protein Coding gene. Diseases associated with LMO4 include Precursor T-Cell Acute Lymphoblastic Leukemia. Among its related pathways are IL-6 signaling pathway and Embryonic and Induced Pluripotent Stem Cell Differentiation Pathways and Lineage-specific Markers. |
| MAPK10 | Mitogen-Activated Protein Kinase 10 | Protein Coding gene. Diseases associated with MAPK10 include Pertussis and Pneumococcal Meningitis. Among its related pathways are PEDF Induced Signaling and Toll-like receptor signaling pathway. |
| MBNL1 | Muscleblind Like Splicing Regulator 1 | Protein Coding gene. Diseases associated with MBNL1 include Myotonic Dystrophy and Myotonic Dystrophy 1. Among its related pathways are Adipogenesis. |
| MYBPC1 | Myosin Binding Protein C, Slow Type | Protein Coding gene. Diseases associated with MYBPC1 include Arthrogryposis, Distal, Type 1B and Lethal Congenital Contracture Syndrome 4. Among its related pathways are Cardiac conduction and Striated Muscle Contraction. |
| MYH1 | Myosin Heavy Chain 1 | Protein Coding gene. Diseases associated with MYH1 include Retinitis Pigmentosa 67. Among its related pathways are PAK Pathway and ERK Signaling. |
| MYO18B | Myosin XVIIIB | Protein Coding gene. Diseases associated with MYO18B include Klippel-Feil Syndrome 4, Autosomal Recessive, With Nemaline Myopathy And Facial Dysmorphism and Lung Large Cell Carcinoma. |
| NCAM1 | Neural Cell Adhesion Molecule 1 | Protein Coding gene. Diseases associated with NCAM1 include Rabies and Blastic Plasmacytoid Dendritic Cell. Among its related pathways are RET signaling and Cytokine Signaling in Immune system. |
| NECTIN2 | Nectin Cell Adhesion Molecule 2 | Protein Coding gene. Diseases associated with NECTIN2 include Herpes Simplex and Ovarian Cystic Teratoma. Among its related pathways are PAK Pathway and Innate Immune System. An important paralog of this gene is PVR. |
| NFKB1 | Nuclear Factor Kappa B Subunit 1 | Protein Coding gene. Diseases associated with NFKB1 include Immunodeficiency, Common Variable, 12and Common Variable Immunodeficiency. Among its related pathways are RANK Signaling in Osteoclasts and PEDF Induced Signaling. |
| NR4A1 | Nuclear Receptor Subfamily 4 Group A Member 1 | Protein Coding gene. Diseases associated with NR4A1 include Fetal Adenoma and Tracheal Cancer. Among its related pathways are Constitutive Signaling by AKT1 E17K in Cancer and Aldosterone synthesis and secretion. |
| NRXN1 | Neurexin 1 | Protein Coding gene. Diseases associated with NRXN1 include Pitt-Hopkins-Like Syndrome 2 and Chromosome 2P16.3 Deletion Syndrome. Among its related pathways are Transmission across Chemical Synapses and Protein-protein interactions at synapses. |
| NTRK2 | Neurotrophic Receptor Tyrosine Kinase 2 | Protein Coding gene. Diseases associated with NTRK2 include Obesity, Hyperphagia, And Developmental Delay and Epileptic Encephalopathy, Early Infantile, 58. Among its related pathways are Apoptotic Pathways in Synovial Fibroblasts and ERK Signaling. |
| PAG1 | Phosphoprotein Membrane Anchor With Giycosphingohpid Microdomains | Protein Coding gene. Among its related pathways are Innate Immune System and B cell receptor signaling pathway (KEGG). |

TABLE 21.c

| Gene | Gene Name | Function |
|------|-----------|----------|
| PCK1 | Phosphoenolpyruvate Carboxykinase 1 | Protein Coding gene. Diseases associated with PCK1 include Phosphoenolpyruvate Carboxykinase Deficiency, Cytosolic and Pepck 1 Deficiency. Among its related pathways are Estrogen Receptor Pathway and Glycosaminoglycan metabolism. |
| PDK3 | Pyruvate Dehydrogenase Kinase 3 | Protein Coding gene. Diseases associated with PDK3 include Charcot-Marie-Tooth Disease, X-Linked Dominant, 6 and X-Linked Charcot-Marie-Tooth Disease. Among its related pathways are Respiratory electron transport, ATP synthesis by chemiosmotic coupling, and heat production by uncoupling proteins, and Metabolism. |
| PHTF2 | Putative Homeodomain Transcription Factor 2 | Protein Coding gene. An important paralog of this gene is PHTF1. May play a role in transcription regulation. |
| PIK3C3 | Phosphatidylinositol 3-Kinase Catalytic Subunit Type 3 | Protein Coding gene. Diseases associated with PIK3C3 include Amyotrophic Lateral Sclerosis 1. Among its related pathways are wtCFTR and deltaF508 traffic/Late endosome and Lysosome (norm and CF) and Delta508-CFTR traffic/Sorting endosome formation in CF. |
| SMAD7 | SMAD Family Member 7 | Protein Coding gene. Diseases associated with SMAD7 include Colorectal Cancer 3 and Keloids. Among its related pathways are Immune response IFN gamma signaling pathway and TGF-beta Receptor Signaling |

TABLE 21.c-continued

| Gene | Gene Name | Function |
|---|---|---|
| STIM1 | Stromal Interaction Molecule 1 | Protein Coding gene. Diseases associated with STIM1 include Myopathy, Tubular Aggregate, 1 and Immunodeficiency 10. Among its related pathways are Cardiac conduction and Platelet homeostasis. |
| STK39 | Serine/Threonine Kinase 39 | Protein Coding gene. Diseases associated with STK39 include Epilepsy, Familial Temporal Lobe, 4 and Renal Tubular Transport Disease. Among its related pathways are Diuretics Pathway, Pharmacodynamics and Sweet Taste Signaling. |
| STXBP4 | Syntaxin Binding Protein 4 | Protein Coding gene. Among its related pathways are Angiopoietin Like Protein 8 Regulatory Pathway and Glucose/Energy Metabolism. |
| SULF2 | Sulfatase 2 | Protein Coding gene. Diseases associated with SULF2 include Juvenile Astrocytoma. Gene Ontology (GO) annotations related to this gene include calcium ion binding and arylsulfatase activity. An important paralog of this gene is SULF1. |
| SYK | Spleen Associated Tyrosine Kinase | Protein Coding gene. Diseases associated with SYK include Hantavirus Pulmonary Syndrome and Mycobacterium Abscessus. Among its related pathways are RANK Signaling in Osteoclasts and Role of phospholipids in phagocytosis. |
| TBX21 | T-Box 21 | Protein Coding gene. Diseases associated with TBX21 include Asthma, Nasal Polyps, And Aspirin Intolerance and Genital Herpes. Among its related pathways are Th1 Differentiation Pathway and Th17 cell differentiation. |
| TGFB2 | Transforming Growth Factor Bets 2 | Protein Coding gene. Diseases associated with TGFB2 include Loeys-Dietz Syndrome 4 and Holt-Oram Syndrome. Among its related pathways are Apoptotic Pathways in Synovial Fibroblasts and PAK Pathway. |
| TGFBR2 | Transforming Growth Factor Beta Receptor 2 | Protein Coding gene. Diseases associated with TGFBR2 include Loeys-Dietz Syndrome 2 and Colorectal Cancer, Hereditary Nonpolyposis, Type 6. Among its related pathways are PAK Pathway and Chronic myeloid leukemia. |
| THADA | THADA, Armadillo Repeat Containing | Protein Coding gene. Diseases associated with THADA include Adenoma. |
| THNSL2 | Threonine Synthase Like 2 | Protein Coding gene. A similar enzyme in mouse can catalyze the degradation of O-phospho-homoserine to a-ketobutyrate, phosphate, and ammonia. This protein also has phospho-lyase activity on both gamma and beta phosphorylated substrates. |
| TLR2 | Toll Like Receptor 2 | Protein Coding gene. Diseases associated with TLR2 include Leprosy 3 and Colorectal Cancer. Among its related pathways are Bacterial infections in CF airways and Toll-like receptor signaling pathway. |
| TNFRSF25 | TNF Receptor Superfamily Member 25 | Protein Coding gene. Diseases associated with TNFRSF25 include Type 1 Diabetes Mellitus 18 and Type 1 Diabetes Mellitus 17. Among its related pathways are PEDF Induced Signaling and Apoptosis Modulation and Signaling. |

TABLE 21.d

| Gene | Gene Name | Function |
|---|---|---|
| TTN | Titin | Protein Coding gene. Diseases associated with TTN include Hereditary Myopathy With Early Respiratory Failure and Tibial Muscular Dystrophy, Tardive. Among its related pathways are Cardiac conduction and Response to elevated platelet cytosolic Ca2+. |
| UACA | Uveal Autoantigen With Coiled-Coil Domains And Ankyrin Repeats | Protein Coding gene. Diseases associated with UACA include Panuveitis and Graves' Disease. An important paralog of this gene is RAI14. |
| WASL | Wiskott-Aldrich Syndrome Like | Protein Coding gene. Diseases associated with WASL include Wiskott-Aldrich Syndrome and Vaccinia. Among its related pathways are Development EGFR signaling via small GTPases and PAK Pathway. |
| ZEB1 | Zinc Finger E-Box Binding Homeobox 1 | Protein Coding gene. Diseases associated with ZEB1 include Corneal Dystrophy, Fuchs Endothelial, 6and Corneal Dystrophy, Posterior Polymorphous, 3. Among its related pathways are PAK Pathway and Cytokine Signaling in Immune system. |
| ZFHX3 | Zinc Finger Homeobox 3 | Protein Coding gene. Diseases associated with ZFHX3 include Prostate Cancer and Atrial Fibrillation. Among its related pathways are Circadian rythm related genes and Signaling pathways regulating pluripotency of stem cells. |
| AGT | Angiotensinogen | Protein Coding gene. Diseases associated with AGT include Renal Tubular Dysgenesis and Hypertension, Essential. Among its related pathways are Signaling events mediated by PRL and Peptide hormone metabolism. |
| BMPR1B | Bone Morphogenetic Protein Receptor Type 1B | Protein Coding gene. Diseases associated with BMPR1B include Acromesomelic Dysplasia, Demirhan Type and Brachydactyly, Type A1, D. Among its related pathways are Akt Signaling and Ovarian Infertility Genes. |

TABLE 21.d-continued

| Gene | Gene Name | Function |
| --- | --- | --- |
| HTR2A | 5-Hydroxytryptamine Receptor 2A | Protein Coding gene. Diseases associated with HTR2A include Major Depressive Disorder and Obsessive-Compulsive Disorder. Among its related pathways are Monoamine GPCRs and Peptide ligand-binding receptors. |
| PPARA | Peroxisome Prollferator Activated Receptor Alpha | Protein Coding gene. Diseases associated with PPARA include Fatty Liver Disease and Alcoholic Cardiomyopathy. Among its related pathways are Estrogen Receptor Pathway and Organelle biogenesis and maintenance. |
| SOS1 | SOS Ras/Rac Guanine Nucleotide Exchange Factor 1 | Protein Coding gene. Diseases associated with SOS1 include Noonan Syndrome 4 and Fibromatosis, Gingival, 1. Among its related pathways are G-protein signaling N-RAS regulation pathway and RET signaling. |
| SVEP1 | Sushi, Von Willebrand Factor Type A, EGF And Pentraxin Domain Containing 1 | Protein Coding gene. Related to calcium ion binding and chromatin binding. |
| UBE3A | Ubiquitin Protein Ligase E3A | Protein Coding gene. Diseases associated with UBE3A include Angelman Syndrome and Angelman Syndrome Due To A Point Mutation. Among its related pathways are PI3K-Akt signaling pathway and Innate Immune System. |
| HADHA | Hydroxyacyl-CoA Dehyrdogenase Trifunctional Multienzyme Complex Subunit Alpha | Protein Coding gene. Diseases associated with HADHA include Long-Chain 3-Hydroxyacyl-Coa Dehydrogenase Deficiency and Mitochondrial Trifunctionai Protein Deficiency. Among its related pathways are Glycerophospholipid biosynthesis and Mitochondrial Fatty Acid Beta-Oxidation. |
| MTFR1 | Mitochondrial Fission Regulator 1 | Protein Coding gene. May play a role in mitochondrial aerobic respiration, organisation and fission. Chicken homolog promotes mitochondrial fission and mouse homolog protects cells from oxadative stress. |
| MYL1 | Myosin Light Chain 1 | Protein Coding gene. Among its related pathways are Cardiac conduction and PAK Pathway. Related to calcium ion binding and structural constituent of muscle. |
| MYOD1 | Myogenic Differentiation 1 | Protein Coding gene. Diseases associated with MYOD1 include Pleomorphic Rhabdomyosarcoma and Spindle Cell Rhabdomyosarcoma. Among its related pathways are Development NOTCHl-mediated pathway for NF-KB activity modulation and miRs in Muscle Cell Differentiation. |
| NECTIN3 | Nectin Cell Adhesion Molecule 3 | Protein Coding gene. Among its related pathways are PAK Pathway and T Cell Co-Signaling Pathway: Ligand-Receptor Interactions. Plays a role in ocular development involving the ciliary body. Mutations are believed to result in congenital ocular defects. |
| PON1 | Paraoxonase 1 | Protein Coding gene. Diseases associated with PON1 include Microvascular Complications Of Diabetes 5 and Amyotrophic Lateral Sclerosis 1. Among its related pathways are Metabolism and Arachidonic acid metabolism. Polymorphisms in the gene may be associated with coronary heart disease and diabetic retinopathy. |
| COL1A2 | Collagen Type 1 Alpha 2 Chain | rotein Coding gene. Diseases associated with COL1A2 include Osteogenesis Imperfecta, Type Iii and Type Iv, atypical Marfan syndrome, Ehlers-Danos syndrome type VIIB and recessive Ehlers-Danos syndrome. Among its related pathways are Cytokine Signaling in Immune system and Integrin Pathway. |
| COX6A1 | Cytochrome C Oxidase Subunit 6A1 | Protein Coding gene. Diseases associated with COX6A1 include Charcot-Marie-Tooth Disease, Recessive Intermediate D and Charcot-Marie-Tooth Disease, Axonal, Type 2R. Among its related pathways are Respiratory electron transport, ATP synthesis by chemiosmotic coupling, and heat production by uncoupling proteins, and Gene Expression. |
| GGPS1 | Geranylgeranyl Diphosphate Synthase 1 | Protein Coding gene. Diseases associated with GGPS1 include Osteogenesis Imperfecta, Type V. Among its related pathways are Regulation of cholesterol biosynthesis by SREBP (SREBF) and Terpenoid backbone biosynthesis. |
| MUSK | Muscle Associated Receptor Tyrosine Kinase | Protein Coding gene. Diseases associated with MUSK include Myasthenic Syndrome, Congenital, 9, Associated With Acetylcholine Receptor Deficiency and Fetal Akinesia Deformation Sequence. Among its related pathways are ERK Signaling and ECM proteoglycans. |
| MYOT | Myotilin | Protein Coding gene. Diseases associated with MYOT include Myopathy, Myofibrillar, 3 and Muscular Dystrophy, Limb-Girdle, Type 1A. |
| PPP1R9A | Protein Phosphatase 1 Regulatory Subunit 9A | Protein Coding gene. Diseases associated with PPP1R9A include Hepatosplenic T-Cell Lymphoma. Among its related pathways are Beta-Adrenergic Signaling and Activation of cAMP-Dependent PKA. Also related to actin binding and cytoiskeleton reorganisation. |
| RB1 | RB Transcriptional Corepressor 1 | Protein Coding gene. Diseases associated with RB1 include Retinoblastoma and Bladder Cancer. Among its related pathways are Mitotic Prophase and Chronic myeloid leukemia. |
| SLC25A13 | Solute Carrier Family 25 Member 13 | Protein Coding gene. Diseases associated with SLC25A13 include Citrullinemia, Type Ii, Neonatal-Onset and Citrullinemia, Type Ii, Adult-Onset. Among its related pathways are Glycosaminoglycan metabolism and Metabolism. |
| ACE2 | Angiotensin 1 Converting Enzyme 2 | Protein Coding gene. Diseases associated with ACE2 include Severe Acute Respiratory Syndrome and Neurogenic Hypertension. Among its related pathways are Peptide hormone metabolism and Collagen chain trimerization. May play a role in the regulation of cardiovasuclar and renal function and fertility. |

TABLE 21.d-continued

| Gene | Gene Name | Function |
|------|-----------|----------|
| DNAH5 | Dynein Axonemal Heavy Chain 5 | Protein Coding gene. Diseases associated with DNAH5 include Ciliary Dyskinesia, Primary, 3, Primary Ciliary Dyskinesia and Kartagener syndrome. Among its related pathways are Respiratory electron transport, ATP synthesis by chemiosmotic coupling, and heat production by uncoupling proteins. |
| ITGAV | Integrin Subunit Alpha V | Protein Coding gene. Diseases associated with ITGAV include West Nile Virus and Cerebral Hypoxia. Among its related pathways are VEGF Signaling Pathway and Primary Focal Segmental Glomerulosclerosis FSGS. Protein may regulate angiogenesis and cancer progression. |
| MSTN | Myostatin | Protein Coding gene. Diseases associated with MSTN include Muscle Hypertrophy and Myostatin-Related Muscle Hypertrophy. Among its related pathways are Hypertrophy Model and Factors and pathways affecting insulin-like growth factor (IGF1)-Akt signaling. |
| SOCS7 | Suppressor Of Cytokine Signaling 7 | Protein Coding gene. Among its related pathways are Jak-STAT signaling pathway (KEGG) and Jak/STAT Signaling Pathway Intracellular Regulation. Functions in insulin signaling and glucose homeostasis. |
| SRI | Sorcin | Protein Coding gene. Regulates intracellular calcium homeostasis. Diseases associated with SRI include Interstitial Myocarditis and Apical Myocardial Infarction. Among its related pathways are Cardiac conduction and Response to elevated platelet cytosolic Ca2+. |

| Marker | Training | Odds Ratio | Training type | | |
|--------|----------|-----------|----------|--------|----------|
| | | | Combined | Cardio | Strength |
| OBD142__029.031__1x | Present in Endurance and Strength | 7.2 | 0.016681 | 0.06669 | 0.01613 |
| OBD142__061.063__1.8x | Present in Endurance and Strength | 8.2 | 0.0185106 | 0.11741 | 0.1068 |
| OBD142__069.071__1.2x | Present in Endurance and Strength | 8 | 0.0025561 | 0.06669 | 0.05767 |
| OBD142__089.091__1x | Present in Endurance and Strength | 2.9 | 0.1237527 | 0.40123 | 0.1806 |
| OBD142__137.139__1.2x | Present in Endurance and Strength | 8 | 0.0627014 | 0.11741 | 0.18262 |
| OBD142__081.083__1.4x | Present in Endurance | 6 | 0.1392395 | 0.07048 | 0.79999 |
| OBD142__189.191__1x | Present in Endurance | 4.5 | 0.1196946 | 0.11741 | 0.84529 |
| OBD142__213.215__1.4x | Present in Endurance | 2.25 | 1 | 0.69409 | 0.13523 |
| OBD142__017.019__1.2x | Present in Strength | 4 | 0.7249505 | 0.54542 | 0.28124 |
| OBD142__037.039__1x | Present in Strength | 12 | 0.1525177 | 1 | 0.02526 |
| OBD142__065.067__1x | Present in Strength | 5 | 0.131911 | 0.54542 | 0.05767 |
| OBD142__133.135__1x | Present in Strength | 4 | 0.4615609 | 1 | 0.01613 |
| OBD142__253.255__1.2x | Present in Strength | 12 | 0.4496075 | 0.6101 | 0.02421 |
| OBD142__353.355__1x | Present in Strength | 9 | 0.1196946 | 1 | 0.01615 |
| OBD142__477.479__1x | Present in Strength | 9 | 0.4275177 | 1 | 0.02526 |
| OBD142__181.183__1.4x | Present in Strength | 2 | 0.7559581 | 0.74071 | 0.17781 |
| OBD142__397.399__1x | Present in Strength | 2 | 0.1516371 | 0.66843 | 0.09668 |

Table 22 shows preferred markers from the equine study and the traits they relate to, which are preferably used to type horses.

| PCR Marker | Phenotype |
|------------|-----------|
| OBD154__125/OBD154__127 | Sprinter |
| OBD154__085/OBD154__087 | Sprinter |
| OBD154__157/OBD154__159 | Stayer |
| OBD154__013/OBD154__015 | Sprinter |
| OBD154__245/OBD154__247 | Sprinter |
| OBD154__229/OBD154__231 | Sprinter |
| OBD154__093/OBD154__095 | Sprinter |
| OBD154__049/OBD154__051 | Sprinter |
| OBD154__201/OBD154__203 | Stayer |

-continued

| PCR Marker | Phenotype |
|------------|-----------|
| OBD154__041/OBD154__043 | Stayer |
| OBD154__073/OBD154__075 | Stayer |
| OBD154__205/OBD154__207 | Sprinter |
| OBD154__009/OBD154__011 | Sprinter |
| OBD154__045/OBD154__047 | Stayer |
| OBD154__141/OBD154__143 | Sprinter |
| OBD154__165/OBD154__167 | Sprinter |
| OBD154__213/OBD154__215 | Stayer |

Table 23 shows preferred markers from the equine study and the traits they relate to, which are preferably used to type horses.

TABLE 24.a

| No. | Probe | GeneLocus |
|-----|-------|-----------|
| 1 | ORF2__1__133335365__133342248__133252663__133254033__RR | ORF2 |
| 2 | ORF17__21__46168522__46170441__46128519__46131714__FR | ORF17 |
| 3 | ORF37__7__80905043__80905799__80946828__80948039__FF | ORF37 |
| 4 | ORF5__22__44079168__44079873__44099430__44101885__RR | ORF5 |
| 5 | ORF33__23__51893485__51894717__51879777__51881452__RR | ORF33 |
| 6 | ORF24__7__26919921__26921163__26962320__26963327__RF | ORF24 |

TABLE 24.a-continued

| No. | Probe | GeneLocus |
|---|---|---|
| 7 | ORF1_3_38982976_38984987_38897821_38902754_RR | ORF1 |
| 8 | ORF39_3_37427338_37427846_37369331_37372145_FF | ORF39 |
| 9 | ORF21_27_18057476_18059723_18216584_18221307_FF | ORF21 |
| 10 | ORF9_9_19477415_19483037_19371208_19377216_RF | ORF9 |
| 11 | ORF11_25_15754740_15756330_15827853_15831235_FR | ORF11 |
| 12 | ORF41_2_44125472_44130831_44114366_44115500_FR | ORF41 |
| 13 | ORF12_28_42033251_42034839_42111316_42112829_FR | ORF12 |
| 14 | ORF42_14_38556059_38561196_38515585_38519701_RR | ORF42 |
| 15 | ORF31_24_18025107_18025879_18089550_18090204_FR | ORF31 |
| 16 | ORF28_19_27971050_27974189_28029396_28030610_FR | ORF28 |
| 17 | ORF3_3_39072647_39081470_38902754_38905559_RR | ORF3 |
| 18 | ORF87_4_38678592_38682251_38712668_38720224_RF | ORF87 |
| 19 | ORF95_2_30297289_30298973_30249858_30251319_RF | ORF95 |
| 20 | ORF72_5_76755446_76755869_76713081_76716746_FR | ORF72 |
| 21 | ORF44_8_11915509_11916086_11887773_11890590_RR | ORF44 |
| 22 | ORF90_5_9229073_9235994_9247952_9249817_FR | ORF90 |
| 23 | ORF51_4_788561_790967_729450_732106_FR | ORF51 |
| 24 | ORF67_15_69928382_69930519_69848008_69851513_FF | ORF67 |
| 25 | ORF109_1_110780529_110783525_110809348_110820887_FF | ORF109 |
| 26 | ORF99_11_29755642_29761616_29820061_29826391_RR | ORF99 |
| 27 | ORF46_27_7694409_7697820_7673458_7673882_FR | ORF46 |
| 28 | ORF107_15_17634193_17641147_17623423_17624089_FR | ORF107 |
| 29 | ORF86_19_45858761_45861211_45775880_45782396_RR | ORF86 |
| 30 | ORF71_5_76755446_76755869_76727262_76728348_FF | ORF71 |
| 31 | ORF62_17_64192230_64193405_64341970_64343229_FF | ORF62 |
| 32 | ORF69_1_104390566_104392857_104321461_104322189_RF | ORF69 |
| 33 | ORF76_7_85946864_85949922_85987651_85988101_FR | ORF76 |
| 34 | ORF79_23_5314583_5315708_5202402_5204544_FR | ORF79 |
| 35 | ORF64_25_24906776_24910177_25031046_25032151_FF | ORF64 |
| 36 | ORF85_X_18614272_18616544_18648509_18649030_FR | ORF85 |
| 37 | ORF58_22_41701255_41702998_41789282_41790782_RF | ORF58 |
| 38 | ORF81_22_44079168_44079873_44118479_44121814_RR | ORF81 |
| 39 | ORF84_X_18614272_18616544_18641258_18647069_FR | ORF84 |
| 40 | ORF73_16_84538528_84540820_84582113_84585716_FR | ORF73 |
| 41 | ORF106_15_55284305_55291596_55156691_55157175_FF | ORF106 |
| 42 | ORF88_3_100800337_100801373_100744664_100751637_FF | ORF88 |

[Table 24 shows markers identified in the equine study, [35] which are preferably used to type horses.]

TABLE 24.b

| No. | Probe sequence 60 mer |
|---|---|
| 1 | TTTAAAACTAAGTCTAACCGCCTGAAAGTCGAGAGGGAAGTGCTACGCATCCCGCGCACA (SEQ ID NO: 2) |
| 2 | AGAGGCTCAAAACTTCTGTCTGGTAAATTCGATTTTCTCCTATTGCTCTACATCACTCGG (SEQ ID NO: 3) |
| 3 | CCCCATAGGAGGCTTCTGGGAAGCCCAGTCGAGATGCATCCATGTTGTCATGGGTATAAG (SEQ ID NO: 4) |
| 4 | TTCCTACCACCCAAATTCTATTATTCTATCGAGAGGCACCAGGATGCTGAGAGGATGAGA (SEQ ID NO: 5) |
| 5 | TCGTGTTAGTTAAATCGGCCGATTTGTCTCGAGAAAAGAGAAGGACTGGGTCATGGTGGG (SEQ ID NO: 6) |
| 6 | CCGCCTCGCCACAGCTCTCCAGTGAGATTCGATCCTTTTAAACTTTGTTAGGCAAGACCA (SEQ ID NO: 7) |
| 7 | TTGATCTTTTTTAAAATAGGGATGGGGTTCGAGAGAAGGAGAATGAAGCAGAAAGCTTGT (SEQ ID NO: 8) |
| 8 | CTGTAACCAGAGGAGCAGAGTCTGCACATCGATTCCTCTTACTGCACTGCAGGTCCAGGG (SEQ ID NO: 9) |
| 9 | ACCCAAAATTTACTTGCAATCACTTTAATCGAGCTCTTGGATGTCTGGGGATTGTTCTGC (SEQ ID NO: 10) |
| 10 | GATAGAATTAAACATTGAAGGCAAACTTTCGATTAGGGTTTTAGTTTTCTTTAAGTTTTT (SEQ ID NO: 11) |
| 11 | GAGCACAGGTGCTGGATTCAGGCTTCCTTCGATTCAAACTTCCCTCACACTGACATTTTT (SEQ ID NO: 12) |
| 12 | GGAGAAAAAGGGGCTTTACGCAGTCCATTCGATGCAGTCAGGAGTCAGGACAGCATCTCC (SEQ ID NO: 13) |
| 13 | CACAATGCCTTCCCCTCTTCCACCCCTTTCGATCACTGTCCTTCGTACACTCAAGATATA (SEQ ID NO: 14) |
| 14 | GTAAAAACCAGCTTCCAGGGACCAGATGTCGAGATCAGTATTGAAATGCACCATTTCATT (SEQ ID NO: 15) |
| 15 | CATAAGAGATGACTGGCCTTTTGCTGTTTCGATGGCCCGGCTTCCTCTTTGGGACTTCAG (SEQ ID NO: 16) |

TABLE 24.b-continued

| No. | Probe sequence 60 mer |
|-----|------------------------|
| 16 | TAATGAAATTGTCTTTTTGTGTCTTTCTTCGAGGATTTCTAGACTTTCTGTGCATCACTA (SEQ ID NO: 17) |
| 17 | AAGCATAAATTCGTTTTCCCCTTGACTTTCGAGACTCCATAAAGCACACGCACAAAGGCC (SEQ ID NO: 18) |
| 18 | GTAACATGCTGAATAACAACATTTCAGTTCGAGCGTTGTGGCAGAGCTTCCTTGTTACTG (SEQ ID NO: 19) |
| 19 | ACAGTGCTGCCTCTTCTGTGCAGATGCTTCGAAACCCATGTAATTTCATAGCTATGATGG (SEQ ID NO: 20) |
| 20 | TTGCCTCCATTTTAAAATTGAAGAAACTTCGAATAAAATTGAAACATCCTACCACCAACA (SEQ ID NO: 21) |
| 21 | CAGCTGGAGCTCAGCCGGATGCGCAACTTCGAGAAGAGATATTTGCACATCCGTGTTCGT (SEQ ID NO: 22) |
| 22 | AGTGGGCCACCACTGCCTAAGAACTACTTCGAGGCCAATACTACTGTCGGCCGCATCCGT (SEQ ID NO: 23) |
| 23 | GCCGTCGGTGGAGAAATTTAAAACTATTTCGAGTCAGTAACTGGACTCAGTTAAGGAAGG (SEQ ID NO: 24) |
| 24 | CACTGAGCTGCACGAAGATGCTGCCATCGATTCTCAATTGGGAAAAGCACATGGGATATG (SEQ ID NO: 25) |
| 25 | TTAAAAGTAAAGTAAGTAGAGGTCAGTCTCGAAGCTTTGAAGATTAGTTTTTGAACAGTG (SEQ ID NO: 26) |
| 26 | CAAGAATCAGTTCTGAGAAATCAATGCCTCGAGAACCAACGAAACACTGGGCCGCCTGCA (SEQ ID NO: 27) |
| 27 | TGAACATTATCCAGGAGCTCATACTGCTTCGATGACCACAGAGGCGCCAGAAGGCCACAG (SEQ ID NO: 28) |
| 28 | CAATGTACAATCTACCAGGAACTGAAGTTCGAGCAGCACTTGGCTTTCTTCCTTTTTAGA (SEQ ID NO: 29) |
| 29 | GAAAGCTGGGTATGGGAGTGTGCACACTTCGAGATCTCAGAAAGGGCATAACTGTATTTT (SEQ ID NO: 30) |
| 30 | ATTGCCTCCATTTTAAAATTGAAGAAACTCGATGGAGTTTGGGTTTAAGCACTGCTTTTT (SEQ ID NO: 31) |
| 31 | AGGCCTCGCCTATGAATAGCATACCAGCTCGATTATTCTTCTCTCACACAATTTCTGAAG (SEQ ID NO: 32) |
| 32 | CTCCGCCCGCCAGCTCTGCAGCTTCCCTTCGACGCTTCCTACTTTTCTCCAGGAAATTAT (SEQ ID NO: 33) |
| 33 | TCACTCCAGGACCCCCCCAGCCCTGTGTTCGAGGTTGTTTTGCCAGTCGTCTGTTTGGCA (SEQ ID NO: 34) |
| 34 | GGAAACACAAAGTTCTTGGCAAAGCTTCGAGTCTTGGAGGTGTTGTTATTTGCCCAAAGC (SEQ ID NO: 35) |
| 35 | GTGGCCTTATTTTGCAAAGGGGCAAACTTCGAAGGTGATGAAACGGAGGCCCAGAGAGGG (SEQ ID NO: 36) |
| 36 | TACCTCCAGTCTTGGTTATTCTGAGAGTTCGAGTCAGGATTCAGACCCAAGTCTAACTCT (SEQ ID NO: 37) |
| 37 | GGGTCCAAACCTGCAAATCCCCAGCTGTTCGAAAATGTGTCTGCTTTTTCATGGACACCA (SEQ ID NO: 38) |
| 38 | TTCCTACCACCCAAATTCTATTATTCTATCGAGAGGCTGAGATGAACAAGGCAGACGCAG (SEQ ID NO: 39) |
| 39 | TACCTCCAGTCTTGGTTATTCTGAGAGTTCGACAAGTGCGCTAGTGCCGCTTGTCAAGAG (SEQ ID NO: 40) |
| 40 | ATAAATTCCTTTGTGAATTTTGATCTCTTCGAAGACTTGTTCTGTTGGAGGCATGTCCCT (SEQ ID NO: 41) |
| 41 | CTTCCCCAAGAATTTTGGATTATATCTCTCGAGAAAGGGTAAGGAAGAGTCAAAGCTGTA (SEQ ID NO: 42) |
| 42 | CAATTTCTGGGGATACAGTAGTGAAGAGTCGATGGCATGGGATCTCTGCTATTTATCTCT (SEQ ID NO: 43) |

TABLE 24.c

| No. | Probe Location | | | | 4 kb Sequence Location | |
|-----|-----|--------|------|--------|------|-----|--------|
| | Chr | Start1 | End1 | Start2 | End2 | Chr | Start1 |
| 1 | 1 | 133335365 | 133335396 | 133252663 | 133252694 | 1 | 133335365 |
| 2 | 21 | 46170410 | 46170441 | 46128519 | 46128550 | 21 | 46166440 |
| 3 | 7 | 80905768 | 80905799 | 80948008 | 80948039 | 7 | 80901798 |
| 4 | 22 | 44079168 | 44079199 | 44099430 | 44099461 | 22 | 44079168 |
| 5 | 23 | 51893485 | 51893516 | 51879777 | 51879808 | 23 | 51893485 |
| 6 | 7 | 26919921 | 26919952 | 26963296 | 26963327 | 7 | 26919921 |
| 7 | 3 | 38982976 | 38983007 | 38897821 | 38897852 | 3 | 38982976 |
| 8 | 3 | 37427815 | 37427846 | 37372114 | 37372145 | 3 | 37423845 |
| 9 | 27 | 18059692 | 18059723 | 18221276 | 18221307 | 27 | 18055722 |
| 10 | 9 | 19477415 | 19477446 | 19377185 | 19377216 | 9 | 19477415 |
| 11 | 25 | 15756299 | 15756330 | 15827853 | 15827884 | 25 | 15752329 |
| 12 | 2 | 44130800 | 44130831 | 44114366 | 44114397 | 2 | 44126830 |
| 13 | 28 | 42034808 | 42034839 | 42111316 | 42111347 | 28 | 42030838 |

TABLE 24.c-continued

| | | Probe Location | | | | 4 kb Sequence Location | |
|---|---|---|---|---|---|---|---|
| No. | Chr | Start1 | End1 | Start2 | End2 | Chr | Start1 |
| 14 | 14 | 38556059 | 38556090 | 38515585 | 38515616 | 14 | 38556059 |
| 15 | 24 | 18025848 | 18025879 | 18089550 | 18089581 | 24 | 18021878 |
| 16 | 19 | 27974158 | 27974189 | 28029396 | 28029427 | 19 | 27970188 |
| 17 | 3 | 39072647 | 39072678 | 38902754 | 38902785 | 3 | 39072647 |
| 18 | 4 | 38678592 | 38678623 | 38720193 | 38720224 | 4 | 38678592 |
| 19 | 2 | 30297289 | 30297320 | 30251288 | 30251319 | 2 | 30297289 |
| 20 | 5 | 76755838 | 76755869 | 76713081 | 76713112 | 5 | 76751868 |
| 21 | 8 | 11915509 | 11915540 | 11887773 | 11887804 | 8 | 11915509 |
| 22 | 5 | 9235963 | 9235994 | 9247952 | 9247983 | 5 | 9231993 |
| 23 | 4 | 790936 | 790967 | 729450 | 729481 | 4 | 786966 |
| 24 | 15 | 69930488 | 69930519 | 69851482 | 69851513 | 15 | 69926518 |
| 25 | 1 | 110783494 | 110783525 | 110820856 | 110820887 | 1 | 110779524 |
| 26 | 11 | 29755642 | 29755673 | 29820061 | 29820092 | 11 | 29755642 |
| 27 | 27 | 7697789 | 7697820 | 7673458 | 7673489 | 27 | 7693819 |
| 28 | 15 | 17641116 | 17641147 | 17623423 | 17623454 | 15 | 17637146 |
| 29 | 19 | 45858761 | 45858792 | 45775880 | 45775911 | 19 | 45858761 |
| 30 | 5 | 76755838 | 76755869 | 76728317 | 76728348 | 5 | 76751868 |
| 31 | 17 | 64193374 | 64193405 | 64343198 | 64343229 | 17 | 64189404 |
| 32 | 1 | 104390566 | 104390597 | 104322158 | 104322189 | 1 | 104390566 |
| 33 | 7 | 85949891 | 85949922 | 85987651 | 85987682 | 7 | 85945921 |
| 34 | 23 | 5315677 | 5315708 | 5202402 | 5202433 | 23 | 5311707 |
| 35 | 25 | 24910146 | 24910177 | 25032120 | 25032151 | 25 | 24906176 |
| 36 | X | 18616513 | 18616544 | 18648509 | 18648540 | X | 18612543 |
| 37 | 22 | 41701255 | 41701286 | 41790751 | 41790782 | 22 | 41701255 |
| 38 | 22 | 44079168 | 44079199 | 44118479 | 44118510 | 22 | 44079168 |
| 39 | X | 18616513 | 18616544 | 18641258 | 18641289 | X | 18612543 |
| 40 | 16 | 84540789 | 84540820 | 84582113 | 84582144 | 16 | 84536819 |
| 41 | 15 | 55291565 | 55291596 | 55157144 | 55157175 | 15 | 55287595 |
| 42 | 3 | 100801342 | 100801373 | 100751606 | 100751637 | 3 | 100797372 |

TABLE 24.d

| | 4 kb Sequence Location | | | | |
|---|---|---|---|---|---|
| No. | End1 | Start2 | End2 | PCR-Primer1_ID | PCR_Primer1 |
| 1 | 133339366 | 133252663 | 133256664 | OBD154_001 | GGTATTGGAACTTCAGAGAGGTAGGC (SEQ ID NO: 44) |
| 2 | 46170441 | 46128519 | 46132520 | OBD154_009 | GAGGAGGGAGAGTGCTACTTGCC (SEQ ID NO: 45) |
| 3 | 80905799 | 80944038 | 80948039 | OBD154_013 | GCCCCATTGAGCATCACAGAGGG (SEQ ID NO: 46) |
| 4 | 44083169 | 44099430 | 44103431 | OBD154_033 | TCCCCACTTCTCCTCCACAAGGC (SEQ ID NO: 47) & (SEQ ID NO: 81) |
| 5 | 51897486 | 51879777 | 51883778 | OBD154_037 | CCCCAGGAGTGATGGCTCAGAAT (SEQ ID NO: 48) |
| 6 | 26923922 | 26959326 | 26963327 | OBD154_041 | GCCTCCCAAACCATTCCCTCGGA (SEQ ID NO: 49) |
| 7 | 38986977 | 38897821 | 38901822 | OBD154_045 | GCCCCATACACTGCTCACTGGCT (SEQ ID NO: 50) |
| 8 | 37427846 | 37368144 | 37372145 | OBD154_049 | CACTCCTGCCGCTGAGATTCCTG (SEQ ID NO: 51) |
| 9 | 18059723 | 18217306 | 18221307 | OBD154_053 | CCGCCATTGGGTTGTTTTGCCCC (SEQ ID NO: 52) |
| 10 | 19481416 | 19373215 | 19377216 | OBD154_057 | GCCTTGAGCATACCCACTGTCAG (SEQ ID NO: 53) |
| 11 | 15756330 | 15827853 | 15831854 | OBD154_061 | ACCAAGCACAGTGGCTGACACATCTG (SEQ ID NO: 54) |
| 12 | 44130831 | 44114366 | 44118367 | OBD154_069 | AAGCCCTGGAGTGGGAGATTGCT (SEQ ID NO: 55) |

TABLE 24.d-continued

| | 4 kb Sequence Location | | | | |
|---|---|---|---|---|---|
| No. | End1 | Start2 | End2 | PCR-Primer1_ID | PCR_Primer1 |
| 13 | 42034839 | 42111316 | 42115317 | OBD154_073 | CAACCTGGAGTCCTGAAGACCCC (SEQ ID NO: 56) |
| 14 | 38560060 | 38515585 | 38519586 | OBD154_077 | CCACCTTGGCAAATGGCTTCTCTGCT (SEQ ID NO: 57) |
| 15 | 18025879 | 18089550 | 18093551 | OBD154_085 | CTCCCTGCCCTCCATTTGCCTTT (SEQ ID NO: 58) |
| 16 | 27974189 | 28029396 | 28033397 | OBD154_093 | GCACTGAGTTGTGGGTTTTCAAAGGT (SEQ ID NO: 59) |
| 17 | 39076648 | 38902754 | 38906755 | OBD154_097 | GCTATTTGCGTGGTGGTGACAATGAT (SEQ ID NO: 60) |
| 18 | 38682593 | 38716223 | 38720224 | OBD154_105 | ATCATCACCTTAGTATCCCCACCTCT (SEQ ID NO: 61) |
| 19 | 30301290 | 30247318 | 30251319 | OBD154_109 | AAGTGTCAGCCTCTGCCCGTAGC (SEQ ID NO: 62) |
| 20 | 76755869 | 76713081 | 76717082 | OBD154_113 | GGGTGAGGTTCTTTCCCTGTAGG (SEQ ID NO: 63) & (SEQ ID NO: 73) |
| 21 | 11919510 | 11887773 | 11891774 | OBD154_117 | GTCTCTTCTTCTCTCTGGTCGGC (SEQ ID NO: 64) |
| 22 | 9235994 | 9247952 | 9251953 | OBD154_121 | CCCACACCTCCAGTTGTCCCACA (SEQ ID NO: 65) |
| 23 | 790967 | 729450 | 733451 | OBD154_125 | TACTCTTCAAAAGCACAGCCAACGGG (SEQ ID NO: 66) |
| 24 | 69930519 | 69847512 | 69851513 | OBD154_133 | GGTGGAAGTCGTCTGCCAAGATG (SEQ ID NO: 67) |
| 25 | 110783525 | 110816886 | 110820887 | OBD154_137 | TGGCTAACTGTCTCCTCAAAATCCTA (SEQ ID NO: 68) |
| 26 | 29759643 | 29820061 | 29824062 | OBD154_141 | CGTAACACCCGAATCAGTGGAAGGAA (SEQ ID NO: 69) |
| 27 | 7697820 | 7673458 | 7677459 | OBD154_149 | GCCTCCTCTCCCTATCTCTGGAT (SEQ ID NO: 70) |
| 28 | 17641147 | 17623423 | 17627424 | OBD154_153 | CAGATGCTGGGTTTTGCCCTCAGG (SEQ ID NO: 71) |
| 29 | 45862762 | 45775880 | 45779881 | OBD154_157 | TGACTCTGCTGTAGATGTCCTGGCTC (SEQ ID NO: 72) |
| 30 | 76755869 | 76724347 | 76728348 | OBD154_161 | GGGTGAGGTTCTTTCCCTGTAGG (SEQ ID NO: 63) & (SEQ ID NO: 73) |
| 31 | 64193405 | 64339228 | 64343229 | OBD154_165 | GGTAGAAAGCGTTTAGCCCTGTATTT (SEQ ID NO: 74) |
| 32 | 104394567 | 104318188 | 104322189 | OBD154_169 | CACCTTCATCCTTCACCAAGTCCTGC (SEQ ID NO: 75) |
| 33 | 85949922 | 85987651 | 85991652 | OBD154_177 | CCCTCAACCCATTTCCTTCACTTGCC (SEQ ID NO: 76) |
| 34 | 5315708 | 5202402 | 5206403 | OBD154_185 | TGAGGATGGTCAGTGAGACTCGTAAA (SEQ ID NO: 77) |
| 35 | 24910177 | 25028150 | 25032151 | OBD154_201 | ACAGTAGACAGACAGCACAGGGTTTA (SEQ ID NO: 78) |
| 36 | 18616544 | 18648509 | 18652510 | OBD154_205 | AAAGGTGGTGGGCAGGACTCCAG (SEQ ID NO: 79) & (SEQ ID NO: 82) |
| 37 | 41705256 | 41786781 | 41790782 | OBD154_209 | ATGTAGGGCATCACCACAGCGTG (SEQ ID NO: 80) |

TABLE 24.d-continued

| No. | | 4 kb Sequence Location | | PCR-Primer1_ID | PCR_Primer1 |
| | End1 | Start2 | End2 | | |
| --- | --- | --- | --- | --- | --- |
| 38 | 44083169 | 44118479 | 44122480 | OBD154_213 | TCCCCACTTCTCCTCCACAAGGC (SEQ ID NO: 47) & (SEQ ID NO: 81) |
| 39 | 18616544 | 18641258 | 18645259 | OBD154_217 | AAAGGTGGTGGGCAGGACTCCAG (SEQ ID NO: 79) & (SEQ ID NO: 82) |
| 40 | 84540820 | 84582113 | 84586114 | OBD154_229 | ACTCGGCTAACCCTCTACTTCAAGGT (SEQ ID NO: 83) |
| 41 | 55291596 | 55153174 | 55157175 | OBD154_237 | GGCGGCTGTGTGAGTTTTGCCAA (SEQ ID NO: 84) |
| 42 | 100801373 | 100747636 | 100751637 | OBD154_245 | ACCATTAGTTGGCTCATCTCCTTGCC (SEQ ID NO: 85) |

TABLE 24.e

| No. | PCR-Primer2_ID | PCR_Primer2 | GLMNET |
| --- | --- | --- | --- |
| 1 | OBD154_003 | GGAGGCAAGGCTGTGATGAAAGTCAA (SEQ ID NO: 86) | 0.044648292 |
| 2 | OBD154_011 | GTGAGTGGGTTTCCCTGCTGAAC (SEQ ID NO: 87) | 0.077266514 |
| 3 | OBD154_015 | GCTGCTGTGGGTTTCTGCGACAT (SEQ ID NO: 88) | 0.10805769 |
| 4 | OBD154_035 | GCCTGGAACAGTTGAGCAAACGC (SEQ ID NO: 89) | 0.052504077 |
| 5 | OBD154_039 | CCAGTGCCTCTCTTCAGCATCCC (SEQ ID NO: 90) | 0.016550856 |
| 6 | OBD154_043 | CTCACACAGAGAGGAGGAGAGGA (SEQ ID NO: 91) | 0.033835679 |
| 7 | OBD154_047 | CCCCAGGTTTGGAAGTTCTCAGC (SEQ ID NO: 92) | -0.031914355 |
| 8 | OBD154_051 | CGGAGCAGAACATTCGCCTAAGC (SEQ ID NO: 93) | 0.073432502 |
| 9 | OBD154_055 | GCAGTGTGACAAGGAAGCAGCAG (SEQ ID NO: 94) | 0.034421206 |
| 10 | OBD154_059 | ACCCTCAGAAATCCCTCCCAGGC (SEQ ID NO: 95) | 0.014137586 |
| 11 | OBD154_063 | TCTTCACCATTTTCTTGAGCACTGTG (SEQ ID NO: 96) | -0.034009396 |
| 12 | OBD154_071 | GCCAGCCACTGTCCCAAGGAGAT (SEQ ID NO: 97) | 0.046480779 |
| 13 | OBD154_075 | CGCAGGGCTAATCTTCCTCAACC (SEQ ID NO: 98) | -0.092997789 |
| 14 | OBD154_079 | TTTTGAGGGAGAGTCCGTGAAGC (SEQ ID NO: 99) | 0.018460556 |
| 15 | OBD154_087 | ATCACGGACAGGCACCTACGGCT (SEQ ID NO: 100) | 0.105247988 |
| 16 | OBD154_095 | ATCAAACTCCAGCAATCTGACTCCAG (SEQ ID NO: 101) | 0.067222042 |
| 17 | OBD154_099 | GCCAGGCTCACTCCTTTCCCTTTTAG (SEQ ID NO: 102) | 0.069540888 |
| 18 | OBD154_107 | GCCCTGAGACAAGCATTTTCCTCGTC (SEQ ID NO: 103) | 0.072250245 |

TABLE 24.e-continued

| No. | PCR-Primer2_ID | PCR_Primer2 | GLMNET |
|---|---|---|---|
| 19 | OBD154_111 | CGGAGTCTCGTCCCGACATTTAC (SEQ ID NO: 104) | -0.021487184 |
| 20 | OBD154_115 | ACTGTGTGGGAGGAAGGTGGAGG (SEQ ID NO: 105) | -0.089547447 |
| 21 | OBD154_119 | CACCCACCTTTGTTCACCCGCTC (SEQ ID NO: 106) | 0.053341863 |
| 22 | OBD154_123 | CCCAGGTAGTCGTGGAAACGGAT (SEQ ID NO: 107) | -0.009481999 |
| 23 | OBD154_127 | CCCCTGGCTTTAGGCTTAGATTCTCT (SEQ ID NO: 108) | 0.184254198 |
| 24 | OBD154_135 | TTCTCGCCTGCTTCCTGCCTGTG (SEQ ID NO: 109) | 0.013549498 |
| 25 | OBD154_139 | GCCATTCGGTGACATCAGGGTGA (SEQ ID NO: 110) | -0.029260042 |
| 26 | OBD154_143 | AGAGTCACGGTTTCTGCCTATCAAGA (SEQ ID NO: 111) | 0.040466078 |
| 27 | OBD154_151 | CCTCTCGCTGAAGTCCCTGCCAT (SEQ ID NO: 112) | -0.026044566 |
| 28 | OBD154_155 | CAGGGAAGGGAGAATAGTCAGGG (SEQ ID NO: 113) | 0.05560739 |
| 29 | OBD154_159 | GGAGAGAAGATAGGCTGGCAATAGAT (SEQ ID NO: 114) | -0.111847127 |
| 30 | OBD154_163 | CACCTCCTCCCTCAACCCCTAAG (SEQ ID NO: 115) | -0.011075719 |
| 31 | OBD154_167 | ATTTAGGCACTTGGGAGAGGAGAGCC (SEQ ID NO: 116) | 0.052703232 |
| 32 | OBD154_171 | CTGATGATAGTTAGGGAGAGGTGAGT (SEQ ID NO: 117) | 0.072817076 |
| 33 | OBD154_179 | AAGGTTTGTGGCTCTTGAACATACCA (SEQ ID NO: 118) | 0.023527 |
| 34 | OBD154_187 | AATGGCACATCCTCCAACCCCAAACC (SEQ ID NO: 119) | -0.028512982 |
| 35 | OBD154_203 | TGTGTGTCTACTGCCAACTCTGCCCT (SEQ ID NO: 120) | -0.076839662 |
| 36 | OBD154_207 | CCTCAGGTCAGGTTTTGTCACGG (SEQ ID NO: 121) | 0.101263033 |
| 37 | OBD154_211 | CCGCCCGCATTGGCATCCGAATA (SEQ ID NO: 122) | 0.048686754 |
| 38 | OBD154_215 | CCGAGCCTTCTCCCTTTTCTCCA (SEQ ID NO: 123) | -0.060839024 |
| 39 | OBD154_219 | CAGAACTCCTCAGGCTCAGACAC (SEQ ID NO: 124) | 0.01900231 |
| 40 | OBD154_231 | CTGGCTCAATAAGAGTGCTTTCCTTG (SEQ ID NO: 125) | 0.10786072 |
| 41 | OBD154_239 | TGGCAGGGAAAGACTCGGAGGTC (SEQ ID NO: 126) | -0.04345676 |
| 42 | OBD154_247 | CCTCTTCCCTAACTGCGAAACAAAC (SEQ ID NO: 127) | 0.059641358 |

TABLE 24.f

| No. | Marker | GLMNET |
|---|---|---|
| 1 | OBD154__001/OBD154__003__1:2x | 0.044648292 |
| 2 | OBD154__009/OBD154__011__1:2x | 0.077266514 |
| 3 | OBD154__013/OBD154__015__1x | 0.10805769 |
| 4 | OBD154__033/OBD154__035__1:4x | 0.052504077 |
| 5 | OBD154__037/OBD154__039__1:8x | 0.016550856 |
| 6 | OBD154__041/OBD154__043__1x | 0.033835679 |
| 7 | OBD154__045/OBD154__047__1x | −0.031914355 |
| 8 | OBD154__049/OBD154__051__1:4x | 0.073432502 |
| 9 | OBD154__053/OBD154__055__1:2x | 0.034421206 |
| 10 | OBD154__057/OBD154__059__1:2x | 0.014137586 |
| 11 | OBD154__061/OBD154__063__1x | −0.034009396 |
| 12 | OBD154__069/OBD154__071__1x | 0.046480779 |
| 13 | OBD154__073/OBD154__075__1x | −0.092997789 |
| 14 | OBD154__077/OBD154__079__1x | 0.018460556 |
| 15 | OBD154__085/OBD154__087__1:2x | 0.105247988 |
| 16 | OBD154__093/OBD154__095__1:2x | 0.067222042 |
| 17 | OBD154__097/OBD154__099__1x | 0.069540888 |
| 18 | OBD154__105/OBD154__107__1:2x | 0.072250245 |
| 19 | OBD154__109/OBD154__111__1:2x | −0.021487184 |
| 20 | OBD154__113/OBD154__115__1:4x | −0.089547447 |
| 21 | OBD154__117/OBD154__119__1x | 0.053341863 |
| 22 | OBD154__121/OBD154__123__1x | −0.009481999 |

TABLE 24.f-continued

| No. | Marker | GLMNET |
|---|---|---|
| 23 | OBD154__125/OBD154__127__1:2x | 0.184254198 |
| 24 | OBD154__133/OBD154__135__1:2x | 0.013549498 |
| 25 | OBD154__137/OBD154__139__1x | −0.029260042 |
| 26 | OBD154__141/OBD154__143__1x | 0.040466078 |
| 27 | OBD154__149/OBD154__151__1:2x | −0.026044566 |
| 28 | OBD154__153/OBD154__155__1:8x | 0.05560739 |
| 29 | OBD154__157/OBD154__159__1:2x | −0.111847127 |
| 30 | OBD154__161/OBD154__163__1:2x | −0.011075719 |
| 31 | OBD154__165/OBD154__167__1x | 0.052703232 |
| 32 | OBD154__169/OBD154__171__1:4x | 0.072817076 |
| 33 | OBD154__177/OBD154__179__1x | 0.023527 |
| 34 | OBD154__185/OBD154__187__1x | −0.028512982 |
| 35 | OBD154__201/OBD154__203__1x | −0.076839662 |
| 36 | OBD154__205/OBD154__207__1:2x | 0.101263033 |
| 37 | OBD154__209/OBD154__211__1:2x | 0.048686754 |
| 38 | OBD154__213/OBD154__215__1:2x | −0.060839024 |
| 39 | OBD154__217/OBD154__219__1x | 0.01900231 |
| 40 | OBD154__229/OBD154__231__1x | 0.10786072 |
| 41 | OBD154__237/OBD154__239__1x | −0.04345676 |
| 42 | OBD154__245/OBD154__247__1x | 0.059641358 |

TABLE 25.a

| No. | Probe | Loci | Probe_Count_Total | Probe_Count_Sig |
|---|---|---|---|---|
| 1 | CBL__11__119249760__119252653__119294588__119299643__RF | CBL | 24 | 19 |
| 2 | DKK3__11__11956071__11968035__11984245__11993733__FR | DKK3 | 54 | 36 |
| 3 | DKK3__11__11956071__11968035__12048403__12051930__FR | DKK3 | 54 | 36 |
| 4 | FBXO32__8__123526212__123527874__123555254__123559065__FR | FBXO32 | 41 | 26 |
| 5 | KDM1A__1__23064655__23070269__23096951__23098159__FR | KDM1A | 25 | 18 |
| 6 | EYA1__8__71216399__71218728__71261816__71267769__RR | EYA1 | 139 | 80 |
| 7 | PCK1__20__57527297__57530814__57579772__57583521__RR | PCK1 | 36 | 26 |
| 8 | PIK3C3__18__42070009__42072187__42088671__42094691__FF | PIK3C3 | 141 | 89 |
| 9 | ALDH1A2__15__58053198__58062371__58157807__58162832__RR | ALDH1A2 | 185 | 100 |
| 10 | CD36__7__80539507__80544315__80679651__80687690__FR | CD36 | 169 | 96 |
| 11 | DKK3__11__11956071__11968035__12010923__12019458__FF | DKK3 | 54 | 36 |
| 12 | IL1RAP__3__190489665__190498302__190560851__190563356__FR | IL1RAP | 160 | 82 |
| 13 | RUNX3__1__24920810__24923822__24973522__24976037__RF | RUNX3 | 51 | 24 |
| 14 | PPARA__22__46101029__46102611__46241078__46244347__FR | PPARA | 44 | 26 |
| 15 | SLC25A13__7__96209525__96214524__96295606__96302029__FF | SLC25A13 | 143 | 99 |
| 16 | PCK1__20__57527297__57530814__57551578__57557205__RR | PCK1 | 36 | 26 |
| 17 | MYL1__2__210288997__210291732__210359762__210362293__FF | MYL1 | 9 | 5 |
| 18 | C1GALT1__7__7113076__7114831__7258228__7260668__FF | C1GALT1 | 89 | 4 |
| 19 | COL25A1__4__109024771__109031337__109090838__109104305__RR | COL25A1 | 134 | 3 |
| 20 | COL5A1__9__134738485__134741113__134811418__134816113__RR | COL5A1 | 180 | 0 |
| 21 | DIAPH3__13__59818047__59823591__59854837__59860534__RR | DIAPH3 | 167 | 1 |
| 22 | FBLN2__3__13512352__13515076__13582406__13590343__RF | FBLN2 | 93 | 1 |
| 23 | GPC6__13__94121445__94133208__94296633__94304225__FF | GPC6 | 166 | 7 |
| 24 | GSN__9__121177548__121180410__121268506__121274144__FR | GSN | 156 | 6 |
| 25 | GSN__9__121227501__121232628__121268506__121274144__FR | GSN | 156 | 6 |
| 26 | GSN__9__121239116__121243347__121268506__121274144__FR | GSN | 156 | 6 |
| 27 | LCK__1__32214585__32217213__32237144__32241139__RF | LCK | 24 | 1 |
| 28 | LMO4__1__87315524__87318670__87343110__87349940__FF | LMO4 | 105 | 0 |
| 29 | MAPK10__4__86572598__86581486__86617317__86621940__FF | MAPK10 | 172 | 2 |
| 30 | MBNL1__3__152229500__152234786__152281057__152285843__FR | MBNL1 | 144 | 2 |
| 31 | NCAM1__11__113019160__113028536__113163748__113168132__FR | NCAM1 | 198 | 3 |
| 32 | PCK1__20__57527297__57530814__57570220__57572870__RR | PCK1 | 36 | 0 |
| 33 | PDK3__X__24441637__24447950__24480152__24481252__FR | PDK3 | 22 | 0 |
| 34 | PDK3__X__24441637__24447950__24490440__24491541__FR | PDK3 | 22 | 0 |
| 35 | PTPRC__1__198595771__198598296__198659753__198666156__RF | PTPRC | 184 | 14 |
| 36 | PTPRC__1__198659753__198666156__198721093__198724578__FF | PTPRC | 184 | 14 |
| 37 | RYR1__19__38410632__38413089__38495982__38499305__RR | RYR1 | 41 | 6 |
| 38 | THNSL2__2__88139809__88146295__88161717__88164554__FR | THNSL2 | 29 | 2 |
| 39 | UACA__15__70715123__70719636__70780754__70784668__RF | UACA | 132 | 1 |
| 40 | ZEB1__10__31273317__31275631__31507470__31524442__FF | ZEB1 | 163 | 11 |
| 41 | ZFHX3__16__73147488__73153243__73182254__73184585__FF | ZFHX3 | 170 | 1 |
| 42 | ADRB3__8__37962724__37965269__37987735__37989039__FR | ADRB3 | 18 | 0 |
| 43 | AGT__1__230724515__230729957__230752057__230757333__RF | AGT | 45 | 3 |
| 44 | HTR2A__13__46860092__46866824__46904346__46907815__RF | HTR2A | 60 | 5 |
| 45 | SOS1__2__38982199__38993639__39061418__39066028__FF | SOS1 | 126 | 0 |
| 46 | ACBD6__1__180431719__180434683__180541491__180549122__RR | ACBD6 | 173 | 4 |
| 47 | MYH1__17__10502067__10505465__10533547__10534931__RF | MYH1 | 103 | 2 |
| 48 | MYOD1__11__17685862__17689487__17729653__17733608__FR | MYOD1 | 15 | 1 |
| 49 | NECTIN3__3__111028574__111034204__111209684__111210764__FR | NECTIN3 | 85 | 4 |

TABLE 25.a-continued

| No. | Probe | Loci | Probe_Count_Total | Probe_Count_Sig |
|---|---|---|---|---|
| 50 | ACACB_12_109146008_109150083_109236052_109237242_RR | ACACB | 133 | 2 |
| 51 | ACACB_12_109236052_109237242_109268078_109273323_RR | ACACB | 133 | 2 |
| 52 | IGF1R_15_98652565_98657862_98731539_98737034_RF | IGF1R | 176 | 2 |
| 53 | SOCS7_17_38347510_38348776_38360864_38363420_FR | SOCS7 | 31 | 1 |
| 54 | STXBP4_17_55035186_55042800_55117598_55123347_RR | STXBP4 | 141 | 4 |
| 55 | SVEP1_9_110397951_110405969_110503630_110509758_FF | SVEP1 | 177 | 7 |
| 56 | EMCN_4_100636305_100649860_100744427_100745788_RR | EMCN | 178 | 2 |
| 57 | ACACB_12_109146008_109150083_109185066_109187324_RR | ACACB | 133 | 2 |
| 58 | FOXO1_13_40524349_40526124_40688580_40690771_RR | FOXO1 | 89 | 0 |
| 59 | FOXO3_6_108603215_108604436_108629992_108635481_FR | FOXO3 | 159 | 2 |
| 60 | FTO_16_53844989_53854574_54045378_54052319_RF | FTO | 153 | 1 |
| 61 | GPC6_13_94054831_94060621_94121445_94133208_RF | GPC6 | 166 | 7 |
| 62 | PPP3CA_4_101055418_101067369_101247819_101259416_RR | PPP3CA | 153 | 2 |
| 63 | SMAD7_18_48917335_48920290_48969505_48974578_RF | SMAD7 | 42 | 0 |
| 64 | SYK_9_90816328_90822228_90832284_90836084_RR | SYK | 160 | 12 |
| 65 | SYK_9_90816328_90822228_90872966_90875740_RR | SYK | 160 | 12 |
| 66 | TGFB2_1_218317687_218325587_218386401_218389011_FR | TGFB2 | 130 | 2 |
| 67 | TGFBR2_3_30566144_30567439_30694718_30698514_RR | TGFBR2 | 191 | 4 |
| 68 | TLR2_4_153659613_153661830_153693586_153700349_RF | TLR2 | 32 | 1 |
| 69 | SVEP1_9_110493529_110499578_110527410_110532406_FR | SVEP1 | 177 | 7 |
| 70 | MTFR1_8_65658401_65661888_65780891_65782535_RF | MTFR1 | 91 | 2 |
| 71 | GSN_9_121182946_121189020_121323589_121328431_FF | GSN | 156 | 6 |
| 72 | MUSK_9_110648469_110652659_110747866_110751903_FR | MUSK | 125 | 1 |
| 73 | PPARA_22_46128634_46134707_46231440_46235124_FR | PPARA | 44 | 0 |
| 74 | PPP1R9A_7_94903925_94908776_94951930_94967018_RF | PPP1R9A | 166 | 1 |
| 75 | PLCXD2_3_111633890_111638317_111672672_111677327_FR | PLCXD2 | 144 | 2 |
| 76 | SGCZ_8_14631157_14642508_14778176_14785491_FF | SGCZ | 191 | 11 |
| 77 | SRI_7_88199682_88203042_88229166_88237101_RF | SRI | 57 | 2 |

TABLE 25.b

| No. | HyperG_Stats | FDR_HyperG | Percent_Sig | logFC | AveExpr | t |
|---|---|---|---|---|---|---|
| 1 | 0.023815147 | 0.261918121 | 79.17 | −0.426375519 | −0.426375519 | −4.618561579 |
| 2 | 0.113222201 | 0.567553327 | 66.67 | −0.452190179 | −0.452190179 | −4.498338722 |
| 3 | 0.113222201 | 0.567553327 | 66.67 | −0.473931719 | −0.473931719 | −4.801248921 |
| 4 | 0.279504208 | 0.898561555 | 63.41 | −0.428908404 | −0.428908404 | −11.06651685 |
| 5 | 0.103914483 | 0.548863748 | 72 | 0.450982494 | 0.450982494 | 11.74211542 |
| 6 | 0.544172978 | 1 | 57.55 | −0.420279402 | −0.420279402 | −6.888734462 |
| 7 | 0.052274012 | 0.438252195 | 72.22 | −0.454377101 | −0.454377101 | −3.146677782 |
| 8 | 0.108139211 | 0.559937306 | 63.12 | 0.349058418 | 0.349058418 | 10.19574365 |
| 9 | 0.85625995 | 1 | 54.05 | −0.42054833 | −0.42054833 | −8.812988665 |
| 10 | 0.618616868 | 1 | 56.8 | 0.355814357 | 0.355814357 | 4.033543511 |
| 11 | 0.113222201 | 0.567553327 | 66.67 | −0.474435884 | −0.474435884 | −4.565896539 |
| 12 | 0.956664907 | 1 | 51.25 | 0.348466077 | 0.348466077 | 11.56470451 |
| 13 | 0.95196413 | 1 | 47.06 | 0.364233402 | 0.364233402 | 10.30993314 |
| 14 | 0.486340587 | 1 | 59.09 | −0.447624697 | −0.447624697 | −6.45833793 |
| 15 | 0.00284877 | 0.08241485 | 69.23 | 0.351229127 | 0.351229127 | 5.941886473 |
| 16 | 0.052274012 | 0.438252195 | 72.22 | −0.427795857 | −0.427795857 | −2.904768228 |
| 17 | 0.682316487 | 1 | 55.56 | −0.389190141 | −0.389190141 | −13.74123239 |
| 18 | 0.024327419 | 0.687064234 | 4.49 | −0.555546218 | −0.555546218 | −11.0417245 |
| 19 | 0.228355538 | 1 | 2.24 | 0.335547043 | 0.335547043 | 5.207330156 |
| 20 | 1 | 1 | 0 | −0.481446393 | −0.481446393 | −3.82029126 |
| 21 | 0.873903179 | 1 | 0.6 | 0.405185839 | 0.405185839 | 2.998972245 |
| 22 | 0.684023987 | 1 | 1.08 | −0.422325738 | −0.422325738 | −8.04265312 |
| 23 | 0.004639027 | 0.223094969 | 4.22 | 0.395980197 | 0.395980197 | 1.793119535 |
| 24 | 0.013014007 | 0.465546506 | 3.85 | −0.435924362 | −0.435924362 | −4.024149814 |
| 25 | 0.013014007 | 0.465546506 | 3.85 | −0.489846734 | −0.489846734 | −3.901621745 |
| 26 | 0.013014007 | 0.465546506 | 3.85 | −0.490566516 | −0.490566516 | −4.064123806 |
| 27 | 0.257000004 | 1 | 4.17 | 0.404856809 | 0.404856809 | 4.029112137 |
| 28 | 1 | 1 | 0 | −0.425303631 | −0.425303631 | −4.334227249 |
| 29 | 0.626639375 | 1 | 1.16 | 0.369477889 | 0.369477889 | 10.62330419 |
| 30 | 0.530285478 | 1 | 1.39 | −0.423225201 | −0.423225201 | −5.762419013 |
| 31 | 0.440361719 | 1 | 1.52 | −0.473418522 | −0.473418522 | −5.252061333 |
| 32 | 1 | 1 | 0 | −0.443750376 | −0.443750376 | −3.069308332 |
| 33 | 1 | 1 | 0 | −0.516209141 | −0.516209141 | −2.912953295 |
| 34 | 1 | 1 | 0 | −0.482956676 | −0.482956676 | −2.845644248 |
| 35 | 7.93E−08 | 3.12E−05 | 7.61 | 0.342871898 | 0.342871898 | 12.24688433 |
| 36 | 7.93E−08 | 3.12E−05 | 7.61 | 0.353200746 | 0.353200746 | 12.71706109 |
| 37 | 1.05E−05 | 0.00164927 | 14.63 | 0.379845454 | 0.379845454 | 3.091066536 |
| 38 | 0.049255392 | 1 | 6.9 | 0.348303621 | 0.348303621 | 5.482854907 |
| 39 | 0.805245253 | 1 | 0.76 | −0.452444827 | −0.452444827 | −6.645114759 |
| 40 | 6.24E−06 | 0.00122739 | 6.75 | 0.341402554 | 0.341402554 | 8.358154799 |
| 41 | 0.878517137 | 1 | 0.59 | −0.437339546 | −0.437339546 | −7.571199723 |
| 42 | 1 | 1 | 0 | −0.431801011 | −0.431801011 | −3.395119054 |

TABLE 25.b-continued

| No. | HyperG_Stats | FDR_HyperG | Percent_Sig | logFC | AveExpr | t |
|---|---|---|---|---|---|---|
| 43 | 0.017905795 | 0.612689599 | 6.67 | −0.462997504 | −0.462997504 | −4.192393926 |
| 44 | 0.000863162 | 0.056609039 | 8.33 | −0.450665703 | −0.450665703 | −8.327533972 |
| 45 | 1 | 1 | 0 | −0.483305844 | −0.483305844 | −11.1896848 |
| 46 | 0.165185813 | 1 | 2.31 | −0.438627353 | −0.438627353 | −7.215605041 |
| 47 | 0.362024499 | 1 | 1.94 | −0.433949544 | −0.433949544 | −7.773631426 |
| 48 | 0.169428566 | 1 | 6.67 | −0.44490366 | −0.44490366 | −11.70445784 |
| 49 | 0.020952195 | 0.683779761 | 4.71 | −0.367763769 | −0.367763769 | −7.284235112 |
| 50 | 0.488070766 | 1 | 1.5 | 0.37639594 | 0.37639594 | 5.784183467 |
| 51 | 0.488070766 | 1 | 1.5 | 0.361980641 | 0.361980641 | 6.812052569 |
| 52 | 0.63908073 | 1 | 1.14 | 0.376793177 | 0.376793177 | 3.580450098 |
| 53 | 0.318687894 | 1 | 3.23 | 0.325631694 | 0.325631694 | 8.979749407 |
| 54 | 0.096791402 | 1 | 2.84 | 0.347975579 | 0.347975579 | 7.974747337 |
| 55 | 0.006539151 | 0.270858531 | 3.95 | 0.328480984 | 0.328480984 | 4.835157675 |
| 56 | 0.645178258 | 1 | 1.12 | 0.319852241 | 0.319852241 | 5.68627836 |
| 57 | 0.488070766 | 1 | 1.5 | −0.639467523 | −0.639467523 | −7.69815267 |
| 58 | 1 | 1 | 0 | 0.393248671 | 0.393248671 | 6.480891366 |
| 59 | 0.583919721 | 1 | 1.26 | 0.365259231 | 0.365259231 | 6.804140703 |
| 60 | 0.849949517 | 1 | 0.65 | −0.434234901 | −0.434234901 | −9.879188206 |
| 61 | 0.004639027 | 0.223094969 | 4.22 | 0.528815395 | 0.528815395 | 2.192030297 |
| 62 | 0.563021006 | 1 | 1.31 | −0.462324823 | −0.462324823 | −10.32420109 |
| 63 | 1 | 1 | 0 | 0.40277223 | 0.40277223 | 2.549597378 |
| 64 | 7.81E−07 | 0.000204861 | 7.5 | 0.454881152 | 0.454881152 | 6.892290381 |
| 65 | 7.81E−07 | 0.000204861 | 7.5 | 0.491854549 | 0.491854549 | 7.332798069 |
| 66 | 0.476152064 | 1 | 1.54 | −0.427835042 | −0.427835042 | −9.631799551 |
| 67 | 0.209498358 | 1 | 2.09 | 0.713766505 | 0.713766505 | 5.020955434 |
| 68 | 0.327072861 | 1 | 3.12 | 0.370613279 | 0.370613279 | 12.69019114 |
| 69 | 0.006539151 | 0.270858531 | 3.95 | −0.425150058 | −0.425150058 | −9.267584464 |
| 70 | 0.308264448 | 1 | 2.2 | −0.373414166 | −0.373414166 | −11.79966649 |
| 71 | 0.013014007 | 0.465546506 | 3.85 | 0.360333931 | 0.360333931 | 7.597970849 |
| 72 | 0.787565452 | 1 | 0.8 | 0.386657089 | 0.386657089 | 7.586923373 |
| 73 | 1 | 1 | 0 | 0.362541486 | 0.362541486 | 2.971365926 |
| 74 | 0.872326654 | 1 | 0.6 | 0.363099567 | 0.363099567 | 3.977705912 |
| 75 | 0.530285478 | 1 | 1.39 | 0.371871445 | 0.371871445 | 9.143459938 |
| 76 | 2.76E−05 | 0.00285196 | 5.76 | 0.351857885 | 0.351857885 | 12.4599802 |
| 77 | 0.155413907 | 1 | 3.51 | 0.345097648 | 0.345097648 | 6.863477929 |

TABLE 25.c

| No. | P.Value | adj.P.Val | B | FC |
|---|---|---|---|---|
| 1 | 0.000204351 | 0.001696324 | 0.420007759 | 0.744128913 |
| 2 | 0.000266954 | 0.002046882 | 0.154483715 | 0.730932365 |
| 3 | 0.000136422 | 0.001270248 | 0.822155807 | 0.719999735 |
| 4 | 0.00000000106 | 0.000000159 | 12.50758304 | 0.742823621 |
| 5 | 0.0000000000057763115753262 | 0.00000024038297446584 | 13.11880883 | 1.366970864 |
| 6 | 0.00000174500366992146 | 0.0000602085318700566 | 5.184417423 | 0.747279887 |
| 7 | 0.005488024 | 0.018949968 | −2.809655881 | 0.729825214 |
| 8 | 0.00000000406 | 0.000000379 | 11.17917387 | 1.27372905 |
| 9 | 0.0000000519795383109141 | 0.00000495299418442526 | 8.693472403 | 0.747140602 |
| 10 | 0.000716034 | 0.003059888 | −0.936521584 | 1.279707733 |
| 11 | 0.000229703 | 0.001841162 | 0.303764249 | 0.719748167 |
| 12 | 0.000000000513 | 0.0000000948 | 13.22969486 | 1.273206191 |
| 13 | 0.0000000464664280056321 | 0.000000961862645683259 | 11.08156058 | 1.287197476 |
| 14 | 0.00000409787235536200 | 0.000109374 | 4.328897959 | 0.733249101 |
| 15 | 0.0000118 | 0.000224511 | 3.269636273 | 1.275646972 |
| 16 | 0.00932387 | 0.028011446 | −3.317120561 | 0.743396676 |
| 17 | 0.0000000000274 | 0.0000000141 | 16.09554078 | 0.763558109 |
| 18 | 0.00000000111 | 0.000000163 | 12.47094565 | 0.680399404 |
| 19 | 0.0000510 | 0.000371158 | 1.696824449 | 1.26185579 |
| 20 | 0.001219666 | 0.006253664 | −1.346303854 | 0.716259169 |
| 21 | 0.007408583 | 0.020028642 | −3.214800278 | 1.324259482 |
| 22 | 0.000000161 | 0.00000491 | 7.493520599 | 0.746220688 |
| 23 | 0.089475491 | 0.154086604 | −5.389247882 | 1.315836464 |
| 24 | 0.000771506 | 0.004457333 | −0.895719572 | 0.739219971 |
| 25 | 0.001015971 | 0.005458351 | −1.166748282 | 0.712100745 |
| 26 | 0.000705273 | 0.004168565 | −0.807203494 | 0.711745556 |
| 27 | 0.0007233 | 0.003084781 | −0.946498319 | 1.323957498 |
| 28 | 0.000385015 | 0.002678159 | −0.20873374 | 0.744681988 |
| 29 | 0.0000000000289295572819759 | 0.00000000681985048919552 | 11.54687815 | 1.291885213 |
| 30 | 0.0000171628795759885 | 0.000292745 | 2.893666517 | 0.745755594 |
| 31 | 0.0000462 | 0.000343634 | 1.795697 | 0.7202559 |
| 32 | 0.006507463 | 0.021473733 | −2.97336687 | 0.73522087 |
| 33 | 0.009159444 | 0.027632407 | −3.300175166 | 0.699206673 |
| 34 | 0.010599052 | 0.030783445 | −3.439002954 | 0.715509746 |
| 35 | 0.000000000196 | 0.0000000539 | 14.17658691 | 1.26827878 |

TABLE 25.c-continued

| No. | P.Value | adj.P.Val | B | FC |
|---|---|---|---|---|
| 36 | 0.000000000104 | 0.0000000375 | 14.80248355 | 1.277391491 |
| 37 | 0.006203474 | 0.020718718 | −2.927451691 | 1.301202459 |
| 38 | 0.0000279 | 0.000231594 | 2.302943346 | 1.273062829 |
| 39 | 0.00000241 | 0.0000352 | 4.766915889 | 0.73080336 |
| 40 | 0.0000000904 | 0.00000323 | 8.071768487 | 1.266987731 |
| 41 | 0.000000474476333843650 | 0.0000231189585700664 | 6.488080595 | 0.738495203 |
| 42 | 0.003161948 | 0.012613791 | −2.27662634 | 0.741335749 |
| 43 | 0.00052891 | 0.00336987 | −0.523006115 | 0.725477359 |
| 44 | 0.000000120499326458705 | 0.0000908377824577704 | 7.856562067 | 0.731705139 |
| 45 | 0.0000000126038126093866 | 0.000004060180470733111 | 12.35960543 | 0.715336596 |
| 46 | 0.000000773 | 0.0000152 | 5.912515816 | 0.737836287 |
| 47 | 0.000000265 | 0.00000692 | 6.989653482 | 0.740232537 |
| 48 | 0.000000000420 | 0.0000000817 | 13.42754235 | 0.734633372 |
| 49 | 0.000000676 | 0.0000139 | 6.047319254 | 0.774982819 |
| 50 | 0.0000163956845883121 | 0.000282973 | 2.939466958 | 1.298094974 |
| 51 | 0.00000202795176244020 | 0.0000670770127555545 | 5.033860861 | 1.285189092 |
| 52 | 0.002089314 | 0.00927894 | −1.873258731 | 1.298452444 |
| 53 | 0.0000000302 | 0.00000149 | 9.171680821 | 1.253213047 |
| 54 | 0.000000182 | 0.00000536 | 7.367278195 | 1.27277339 |
| 55 | 0.000116599 | 0.000719355 | 0.868191804 | 1.25569056 |
| 56 | 0.0000179 | 0.000164182 | 2.745641844 | 1.248202703 |
| 57 | 0.000000306 | 0.00000769 | 6.846486395 | 0.641949839 |
| 58 | 0.00000391616567926034 | 0.000106263 | 4.374356285 | 1.313347482 |
| 59 | 0.00000205973252071508 | 0.0000679202407840129 | 5.018280323 | 1.288113063 |
| 60 | 0.0000000000906782907573557 | 0.00000142181714589480 | 10.42301097 | 0.740086138 |
| 61 | 0.041519144 | 0.085450094 | −4.70897528 | 1.442744064 |
| 62 | 0.0000000000454643610867096 | 0.000000946006652142489 | 11.10299558 | 0.725815704 |
| 63 | 0.019933628 | 0.04923408 | −4.033722222 | 1.322045866 |
| 64 | 0.00000146 | 0.0000245 | 5.268722172 | 1.370669886 |
| 65 | 0.000000615 | 0.0000130 | 6.142312649 | 1.406251416 |
| 66 | 0.0000000101 | 0.000000678 | 10.2711503 | 0.743376485 |
| 67 | 0.0000842245621504624 | 0.000906383 | 1.302982598 | 1.640080359 |
| 68 | 0.0000000000161476307566624 | 0.00000000940784035927087 | 14.34965814 | 1.292902317 |
| 69 | 0.0000000242868020514695 | 0.00000282996756590024 | 9.44872473 | 0.744761263 |
| 70 | 0.000000000367 | 0.0000000760 | 13.56117136 | 0.771953491 |
| 71 | 0.00000451423921266660 | 0.0000224517338792905 | 6.53788422 | 1.283722998 |
| 72 | 0.0000000460792529508426 | 0.0000227787899768996 | 6.517344279 | 1.307360568 |
| 73 | 0.008064742 | 0.025126002 | −3.178757551 | 1.285688803 |
| 74 | 0.000856336 | 0.004819753 | −0.998511342 | 1.286186246 |
| 75 | 0.0000000228 | 0.00000120 | 9.452862589 | 1.294030342 |
| 76 | 0.000000000146 | 0.0000000458 | 14.46288268 | 1.276203048 |
| 77 | 0.00000155 | 0.0000255 | 5.210654526 | 1.270236955 |

TABLE 25.d

| No. | FC 1 | LS | Loop detected | Probe sequence 60 mer |
|---|---|---|---|---|
| 1 | −1.343853172 | −1 | Str_train | ACCGCCTCACCTCAGCTCTCCAGTGAGATCGATCCTCCCACCTAAGCTTCCCAAGTTGCT (SEQ ID NO: 128) & (SEQ ID NO: 376) & (SEQ ID NO: 618) |
| 2 | −1.36811564 | −1 | Str_train | GACACCTCCTCTCCCTTCCCTCCCCTTCTCGAGTTATCAAAATATTTTGAGAGACAGTAT (SEQ ID NO: 129) & (SEQ ID NO: 390) & (SEQ ID NO: 562) & (SEQ ID NO: 617) |
| 3 | −1.3888894 | −1 | Str_train | GACACCTCCTCTCCCTTCCCTCCCCTTCTCGATGGCCACATGTGGCCAGTGGCTCTCATG (SEQ ID NO: 130) & (SEQ ID NO: 393) |
| 4 | −1.346214596 | −1 | End_train | TGCAGAAAGTACTACAAAAAAAGAAGCTTCGAAAATGTTGGAGATGAGAGTTTCTTCA CC (SEQ ID NO: 131) & (SEQ ID NO: 402) & (SEQ ID NO: 563) |
| 5 | 1.366970864 | 1 | Str_control | GGCAGGTGGATCATTTGAGGTCAAGAGCTCGACAGAGCAAGACACCATCTCCAAAAA GAA (SEQ ID NO: 132) & (SEQ ID NO: 421) |
| 6 | −1.338186692 | −1 | Str_train | TGTCCTTTCAAGGAAGGATTAGCATCCTTCGAAAGACCTATCAGGATTTCATTTGTAAT G (SEQ ID NO: 133) & (SEQ ID NO: 400) & (SEQ ID NO: 619) |
| 7 | −1.370191083 | −1 | Str_train | CCTCGTCGTCCCCTCTCTTCCTCGTTCCTCGAACATCTCCAAGTCAGATAATCATAACAA (SEQ ID NO: 134) & (SEQ ID NO: 448) & (SEQ ID NO: 569) |
| 8 | 1.27372905 | 1 | End_control | ATCTATTATAATGATGCAATATTGTTAATCGATTCAAAGATCAAATTAATTATTAAAGCT (SEQ ID NO: 135) & (SEQ ID NO: 455) & (SEQ ID NO: 570) |
| 9 | −1.338436162 | −1 | Str_train | ATTTTAAATGTGGCATTTTAGGTTTATTTCGATTTTGCATAAATTGAAAAAGCTGGAGAT (SEQ ID NO: 136) & (SEQ ID NO: 364) |

TABLE 25.d-continued

| No. | FC 1 | LS | Loop detected | Probe sequence 60 mer |
|-----|------|----|----|------------------------|
| 10 | 1.279707733 | 1 | End_control | TGCTGAAAGAAAACACAATTTATTTAAGTCGAAATTTTGGAAAAGCCCTGATTTAAGTCA (SEQ ID NO: 137) & (SEQ ID NO: 378) |
| 11 | -1.389374847 | -1 | Str_train | GACACCTCCTCTCCCTTCCCTCCCCTTCTCGATCACTTTGCAAAGCTTTGTTGGCTAGGC (SEQ ID NO: 138) & (SEQ ID NO: 391) |
| 12 | 1.273206191 | 1 | End_control | TAAATAAAATTGTCTTTTTTTGTCTTTCTCGATTACAGAGAACTAAGTACATTTTAAATC (SEQ ID NO: 139) & (SEQ ID NO: 420) |
| 13 | 1.287197476 | 1 | Str_control | CTTAATTTTTTTTTCTTTGAATGCCTCTATCGACAGTCTTCTCTCTACTTTCTACAGTGAA (SEQ ID NO: 140) & (SEQ ID NO: 474) & (SEQ ID NO: 573) |
| 14 | -1.363793011 | -1 | Str_train | ACACCTCACCCACCCAGCTGGGCTGGCCTCGATGCCATTAAATCATCCCGTGACCTTCCT (SEQ ID NO: 141) & (SEQ ID NO: 516) |
| 15 | 1.275646972 | 1 | Str_control | GGCAGGCGGATCATTTCAGGTCAGGAGTTCGACCTGAAATTTCCATACTAAATTTAAATA (SEQ ID NO: 142) & (SEQ ID NO: 548) |
| 16 | -1.345176851 | -1 | Str_train | CCTCGTCGTCCCCTCTCTTCCTCGTTCCTCGACAGGAAAGCATACGGAAAAAGTTAAAGA (SEQ ID NO: 143) & (SEQ ID NO: 446) |
| 17 | -1.309658019 | -1 | End-Train | AATTTCACATTGATACATTGATAGACATTCGAAATCATACACAGCATACTCTCAAACCAT (SEQ ID NO: 144) & (SEQ ID NO: 528) & (SEQ ID NO: 577) |
| 18 | -1.469724979 | -1 | END_Train | AAATGTATAAGAACAGAAGAGAATTATCTCGACATGTCTGAAAAGTATTATCAGCCCTCT (SEQ ID NO: 145) & (SEQ ID NO: 372) & (SEQ ID NO: 561) |
| 19 | 1.26185579 | 1 | END_Control | AAAACACCCTGAATTGGAAGAAAGAAACTCGAGGGATGAGTGTGTATCATCAAAGTCAAA (SEQ ID NO: 146) & (SEQ ID NO: 380) |
| 20 | -1.396142686 | -1 | Str_Train | CGCGGGGCCTTCTGGGCCAGGCGGGCCCTCGAAAAGCCCCACGCCCCCCCAGAGCTGCTG (SEQ ID NO: 147) & (SEQ ID NO: 383) |
| 21 | 1.324259482 | 1 | END_Control | AATACGTGGTCAATCTAAGGATTATAGTTCGAAAAGATTAATGATGTATTGATGACACTT (SEQ ID NO: 148) & (SEQ ID NO: 389) |
| 22 | -1.340086139 | -1 | END_Train | CTTGCCTAGTCTTTAATTTATTTATTTATCGACATTTTTTTCTTATCAACGAGACGATGT (SEQ ID NO: 149) & (SEQ ID NO: 401) |
| 23 | 1.315836464 | 1 | Str_Control | AATTAGACAACGACTATATGACTCTGTCTCGAGATTGGTCTTAACACACTATTGATTATT (SEQ ID NO: 150) & (SEQ ID NO: 409) |
| 24 | -1.352777305 | -1 | Str_Train | AAAAAGAGAAAAGCAGGTTAGCACATTGTCGACCCCGCCCCCGGGATGGGGGAACTGGCC (SEQ ID NO: 151) & (SEQ ID NO: 411) & (SEQ ID NO: 565) |
| 25 | -1.404295681 | -1 | Str_Train | AAATTTTCAAGTGTACGATATGGTATCATCGACCCCGCCCCCGGGATGGGGGAACTGGCC (SEQ ID NO: 152) & (SEQ ID NO: 413) |
| 26 | -1.40499648 | -1 | Str_Train | AAACTTACGATTACATTTAGAGATCACTTCGACCCCGCCCCCGGGATGGGGGAACTGGCC (SEQ ID NO: 153) & (SEQ ID NO: 414) |
| 27 | 1.323957498 | 1 | END_Control | AAGGGCTCGGGAGCTCCCTCGGCACACCTCGAGGAGTGCCAGGCATCTACTGCTCTGTCC (SEQ ID NO: 154) & (SEQ ID NO: 424) |
| 28 | -1.342855092 | -1 | Str_Train | CCCCTGGCTCACCTACACAAAATTGTGCTCGACTCTACTCTTAGCCCTGCTAAATAAGTA (SEQ ID NO: 155) & (SEQ ID NO: 426) & (SEQ ID NO: 566) |
| 29 | 1.291885213 | 1 | Str_Control | ATTATATTAGTGCTGTAATAAAATTAAGTCGACACATTTGATACTGCTTATTGGGTTATT (SEQ ID NO: 156) & (SEQ ID NO: 428) & (SEQ ID NO: 567) |
| 30 | -1.34092189 | -1 | Str_Train | TACCTTGAAAAGCTCTTCAGTATGATTATCGAGCTTTAGCCATTCTAGTAATTATTAAAA (SEQ ID NO: 157) & (SEQ ID NO: 430) & (SEQ ID NO: 568) |
| 31 | -1.38839543 | -1 | END_Train | ATGAATTAATGTTTCCTAGAAAGTTGTCTCGAAAGAAGAAAGTGTCAGGGTTCAACTGCC (SEQ ID NO: 158) & (SEQ ID NO: 435) |
| 32 | -1.360135493 | -1 | Str_Train | CCTCGTCGTCCCCTCTCTTCCTCGTTCCTCGATGCGGGACTGATTGTTACAGAACTGTTT (SEQ ID NO: 159) & (SEQ ID NO: 447) |
| 33 | -1.4301923 | -1 | Str_Train | GGGGATGGGGCCGAAATATGATTGCACTTCGAGTTTGTTTAGTTTTTATCTTCCCCATTT (SEQ ID NO: 160) & (SEQ ID NO: 450) |
| 34 | -1.397605002 | -1 | Str_Train | GGGGATGGGGCCGAAATATGATTGCACTTCGAACTTCAGCACCTGACCTTTGTCATCAAC (SEQ ID NO: 161) & (SEQ ID NO: 451) |

TABLE 25.d-continued

| No. | FC 1 | LS | Loop detected | Probe sequence 60 mer |
|---|---|---|---|---|
| 35 | 1.26827878 | 1 | END_Control | AGAGGCTGAGGTGAAAAGATTGTTTGAGTCGAAGATCATTGTCTCATTTTTTTACTTGT T (SEQ ID NO: 162) & (SEQ ID NO: 465) & (SEQ ID NO: 571) & (SEQ ID NO: 621) |
| 36 | 1.277391491 | 1 | END_Control | AGAGGCTGAGGTGAAAAGATTGTTTGAGTCGATACACTGAACAAGTGCCAGAGCAGA ATA (SEQ ID NO: 163) & (SEQ ID NO: 469) |
| 37 | 1.301202459 | 1 | Str_Control | GGTGGGAGGATCACTTGAGGTCAGAAGTTCGATCTCCTGACCTCAAGTGATCCTCTAG CT (SEQ ID NO: 164) & (SEQ ID NO: 475) |
| 38 | 1.273062829 | 1 | END_Control | TATCAAGTTAAACATTCAGACGTCTAGGTCGACTTGAAGTTCACCTAAAGTTTTCCAGTC (SEQ ID NO: 165) & (SEQ ID NO: 499) & (SEQ ID NO: 615) |
| 39 | -1.368357145 | -1 | END_Train | ATAGTATAGAATGACAGCATGCTGGTTATCGACAAGAGTTCTTAAAAAGCCTAAATGTC A (SEQ ID NO: 166) & (SEQ ID NO: 503) |
| 40 | 1.266987731 | 1 | END_Control | ATTCCACAAATATTTGTGAGCACCATCTTCGAGCTCATTAGTTCAAGACCAGCCTGGGC A (SEQ ID NO: 167) & (SEQ ID NO: 506) |
| 41 | -1.354104937 | -1 | Str_Train | CTCTCAACTTTGGATGTAAGAATCATCTTCGAGATTTTGACTCTCCACCTGCCCCACAGG (SEQ ID NO: 168) & (SEQ ID NO: 509) & (SEQ ID NO: 574) |
| 42 | -1.348916468 | -1 | Str_Train | CGGTCCCTCTGCCCCGGTTACCTACCCGTCGACATGACACTTGGGTGGGGATACAGGG CC (SEQ ID NO: 169) & (SEQ ID NO: 510) |
| 43 | -1.378402768 | -1 | Str_Train | TCCCCCTCTTCCTCTGCCTCCCTTCCCCTCGAAAACTGATTAAAAAGAATATTGCTGGCT (SEQ ID NO: 170) & (SEQ ID NO: 513) & (SEQ ID NO: 576) |
| 44 | -1.366670735 | -1 | Str_Train | TCACTTTTATTTATCTTACTCACTTTTCTCGAGGAATTCTCAGAATTCTCCTCAACCCAC (SEQ ID NO: 171) & (SEQ ID NO: 515) |
| 45 | -1.397943297 | -1 | Str_Train | TTTCTTCCAACTGAGAGAATCTTAAAAATCGAAATTGGATAAGGAAAAAAGTGAAATG TG (SEQ ID NO: 172) & (SEQ ID NO: 517) |
| 46 | -1.355314205 | -1 | END_Train | TTTTAGTTTTATTTATTTAGTTATCATCTCGAAAAACAAACAACAATAACAGCAACCCTC (SEQ ID NO: 173) & (SEQ ID NO: 521) |
| 47 | -1.350926837 | -1 | END_train | GCAAGACTTTGTCTCAAAACAAAAGTGTTCGAAAAAGTCATCGTTTAAAAGGTAAAAT GT (SEQ ID NO: 174) & (SEQ ID NO: 527) |
| 48 | -1.361223214 | -1 | END_Train | TCCATTAGCTCTGCTTTCAAATACTATATCGATGTAGCTTATGTAAAATAAATGTATTAA (SEQ ID NO: 175) & (SEQ ID NO: 529) |
| 49 | -1.290351187 | -1 | END_Train | TCAAAGTTACAGTTTATATAATTAGAAATCGATCTAACCTCAATTCCAGTCCCACAAATG (SEQ ID NO: 176) & (SEQ ID NO: 530) |
| 50 | 1.298094974 | 1 | Str_Control | TCAAGAAAAAATAATAATAATTTTTTTTTTCGAACTTATGGCTCAAGCGATTCTCTTGCTT (SEQ ID NO: 177) & (SEQ ID NO: 532) |
| 51 | 1.285189092 | 1 | Str_Control | AAGCAAGAGAATCGCTTGAGCCATAAGTTCGATGCTGCTTTGGGAACTGAAGGTTTTT CT (SEQ ID NO: 178) & (SEQ ID NO: 533) & (SEQ ID NO: 620) |
| 52 | 1.298452444 | 1 | Str_Control | CGTAGAACTAAGATGTATTCAAAGTCAGTCGAAAAAGATTAGAAAAGTTCAACTCTAA GA (SEQ ID NO: 179) & (SEQ ID NO: 540) & (SEQ ID NO: 616) |
| 53 | 1.253213047 | 1 | END_Control | AGGCAGGCAGATCAATGAGGTTGGGAGATCGACAAGTTCAGTAATTCTGAGGTGAGT TTT (SEQ ID NO: 180) & (SEQ ID NO: 557) |
| 54 | 1.27277339 | 1 | END_Control | GTTGTTATAACTATATCATGAGACTAAGTCGAAAAAAAAAAACAATAATTTCAGCTGTA T (SEQ ID NO: 181) & (SEQ ID NO: 559) |
| 55 | 1.25569056 | 1 | END_Control | TATATTAGAAACATGTCTGAAAAAAGTATCGATAAATGTATACGTTGATGTACATTGAT A (SEQ ID NO: 182) & (SEQ ID NO: 560) |
| 56 | 1.248202703 | 1 | END_Ctrl | GGTATTACCTTGATGGCCTTAAAGAAGATCGAGCCAGAGGGCCTCTGTTCATGTTTGG GC (SEQ ID NO: 183) & (SEQ ID NO: 551) |
| 57 | -1.55775411 | -1 | END_train | TCAAGAAAAAATAATAATAATTTTTTTTTTCGATTCCTGCTACACATTTTGGCAGAATACT (SEQ ID NO: 184) & (SEQ ID NO: 359) |
| 58 | 1.313347482 | 1 | STR_Ctrl | CATGGTTTATAATCCTTTTTATACATTGTCGACACTGTATTTTCACAGATCACTCTGGAG (SEQ ID NO: 185) & (SEQ ID NO: 403) |
| 59 | 1.288113063 | 1 | STR_Ctrl | AGAACTTCCTGATATATTTTTTTTTCTTTTCGAAGGTCTTAAAATGTTTTTAAACATGACC (SEQ ID NO: 186) & (SEQ ID NO: 404) |

TABLE 25.d-continued

| No. | FC 1 | LS | Loop detected | Probe sequence 60 mer |
|---|---|---|---|---|
| 60 | -1.351194069 | -1 | STR_train | GACTCTTAAAACAATAATATCAAACAACTCGACTTGTCATTTAGTTCTTTGGGAAGCAGT (SEQ ID NO: 187) & (SEQ ID NO: 405) |
| 61 | 1.442744064 | 1 | STR_Ctrl | AATTAGACAACGACTATATGACTCTGTCTCGACTTTAAAGCAAGTACTTCTTGTATGCTC (SEQ ID NO: 188) & (SEQ ID NO: 408) & (SEQ ID NO: 564) |
| 62 | -1.377760215 | -1 | STR_train | TCTTTGTTTCCTGTTTCCACTTCTTATTTCGATATTTATTGAGTGCTACTATATATATGC (SEQ ID NO: 189) & (SEQ ID NO: 460) |
| 63 | 1.322045866 | 1 | STR_Ctrl | TATGAATCCCTAAATGTCACACATCAAGTCGAATTATATAAGATACCCTGAAATTTAAG G (SEQ ID NO: 190) & (SEQ ID NO: 479) |
| 64 | 1.370669886 | 1 | END_Ctrl | ATGACTGTGGAAGGTTCTGATGTCTCTGTCGATGAAATGGAGAGAGGAGAAAGAAAA GAA (SEQ ID NO: 191) & (SEQ ID NO: 486) |
| 65 | 1.406251416 | 1 | END_Ctrl | ATGACTGTGGAAGGTTCTGATGTCTCTGTCGACATCATTTTTACAAATAAGACCAGATG T (SEQ ID NO: 192) & (SEQ ID NO: 489) |
| 66 | -1.345213388 | -1 | END_train | AATATTGCTACTGGAAAATCTGAATCTTTCGAAGAAAGCCCTTTGTAAGTTGTTTTCAAA (SEQ ID NO: 193) & (SEQ ID NO: 491) |
| 67 | 1.640080359 | 1 | STR_Ctrl | AACTATGTGACTTTTAGCTATACGAGTTTCGACTGGGTTCTAAATAGTTAATGTCATAGT (SEQ ID NO: 194) & (SEQ ID NO: 494) |
| 68 | 1.292902317 | 1 | STR_Ctrl | TAAAACTATTTTAAATGTTTTTAAAGTATCGATGTGTACTTTGACATCTGTGATGATGAT (SEQ ID NO: 195) & (SEQ ID NO: 500) |
| 69 | -1.342712154 | -1 | STR_train | TTATGGCTTAGAAGTAGAAAGTCATAAATCGATTCCTAAAAATTAATGAGGTGAATAGT A (SEQ ID NO: 196) & (SEQ ID NO: 518) |
| 70 | -1.29541483 | -1 | END_train | TTTCTATGAAGAATGTTCAAGATGCAATTCGAGCTACATACTATTATATATTTTCACAGT (SEQ ID NO: 197) & (SEQ ID NO: 525) |
| 71 | 1.283722998 | 1 | STR_Ctrl | CTCTATAAATTTACCAGAATATAAATTCTCGACTAAAAGTTCAGTTCTTCATTCCCACTA (SEQ ID NO: 198) & (SEQ ID NO: 537) |
| 72 | 1.307360568 | 1 | STR_Ctrl | ATCTTACAAAGAATAATTCTAAGAAAAGTCGAGCATTGGAGAAAATCTCCCTTTTCTTTT (SEQ ID NO: 199) & (SEQ ID NO: 541) |
| 73 | 1.285688803 | 1 | STR_Ctrl | TGTTTTTATTTTCATGTTTTAATTTTGTTCGAACTCTTGACCTCAGGTAAACCACCCACC (SEQ ID NO: 200) & (SEQ ID NO: 543) |
| 74 | 1.286186246 | 1 | STR_Ctrl | AGAACTGGTTATTGATCTATTCAGGGATTCGAAATAATAGATTATGAATAAATTATTCT G (SEQ ID NO: 201) & (SEQ ID NO: 544) |
| 75 | 1.294030342 | 1 | END_Ctrl | CTTTTTGAAGATTATAATCTATTAGTGATCGAGGCTTTTTTGCTTTTTTTTTTTTGAGAT (SEQ ID NO: 202) & (SEQ ID NO: 554) |
| 76 | 1.276203048 | 1 | END_Ctrl | CTATATGTAAGTTACAATATGTAAGGTATCGATAGTCACTGAGACTAATTTAATGTTAT A (SEQ ID NO: 203) & (SEQ ID NO: 555) |
| 77 | 1.270236955 | 1 | END_Ctrl | TGTAGGCAGATTACCTGAAGTTAGGAGTTCGATTAGGAATAACCTATCATTAGAGTTGT T (SEQ ID NO: 204) & (SEQ ID NO: 558) & (SEQ ID NO: 578) |

TABLE 25.e

| No. | | Probe Location | | | | 4 kb Sequence Location | | |
|---|---|---|---|---|---|---|---|---|
| | Chr | Start1 | End1 | Start2 | End2 | Chr | Start1 | End1 |
| 1 | 11 | 119249760 | 119249791 | 119299612 | 119299643 | 11 | 119249760 | 119253761 |
| 2 | 11 | 11968004 | 11968035 | 11984245 | 11984276 | 11 | 11964034 | 11968035 |
| 3 | 11 | 11968004 | 11968035 | 12048403 | 12048434 | 11 | 11964034 | 11968035 |
| 4 | 8 | 123527843 | 123527874 | 123555254 | 123555285 | 8 | 123523873 | 123527874 |
| 5 | 1 | 23070238 | 23070269 | 23096951 | 23096982 | 1 | 23066268 | 23070269 |
| 6 | 8 | 71216399 | 71216430 | 71261816 | 71261847 | 8 | 71216399 | 71220400 |
| 7 | 20 | 57527297 | 57527328 | 57579772 | 57579803 | 20 | 57527297 | 57531298 |
| 8 | 18 | 42072156 | 42072187 | 42094660 | 42094691 | 18 | 42068186 | 42072187 |
| 9 | 15 | 58053198 | 58053229 | 58157807 | 58157838 | 15 | 58053198 | 58057199 |
| 10 | 7 | 80544284 | 80544315 | 80679651 | 80679682 | 7 | 80540314 | 80544315 |
| 11 | 11 | 11968004 | 11968035 | 12019427 | 12019458 | 11 | 11964034 | 11968035 |
| 12 | 3 | 190498271 | 190498302 | 190560851 | 190560882 | 3 | 190494301 | 190498302 |
| 13 | 1 | 24920810 | 24920841 | 24976006 | 24976037 | 1 | 24920810 | 24924811 |
| 14 | 22 | 46102580 | 46102611 | 46241078 | 46241109 | 22 | 46098610 | 46102611 |

TABLE 25.e-continued

| No. | | Probe Location | | | | | 4 kb Sequence Location | |
| --- | --- | --- | --- | --- | --- | --- | --- | --- |
| | Chr | Start1 | End1 | Start2 | End2 | Chr | Start1 | End1 |
| 15 | 7 | 96214493 | 96214524 | 96301998 | 96302029 | 7 | 96210523 | 96214524 |
| 16 | 20 | 57527297 | 57527328 | 57551578 | 57551609 | 20 | 57527297 | 57531298 |
| 17 | 2 | 210291701 | 210291732 | 210362262 | 210362293 | 2 | 210287731 | 210291732 |
| 18 | 7 | 7114800 | 7114831 | 7260637 | 7260668 | 7 | 7110830 | 7114831 |
| 19 | 4 | 109024771 | 109024802 | 109090838 | 109090869 | 4 | 109024771 | 109028772 |
| 20 | 9 | 134738485 | 134738516 | 134811418 | 134811449 | 9 | 134738485 | 134742486 |
| 21 | 13 | 59818047 | 59818078 | 59854837 | 59854868 | 13 | 59818047 | 59822048 |
| 22 | 3 | 13512352 | 13512383 | 13590312 | 13590343 | 3 | 13512352 | 13516353 |
| 23 | 13 | 94133177 | 94133208 | 94304194 | 94304225 | 13 | 94129207 | 94133208 |
| 24 | 9 | 121180379 | 121180410 | 121268506 | 121268537 | 9 | 121176409 | 121180410 |
| 25 | 9 | 121232597 | 121232628 | 121268506 | 121268537 | 9 | 121228627 | 121232628 |
| 26 | 9 | 121243316 | 121243347 | 121268506 | 121268537 | 9 | 121239346 | 121243347 |
| 27 | 1 | 32214585 | 32214616 | 32241108 | 32241139 | 1 | 32214585 | 32218586 |
| 28 | 1 | 87318639 | 87318670 | 87349909 | 87349940 | 1 | 87314669 | 87318670 |
| 29 | 4 | 86581455 | 86581486 | 86621909 | 86621940 | 4 | 86577485 | 86581486 |
| 30 | 3 | 152234755 | 152234786 | 152281057 | 152281088 | 3 | 152230785 | 152234786 |
| 31 | 11 | 113028505 | 113028536 | 113163748 | 113163779 | 11 | 113024535 | 113028536 |
| 32 | 20 | 57527297 | 57527328 | 57570220 | 57570251 | 20 | 57527297 | 57531298 |
| 33 | X | 24447919 | 24447950 | 24480152 | 24480183 | X | 24443949 | 24447950 |
| 34 | X | 24447919 | 24447950 | 24490440 | 24490471 | X | 24443949 | 24447950 |
| 35 | 1 | 198595771 | 198595802 | 198666125 | 198666156 | 1 | 198595771 | 198599772 |
| 36 | 1 | 198666125 | 198666156 | 198724547 | 198724578 | 1 | 198662155 | 198666156 |
| 37 | 19 | 38410632 | 38410663 | 38495982 | 38496013 | 19 | 38410632 | 38414633 |
| 38 | 2 | 88146264 | 88146295 | 88161717 | 88161748 | 2 | 88142294 | 88146295 |
| 39 | 15 | 70715123 | 70715154 | 70784637 | 70784668 | 15 | 70715123 | 70719124 |
| 40 | 10 | 31275600 | 31275631 | 31524411 | 31524442 | 10 | 31271630 | 31275631 |
| 41 | 16 | 73153212 | 73153243 | 73184554 | 73184585 | 16 | 73149242 | 73153243 |
| 42 | 8 | 37965238 | 37965269 | 37987735 | 37987766 | 8 | 37961268 | 37965269 |
| 43 | 1 | 230724515 | 230724546 | 230757302 | 230757333 | 1 | 230724515 | 230728516 |
| 44 | 13 | 46860092 | 46860123 | 46907784 | 46907815 | 13 | 46860092 | 46864093 |
| 45 | 2 | 38993608 | 38993639 | 39065997 | 39066028 | 2 | 38989638 | 38993639 |
| 46 | 1 | 180431719 | 180431750 | 180541491 | 180541522 | 1 | 180431719 | 180435720 |
| 47 | 17 | 10502067 | 10502098 | 10534900 | 10534931 | 17 | 10502067 | 10506068 |
| 48 | 11 | 17689456 | 17689487 | 17729653 | 17729684 | 11 | 17685486 | 17689487 |
| 49 | 3 | 111034173 | 111034204 | 111209684 | 111209715 | 3 | 111030203 | 111034204 |
| 50 | 12 | 109146008 | 109146039 | 109236052 | 109236083 | 12 | 109146008 | 109150009 |
| 51 | 12 | 109236052 | 109236083 | 109268078 | 109268109 | 12 | 109236052 | 109240053 |
| 52 | 15 | 98652565 | 98652596 | 98737003 | 98737034 | 15 | 98652565 | 98656566 |
| 53 | 17 | 38348745 | 38348776 | 38360864 | 38360895 | 17 | 38344775 | 38348776 |
| 54 | 17 | 55035186 | 55035217 | 55117598 | 55117629 | 17 | 55035186 | 55039187 |
| 55 | 9 | 110405938 | 110405969 | 110509727 | 110509758 | 9 | 110401968 | 110405969 |
| 56 | 4 | 100636305 | 100636336 | 100744427 | 100744458 | 4 | 100636305 | 100640306 |
| 57 | 12 | 109146008 | 109146039 | 109185066 | 109185097 | 12 | 109146008 | 109150009 |
| 58 | 13 | 40524349 | 40524380 | 40688580 | 40688611 | 13 | 40524349 | 40528350 |
| 59 | 6 | 108604405 | 108604436 | 108629992 | 108630023 | 6 | 108600435 | 108604436 |
| 60 | 16 | 53844989 | 53845020 | 54052288 | 54052319 | 16 | 53844989 | 53848990 |
| 61 | 13 | 94054831 | 94054862 | 94133177 | 94133208 | 13 | 94054831 | 94058832 |
| 62 | 4 | 101055418 | 101055449 | 101247819 | 101247850 | 4 | 101055418 | 101059419 |
| 63 | 18 | 48917335 | 48917366 | 48974547 | 48974578 | 18 | 48917335 | 48921336 |
| 64 | 9 | 90816328 | 90816359 | 90832284 | 90832315 | 9 | 90816328 | 90820329 |
| 65 | 9 | 90816328 | 90816359 | 90872966 | 90872997 | 9 | 90816328 | 90820329 |
| 66 | 1 | 218325556 | 218325587 | 218386401 | 218386432 | 1 | 218321586 | 218325587 |
| 67 | 3 | 30566144 | 30566175 | 30694718 | 30694749 | 3 | 30566144 | 30570145 |
| 68 | 4 | 153659613 | 153659644 | 153700318 | 153700349 | 4 | 153659613 | 153663614 |
| 69 | 9 | 110499547 | 110499578 | 110527410 | 110527441 | 9 | 110495577 | 110499578 |
| 70 | 8 | 65658401 | 65658432 | 65782504 | 65782535 | 8 | 65658401 | 65662402 |
| 71 | 9 | 121188989 | 121189020 | 121328400 | 121328431 | 9 | 121185019 | 121189020 |
| 72 | 9 | 110652628 | 110652659 | 110747866 | 110747897 | 9 | 110648658 | 110652659 |
| 73 | 22 | 46134676 | 46134707 | 46231440 | 46231471 | 22 | 46130706 | 46134707 |
| 74 | 7 | 94903925 | 94903956 | 94966987 | 94967018 | 7 | 94903925 | 94907926 |
| 75 | 3 | 111638286 | 111638317 | 111672672 | 111672703 | 3 | 111634316 | 111638317 |
| 76 | 8 | 14642477 | 14642508 | 14785460 | 14785491 | 8 | 14638507 | 14642508 |
| 77 | 7 | 88199682 | 88199713 | 88237070 | 88237101 | 7 | 88199682 | 88203683 |

Table 25.f

| | 4 kb Sequence Location | | | |
| --- | --- | --- | --- | --- |
| No. | Start2 | End2 | PCR-Primer1_ID | PCR_Primer1 |
| 1 | 119295642 | 119299643 | OBD142_029 | ACTGAAGGTTCCCAAGTTCCCGAGAG (SEQ ID NO: 205) & (SEQ ID NO: 625) |

Table 25.f-continued

| | 4 kb Sequence Location | | | |
|---|---|---|---|---|
| No. | Start2 | End2 | PCR-Primer1_ID | PCR_Primer1 |
| 2 | 11984245 | 11988246 | OBD142_061 | GCTCCACATTTCCCAATCTAACCTGC (SEQ ID NO: 206) & (SEQ ID NO: 580) & (SEQ ID NO: 624) & (SEQ ID NO: 1597) |
| 3 | 12048403 | 12052404 | OBD142_069 | GTCCCTCTGCCCTCTCTTATTGGC (SEQ ID NO: 207) |
| 4 | 123555254 | 123559255 | OBD142_089 | AATCTCTGTCCCCAACTGTATCTGGC (SEQ ID NO: 208) & (SEQ ID NO: 581) & (SEQ ID NO: 1598) |
| 5 | 23096951 | 23100952 | OBD142_137 | CCCAGTCTCAGGCTTTGTCACTC (SEQ ID NO: 209) |
| 6 | 71261816 | 71265817 | OBD142_081 | GGCAAGTTTCCTGACCTCTCTGACAT (SEQ ID NO: 210) & (SEQ ID NO: 626) |
| 7 | 57579772 | 57583773 | OBD142_189 | TTCTCCCTCGGACGCTCATCCTC (SEQ ID NO: 211) & (SEQ ID NO: 587) & (SEQ ID NO: 1604) |
| 8 | 42090690 | 42094691 | OBD142_213 | CTGGAACTTGTTTAGGCACTGAAGCA (SEQ ID NO: 212) & (SEQ ID NO: 588) & (SEQ ID NO: 1605) |
| 9 | 58157807 | 58161808 | OBD142_017 | GCTGTCATTTTCAGTGATAGGCACAC (SEQ ID NO: 213) |
| 10 | 80679651 | 80683652 | OBD142_037 | GCTGGTTTCCTGAGAAGGTAACTC (SEQ ID NO: 214) |
| 11 | 12015457 | 12019458 | OBD142_065 | TTCTTGCCCTGTCCCTCTGCCCT (SEQ ID NO: 215) |
| 12 | 190560851 | 190564852 | OBD142_133 | AGATGCTGGCAGTCTCCCTCTTGAG (SEQ ID NO: 216) |
| 13 | 24972036 | 24976037 | OBD142_253 | CTGAAATCCCATAGTGAGATGCCTTC (SEQ ID NO: 217) & (SEQ ID NO: 591) & (SEQ ID NO: 1608) |
| 14 | 46241078 | 46245079 | OBD142_353 | GCCCTTCTCCAAAAACACCTCAC (SEQ ID NO: 218) |
| 15 | 96298028 | 96302029 | OBD142_477 | CAGGCGGATCATTTCAGGTC (SEQ ID NO: 219) & (SEQ ID NO: 221) |
| 16 | 57551578 | 57555579 | OBD142_181 | TCATCCTCCTCCACACCCGCCTA (SEQ ID NO: 220) & (SEQ ID NO: 236) |
| 17 | 210358292 | 210362293 | OBD142_397 | CAGGCGGATCATTTCAGGTC (SEQ ID NO: 219) & (SEQ ID NO: 221) |
| 18 | 7256667 | 7260668 | OBD142_025 | CACCTCAAAAGACAACCCCAGACCCA (SEQ ID NO: 222) & (SEQ ID NO: 579) & (SEQ ID NO: 1596) |
| 19 | 109090838 | 109094839 | OBD142_041 | CTGCCCCTTTCTTTATTCCTACTTCC (SEQ ID NO: 223) |
| 20 | 134811418 | 134815419 | OBD142_045 | ACCCCACCAAGAGCACCTTCTGC (SEQ ID NO: 224) |
| 21 | 59854837 | 59858838 | OBD142_057 | CAGTCTCTGTGGCAACTCTCGTG (SEQ ID NO: 225) |
| 22 | 13586342 | 13590343 | OBD142_085 | CCCCATCGCTGCTGGAAACCATT (SEQ ID NO: 226) |
| 23 | 94300224 | 94304225 | OBD142_113 | GAGTATTTACGATGGTCAGGTGCTGC (SEQ ID NO: 227) & (SEQ ID NO: 265) & (SEQ ID NO: 582) & (SEQ ID NO: 1599) |
| 24 | 121268506 | 121272507 | OBD142_117 | GACCTGTGGTTCTGACTGTCCAG (SEQ ID NO: 228) & (SEQ ID NO: 583) & (SEQ ID NO: 1600) |

Table 25.f-continued

| | 4 kb Sequence Location | | | |
|---|---|---|---|---|
| No. | Start2 | End2 | PCR-Primer1_ID | PCR_Primer1 |
| 25 | 121268506 | 121272507 | OBD142_121 | GGGCTGGTTAGTCAGTTATCCCTTTT (SEQ ID NO: 229) |
| 26 | 121268506 | 121272507 | OBD142_125 | CCACTTCCCTGCCTTTTCTGGCT (SEQ ID NO: 230) |
| 27 | 32237138 | 32241139 | OBD142_141 | GCGGAGCCTCTTTGAACAGAAGC (SEQ ID NO: 231) |
| 28 | 87345939 | 87349940 | OBD142_145 | GCAACCTGGTCTCCTACCTGCTTCTA (SEQ ID NO: 232) & (SEQ ID NO: 584) & (SEQ ID NO: 1601) |
| 29 | 86617939 | 86621940 | OBD142_153 | TAGCAGACAATCAGAGGGTTTTGC (SEQ ID NO: 233) & (SEQ ID NO: 585) & (SEQ ID NO: 1602) |
| 30 | 152281057 | 152285058 | OBD142_157 | GCTGGTAGTTGGCTTTTGGGAAGAAC (SEQ ID NO: 234) & (SEQ ID NO: 586) & (SEQ ID NO: 1603) |
| 31 | 113163748 | 113167749 | OBD142_165 | CAGGAGGTGTGGATTTGACTCATACT (SEQ ID NO: 235) |
| 32 | 57570220 | 57574221 | OBD142_185 | TCATCCTCCTCCACACCCGCCTA (SEQ ID NO: 220) & (SEQ ID NO: 236) |
| 33 | 24480152 | 24484153 | OBD142_197 | GGGAGTAGGGAGCAGAACCAGGA (SEQ ID NO: 237) |
| 34 | 24490440 | 24494441 | OBD142_201 | CAACAAGGAGGGAGTGACCACAAGAT (SEQ ID NO: 238) |
| 35 | 198662155 | 198666156 | OBD142_233 | GCAAAGGGCAGGTCATCATCATTCAA (SEQ ID NO: 239) & (SEQ ID NO: 589) & (SEQ ID NO: 628) & (SEQ ID NO: 1606) |
| 36 | 198720577 | 198724578 | OBD142_241 | AAGACATAGGCACTTTGAGAGGC (SEQ ID NO: 240) |
| 37 | 38495982 | 38499983 | OBD142_257 | GGACAGATTTGGAGACCCATAGAAAG (SEQ ID NO: 241) |
| 38 | 88161717 | 88165718 | OBD142_297 | GTAACACAGGTAGGAAGGAGTGGAGC (SEQ ID NO: 242) & (SEQ ID NO: 622) |
| 39 | 70780667 | 70784668 | OBD142_309 | GTGAGGAAGGTGTAGAAGAACAGACT (SEQ ID NO: 243) |
| 40 | 31520441 | 31524442 | OBD142_321 | CTTGTCGTAGAGGATGCTCAGGC (SEQ ID NO: 244) |
| 41 | 73180584 | 73184585 | OBD142_325 | CCTGGATGTTCATTCCCACCTGG (SEQ ID NO: 245) & (SEQ ID NO: 592) & (SEQ ID NO: 1609) |
| 42 | 37987735 | 37991736 | OBD142_329 | TACTCCTCGTTCCCTTTTCTCTC (SEQ ID NO: 246) & (SEQ ID NO: 623) |
| 43 | 230753332 | 230757333 | OBD142_337 | GCAGATTCCACAGGGCTTAC (SEQ ID NO: 247) & (SEQ ID NO: 593) & (SEQ ID NO: 1610) |
| 44 | 46903814 | 46907815 | OBD142_349 | TTTGTCATGTTGTCCAGGCTG (SEQ ID NO: 248) |
| 45 | 39062027 | 39066028 | OBD142_357 | GCTGGTCTCAAAGTCCTGGC (SEQ ID NO: 249) |
| 46 | 180541491 | 180545492 | OBD142_373 | GCTGGTCTCAAACTCCTGGC (SEQ ID NO: 250) |
| 47 | 10530930 | 10534931 | OBD142_393 | AGTATTTGAGGCTGGGCATG (SEQ ID NO: 251) |

Table 25.f-continued

| | 4 kb Sequence Location | | | |
|---|---|---|---|---|
| No. | Start2 | End2 | PCR-Primer1_ID | PCR_Primer1 |
| 48 | 17729653 | 17733654 | OBD142_401 | TTCTTTGTCTCCCCTCTCTACTCCT (SEQ ID NO: 252) |
| 49 | 111209684 | 111213685 | OBD142_405 | ACAGGAAATCCAGTATCTTGGGGAAA (SEQ ID NO: 253) |
| 50 | 109236052 | 109240053 | OBD142_413 | ACGGTTAGAAGATTTGCCAGAGGAT (SEQ ID NO: 254) |
| 51 | 109268078 | 109272079 | OBD142_417 | GAATATCAAAGATGCCAGGGAGCTG (SEQ ID NO: 255) & (SEQ ID NO: 331) |
| 52 | 98733033 | 98737034 | OBD142_445 | GACGTTTCACCATGTTGCCC (SEQ ID NO: 256) |
| 53 | 38360864 | 38364865 | OBD142_509 | GAATGAAACTCTGAGGCCGG (SEQ ID NO: 257) & (SEQ ID NO: 596) & (SEQ ID NO: 1613) |
| 54 | 55117598 | 55121599 | OBD142_517 | TGTGTTATCAGGATAAGATTCCAGGT (SEQ ID NO: 258) |
| 55 | 110505757 | 110509758 | OBD142_521 | AGGATCTTGCTGTTTGTTTCACG (SEQ ID NO: 259) |
| 56 | 100744427 | 100748428 | OBD142_005 | CCCTAAACCCAGTAATCCTGTGCTTC (SEQ ID NO: 260) |
| 57 | 109185066 | 109189067 | OBD142_009 | GCAGAAACAGGACCTCAAACGGTTAG (SEQ ID NO: 261) |
| 58 | 40688580 | 40692581 | OBD142_093 | AGTTTCTCTCTGTTCCCAGTTTGCTG (SEQ ID NO: 262) |
| 59 | 108629992 | 108633993 | OBD142_097 | GTTCCTTTGCCCTCTTCAGTGGC (SEQ ID NO: 263) |
| 60 | 54048318 | 54052319 | OBD142_101 | TAGCATCCTGCCTTGACTGAGGGTGA (SEQ ID NO: 264) |
| 61 | 94129207 | 94133208 | OBD142_109 | GAGTATTTACGATGGTCAGGTGCTGC (SEQ ID NO: 227) & (SEQ ID NO: 265) & (SEQ ID NO: 582) & (SEQ ID NO: 1599) |
| 62 | 101247819 | 101251820 | OBD142_225 | GGCTCACACAGGCTTCTGGATAGGAA (SEQ ID NO: 266) |
| 63 | 48970577 | 48974578 | OBD142_261 | ATTACTCAGCCCCTCGGAGCCAT (SEQ ID NO: 267) |
| 64 | 90832284 | 90836285 | OBD142_265 | GACTCAGGGCTGGCAGTGAACGA (SEQ ID NO: 268) & (SEQ ID NO: 269) |
| 65 | 90872966 | 90876967 | OBD142_273 | GACTCAGGGCTGGCAGTGAACGA (SEQ ID NO: 268) & (SEQ ID NO: 269) |
| 66 | 218386401 | 218390402 | OBD142_277 | TTATGGAGAACATCCTCAGTGTCCTG (SEQ ID NO: 270) |
| 67 | 30694718 | 30698719 | OBD142_285 | CAAGAACTGACCCCAAGTCCCTG (SEQ ID NO: 271) |
| 68 | 153696348 | 153700349 | OBD142_313 | GGCAGCCACTTCATCCATCCAGAATC (SEQ ID NO: 272) |
| 69 | 110527410 | 110531411 | OBD142_361 | TGTGTTCCCACAAATTGGAAATGCC (SEQ ID NO: 273) |
| 70 | 65778534 | 65782535 | OBD142_389 | CCATGCTGGCATTCATCTATTTGGT (SEQ ID NO: 274) |
| 71 | 121324430 | 121328431 | OBD142_433 | TAGAAGTCACTCACTCCCATCCTCT (SEQ ID NO: 275) |

Table 25.f-continued

| | 4 kb Sequence Location | | | |
|---|---|---|---|---|
| No. | Start2 | End2 | PCR-Primer1_ID | PCR_Primer1 |
| 72 | 110747866 | 110751867 | OBD142_449 | ACAGTCAGTGATTGGCACAGAGTAA (SEQ ID NO: 276) & (SEQ ID NO: 595) & (SEQ ID NO: 1612) |
| 73 | 46231440 | 46235441 | OBD142_457 | ACACTTTAGACAGAGTGACAGGGTC (SEQ ID NO: 277) |
| 74 | 94963017 | 94967018 | OBD142_461 | AGGAATGGTTACTGCTCCTCTTTGT (SEQ ID NO: 278) & (SEQ ID NO: 627) |
| 75 | 111672672 | 111676673 | OBD142_497 | AGTCCCCACAACTGCCAATG (SEQ ID NO: 279) |
| 76 | 14781490 | 14785491 | OBD142_501 | AGTCTAAGAGATGGTCACACCCATT (SEQ ID NO: 280) |
| 77 | 88233100 | 88237101 | OBD142_513 | GTTTGGGAGGCCAATGTAGG (SEQ ID NO: 281) |

TABLE 25.g

| No. | PCR-Primer2_ID | PCR_Primer2 | GLMNET | Marker |
|---|---|---|---|---|
| 1 | OBD142_031 | TTAGTCTGTATGGTAGTGTGTGCCTG (SEQ ID NO: 282) & (SEQ ID NO: 632) | 0.027324192 | OBD142_029.031_1x |
| 2 | OBD142_063 | GTCAGAGTTGCCGATAGGTCTTGCTA (SEQ ID NO: 283) & (SEQ ID NO: 598) & (SEQ ID NO: 631) & (SEQ ID NO: 1615) | 0.066643802 | OBD142_061.063_1.8x |
| 3 | OBD142_071 | GGTGGGTCTGACTGCCTTTCTCA (SEQ ID NO: 284) | -0.093076823 | OBD142_069.071_1.2x |
| 4 | OBD142_091 | ACATCTATCTTGCCCCTCACTCAGGT (SEQ ID NO: 285) & (SEQ ID NO: 599) & (SEQ ID NO: 1616) | 0.004873633 | OBD142_089.091_1x |
| 5 | OBD142_139 | GCCTGAGGGAGCAAGTTCAACCC (SEQ ID NO: 286) | -0.019817526 | OBD142_137.139_1.2x |
| 6 | OBD142_083 | GAAGGAGGGAGGTAGGAGAGTCATTA (SEQ ID NO: 287) & (SEQ ID NO: 633) | 0.030332059 | OBD142_081.083_1.4x |
| 7 | OBD142_191 | GAGGAGGAGAAACTCAGAAGCCC (SEQ ID NO: 288) & (SEQ ID NO: 605) & (SEQ ID NO: 1622) | 0.03066036 | OBD142_189.191_1x |
| 8 | OBD142_215 | GCACAAGACCTCACATTCTGATGGGC (SEQ ID NO: 289) & (SEQ ID NO: 606) & (SEQ ID NO: 1623) | 0.006242977 | OBD142_213.215_1.4x |
| 9 | OBD142_019 | CAAAGAGAAAGGGCTGAGGATGAAGC (SEQ ID NO: 290) | 0.017005669 | OBD142_017.019_1.2x |
| 10 | OBD142_039 | CCCCTCATCTCAGTATGTTTATGTCC (SEQ ID NO: 291) | 0.014942824 | OBD142_037.039_1x |
| 11 | OBD142_067 | GCCTGGCAAGGAGTAAGCATTCG (SEQ ID NO: 292) | 0.067763605 | OBD142_065.067_1x |
| 12 | OBD142_135 | ATGCTCCCTCCCTTATCTTTTGGTA (SEQ ID NO: 293) | 0.006222197 | OBD142_133.135_1x |
| 13 | OBD142_255 | CCCCAAACTCCCAGACACATCAGAGA (SEQ ID NO: 294) & (SEQ ID NO: 609) & (SEQ ID NO: 1626) | 0.066746082 | OBD142_253.255_1.2x |
| 14 | OBD142_355 | TGCTGTCAAAATGGTGCCTGAAAAT (SEQ ID NO: 295) | -0.026372512 | OBD142_353.355_1x |
| 15 | OBD142_479 | CTTACTGCAGCCTCACACTC (SEQ ID NO: 296) & (SEQ ID NO: 298) | 0.015126312 | OBD142_477.479_1x |

TABLE 25.g-continued

| No. | PCR-Primer2_ID | PCR_Primer2 | GLMNET | Marker |
|---|---|---|---|---|
| 16 | OBD142_183 | GACAGTAAACACACCCACTCCCC (SEQ ID NO: 297) | 0.04064456 | OBD142_181.183_1.4x |
| 17 | OBD142_399 | CTTACTGCAGCCTCACACTC (SEQ ID NO: 296) & (SEQ ID NO: 298) | 0.006805912 | OBD142_397.399_1x |
| 18 | OBD142_027 | CCCTCACTTTCCTTCTACTCTTCAAG (SEQ ID NO: 299) & (SEQ ID NO: 597) & (SEQ ID NO: 1614) | 0.000572834 | OBD142_025.027_1/2X |
| 19 | OBD142_043 | TGTTCCCTTTGTTCAACCCAGGCTAT (SEQ ID NO: 300) | 0.003754206 | OBD142_041.043_1/2X |
| 20 | OBD142_047 | ATGGGTGAGGATGCTGGCAATGC (SEQ ID NO: 301) | 0.002011981 | OBD142_045.047_1/2X |
| 21 | OBD142_059 | CCTGAATCTGCTGTGGCTTGGGC (SEQ ID NO: 302) | -0.003337259 | OBD142_057.059_1/4X |
| 22 | OBD142_087 | CCAGTAGGAGGGAAGACACGGTC (SEQ ID NO: 303) | 0.007164008 | OBD142_085.087_1/4X |
| 23 | OBD142_115 | GATTTAGGCACTACGGAGAAAAGGGC (SEQ ID NO: 304) | -0.005249258 | OBD142_113.115_1/2X |
| 24 | OBD142_119 | TATCGTCCAGGAGGCAAGGGTCC (SEQ ID NO: 305) & (SEQ ID NO: 307) & (SEQ ID NO: 601) & (SEQ ID NO: 1618) | -0.001120031 | OBD142_117.119_1/2X |
| 25 | OBD142_123 | AGAGGAGAGCAGGCACAGGTATCGT (SEQ ID NO: 306) | 0.003244236 | OBD142_121.123_1/8X |
| 26 | OBD142_127 | TATCGTCCAGGAGGCAAGGGTCC (SEQ ID NO: 305) & (SEQ ID NO: 307) & (SEQ ID NO: 601) & (SEQ ID NO: 1618) | -0.007783392 | OBD142_125.127_1/2X |
| 27 | OBD142_143 | GCCTCTTCCCACCAGCCTGACTT (SEQ ID NO: 308) | -0.005778408 | OBD142_141.143_1/4X |
| 28 | OBD142_147 | GATGAGGTAACCAAAGTTCAGGGAGA (SEQ ID NO: 309) & (SEQ ID NO: 602) & (SEQ ID NO: 1619) | -0.005269663 | OBD142_145.147_1/2X |
| 29 | OBD142_155 | CTCTCTCCTCATCCTCCCTCCTAATA (SEQ ID NO: 310) & (SEQ ID NO: 603) & (SEQ ID NO: 1620) | 0.003978216 | OBD142_153.155_1/2X |
| 30 | OBD142_159 | GGGAGCCAGAAAGATAGCAATGCCTA (SEQ ID NO: 311) & (SEQ ID NO: 604) & (SEQ ID NO: 1621) | -0.003656603 | OBD142_157.159_1/4X |
| 31 | OBD142_167 | TCACTCCCTCTCTTCTCCCCTTCACT (SEQ ID NO: 312) | -0.005244916 | OBD142_165.167_1X |
| 32 | OBD142_187 | CTCTGTGGCATCCCTAAATCCCG (SEQ ID NO: 313) | -0.005243145 | OBD142_185.187_1/4X |
| 33 | OBD142_199 | ACTCCTCAAGCCCAGACAATGGC (SEQ ID NO: 314) | -0.000856647 | OBD142_197.199_1/4X |
| 34 | OBD142_203 | GTCAGTTCAGGTCTGGTTTTGCCACA (SEQ ID NO: 315) | -0.005241372 | OBD142_201.203_1/4X |
| 35 | OBD142_235 | CTCTCCTTTATCCCTACCCTGCTCA (SEQ ID NO: 316) & (SEQ ID NO: 607) & (SEQ ID NO: 635) & (SEQ ID NO: 1624) | -0.003634106 | OBD142_233.235_1/2X |
| 36 | OBD142_243 | GGGACCCTTTCTTCTTGCTCTGAT (SEQ ID NO: 317) | -0.002467172 | OBD142_241.243_1X |
| 37 | OBD142_259 | CATTCTTGACCCTCTCACTCTGTGCC (SEQ ID NO: 318) | -0.009961655 | OBD142_257.259_1/2X |
| 38 | OBD142_299 | CACCATAAAATAGGGCAAGGTCAGCA (SEQ ID NO: 319) & (SEQ ID NO: 629) | 0.004963311 | OBD142_297.299_1/2X |

TABLE 25.g-continued

| No. | PCR-Primer2_ID | PCR_Primer2 | GLMNET | Marker |
|---|---|---|---|---|
| 39 | OBD142_311 | GGATAGAAGGCACAGTGACCCTCCT (SEQ ID NO: 320) | 0.002101178 | OBD142_309.311_1/2X |
| 40 | OBD142_323 | GGCACGCAATCTCAATCTCGGCTC (SEQ ID NO: 321) | -0.005202079 | OBD142_321.323_1X |
| 41 | OBD142_327 | AGAGGGAAAGGCAGGTCGTGAGC (SEQ ID NO: 322) & (SEQ ID NO: 610) & (SEQ ID NO: 1627) | -0.003264119 | OBD142_325.327_1/4 |
| 42 | OBD142_331 | TGTGTGCTAGGCTGATATGGTTTG (SEQ ID NO: 323) & (SEQ ID NO: 630) | 0.001018411 | OBD142_329.331_1X |
| 43 | OBD142_339 | AGTCTAAAGCCCATGTGAGCC (SEQ ID NO: 324) | -0.000807541 | OBD142_337.339_1X |
| 44 | OBD142_351 | CTCAGCACCAGAACTAGGGC (SEQ ID NO: 325) | -0.005203446 | OBD142_349.351_1X |
| 45 | OBD142_359 | GCTCTAGGTGCTGATGATTCAAC (SEQ ID NO: 326) | -0.003795912 | OBD142_357.359_1/4X |
| 46 | OBD142_375 | GGTCCCCACATTACATTTTGGC (SEQ ID NO: 327) | -0.006643376 | OBD142_373.375_1X |
| 47 | OBD142_395 | AGGGTGTTCTAAGAAGGCAGC (SEQ ID NO: 328) | -0.006900338 | OBD142_393.395_1/2X |
| 48 | OBD142_403 | TTTTTATTAACTGCACGGCACACCT (SEQ ID NO: 329) | -0.001296151 | OBD142_401.403_1X |
| 49 | OBD142_407 | ACTAAGAATGGATGGGGCCAATTAT (SEQ ID NO: 330) | -0.00075487 | OBD142_405.407_1X |
| 50 | OBD142_415 | GAATATCAAAGATGCCAGGGAGCTG (SEQ ID NO: 255) & (SEQ ID NO: 331) | -0.005201838 | OBD142_413.415_1/2X |
| 51 | OBD142_419 | CTGCACATTTCCTAGTAGGCTCTCT (SEQ ID NO: 332) | -0.000282666 | OBD142_417.419_1X |
| 52 | OBD142_447 | GTCACTCCCCATTCCATCCG (SEQ ID NO: 333) | 0.001436473 | OBD142_445.447_1/2X |
| 53 | OBD142_511 | CCCATTCGTCTCTCTGAGCTG (SEQ ID NO: 334) & (SEQ ID NO: 614) & (SEQ ID NO: 1631) | -0.001530558 | OBD142_509.511_1/8X |
| 54 | OBD142_519 | TTGGTGAAAGGAAGGGAGTAGAAGT (SEQ ID NO: 335) | 0.005722578 | OBD142_517.519_1X, 1/2X |
| 55 | OBD142_523 | TGCCATCACACCCATGCATG (SEQ ID NO: 336) | -0.005188075 | OBD142_521.523_1/4X |
| 56 | OBD142_007 | ATTGCTGTGGAGGGAATGGTGTGC (SEQ ID NO: 337) | -0.003614434 | OBD142_005.007_1X |
| 57 | OBD142_011 | TTTTGTAAAGGGCACCCGAAGGG (SEQ ID NO: 338) | 0.00909588 | OBD142_009.011_1/4X |
| 58 | OBD142_095 | AGCATCACCTTCGTATCTTCCCCAAG (SEQ ID NO: 339) | -0.002626343 | OBD142_093.095_1X |
| 59 | OBD142_099 | GCCTGCTCTTCCCTGTTTCTGCC (SEQ ID NO: 340) | 0.003599622 | OBD142_097.099_1/8X |
| 60 | OBD142_103 | AAACAAAGCCTCACAAACTCCACAGC (SEQ ID NO: 341) | -0.005544516 | OBD142_101.103_1X |
| 61 | OBD142_111 | ATCCAAACACAGGACGAGAATAAAGC (SEQ ID NO: 342) & (SEQ ID NO: 600) & (SEQ ID NO: 1617) | -0.010787892 | OBD142_109.111_1/2X |
| 62 | OBD142_227 | TTTTGTCCCTCTTCAGGCAGTGC (SEQ ID NO: 343) | -0.004657708 | OBD142_225.227_1/2X |
| 63 | OBD142_263 | GCAGAGGAGGTGGGACTTTCAGC (SEQ ID NO: 344) | -0.003808119 | OBD142_261.263_1/X |

TABLE 25.g-continued

| No. | PCR-Primer2_ID | PCR_Primer2 | GLMNET | Marker |
|---|---|---|---|---|
| 64 | OBD142_267 | CTGCCTCACCCTGGCTTCTTTCA (SEQ ID NO: 345) | 0.005232196 | OBD142_265.267_1/4X |
| 65 | OBD142_275 | CCGCCACTCAGCCATTGTTTCCA (SEQ ID NO: 346) | −0.003175937 | OBD142_273.275_1/4X |
| 66 | OBD142_279 | GCTACACAAAGAGACTTCCAGTGATT (SEQ ID NO: 347) | 0.00931825 | OBD142_277.279_1/2X |
| 67 | OBD142_287 | GGTGGAGGCGAGGGATACTGCTA (SEQ ID NO: 348) | −0.004573651 | OBD142_285.287_1/4X |
| 68 | OBD142_315 | GCAAATGCTTAGGACCCAAACCCTTT (SEQ ID NO: 349) | 0.004668104 | OBD142_313.315_1X |
| 69 | OBD142_363 | CACTTGCACCCCTAAAGCTATTGAAA (SEQ ID NO: 350) | −0.006335271 | OBD142_361.363_1/2X |
| 70 | OBD142_391 | AATTTTGGTTGGCAGCTGGTAGAAG (SEQ ID NO: 351) | 0.008864459 | OBD142_389.391_1X |
| 71 | OBD142_435 | CTTGAAATGCGACCAGTGGGAATTA (SEQ ID NO: 352) | −0.002735702 | OBD142_433.435_1X |
| 72 | OBD142_451 | AGGAAATAGCCCAAATGCAACTGAA (SEQ ID NO: 353) & (SEQ ID NO: 613) & (SEQ ID NO: 1630) | −0.004744695 | OBD142_449.451_1X |
| 73 | OBD142_459 | CTCAACTTCAAAATCGGTTGGGGAA (SEQ ID NO: 354) | −0.006822261 | OBD142_457.459_1X |
| 74 | OBD142_463 | TTTCTGTCTGCAAATCCTCCACCTA (SEQ ID NO: 355) | −0.002268338 | OBD142_461.463_1/4X |
| 75 | OBD142_499 | CGAGAAGGGTGGCTCATGAG (SEQ ID NO: 356) | −0.00572004 | OBD142_497.499_1/2X |
| 76 | OBD142_503 | ATGGAAACCCAAGTTTGCAAGGAA (SEQ ID NO: 357) | −0.004756155 | OBD142_501.503_1X |
| 77 | OBD142_515 | GCCACAAGAGATCTGGGAC (SEQ ID NO: 358) | −0.005511591 | OBD142_513.515_1/2X |

Table 25.g

TABLE 25.h

| No. | Location | Training | Odds Ratio | Glmnet |
|---|---|---|---|---|
| 1 | CBL | Any | 7.2 | 0.027324192 |
| 2 | DKK3 | Any | 8.2 | 0.066643802 |
| 3 | DKK3 | Any | 8 | −0.093076823 |
| 4 | FBXO32 | Any | 2.9 | 0.004873633 |
| 5 | KDM1A | Any | 8 | −0.019817526 |
| 6 | EYA1 | Endurance | 6 | 0.030332059 |
| 7 | PCK1 | Endurance | 4.5 | 0.03066036 |
| 8 | PIK3C3 | Endurance | 2.25 | 0.006242977 |
| 9 | ALDH1A2 | Strength | 4 | 0.017005669 |
| 10 | CD36 | Strength | 12 | 0.014942824 |
| 11 | DKK3 | Strength | 5 | 0.067763605 |
| 12 | IL1RAP | Strength | 4 | 0.006222197 |
| 13 | RUNX3 | Strength | 12 | 0.066746082 |
| 14 | ADRB3 | Strength | 9 | −0.026372512 |
| 15 | PLCXD2 | Strength | 9 | 0.015126312 |
| 16 | PCK1 | Strength | 2 | 0.04064456 |
| 17 | SLC25A13 | Strength | 2 | 0.006805912 |
| 18 | C1GALT1 | Any | n/a | 0.000572834 |
| 19 | COL25A1 | Any | n/a | 0.003754206 |
| 20 | COL5A1 | Any | n/a | 0.002011981 |
| 21 | DIAPH3 | Any | n/a | −0.003337259 |
| 22 | FBLN2 | Any | n/a | 0.007164008 |
| 23 | GPC6 | Any | n/a | −0.005249258 |
| 24 | GSN | Any | n/a | −0.001120031 |

TABLE 25.h-continued

| No. | Location | Training | Odds Ratio | Glmnet |
|---|---|---|---|---|
| 25 | GSN | Any | n/a | 0.003244236 |
| 26 | GSN | Strength | n/a | −0.007783392 |
| 27 | LCK | Endurance | n/a | −0.005778408 |
| 28 | LMO4 | Any | n/a | −0.005269663 |
| 29 | MAPK10 | Any | n/a | 0.003978216 |
| 30 | MBNL1 | Any | n/a | −0.003656603 |
| 31 | NCAM1 | Endurance | n/a | −0.005244916 |
| 32 | PCK1 | Any | n/a | −0.005243145 |
| 33 | PDK3 | Any | n/a | −0.000856647 |
| 34 | PDK3 | Any | n/a | −0.005241372 |
| 35 | PTPRC | Any | n/a | −0.003634106 |
| 36 | PTPRC | Any | n/a | −0.002467172 |
| 37 | RYR1 | Any | n/a | −0.009961655 |
| 38 | THNSL2 | Endurance | n/a | 0.004963311 |
| 39 | UACA | Any | n/a | 0.002101178 |
| 40 | ZEB1 | Any | n/a | −0.005202079 |
| 41 | ZFHX3 | Any | n/a | −0.003264119 |
| 42 | ADRB3 | Any | n/a | 0.001018411 |
| 43 | AGT | Endurance | n/a | −0.000807541 |
| 44 | HTR2A | Any | n/a | −0.005203446 |
| 45 | SOS1 | Endurance | n/a | −0.003795912 |
| 46 | ACBD6 | Any | n/a | −0.006643376 |
| 47 | MYH1 | Any | n/a | −0.006900338 |
| 48 | MYOD1 | Endurance | n/a | −0.001296151 |
| 49 | NECTIN3 | Endurance | n/a | −0.00075487 |
| 50 | ACACB | Endurance | n/a | −0.005201838 |

TABLE 25.h-continued

| No. | Location | Training | Odds Ratio | Glmnet |
|---|---|---|---|---|
| 51 | ACACB | Strength | n/a | −0.000282666 |
| 52 | IGF1R | Any | n/a | 0.001436473 |
| 53 | SOCS7 | Any | n/a | −0.001530558 |
| 54 | STXBP4 | Any | n/a | 0.005722578 |
| 55 | SVEP1 | Any | n/a | −0.005188075 |
| 56 | EMCN | Endurance | n/a | −0.003614434 |
| 57 | ACACB | Endurance | n/a | 0.00909588 |
| 58 | FOXO1 | Strength | n/a | −0.002626343 |
| 59 | FOXO3 | Endurance | n/a | 0.003599622 |
| 60 | FTO | Any | n/a | −0.005544516 |
| 61 | GPC6 | Endurance | n/a | −0.010787892 |
| 62 | PPP3CA | Any | n/a | −0.004657708 |
| 63 | SMAD7 | Any | n/a | −0.003808119 |
| 64 | SYK | Endurance | n/a | 0.005232196 |

TABLE 25.h-continued

| No. | Location | Training | Odds Ratio | Glmnet |
|---|---|---|---|---|
| 65 | SYK | Any | n/a | −0.003175937 |
| 66 | TGFB2 | Endurance | n/a | 0.00931825 |
| 67 | TGFBR2 | Strength | n/a | −0.004573651 |
| 68 | TLR2 | Endurance | n/a | 0.004668104 |
| 69 | SVEP1 | Any | n/a | −0.006335271 |
| 70 | MTFR1 | Any | n/a | 0.008864459 |
| 71 | GSN | Any | n/a | −0.002735702 |
| 72 | MUSK | Strength | n/a | −0.004744695 |
| 73 | PPARA | Endurance | n/a | −0.006822261 |
| 74 | PPP1R9A | Any | n/a | −0.002268338 |
| 75 | PLCXD2 | Any | n/a | −0.00572004 |
| 76 | SGC2 | Endurance | n/a | −0.004756155 |
| 77 | SRI | Strength | n/a | −0.005511591 |

TABLE 26

| Gene | Gene name | Function |
|---|---|---|
| CBL | Cbl Proto-Oncogene | Pretein coding, associated with noonan syndrome-like disorder with or without juvenile myelomonocytic leukemia and juvenile myelomonocytic leukemia, related to immune response Fc epsilon RI pathway and EGF/EGFR signaling pathway |
| DKK3 | Dickkopf WNT Signaling Pathway Inhibitor 3 | Pretein coding, associated with oral submucous fibrosis disease, related to regulation of Wnt/B-catenin signaling pathways |
| FBXO32 | F-Box Protein 32 | Protein coding, accociated with muscle hypertrophy and muscle tissue disease, related to class I MHC mediated antigen processing and presentation and FoxO signaling pathway |
| KDM1A | Lysine Demethylase 1A | Proteing coding; Associated with cleft palate, psychomotor retardation, and distinctive facial features and Kbg syndrome; Related to signaling by Rho GTPases and coregulation of androgen receptor activity |
| EYA1 | EYA Transcriptional Coactivator And Phosphatase 1 | Protein coding, associated with otofaciocervical syndrome 1 and branchiootorenal syndrome 1, related to transcriptional misregulation in cancer and DNA double-strand break repair |
| PCK1 | Phosphoenolpyruvate Carboxykinase 1 | Protein coding; Associated with phosphoenolpyruvate carboxykinase deficiency, cytosolic and pepck 1 deficiency; Related to adipogenesis and AMP-activated protein kinase (AMPK) signaling |
| PIK3C3 | Phosphatidylinositol 3-Kinase Catalytic Subunit Type 3 | Protein coding, associated with amyotrophic lateral sclerosis 1 disease, related to mTOR and MAPK Pathway, involved in regulation of degradative endocytic trafficking and required for the abcission step in cytokinesis, involved in trasport from early to late endosomes |
| ALDH1A2 | Aldehyde Dehydrogenase 1 Family Member A2 | Protein coding, associated with diaphragm disease and neural tube defects, related to drug metabolism cytochrome P450 and vitamin A and carotenoid metabolism |
| CD36 | CD36 Molecule | Protein coding, associated with platelet glycoprotein Iv deficiency and coronary heart disease 7, related to activated TLR4 signaling and hematopoietic stem cell differentiation pathways and lineage-specific markers |
| IL1RAP | Interleukin 1 Receptor Accessory Protein | Protein coding, associated with chromosome Xp21 deletion syndrome and stromal keratitis, relared to bacterial infections in CF airways and IL-1 family signaling pathways |
| RUNX3 | Runt Related Transcription Factor 3 | Protein coding, associated with testicular yolk sac tumor and cleidocranial dysplasia, related to sudden infant death syndrome (SIDS) susceptibility pathways and Wnt/Hedgehog/Notch |
| PPARA | Peroxisome Proliferator Activated Receptor Alpha | Protein coding, associated with fatty liver disease and alcoholic cardiomyopathy, related to gene expression and regulation of cholesterol biosynthesis by SREBP |
| SLC25A13 | Solute Carrier Family 25 Member 13 | Protein coding, related to metabolism and protein metabolism pathways, associated with Citrullinemia, Type Ii, Neonatal-Onset and Citrullinemia, Type Ii, Adult-Onset |
| MYL1 | Myosin Light Chain 1 | Protein coding, related to ERK signaling and cytoskeleton remodeling regulation of actin cytoskeleton by Rho GTPases |

TABLE 27

| GeneSet | Number Of Protein In Gene Set | Protein From Network | FDR | Nodes |
|---|---|---|---|---|
| Th17 cell differentiation(K) | 107 | 14 | 1.52E–10 | RORA, FOXP3, GATA3, SMAD3, NFATC3, NFATC2, NFKB1, NFKBIE, LAT, IKBKB, PPP3CA, TGFBR2,CD247, IL17A |
| T cell receptor signaling pathway(K) | 105 | 12 | 1.99E–08 | GRAP2, PIK3R1, NFATC3, NFATC2, NFKB1, NFKBIE, LAT, IKBKB, PPP3CA, LCP2, CBL, CD247 |
| Pathways in cancer(K) | 397 | 19 | 7.44E–08 | RB1, ETS1, IGF1R, RASSF1, CDH1, COL4A1, PIK3R1, TGFB2, SMAD3, NFKB1, BCL2, ITGB1, IKBKB, TGFBR2, LAMA2, LAMA4, CBL, TCF7L2, APC |
| T cell activation(P) | 81 | 10 | 2.03E–07 | GRAP2, PIK3R1, NFATC3, NFATC2, NFKB1, LAT, IKBKB, PPP3CA, LCP2, CD247 |
| Th1 and Th2 cell differentiation(K) | 92 | 10 | 4.55E–07 | GATA3, NFATC3, NFATC2, NFKB1, NFKBIE, LAT, IKBKB, PPP3CA, DLL1, CD247 |
| TCR signaling in naïve CD4+ T cells(N) | 67 | 9 | 4.55E–07 | GRAP2, PRKCE, STIM1, LAT, IKBKB, LCP2, CBL, PTPN11, CD247 |
| Chronic myeloid leukemia(K) | 73 | 9 | 8.09E–07 | RB1, PIK3R1, TGFB2, SMAD3, NFKB1, IKBKB, TGFBR2, CBL, PTPN11 |
| TCR signaling in naïve CD8+ T cells(N) | 54 | 8 | 1.21E–06 | GRAP2, PRKCE, STIM1, LAT, IKBKB, LCP2, CBL, CD247 |
| Small cell lung cancer(K) | 86 | 9 | 2.54E–06 | RB1, COL4A1, PIK3R1, NFKB1, BCL2, ITGB1, IKBKB, LAMA2, LAMA4 |
| Fc-epsilon receptor I signaling in mast cells(N) | 62 | 8 | 2.74E–06 | PIK3R1, NFATC2, NFKB1, LAT, IKBKB, LCP2, CBL, PTPN11 |
| Inflammatory bowel disease (IBD)(K) | 65 | 8 | 3.58E–06 | RORA, IL18RAP, FOXP3, GATA3, TGFB2, SMAD3, NFKB1, IL17A |
| Adherens junction(K) | 72 | 8 | 7.15E–06 | IGF1R, CDH1, LMO7, SMAD3, WASL, TGFBR2, TCF7L2, NECTIN3 |
| Hepatitis B(K) | 146 | 10 | 1.47E–05 | RB1, PIK3R1, TGFB2, SMAD3, EGR3, NFATC3, NFATC2, NFKB1, BCL2, IKBKB |
| TGF-beta signaling pathway(K) | 84 | 8 | 1.94E–05 | ACVR1, TGFB2, SMAD3, SMAD9, BMPR1B, BMPR1A, DCN, TGFBR2 |
| Neurotrophin signaling pathway(K) | 121 | 9 | 2.59E–05 | PIK3R1, FOXO3, NFKB1, BCL2, NFKBIE, IKBKB, IRAK3, NTRK2, PTPN11 |
| Colorectal cancer(K) | 62 | 7 | 2.85E–05 | PIK3R1, TGFB2, SMAD3, BCL2, TGFBR2, TCF7L2, APC |
| Signaling by Interleukins(R) | 460 | 16 | 2.85E–05 | RORA, IL18RAP, PIK3R1, GATA3, FOXO3, NFKB1, BCL2, LAT, ITGB1, IKBKB, IRAK3, ZEB1, CBL, NCAM1, PTPN11, IL17A |
| HTLV-I infection(K) | 258 | 12 | 3.78E–05 | RB1, ETS1, PIK3R1, TGFB2, SMAD3, NFATC3, NFATC2, NFKB1, IKBKB, PPP3CA, TGFBR2, APC |
| Pancreatic cancer(K) | 66 | 7 | 3.78E–05 | RB1, PIK3R1, TGFB2, SMAD3, NFKB1, IKBKB, TGFBR2 |
| Osteoclast differentiation(K) | 132 | 9 | 3.88E–05 | PIK3R1, TGFB2, NFATC2, NFKB1, IKBKB, PPP3CA, FCGR3A,TGFBR2, LCP2 |
| Natural killer cell mediated cytotoxicity(K) | 135 | 9 | 4.44E–05 | PIK3R1, NFATC2, KLRD1, LAT, PPP3CA, FCGR3A, LCP2, PTPN11, CD247 |
| AGE-RAGE signaling pathway in diabetic complications(K) | 101 | 8 | 4.44E–05 | PRKCE, COL4A1, PIK3R1, TGFB2, SMAD3, NFKB1, BCL2, TGFBR2 |
| AP-1 transcription factor network(N) | 70 | 7 | 4.44E–05 | ETS1, BCL2L11, NFATC3, NFATC2, ELF1, TCF7L2, AGT |
| CDC42 signaling events(N) | 70 | 7 | 4.44E–05 | CDH1, PRKCE, PIK3R1, WASL, PAX6, CBL, APC |
| ras-independent pathway in nk cell-mediated cytotoxicity(B) | 25 | 5 | 4.95E–05 | PIK3R1, KLRD1, LAT, FCGR3A, PTPN11 |
| B cell receptor signaling pathway(K) | 73 | 7 | 5.26E–05 | PIK3R1, NFATC3, NFATC2, NFKB1, NFKBIE, IKBKB, PPP3CA |
| Signaling pathways regulating pluripotency of stem cells(K) | 142 | 9 | 5.26E–05 | IGF1R, ACVR1, PIK3R1, SMAD3, SMAD9, BMPR1B, BMPR1A, PAX6, APC |

TABLE 27-continued

| GeneSet | Number Of Protein In Gene Set | Protein From Network | FDR | Nodes |
|---|---|---|---|---|
| Angiopoietin receptor Tie2-mediated signaling(N) | 50 | 6 | 7.08E−05 | ETS1, PIK3R1, NFKB1, ITGB1, ELF1, PTPN11 |
| IL2 signaling events mediated by STAT5(N) | 28 | 5 | 7.08E−05 | FOXP3, PIK3R1, BCL2, ELF1, PTPN11 |
| TGF-beta signaling pathway(P) | 80 | 7 | 7.95E−05 | ACVR1, TGFB2, SMAD3, SMAD9, BMPR1B, BMPR1A, TGFBR2 |
| Signaling events mediated by Hepatocyte Growth Factor Receptor (c-Met)(N) | 80 | 7 | 7.95E−05 | ETS1, CDH1, PIK3R1, WASL, CBL, PTPN11, APC |
| Signaling events mediated by Stem cell factor receptor (c-Kit)(N) | 52 | 6 | 8.17E−05 | GRAP2, PIK3R1, FOXO3, BCL2, CBL, PTPN11 |
| Hippo signaling pathway(K) | 154 | 9 | 8.17E−05 | RASSF1, CDH1, TGFB2, SMAD3, BMPR1B, BMPR1A, TGFBR2, TCF7L2, APC |
| Toxoplasmosis(K) | 118 | 8 | 9.76E−05 | PIK3R1, TGFB2, NFKB1, BCL2, ITGB1, IKBKB, LAMA2, LAMA4 |
| EPO signaling pathway(N) | 33 | 5 | 1.31E−04 | PIK3R1, NFKB1, BCL2, CBL, PTPN11 |
| Prostate cancer(K) | 89 | 7 | 1.41E−04 | RB1, IGF1R, PIK3R1, NFKB1, BCL2, IKBKB, TCF7L2 |
| IL2 signaling events mediated by PI3K(N) | 35 | 5 | 1.63E−04 | PIK3R1, FOXO3, NFKB1, BCL2, PTPN11 |
| FoxO signaling pathway(K) | 134 | 8 | 2.14E−04 | IGF1R, PIK3R1, FOXO3, BCL2L11, TGFB2, SMAD3, IKBKB, TGFBR2 |
| Chagas disease (American trypanosomiasis)(K) | 104 | 7 | 3.32E−04 | PIK3R1, TGFB2, SMAD3, NFKB1, IKBKB, TGFBR2, CD247 |
| Adipocytokine signaling pathway(K) | 70 | 6 | 3.45E−04 | ACACB, PPARGC1A, NFKB1, NFKBIE, IKBKB, PTPN11 |
| sumoylation as a mechanism to modulate ctbp-dependent gene responses(B) | 7 | 3 | 3.94E−04 | UBE3A, CDH1, ZEB1 |
| Insulin resistance(K) | 109 | 7 | 4.15E−04 | PRKCE, PIK3R1, ACACB, PPARGC1A, NFKB1, IKBKB, PTPN11 |
| Calcineurin-regulated NFAT-dependent transcription in lymphocytes(N) | 46 | 5 | 5.17E−04 | FOXP3, GATA3, EGR3, NFATC3, NFATC2 |
| MAPK signaling pathway(K) | 255 | 10 | 5.28E−04 | CACNB1, DDIT3, CACNA1E, TGFB2, NFATC3, NFKB1, IKBKB, PPP3CA, TGFBR2, NTRK2 |
| FGF signaling pathway(N) | 47 | 5 | 5.28E−04 | CDH1, PIK3R1, CBL, NCAM1, PTPN11 |
| Integrins in angiogenesis(N) | 47 | 5 | 5.28E−04 | IGF1R, PIK3R1, TGFBR2, CBL, PTPN11 |
| TCR signaling(R) | 123 | 7 | 8.14E−04 | GRAP2, PIK3R1, NFKB1, LAT, IKBKB, LCP2, CD247 |
| Endometrial cancer(K) | 52 | 5 | 8.48E−04 | CDH1, PIK3R1, FOXO3, TCF7L2, APC |
| PI3K-Akt signaling pathway(K) | 341 | 11 | 1.10E−03 | IGF1R, COL4A1, PIK3R1, FOXO3, BCL2L11, NFKB1, BCL2, ITGB1, IKBKB, LAMA2, LAMA4 |
| Fc epsilon receptor (FCERI) signaling(R) | 405 | 12 | 1.16E−03 | GRAP2, PIK3R1, FOXO3, NFATC3, NFATC2, NFKB1, LAT, IKBKB, PPP3CA, LCP2, NCAM1, PTPN11 |
| Transcriptional misregulation in cancer(K) | 180 | 8 | 1.17E−03 | IGF1R, DDIT3, NFKB1, NR4A3, TGFBR2, ZEB1, PAX7, EYA1 |
| Fc gamma R-mediated phagocytosis(K) | 93 | 6 | 1.17E−03 | PRKCE, PIK3R1, LAT, WASL, FCGR3A, GSN |
| ATF-2 transcription factor network(N) | 58 | 5 | 1.17E−03 | RB1, DDIT3, PPARGC1A, TGFB2, BCL2 |
| Validated targets of C-MYC transcriptional repression(N) | 60 | 5 | 1.37E−03 | DDIT3, FOXO3, SMAD3, BCL2, ITGB1 |
| Amoebiasis(K) | 98 | 6 | 1.55E−03 | COL4A1, PIK3R1, TGFB2, NFKB1, LAMA2, LAMA4 |
| IL1-mediated signaling events(N) | 34 | 4 | 1.81E−03 | PIK3R1, NFKB1, IKBKB, IRAK3 |

TABLE 27-continued

| GeneSet | Number Of Protein In Gene Set | Protein From Network | FDR | Nodes |
|---|---|---|---|---|
| BCR signaling pathway(N) | 65 | 5 | 1.95E-03 | ETS1, PIK3R1, NFKB1, IKBKB, PPP3CA |
| JNK signaling in the CD4+ TCR pathway(N) | 14 | 3 | 1.95E-03 | GRAP2, LAT, LCP2 |
| Atypical NF-kappaB pathway(N) | 14 | 3 | 1.95E-03 | PIK3R1, NFKB1, IKBKB |
| Extracellular matrix organization(R) | 255 | 9 | 2.09E-03 | CDH1, COL4A1, TGFB2, ITGB1, DCN, LAMA2, LAMA4, NRXN1, NCAM1 |
| IL23-mediated signaling events(N) | 37 | 4 | 2.25E-03 | IL18RAP, PIK3R1, NFKB1, IL17A |
| Proteoglycans in cancer(K) | 205 | 8 | 2.43E-03 | IGF1R, PIK3R1, TGFB2, ITGB1, DCN, CBL, GPC1, PTPN11 |
| Wnt signaling pathway(P) | 268 | 9 | 3.00E-03 | CDH1, PRKCE, NFATC3, NFATC2, BMPR1B, BMPR1A, PPP3CA, TCF7L2, APC |
| FOXM1 transcription factor network(N) | 40 | 4 | 3.01E-03 | RB1, NFATC3, LAMA4, CENPF |
| Bacterial invasion of epithelial cells(K) | 78 | 5 | 3.64E-03 | CDH1, PIK3R1, ITGB1, WASL, CBL |
| il-2 receptor beta chain in t cell activation(B) | 44 | 4 | 3.82E-03 | RB1, PIK3R1, CBL, PTPN11 |
| Axon guidance mediated by netrin(P) | 4 | 2 | 4.06E-03 | NFATC3, NFATC2 |
| Insulin Pathway(N) | 45 | 4 | 4.16E-03 | PIK3R1, FOXO3, CBL, PTPN11 |
| AMPK signaling pathway(K) | 124 | 6 | 4.26E-03 | IGF1R, PIK3R1, FOXO3, ACACB, ACACA, PPARGC1A |
| EGFR tyrosine kinase inhibitor resistance(K) | 81 | 5 | 4.26E-03 | IGF1R, PIK3R1, FOXO3, BCL2L11, BCL2 |
| Ras signaling pathway(K) | 229 | 8 | 4.26E-03 | ETS1, IGF1R, RASSF1, PIK3R1, NFKB1, LAT, IKBKB, PTPN11 |
| Hypertrophic cardiomyopathy (HCM)(K) | 83 | 5 | 4.26E-03 | CACNB1, TGFB2, ITGB1, LAMA2, TTN |
| the co-stimulatory signal during t-cell activation(B) | 20 | 3 | 4.26E-03 | PIK3R1, PTPN11, CD247 |
| Axon guidance(K) | 177 | 7 | 4.27E-03 | PIK3R1, NFATC3, NFATC2, BMPR1B, ITGB1, PPP3CA, PTPN11 |
| Type II diabetes mellitus(K) | 48 | 4 | 4.62E-03 | PRKCE, PIK3R1, CACNA1E, IKBKB |
| t cell receptor signaling pathway(B) | 48 | 4 | 4.62E-03 | PIK3R1, LAT, PTPN11, CD247 |
| GPVI-mediated activation cascade(R) | 49 | 4 | 4.99E-03 | PIK3R1, LAT, LCP2, PTPN11 |
| MicroRNAs in cancer(K) | 299 | 9 | 5.10E-03 | RASSF1, PRKCE, BCL2L11, TGFB2, NFKB1, BCL2, IKBKB, ZEB1, APC |
| influence of ras and rho proteins on g1 to s transition(B) | 22 | 3 | 5.46E-03 | RB1, PIK3R1, IKBKB |
| Dilated cardiomyopathy(K) | 90 | 5 | 5.46E-03 | CACNB1, TGFB2, ITGB1, LAMA2, TTN |
| Role of Calcineurin-dependent NFAT signaling in lymphocytes(N) | 52 | 4 | 5.46E-03 | PRKCE, NFATC3, NFATC2, BCL2 |
| Signaling by MET(R) | 52 | 4 | 5.46E-03 | PIK3R1, ITGB1, CBL, PTPN11 |
| Signaling by BMP(R) | 23 | 3 | 5.46E-03 | SMAD9, BMPR1B, BMPR1A |
| role of mef2d in t-cell apoptosis(B) | 23 | 3 | 5.46E-03 | LAT, PTPN11, CD247 |
| Apoptosis(K) | 140 | 6 | 6.04E-03 | DDIT3, PIK3R1, BCL2L11, NFKB1, BCL2, IKBKB |
| Insulin signaling pathway(K) | 140 | 6 | 6.04E-03 | PIK3R1, ACACB, ACACA, PPARGC1A, IKBKB, CBL |
| IL2-mediated signaling events(N) | 54 | 4 | 6.12E-03 | PRKCE, PIK3R1, BCL2, PTPN11 |
| Longevity regulating pathway(K) | 94 | 5 | 6.28E-03 | IGF1R, PIK3R1, FOXO3, PPARGC1A, NFKB1 |
| Wnt signaling pathway(K) | 143 | 6 | 6.46E-03 | SMAD3, NFATC3, NFATC2, PPP3CA, TCF7L2, APC |
| Non-small cell lung cancer(K) | 56 | 4 | 6.46E-03 | RB1, RASSF1, PIK3R1, FOXO3 |
| Cell adhesion molecules (CAMs)(K) | 145 | 6 | 6.46E-03 | CDH1, CD226, ITGB1, NRXN1, NCAM1, NECTIN3 |

TABLE 27-continued

| GeneSet | Number Of Protein In Gene Set | Protein From Network | FDR | Nodes |
|---|---|---|---|---|
| Acute myeloid leukemia(K) | 57 | 4 | 6.46E−03 | PIK3R1, NFKB1, IKBKB, TCF7L2 |
| Breast cancer(K) | 146 | 6 | 6.46E−03 | RB1, IGF1R, PIK3R1, DLL1, TCF7L2, APC |
| DAP12 interactions(R) | 323 | 9 | 6.46E−03 | GRAP2, PRKCE, PIK3R1, FOXO3, KLRD1, LAT, LCP2, NCAM1, PTPN11 |
| Endocrine resistance(K) | 98 | 5 | 6.46E−03 | RB1, IGF1R, PIK3R1, BCL2, DLL1 |
| Focal adhesion(K) | 201 | 7 | 6.46E−03 | IGF1R, COL4A1, PIK3R1, BCL2, ITGB1, LAMA2, LAMA4 |
| ALK1 signaling events(N) | 26 | 3 | 6.46E−03 | ACVR1, SMAD9, TGFBR2 |
| Apoptosis signaling pathway(P) | 26 | 3 | 6.46E−03 | PRKCE, BCL2L11, BCL2 |
| B cell activation(P) | 59 | 4 | 7.05E−03 | NFATC3, NFATC2, IKBKB, PPP3CA |
| Cytokine-cytokine receptor interaction(K) | 265 | 8 | 7.11E−03 | IL18RAP, ACVR1, TGFB2, BMPR1B, BMPR1A, TGFBR2, TNFRSF25, IL17A |
| VEGFR1 specific signals(N) | 27 | 3 | 7.19E−03 | PIK3R1, CBL, PTPN11 |
| Signaling events mediated by focal adhesion kinase(N) | 60 | 4 | 7.49E−03 | ETS1, PIK3R1, ITGB1, WASL |
| Signaling by the B Cell Receptor (BCR)(R) | 270 | 8 | 7.99E−03 | STIM1, PIK3R1, FOXO3, NFKB1, NFKBIE, IKBKB, CBL, PTPN11 |
| Rap1 signaling pathway(K) | 212 | 7 | 8.61E−03 | IGF1R, CDH1, PIK3R1, DRD2, LAT, ITGB1, LCP2 |
| EGF receptor (ErbB1) signaling pathway(N) | 29 | 3 | 8.80E−03 | WASL, GSN, PTPN11 |
| Osteopontin-mediated events(N) | 29 | 3 | 8.80E−03 | PIK3R1, NFKB1, GSN |
| Costimulation by the CD28 family(R) | 63 | 4 | 8.94E−03 | GRAP2, PIK3R1, PTPN11, CD247 |
| Downstream signaling in naïve CD8+ T cells(N) | 64 | 4 | 9.47E−03 | PRKCE, NFATC3, NFATC2, CD247 |
| IGF1 pathway(N) | 30 | 3 | 9.69E−03 | IGF1R, PIK3R1, PTPN11 |
| Nectin adhesion pathway(N) | 30 | 3 | 9.69E−03 | CDH1, PIK3R1, NECTIN3 |
| Shigellosis(K) | 65 | 4 | 0.01 | NFKB1, ITGB1, WASL, IKBKB |
| Beta1 integrin cell surface interactions(N) | 66 | 4 | 0.0101 | COL4A1, ITGB1, LAMA2, LAMA4 |
| Signalling by NGF(R) | 421 | 10 | 0.0101 | PRKCE, PIK3R1, FOXO3, BCL2L11, NFKB1, LAT, IKBKB, NCAM1, NTRK2, PTPN11 |
| Renal cell carcinoma(K) | 67 | 4 | 0.0101 | ETS1, PIK3R1, TGFB2, PTPN11 |
| N-cadherin signaling events(N) | 33 | 3 | 0.0101 | PIK3R1, GSN, PTPN11 |
| HIV-1 Nef: Negative effector of Fas and TNF-alpha(N) | 33 | 3 | 0.0101 | NFKB1, BCL2, CD247 |
| Melanoma(K) | 71 | 4 | 0.011 | RB1, IGF1R, CDH1, PIK3R1 |
| Arrhythmogenic right ventricular cardiomyopathy (ARVC)(K) | 72 | 4 | 0.0116 | CACNB1, ITGB1, LAMA2, TCF7L2 |
| a6b1 and a6b4 Integrin signaling(N) | 35 | 3 | 0.012 | CDH1, PIK3R1, ITGB1 |
| Leishmaniasis(K) | 73 | 4 | 0.0121 | TGFB2, NFKB1, ITGB1, FCGR3A |
| Validated transcriptional targets of AP1 family members Fra1 and Fra2(N) | 37 | 3 | 0.014 | NFATC3, NFATC2, DCN |
| GMCSF-mediated signaling events(N) | 37 | 3 | 0.014 | PIK3R1, IKBKB, PTPN11 |
| ALK2 signaling events(N) | 11 | 2 | 0.0148 | ACVR1, SMAD9 |
| lck and fyn tyrosine kinases in initiation of tcr activation(B) | 11 | 2 | 0.0148 | PTPN11, CD247 |
| Immunoregulatory interactions between | 187 | 6 | 0.0169 | CDH1, CD226, KLRD1, ITGB1, FCGR3A, CD247 |

TABLE 27-continued

| GeneSet | Number Of Protein In Gene Set | Protein From Network | FDR | Nodes |
|---|---|---|---|---|
| a Lymphoid and a non-Lymphoid cell(R) | | | | |
| IFN-gamma pathway(N) | 40 | 3 | 0.0173 | PIK3R1, CBL, PTPN11 |
| Signaling by FGFR3(R) | 40 | 3 | 0.0173 | PIK3R1, CBL, PTPN11 |
| insulin signaling pathway(B) | 12 | 2 | 0.0175 | PIK3R1, PTPN11 |
| C-MYB transcription factor network(N) | 82 | 4 | 0.0183 | ETS1, GATA3, BCL2, PPP3CA |
| ECM-receptor interaction(K) | 82 | 4 | 0.0183 | COL4A1, ITGB1, LAMA2, LAMA4 |
| Bladder cancer(K) | 41 | 3 | 0.0186 | RB1, RASSF1, CDH1 |
| Signaling by FGFR4(R) | 41 | 3 | 0.0186 | PIK3R1, CBL, PTPN11 |
| BMP receptor signaling(N) | 41 | 3 | 0.0186 | SMAD9, BMPR1B, BMPR1A |
| human cytomegalovirus and map kinase pathways(B) | 13 | 2 | 0.0205 | RB1, PIK3R1 |
| Metabolism of Angiotensinogen to Angiotensins(R) | 13 | 2 | 0.0205 | ACE2, AGT |
| Fatty acid biosynthesis(K) | 13 | 2 | 0.0205 | ACACB, ACACA |
| b cell survival pathway(B) | 13 | 2 | 0.0205 | PIK3R1, ITGB1 |
| Beta3 integrin cell surface interactions(N) | 43 | 3 | 0.0212 | COL4A1, TGFBR2, LAMA4 |
| C-type lectin receptors (CLRs)(R) | 139 | 5 | 0.0215 | NFATC3, NFATC2, NFKB1, IKBKB, PPP3CA |
| IL5-mediated signaling events(N) | 14 | 2 | 0.0215 | PIK3R1, PTPN11 |
| Viral carcinogenesis(K) | 203 | 6 | 0.0215 | RB1, UBE3A, PIK3R1, EGR3, NFKB1, GSN |
| Epstein-Barr virus infection(K) | 204 | 6 | 0.0215 | RB1, PIK3R1, NFKB1, BCL2, NFKBIE, IKBKB |
| keratinocyte differentiation(B) | 47 | 3 | 0.0215 | ETS1, PRKCE, IKBKB |
| Apoptotic execution phase(R) | 47 | 3 | 0.0215 | CDH1, GSN, APC |
| Ceramide signaling pathway(N) | 48 | 3 | 0.0215 | RB1, NFKB1, BCL2 |
| Posttranslational regulation of adherens junction stability and dissassembly(N) | 48 | 3 | 0.0215 | IGF1R, CDH1, NTRK2 |
| FoxO family signaling(N) | 48 | 3 | 0.0215 | FOXO3, BCL2L11, IKBKB |
| Signaling by FGFR1(R) | 49 | 3 | 0.0227 | PIK3R1, CBL, PTPN11 |
| NF-kappa B signaling pathway(K) | 95 | 4 | 0.0228 | NFKB1, BCL2, LAT, IKBKB |
| role of pi3k subunit p85 in regulation of actin organization and cell migration(B) | 16 | 2 | 0.0229 | PIK3R1, WASL |
| Non-alcoholic fatty liver disease (NAFLD)(K) | 151 | 5 | 0.0235 | DDIT3, PIK3R1, BCL2L11, NFKB1, IKBKB |
| SHP2 signaling(N) | 51 | 3 | 0.0253 | IGF1R, PIK3R1, PTPN11 |
| pten dependent cell cycle arrest and apoptosis(B) | 17 | 2 | 0.0257 | PIK3R1, ITGB1 |
| Signaling by SCF-KIT(R) | 290 | 7 | 0.028 | GRAP2, PIK3R1, FOXO3, LAT, CBL, NCAM1, PTPN11 |
| Fcgamma receptor (FCGR) dependent phagocytosis(R) | 159 | 5 | 0.0289 | PRKCE, PIK3R1, WASL, FCGR3A, CD247 |
| Oxytocin signaling pathway(K) | 159 | 5 | 0.0289 | CACNB1, PIK3R1, NFATC3, NFATC2, PPP3CA |
| Glucagon signaling pathway(K) | 103 | 4 | 0.0301 | ACACB, ACACA, PPARGC1A, PPP3CA |
| HIF-1 signaling pathway(K) | 103 | 4 | 0.0301 | IGF1R, PIK3R1, NFKB1, BCL2 |
| Pathogenic *Escherichia coli* infection(K) | 55 | 3 | 0.031 | CDH1, ITGB1, WASL |

TABLE 27-continued

| GeneSet | Number Of Protein In Gene Set | Protein From Network | FDR | Nodes |
|---|---|---|---|---|
| cyclins and cell cycle regulation(B) | 19 | 2 | 0.0318 | RB1, PTPN11 |
| tgf beta signaling pathway(B) | 19 | 2 | 0.0318 | CDH1, TGFB2 |
| Signaling by NODAL(R) | 19 | 2 | 0.0318 | FOXO3, SMAD3 |
| fas signaling pathway (cd95)(B) | 19 | 2 | 0.0318 | RB1, PTPN11 |
| tumor suppressor arf inhibits ribosomal biogenesis(B) | 19 | 2 | 0.0318 | RB1, PIK3R1 |
| cGMP-PKG signaling pathway(K) | 168 | 5 | 0.0346 | PRKCE, PIK3R1, NFATC3, NFATC2, PPP3CA |
| cell cycle: g1/s check point(B) | 21 | 2 | 0.0346 | RB1, PTPN11 |
| growth hormone signaling pathway(B) | 21 | 2 | 0.0346 | PIK3R1, PTPN11 |
| E-cadherin signaling in keratinocytes(N) | 21 | 2 | 0.0346 | CDH1, PIK3R1 |
| igf-1 signaling pathway(B) | 21 | 2 | 0.0346 | PIK3R1, PTPN11 |
| nf-kb signaling pathway(B) | 21 | 2 | 0.0346 | NFKB1, IKBKB |
| Neurotrophic factor-mediated Trk receptor signaling(N) | 60 | 3 | 0.0346 | PIK3R1, NTRK2, PTPN11 |
| IL12-mediated signaling events(N) | 61 | 3 | 0.0346 | IL18RAP, NFKB1, CD247 |
| VEGF signaling pathway(K) | 61 | 3 | 0.0346 | PIK3R1, NFATC2, PPP3CA |
| ctcf: first multivalent nuclear factor(B) | 22 | 2 | 0.0346 | PIK3R1, TGFB2 |
| Nephrin interactions(R) | 22 | 2 | 0.0346 | PIK3R1, WASL |
| Incretin synthesis, secretion, and inactivation(R) | 22 | 2 | 0.0346 | PAX6, TCF7L2 |
| Signaling by EGFR(R) | 317 | 7 | 0.0346 | PRKCE, PIK3R1, FOXO3, LAT, CBL, NCAM1, PTPN11 |
| IL4-mediated signaling events(N) | 63 | 3 | 0.0346 | ETS1, PIK3R1, CBL |
| Signaling events mediated by VEGFR1 and VEGFR2(N) | 63 | 3 | 0.0346 | PIK3R1, CBL, PTPN11 |
| LPA receptor mediated events(N) | 63 | 3 | 0.0346 | PRKCE, PIK3R1, NFKB1 |
| Canonical NF-kappaB pathway(N) | 23 | 2 | 0.0346 | NFKB1, IKBKB |
| Signaling events mediated by the Hedgehog family(N) | 23 | 2 | 0.0346 | PIK3R1, TGFB2 |
| Renin-angiotensin system(K) | 23 | 2 | 0.0346 | ACE2, AGT |
| Signaling events mediated by PRL(N) | 23 | 2 | 0.0346 | ITGB1, AGT |
| Tuberculosis(K) | 179 | 5 | 0.0346 | TGFB2, NFKB1, BCL2, PPP3CA, FCGR3A |
| Longevity regulating pathway - multiple species(K) | 64 | 3 | 0.0346 | IGF1R, PIK3R1, FOXO3 |
| Regulation of retinoblastoma protein(N) | 64 | 3 | 0.0346 | RB1, TGFB2, ELF1 |
| HIF-1-alpha transcription factor network(N) | 65 | 3 | 0.0346 | RORA, ETS1, SMAD3 |
| nfkb activation by nontypeable hemophilus influenzae(B) | 24 | 2 | 0.0346 | TGFB2, IKBKB |
| PDGFR-beta signaling pathway(N) | 120 | 4 | 0.0346 | PRKCE, WASL, CBL, PTPN11 |
| Sphingolipid signaling pathway(K) | 120 | 4 | 0.0346 | PRKCE, PIK3R1, NFKB1, BCL2 |

TABLE 27-continued

| GeneSet | Number Of Protein In Gene Set | Protein From Network | FDR | Nodes |
| --- | --- | --- | --- | --- |
| Glioma(K) | 66 | 3 | 0.0346 | RB1, IGF1R, PIK3R1 |
| Angiogenesis(P) | 66 | 3 | 0.0346 | ETS1, TCF7L2, APC |
| Signaling by PDGF(R) | 328 | 7 | 0.0346 | PRKCE, COL4A1, PIK3R1, FOXO3, LAT, NCAM1, PTPN11 |
| Platelet activation(K) | 122 | 4 | 0.0352 | STIM1, PIK3R1, ITGB1, LCP2 |
| VEGFR3 signaling in lymphatic endothelium(N) | 25 | 2 | 0.0355 | PIK3R1, ITGB1 |
| Glypican 1 network(N) | 25 | 2 | 0.0355 | TGFBR2, GPC1 |
| Epithelial cell signaling in *Helicobacter pylori* infection(K) | 68 | 3 | 0.0362 | NFKB1, IKBKB, PTPN11 |
| Regulation of Telomerase(N) | 68 | 3 | 0.0362 | UBE3A, SMAD3, NFKB1 |
| Chemokine signaling pathway(K) | 187 | 5 | 0.0365 | PIK3R1, FOXO3, NFKB1, WASL, IKBKB |
| p75(NTR)-mediated signaling(N) | 69 | 3 | 0.0377 | PIK3R1, BCL2L11, IKBKB |
| IL3-mediated signaling events(N) | 26 | 2 | 0.0382 | PIK3R1, PTPN11 |
| IL27-mediated signaling events(N) | 26 | 2 | 0.0382 | GATA3, IL17A |
| Signaling events mediated by HDAC Class III(N) | 26 | 2 | 0.0382 | FOXO3, PPARGC1A |
| Endocytosis(K) | 260 | 6 | 0.0384 | IGF1R, TGFB2, SMAD3, WASL, TGFBR2, CBL |
| Fc epsilon Rl signaling pathway(K) | 70 | 3 | 0.0391 | PIK3R1, LAT, LCP2 |
| Cell junction organization(R) | 70 | 3 | 0.0391 | CDH1, ITGB1, NECTIN3 |
| Signaling by FGFR2(R) | 71 | 3 | 0.0406 | PIK3R1, CBL, PTPN11 |
| Calcium signaling in the CD4+ TCR pathway(N) | 27 | 2 | 0.041 | NFATC3, NFATC2 |
| Prolactin signaling pathway(K) | 72 | 3 | 0.0421 | PIK3R1, FOXO3, NFKB1 |
| Signaling by TGF-beta Receptor Complex(R) | 73 | 3 | 0.0436 | SMAD3, TGFBR2, CBL |
| Reelin signaling pathway(N) | 28 | 2 | 0.0439 | PIK3R1, ITGB1 |
| IL8- and CXCR1-mediated signaling events(N) | 28 | 2 | 0.0439 | PRKCE, CBL |
| p73 transcription factor network(N) | 75 | 3 | 0.0467 | RB1, FOXO3, BCL2L11 |
| Thyroid cancer(K) | 29 | 2 | 0.0468 | CDH1, TCF7L2 |
| AlphaE beta7 integrin cell surface interactions(N) | 3 | 1 | 0.048 | CDH1 |
| erk and pi-3 kinase are necessary for collagen binding in corneal epithelia(B) | 30 | 2 | 0.0499 | PIK3R1, ITGB1 |
| Regulation of nuclear SMAD2/3 signaling(N) | 77 | 3 | 0.05 | GATA3, FOXO3, SMAD3 |
| IL12 signaling mediated by STAT4(N) | 31 | 2 | 0.053 | IL18RAP, CD247 |
| Antifolate resistance(K) | 31 | 2 | 0.053 | NFKB1, IKBKB |
| trefoil factors initiate mucosal healing(B) | 31 | 2 | 0.053 | PIK3R1, IKBKB |
| Regulation of nuclear beta catenin signaling and target gene transcription(N) | 80 | 3 | 0.0551 | CDH1, TCF7L2, APC |
| Toll-Like Receptors Cascades(R) | 141 | 4 | 0.056 | NFKB1, IKBKB, IRAK3, PTPN11 |
| Netrin-mediated signaling events(N) | 32 | 2 | 0.0562 | PIK3R1, WASL |
| Propanoate metabolism(K) | 32 | 2 | 0.0562 | ACACB, ACACA |
| L1CAM interactions(R) | 82 | 3 | 0.0587 | ITGB1, CHL1, NCAM1 |
| Apoptosis - multiple species(K) | 33 | 2 | 0.0594 | BCL2L11, BCL2 |

TABLE 27-continued

| GeneSet | Number Of Protein In Gene Set | Protein From Network | FDR | Nodes |
|---|---|---|---|---|
| Regulation of actin cytoskeleton(K) | 214 | 5 | 0.0605 | PIK3R1, ITGB1, WASL, GSN, APC |
| phospholipase c signaling pathway(B) | 4 | 1 | 0.0638 | PIK3R1 |
| signal transduction through il1r(B) | 35 | 2 | 0.0662 | TGFB2, IKBKB |
| Signaling mediated by p38-alpha and p38-beta(N) | 35 | 2 | 0.0662 | DDIT3, PPARGC1A |
| Salmonella infection(K) | 86 | 3 | 0.0662 | NFKB1, WASL, DYNC1I1 |
| Trk receptor signaling mediated by PI3K and PLC-gamma(N) | 36 | 2 | 0.0696 | PIK3R1, FOXO3 |
| mechanism of gene regulation by peroxisome proliferators via ppara(B) | 36 | 2 | 0.0696 | RB1, PPARGC1A |
| inactivation of gsk3 by akt causes accumulation of b-catenin in alveolar macrophages(B) | 36 | 2 | 0.0696 | PIK3R1, IKBKB |
| E-cadherin signaling in the nascent adherens junction(N) | 36 | 2 | 0.0696 | CDH1, PIK3R1 |
| Retinoid metabolism and transport(R) | 38 | 2 | 0.0768 | GPC1, GPC6 |
| Nucleotide-binding domain, leucine rich repeat containing receptor (NLR) signaling pathways(R) | 38 | 2 | 0.0768 | BCL2, IKBKB |
| EPHB forward signaling(N) | 38 | 2 | 0.0768 | PIK3R1, WASL |
| Integration of energy metabolism(R) | 92 | 3 | 0.0783 | ACACB, CACNA1E, ACACA |
| cyclin e destruction pathway(B) | 5 | 1 | 0.0794 | RB1 |
| Signaling events regulated by Ret tyrosine kinase(N) | 39 | 2 | 0.0805 | PIK3R1, PTPN11 |
| Pyruvate metabolism(K) | 39 | 2 | 0.0805 | ACACB, ACACA |
| Oxidative stress response(P) | 40 | 2 | 0.0842 | DDIT3, BCL2 |
| Class I PI3K signaling events(N) | 40 | 2 | 0.0842 | FOXO3, LAT |
| Intrinsic Pathway for Apoptosis(R) | 41 | 2 | 0.0849 | BCL2L11, BCL2 |
| Netrin-1 signaling(R) | 42 | 2 | 0.0849 | WASL, PTPN11 |
| Stabilization and expansion of the E-cadherin adherens junction(N) | 42 | 2 | 0.0849 | IGF1R, CDH1 |
| Plasma membrane estrogen receptor signaling(N) | 42 | 2 | 0.0849 | IGF1R, PIK3R1 |
| Inflammatory mediator regulation of TRP channels(K) | 99 | 3 | 0.0849 | PRKCE, PIK3R1, HTR2A |
| proteolysis and signaling pathway of notch(B) | 6 | 1 | 0.0849 | DLL1 |
| overview of telomerase rna component gene hterc transcriptional regulation(B) | 6 | 1 | 0.0849 | RB1 |
| e2f1 destruction pathway(B) | 6 | 1 | 0.0849 | RB1 |
| regulation of p27 phosphorylation during cell cycle progression(B) | 6 | 1 | 0.0849 | RB1 |

TABLE 27-continued

| GeneSet | Number Of Protein In Gene Set | Protein From Network | FDR | Nodes |
|---|---|---|---|---|
| cell to cell adhesion signaling(B) | 6 | 1 | 0.0849 | PTPN11 |
| Alternative NF-kappaB pathway(N) | 6 | 1 | 0.0849 | NFKB1 |
| Presenilin action in Notch and Wnt signaling(N) | 45 | 2 | 0.0849 | DLL1, APC |
| TNF receptor signaling pathway(N) | 46 | 2 | 0.0849 | NFKB1, IKBKB |
| cbl mediated ligand-induced downregulation of egf receptors pathway(B) | 7 | 1 | 0.0849 | CBL |
| Depolarization of the Presynaptic Terminal Triggers the Opening of Calcium Channels(R) | 7 | 1 | 0.0849 | CACNA1E |
| Toll-like receptor signaling pathway(K) | 106 | 3 | 0.0849 | PIK3R1, NFKB1, IKBKB |
| IL6-mediated signaling events(N) | 47 | 2 | 0.0849 | PIK3R1, PTPN11 |
| TGF-beta receptor signaling(N) | 47 | 2 | 0.0849 | SMAD3, TGFBR2 |
| Signaling by Type 1 Insulin-like Growth Factor 1 Receptor (IGF1R)(R) | 255 | 5 | 0.0849 | IGF1R, PIK3R1, LAT, NCAM1, PTPN11 |
| Cardiac conduction(R) | 107 | 3 | 0.0849 | CACNB1, STIM1, TRDN |
| Heterotrimeric G-protein signaling pathway-Gq alpha and Go alpha mediated pathway(P) | 108 | 3 | 0.0849 | PRKCE, CACNA1E, DRD2 |
| Cocaine addiction(K) | 49 | 2 | 0.0849 | DRD2, NFKB1 |
| TNF signaling pathway(K) | 110 | 3 | 0.0849 | PIK3R1, NFKB1, IKBKB |
| Calcium signaling pathway(K) | 182 | 4 | 0.0849 | STIM1, CACNA1E, HTR2A, PPP3CA |
| PIP3 activates AKT signaling(R) | 111 | 3 | 0.0849 | PIK3R1, FOXO3, PTPN11 |
| chaperones modulate interferon signaling pathway(B) | 8 | 1 | 0.0849 | RB1 |
| a4b7 Integrin signaling(N) | 8 | 1 | 0.0849 | ITGB1 |
| Amyotrophic lateral sclerosis (ALS)(K) | 51 | 2 | 0.0849 | BCL2, PPP3CA |
| Signaling events mediated by PTP1B(N) | 52 | 2 | 0.0849 | PIK3R1, LAT |
| Caspase cascade in apoptosis(N) | 52 | 2 | 0.0849 | BCL2, GSN |
| Notch signaling pathway(N) | 52 | 2 | 0.0849 | GATA3, DLL1 |
| Leukocyte transendothelial migration(K) | 116 | 3 | 0.0849 | PIK3R1, ITGB1, PTPN11 |
| Regulation of cholesterol biosynthesis by SREBP (SREBF)(R) | 53 | 2 | 0.0849 | ACACB, ACACA |
| btg family proteins and cell cycle regulation(B) | 9 | 1 | 0.0849 | RB1 |
| proteasome complex(B) | 9 | 1 | 0.0849 | UBE3A |
| Interleukin signaling pathway(P) | 55 | 2 | 0.0849 | FOXO3, IKBKB |
| Basal cell carcinoma(K) | 55 | 2 | 0.0849 | TCF7L2, APC |
| Fatty acid, triacylglycerol, and ketone body metabolism(R) | 195 | 4 | 0.0849 | RORA, ACACA, PPARGC1A, AGT |
| GP1b-IX-V activation signalling(R) | 10 | 1 | 0.0849 | PIK3R1 |

TABLE 27-continued

| GeneSet | Number Of Protein In Gene Set | Protein From Network | FDR | Nodes |
|---|---|---|---|---|
| cxcr4 signaling pathway(B) | 10 | 1 | 0.0849 | PIK3R1 |
| cardiac protection against ros(B) | 10 | 1 | 0.0849 | PRKCE |
| Cell cycle(K) | 124 | 3 | 0.0849 | RB1, TGFB2, SMAD3 |
| Platelet homeostasis(R) | 59 | 2 | 0.0849 | STIM1, PTPN11 |
| PI Metabolism(R) | 59 | 2 | 0.0849 | PIK3R1, MTMR7 |
| Gastrin-CREB signalling pathway via PKC and MAPK(R) | 376 | 6 | 0.0849 | PRKCE, PIK3R1, LAT, HTR2A, NCAM1, AGT |
| il-7 signal transduction(B) | 11 | 1 | 0.0853 | PIK3R1 |
| Signaling by NOTCH4(R) | 11 | 1 | 0.0853 | DLL1 |
| Signaling by NOTCH3(R) | 11 | 1 | 0.0853 | DLL1 |
| protein kinase a at the centrosome(B) | 11 | 1 | 0.0853 | PRKCE |
| rb tumor suppressor/checkpoint signaling in response to dna damage(B) | 11 | 1 | 0.0853 | RB1 |
| regulation of transcriptional activity by pml(B) | 11 | 1 | 0.0853 | RB1 |
| Alpha6 beta4 integrin-ligand interactions(N) | 11 | 1 | 0.0853 | LAMA2 |
| how does *salmonella* hijack a cell(B) | 11 | 1 | 0.0853 | WASL |
| Coregulation of Androgen receptor activity(N) | 60 | 2 | 0.0855 | UBE3A, GSN |
| Cell surface interactions at the vascular wall(R) | 208 | 4 | 0.089 | PIK3R1, ITGB1, GPC1, PTPN11 |
| Direct p53 effectors(N) | 132 | 3 | 0.0923 | RB1, BCL2, APC |
| epo signaling pathway(B) | 12 | 1 | 0.0927 | PTPN11 |
| trka receptor signaling pathway(B) | 12 | 1 | 0.0927 | PIK3R1 |
| Signal regulatory protein (SIRP) family interactions(R) | 12 | 1 | 0.0927 | PTPN11 |
| p53 signaling pathway(B) | 12 | 1 | 0.0927 | RB1 |
| Hepatitis C(K) | 133 | 3 | 0.0939 | PIK3R1, NFKB1, IKBKB |
| Cytosolic DNA-sensing pathway(K) | 64 | 2 | 0.0954 | NFKB1, IKBKB |
| mTOR signaling pathway(N) | 64 | 2 | 0.0954 | PPARGC1A, IKBKB |
| Renin secretion(K) | 65 | 2 | 0.0979 | PPP3CA, AGT |
| il 6 signaling pathway(B) | 13 | 1 | 0.1 | PTPN11 |
| il 3 signaling pathway(B) | 13 | 1 | 0.1 | PTPN11 |
| Platelet Adhesion to exposed collagen(R) | 13 | 1 | 0.1 | ITGB1 |
| Signaling by Activin(R) | 13 | 1 | 0.1 | SMAD3 |
| double stranded rna induced gene expression(B) | 13 | 1 | 0.1 | IKBKB |
| multiple antiapoptotic pathways from igf-1r signaling lead to bad phosphorylation(B) | 13 | 1 | 0.1 | PIK3R1 |
| Circadian Clock(R) | 67 | 2 | 0.1029 | RORA, PPARGC1A |
| Cytosolic sensors of pathogen-associated DNA (R) | 67 | 2 | 0.1029 | NFKB1, IKBKB |
| RET signaling(R) | 222 | 4 | 0.1063 | PIK3R1, LAT, NCAM1, PTPN11 |
| Degradation of beta-catenin by the destruction complex(R) | 70 | 2 | 0.1107 | TCF7L2, APC |

TABLE 27-continued

| GeneSet | Number Of Protein In Gene Set | Protein From Network | FDR | Nodes |
|---|---|---|---|---|
| RIG-I-like receptor signaling pathway(K) | 70 | 2 | 0.1107 | NFKB1, IKBKB |
| Deubiquitination(R) | 226 | 4 | 0.1116 | GATA3, SMAD3, TGFBR2, APC |
| Inflammation mediated by chemokine and cytokine signaling pathway(P) | 71 | 2 | 0.1133 | PRKCE, IKBKB |
| telomeres telomerase cellular aging and immortality(B) | 15 | 1 | 0.1145 | RB1 |
| Prolactin receptor signaling(R) | 15 | 1 | 0.1145 | PTPN11 |
| ucalpain and friends in cell spread(B) | 15 | 1 | 0.1145 | ITGB1 |
| Interferon-gamma signaling pathway(P) | 15 | 1 | 0.1145 | PTPN11 |
| NCAM signaling for neurite out-growth(R) | 231 | 4 | 0.1183 | CACNB1, COL4A1, LAT, NCAM1 |
| Interferon gamma signaling(R) | 73 | 2 | 0.1185 | NCAM1, PTPN11 |
| Metabolism of water-soluble vitamins and cofactors(R) | 73 | 2 | 0.1185 | ACACB, ACACA |
| Adrenergic signaling in cardiomyocytes(K) | 149 | 3 | 0.1207 | CACNB1, PIK3R1, BCL2 |
| bone remodeling(B) | 16 | 1 | 0.1216 | IKBKB |
| nerve growth factor pathway (ngf)(B) | 16 | 1 | 0.1216 | PIK3R1 |
| LPA4-mediated signaling events(N) | 16 | 1 | 0.1216 | PRKCE |
| RAF-independent MAPK1/3 activation(R) | 16 | 1 | 0.1216 | PTPN11 |
| downregulated of mta-3 in er-negative breast tumors(B) | 16 | 1 | 0.1216 | CDH1 |
| y branching of actin filaments(B) | 16 | 1 | 0.1216 | WASL |
| akt signaling pathway(B) | 16 | 1 | 0.1216 | PIK3R1 |
| the igf-1 receptor and longevity(B) | 16 | 1 | 0.1216 | PIK3R1 |
| role of nicotinic acetylcholine receptors in the regulation of apoptosis(B) | 16 | 1 | 0.1216 | PIK3R1 |
| Platinum drug resistance(K) | 75 | 2 | 0.1239 | PIK3R1, BCL2 |
| Pertussis(K) | 76 | 2 | 0.1266 | NFKB1, ITGB1 |
| control of skeletal myogenesis by hdac and calcium/calmodulin-dependent kinase (camk)(B) | 17 | 1 | 0.1287 | PIK3R1 |
| phosphoinositides and their downstream targets(B) | 17 | 1 | 0.1287 | PRKCE |
| Peroxisomal lipid metabolism(R) | 17 | 1 | 0.1287 | AGPS |
| gata3 participate in activating the th2 cytokine genes expression(B) | 17 | 1 | 0.1287 | GATA3 |
| RIG-I/MDA5 mediated induction of IFN-alpha/beta pathways(R) | 77 | 2 | 0.1293 | NFKB1, IKBKB |
| Phagosome(K) | 154 | 3 | 0.1297 | ITGB1, FCGR3A, DYNC1I1 |
| mTOR signaling pathway(K) | 154 | 3 | 0.1297 | IGF1R, PIK3R1, IKBKB |
| Glucocorticoid receptor regulatory network(N) | 78 | 2 | 0.132 | GATA3, NFKB1 |

TABLE 27-continued

| GeneSet | Number Of Protein In Gene Set | Protein From Network | FDR | Nodes |
|---|---|---|---|---|
| EPHA2 forward signaling(N) | 18 | 1 | 0.1357 | PIK3R1 |
| Metabolism of nitric oxide(R) | 18 | 1 | 0.1357 | WASL |
| Degradation of beta catenin(N) | 18 | 1 | 0.1357 | APC |
| Regulation of cytoplasmic and nuclear SMAD2/3 signaling(N) | 18 | 1 | 0.1357 | SMAD3 |
| mets affect on macrophage differentiation(B) | 18 | 1 | 0.1357 | ETS1 |
| VEGF signaling pathway(P) | 18 | 1 | 0.1357 | ETS1 |
| regulation of pgc-1a(B) | 18 | 1 | 0.1357 | PPARGC1A |
| Integrin signalling pathway(P) | 158 | 3 | 0.137 | COL4A1, PIK3R1, ITGB1 |
| Jak-STAT signaling pathway(K) | 158 | 3 | 0.137 | PIK3R1, BCL2, PTPN11 |
| CXCR4-mediated signaling events(N) | 80 | 2 | 0.1374 | PTPN11, CD247 |
| sprouty regulation of tyrosine kinase signals(B) | 19 | 1 | 0.1427 | CBL |
| EGF receptor signaling pathway(P) | 82 | 2 | 0.143 | PRKCE, CBL |
| Visual phototransduction(R) | 83 | 2 | 0.1457 | GPC1, GPC6 |
| Transcriptional regulation of white adipocyte differentiation(R) | 84 | 2 | 0.1485 | PPARGC1A, NFKB1 |
| Canonical Wnt signaling pathway(N) | 20 | 1 | 0.1497 | APC |
| tnf/stress related signaling(B) | 20 | 1 | 0.1497 | IKBKB |
| regulation of bad phosphorylation(B) | 20 | 1 | 0.1497 | PIK3R1 |
| egf signaling pathway(B) | 21 | 1 | 0.1565 | PIK3R1 |
| erk1/erk2 mapk signaling pathway(B) | 21 | 1 | 0.1565 | PTPN11 |
| segmentation clock(B) | 21 | 1 | 0.1565 | DLL1 |
| PDGFR-alpha signaling pathway(N) | 21 | 1 | 0.1565 | PIK3R1 |
| how progesterone initiates the oocyte maturation(B) | 21 | 1 | 0.1565 | PTPN11 |
| regulation of ck1/cdk5 by type 1 glutamate receptors(B) | 21 | 1 | 0.1565 | DRD2 |
| NOD-like receptor signaling pathway(K) | 170 | 3 | 0.1597 | NFKB1, BCL2, IKBKB |
| ErbB signaling pathway(K) | 88 | 2 | 0.1598 | PIK3R1, CBL |
| Gap junction(K) | 88 | 2 | 0.1598 | DRD2, HTR2A |
| stathmin and breast cancer resistance to antimicrotubule agents(B) | 22 | 1 | 0.1633 | CD247 |
| ras signaling pathway(B) | 22 | 1 | 0.1633 | PIK3R1 |
| inhibition of cellular proliferation by gleevec(B) | 22 | 1 | 0.1633 | PIK3R1 |
| Other types of O-glycan biosynthesis(K) | 22 | 1 | 0.1633 | COLGALT2 |
| TRAIL signaling pathway(N) | 22 | 1 | 0.1633 | IKBKB |
| Protein digestion and absorption(K) | 90 | 2 | 0.1655 | ACE2, COL4A1 |
| Rheumatoid arthritis(K) | 90 | 2 | 0.1655 | TGFB2, IL17A |
| Influenza A(K) | 175 | 3 | 0.1695 | PIK3R1, NFKB1, IKBKB |

TABLE 27-continued

| GeneSet | Number Of Protein In Gene Set | Protein From Network | FDR | Nodes |
|---|---|---|---|---|
| Signaling by Robo receptor(R) | 23 | 1 | 0.1701 | GPC1 |
| Effects of PIP2 hydrolysis(R) | 23 | 1 | 0.1701 | PRKCE |
| alk in cardiac myocytes(B) | 23 | 1 | 0.1701 | TGFB2 |
| regulation of eif-4e and p70s6 kinase(B) | 23 | 1 | 0.1701 | PIK3R1 |
| role of erk5 in neuronal survival pathway(B) | 23 | 1 | 0.1701 | PIK3R1 |
| FGF signaling pathway(P) | 92 | 2 | 0.1712 | PRKCE, PTPN11 |
| corticosteroids and cardioprotection(B) | 24 | 1 | 0.1768 | PIK3R1 |
| mtor signaling pathway(B) | 24 | 1 | 0.1768 | PIK3R1 |
| Hypoxia response via HIF activation(P) | 24 | 1 | 0.1768 | PIK3R1 |
| transcription factor creb and its extracellular signals(B) | 24 | 1 | 0.1768 | PIK3R1 |
| Ephrin B reverse signaling(N) | 24 | 1 | 0.1768 | PIK3R1 |
| skeletal muscle hypertrophy is regulated via akt-mtor pathway(B) | 24 | 1 | 0.1768 | PIK3R1 |
| Alpha9 beta1 integrin signaling events(N) | 24 | 1 | 0.1768 | ITGB1 |
| Nongenotropic Androgen signaling(N) | 25 | 1 | 0.1835 | PIK3R1 |
| EndogenousTLR signaling(N) | 25 | 1 | 0.1835 | IKBKB |
| fc epsilon receptor i signaling in mast cells(B) | 25 | 1 | 0.1835 | PIK3R1 |
| Nephrin/Neph1 signaling in the kidney podocyte(N) | 25 | 1 | 0.1835 | WASL |
| tpo signaling pathway(B) | 25 | 1 | 0.1835 | PIK3R1 |
| Signaling by Insulin receptor(R) | 277 | 4 | 0.1872 | PIK3R1, LAT, NCAM1, PTPN11 |
| Progesterone-mediated oocyte maturation(K) | 98 | 2 | 0.1886 | IGF1R, PIK3R1 |
| Herpes simplex infection(K) | 185 | 3 | 0.1896 | NFKB1, IKBKB, PTPN11 |
| S1P2 pathway(N) | 26 | 1 | 0.1901 | PIK3R1 |
| mcalpain and friends in cell motility(B) | 26 | 1 | 0.1901 | ITGB1 |
| Maturity onset diabetes of the young(K) | 26 | 1 | 0.1901 | PAX6 |
| bioactive peptide induced signaling pathway(B) | 26 | 1 | 0.1901 | PIK3R1 |
| RXR and RAR heterodimerization with other nuclear receptor(N) | 26 | 1 | 0.1901 | BCL2 |
| pdgf signaling pathway(B) | 26 | 1 | 0.1901 | PIK3R1 |
| PI3 kinase pathway(P) | 26 | 1 | 0.1901 | FOXO3 |
| Phosphatidylinositol signaling system(K) | 99 | 2 | 0.1915 | PIK3R1, MTMR7 |
| DNA Damage/Telomere Stress Induced Senescence(R) | 27 | 1 | 0.1966 | RB1 |
| thrombin signaling and protease-activated receptors(B) | 27 | 1 | 0.1966 | PIK3R1 |
| Choline metabolism in cancer(K) | 101 | 2 | 0.1973 | PIK3R1, WASL |

TABLE 27-continued

| GeneSet | Number Of Protein In Gene Set | Protein From Network | FDR | Nodes |
|---|---|---|---|---|
| Signaling by NOTCH2(R) | 28 | 1 | 0.2031 | DLL1 |
| role of erbb2 in signal transduction and oncology(B) | 28 | 1 | 0.2031 | PIK3R1 |
| vegf hypoxia and angiogenesis(B) | 28 | 1 | 0.2031 | PIK3R1 |
| Dorso-ventral axis formation(K) | 28 | 1 | 0.2031 | ETS1 |
| Hippo signaling pathway-multiple species(K) | 29 | 1 | 0.2096 | RASSF1 |
| CD40/CD40L signaling(N) | 29 | 1 | 0.2096 | NFKB1 |
| Response to elevated platelet cytosolic Ca2+(R) | 106 | 2 | 0.2121 | TGFB2, TTN |
| ceramide signaling pathway(B) | 30 | 1 | 0.2159 | IKBKB |
| Regulation of CDC42 activity(N) | 30 | 1 | 0.2159 | APC |
| cAMP signaling pathway(K) | 200 | 3 | 0.2208 | PIK3R1, DRD2, NFKB1 |
| Circadian rhythm(K) | 31 | 1 | 0.2223 | RORA |
| amb2 Integrin signaling(N) | 31 | 1 | 0.2223 | NFKB1 |
| Striated Muscle Contraction(R) | 31 | 1 | 0.2223 | TTN |
| Detoxification of Reactive Oxygen Species(R) | 31 | 1 | 0.2223 | PRDX6 |
| phospholipids as signalling intermediaries(B) | 31 | 1 | 0.2223 | PIK3R1 |
| Regulation of beta-cell development(R) | 31 | 1 | 0.2223 | PAX6 |
| Mucin type O-glycan biosynthesis(K) | 31 | 1 | 0.2223 | C1GALT1 |
| p38 mapk signaling pathway(B) | 31 | 1 | 0.2223 | DDIT3 |
| role of egf receptor transactivation by gpcrs in cardiac hypertrophy(B) | 31 | 1 | 0.2223 | IKBKB |
| EPHA forward signaling(N) | 31 | 1 | 0.2223 | CBL |
| Alzheimer disease-presenilin pathway(P) | 111 | 2 | 0.2269 | CDH1, TCF7L2 |
| Cholinergic synapse(K) | 111 | 2 | 0.2269 | PIK3R1, BCL2 |
| Oncogene Induced Senescence(R) | 32 | 1 | 0.2286 | ETS1 |
| HIF-2-alpha transcription factor network(N) | 32 | 1 | 0.2286 | ETS1 |
| Syndecan-4-mediated signaling events(N) | 32 | 1 | 0.2286 | ITGB1 |
| FAS (CD95) signaling pathway(N) | 32 | 1 | 0.2286 | IKBKB |
| DAG and IP3 signaling(R) | 32 | 1 | 0.2286 | PRKCE |
| toll-like receptor pathway(B) | 32 | 1 | 0.2286 | IKBKB |
| Syndecan-2-mediated signaling events(N) | 32 | 1 | 0.2286 | ITGB1 |
| Noncanonical Wnt signaling pathway(N) | 32 | 1 | 0.2286 | NFATC2 |
| Beta-catenin independent WNT signaling(R) | 112 | 2 | 0.2299 | PPP3CA, TCF7L2 |
| Alpha4 beta1 integrin signaling events(N) | 33 | 1 | 0.2348 | ITGB1 |
| integrin signaling pathway(B) | 33 | 1 | 0.2348 | ITGB1 |
| FAS signaling pathway(P) | 33 | 1 | 0.2348 | GSN |
| Signaling by Leptin(R) | 209 | 3 | 0.24 | LAT, NCAM1, PTPN11 |

TABLE 27-continued

| GeneSet | Number Of Protein In Gene Set | Protein From Network | FDR | Nodes |
|---|---|---|---|---|
| IL8- and CXCR2-mediated signaling events(N) | 34 | 1 | 0.241 | CBL |
| actions of nitric oxide in the heart(B) | 34 | 1 | 0.241 | PIK3R1 |
| Arf6 trafficking events(N) | 34 | 1 | 0.241 | CDH1 |
| Clathrin-mediated endocytosis(R) | 117 | 2 | 0.2448 | WASL, CBL |
| Prion diseases(K) | 35 | 1 | 0.2471 | NCAM1 |
| Internalization of ErbB1(N) | 35 | 1 | 0.2471 | CBL |
| Class I PI3K signaling events mediated by Akt(N) | 35 | 1 | 0.2471 | FOXO3 |
| African trypanosomiasis(K) | 35 | 1 | 0.2471 | LAMA4 |
| Signaling events mediated by TCPTP(N) | 35 | 1 | 0.2471 | ITGB1 |

TABLE 28

| GeneSet | Number Of Protein In Gene Set | Protein From Network | FDR | Nodes |
|---|---|---|---|---|
| BCR signaling pathway(N) | 65 | 7 | 1.04E−05 | ETS1, SYK, CARD11, PIK3R1, PAG1, NFKB1, PTPRC |
| Pathways in cancer(K) | 397 | 13 | 1.04E−05 | GSK3B, ETS1, FGF2, IGF1R, CASP9, TGFBR2, COL4A2, COL4A1, LAMA2, CXCR4, PIK3R1, TGFB2, NFKB1 |
| T cell receptor signaling pathway(K) | 105 | 7 | 1.16E−04 | GSK3B, PRKCQ, CARD11, PIK3R1, NFATC2, NFKB1, PTPRC |
| TCR signaling in naïve CD4+ T cells(N) | 67 | 6 | 1.16E−04 | STIM1, PRKCQ, CARD11, STK39, PAG1, PTPRC |
| B cell receptor signaling pathway(K) | 73 | 6 | 1.51E−04 | GSK3B, SYK, CARD11, PIK3R1, NFATC2, NFKB1 |
| Extracellular matrix organization(R) | 255 | 9 | 2.72E−04 | FGF2, DCN, COL4A2, COL4A1, LAMA2, COL13A1, FBLN2, NCAM1, TGFB2 |
| Small cell lung cancer(K) | 86 | 6 | 2.72E−04 | CASP9, COL4A2, COL4A1, LAMA2, PIK3R1, NFKB1 |
| Angiopoietin receptor Tie2-mediated signaling(N) | 50 | 5 | 2.72E−04 | ETS1, FGF2, ELF1, PIK3R1, NFKB1 |
| PI3K-Akt signaling pathway(K) | 341 | 10 | 2.72E−04 | GSK3B, FGF2, IGF1R, CASP9, SYK, COL4A2, COL4A1, LAMA2, PIK3R1, NFKB1 |
| TCR signaling in naïve CD8+ T cells(N) | 54 | 5 | 3.35E−04 | STIM1, PRKCQ, CARD11, PAG1, PTPRC |
| Amoebiasis(K) | 98 | 6 | 3.61E−04 | COL4A2, COL4A1, LAMA2, PIK3R1, TGFB2, NFKB1 |
| AGE-RAGE signaling pathway in diabetic complications(K) | 101 | 6 | 3.97E−04 | TGFBR2, COL4A2, COL4A1, PIK3R1, TGFB2, NFKB1 |
| Colorectal cancer(K) | 62 | 5 | 4.64E−04 | GSK3B, CASP9, TGFBR2, PIK3R1, TGFB2 |
| Th17 cell differentiation(K) | 107 | 6 | 4.64E−04 | RORA, IL1RAP, TGFBR2, PRKCQ, NFATC2, NFKB1 |
| Insulin resistance(K) | 109 | 6 | 4.84E−04 | GSK3B, PYGM, PRKCQ, PIK3R1, ACACB, NFKB1 |
| Pancreatic cancer(K) | 66 | 5 | 5.40E−04 | CASP9, TGFBR2, PIK3R1, TGFB2, NFKB1 |
| Fc epsilon receptor (FCERI) signaling(R) | 405 | 10 | 6.24E−04 | GSK3B, FGF2, CASP9, SYK, PRKCQ, CARD11, PIK3R1, NCAM1, NFATC2, NFKB1 |
| TCR signaling(R) | 123 | 6 | 7.96E−04 | PRKCQ, CARD11, PIK3R1, PAG1, NFKB1, PTPRC |
| Osteoclast differentiation(K) | 132 | 6 | 1.03E−03 | SYK, TGFBR2, PIK3R1, TGFB2, NFATC2, NFKB1 |
| Signaling by the B Cell Receptor (BCR)(R) | 270 | 8 | 1.03E−03 | GSK3B, FGF2, CASP9, SYK, STIM1, CARD11, PIK3R1, NFKB1 |
| Atypical NF-kappaB pathway(N) | 14 | 3 | 1.03E−03 | SYK, PIK3R1, NFKB1 |

TABLE 28-continued

| GeneSet | Number Of Protein In Gene Set | Protein From Network | FDR | Nodes |
|---|---|---|---|---|
| T cell activation(P) | 81 | 5 | 1.03E−03 | PRKCQ, PIK3R1, NFATC2, NFKB1, PTPRC |
| Prostate cancer(K) | 89 | 5 | 1.49E−03 | GSK3B, IGF1R, CASP9, PIK3R1, NFKB1 |
| Hepatitis B(K) | 146 | 6 | 1.49E−03 | CASP9, PIK3R1, TGFB2, EGR3, NFATC2, NFKB1 |
| Integrins in angiogenesis(N) | 47 | 4 | 1.56E−03 | FGF2, IGF1R, TGFBR2, PIK3R1 |
| Fc-epsilon receptor I signaling in mast cells(N) | 62 | 4 | 4.28E−03 | SYK, PIK3R1, NFATC2, NFKB1 |
| HTLV-I infection(K) | 258 | 7 | 4.28E−03 | GSK3B, ETS1, TGFBR2, PIK3R1, TGFB2, NFATC2, NFKB1 |
| Regulation of retinoblastoma protein(N) | 64 | 4 | 4.48E−03 | ELF1, MYL1, MYOD1, TGFB2 |
| Toxoplasmosis(K) | 118 | 5 | 4.49E−03 | CASP9, LAMA2, PIK3R1, TGFB2, NFKB1 |
| Osteopontin-mediated events(N) | 29 | 3 | 5.96E−03 | SYK, PIK3R1, NFKB1 |
| Adherens junction(K) | 72 | 4 | 5.96E−03 | WASL, IGF1R, TGFBR2, NECTIN3 |
| Focal adhesion(K) | 201 | 6 | 5.96E−03 | GSK3B, IGF1R, COL4A2, COL4A1, LAMA2, PIK3R1 |
| IGF1 pathway(N) | 30 | 3 | 5.96E−03 | IGF1R, GRB10, PIK3R1 |
| Chronic myeloid leukemia(K) | 73 | 4 | 5.96E−03 | TGFBR2, PIK3R1, TGFB2, NFKB1 |
| FoxO signaling pathway(K) | 134 | 5 | 6.50E−03 | IGF1R, TGFBR2, PIK3R1, TGFB2, FBXO32 |
| IL1-mediated signaling events(N) | 34 | 3 | 7.79E−03 | IL1RAP, PIK3R1, NFKB1 |
| Signaling pathways regulating pluripotency of stem cells(K) | 142 | 5 | 7.79E−03 | GSK3B, FGF2, IGF1R, PIK3R1, BMPR1B |
| EGFR tyrosine kinase inhibitor resistance(K) | 81 | 4 | 8.11E−03 | GSK3B, FGF2, IGF1R, PIK3R1 |
| TGF-beta signaling pathway(K) | 84 | 4 | 9.27E−03 | DCN, TGFBR2, TGFB2, BMPR1B |
| Signaling by PDGF(R) | 328 | 7 | 0.0113 | GSK3B, FGF2, CASP9, COL4A2, COL4A1, PIK3R1, NCAM1 |
| Th1 and Th2 cell differentiation(K) | 92 | 4 | 0.0113 | MAML2, PRKCQ, NFATC2, NFKB1 |
| Fc gamma R-mediated phagocytosis(K) | 93 | 4 | 0.0113 | WASL, SYK, PIK3R1, PTPRC |
| cxcr4 signaling pathway(B) | 10 | 2 | 0.0113 | CXCR4, PIK3R1 |
| NF-kappa B signaling pathway(K) | 95 | 4 | 0.0122 | SYK, PRKCQ, CARD11, NFKB1 |
| Calcineurin-regulated NFAT-dependent transcription in lymphocytes(N) | 46 | 3 | 0.0152 | PRKCQ, EGR3, NFATC2 |
| Endocytosis(K) | 260 | 6 | 0.0155 | WASL, IGF1R, TGFBR2, CXCR4, TGFB2, EHD1 |
| Chagas disease (American trypanosomiasis)(K) | 104 | 4 | 0.0155 | TGFBR2, PIK3R1, TGFB2, NFKB1 |
| Axon guidance(K) | 177 | 5 | 0.0155 | GSK3B, CXCR4, PIK3R1, NFATC2, BMPR1B |
| SHP2 signaling(N) | 51 | 3 | 0.0172 | IGF1R, PIK3R1, PAG1 |
| PIP3 activates AKT signaling(R) | 111 | 4 | 0.0172 | GSK3B, FGF2, CASP9, PIK3R1 |
| Role of Calcineurin-dependent NFAT signaling in lymphocytes(N) | 52 | 3 | 0.0172 | GSK3B, PRKCQ, NFATC2 |
| Signaling events mediated by Stem cell factor receptor (c-Kit)(N) | 52 | 3 | 0.0172 | GSK3B, GRB10, PIK3R1 |
| Endometrial cancer(K) | 52 | 3 | 0.0172 | GSK3B, CASP9, PIK3R1 |
| Chemokine signaling pathway(K) | 187 | 5 | 0.0174 | GSK3B, WASL, CXCR4, PIK3R1, NFKB1 |
| Signaling by SCF-KIT(R) | 290 | 6 | 0.0224 | GSK3B, FGF2, CASP9, GRB10, PIK3R1, NCAM1 |
| role of pi3k subunit p85 in regulation of actin organization and cell migration(B) | 16 | 2 | 0.0224 | WASL, PIK3R1 |

TABLE 28-continued

| GeneSet | Number Of Protein In Gene Set | Protein From Network | FDR | Nodes |
|---|---|---|---|---|
| B cell activation(P) | 59 | 3 | 0.0224 | SYK, NFATC2, PTPRC |
| Viral carcinogenesis(K) | 203 | 5 | 0.0224 | SYK, HDAC4, PIK3R1, EGR3, NFKB1 |
| Epstein-Barr virus infection(K) | 204 | 5 | 0.0224 | GSK3B, SYK, HDAC4, PIK3R1, NFKB1 |
| control of skeletal myogenesis by hdac and calcium/calmodulin-dependent kinase (camk)(B) | 17 | 2 | 0.0224 | MYOD1, PIK3R1 |
| Signaling events mediated by focal adhesion kinase(N) | 60 | 3 | 0.0225 | WASL, ETS1, PIK3R1 |
| Proteoglycans in cancer(K) | 205 | 5 | 0.0226 | FGF2, IGF1R, DCN, PIK3R1, TGFB2 |
| VEGF signaling pathway(K) | 61 | 3 | 0.0235 | CASP9, PIK3R1, NFATC2 |
| VEGF signaling pathway(P) | 18 | 2 | 0.025 | ETS1, CASP9 |
| LPA receptor mediated events(N) | 63 | 3 | 0.0251 | GSK3B, PIK3R1, NFKB1 |
| Inflammatory bowel disease (IBD)(K) | 65 | 3 | 0.0251 | RORA, TGFB2, NFKB1 |
| HIF-1-alpha transcription factor network(N) | 65 | 3 | 0.0251 | RORA, ETS1, CXCR4 |
| Angiogenesis(P) | 66 | 3 | 0.0251 | GSK3B, ETS1, CASP9 |
| Renal cell carcinoma(K) | 67 | 3 | 0.0258 | ETS1, PIK3R1, TGFB2 |
| Signaling by EGFR(R) | 317 | 6 | 0.0258 | GSK3B, FGF2, CASP9, PIK3R1, NCAM1, PAG1 |
| Measles(K) | 136 | 4 | 0.0258 | GSK3B, PRKCQ, PIK3R1, NFKB1 |
| C-type lectin receptors (CLRs)(R) | 139 | 4 | 0.0258 | SYK, CARD11, NFATC2, NFKB1 |
| DAP12 interactions(R) | 323 | 6 | 0.0258 | GSK3B, FGF2, CASP9, SYK, PIK3R1, NCAM1 |
| Insulin signaling pathway(K) | 140 | 4 | 0.0258 | GSK3B, PYGM, PIK3R1, ACACB |
| AP-1 transcription factor network(N) | 70 | 3 | 0.0258 | ETS1, ELF1, NFATC2 |
| CDC42 signaling events(N) | 70 | 3 | 0.0258 | GSK3B, WASL, PIK3R1 |
| Adipocytokine signaling pathway(K) | 70 | 3 | 0.0258 | PRKCQ, ACACB, NFKB1 |
| Melanoma(K) | 71 | 3 | 0.0258 | FGF2, IGF1R, PIK3R1 |
| Ras signaling pathway(K) | 229 | 5 | 0.0258 | ETS1, FGF2, IGF1R, PIK3R1, NFKB1 |
| ctcf: first multivalent nuclear factor(B) | 22 | 2 | 0.0264 | PIK3R1, TGFB2 |
| Nephrin interactions(R) | 22 | 2 | 0.0264 | WASL, PIK3R1 |
| Prolactin signaling pathway(K) | 72 | 3 | 0.0266 | GSK3B, PIK3R1, NFKB1 |
| Breast cancer(K) | 146 | 4 | 0.0283 | GSK3B, FGF2, IGF1R, PIK3R1 |
| Effects of PIP2 hydrolysis(R) | 23 | 2 | 0.0287 | PRKCQ, DGKH |
| Signaling events mediated by the Hedgehog family(N) | 23 | 2 | 0.0287 | PIK3R1, TGFB2 |
| Glypican 1 network(N) | 25 | 2 | 0.0304 | FGF2, TGFBR2 |
| Signaling by Interleukins(R) | 460 | 7 | 0.0304 | RORA, IL1RAP, FGF2, SYK, PIK3R1, NCAM1, NFKB1 |
| Hippo signaling pathway(K) | 154 | 4 | 0.0304 | GSK3B, TGFBR2, TGFB2, BMPR1B |
| mTOR signaling pathway(K) | 154 | 4 | 0.0304 | GSK3B, IGF1R, GRB10, PIK3R1 |
| TGF-beta signaling pathway(P) | 80 | 3 | 0.0304 | TGFBR2, TGFB2, BMPR1B |
| CXCR4-mediated signaling events(N) | 80 | 3 | 0.0304 | CXCR4, PAG1, PTPRC |
| Signaling events mediated by Hepatocyte Growth Factor Receptor (c-Met)(N) | 80 | 3 | 0.0304 | WASL, ETS1, PIK3R1 |
| Signaling events mediated by HDAC Class III(N) | 26 | 2 | 0.0304 | MYOD1, HDAC4 |

TABLE 28-continued

| GeneSet | Number Of Protein In Gene Set | Protein From Network | FDR | Nodes |
|---|---|---|---|---|
| Integrin signalling pathway(P) | 158 | 4 | 0.0304 | COL4A2, COL4A1, COL13A1, PIK3R1 |
| ECM-receptor interaction(K) | 82 | 3 | 0.0304 | COL4A2, COL4A1, LAMA2 |
| Insulin-mediated glucose transport(N) | 27 | 2 | 0.0313 | GSK3B, STXBP4 |
| Reelin signaling pathway(N) | 28 | 2 | 0.0335 | GSK3B, PIK3R1 |
| IL2 signaling events mediated by STAT5(N) | 28 | 2 | 0.0335 | ELF1, PIK3R1 |
| Cytokine-cytokine receptor interaction(K) | 265 | 5 | 0.0375 | IL1RAP, TGFBR2, CXCR4, TGFB2, BMPR1B |
| Nectin adhesion pathway(N) | 30 | 2 | 0.0383 | PIK3R1, NECTIN3 |
| Protein digestion and absorption(K) | 90 | 3 | 0.0391 | COL4A2, COL4A1, COL13A1 |
| Wnt signaling pathway(P) | 268 | 5 | 0.0392 | GSK3B, MYH1, PRKCQ, NFATC2, BMPR1B |
| Striated Muscle Contraction(R) | 31 | 2 | 0.0407 | MYBPC1, MYL1 |
| Influenza A(K) | 175 | 4 | 0.0421 | GSK3B, CASP9, PIK3R1, NFKB1 |
| Syndecan-4-mediated signaling events(N) | 32 | 2 | 0.0427 | FGF2, CXCR4 |
| Netrin-mediated signaling events(N) | 32 | 2 | 0.0427 | WASL, PIK3R1 |
| Propanoate metabolism(K) | 32 | 2 | 0.0427 | HADHA, ACACB |
| Longevity regulating pathway(K) | 94 | 3 | 0.0427 | IGF1R, PIK3R1, NFKB1 |
| Tuberculosis(K) | 179 | 4 | 0.0427 | CASP9, SYK, TGFB2, NFKB1 |
| EPO signaling pathway(N) | 33 | 2 | 0.0427 | PIK3R1, NFKB1 |
| HIV-1 Nef: Negative effector of Fas and TNF-alpha(N) | 33 | 2 | 0.0427 | CASP9, NFKB1 |
| Inflammatory mediator regulation of TRP channels(K) | 99 | 3 | 0.0427 | IL1RAP, PRKCQ, PIK3R1 |
| IL2 signaling events mediated by PI3K(N) | 35 | 2 | 0.0427 | PIK3R1, NFKB1 |
| signal transduction through il1r(B) | 35 | 2 | 0.0427 | IL1RAP, TGFB2 |
| Class I PI3K signaling events mediated by Akt(N) | 35 | 2 | 0.0427 | GSK3B, CASP9 |
| Choline metabolism in cancer(K) | 101 | 3 | 0.0427 | WASL, DGKH, PIK3R1 |
| Trk receptor signaling mediated by PI3K and PLC-gamma(N) | 36 | 2 | 0.0427 | GSK3B, PIK3R1 |
| HIF-1 signaling pathway(K) | 103 | 3 | 0.0427 | IGF1R, PIK3R1, NFKB1 |
| Validated transcriptional targets of API family members Fra1 and Fra2(N) | 37 | 2 | 0.0427 | DCN, NFATC2 |
| IL23-mediated signaling events(N) | 37 | 2 | 0.0427 | PIK3R1, NFKB1 |
| GMCSF-mediated signaling events(N) | 37 | 2 | 0.0427 | SYK, PIK3R1 |
| hiv-1 defeats host-mediated resistance by cem15(B) | 3 | 1 | 0.0436 | CXCR4 |
| EPHB forward signaling(N) | 38 | 2 | 0.0449 | WASL, PIK3R1 |
| Signaling events regulated by Ret tyrosine kinase(N) | 39 | 2 | 0.0472 | GRB10, PIK3Rl |
| Signalling by NGF(R) | 421 | 6 | 0.049 | GSK3B, FGF2, CASP9, PIK3R1, NCAM1, NFKB1 |
| Signaling by FGFR3(R) | 40 | 2 | 0.0495 | FGF2, PIK3R1 |
| activation of csk by camp-dependent protein kinase inhibits signaling through the t cell receptor(B) | 41 | 2 | 0.0518 | CXCR4, PTPRC |

TABLE 28-continued

| GeneSet | Number Of Protein In Gene Set | Protein From Network | FDR | Nodes |
|---|---|---|---|---|
| Signaling by FGFR4(R) | 41 | 2 | 0.0518 | FGF2, PIK3R1 |
| Netrin-1 signaling(R) | 42 | 2 | 0.0542 | WASL, PRKCQ |
| Plasma membrane estrogen receptor signaling(N) | 42 | 2 | 0.0542 | IGF1R, PIK3R1 |
| Beta3 integrin cell surface interactions(N) | 43 | 2 | 0.0566 | TGFBR2, COL4A1 |
| Axon guidance mediated by netrin(P) | 4 | 1 | 0.058 | NFATC2 |
| phospholipase c signaling pathway(B) | 4 | 1 | 0.058 | PIK3R1 |
| Thyroid hormone signaling pathway(K) | 118 | 3 | 0.0601 | GSK3B, CASP9, PIK3R1 |
| Validated transcriptional targets of deltaNp63 isoforms(N) | 45 | 2 | 0.0616 | GSK3B, STXBP4 |
| Insulin Pathway(N) | 45 | 2 | 0.0616 | GRB10, PIK3R1 |
| PDGFR-beta signaling pathway(N) | 120 | 3 | 0.0628 | WASL, GRB10, PAG1 |
| Neurotrophin signaling pathway(K) | 121 | 3 | 0.0642 | GSK3B, PIK3R1, NFKB1 |
| Platelet activation(K) | 122 | 3 | 0.0656 | SYK, STIM1, PIK3R1 |
| FGF signaling pathway(N) | 47 | 2 | 0.0667 | PIK3R1, NCAM1 |
| Notch-mediated HES/HEY network(N) | 47 | 2 | 0.0667 | MAML2, MYOD1 |
| keratinocyte differentiation(B) | 47 | 2 | 0.0667 | ETS1, PRKCQ |
| AMPK signaling pathway(K) | 124 | 3 | 0.0667 | IGF1R, PIK3R1, ACACB |
| RET signaling(R) | 222 | 4 | 0.0667 | FGF2, GRB10, PIK3R1, NCAM1 |
| GPVI-mediated activation cascade(R) | 49 | 2 | 0.0667 | SYK, PIK3R1 |
| Signaling by FGFR1(R) | 49 | 2 | 0.0667 | FGF2, PIK3R1 |
| NCAM signaling for neurite out-growth(R) | 231 | 4 | 0.0667 | FGF2, COL4A2, COL4A1, NCAM1 |
| Metabolism of carbohydrates(R) | 233 | 4 | 0.0667 | PYGM, DCN, GPC5, B3GAT2 |
| Hepatitis C(K) | 133 | 3 | 0.0667 | GSK3B, PIK3R1, NFKB1 |
| Natural killer cell mediated cytotoxicity(K) | 135 | 3 | 0.0667 | SYK, PIK3R1, NFATC2 |
| Thromboxane A2 receptor signaling(N) | 54 | 2 | 0.0667 | SYK, PRKCQ |
| IL2-mediated signaling events(N) | 54 | 2 | 0.0667 | SYK, PIK3R1 |
| Alternative NF-kappaB pathway(N) | 6 | 1 | 0.0667 | NFKB1 |
| Legionellosis(K) | 55 | 2 | 0.0667 | CASP9, NFKB1 |
| Non-small cell lung cancer(K) | 56 | 2 | 0.0667 | CASP9, PIK3R1 |
| Apoptosis(K) | 140 | 3 | 0.0667 | CASP9, PIK3R1, NFKB1 |
| Acute myeloid leukemia(K) | 57 | 2 | 0.0667 | PIK3R1, NFKB1 |
| Phospholipase D signaling pathway(K) | 144 | 3 | 0.0667 | SYK, DGKH, PIK3R1 |
| Viral myocarditis(K) | 59 | 2 | 0.0677 | CASP9, LAMA2 |
| Cell adhesion molecules (CAMs)(K) | 145 | 3 | 0.0679 | NCAM1, PTPRC, NECTIN3 |
| MAPK signaling pathway(K) | 255 | 4 | 0.0715 | FGF2, TGFBR2, TGFB2, NFKB1 |
| Signaling by Type 1 Insulin-like Growth Factor 1 Receptor (IGF1R)(R) | 255 | 4 | 0.0715 | FGF2, IGF1R, PIK3R1, NCAM1 |
| Gastrin-CREB signalling pathway via PKC and MAPK(R) | 376 | 5 | 0.0721 | FGF2, PRKCQ, DGKH, PIK3R1, NCAM1 |
| Non-alcoholic fatty liver disease (NAFLD)(K) | 151 | 3 | 0.0751 | GSK3B, PIK3R1, NFKB1 |
| IL4-mediated signaling events(N) | 63 | 2 | 0.0762 | ETS1, PIK3R1 |
| Ras Pathway(P) | 63 | 2 | 0.0762 | GSK3B, ETS1 |
| Ligand-independent caspase activation via DCC(R) | 8 | 1 | 0.0766 | CASP9 |

TABLE 28-continued

| GeneSet | Number Of Protein In Gene Set | Protein From Network | FDR | Nodes |
|---|---|---|---|---|
| pertussis toxin-insensitive ccr5 signaling in macrophage(B) | 8 | 1 | 0.0766 | CXCR4 |
| signal dependent regulation of myogenesis by corepressor mitr(B) | 8 | 1 | 0.0766 | MYOD1 |
| Downstream signaling in naïve CD8+ T cells(N) | 64 | 2 | 0.0784 | PRKCQ, NFATC2 |
| Longevity regulating pathway - multiple species(K) | 64 | 2 | 0.0784 | IGF1R, PIK3R1 |
| Semaphorin interactions(R) | 65 | 2 | 0.0806 | GSK3B, PTPRC |
| Shigellosis(K) | 65 | 2 | 0.0806 | WASL, NFKB1 |
| Glioma(K) | 66 | 2 | 0.0829 | IGF1R, PIK3R1 |
| Beta1 integrin cell surface interactions(N) | 66 | 2 | 0.0829 | COL4A1, LAMA2 |
| Fcgamma receptor (FCGR) dependent phagocytosis(R) | 159 | 3 | 0.0854 | WASL, SYK, PIK3R1 |
| regulators of bone mineralization(B) | 9 | 1 | 0.0859 | COL4A2 |
| 5-Hydroxytryptamine degredation(P) | 9 | 1 | 0.0859 | ALDH1A2 |
| p75(NTR)-mediated signaling(N) | 69 | 2 | 0.0898 | CASP9, PIK3R1 |
| Fc epsilon RI signaling pathway(K) | 70 | 2 | 0.0921 | SYK, PIK3R1 |
| Signaling by Insulin receptor(R) | 277 | 4 | 0.0922 | FGF2, GRB10, PIK3R1, NCAM1 |
| Signaling by FGFR2(R) | 71 | 2 | 0.0945 | FGF2, PIK3R1 |
| GP1b-IX-V activation signalling(R) | 10 | 1 | 0.0952 | PIK3R1 |
| Leishmaniasis(K) | 73 | 2 | 0.0992 | TGFB2, NFKB1 |
| Platinum drug resistance(K) | 75 | 2 | 0.1007 | CASP9, PIK3R1 |
| il-7 signal transduction(B) | 11 | 1 | 0.1007 | PIK3R1 |
| Alpha6 beta4 integrin-ligand interactions(N) | 11 | 1 | 0.1007 | LAMA2 |
| how does *salmonella* hijack a cell(B) | 11 | 1 | 0.1007 | WASL |
| Glucocorticoid receptor regulatory network(N) | 78 | 2 | 0.1007 | GSK3B, NFKB1 |
| Bacterial invasion of epithelial cells(K) | 78 | 2 | 0.1007 | WASL, PIK3R1 |
| insulin signaling pathway(B) | 12 | 1 | 0.1007 | PIK3R1 |
| trka receptor signaling pathway(B) | 12 | 1 | 0.1007 | PIK3R1 |
| Transcriptional misregulation in cancer(K) | 180 | 3 | 0.1007 | IGF1R, TGFBR2, NFKB1 |
| C-MYB transcription factor network(N) | 82 | 2 | 0.1007 | ETS1, MYOD1 |
| human cytomegalovirus and map kinase pathways(B) | 13 | 1 | 0.1007 | PIK3R1 |
| Fatty acid biosy nthesis(K) | 13 | 1 | 0.1007 | ACACB |
| b cell survival pathway(B) | 13 | 1 | 0.1007 | PIK3R1 |
| multiple antiapoptotic pathways from igf-1r signaling lead to bad phosphorylation(B) | 13 | 1 | 0.1007 | PIK3R1 |
| Visual phototransduction(R) | 83 | 2 | 0.1007 | PRKCQ, GPC5 |
| Hypertrophic cardiomyopathy (HCM)(K) | 83 | 2 | 0.1007 | LAMA2, TGFB2 |
| IL5-mediated signaling events(N) | 14 | 1 | 0.1007 | PIK3R1 |
| *Salmonella* infection(K) | 86 | 2 | 0.1007 | WASL, NFKB1 |

TABLE 28-continued

| GeneSet | Number Of Protein In Gene Set | Protein From Network | FDR | Nodes |
|---|---|---|---|---|
| ErbB signaling pathway(K) | 88 | 2 | 0.1007 | GSK3B, PIK3R1 |
| Sumoylation by RanBP2 regulates transcriptional repression(N) | 15 | 1 | 0.1007 | HDAC4 |
| Dilated cardiomyopathy(K) | 90 | 2 | 0.1007 | LAMA2, TGFB2 |
| FGF signaling pathway(P) | 92 | 2 | 0.1007 | FGF2, PRKCQ |
| nerve growth factor pathway (ngf)(B) | 16 | 1 | 0.1007 | PIK3R1 |
| y branching of actin filaments(B) | 16 | 1 | 0.1007 | WASL |
| a kt signaling pathway(B) | 16 | 1 | 0.1007 | PIK3R1 |
| the igf-1 receptor and longevity(B) | 16 | 1 | 0.1007 | PIK3R1 |
| role of nicotinic acetylcholine receptors in the regulation of apoptosis(B) | 16 | 1 | 0.1007 | PIK3R1 |
| pten dependent cell cycle arrest and apoptosis(B) | 17 | 1 | 0.1007 | PIK3R1 |
| Endocrine resistance(K) | 98 | 2 | 0.1007 | IGF1R, PIK3R1 |
| Progesterone-mediated oocyte maturation(K) | 98 | 2 | 0.1007 | IGF1R, PIK3R1 |
| EPHA2 forward signaling(N) | 18 | 1 | 0.1007 | PIK3R1 |
| Metabolism of nitric oxide(R) | 18 | 1 | 0.1007 | WASL |
| Degradation of beta catenin(N) | 18 | 1 | 0.1007 | GSK3B |
| mets affect on macrophage differentiation(B) | 18 | 1 | 0.1007 | ETS1 |
| Phosphatidylinositol signaling system(K) | 99 | 2 | 0.1007 | DGKH, PIK3R1 |
| Rap1 signaling pathway(K) | 212 | 3 | 0.1007 | FGF2, IGF1R, PIK3R1 |
| Regulation of actin cytoskeleton(K) | 214 | 3 | 0.1007 | WASL, FGF2, PIK3R1 |
| sprouty regulation of tyrosine kinase signals(B) | 19 | 1 | 0.1007 | PTPRC |
| tgf beta signaling pathway(B) | 19 | 1 | 0.1007 | TGFB2 |
| tumor suppressor arf inhibits ribosomal biogenesis(B) | 19 | 1 | 0.1007 | PIK3R1 |
| Glucagon signaling pathway(K) | 103 | 2 | 0.1007 | PYGM, ACACB |
| Canonical Wnt signaling pathway(N) | 20 | 1 | 0.1007 | GSK3B |
| the co-stimulatory signal during t-cell activation(B) | 20 | 1 | 0.1007 | PIK3R1 |
| regulation of bad phosphorylation(B) | 20 | 1 | 0.1007 | PIK3R1 |
| Toll-like receptor signaling pathway(K) | 106 | 2 | 0.1007 | PIK3R1, NFKB1 |
| Cardiac conduction(R) | 107 | 2 | 0.1007 | TRDN, STIM1 |
| egf signaling pathway(B) | 21 | 1 | 0.1007 | PIK3R1 |
| growth hormone signaling pathway(B) | 21 | 1 | 0.1007 | PIK3R1 |
| E-cadherin signaling in keratinocytes(N) | 21 | 1 | 0.1007 | PIK3R1 |
| igf-1 signaling pathway(B) | 21 | 1 | 0.1007 | PIK3R1 |
| PDGFR-alpha signaling pathway(N) | 21 | 1 | 0.1007 | PIK3R1 |
| nf-kb signaling pathway(B) | 21 | 1 | 0.1007 | NFKB1 |
| TNF signaling pathway(K) | 110 | 2 | 0.1007 | PIK3R1, NFKB1 |
| intrinsic prothrombin activation pathway(B) | 22 | 1 | 0.1018 | COL4A2 |

TABLE 28-continued

| GeneSet | Number Of Protein In Gene Set | Protein From Network | FDR | Nodes |
|---|---|---|---|---|
| ras signaling pathway(B) | 22 | 1 | 0.1018 | PIK3R1 |
| inhibition of cellular proliferation by gleevec(B) | 22 | 1 | 0.1018 | PIK3R1 |
| influence of ras and rho proteins on g1 to s transition(B) | 22 | 1 | 0.1018 | PIK3R1 |
| Nicotinic acetylcholine receptor signaling pathway(P) | 22 | 1 | 0.1018 | MYH1 |
| alk in cardiac myocytes(B) | 23 | 1 | 0.1062 | TGFB2 |
| Signaling by BMP(R) | 23 | 1 | 0.1062 | BMPR1B |
| Canonical NF-kappaB pathway(N) | 23 | 1 | 0.1062 | NFKB1 |
| Biosynthesis of unsaturated fatty acids(K) | 23 | 1 | 0.1062 | HADHA |
| regulation of eif-4e and p70s6 kinase(B) | 23 | 1 | 0.1062 | PIK3R1 |
| role of erk5 in neuronal survival pathway(B) | 23 | 1 | 0.1062 | PIK3R1 |
| Mannose type O-glycan biosynthesis(K) | 23 | 1 | 0.1062 | B3GAT2 |
| Leukocyte transendothelial migration(K) | 116 | 2 | 0.11 | CXCR4, PIK3R1 |
| corticosteroids and cardioprotection(B) | 24 | 1 | 0.1106 | PIK3R1 |
| mtor signaling pathway(B) | 24 | 1 | 0.1106 | PIK3R1 |
| nfkb activation by nontypeable hemophilus influenzae(B) | 24 | 1 | 0.1106 | TGFB2 |
| Hypoxia response via HIF activation(P) | 24 | 1 | 0.1106 | PIK3R1 |
| transcription factor creb and its extracellular signals(B) | 24 | 1 | 0.1106 | PIK3R1 |
| Myogenesis(R) | 24 | 1 | 0.1106 | MYOD1 |
| Ephrin B reverse signaling(N) | 24 | 1 | 0.1106 | PIK3R1 |
| skeletal muscle hypertrophy is regulated via akt-mtor pathway(B) | 24 | 1 | 0.1106 | PIK3R1 |
| VEGFR3 signaling in lymphatic endothelium(N) | 25 | 1 | 0.1149 | PIK3R1 |
| Fatty acid elongation(K) | 25 | 1 | 0.1149 | HADHA |
| Nongenotropic Androgen signaling(N) | 25 | 1 | 0.1149 | PIK3R1 |
| ras-independent pathway in nk cell-mediated cytotoxicity(B) | 25 | 1 | 0.1149 | PIK3R1 |
| S1P3 pathway(N) | 25 | 1 | 0.1149 | CXCR4 |
| C-MYC pathway(N) | 25 | 1 | 0.1149 | GSK3B |
| fc epsilon receptor i signaling in mast cells(B) | 25 | 1 | 0.1149 | PIK3R1 |
| Nephrin/Neph1 signaling in the kidney podocyte(N) | 25 | 1 | 0.1149 | WASL |
| tpo signaling pathway(B) | 25 | 1 | 0.1149 | PIK3R1 |
| Sphingolipid signaling pathway(K) | 120 | 2 | 0.1163 | PIK3R1, NFKB1 |
| S1P2 pathway(N) | 26 | 1 | 0.1192 | PIK3R1 |
| IL3-mediated signaling events(N) | 26 | 1 | 0.1192 | PIK3R1 |
| bioactive peptide induced signaling pathway(B) | 26 | 1 | 0.1192 | PIK3R1 |
| pdgf signaling pathway(B) | 26 | 1 | 0.1192 | PIK3R1 |

TABLE 28-continued

| GeneSet | Number Of Protein In Gene Set | Protein From Network | FDR | Nodes |
|---|---|---|---|---|
| PI3 kinase pathway(P) | 26 | 1 | 0.1192 | GSK3B |
| ALK1 signaling events(N) | 26 | 1 | 0.1192 | TGFBR2 |
| Apoptosis signaling pathway(P) | 26 | 1 | 0.1192 | PRKCQ |
| activation of camp-dependent protein kinase pka(B) | 26 | 1 | 0.1192 | CXCR4 |
| β-arrestins in gpcr desensitization(B) | 26 | 1 | 0.1192 | CXCR4 |
| Binding and Uptake of Ligands by Scavenger Receptors(R) | 124 | 2 | 0.1227 | COL4A2, COL4A1 |
| Cell cycle(K) | 124 | 2 | 0.1227 | GSK3B, TGFB2 |
| Calcium signaling in the CD4+ TCR pathway(N) | 27 | 1 | 0.1235 | NFATC2 |
| thrombin signaling and protease-activated receptors(B) | 27 | 1 | 0.1235 | PIK3R1 |
| VEGFR1 specific signals(N) | 27 | 1 | 0.1235 | PIK3R1 |
| Integrin alphaIIb beta3 signaling(R) | 27 | 1 | 0.1235 | SYK |
| role of β-arrestins in the activation and targeting of map kinases(B) | 28 | 1 | 0.1278 | CXCR4 |
| Signaling by NOTCH2(R) | 28 | 1 | 0.1278 | MAML2 |
| role of erbb2 in signal transduction and oncology(B) | 28 | 1 | 0.1278 | PIK3R1 |
| Butanoate metabolism(K) | 28 | 1 | 0.1278 | HADHA |
| vegf hypoxia and angiogenesis(B) | 28 | 1 | 0.1278 | PIK3R1 |
| Dorso-ventral axis formation(K) | 28 | 1 | 0.1278 | ETS1 |
| EGF receptor (ErbB1) signaling pathway(N) | 29 | 1 | 0.1321 | WASL |
| CD40/CD40L signaling(N) | 29 | 1 | 0.1321 | NFKB1 |
| erk and pi-3 kinase are necessary for collagen binding in corneal epithelia(B) | 30 | 1 | 0.1363 | PIK3R1 |
| Alpha-synuclein signaling(N) | 30 | 1 | 0.1363 | SYK |
| Circadian rhythm(K) | 31 | 1 | 0.1405 | RORA |
| Aurora A signaling(N) | 31 | 1 | 0.1405 | GSK3B |
| beta-Alanine metabolism(K) | 31 | 1 | 0.1405 | HADHA |
| amb2 Integrin signaling(N) | 31 | 1 | 0.1405 | NFKB1 |
| Detoxification of Reactive Oxygen Species(R) | 31 | 1 | 0.1405 | PRDX6 |
| phospholipids as signalling intermediaries(B) | 31 | 1 | 0.1405 | PIK3R1 |
| Mucin type O-glycan biosynthesis(K) | 31 | 1 | 0.1405 | C1GALT1 |
| Antifolate resistance(K) | 31 | 1 | 0.1405 | NFKB1 |
| trefoil factors initiate mucosal healing(B) | 31 | 1 | 0.1405 | PIK3R1 |
| Tight junction(K) | 137 | 2 | 0.1441 | MYH1, PRKCQ |
| Oncogene Induced Senescence(R) | 32 | 1 | 0.1447 | ETS1 |
| HIF-2-alpha transcription factor network(N) | 32 | 1 | 0.1447 | ETS1 |
| roles of β arrestin dependent recruitment of src kinases in gpcr signaling(B) | 32 | 1 | 0.1447 | CXCR4 |

TABLE 28-continued

| GeneSet | Number Of Protein In Gene Set | Protein From Network | FDR | Nodes |
|---|---|---|---|---|
| FAS (CD95) signaling pathway(N) | 32 | 1 | 0.1447 | SYK |
| Noncanonical Wnt signaling pathway(N) | 32 | 1 | 0.1447 | NFATC2 |
| N-cadherin signaling events(N) | 33 | 1 | 0.1489 | PIK3R1 |
| Apoptosis - multiple species(K) | 33 | 1 | 0.1489 | CASP9 |
| FAS signaling pathway(P) | 33 | 1 | 0.1489 | CASP9 |
| actions of nitric oxide in the heart(B) | 34 | 1 | 0.153 | PIK3R1 |
| Signaling by Retinoic Acid(R) | 34 | 1 | 0.153 | ALDH1A2 |
| Wnt signaling pathway(K) | 143 | 2 | 0.1542 | GSK3B, NFATC2 |
| a6b1 and a6b4 Integrin signaling(N) | 35 | 1 | 0.1572 | PIK3R1 |
| B-WICH complex positively regulates rRNA expression(R) | 35 | 1 | 0.1572 | GSK3B |
| Prion diseases(K) | 35 | 1 | 0.1572 | NCAM1 |
| Metabolic pathways(K) | 1266 | 9 | 0.1586 | PYGM, HADHA, ALDH1A2, DGKH, PON1, ACACB, B3GAT2, C1GALT1, PRDX6 |
| Heterotrimeric G-protein signaling pathway-Gi alpha and Gs alpha mediated pathway(P) | 147 | 2 | 0.161 | GSK3B, PYGM |
| Transcriptional regulation of pluripotent stem cells(R) | 36 | 1 | 0.1613 | FGF2 |
| chrebp regulation by carbohydrates and camp(B) | 36 | 1 | 0.1613 | CXCR4 |
| Arachidonic acid metabolism(R) | 36 | 1 | 0.1613 | PON1 |
| Starch and sucrose metabolism(K) | 36 | 1 | 0.1613 | PYGM |
| inactivation of gsk3 by akt causes accumulation of b-catenin in alveolar macrophages(B) | 36 | 1 | 0.1613 | PIK3R1 |
| E-cadherin signaling in the nascent adherens junction(N) | 36 | 1 | 0.1613 | PIK3R1 |
| Signaling by VEGF(R) | 287 | 3 | 0.1645 | FGF2, PIK3R1, NCAM1 |
| Primary immunodeficiency(K) | 37 | 1 | 0.1654 | PTPRC |
| Platelet Aggregation (Plug Formation)(R) | 37 | 1 | 0.1654 | SYK |
| rac1 cell motility signaling pathway(B) | 37 | 1 | 0.1654 | PIK3R1 |
| nfat and hypertrophy of the heart (B) | 37 | 1 | 0.1654 | PIK3R1 |
| Retinoid metabolism and transport(R) | 38 | 1 | 0.1694 | GPC5 |
| Pre-NOTCH Expression and Processing(R) | 38 | 1 | 0.1694 | MAML2 |
| Signaling events mediated by HDAC Class II(N) | 38 | 1 | 0.1694 | HDAC4 |
| Aldosterone-regulated sodium reabsorption(K) | 39 | 1 | 0.1735 | PIK3R1 |
| Pyruvate metabolism(K) | 39 | 1 | 0.1735 | ACACB |
| IFN-gamma pathway(N) | 40 | 1 | 0.1775 | PIK3R1 |
| Tryptophan metabolism(K) | 40 | 1 | 0.1775 | HADHA |
| Class I PI3K signaling events(N) | 40 | 1 | 0.1775 | SYK |

TABLE 28-continued

| GeneSet | Number Of Protein In Gene Set | Protein From Network | FDR | Nodes |
|---|---|---|---|---|
| MicroRNAs in cancer(K) | 299 | 3 | 0.1788 | HDAC4, TGFB2, NFKB1 |
| Intrinsic Pathway for Apoptosis(R) | 41 | 1 | 0.1815 | CASP9 |
| BMP receptor signaling(N) | 41 | 1 | 0.1815 | BMPR1B |
| Oxytocin signaling pathway(K) | 159 | 2 | 0.1818 | PIK3R1, NFATC2 |
| Stabilization and expansion of the E-cadherin adherens junction(N) | 42 | 1 | 0.1855 | IGF1R |
| Signaling by ERBB4(R) | 42 | 1 | 0.1855 | PIK3R1 |
| ion channels and their functional role in vascular endothelium(B) | 43 | 1 | 0.1895 | CXCR4 |
| Signaling by ERBB2(R) | 43 | 1 | 0.1895 | PIK3R1 |
| PAR1-mediated thrombin signaling events(N) | 43 | 1 | 0.1895 | PIK3R1 |
| LKB1 signaling events(N) | 43 | 1 | 0.1895 | GSK3B |
| Fatty acid degradation(K) | 44 | 1 | 0.1935 | HADHA |
| il-2 receptor beta chain in t cell activation(B) | 44 | 1 | 0.1935 | PIK3R1 |
| Integrin-linked kinase signaling(N) | 45 | 1 | 0.1974 | GSK3B |
| Presenilin action in Notch and Wnt signaling(N) | 45 | 1 | 0.1974 | GSK3B |
| cGMP-PKG signaling pathway(K) | 168 | 2 | 0.1977 | PIK3R1, NFATC2 |
| Carbohydrate digestion and absorption(K) | 46 | 1 | 0.2013 | PIK3R1 |
| TNF receptor signaling pathway(N) | 46 | 1 | 0.2013 | NFKB1 |
| Alzheimer's disease(K) | 171 | 2 | 0.203 | GSK3B, CASP9 |
| Hedgehog signaling pathway(K) | 47 | 1 | 0.2052 | GSK3B |
| IL6-mediated signaling events(N) | 47 | 1 | 0.2052 | PIK3R1 |
| TGF-beta receptor signaling(N) | 47 | 1 | 0.2052 | TGFBR2 |
| Apoptotic execution phase(R) | 47 | 1 | 0.2052 | PRKCQ |
| Hedgehog signaling events mediated by Gli proteins(N) | 48 | 1 | 0.2091 | GSK3B |
| Ceramide signaling pathway(N) | 48 | 1 | 0.2091 | NFKB1 |
| Fatty acid metabolism(K) | 48 | 1 | 0.2091 | HADHA |
| Posttranslational regulation of adherens junction stability and dissassembly(N) | 48 | 1 | 0.2091 | IGF1R |
| Type II diabetes mellitus(K) | 48 | 1 | 0.2091 | PIK3R1 |
| t cell receptor signaling pathway(B) | 48 | 1 | 0.2091 | PIK3R1 |
| FoxO family signaling(N) | 48 | 1 | 0.2091 | FBXO32 |
| Valine, leucine and isoleucine degradation(K) | 48 | 1 | 0.2091 | HADHA |
| Notch signaling pathway(K) | 48 | 1 | 0.2091 | MAML2 |
| Cocaine addiction(K) | 49 | 1 | 0.213 | NFKB1 |
| Regulation of Androgen receptor activity(N) | 49 | 1 | 0.213 | GSK3B |
| Malaria(K) | 49 | 1 | 0.213 | TGFB2 |
| Intestinal immune network for IgA production(K) | 49 | 1 | 0.213 | CXCR4 |
| Ovarian steroidogenesis(K) | 50 | 1 | 0.2168 | IGF1R |
| Amyotrophic lateral sclerosis (ALS)(K) | 51 | 1 | 0.2207 | CASP9 |

TABLE 28-continued

| GeneSet | Number Of Protein In Gene Set | Protein From Network | FDR | Nodes |
|---|---|---|---|---|
| Senescence-Associated Secretory Phenotype (SASP)(R) | 52 | 1 | 0.2245 | NFKB1 |
| Signaling events mediated by PTP1B(N) | 52 | 1 | 0.2245 | PIK3R1 |
| Caspase cascade in apoptosis(N) | 52 | 1 | 0.2245 | CASP9 |
| Notch signaling pathway(N) | 52 | 1 | 0.2245 | MAML2 |
| Signaling by MET(R) | 52 | 1 | 0.2245 | PIK3R1 |
| Regulation of cholesterol biosynthesis by SREBP (SREBF)(R) | 53 | 1 | 0.2283 | ACACB |
| Interleukin signaling pathway(P) | 55 | 1 | 0.2358 | GSK3B |
| Endothelin signaling pathway(P) | 55 | 1 | 0.2358 | PRKCQ |
| Basal cell carcinoma(K) | 55 | 1 | 0.2358 | GSK3B |
| Pathogenic *Escherichia coli* infection(K) | 55 | 1 | 0.2358 | WASL |
| Regulation of lipolysis in adipocytes(K) | 56 | 1 | 0.2395 | PIK3R1 |
| Signaling events mediated by HDAC Class I(N) | 56 | 1 | 0.2395 | NFKB1 |
| p53 pathway(N) | 57 | 1 | 0.2433 | GSK3B |
| Fatty acid, triacylglycerol, and ketone body metabolism(R) | 195 | 2 | 0.2461 | RORA, HADHA |
| ATF-2 transcription factor network(N) | 58 | 1 | 0.247 | TGFB2 |

TABLE 29

| GeneSet | Number Of Protein In Gene Set | Protein From Network | FDR | Nodes |
|---|---|---|---|---|
| T cell receptor signaling pathway(K) | 105 | 6 | 1.54E−04 | PIK3R1, CBL, PPP3CA, PPP3CC, PLCG1, SOS1 |
| Th17 cell differentiation(K) | 107 | 6 | 1.54E−04 | PPP3CA, PPP3CC, TBX21, PLCG1, IRF4, 1 LUA |
| BCR signaling pathway(N) | 65 | 5 | 2.02E−04 | PIK3R1, PPP3CA, PPP3CC, TRAF6, SOS1 |
| EPO signaling pathway(N) | 33 | 4 | 3.11E−04 | PIK3R1, CBL, PLCG1, SOS1 |
| T cell activation(P) | 81 | 5 | 3.49E−04 | PIK3R1, PPP3CA, PPP3CC, PLCG1, SOS1 |
| Signaling by FGFR3(R) | 40 | 4 | 4.10E−04 | PIK3R1, CBL, PLCG1, SOS1 |
| Signaling by FGFR4(R) | 41 | 4 | 4.10E−04 | PIK3R1, CBL, PLCG1, SOS1 |
| FGF signaling pathway(N) | 47 | 4 | 6.22E−04 | PIK3R1, CBL, PLCG1, SOS1 |
| Signaling by FGFR1(R) | 49 | 4 | 6.40E−04 | PIK3R1, CBL, PLCG1, SOS1 |
| TCR signaling in naïve CD8+ T cells(N) | 54 | 4 | 8.45E−04 | CBL, PLCG1, TRAF6, SOS1 |
| VEGF signaling pathway(K) | 61 | 4 | 1.10E−03 | PIK3R1, PPP3CA, PPP3CC, PLCG1 |
| PDGFR-alpha signaling pathway(N) | 21 | 3 | 1.10E−03 | PIK3R1, PLCG1, SOS1 |
| Fc-epsilon receptor I signaling in mast cells(N) | 62 | 4 | 1.10E−03 | PIK3R1, CBL, PLCG1, SOS1 |
| Renin secretion(K) | 65 | 4 | 1.23E−03 | PPP3CA, PPP3CC, AGT, ADRB3 |
| TCR signaling in naïve CD4+ T cells(N) | 67 | 4 | 1.26E−03 | CBL, PLCG1, TRAF6, SOS1 |
| Natural killer cell mediated cytotoxicity(K) | 135 | 5 | 1.26E−03 | PIK3R1, PPP3CA, PPP3CC, PLCG1, SOS1 |

TABLE 29-continued

| GeneSet | Number Of Protein In Gene Set | Protein From Network | FDR | Nodes |
|---|---|---|---|---|
| Signaling by FGFR2(R) | 71 | 4 | 1.41E−03 | PIK3R1, CBL, PLCG1, SOS1 |
| B cell receptor signaling pathway(K) | 73 | 4 | 1.50E−03 | PIK3R1, PPP3CA, PPP3CC, SOS1 |
| VEGFR1 specific signals(N) | 27 | 3 | 1.58E−03 | PIK3R1, CBL, PLCG1 |
| EGF receptor (ErbB1) signaling pathway(N) | 29 | 3 | 1.82E−03 | PLCG1, GSN, SOS1 |
| Signaling events mediated by Hepatocyte Growth Factor Receptor (c-Met)(N) | 80 | 4 | 1.82E−03 | PIK3R1, CBL, PLCG1, SOS1 |
| N-cadherin signaling events(N) | 33 | 3 | 2.33E−03 | PIK3R1, PLCG1, GSN |
| ErbB signaling pathway(K) | 88 | 4 | 2.33E−03 | PIK3R1, CBL, PLCG1, SOS1 |
| Th1 and Th2 cell differentiation(K) | 92 | 4 | 2.60E−03 | PPP3CA, PPP3CC, TBX21, PLCG1 |
| Trk receptor signaling mediated by PI3K and PLC-gamma(N) | 36 | 3 | 2.60E−03 | PIK3R1, PLCG1, SOS1 |
| Axon guidance(K) | 177 | 5 | 2.60E−03 | PIK3R1, PPP3CA, PPP3CC, PLCG1, BMPR1B |
| Calcium signaling pathway(K) | 182 | 5 | 2.96E−03 | HTR2A, PPP3CA, PPP3CC, PLCG1, ADRB3 |
| Glucagon signaling pathway(K) | 103 | 4 | 3.45E−03 | PPP3CA, PPP3CC, PCK1, PPARA |
| Signaling by ERBB2(R) | 43 | 3 | 4.02E−03 | PIK3R1, PLCG1, SOS1 |
| Insulin Pathway(N) | 45 | 3 | 4.24E−03 | PIK3R1, CBL, SOS1 |
| IL6-mediated signaling events(N) | 47 | 3 | 4.81E−03 | PIK3R1, LMO4, SOS1 |
| Neurotrophin signaling pathway(K) | 121 | 4 | 5.37E−03 | PIK3R1, PLCG1, TRAF6, SOS1 |
| SHP2 signaling(N) | 51 | 3 | 5.37E−03 | PIK3R1, LMO4, SOS1 |
| Signaling events mediated by Stem cell factor receptor (c-Kit)(N) | 52 | 3 | 5.37E−03 | PIK3R1, CBL, SOS1 |
| Signaling by MET(R) | 52 | 3 | 5.37E−03 | PIK3R1, CBL, SOS1 |
| Non-small cell lung cancer(K) | 56 | 3 | 6.65E−03 | PIK3R1, PLCG1, SOS1 |
| Osteoclast differentiation(K) | 132 | 4 | 6.72E−03 | PIK3R1, PPP3CA, PPP3CC, TRAF6 |
| Hepatitis C(K) | 133 | 4 | 6.91E−03 | PIK3R1, TRAF6, SOS1, PPARA |
| Neurotrophic factor-mediated Trk receptor signaling(N) | 60 | 3 | 7.30E−03 | PIK3R1, PLCG1, SOS1 |
| Signaling events mediated by focal adhesion kinase(N) | 60 | 3 | 7.30E−03 | PIK3R1, PLCG1, SOS1 |
| Insulin signaling pathway(K) | 140 | 4 | 7.47E−03 | PIK3R1, CBL, PCK1, SOS1 |
| Signaling pathways regulating pluripotency of stem cells(K) | 142 | 4 | 7.47E−03 | PIK3R1, ZFHX3, BMPR1B, BMPR1A |
| IL4-mediated signaling events(N) | 63 | 3 | 7.47E−03 | PIK3R1, CBL, IRF4 |
| Signaling events mediated by VEGFR1 and VEGFR2(N) | 63 | 3 | 7.47E−03 | PIK3R1, CBL, PLCG1 |
| MAPK signaling pathway(K) | 255 | 5 | 7.81E−03 | PPP3CA, PPP3CC, NR4A1, TRAF6, SOS1 |
| Glioma(K) | 66 | 3 | 8.53E−03 | PIK3R1, PLCG1, SOS1 |
| Wnt signaling pathway(P) | 268 | 5 | 8.80E−03 | PPP3CA, PPP3CC, MYH1, BMPR1B, BMPR1A |
| Fc epsilon receptor (FCERI) signaling(R) | 405 | 6 | 8.80E−03 | PIK3R1, PPP3CA, PLCG1, NR4A1, TRAF6, SOS1 |
| Signaling by the B Cell Receptor (BCR)(R) | 270 | 5 | 8.80E−03 | PIK3R1, CBL, PLCG1, NR4A1, SOS1 |
| Fc epsilon RI signaling pathway(K) | 70 | 3 | 8.83E−03 | PIK3R1, PLCG1, SOS1 |
| Chronic myeloid leukemia(K) | 73 | 3 | 9.96E−03 | PIK3R1, CBL, SOS1 |
| cGMP-PKG signaling pathway(K) | 168 | 4 | 0.0114 | PIK3R1, PPP3CA, PPP3CC, ADRB3 |

TABLE 29-continued

| GeneSet | Number Of Protein In Gene Set | Protein From Network | FDR | Nodes |
|---|---|---|---|---|
| E-cadherin signaling in keratinocytes(N) | 21 | 2 | 0.0119 | PIK3R1, PLCG1 |
| EGFR tyrosine kinase inhibitor resistance(K) | 81 | 3 | 0.0119 | PIK3R1, PLCG1, SOS1 |
| EGF receptor signaling pathway(P) | 82 | 3 | 0.0119 | CBL, PLCG1, SOS1 |
| Signaling by BMP(R) | 23 | 2 | 0.0136 | BMPR1B, BMPR1A |
| Signaling by Interleukins(R) | 460 | 6 | 0.0143 | PIK3R1, CBL, IRF4, TRAF6, SOS1, IL17A |
| Signaling by EGFR(R) | 317 | 5 | 0.0152 | PIK3R1, CBL, PLCG1, NR4A1, SOS1 |
| VEGFR3 signaling in lymphatic endothelium(N) | 25 | 2 | 0.016 | PIK3R1, SOS1 |
| Fc gamma R-mediated phagocytosis(K) | 93 | 3 | 0.0168 | PIK3R1, PLCG1, GSN |
| IL27-mediated signaling events(N) | 26 | 2 | 0.0168 | TBX21JL17A |
| RXR and RAR heterodimerization with other nuclear receptor(N) | 26 | 2 | 0.0168 | NR4A1, PPARA |
| IL2 signaling events mediated by STAT5(N) | 28 | 2 | 0.0168 | PIK3R1, SOS1 |
| Proteoglycans in cancer(K) | 205 | 4 | 0.0168 | PIK3R1, CBL, PLCG1, SOS1 |
| Inflammatory mediator regulation of TRP channels(K) | 99 | 3 | 0.0168 | PIK3R1, HTR2A, PLCG1 |
| Choline metabolism in cancer(K) | 101 | 3 | 0.0178 | PIK3R1, PLCG1, SOS1 |
| Osteopontin-mediated events(N) | 29 | 2 | 0.0178 | PIK3R1, GSN |
| IGF1 pathway(N) | 30 | 2 | 0.019 | PIK3R1, SOS1 |
| EPHA forward signaling(N) | 31 | 2 | 0.0203 | CBL, PLCG1 |
| Netrin-mediated signaling events(N) | 32 | 2 | 0.0215 | PIK3R1, PLCG1 |
| toll-like receptor pathway(B) | 32 | 2 | 0.0215 | TRAF6, PPARA |
| Insulin resistance(K) | 109 | 3 | 0.022 | PIK3R1, PCK1, PPARA |
| Signaling by Retinoic Acid(R) | 34 | 2 | 0.0228 | PDK3, ALDH1A2 |
| IL1-mediated signaling events(N) | 34 | 2 | 0.0228 | PIK3R1, TRAF6 |
| Internalization of ErbB1(N) | 35 | 2 | 0.0228 | CBL, SOS1 |
| IL2 signaling events mediated by PI3K(N) | 35 | 2 | 0.0228 | PIK3R1, SOS1 |
| GMCSF-mediated signaling events(N) | 37 | 2 | 0.0228 | PIK3R1, SOS1 |
| IL23-mediated signaling events(N) | 37 | 2 | 0.0228 | PIK3R1JL17A |
| PDGFR-beta signaling pathway(N) | 120 | 3 | 0.0229 | CBL, PLCG1, SOS1 |
| TCR signaling(R) | 123 | 3 | 0.0246 | PIK3R1, PLCG1, TRAF6 |
| Signaling events regulated by Ret tyrosine kinase(N) | 39 | 2 | 0.0253 | PIK3R1, SOS1 |
| Pathways in cancer(K) | 397 | 5 | 0.0263 | PIK3R1, CBL, PLCG1, TRAF6, SOS1 |
| FOXA2 and FOXA3 transcription factor networks(N) | 40 | 2 | 0.0265 | PCK1, DLK1 |
| IFN-gamma pathway(N) | 40 | 2 | 0.0265 | PIK3R1, CBL |
| BMP receptor signaling(N) | 41 | 2 | 0.0278 | BMPR1B, BMPR1A |
| Plasma membrane estrogen receptor signaling(N) | 42 | 2 | 0.0291 | PIK3R1, SOS1 |
| Signaling by ERBB4(R) | 42 | 2 | 0.0291 | PIK3R1, SOS1 |
| FoxO signaling pathway(K) | 134 | 3 | 0.031 | PIK3R1, PCK1, SOS1 |
| il-2 receptor beta chain in t cell activation(B) | 44 | 2 | 0.0319 | PIK3R1, CBL |

TABLE 29-continued

| GeneSet | Number Of Protein In Gene Set | Protein From Network | FDR | Nodes |
|---|---|---|---|---|
| Cytokine-cytokine receptor interaction(K) | 265 | 4 | 0.0329 | TNFRSF25, BMPR1B, IL17A, BMPR1A |
| Ubiquitin mediated proteolysis(K) | 137 | 3 | 0.0329 | UBE3A, CBL, TRAF6 |
| Signalling by NGF(R) | 421 | 5 | 0.0329 | PIK3R1, PLCG1, NR4A1, TRAF6, SOS1 |
| Calcineurin-regulated NFAT-dependent transcription in lymphocytes(N) | 46 | 2 | 0.0329 | TBX21, IRF4 |
| Integrins in angiogenesis(N) | 47 | 2 | 0.0329 | PIK3R1, CBL |
| Phospholipase D signaling pathway(K) | 144 | 3 | 0.0329 | PIK3R1, PLCG1, SOS1 |
| Amyotrophic lateral sclerosis (ALS)(K) | 51 | 2 | 0.0329 | PPP3CA, PPP3CC |
| Endometrial cancer(K) | 52 | 2 | 0.0329 | PIK3R1, SOS1 |
| Signaling by SCF-KIT(R) | 290 | 4 | 0.0336 | PIK3R1, CBL, NR4A1, SOS1 |
| IL2-mediated signaling events(N) | 54 | 2 | 0.0353 | PIK3R1, SOS1 |
| phospholipase c signaling pathway(B) | 4 | 1 | 0.0362 | PIK3R1 |
| Integrin signalling pathway(P) | 158 | 3 | 0.0363 | PIK3R1, COL5A1, SOS1 |
| Oxytocin signaling pathway(K) | 159 | 3 | 0.037 | PIK3R1, PPP3CA, PPP3CC |
| Regulation of lipolysis in adipocytes(K) | 56 | 2 | 0.0378 | PIK3R1, ADRB3 |
| Acute myeloid leukemia(K) | 57 | 2 | 0.0391 | PIK3R1, SOS1 |
| B cell activation(P) | 59 | 2 | 0.0418 | PPP3CA, SOS1 |
| Coregulation of Androgen receptor activity(N) | 60 | 2 | 0.0431 | UBE3A, GSN |
| basic mechanism of action of ppara pparb(d) and pparg and effects on gene expression(B) | 5 | 1 | 0.0452 | PPARA |
| Opioid Signalling(R) | 62 | 2 | 0.0459 | PPP3CA, PPP3CC |
| LPA receptor mediated events(N) | 63 | 2 | 0.0469 | PIK3R1, PLCG1 |
| DAP12 interactions(R) | 323 | 4 | 0.0469 | PIK3R1, PLCG1, NR4A1, SOS1 |
| Inflammatory bowel disease (IBD)(K) | 65 | 2 | 0.0469 | TBX21, IL17A |
| Tuberculosis(K) | 179 | 3 | 0.0469 | PPP3CA, PPP3CC, TRAF6 |
| Signaling by PDGF(R) | 328 | 4 | 0.0469 | PIK3R1, PLCG1, NR4A1, SOS1 |
| Angiogenesis(P) | 66 | 2 | 0.0469 | PLCG1, SOS1 |
| Renal cell carcinoma(K) | 67 | 2 | 0.0469 | PIK3R1, SOS1 |
| Long-term potentiation(K) | 67 | 2 | 0.0469 | PPP3CA, PPP3CC |
| cd40l signaling pathway(B) | 6 | 1 | 0.0469 | TRAF6 |
| Amphetamine addiction(K) | 68 | 2 | 0.0469 | PPP3CA, PPP3CC |
| p75(NTR)-mediated signaling(N) | 69 | 2 | 0.0469 | PIK3R1, TRAF6 |
| CDC42 signaling events(N) | 70 | 2 | 0.0469 | PIK3R1, CBL |
| Adipocytokine signaling pathway(K) | 70 | 2 | 0.0469 | PCK1, PPARA |
| PI3K-Akt signaling pathway(K) | 341 | 4 | 0.0469 | PIK3R1, PCK1, NR4A1, SOS1 |
| Inflammation mediated by chemokine and cytokine signaling pathway(P) | 71 | 2 | 0.0469 | PLCG1, SOS1 |
| PPAR signaling pathway(K) | 72 | 2 | 0.0469 | PCK1, PPARA |
| Prolactin signaling pathway(K) | 72 | 2 | 0.0469 | PIK3R1, SOS1 |
| sumoylation as a mechanism to | 7 | 1 | 0.0469 | UBE3A |

TABLE 29-continued

| GeneSet | Number Of Protein In Gene Set | Protein From Network | FDR | Nodes |
|---|---|---|---|---|
| modulate ctbp-dependent gene responses(B) | | | | |
| Abacavir transport and metabolism(R) | 7 | 1 | 0.0469 | PCK1 |
| cbI mediated ligand-induced downregulation of egf receptors pathway(B) | 7 | 1 | 0.0469 | CBL |
| Viral carcinogenesis(K) | 203 | 3 | 0.0469 | UBE3A, PIK3R1, GSN |
| Glucocorticoid receptor regulatory network(N) | 78 | 2 | 0.047 | TBX21, NR4A1 |
| Bacterial invasion of epithelial cells(K) | 78 | 2 | 0.047 | PIK3R1, CBL |
| Epstein-Barr virus infection(K) | 204 | 3 | 0.0475 | PIK3R1, PLCG1, TRAF6 |
| yaci and bcma stimulation of b cell immune responses(B) | 8 | 1 | 0.048 | TRAF6 |
| TGF-beta signaling pathway(P) | 80 | 2 | 0.0492 | BMPR1B, BMPR1A |
| Cell surface interactions at the vascular wall(R) | 208 | 3 | 0.0499 | PIK3R1, PLCG1, SOS1 |
| C-MYB transcription factor network(N) | 82 | 2 | 0.0515 | PPP3CA, ZFHX3 |
| Gastrin-CREB signalling pathway via PKC and MAPK(R) | 376 | 4 | 0.0527 | PIK3R1, HTR2A, AGT, SOS1 |
| Regulation of actin cytoskeleton(K) | 214 | 3 | 0.0537 | PIK3R1, GSN, SOS1 |
| TGF-beta signaling pathway(K) | 84 | 2 | 0.0538 | BMPR1B, BMPR1A |
| Transcriptional regulation of white adipocyte differentiation(R) | 84 | 2 | 0.0538 | PCK1, PPARA |
| EGFR-dependent Endothelin signaling events(N) | 9 | 1 | 0.0539 | SOS1 |
| proteasome complex(B) | 9 | 1 | 0.0539 | UBE3A |
| 5-Hydroxytryptamine degredation(P) | 9 | 1 | 0.0539 | ALDH1A2 |
| Small cell lung cancer(K) | 86 | 2 | 0.0561 | PIK3R1, TRAF6 |
| Gap junction(K) | 88 | 2 | 0.0561 | HTR2A, SOS1 |
| RET signaling(R) | 222 | 3 | 0.0561 | PIK3R1, PLCG1, SOS1 |
| GP1b-IX-V activation signalling(R) | 10 | 1 | 0.0561 | PIK3R1 |
| cxcr4 signaling pathway(B) | 10 | 1 | 0.0561 | PIK3R1 |
| Prostate cancer(K) | 89 | 2 | 0.0561 | PIK3R1, SOS1 |
| FGF signaling pathway(P) | 92 | 2 | 0.0561 | PLCG1, SOS1 |
| Ras signaling pathway(K) | 229 | 3 | 0.0561 | PIK3R1, PLCG1, SOS1 |
| il-7 signal transduction(B) | 11 | 1 | 0.0561 | PIK3R1 |
| Metabolism of carbohydrates(R) | 233 | 3 | 0.0561 | PCK1, GPC6, B3GAT1 |
| NF-kappa B signaling pathway(K) | 95 | 2 | 0.0561 | PLCG1, TRAF6 |
| Endocrine resistance(K) | 98 | 2 | 0.0561 | PIK3R1, SOS1 |
| insulin signaling pathway(B) | 12 | 1 | 0.0561 | PIK3R1 |
| trka receptor signaling pathway(B) | 12 | 1 | 0.0561 | PIK3R1 |
| Phosphatidylinositol signaling system(K) | 99 | 2 | 0.0561 | PIK3R1, PLCG1 |
| Estrogen signaling pathway(K) | 100 | 2 | 0.0561 | PIK3R1, SOS1 |
| AGE-RAGE signaling pathway in diabetic | 101 | 2 | 0.0561 | PIK3R1, PLCG1 |

| GeneSet | Number Of Protein In Gene Set | Protein From Network | FDR | Nodes |
|---|---|---|---|---|
| complications(K) | | | | |
| human cytomegalovirus and map kinase pathways(B) | 13 | 1 | 0.0561 | PIK3R1 |
| Metabolism of Angiotensinogen to Angiotensins(R) | 13 | 1 | 0.0561 | AGT |
| b cell survival pathway(B) | 13 | 1 | 0.0561 | PIK3R1 |
| multiple antiapoptotic pathways from igf-1r signaling lead to bad phosphorylation(B) | 13 | 1 | 0.0561 | PIK3R1 |
| HIF-1 signaling pathway(K) | 103 | 2 | 0.0561 | PIK3R1, PLCG1 |
| Chagas disease (American trypanosomiasis)(K) | 104 | 2 | 0.0561 | PIK3R1, TRAF6 |
| Toll-like receptor signaling pathway(K) | 106 | 2 | 0.0561 | PIK3R1, TRAF6 |
| S1P4 pathway(N) | 14 | 1 | 0.0561 | PLCG1 |
| Atypical NF-kappaB pathway(N) | 14 | 1 | 0.0561 | PIK3R1 |
| IL5-mediated signaling events(N) | 14 | 1 | 0.0561 | PIK3R1 |
| HTLV-I infection(K) | 258 | 3 | 0.0561 | PIK3R1, PPP3CA, PPP3CC |
| Endocytosis(K) | 260 | 3 | 0.0561 | CBL, ADRB3, TRAF6 |
| PIP3 activates AKT signaling(R) | 111 | 2 | 0.0561 | PIK3R1, NR4A1 |
| Glutamatergic synapse(K) | 114 | 2 | 0.0561 | PPP3CA, PPP3CC |
| bone remodeling(B) | 16 | 1 | 0.0561 | TRAF6 |
| akt signaling pathway(B) | 16 | 1 | 0.0561 | PIK3R1 |
| the igf-1 receptor and longevity(B) | 16 | 1 | 0.0561 | PIK3R1 |
| nerve growth factor pathway (ngf)(B) | 16 | 1 | 0.0561 | PIK3R1 |
| role of nicotinic acetylcholine receptors in the regulation of apoptosis(B) | 16 | 1 | 0.0561 | PIK3R1 |
| role of pi3k subunit p85 in regulation of actin organization and cell migration(B) | 16 | 1 | 0.0561 | PIK3R1 |
| Leukocyte transendothelial migration(K) | 116 | 2 | 0.0561 | PIK3R1, PLCG1 |
| Toxoplasmosis(K) | 118 | 2 | 0.0561 | PIK3R1, TRAF6 |
| Thyroid hormone signaling pathway(K) | 118 | 2 | 0.0561 | PIK3R1, PLCG1 |
| control of skeletal myogenesis by hdac and calcium/calmodulin-dependent kinase (camk)(B) | 17 | 1 | 0.0561 | PIK3R1 |
| pten dependent cell cycle arrest and apoptosis(B) | 17 | 1 | 0.0561 | PIK3R1 |
| EPHA2 forward signaling(N) | 18 | 1 | 0.0561 | PIK3R1 |
| S1P1 pathway(N) | 18 | 1 | 0.0561 | PLCG1 |
| VEGF signaling pathway(P) | 18 | 1 | 0.0561 | PLCG1 |
| regulation of pgc-1a(B) | 18 | 1 | 0.0561 | PPARA |
| AMPK signaling pathway(K) | 124 | 2 | 0.0561 | PIK3R1, PCK1 |
| Oocyte meiosis(K) | 124 | 2 | 0.0561 | PPP3CA, PPP3CC |

TABLE 29-continued

| GeneSet | Number Of Protein In Gene Set | Protein From Network | FDR | Nodes |
|---|---|---|---|---|
| Signaling by VEGF(R) | 287 | 3 | 0.0561 | PIK3R1, PLCG1, SOS1 |
| sprouty regulation of tyrosine kinase signals(B) | 19 | 1 | 0.0561 | CBL |
| tumor suppressor arf inhibits ribosomal biogenesis(B) | 19 | 1 | 0.0561 | PIK3R1 |
| the co-stimulatory signal during t-cell activation(B) | 20 | 1 | 0.059 | PIK3R1 |
| regulation of bad phosphorylation(B) | 20 | 1 | 0.059 | PIK3R1 |
| Dopaminergic synapse(K) | 130 | 2 | 0.0592 | PPP3CA, PPP3CC |
| egf signaling pathway(B) | 21 | 1 | 0.0618 | PIK3R1 |
| growth hormone signaling pathway(B) | 21 | 1 | 0.0618 | PIK3R1 |
| nf-kb signaling pathway(B) | 21 | 1 | 0.0618 | TRAF6 |
| igf-1 signaling pathway(B) | 21 | 1 | 0.0618 | PIK3R1 |
| Measles(K) | 136 | 2 | 0.064 | PIK3R1, TRAF6 |
| ctcf: first multivalent nuclear factor(B) | 22 | 1 | 0.0647 | PIK3R1 |
| ras signaling pathway(B) | 22 | 1 | 0.0647 | PIK3R1 |
| inhibition of cellular proliferation by gleevec(B) | 22 | 1 | 0.0647 | PIK3R1 |
| Nephrin interactions(R) | 22 | 1 | 0.0647 | PIK3R1 |
| influence of ras and rho proteins on g1 to s transition(B) | 22 | 1 | 0.0647 | PIK3R1 |
| Nicotinic acetylcholine receptor signaling pathway(P) | 22 | 1 | 0.0647 | MYH1 |
| C-type lectin receptors (CLRs)(R) | 139 | 2 | 0.0665 | PPP3CA, TRAF6 |
| Renin-angiotensin system(K) | 23 | 1 | 0.0675 | AGT |
| Signaling by Robo receptor(R) | 23 | 1 | 0.0675 | SOS1 |
| regulation of eif-4e and p70s6 kinase(B) | 23 | 1 | 0.0675 | PIK3R1 |
| Canonical NF-kappaB pathway(N) | 23 | 1 | 0.0675 | TRAF6 |
| Signaling events mediated by PRL(N) | 23 | 1 | 0.0675 | AGT |
| role of erk5 in neuronal survival pathway(B) | 23 | 1 | 0.0675 | PIK3R1 |
| Mannose type O-glycan biosynthesis(K) | 23 | 1 | 0.0675 | B3GAT1 |
| Proximal tubule bicarbonate reclamation(K) | 23 | 1 | 0.0675 | PCK1 |
| Signaling events mediated by the Hedgehog family(N) | 23 | 1 | 0.0675 | PIK3R1 |
| Wnt signaling pathway(K) | 143 | 2 | 0.0699 | PPP3CA, PPP3CC |
| corticosteroids and cardioprotection(B) | 24 | 1 | 0.0704 | PIK3R1 |
| Ephrin B reverse signaling(N) | 24 | 1 | 0.0704 | PIK3R1 |
| skeletal muscle hypertrophy is regulated via akt-mtor pathway(B) | 24 | 1 | 0.0704 | PIK3R1 |
| mtor signaling pathway(B) | 24 | 1 | 0.0704 | PIK3R1 |
| Hypoxia response via HIF activation(P) | 24 | 1 | 0.0704 | PIK3R1 |

TABLE 29-continued

| GeneSet | Number Of Protein In Gene Set | Protein From Network | FDR | Nodes |
|---|---|---|---|---|
| transcription factor creb and its extracellular signals(B) | 24 | 1 | 0.0704 | PIK3R1 |
| Breast cancer(K) | 146 | 2 | 0.0725 | PIK3R1, SOS1 |
| fc epsilon receptor i signaling in mast cells(B) | 25 | 1 | 0.0732 | PIK3R1 |
| Nephrin/Neph1 signaling in the kidney podocyte(N) | 25 | 1 | 0.0732 | PLCG1 |
| tpo signaling pathway(B) | 25 | 1 | 0.0732 | PIK3R1 |
| Nongenotropic Androgen signaling(N) | 25 | 1 | 0.0732 | PIK3R1 |
| ras-independent pathway in nk cell-mediated cytotoxicity(B) | 25 | 1 | 0.0732 | PIK3R1 |
| Heterotrimeric G-protein signaling pathway-Gi alpha and Gs alpha mediated pathway(P) | 147 | 2 | 0.0733 | HTR2A, ADRB3 |
| S1P2 pathway(N) | 26 | 1 | 0.076 | PIK3R1 |
| IL3-mediated signaling events(N) | 26 | 1 | 0.076 | PIK3R1 |
| bioactive peptide induced signaling pathway(B) | 26 | 1 | 0.076 | PIK3R1 |
| β-arrestins in gpcr desensitization(B) | 26 | 1 | 0.076 | PPARA |
| pdgf signaling pathway(B) | 26 | 1 | 0.076 | PIK3R1 |
| Non-alcoholic fatty liver disease (NAFLD)(K) | 151 | 2 | 0.0768 | PIK3R1, PPARA |
| thrombin signaling and protease-activated receptors(B) | 27 | 1 | 0.0788 | PIK3R1 |
| Integrin alphaIIb beta3 signaling(R) | 27 | 1 | 0.0788 | SOS1 |
| p38 MAPK signaling pathway(N) | 27 | 1 | 0.0788 | TRAF6 |
| Hippo signaling pathway(K) | 154 | 2 | 0.0794 | BMPR1B, BMPR1A |
| mTOR signaling pathway(K) | 154 | 2 | 0.0794 | PIK3R1, SOS1 |
| role of erbb2 in signal transduction and oncology(B) | 28 | 1 | 0.0816 | PIK3R1 |
| IL8- and CXCR1-mediated signaling events(N) | 28 | 1 | 0.0816 | CBL |
| Reelin signaling pathway(N) | 28 | 1 | 0.0816 | PIK3R1 |
| Dorso-ventral axis formation(K) | 28 | 1 | 0.0816 | SOS1 |
| vegf hypoxia and angiogenesis(B) | 28 | 1 | 0.0816 | PIK3R1 |
| Jak-STAT signaling pathway(K) | 158 | 2 | 0.083 | PIK3R1, SOS1 |
| Fcgamma receptor (FCGR) dependent phagocytosis(R) | 159 | 2 | 0.0839 | PIK3R1, PLCG1 |
| CD40/CD40L signaling(N) | 29 | 1 | 0.0844 | TRAF6 |
| Regulation of CDC42 activity(N) | 30 | 1 | 0.0872 | PLCG1 |
| Nectin adhesion pathway(N) | 30 | 1 | 0.0872 | PIK3R1 |
| erk and pi-3 kinase are necessary for collagen binding in corneal epithelia(B) | 30 | 1 | 0.0872 | PIK3R1 |
| Citrate cycle (TCA cycle)(K) | 30 | 1 | 0.0872 | PCK1 |

TABLE 29-continued

| GeneSet | Number Of Protein In Gene Set | Protein From Network | FDR | Nodes |
|---|---|---|---|---|
| IL12 signaling mediated by STAT4(N) | 31 | 1 | 0.09 | TBX21 |
| Detoxification of Reactive Oxygen Species(R) | 31 | 1 | 0.09 | PRDX6 |
| phospholipids as signalling intermediaries(B) | 31 | 1 | 0.09 | PIK3R1 |
| Regulation of p38-alpha and p38-beta(N) | 31 | 1 | 0.09 | TRAF6 |
| trefoil factors initiate mucosal healing(B) | 31 | 1 | 0.09 | PIK3R1 |
| DAG and IP3 signaling(R) | 32 | 1 | 0.0927 | PLCG1 |
| Alzheimer's disease(K) | 171 | 2 | 0.0949 | PPP3CA, PPP3CC |
| FAS signaling pathway(P) | 33 | 1 | 0.0955 | GSN |
| IL8- and CXCR2-mediated signaling events(N) | 34 | 1 | 0.0982 | CBL |
| actions of nitric oxide in the heart(B) | 34 | 1 | 0.0982 | PIK3R1 |
| a6b1 and a6b4 Integrin signaling(N) | 35 | 1 | 0.101 | PIK3R1 |
| signal transduction through il1r(B) | 35 | 1 | 0.101 | TRAF6 |
| Signaling events mediated by TCPTP(N) | 35 | 1 | 0.101 | SOS1 |
| inactivation of gsk3 by akt causes accumulation of b-catenin in alveolar macrophages(B) | 36 | 1 | 0.1037 | PIK3R1 |
| mechanism of gene regulation by peroxisome proliferators via ppara(B) | 36 | 1 | 0.1037 | PPARA |
| E-cadherin signaling in the nascent adherens junction(N) | 36 | 1 | 0.1037 | PIK3R1 |
| rac1 cell motility signaling pathway(B) | 37 | 1 | 0.1064 | PIK3R1 |
| ErbB2/ErbB3 signaling events(N) | 37 | 1 | 0.1064 | SOS1 |
| Inositol phosphate metabolism(R) | 37 | 1 | 0.1064 | PLCG1 |
| Platelet Aggregation (Plug Formation)(R) | 37 | 1 | 0.1064 | SOS1 |
| nfat and hypertrophy of the heart (B) | 37 | 1 | 0.1064 | PIK3R1 |
| Nucleotide-binding domain, leucine rich repeat containing receptor (NLR) signaling pathways(R) | 38 | 1 | 0.1092 | TRAF6 |
| Retinoid metabolism and transport(R) | 38 | 1 | 0.1092 | GPC6 |
| EPHB forward signaling(N) | 38 | 1 | 0.1092 | PIK3R1 |
| Regulation of RAC1 activity(N) | 38 | 1 | 0.1092 | SOS1 |
| Chemokine signaling pathway(K) | 187 | 2 | 0.1102 | PIK3R1, SOS1 |
| Aldosterone-regulated sodium reabsorption(K) | 39 | 1 | 0.1119 | PIK3R1 |
| Pyruvate metabolism(K) | 39 | 1 | 0.1119 | PCK1 |
| Class I PI3K signaling events(N) | 40 | 1 | 0.1146 | PLCG1 |
| GPCR ligand binding(R) | 395 | 3 | 0.1171 | HTR2A, AGT, ADRB3 |
| Intrinsic Pathway for Apoptosis(R) | 41 | 1 | 0.1173 | PPP3CC |

TABLE 29-continued

| GeneSet | Number Of Protein In Gene Set | Protein From Network | FDR | Nodes |
|---|---|---|---|---|
| Fatty acid, triacylglycerol, and ketone body metabolism(R) | 195 | 2 | 0.1181 | AGT, PPARA |
| Netrin-1 signaling(R) | 42 | 1 | 0.12 | PLCG1 |
| PAR1-mediated thrombin signaling events(N) | 43 | 1 | 0.1226 | PIK3R1 |
| cAMP signaling pathway(K) | 200 | 2 | 0.1231 | PIK3R1, PPARA |
| Focal adhesion(K) | 201 | 2 | 0.1241 | PIK3R1, SOS1 |
| Validated transcriptional targets of deltaNp63 isoforms(N) | 45 | 1 | 0.128 | COL5A1 |
| DNA Double Strand Break Response(R) | 45 | 1 | 0.128 | EYA1 |
| Carbohydrate digestion and absorption(K) | 46 | 1 | 0.1306 | PIK3R1 |
| Amyloid fiber formation(R) | 47 | 1 | 0.1333 | GSN |
| TGF-beta receptor signaling(N) | 47 | 1 | 0.1333 | SOS1 |
| Apoptotic execution phase(R) | 47 | 1 | 0.1333 | GSN |
| Rapl signaling pathway(K) | 212 | 2 | 0.1353 | PIK3R1, PLCG1 |
| t cell receptor signaling pathway(B) | 48 | 1 | 0.1359 | PIK3R1 |
| Type II diabetes mellitus(K) | 48 | 1 | 0.1359 | PIK3R1 |
| GPVI-mediated activation cascade(R) | 49 | 1 | 0.1385 | PIK3R1 |
| GPCR downstream signaling(R) | 915 | 5 | 0.1405 | PIK3R1, HTR2A, AGT, ADRB3, SOS1 |
| Angiopoietin receptor Tie2-mediated signaling(N) | 50 | 1 | 0.1412 | PIK3R1 |
| Vibrio cholerae infection(K) | 51 | 1 | 0.1438 | PLCG1 |
| Caspase cascade in apoptosis(N) | 52 | 1 | 0.1464 | GSN |
| Notch signaling pathway(N) | 52 | 1 | 0.1464 | DLK1 |
| Role of Calcineurin-dependent NFAT signaling in lymphocytes(N) | 52 | 1 | 0.1464 | NR4A1 |
| Mitochondrial biogenesis(R) | 52 | 1 | 0.1464 | PPARA |
| Signaling events mediated by PTPIB(N) | 52 | 1 | 0.1464 | PIK3R1 |
| Regulation of cholesterol biosynthesis by SREBP (SREBF)(R) | 53 | 1 | 0.149 | PPARA |
| Interleukin signaling pathway(P) | 55 | 1 | 0.1542 | SOS1 |
| Signaling by NOTCH1(R) | 59 | 1 | 0.1644 | DLK1 |
| PI Metabolism(R) | 59 | 1 | 0.1644 | PIK3R1 |
| Signaling by PTK6(R) | 61 | 1 | 0.1695 | CBL |
| IL12-mediated signaling events(N) | 61 | 1 | 0.1695 | TBX21 |
| Colorectal cancer(K) | 62 | 1 | 0.1721 | PIK3R1 |
| Validated nuclear estrogen receptor alpha network(N) | 62 | 1 | 0.1721 | LMO4 |
| Costimulation by the CD28 family(R) | 63 | 1 | 0.1746 | PIK3R1 |
| Ras Pathway(P) | 63 | 1 | 0.1746 | SOS1 |
| Longevity regulating pathway - multiple species(K) | 64 | 1 | 0.1771 | PIK3R1 |

TABLE 29-continued

| GeneSet | Number Of Protein In Gene Set | Protein From Network | FDR | Nodes |
|---|---|---|---|---|
| Retinol metabolism(K) | 65 | 1 | 0.1796 | ALDH1A2 |
| Signaling by Type 1 Insulin-like Growth Factor 1 Receptor (IGF1R)(R) | 255 | 2 | 0.181 | PIK3R1, SOS1 |
| Pancreatic cancer(K) | 66 | 1 | 0.1821 | PIK3R1 |
| Beta1 integrin cell surface interactions(N) | 66 | 1 | 0.1821 | COL5A1 |
| ISG15 antiviral mechanism(R) | 67 | 1 | 0.1846 | PLCG1 |
| Circadian Clock(R) | 67 | 1 | 0.1846 | PPARA |
| Central carbon metabolism in cancer(K) | 67 | 1 | 0.1846 | PIK3R1 |
| Glycolysis/ Gluconeogenesis(K) | 67 | 1 | 0.1846 | PCK1 |
| Interferon alpha/beta signaling(R) | 68 | 1 | 0.1871 | IRF4 |
| Epithelial cell signaling in *Helicobacter pylori* infection(K) | 68 | 1 | 0.1871 | PLCG1 |
| Regulation of Telomerase(N) | 68 | 1 | 0.1871 | UBE3A |
| AP-1 transcription factor network(N) | 70 | 1 | 0.1921 | AGT |
| RIG-I-like receptor signaling pathway(K) | 70 | 1 | 0.1921 | TRAF6 |
| Inositol phosphate metabolism(K) | 71 | 1 | 0.1945 | PLCG1 |
| Melanoma(K) | 71 | 1 | 0.1945 | PIK3R1 |
| Signaling by TGF-beta Receptor Complex(R) | 73 | 1 | 0.1994 | CBL |
| Leishmaniasis(K) | 73 | 1 | 0.1994 | TRAF6 |
| Interferon gamma signaling(R) | 73 | 1 | 0.1994 | IRF4 |
| Platinum drug resistance(K) | 75 | 1 | 0.2043 | PIK3R1 |
| Signaling by Insulin receptor(R) | 277 | 2 | 0.2053 | PIK3R1, SOS1 |
| Neuroactive ligand- receptor interaction(K) | 278 | 2 | 0.2064 | HTR2A, ADRB3 |
| Pertussis(K) | 76 | 1 | 0.2067 | TRAF6 |
| RIG-I/MDA5 mediated induction of IFN- alpha/beta pathways(R) | 77 | 1 | 0.2092 | TRAF6 |
| Aldosterone synthesis and secretion(K) | 82 | 1 | 0.2212 | NR4A1 |
| Visual phototransduction(R) | 83 | 1 | 0.2235 | GPC6 |
| MicroRNAs in cancer(K) | 299 | 2 | 0.2299 | PLCG1, SOS1 |
| Rheumatoid arthritis(K) | 90 | 1 | 0.24 | IL17A |
| Salivary secretion(K) | 90 | 1 | 0.24 | ADRB3 |
| Protein digestion and absorption(K) | 90 | 1 | 0.24 | COL5A1 |
| GnRH signaling pathway(K) | 92 | 1 | 0.2446 | SOS1 |
| Longevity regulating pathway(K) | 94 | 1 | 0.2493 | PIK3R1 |

TABLE 30.A1

| | probe | GeneLocus |
|---|---|---|
| 1 | ACACB__12__109146008__109150083__109185066__109187324__RR | ACACB |
| 2 | ACBD6__1__180269638__180272765__180371571__180375410__RR | ACBD6 |
| 3 | ACBD6__1__180337907__180340909__180371571__180375410__FR | ACBD6 |
| 4 | ADRB3__8__37962724__37965269__37984580__37986052__FF | ADRB3 |
| 5 | ADRB3__8__37962724__37965269__37996522__37999233__FR | ADRB3 |
| 6 | ALDH1A2__15__58053198__58062371__58157807__58162832__RR | ALDH1A2 |

TABLE 30.A1-continued

| | | |
|---|---|---|
| 7 | ALDH1A2__15__58053198__58062371__58229591__58234474__RF | ALDH1A2 |
| 8 | ANO2__12__5767708__5775129__5922387__5930466__RR | ANO2 |
| 9 | ANO2__12__5872622__5877860__5922387__5930466__RR | ANO2 |
| 10 | B3GAT1__11__134376219__134382136__134419343__134423366__FF | B3GAT1 |
| 11 | B3GAT2__6__70837358__70839856__70855194__70857991__FR | B3GAT2 |
| 12 | B3GAT2__6__70837358__70839856__70933019__70941366__FF | B3GAT2 |
| 13 | BMP7__20__57274840__57277666__57290751__57294583__RF | BMP7 |
| 14 | C1GALT1__7__7113076__7114831__7258228__7260668__FF | C1GALT1 |
| 15 | CALCR__7__93553156__93563952__93593898__93597071__RF | CALCR |
| 16 | CARD11__7__2966372__2970772__3066095__3073017__RR | CARD11 |
| 17 | CASP9__1__15526774__15533191__15569002__15572579__FR | CASP9 |
| 18 | CBL__11__119249760__119252653__119294588__119299643__RF | CBL |
| 19 | CD36__7__80539507__80544315__80603212__80611693__FR | CD36 |
| 20 | CD36__7__80539507__80544315__80679651__80687690__FR | CD36 |
| 21 | COL13A1__10__69769669__69775141__69840301__69843474__RF | COL13A1 |
| 22 | COL25A1__4__109024771__109031337__109090838__109104305__RR | COL25A1 |
| 23 | COL25A1__4__109090838__109104305__109307411__109309712__RF | COL25A1 |
| 24 | COL4A2__13__110272408__110277108__110487749__110493325__FR | COL4A2 |
| 25 | COL5A1__9__134738485__134741113__134811418__134816113__RR | COL5A1 |
| 26 | CYGB__17__76511049__76513649__76555120__76557454__RF | CYGB |
| 27 | CYGB__17__76533052__76534398__76555120__76557454__RF | CYGB |
| 28 | CYGB__17__76555120__76557454__76593886__76595265__FF | CYGB |
| 29 | CYGB__17__76555120__76557454__76593886__76595265__FR | CYGB |

| | Probe__Count__Total | Probe__Count__Sig | HyperG_Stats | FDR_HyperG |
|---|---|---|---|---|
| 1 | 191 | 87 | 0.388279548 | 1 |
| 2 | 200 | 111 | 0.00091339 | 0.014340227 |
| 3 | 200 | 111 | 0.00091339 | 0.014340227 |
| 4 | 29 | 12 | 0.689607935 | 1 |
| 5 | 29 | 12 | 0.689607935 | 1 |
| 6 | 200 | 111 | 0.00091339 | 0.014340227 |
| 7 | 200 | 111 | 0.00091339 | 0.014340227 |
| 8 | 200 | 111 | 0.00091339 | 0.014340227 |
| 9 | 200 | 111 | 0.00091339 | 0.014340227 |
| 10 | 110 | 65 | 0.001249162 | 0.018857547 |
| 11 | 97 | 39 | 0.81848692 | 1 |
| 12 | 97 | 39 | 0.81848692 | 1 |
| 13 | 79 | 37 | 0.363905679 | 1 |
| 14 | 109 | 57 | 0.056359167 | 0.291065435 |
| 15 | 45 | 37 | 1.92096E−07 | 1.37086E−05 |
| 16 | 122 | 41 | 0.993686632 | 1 |
| 17 | 49 | 22 | 0.520298425 | 1 |
| 18 | 76 | 20 | 0.999603201 | 1 |
| 19 | 200 | 101 | 0.044617305 | 0.247106631 |
| 20 | 200 | 101 | 0.044617305 | 0.247106631 |
| 21 | 200 | 73 | 0.989437228 | 1 |
| 22 | 200 | 73 | 0.989437228 | 1 |
| 23 | 200 | 73 | 0.989437228 | 1 |
| 24 | 47 | 26 | 0.08460057 | 0.378025067 |
| 25 | 200 | 94 | 0.240043966 | 0.795082334 |
| 26 | 33 | 21 | 0.01973308 | 0.135639073 |
| 27 | 33 | 21 | 0.01973308 | 0.135639073 |
| 28 | 33 | 21 | 0.01973308 | 0.135639073 |
| 29 | 33 | 21 | 0.01973308 | 0.135639073 |

TABLE 30.A2

| | Percent__Sig | logFC | AveExpr | t | P.Value | adj.P.Val | B | FC | FC__1 | LS | Loop detected |
|---|---|---|---|---|---|---|---|---|---|---|---|
| 1 | 45.55 | −0.63947 | −0.63947 | −7.69815 | 3.1E−07 | 7.7E−06 | 6.84649 | 0.64195 | −1.55775 | −1 | E__Trn |
| 2 | 55.5 | −0.40863 | −0.40863 | −8.71959 | 4.8E−08 | 2E−06 | 8.7176 | 0.75334 | −1.32742 | −1 | E__Trn |
| 3 | 55.5 | −0.37204 | −0.37204 | −4.7404 | 0.00014 | 0.00085 | 0.65579 | 0.77269 | −1.29418 | −1 | E__Trn |
| 4 | 41.38 | −0.43258 | −0.43258 | −3.39837 | 0.00314 | 0.01255 | −2.26959 | 0.74093 | −1.34965 | −1 | Str__Trn |
| 5 | 41.38 | −0.41009 | −0.41009 | −3.34476 | 0.00354 | 0.0137 | −2.38547 | 0.75257 | −1.32877 | −1 | Str__Trn |
| 6 | 55.5 | −0.42055 | −0.42055 | −8.81299 | 5.2E−08 | 5E−06 | 8.69347 | 0.74714 | −1.33844 | −1 | Str__Trn |
| 7 | 55.5 | −0.38345 | −0.38345 | −10.298 | 3.5E−09 | 3.4E−07 | 11.3398 | 0.7666 | −1.30445 | −1 | E__Trn |
| 8 | 55.5 | −0.41242 | −0.41242 | −5.49229 | 3E−05 | 0.00044 | 2.3207 | 0.75136 | −1.33092 | −1 | Str__Trn |
| 9 | 55.5 | −0.41127 | −0.41127 | −5.12273 | 6.7E−05 | 0.00077 | 1.52446 | 0.75196 | −1.32986 | −1 | Str__Trn |
| 10 | 59.09 | −0.41969 | −0.41969 | −10.1091 | 6.3E−09 | 1.1E−06 | 10.7772 | 0.74758 | −1.33764 | −1 | Str__Trn |
| 11 | 40.21 | −0.37049 | −0.37049 | −9.68101 | 9.3E−09 | 6.4E−07 | 10.3519 | 0.77352 | −1.29279 | −1 | E__Trn |
| 12 | 40.21 | 0.37079 | 0.37079 | 12.5019 | 2.1E−10 | 1.1E−07 | 14.1122 | 1.29306 | 1.29306 | 1 | Str__Ctrl |
| 13 | 46.84 | 0.32369 | 0.32369 | 7.23249 | 7.5E−07 | 1.5E−05 | 5.94574 | 1.25153 | 1.25153 | 1 | E__Ctrl |
| 14 | 52.29 | −0.55555 | −0.55555 | −11.0417 | 1.1E−09 | 1.6E−07 | 12.4709 | 0.6804 | −1.46972 | −1 | E__Trn |
| 15 | 82.22 | 0.32372 | 0.32372 | 7.81516 | 2.5E−07 | 6.6E−06 | 7.06808 | 1.25156 | 1.25156 | 1 | E__Ctrl |
| 16 | 33.61 | −0.37618 | −0.37618 | −8.25898 | 1.1E−07 | 3.7E−06 | 7.89147 | 0.77047 | −1.2979 | −1 | E__Trn |

TABLE 30.A2-continued

| | Percent_Sig | logFC | AveExpr | t | P.Value | adj.P.Val | B | FC | FC_1 | LS | Loop detected |
|---|---|---|---|---|---|---|---|---|---|---|---|
| 17 | 44.9 | −0.3658 | −0.3658 | −7.08702 | 9.9E−07 | 1.8E−05 | 5.6582 | 0.77604 | −1.28859 | −1 | E_Trn |
| 18 | 26.32 | −0.42638 | −0.42638 | −4.61856 | 0.0002 | 0.0017 | 0.42001 | 0.74413 | −1.34385 | −1 | Str_Trn |
| 19 | 50.5 | 0.36751 | 0.36751 | 3.11685 | 0.0057 | 0.01625 | −2.96367 | 1.29012 | 1.29012 | 1 | E_Ctrl |
| 20 | 50.5 | 0.35581 | 0.35581 | 4.03354 | 0.00072 | 0.00306 | −0.93652 | 1.27971 | 1.27971 | 1 | E_Ctrl |
| 21 | 36.5 | −0.39187 | −0.39187 | −7.41112 | 5.3E−07 | 1.2E−05 | 6.29483 | 0.76214 | −1.31209 | −1 | E_Trn |
| 22 | 36.5 | 0.33555 | 0.33555 | 5.20733 | 5.1E−05 | 0.00037 | 1.69682 | 1.26186 | 1.26186 | 1 | E_Ctrl |
| 23 | 36.5 | 0.32915 | 0.32915 | 4.61978 | 0.00019 | 0.00106 | 0.38479 | 1.25627 | 1.25627 | 1 | E_Ctrl |
| 24 | 55.32 | −0.36515 | −0.36515 | −5.22977 | 4.9E−05 | 0.00036 | 1.74644 | 0.77639 | −1.28802 | −1 | E_Trn |
| 25 | 47 | −0.48145 | −0.48145 | −3.82029 | 0.00122 | 0.00625 | −1.3463 | 0.71626 | −1.39614 | −1 | Str_Trn |
| 26 | 63.64 | −0.47142 | −0.47142 | −3.45234 | 0.00278 | 0.01148 | −2.15253 | 0.72126 | −1.38647 | −1 | Str_Trn |
| 27 | 63.64 | −0.48149 | −0.48149 | −3.45927 | 0.00274 | 0.01134 | −2.13747 | 0.71624 | −1.39618 | −1 | Str_Trn |
| 28 | 63.64 | −0.41585 | −0.41585 | −2.94096 | 0.00862 | 0.02643 | −3.24207 | 0.74958 | −1.33409 | −1 | Str_Trn |
| 29 | 63.64 | −0.41368 | −0.41368 | −2.8539 | 0.01041 | 0.03037 | −3.42204 | 0.75071 | −1.33208 | −1 | Str_Trn |

TABLE 30.A3

| | Probe sequence 60 mer | Probe Location | | | | |
|---|---|---|---|---|---|---|
| | | Chr | Start1 | End1 | Start2 | End2 |
| 1 | TCAAGAAAAAATAATAATAATTTTTTTTTCGATTCCTGCTACACATTT TGGCAGAATACT (SEQ ID NO: 184) & (SEQ ID NO: 359) | 12 | 109146008 | 109146039 | 109185066 | 109185097 |
| 2 | ATGCAATCACCAAAAATGTTTTAATTTCTCGACTCTTGGTGATCCAGG TTTCAGAACTTC (SEQ ID NO: 360) | 1 | 180269638 | 180269669 | 180371571 | 180371602 |
| 3 | GGTCACCAGCACAGAATGATGATGAGGATCGACTCTTGGTGATCCAGG TTTCAGAACTTC (SEQ ID NO: 361) | 1 | 180340878 | 180340909 | 180371571 | 180371602 |
| 4 | CGGTCCCTCTGCCCCGGTTACCTACCCGTCGACATTGGAATCACTTTC TAATCCGGGACA (SEQ ID NO: 362) | 8 | 37965238 | 37965269 | 37986021 | 37986052 |
| 5 | CGGTCCCTCTGCCCCGGTTACCTACCCGTCGAGGACATTCCGGCTACC CCTTCCCATCAC (SEQ ID NO: 363) | 8 | 37965238 | 37965269 | 37996522 | 37996553 |
| 6 | ATTTTAAATGTGGCATTTTAGGTTTATTTCGATTTTGCATAAATTGAA AAAGCTGGAGAT (SEQ ID NO: 136) & (SEQ ID NO: 364) | 15 | 58053198 | 58053229 | 58157807 | 58157838 |
| 7 | CCTTGTCTATGAAGTAAGAGATTAAATCTCGAAATAAACCTAAAATGC CACATTTAAAAT (SEQ ID NO: 365) | 15 | 58053198 | 58053229 | 58234443 | 58234474 |
| 8 | GGGGGAAGGGCCCATGCGGACAAGTAGCTCGACTGGCCTCCCACGCCT CCTCCTTTCCTG (SEQ ID NO: 366) | 12 | 5767708 | 5767739 | 5922387 | 5922418 |
| 9 | ATATTTAAAAAAAATTAAGATGTAATTTTCGACTGGCCTCCCACGCCT CCTCCTTTCCTG (SEQ ID NO: 367) | 12 | 5872622 | 5872653 | 5922387 | 5922418 |
| 10 | AAACATTTCTCCTGCCCCTCCTTTTCCTTCGAGCAGCAGCGAACTGTG ATTGCTGTGAGT (SEQ ID NO: 368) | 11 | 134382105 | 134382136 | 134423335 | 134423366 |
| 11 | TTTAAAAAAGCTATGTTTCAGCATAAAATCGATTAGATGCTCTGCAGC TTCCTGAAGTGT (SEQ ID NO: 369) | 6 | 70839825 | 70839856 | 70855194 | 70855225 |
| 12 | TTTAAAAAAGCTATGTTTCAGCATAAAATCGAGTGATTGTTTTAAGTG CTCTAGGCAAGT (SEQ ID NO: 370) | 6 | 70839825 | 70839856 | 70941335 | 70941366 |
| 13 | TTATAGTGAGAATATATGACTTTTGTAATCGAGTTTTATCTTTATTCC CTCCCCATTGGT (SEQ ID NO: 371) | 20 | 57274840 | 57274871 | 57294552 | 57294583 |
| 14 | AAATGTATAAGAACAGAAGAGAATTATCTCGACATGTCTGAAAAGTAT TATCAGCCCTCT (SEQ ID NO: 145) & (SEQ ID NO: 372) & (SEQ ID NO: 561) | 7 | 7114800 | 7114831 | 7260637 | 7260668 |
| 15 | TATAAAGGTGGTTAGGGACAGATTTTCATCGAATTTCACCCATGGTGG AGATATTTCACT (SEQ ID NO: 373) | 7 | 93553156 | 93553187 | 93597040 | 93597071 |
| 16 | CTAGGAAAAAAGAATGGGAAGGAATAGATCGATATAGAATCTCAGTTA TTCCTCAGGAAA (SEQ ID NO: 374) | 7 | 2966372 | 2966403 | 3066095 | 3066126 |
| 17 | TTCAAGGAATTAAACCTAGCCCTTACTATCGATTTTAGGGTATGGATA TTAGGAGCCATA (SEQ ID NO: 375) | 1 | 15533160 | 15533191 | 15569002 | 15569033 |
| 18 | ACCGCCTCACCTCAGCTCTCCAGTGAGATCGATCCTCCCACCTAAGCT TCCCAAGTTGCT (SEQ ID NO: 128) & (SEQ ID NO: 376) & (SEQ ID NO: 618) | 11 | 119249760 | 119249791 | 119299612 | 119299643 |

TABLE 30.A3-continued

| | Probe sequence | | Probe Location | | | |
|---|---|---|---|---|---|---|
| | 60 mer | Chr | Start1 | End1 | Start2 | End2 |
| 19 | TGCTGAAAGAAAACACAATTTATTTAAGTCGAGACACAATTAAGGTTG ATACAAAAAAG (SEQ ID NO: 377) | 7 | 80544284 | 80544315 | 80603212 | 80603243 |
| 20 | TGCTGAAAGAAAACACAATTTATTTAAGTCGAAATTTTGGAAAAGCCC TGATTTAAGTCA (SEQ ID NO: 137) & (SEQ ID NO: 378) | 7 | 80544284 | 80544315 | 80679651 | 80679682 |
| 21 | CCACACATGACTGTATATTTAAATTAATTCGATGCCCAAAGGACTGTC ATAATCACTCAG (SEQ ID NO: 379) | 10 | 69769669 | 69769700 | 69843443 | 69843474 |
| 22 | AAAACACCCTGAATTGGAAGAAAGAAACTCGAGGGATGAGTGTGTATC ATCAAAGTCAAA (SEQ ID NO: 146) & (SEQ ID NO: 380) | 4 | 109024771 | 109024802 | 109090838 | 109090869 |
| 23 | CATGTTTTGAAAAAACTATGCATGGATTTCGAGGGATGAGTGTGTATC ATCAAAGTCAAA (SEQ ID NO: 381) | 4 | 109090838 | 109090869 | 109309681 | 109309712 |
| 24 | TTTAGATAACCAATGTATAGTACGTTAATCGATGTGAAGTTCAAGAAC TGACAAGGCTGT (SEQ ID NO: 382) | 13 | 110277077 | 110277108 | 110487749 | 110487780 |
| 25 | CGCGGGGCCTTCTGGGCCAGGCGGGCCCTCGAAAAGCCCCACGCCCCC CCAGAGCTGCTG (SEQ ID NO: 147) & (SEQ ID NO: 383) | 9 | 134738485 | 134738516 | 134811418 | 134811449 |
| 26 | CCCGGTTTCCTCATCTGTCCCTGCCCCCTCGAGACTTGACTGGGGGAC AATCCACTTTGA (SEQ ID NO: 384) | 17 | 76511049 | 76511080 | 76557423 | 76557454 |
| 27 | CCCGGTTTCCTCATCTGTCCCTGCCCCCTCGAGTCTCAGATGTGAGGG CTGGAACAGATG (SEQ ID NO: 385) | 17 | 76533052 | 76533083 | 76557423 | 76557454 |
| 28 | CCCGGTTTCCTCATCTGTCCCTGCCCCCTCGAACAATCTTGAGCATAG AGAACCAGACCC (SEQ ID NO: 386) | 17 | 76557423 | 76557454 | 76595234 | 76595265 |
| 29 | CCCGGTTTCCTCATCTGTCCCTGCCCCCTCGAAGTATGGAGGTAAATG CCAAAGGCTCAG (SEQ ID NO: 387) | 17 | 76557423 | 76557454 | 76593886 | 76593917 |

TABLE 30.A4

| | Chr.1 | Start1.1 | End1.1 | Start2.1 | End2.1 |
|---|---|---|---|---|---|
| | | 4 kb Sequence Location | | | |
| 1 | 12 | 109146008 | 109150009 | 1.1E+08 | 109189067 |
| 2 | 1 | 180269638 | 180273639 | 1.8E+08 | 180375572 |
| 3 | 1 | 180336908 | 180340909 | 1.8E+08 | 180375572 |
| 4 | 8 | 37961268 | 37965269 | 3.8E+07 | 37986052 |
| 5 | 8 | 37961268 | 37965269 | 3.8E+07 | 38000523 |
| 6 | 15 | 58053198 | 58057199 | 5.8E+07 | 58161808 |
| 7 | 15 | 58053198 | 58057199 | 5.8E+07 | 58234474 |
| 8 | 12 | 5767708 | 5771709 | 5922387 | 5926388 |
| 9 | 12 | 5872622 | 5876623 | 5922387 | 5926388 |
| 10 | 11 | 134378135 | 134382136 | 1.3E+08 | 134423366 |
| 11 | 6 | 70835855 | 70839856 | 7.1E+07 | 70859195 |
| 12 | 6 | 70835855 | 70839856 | 7.1E+07 | 70941366 |
| 13 | 20 | 57274840 | 57278841 | 5.7E+07 | 57294583 |
| 14 | 7 | 7110830 | 7114831 | 7256667 | 7260668 |
| 15 | 7 | 93553156 | 93557157 | 9.4E+07 | 93597071 |

TABLE 30.A4-continued

| | Chr.1 | Start1.1 | End1.1 | Start2.1 | End2.1 |
|---|---|---|---|---|---|
| | | 4 kb Sequence Location | | | |
| 16 | 7 | 2966372 | 2970373 | 3066095 | 3070096 |
| 17 | 1 | 15529190 | 15533191 | 1.6E+07 | 15573003 |
| 18 | 11 | 119249760 | 119253761 | 1.2E+08 | 119299643 |
| 19 | 7 | 80540314 | 80544315 | 8.1E+07 | 80607213 |
| 20 | 7 | 80540314 | 80544315 | 8.1E+07 | 80683652 |
| 21 | 10 | 69769669 | 69773670 | 7E+07 | 69843474 |
| 22 | 4 | 109024771 | 109028772 | 1.1E+08 | 109094839 |
| 23 | 4 | 109090838 | 109094839 | 1.1E+08 | 109309712 |
| 24 | 13 | 110273107 | 110277108 | 1.1E+08 | 110491750 |
| 25 | 9 | 134738485 | 134742486 | 1.3E+08 | 134815419 |
| 26 | 17 | 76511049 | 76515050 | 7.7E+07 | 76557454 |
| 27 | 17 | 76533052 | 76537053 | 7.7E+07 | 76557454 |
| 28 | 17 | 76553453 | 76557454 | 7.7E+07 | 76595265 |
| 29 | 17 | 76553453 | 76557454 | 7.7E+07 | 76597887 |

TABLE 30.B1

| | | | | | |
|---|---|---|---|---|---|
| 30 | DGKH_13_42011104_42015078_42235825_42240914_RR | DGKH | 200 | 99 | 0.078405901 | 0.370774891 |
| 31 | DIAPH3_13_59818047_59823591_59854837_59860534_RR | DIAPH3 | 200 | 91 | 0.389926943 | 1 |
| 32 | DKK3_11_11956071_11968035_11984245_11993733_FR | DKK3 | 62 | 37 | 0.010531285 | 0.08702167 |
| 33 | DKK3_11_11956071_11968035_12010923_12019458_FF | DKK3 | 62 | 37 | 0.010531285 | 0.08702167 |
| 34 | DKK3_11_11956071_11968035_12010923_12019458_FR | DKK3 | 62 | 37 | 0.010531285 | 0.08702167 |
| 35 | DKK3_11_11956071_11968035_12048403_12051930_FR | DKK3 | 62 | 37 | 0.010531285 | 0.08702167 |
| 36 | DLK1_14_100687837_100692867_100749541_100751577_RF | DLK1 | 47 | 28 | 0.025050129 | 0.159872776 |
| 37 | DOK5_20_54466479_54470848_54572383_54577350_RF | DOK5 | 200 | 107 | 0.005388757 | 0.052676227 |
| 38 | EGR3_8_22681793_22682820_22737091_22739184_FF | EGR3 | 33 | 16 | 0.375730688 | 1 |
| 39 | EHD1_11_64868178_64874017_64914431_64916090_RF | EHD1 | 47 | 8 | 0.999981792 | 1 |
| 40 | EMCN_4_100525710_100532027_100732651_100738720_RR | EMCN | 200 | 121 | 2.82028E-06 | 0.000158137 |
| 41 | ETS1_11_128476761_128480323_128561632_128566579_RR | ETS1 | 200 | 112 | 0.000559145 | 0.010705579 |
| 42 | EYA1_8_71216399_71218728_71261816_71267769_RR | EYA1 | 139 | 89 | 2.12839E-06 | 0.000128522 |
| 43 | FBLN2_3_13512352_13515076_13582406_13590343_RF | FBLN2 | 193 | 61 | 0.999882361 | 1 |

TABLE 30.B1-continued

| 44 | FBXO32__8__123526212__123527874__123555254__123559065__FR | FBXO32 | 48 | 27 | 0.06408635 | 0.316104415 |
|---|---|---|---|---|---|---|
| 45 | FOXO1__13__40524349__40526124__40688580__40690771__RR | FOXO1 | 199 | 76 | 0.964953638 | 1 |
| 46 | FOXO3__6__108603215__108604436__108629992__108635481__FR | FOXO3 | 200 | 94 | 0.240043966 | 0.795082334 |
| 47 | FTO__16__53844989__53854574__54045378__54052319__RF | FTO | 200 | 100 | 0.059654823 | 0.302381977 |
| 48 | GPC5__13__91724432__91728749__91910388__91925040__FR | GPC5 | 200 | 102 | 0.032796361 | 0.195038964 |
| 49 | GPC5__13__91794062__91815301__91953115__91957441__RR | GPC5 | 200 | 102 | 0.032796361 | 0.195038964 |
| 50 | GPC6__13__94054831__94060621__94121445__94133208__RF | GPC6 | 200 | 109 | 0.002303017 | 0.026200987 |
| 51 | GPC6__13__94121445__94133208__94296633__94304225__FF | GPC6 | 200 | 109 | 0.002303017 | 0.026200987 |
| 52 | GRB10__7__50706363__50709345__50775503__50780905__RF | GRB10 | 200 | 95 | 0.198157163 | 0.697548759 |
| 53 | GSN__9__121177548__121180410__121268506__121274144__FR | GSN | 200 | 80 | 0.902128149 | 1 |
| 54 | GSN__9__121182946__121189020__121239116__121243347__FF | GSN | 200 | 80 | 0.902128149 | 1 |
| 55 | GSN__9__121227501__121232628__121268506__121274144__FR | GSN | 200 | 80 | 0.902128149 | 1 |
| 56 | GSN__9__121239116__121243347__121268506__121274144__FR | GSN | 200 | 80 | 0.902128149 | 1 |
| 57 | GSN__9__121253564__121256485__121268506__121274144__RR | GSN | 200 | 80 | 0.902128149 | 1 |
| 58 | HDAC9__7__18055950__18064786__18135886__18142010__RF | HDAC9 | 200 | 75 | 0.9780749 | 1 |
| 59 | HOXC6__12__53956382__53960014__53992251__53994278__FF | HOXC6 | 120 | 71 | 0.000728297 | 0.012823129 |

TABLE 30.B2

| 30 | 49.5 | −0.40058 | −0.40058 | −5.54747 | 2.4E−05 | 0.00021 | 2.44404 | 0.75755 | −1.32004 | −1 | E_Trn |
|---|---|---|---|---|---|---|---|---|---|---|---|
| 31 | 45.5 | 0.40519 | 0.40519 | 2.99897 | 0.00741 | 0.02003 | −3.2148 | 1.32426 | 1.32426 | 1 | E_Ctrl |
| 32 | 59.68 | −0.45219 | −0.45219 | −4.49834 | 0.00027 | 0.00205 | 0.15448 | 0.73093 | −1.36812 | −1 | Str_Trn |
| 33 | 59.68 | −0.47444 | −0.47444 | −4.5659 | 0.00023 | 0.00184 | 0.30376 | 0.71975 | −1.38937 | −1 | Str_Trn |
| 34 | 59.68 | −0.43473 | −0.43473 | −4.56246 | 0.00023 | 0.00185 | 0.29618 | 0.73983 | −1.35166 | −1 | Str_Trn |
| 35 | 59.68 | −0.47393 | −0.47393 | −4.80125 | 0.00014 | 0.00127 | 0.82216 | 0.72 | −1.38889 | −1 | Str_Trn |
| 36 | 59.57 | −0.4092 | −0.4092 | −4.72064 | 0.00016 | 0.00144 | 0.64495 | 0.75304 | −1.32794 | −1 | Str_Trn |
| 37 | 53.5 | 0.363 | 0.363 | 12.7216 | 1.5E−10 | 9.4E−08 | 14.389 | 1.28609 | 1.28609 | 1 | Str_Ctrl |
| 38 | 48.48 | −0.37008 | −0.37008 | −9.47862 | 1.3E−08 | 8.1E−07 | 10.0177 | 0.77374 | −1.29242 | −1 | E_Trn |
| 39 | 17.02 | −0.39552 | −0.39552 | −9.28016 | 1.8E−08 | 1E−06 | 9.68498 | 0.76022 | −1.31541 | −1 | E_Trn |
| 40 | 60.5 | 0.37461 | 0.37461 | 6.40303 | 4.6E−06 | 0.00012 | 4.21714 | 1.29649 | 1.29649 | 1 | Str_Ctrl |
| 41 | 56 | −0.37402 | −0.37402 | −9.59542 | 1.1E−08 | 7.1E−07 | 10.2112 | 0.77163 | −1.29596 | −1 | E_Trn |
| 42 | 64.03 | −0.42028 | −0.42028 | −6.88873 | 1.7E−06 | 6E−05 | 5.18442 | 0.74728 | −1.33819 | −1 | Str_Trn |
| 43 | 31.61 | −0.42233 | −0.42233 | −8.04265 | 1.6E−07 | 4.9E−06 | 7.49352 | 0.74622 | −1.34009 | −1 | E_Trn |
| 44 | 56.25 | −0.42891 | −0.42891 | −11.0665 | 1.1E−09 | 1.6E−07 | 12.5076 | 0.74282 | −1.34621 | −1 | E_Trn |
| 45 | 38.19 | 0.39325 | 0.39325 | 6.48089 | 3.9E−06 | 0.00011 | 4.37436 | 1.31335 | 1.31335 | 1 | Str_Ctrl |
| 46 | 47 | 0.36526 | 0.36526 | 6.80414 | 2.1E−06 | 6.8E−05 | 5.01828 | 1.28811 | 1.28811 | 1 | Str_Ctrl |
| 47 | 50 | −0.43423 | −0.43423 | −9.87919 | 9.1E−09 | 1.4E−06 | 10.423 | 0.74009 | −1.35119 | −1 | Str_Trn |
| 48 | 51 | −0.46546 | −0.46546 | −5.10325 | 6.4E−05 | 0.00045 | 1.46612 | 0.72424 | −1.38075 | −1 | Str_Trn |
| 49 | 51 | −0.36364 | −0.36364 | −5.17542 | 5.5E−05 | 0.00039 | 1.62618 | 0.7772 | −1.28667 | −1 | E_Trn |
| 50 | 54.5 | 0.52882 | 0.52882 | 2.19203 | 0.04152 | 0.08545 | −4.70898 | 1.44274 | 1.44274 | 1 | Str_Ctrl |
| 51 | 54.5 | 0.39598 | 0.39598 | 1.79312 | 0.08948 | 0.15409 | −5.38925 | 1.31584 | 1.31584 | 1 | Str_Ctrl |
| 52 | 47.5 | −0.3813 | −0.3813 | −6.54839 | 2.9E−06 | 4.1E−05 | 4.56832 | 0.76775 | −1.30252 | −1 | E_Trn |
| 53 | 40 | −0.43592 | −0.43592 | −4.02415 | 0.00077 | 0.00446 | −0.89572 | 0.73922 | −1.35278 | −1 | Str_Trn |
| 54 | 40 | 0.38727 | 0.38727 | 10.2623 | 5E−09 | 1E−06 | 11.0098 | 1.30792 | 1.30792 | 1 | Str_Ctrl |
| 55 | 40 | −0.48985 | −0.48985 | −3.90162 | 0.00102 | 0.00546 | −1.16675 | 0.7121 | −1.4043 | −1 | Str_Trn |
| 56 | 40 | −0.49057 | −0.49057 | −4.06412 | 0.00071 | 0.00417 | −0.8072 | 0.71175 | −1.405 | −1 | Str_Trn |
| 57 | 40 | −0.46894 | −0.46894 | −3.75332 | 0.00142 | 0.00697 | −1.49388 | 0.72249 | −1.3841 | −1 | Str_Trn |
| 58 | 37.5 | 0.32134 | 0.32134 | 2.04678 | 0.05484 | 0.10013 | −5.07725 | 1.24949 | 1.24949 | 1 | E_Ctrl |
| 59 | 59.17 | −0.41983 | −0.41983 | −3.39948 | 0.00313 | 0.01253 | −2.26719 | 0.74751 | −1.33777 | −1 | Str_Trn |

TABLE 30.B3

| 30 | AGAAACCACAAAGCTAGGAATTAAATTTTCGAATGTTTTTCTTCCTCTTA AGTGAGATAA (SEQ ID NO: 388) | 13 | 42011104 | 42011135 | 42235825 | 42235856 |
|---|---|---|---|---|---|---|
| 31 | AATACGTGGTCAATCTAAGGATTATAGTTCGAAAAGATTAATGATGTATT GATGACACTT (SEQ ID NO: 148) & (SEQ ID NO: 389) | 13 | 59818047 | 59818078 | 59854837 | 59854868 |
| 32 | GACACCTCCTCTCCCTTCCCTCCCCTTCTCGAGTTATCAAAATATTTTGA GAGACAGTAT (SEQ ID NO: 129) & (SEQ ID NO: 390) & (SEQ ID NO: 562) & (SEQ ID NO: 617) | 11 | 11968004 | 11968035 | 11984245 | 11984276 |
| 33 | GACACCTCCTCTCCCTTCCCTCCCCTTCTCGATCACTTTGCAAAGCTTTG TTGGCTAGGC (SEQ ID NO: 138) & (SEQ ID NO: 391) | 11 | 11968004 | 11968035 | 12019427 | 12019458 |
| 34 | GACACCTCCTCTCCCTTCCCTCCCCTTCTCGAAGGAAAAGCCCTGGGGCC AGCTGTAGAG (SEQ ID NO: 392) | 11 | 11968004 | 11968035 | 12010923 | 12010954 |
| 35 | GACACCTCCTCTCCCTTCCCTCCCCTTCTCGATGGCCACATGTGGCCAGT GGCTCTCATG (SEQ ID NO: 130) & (SEQ ID NO: 393) | 11 | 11968004 | 11968035 | 12048403 | 12048434 |
| 36 | CCGCTCTGCTATGGACCCCGGCTCGCTCTCGACTTGGCCCCCAGCATGTC CTCAGCCACC (SEQ ID NO: 394) | 14 | 100687837 | 100687868 | 100751546 | 100751577 |

TABLE 30.B3-continued

| | | | | | | |
|---|---|---|---|---|---|---|
| 37 | TTATAATTGTTACTATTGGGAAGAGGATTCGACACAGAAACTAAGTTTTC AAAATAAAAA (SEQ ID NO: 395) | 20 | 54466479 | 54466510 | 54577319 | 54577350 |
| 38 | GCCAAGAGGGGAAAGGACTCATGTTCTCTCGACTGCCTCCTCTCCCACCT CTGCTCGGAT (SEQ ID NO: 396) | 8 | 22682789 | 22682820 | 22739153 | 22739184 |
| 39 | CCACCCCTGCTGCTCTGGACCTGGTGGATCGACTTTTGTTTCCTGTCATT CAAGCTGCGT (SEQ ID NO: 397) | 11 | 64868178 | 64868209 | 64916059 | 64916090 |
| 40 | TTTGGTGATGAAATGAAAATAATTTATTTCGAAGAGCTCCTTATTCCAGT AGAAACACAA (SEQ ID NO: 398) | 4 | 100525710 | 100525741 | 100732651 | 100732682 |
| 41 | ACCATCAGAAAGCTCCATTTTCTTTTGTTCGACATGATTTTATGACTGAT TGGTCATAGG (SEQ ID NO: 399) | 11 | 128476761 | 128476792 | 128561632 | 128561663 |
| 42 | TGTCCTTTCAAGGAAGGATTAGCATCCTTCGAAAGACCTATCAGGATTTC ATTTGTAATG (SEQ ID NO: 133) & (SEQ ID NO: 400) & (SEQ ID NO: 619) | 8 | 71216399 | 71216430 | 71261816 | 71261847 |
| 43 | CTTGCCTAGTCTTTAATTTATTTATTTATCGACATTTTTTTCTTATCAAC GAGACGATGT (SEQ ID NO: 149) & (SEQ ID NO: 401) | 3 | 13512352 | 13512383 | 13590312 | 13590343 |
| 44 | TGCAGAAAGTACTACAAAAAAAGAAGCTTCGAAAATGTTGGAGATGAGAG TTTCTTCACC (SEQ ID NO: 131) & (SEQ ID NO: 402) & (SEQ ID NO: 563) | 8 | 123527843 | 123527874 | 123555254 | 123555285 |
| 45 | CATGGTTTATAATCCTTTTTATACATTGTCGACACTGTATTTTCACAGAT CACTCTGGAG (SEQ ID NO: 185) & (SEQ ID NO: 403) | 13 | 40524349 | 40524380 | 40688580 | 40688611 |
| 46 | AGAACTTCCTGATATATTTTTTTTCTTTTCGAAGGTCTTAAAATGTTTTT AAACATGACC (SEQ ID NO: 186) & (SEQ ID NO: 404) | 6 | 108604405 | 108604436 | 108629992 | 108630023 |
| 47 | GACTCTTAAAACAATAATATCAAACAACTCGACTTGTCATTTAGTTCTTT GGGAAGCAGT (SEQ ID NO: 187) & (SEQ ID NO: 405) | 16 | 53844989 | 53845020 | 54052288 | 54052319 |
| 48 | ACAACAGAATAGAACATATTCAATTAAATCGACATAGGAATAGGTTTCAG ATCCTAGTCT (SEQ ID NO: 406) | 13 | 91728718 | 91728749 | 91910388 | 91910419 |
| 49 | TAATAATTTTATATAATAGAATTTTGACTCGAAGTTGATGTCAAGATTTA TGGCTTACAT (SEQ ID NO: 407) | 13 | 91794062 | 91794093 | 91953115 | 91953146 |
| 50 | AATTAGACAACGACTATATGACTCTGTCTCGACTTTAAAGCAAGTACTTC TTGTATGCTC (SEQ ID NO: 188) & (SEQ ID NO: 408) & (SEQ ID NO: 564) | 13 | 94054831 | 94054862 | 94133177 | 94133208 |
| 51 | AATTAGACAACGACTATATGACTCTGTCTCGAGATTGGTCTTAACACACT ATTGATTATT (SEQ ID NO: 150) & (SEQ ID NO: 409) | 13 | 94133177 | 94133208 | 94304194 | 94304225 |
| 52 | GCAAATTTTGGAGCCTAACCTCCAAAATTCGAGCACAAAACTTTGTCCAC ATTTCTGATT (SEQ ID NO: 410) | 7 | 50706363 | 50706394 | 50780874 | 50780905 |
| 53 | AAAAAGAGAAAAGCAGGTTAGCACATTGTCGACCCCGCCCCCGGGATGGG GGAACTGGCC (SEQ ID NO: 151) & (SEQ ID NO: 411) & (SEQ ID NO: 565) | 9 | 121180379 | 121180410 | 121268506 | 121268537 |
| 54 | CTCTATAAATTTACCAGAATATAAATTCTCGAAGTGATCTCTAAATGTAA TCGTAAGTTT (SEQ ID NO: 412) | 9 | 121188989 | 121189020 | 121243316 | 121243347 |
| 55 | AAATTTTCAAGTGTACGATATGGTATCATCGACCCCGCCCCCGGGATGGG GGAACTGGCC (SEQ ID NO: 152) & (SEQ ID NO: 413) | 9 | 121232597 | 121232628 | 121268506 | 121268537 |
| 56 | AAACTTACGATTACATTTAGAGATCACTTCGACCCCGCCCCCGGGATGGG GGAACTGGCC (SEQ ID NO: 153) & (SEQ ID NO: 414) | 9 | 121243316 | 121243347 | 121268506 | 121268537 |
| 57 | GAGAGATGCCCACTCATACCATATAACTTCGACCCCGCCCCCGGGATGGG GGAACTGGCC (SEQ ID NO: 415) | 9 | 121253564 | 121253595 | 121268506 | 121268537 |
| 58 | CCACATAAAACCTTGGGTTCTTAATTTATCGAAGTTGAGTTACGTGTTTA AAAAAGAAA (SEQ ID NO: 416) | 7 | 18055950 | 18055981 | 18141979 | 18142010 |
| 59 | TCATATAAATGCCCCACAGAGTGCAGCATCGAACCTCGCCCCCTGCACGA CCCACACAAA (SEQ ID NO: 417) | 12 | 53959983 | 53960014 | 53994247 | 53994278 |

TABLE 30.B4

| | | | | | |
|---|---|---|---|---|---|
| 30 | 13 | 42011104 | 42015105 | 4.2E+07 | 42239826 |
| 31 | 13 | 59818047 | 59822048 | 6E+07 | 59858838 |
| 32 | 11 | 11964034 | 11968035 | 1.2E+07 | 11988246 |
| 33 | 11 | 11964034 | 11968035 | 1.2E+07 | 12019458 |
| 34 | 11 | 11964034 | 11968035 | 1.2E+07 | 12014924 |
| 35 | 11 | 11964034 | 11968035 | 1.2E+07 | 12052404 |
| 36 | 14 | 100687837 | 100691838 | 1E+08 | 100751577 |
| 37 | 20 | 54466479 | 54470480 | 5.5E+07 | 54577350 |
| 38 | 8 | 22678819 | 22682820 | 2.3E+07 | 22739184 |
| 39 | 11 | 64868178 | 64872179 | 6.5E+07 | 64916090 |
| 40 | 4 | 100525710 | 100529711 | 1E+08 | 100736652 |
| 41 | 11 | 128476761 | 128480762 | 1.3E+08 | 128565633 |
| 42 | 8 | 71216399 | 71220400 | 7.1E+07 | 71265817 |
| 43 | 3 | 13512352 | 13516353 | 1.4E+07 | 13590343 |
| 44 | 8 | 123523873 | 123527874 | 1.2E+08 | 123559255 |
| 45 | 13 | 40524349 | 40528350 | 4.1E+07 | 40692581 |

TABLE 30.B4-continued

| | | | | | |
|---|---|---|---|---|---|
| 46 | 6 | 108600435 | 108604436 | 1.1E+08 | 108633993 |
| 47 | 16 | 53844989 | 53848990 | 5.4E+07 | 54052319 |
| 48 | 13 | 91724748 | 91728749 | 9.2E+07 | 91914389 |
| 49 | 13 | 91794062 | 91798063 | 9.2E+07 | 91957116 |
| 50 | 13 | 94054831 | 94058832 | 9.4E+07 | 94133208 |
| 51 | 13 | 94129207 | 94133208 | 9.4E+07 | 94304225 |
| 52 | 7 | 50706363 | 50710364 | 5.1E+07 | 50780905 |
| 53 | 9 | 121176409 | 121180410 | 1.2E+08 | 121272507 |
| 54 | 9 | 121185019 | 121189020 | 1.2E+08 | 121243347 |
| 55 | 9 | 121228627 | 121232628 | 1.2E+08 | 121272507 |
| 56 | 9 | 121239346 | 121243347 | 1.2E+08 | 121272507 |
| 57 | 9 | 121253564 | 121257565 | 1.2E+08 | 121272507 |
| 58 | 7 | 18055950 | 18059951 | 1.8E+07 | 18142010 |
| 59 | 12 | 53956013 | 53960014 | 5.4E+07 | 53994278 |

TABLE 30.C1

| | | | | | | |
|---|---|---|---|---|---|---|
| 60 | IGF1R__15__98659065__98662585__98893484__98899517__FR | IGF1R | 200 | 106 | 0.008018013 | 0.06952724 |
| 61 | IL1RAP__3__190465562__190469171__190489665__190498302__RF | IL1RAP | 200 | 89 | 0.502149894 | 1 |
| 62 | IL1RAP__3__190489665__190498302__190560851__190563356__FR | IL1RAP | 200 | 89 | 0.502149894 | 1 |
| 63 | KDM1A__1__23064655__23070269__23096951__23098159__FR | KDM1A | 47 | 20 | 0.647904687 | 1 |
| 64 | LAMA2__6__128920996__128927003__129105731__129113311__FF | LAMA2 | 200 | 150 | 9.1067E-19 | 7.14876E-16 |
| 65 | LAMA2__6__129342029__129351351__129383008__129389769__FR | LAMA2 | 200 | 150 | 9.1067E-19 | 7.14876E-16 |
| 66 | LCK__1__32214585__32217213__32237144__32241139__RF | LCK | 47 | 19 | 0.750202183 | 1 |
| 67 | LDB2__4__16489298__16494220__16535160__16542582__RR | LDB2 | 200 | 108 | 0.003555653 | 0.038235451 |
| 68 | LMO4__1__87315524__87318670__87343110__87349940__FF | LMO4 | 106 | 81 | 1.57736E-11 | 3.09557E-09 |
| 69 | LMO4__1__87315524__87318670__87355277__87360229__FF | LMO4 | 106 | 81 | 1.57736E-11 | 3.09557E-09 |
| 70 | MAPK10__4__86572598__86581486__86617317__86621940__FF | MAPK10 | 200 | 114 | 0.000197862 | 0.005547208 |
| 71 | MBNL1__3__152229500__152234786__152252961__152257281__FR | MBNL1 | 200 | 91 | 0.389926943 | 1 |
| 72 | MBNL1__3__152229500__152234786__152281057__152285843__FR | MBNL1 | 200 | 91 | 0.389926943 | 1 |
| 73 | MYBPC1__12__101527342__101530065__101646571__101655128__RF | MYBPC1 | 186 | 94 | 0.05009075 | 0.263900932 |
| 74 | MYH1__17__10491098__10496051__10520297__10523271__RR | MYH1 | 103 | 52 | 0.121185055 | 0.485358512 |
| 75 | MYH1__17__10523271__10524567__10560779__10565755__FF | MYH1 | 103 | 52 | 0.121185055 | 0.485358512 |
| 76 | MYO18B__22__26004818__26009467__26030914__26037279__FF | MYO18B | 200 | 73 | 0.989437228 | 1 |
| 77 | NCAM1__11__113019160__113028516__113163748__113168132__FR | NCAM1 | 200 | 111 | 0.00091339 | 0.014340227 |
| 78 | NECTIN2__19__44815042__44816736__44827160__44828776__RR | NECTIN2 | 47 | 12 | 0.997525539 | 1 |
| 79 | NFKB1__4__102504137__102509238__102557818__102560252__FF | NFKB1 | 120 | 73 | 0.00019192 | 0.005547208 |
| 80 | NFKB1__4__102557818__102560252__102627099__102634363__FR | NFKB1 | 120 | 73 | 0.00019192 | 0.005547208 |
| 81 | NFKB1__4__102599188__102601960__102627099__102634363__FR | NFKB1 | 120 | 73 | 0.00019192 | 0.005547208 |
| 82 | NR4A1__12__51995149__51997631__52041793__52046779__RR | NR4A1 | 47 | 13 | 0.993704481 | 1 |
| 83 | NRXN1__2__50580957__50583587__50867546__50884047__RF | NRXN1 | 200 | 110 | 0.00146407 | 0.020081546 |
| 84 | NTRK2__9__84804816__84814325__84917519__84924935__FR | NTRK2 | 200 | 108 | 0.003555653 | 0.038235451 |
| 85 | NTRK2__9__84804816__84814325__84934592__84942655__RF | NTRK2 | 200 | 108 | 0.003555653 | 0.038235451 |
| 86 | PAG1__8__81007411__81018107__81069439__81070856__FR | PAG1 | 200 | 126 | 7.40996E-08 | 5.81682E-06 |
| 87 | PAG1__8__81007411__81018107__81126745__81129448__FR | PAG1 | 200 | 126 | 7.40996E-08 | 5.81682E-06 |
| 88 | PCK1__20__57527297__57530814__57551578__57557205__RR | PCK1 | 47 | 27 | 0.047791071 | 0.253486424 |
| 89 | PCK1__20__57527297__57530814__57570220__57572870__RR | PCK1 | 47 | 27 | 0.047791071 | 0.253486424 |

TABLE 30.C2

| | | | | | | | | | | |
|---|---|---|---|---|---|---|---|---|---|---|
| 60 | 53 | -0.3995 | -0.3995 | -9.07793 | 2.6E-08 | 1.3E-06 | 9.34074 | 0.75812 | -1.31905 | -1 E_Trn |
| 61 | 44.5 | -0.37779 | -0.37779 | -9.55782 | 1.1E-08 | 7.4E-07 | 10.1491 | 0.76962 | -1.29935 | -1 E_Trn |
| 62 | 44.5 | 0.34847 | 0.34847 | 11.5647 | 5.1E-10 | 9.5E-08 | 13.3297 | 1.27321 | 1.27321 | 1 E_Ctrl |
| 63 | 42.55 | 0.45098 | 0.45098 | 11.7421 | 5.8E-10 | 2.4E-07 | 13.1188 | 1.36697 | 1.36697 | 1 Str_Ctrl |
| 64 | 75 | -0.38825 | -0.38825 | -5.36236 | 3.6E-05 | 0.00028 | 2.03874 | 0.76406 | -1.3088 | -1 E_Trn |
| 65 | 75 | -0.40794 | -0.40794 | -12.0446 | 2.6E-10 | 6.4E-08 | 13.9006 | 0.7537 | -1.32679 | -1 E_Trn |
| 66 | 40.43 | 0.40486 | 0.40486 | 4.02911 | 0.00072 | 0.00308 | -0.9465 | 1.32396 | 1.32396 | 1 E_Ctrl |
| 67 | 54 | 0.33023 | 0.33023 | 5.78958 | 1.4E-05 | 0.00014 | 2.96874 | 1.25721 | 1.25721 | 1 E_Ctrl |
| 68 | 76.42 | -0.4253 | -0.4253 | -4.33423 | 0.00039 | 0.00268 | -0.20873 | 0.74468 | -1.34286 | -1 Str_Trn |
| 69 | 76.42 | -0.45509 | -0.45509 | -5.12331 | 6.7E-05 | 0.00077 | 1.52571 | 0.72946 | -1.37087 | -1 Str_Trn |
| 70 | 57 | 0.36948 | 0.36948 | 10.6233 | 2.9E-09 | 6.8E-07 | 11.5469 | 1.29189 | 1.29189 | 1 Str_Ctrl |
| 71 | 45.5 | -0.38329 | -0.38329 | -8.65576 | 5.3E-08 | 2.2E-06 | 8.60483 | 0.76669 | -1.30431 | -1 E_Trn |
| 72 | 45.5 | -0.42323 | -0.42323 | -5.76242 | 1.7E-05 | 0.00029 | 2.89367 | 0.74576 | -1.34092 | -1 Str_Trn |
| 73 | 50.54 | 0.38033 | 0.38033 | 2.20515 | 0.04044 | 0.08374 | -4.68518 | 1.30164 | 1.30164 | 1 Str_Ctrl |
| 74 | 50.49 | -0.41206 | -0.41206 | -6.14494 | 7.8E-06 | 0.00017 | 3.69022 | 0.75155 | -1.33058 | -1 Str_Trn |
| 75 | 50.49 | 0.32004 | 0.32004 | 7.50348 | 4.4E-07 | 1E-05 | 6.47359 | 1.24836 | 1.24836 | 1 E_Ctrl |
| 76 | 36.5 | -0.36797 | -0.36797 | -5.42926 | 3.1E-05 | 0.00025 | 2.18559 | 0.77487 | -1.29054 | -1 E_Trn |
| 77 | 55.5 | -0.47342 | -0.47342 | -5.25206 | 4.6E-05 | 0.00034 | 1.7957 | 0.72026 | -1.3884 | -1 E_Trn |
| 78 | 25.53 | 0.32241 | 0.32241 | 8.11688 | 1.4E-07 | 4.5E-06 | 7.63079 | 1.25042 | 1.25042 | 1 E_Ctrl |
| 79 | 60.83 | 0.35343 | 0.35343 | 7.56553 | 4.8E-07 | 2.3E-05 | 6.47751 | 1.2776 | 1.2776 | 1 Str_Ctrl |
| 80 | 60.83 | -0.40158 | -0.40158 | -7.53437 | 4.2E-07 | 9.8E-06 | 6.5331 | 0.75703 | -1.32096 | -1 E_Trn |
| 81 | 60.83 | -0.41977 | -0.41977 | -16.809 | 8E-13 | 1.4E-09 | 19.4697 | 0.74754 | -1.33772 | -1 E_Trn |
| 82 | 27.66 | -0.40863 | -0.40863 | -6.84429 | 1.9E-06 | 6.4E-05 | 5.09725 | 0.75334 | -1.32742 | -1 Str_Trn |
| 83 | 55 | 0.32026 | 0.32026 | 5.92682 | 1.1E-05 | 0.00011 | 3.26326 | 1.24856 | 1.24856 | 1 E_Ctrl |

TABLE 30.C2-continued

| 84 | 54 | 0.37084 | 0.37084 | 6.52335 | 3.1E−06 | 4.3E−05 | 4.5167 | 1.2931 | 1.2931 | 1 | E_Ctrl |
| 85 | 54 | 0.35785 | 0.35785 | 10.4559 | 2.7E−09 | 2.9E−07 | 11.5853 | 1.28152 | 1.28152 | 1 | E_Ctrl |
| 86 | 63 | −0.38914 | −0.38914 | −8.8407 | 3.9E−08 | 1.8E−06 | 8.93009 | 0.76359 | −1.30961 | −1 | E_Trn |
| 87 | 63 | −0.38118 | −0.38118 | −6.54771 | 2.9E−06 | 4.1E−05 | 4.56692 | 0.76781 | −1.30241 | −1 | E_Trn |
| 88 | 57.45 | −0.4278 | −0.4278 | −2.90477 | 0.00932 | 0.02801 | −3.31712 | 0.7434 | −1.34518 | −1 | Str_Trn |
| 89 | 57.45 | −0.44375 | −0.44375 | −3.06931 | 0.00651 | 0.02147 | −2.97337 | 0.73522 | −1.36014 | −1 | Str_Trn |

TABLE 30.C3

| 60 | ATGAAAGAATATGATTTTTTTTTTTACTCGAGTGTAAAAGGGCTTTTAC TGGTGCACAC (SEQ ID NO: 418) | 15 | 98662554 | 98662585 | 98893484 | 98893515 |
| 61 | TAAATAAAATTGTCTTTTTTTGTCTTTCTCGAGATTTTGAAACACCTTCA GTTTGAAGAC (SEQ ID NO: 419) | 3 | 190465562 | 190465593 | 190498271 | 190498302 |
| 62 | TAAATAAAATTGTCTTTTTTTGTCTTTCTCGATTACAGAGAACTAAGTAC ATTTTAAATC (SEQ ID NO: 139) & (SEQ ID NO: 420) | 3 | 190498271 | 190498302 | 190560851 | 190560882 |
| 63 | GGCAGGTGGATCATTTGAGGTCAAGAGCTCGACAGAGCAAGCACCATCT CCAAAAAGAA (SEQ ID NO: 132) & (SEQ ID NO: 421) | 1 | 23070238 | 23070269 | 23096951 | 23096982 |
| 64 | TCTAAGGTATAGTTTTGGGTATAAACCATCGAACATTACCCCCGATTGTT TTGGAAATTA (SEQ ID NO: 422) | 6 | 128926972 | 128927003 | 129113280 | 129113311 |
| 65 | TTATTTGTTAATATCCAGTAGTATTTAATCGATTGCCGTTGGCTCAAAGT AATATTTGAA (SEQ ID NO: 423) | 6 | 129351320 | 129351351 | 129383008 | 129383039 |
| 66 | AAGGGCTCGGGAGCTCCCTCGGCACACCTCGAGGAGTGCCAGGCATCTAC TGCTCTGTCC (SEQ ID NO: 154) & (SEQ ID NO: 424) | 1 | 32214585 | 32214616 | 32241108 | 32241139 |
| 67 | AGGAATCCATTTTCAGATCACACCCCAGTCGAAAGAAAACCATTTGGATG ACCGTGGAAG (SEQ ID NO: 425) | 4 | 16489298 | 16489329 | 16535160 | 16535191 |
| 68 | CCCCTGGCTCACCTACACAAAATTGTGCTCGACTCTACTCTTAGCCCTGC TAAATAAGTA (SEQ ID NO: 155) & (SEQ ID NO: 426) & (SEQ ID NO: 566) | 1 | 87318639 | 87318670 | 87349909 | 87349940 |
| 69 | CCCCTGGCTCACCTACACAAAATTGTGCTCGAATGTCTGAACAAGTGAAT GAACAAATGA (SEQ ID NO: 427) | 1 | 87318639 | 87318670 | 87355277 | 87355308 |
| 70 | ATTATATTAGTGCTGTAATAAAATTAAGTCGACACATTTGATACTGCTTA TTGGGTTATT (SEQ ID NO: 156) & (SEQ ID NO: 428) & (SEQ ID NO: 567) | 4 | 86581455 | 86581486 | 86621909 | 86621940 |
| 71 | TACCTTGAAAAGCTCTTCAGTATGATTATCGAAAGATTCATTTTCATGTT CCGTTTTATC (SEQ ID NO: 429) | 3 | 152234755 | 152234786 | 152252961 | 152252992 |
| 72 | TACCTTGAAAAGCTCTTCAGTATGATTATCGAGCTTTAGCCATTCTAGTA ATTATTAAAA (SEQ ID NO: 157) & (SEQ ID NO: 430) & (SEQ ID NO: 568) | 3 | 152234755 | 152234786 | 152281057 | 152281088 |
| 73 | AGATCTCACATGTAAATTAGAATAGCAGTCGACTAAATATAAAGACTCAA TAACCACCAT (SEQ ID NO: 431) | 12 | 101527342 | 101527373 | 101655097 | 101655128 |
| 74 | TTTTCTCCCAAAGTTTATATCCTAATATTCGAGGAAGGTTATATTTTTGG CTATGCATCT (SEQ ID NO: 432) | 17 | 10491098 | 10491129 | 10520297 | 10520328 |
| 75 | TGTCTGTTCCAGAGTGGCCCGCAGCTCCTCGAGGAGCTGGCACTCTTATA CACCTCTGGG (SEQ ID NO: 433) | 17 | 10524536 | 10524567 | 10565724 | 10565755 |
| 76 | TGAGTTACTGTTTTTCCTTCCTTTTGATTCGAGAAGAAACCAAGAATTAG AGGGATTAA (SEQ ID NO: 434) | 22 | 26009436 | 26009467 | 26037248 | 26037279 |
| 77 | ATGAATTAATGTTTCCTAGAAAGTTGTCTCGAAAGAAGAAAGTGTCAGGG TTCAACTGCC (SEQ ID NO: 158) & (SEQ ID NO: 435) | 11 | 113028505 | 113028536 | 113163748 | 113163779 |
| 78 | GGTCAGGTCTGTGCTATGGAAAGAGCTCTCGACCTCCAGTCTTTCCTCTC GCATAAATGG (SEQ ID NO: 436) | 19 | 44815042 | 44815073 | 44827160 | 44827191 |
| 79 | TCTTTATGGTGTCTCTTTATATATTTACTCGAGAAAGAAGTAACACACTA TTGCTAATTC (SEQ ID NO: 437) | 4 | 102509207 | 102509238 | 102560221 | 102560252 |
| 80 | GAATTAGCAATAGTGTGTTACTTCTTTCTCGATATTTTACATGGAATCTT TCCCTTTTTA (SEQ ID NO: 438) | 4 | 102560221 | 102560252 | 102627099 | 102627130 |
| 81 | TACCTTTCCATTTGTCTCCTTCCCTTCATCGATATTTTACATGGAATCTT TCCCTTTTTA (SEQ ID NO: 439) | 4 | 102601929 | 102601960 | 102627099 | 102627130 |

TABLE 30.C3-continued

| 82 | ATCTGGCTTCACATTCCTCGGCCCTTCCTCGACTCTCCCTCTGTAGGCCT CCACCATGGA (SEQ ID NO: 440) | 12 | 51995149 | 51995180 | 52041793 | 52041824 |
| 83 | ATTCATTTATCTGTATTCTTAGTATGCTTCGAAGGTAATATAACCTTGAA AATGTAACAA (SEQ ID NO: 441) | 2 | 50580957 | 50580988 | 50884016 | 50884047 |
| 84 | CTCTTCAGGGGTGTGTGGAGTAAATAGCTCGAGTTTGTCCACAGCCCTCA CAGCCCTTGG (SEQ ID NO: 442) | 9 | 84814294 | 84814325 | 84917519 | 84917550 |
| 85 | TAAAAAGAAACATATGAAACTTATTTTATCGACCCTATAGATTTTTCAAT ATATGTTTAT (SEQ ID NO: 443) | 9 | 84804816 | 84804847 | 84942624 | 84942655 |
| 86 | TCAGATAAGTAACTTCCTGATAATTAACTCGAAGTCCAGGATTCATTATA AACACTGATA (SEQ ID NO: 444) | 8 | 81018076 | 81018107 | 81069439 | 81069470 |
| 87 | TCAGATAAGTAACTTCCTGATAATTAACTCGAGAAACATTTATTGGTTGT CCAATTGTTT (SEQ ID NO: 445) | 8 | 81018076 | 81018107 | 81126745 | 81126776 |
| 88 | CCTCGTCGTCCCCTCTCTTCCTCGTTCCTCGACAGGAAAGCATACGGAAA AAGTTAAAGA (SEQ ID NO: 143) & (SEQ ID NO: 446) | 20 | 57527297 | 57527328 | 57551578 | 57551609 |
| 89 | CCTCGTCGTCCCCTCTCTTCCTCGTTCCTCGATGCGGGACTGATTGTTAC AGAACTGTTT (SEQ ID NO: 159) & (SEQ ID NO: 447) | 20 | 57527297 | 57527328 | 57570220 | 57570251 |

TABLE 30.C4     TABLE 30.C4-continued

| 60 | 15 | 98658584 | 98662585 | 9.9E+07 | 98897485 |
| 61 | 3 | 190465562 | 190469563 | 1.9E+08 | 190498302 |
| 62 | 3 | 190494301 | 190498302 | 1.9E+08 | 190564852 |
| 63 | 1 | 23066268 | 23070269 | 2.3E+07 | 23100952 |
| 64 | 6 | 128923002 | 128927003 | 1.3E+08 | 129113311 |
| 65 | 6 | 129347350 | 129351351 | 1.3E+08 | 129387009 |
| 66 | 1 | 32214585 | 32218586 | 3.2E+07 | 32241139 |
| 67 | 4 | 16489298 | 16493299 | 1.7E+07 | 16539161 |
| 68 | 1 | 87314669 | 87318670 | 8.7E+07 | 87349940 |
| 69 | 1 | 87314669 | 87318670 | 8.7E+07 | 87359278 |
| 70 | 4 | 86577485 | 86581486 | 8.7E+07 | 86621940 |
| 71 | 3 | 152230785 | 152234786 | 1.5E+08 | 152256962 |
| 72 | 3 | 152230785 | 152234786 | 1.5E+08 | 152285058 |
| 73 | 12 | 101527342 | 101531343 | 1E+08 | 101655128 |
| 74 | 17 | 10491098 | 10495099 | 1.1E+07 | 10524298 |
| 75 | 17 | 10520566 | 10524567 | 1.1E+07 | 10565755 |
| 76 | 22 | 26005466 | 26009467 | 2.6E+07 | 26037279 |
| 77 | 11 | 113024535 | 113028536 | 1.1E+08 | 113167749 |
| 78 | 19 | 44815042 | 44819043 | 4.5E+07 | 44831161 |
| 79 | 4 | 102505237 | 102509238 | 1E+08 | 102560252 |
| 80 | 4 | 102556251 | 102560252 | 1E+08 | 102631100 |
| 81 | 4 | 102597959 | 102601960 | 1E+08 | 102631100 |
| 82 | 12 | 51995149 | 51999150 | 5.2E+07 | 52045794 |
| 83 | 2 | 50580957 | 50584958 | 5.1E+07 | 50884047 |
| 84 | 9 | 84810324 | 84814325 | 8.5E+07 | 84921520 |
| 85 | 9 | 84804816 | 84808817 | 8.5E+07 | 84942655 |
| 86 | 8 | 81014106 | 81018107 | 8.1E+07 | 81073440 |
| 87 | 8 | 81014106 | 81018107 | 8.1E+07 | 81130746 |
| 88 | 20 | 57527297 | 57531298 | 5.8E+07 | 57555579 |
| 89 | 20 | 57527297 | 57531298 | 5.8E+07 | 57574221 |

TABLE 30.D1

| 90 | PCK1_20_57527297_57530814_57579772_57583521_RR | PCK1 | 47 | 27 | 0.047791071 | 0.253486424 |
| 91 | PCK1_20_57527297_57530814_57583521_57585923_RR | PCK1 | 47 | 27 | 0.047791071 | 0.253486424 |
| 92 | PDK3_X_24441637_24447950_24480152_24481252_FR | PDK3 | 42 | 14 | 0.945004612 | 1 |
| 93 | PDK3_X_24441637_24447950_24490440_24491541_FR | PDK3 | 42 | 14 | 0.945004612 | 1 |
| 94 | PHTF2_7_77800747_77805972_77956111_77960107_RR | PHTF2 | 200 | 99 | 0.078405901 | 0.370774891 |
| 95 | PHTF2_7_77846910_77851576_77956111_77960107_RR | PHTF2 | 200 | 99 | 0.078405901 | 0.370774891 |
| 96 | PIK3C3_18_42033052_42039159_42070009_42072187_RF | PIK3C3 | 174 | 92 | 0.013813418 | 0.105277024 |
| 97 | PIK3C3_18_42070009_42072187_42088671_42094691_FF | PIK3C3 | 174 | 92 | 0.013813418 | 0.105277024 |
| 98 | PIK3R1_5_68187850_68194388_68237549_68241297_FF | PIK3R1 | 146 | 71 | 0.164362225 | 0.605748107 |
| 99 | PIK3R1_5_68203536_68213336_68237549_68241297_FR | PIK3R1 | 146 | 71 | 0.164362225 | 0.605748107 |
| 100 | PLCXD2_3_111719030_111722119_111809065_111815838_RR | PLCXD2 | 200 | 76 | 0.969310539 | 1 |
| 101 | PPARGC1A_4_23871872_23880181_23925180_23932379_FF | PPARGC1A | 200 | 109 | 0.002303017 | 0.026200987 |
| 102 | PPP3CA_4_101055418_101067369_101247819_101259416_RR | PPP3CA | 200 | 95 | 0.198157163 | 0.697548759 |
| 103 | PRDX6_1_173434669_173438537_173475099_173476805_FR | PRDX6 | 38 | 21 | 0.115306099 | 0.474801595 |
| 104 | PRDX6_1_173434669_173438537_173477717_173485417_FR | PRDX6 | 38 | 21 | 0.115306099 | 0.474801595 |
| 105 | PRDX6_1_173450908_173452763_173477717_173485417_FR | PRDX6 | 38 | 21 | 0.115306099 | 0.474801595 |
| 106 | PRKCQ_10_6432893_6439235_6488207_6489596_FF | PRKCQ | 200 | 106 | 0.008018013 | 0.06952724 |
| 107 | PTPRC_1_198595771_198598296_198659753_198666156_RF | PTPRC | 200 | 98 | 0.101325207 | 0.434758425 |
| 108 | PTPRC_1_198631562_198634915_198659753_198666156_RF | PTPRC | 200 | 98 | 0.101325207 | 0.434758425 |
| 109 | PTPRC_1_198659753_198666156_198697386_198704777_FR | PTPRC | 200 | 98 | 0.101325207 | 0.434758425 |
| 110 | PTPRC_1_198659753_198666156_198704777_198709653_FR | PTPRC | 200 | 98 | 0.101325207 | 0.434758425 |
| 111 | PTPRC_1_198659753_198666156_198721093_198724578_FF | PTPRC | 200 | 98 | 0.101325207 | 0.434758425 |
| 112 | PTPRC_1_198659753_198666156_198768850_198775826_FF | PTPRC | 200 | 98 | 0.101325207 | 0.434758425 |
| 113 | PYGM_11_64747174_64749438_64762879_64765587_RF | PYGM | 16 | 8 | 0.413940883 | 1 |
| 114 | RGS6_14_72139099_72144564_72213251_72222544_FR | RGS6 | 200 | 110 | 0.00146407 | 0.020081546 |
| 115 | RORA_15_60902137_60909221_61019417_61030714_RR | RORA | 200 | 102 | 0.032796361 | 0.195038964 |
| 116 | RUNX3_1_24920810_24923822_24973522_24976037_RF | RUNX3 | 94 | 25 | 0.999868187 | 1 |

TABLE 30.D1-continued

| | | | | | | |
|---|---|---|---|---|---|---|
| 117 | RYR1__19__38410632__38413089__38495982__38499305__RR | RYR1 | 75 | 31 | 0.734667715 | 1 |
| 118 | SGCZ__8__14631157__14642508__14656955__14664444__RF | SGCZ | 200 | 131 | 1.15564E−09 | 1.13397E−07 |
| 119 | SLC35B1__17__49700402__49702340__49724264__49725934__RR | SLC35B1 | 34 | 9 | 0.989799814 | 1 |

TABLE 30.D2

| | | | | | | | | | | | |
|---|---|---|---|---|---|---|---|---|---|---|---|
| 90 | 57.45 | −0.45438 | −0.45438 | −3.14668 | 0.00549 | 0.01895 | −2.80966 | 0.72983 | −1.37019 | −1 | Str_Trn |
| 91 | 57.45 | −0.46711 | −0.46711 | −3.5423 | 0.00228 | 0.00989 | −1.95661 | 0.72341 | −1.38233 | −1 | Str_Trn |
| 92 | 33.33 | −0.51621 | −0.51621 | −2.91295 | 0.00916 | 0.02763 | −3.30018 | 0.69921 | −1.43019 | −1 | Str_Trn |
| 93 | 33.33 | −0.48296 | −0.48296 | −2.84564 | 0.0106 | 0.03078 | −3.439 | 0.71551 | −1.39761 | −1 | Str_Trn |
| 94 | 49.5 | −0.37906 | −0.37906 | −7.13828 | 9E−07 | 1.7E−05 | 5.75985 | 0.76894 | −1.3005 | −1 | E_Trn |
| 95 | 49.5 | 0.40917 | 0.40917 | 9.25447 | 2.5E−08 | 2.9E−06 | 9.42731 | 1.32792 | 1.32792 | 1 | Str_Ctrl |
| 96 | 52.87 | 0.36058 | 0.36058 | 10.1197 | 6.2E−09 | 1.1E−06 | 10.7935 | 1.28394 | 1.28394 | 1 | Str_Ctrl |
| 97 | 52.87 | 0.34906 | 0.34906 | 10.1957 | 4.1E−09 | 3.8E−07 | 11.1792 | 1.27373 | 1.27373 | 1 | E_Ctrl |
| 98 | 48.63 | −0.40001 | −0.40001 | −7.21891 | 7.7E−07 | 1.5E−05 | 5.91903 | 0.75785 | −1.31952 | −1 | E_Trn |
| 99 | 48.63 | −0.37383 | −0.37383 | −6.77717 | 1.8E−06 | 2.9E−05 | 5.03603 | 0.77173 | −1.29578 | −1 | E_Trn |
| 100 | 38 | 0.36966 | 0.36966 | 10.925 | 1.3E−09 | 1.8E−07 | 12.2976 | 1.29205 | 1.29205 | 1 | E_Ctrl |
| 101 | 54.5 | 0.3467 | 0.3467 | 10.5435 | 2.4E−09 | 2.6E−07 | 11.7202 | 1.27165 | 1.27165 | 1 | E_Ctrl |
| 102 | 47.5 | −0.46232 | −0.46232 | −10.3242 | 4.5E−09 | 9.5E−07 | 11.103 | 0.72582 | −1.37776 | −1 | Str_Trn |
| 103 | 55.26 | −0.37846 | −0.37846 | −6.54322 | 3E−06 | 4.2E−05 | 4.55767 | 0.76926 | −1.29995 | −1 | E_Trn |
| 104 | 55.26 | −0.36712 | −0.36712 | −9.7319 | 8.6E−09 | 6E−07 | 10.4352 | 0.77533 | −1.28977 | −1 | E_Trn |
| 105 | 55.26 | −0.43334 | −0.43334 | −6.62265 | 2.9E−06 | 8.8E−05 | 4.6585 | 0.74054 | −1.35036 | −1 | Str_Trn |
| 106 | 53 | −0.39208 | −0.39208 | −8.21682 | 1.2E−07 | 3.9E−06 | 7.81442 | 0.76203 | −1.31228 | −1 | E_Trn |
| 107 | 49 | 0.34287 | 0.34287 | 12.2469 | 2E−10 | 5.4E−08 | 14.1766 | 1.26828 | 1.26828 | 1 | E_Ctrl |
| 108 | 49 | 0.3635 | 0.3635 | 12.1633 | 2.2E−10 | 5.8E−08 | 14.0631 | 1.28654 | 1.28654 | 1 | E_Ctrl |
| 109 | 49 | 0.32003 | 0.32003 | 11.7784 | 3.8E−10 | 7.8E−08 | 13.5313 | 1.24836 | 1.24836 | 1 | E_Ctrl |
| 110 | 49 | 0.33346 | 0.33346 | 13.2487 | 5.1E−11 | 2.3E−08 | 15.4853 | 1.26003 | 1.26003 | 1 | E_Ctrl |
| 111 | 49 | 0.3532 | 0.3532 | 12.7171 | 1E−10 | 3.8E−08 | 14.8025 | 1.27739 | 1.27739 | 1 | E_Ctrl |
| 112 | 49 | 0.33194 | 0.33194 | 12.0445 | 2.6E−10 | 6.4E−08 | 13.9006 | 1.25871 | 1.25871 | 1 | E_Ctrl |
| 113 | 50 | −0.38806 | −0.38806 | −9.61961 | 1E−08 | 6.9E−07 | 10.2511 | 0.76415 | −1.30864 | −1 | E_Trn |
| 114 | 55 | 0.37355 | 0.37355 | 9.04986 | 3.5E−08 | 3.6E−06 | 9.09037 | 1.29554 | 1.29554 | 1 | Str_Ctrl |
| 115 | 51 | −0.47031 | −0.47031 | −3.83332 | 0.00113 | 0.00442 | −1.38642 | 0.72181 | −1.38541 | −1 | E_Trn |
| 116 | 26.6 | 0.36423 | 0.36423 | 10.3099 | 4.6E−09 | 9.6E−07 | 11.0816 | 1.2872 | 1.2872 | 1 | Str_Ctrl |
| 117 | 41.33 | 0.37985 | 0.37985 | 3.09107 | 0.0062 | 0.02072 | −2.92745 | 1.3012 | 1.3012 | 1 | Str_Ctrl |
| 118 | 65.5 | −0.39071 | −0.39071 | −7.31446 | 6.4E−07 | 1.3E−05 | 6.10649 | 0.76275 | −1.31104 | −1 | E_Trn |
| 119 | 26.47 | −0.41926 | −0.41926 | −4.89024 | 0.00011 | 0.00111 | 1.01732 | 0.74781 | −1.33724 | −1 | Str_Trn |

TABLE 30.D3

90 CCTCGTCGTCCCCTCTCTTCCTCGTTCCTCGAACATCTCCAAGTCAGATA 20 57527297 57527328 57579772 57579803
ATCATAACAA (SEQ ID NO: 134) & (SEQ ID NO: 448) &
(SEQ ID NO: 569)

91 CCTCGTCGTCCCCTCTCTTCCTCGTTCCTCGAGCCTCTGTCCCAATGTCA 20 57527297 57527328 57583521 57583552
CCTCTTCAGA (SEQ ID NO: 449)

92 GGGGATGGGGCCGAAATATGATTGCACTTCGAGTTTGTTTAGTTTTTATC X 24447919 24447950 24480152 24480183
TTCCCCATTT (SEQ ID NO: 160) & (SEQ ID NO: 450)

93 GGGGATGGGGCCGAAATATGATTGCACTTCGAACTTCAGCACCTGACCTT X 24447919 24447950 24490440 24490471
TGTCATCAAC (SEQ ID NO: 161) & (SEQ ID NO: 451)

94 AAATAATATACAAGTAGTCCAACTATTTTCGAGTATTTTAGAAATTACAT 7 77800747 77800778 77956111 77956142
GAAACATGAA (SEQ ID NO: 452)

95 TCAGGCTTGCAGGCTCATGCCTGCAATGTCGAGTATTTTAGAAATTACAT 7 77846910 77846941 77956111 77956142
GAAACATGAA (SEQ ID NO: 453)

96 ATCTATTATAATGATGCAATATTGTTAATCGAGTTTTCCTTCTTAAAGAA 18 42033052 42033083 42072156 42072187
CAAACTCACC (SEQ ID NO: 454)

97 ATCTATTATAATGATGCAATATTGTTAATCGATTCAAAGATCAAATTAAT 18 42072156 42072187 42094660 42094691
TATTAAAGCT (SEQ ID NO: 135) & (SEQ ID NO: 455) &
(SEQ ID NO: 570)

98 CTGAGTCTTCATTACCAAAAAAAAAAGTTCGAACATGCACTGGGGTTTTA 5 68194357 68194388 68241266 68241297
CTAAAACTAT (SEQ ID NO: 456)

99 CGTTGCAAATTGTACATCTTCTGCTATTTCGAATGCGAAGTTGAGAAATT 5 68213305 68213336 68237549 68237580
TTACTTATTT (SEQ ID NO: 457)

100 TACTTTTTTCATATGGATATACAGTTATTCGAGGAGGAATAGTCACATAA 3 111719030 111719061 111809065 111809096
ATAAATTATT (SEQ ID NO: 458)

TABLE 30.D3-continued

| | | | | | | |
|---|---|---|---|---|---|---|
| 101 | TACATGAATATACAGTCTTGTATTGTTTTCGATCTATAGAATGGAAGGAT AGCATTAGCT (SEQ ID NO: 459) | 4 | 23880150 | 23880181 | 23932348 | 23932379 |
| 102 | TCTTTGTTTCCTGTTTCCACTTCTTATTTCGATATTTATTGAGTGCTACT ATATATATGC (SEQ ID NO: 189) & (SEQ ID NO: 460) | 4 | 101055418 | 101055449 | 101247819 | 101247850 |
| 103 | ACTGTATCTTTTGCTTATTTTCTATACTTCGAGGCATAGAACCTTTCCTT AAACTTATTT (SEQ ID NO: 461) | 1 | 173438506 | 173438537 | 173475099 | 173475130 |
| 104 | ACTGTATCTTTTGCTTATTTTCTATACTTCGATCCCTCCTGGCCTCCCCG CCTCCGGCGT (SEQ ID NO: 462) | 1 | 173438506 | 173438537 | 173477717 | 173477748 |
| 105 | TAATGCTGGAGCAAGACAAAGATAGACTTCGATCCCTCCTGGCCTCCCCG CCTCCGGCGT (SEQ ID NO: 463) | 1 | 173452732 | 173452763 | 173477717 | 173477748 |
| 106 | TTCCACCTGTAATACTGTGCCTGTATTCTCGACTCTTCTCGCCCTCTTCT CCAGCTCTCT (SEQ ID NO: 464) | 10 | 6439204 | 6439235 | 6489565 | 6489596 |
| 107 | AGAGGCTGAGGTGAAAAGATTGTTTGAGTCGAAGATCATTGTCTCATTTT TTTACTTGTT (SEQ ID NO: 162) & (SEQ ID NO: 465) & (SEQ ID NO: 571) & (SEQ ID NO: 621) | 1 | 198595771 | 198595802 | 198666125 | 198666156 |
| 108 | AGAGGCTGAGGTGAAAAGATTGTTTGAGTCGACAAATGTTATACATGGCT TGTAACACTG (SEQ ID NO: 466) | 1 | 198631562 | 198631593 | 198666125 | 198666156 |
| 109 | AGAGGCTGAGGTGAAAAGATTGTTTGAGTCGACAACCCAATTTTGTTATT TGAGTTTCTT (SEQ ID NO: 467) | 1 | 198666125 | 198666156 | 198697386 | 198697417 |
| 110 | AGAGGCTGAGGTGAAAAGATTGTTTGAGTCGAATTCAATTTTACTGCAAA CCTCAGCATC (SEQ ID NO: 468) | 1 | 198666125 | 198666156 | 198704777 | 198704808 |
| 111 | AGAGGCTGAGGTGAAAAGATTGTTTGAGTCGATACACTGAACAAGTGCCA GAGCAGAATA (SEQ ID NO: 163) & (SEQ ID NO: 469) | 1 | 198666125 | 198666156 | 198724547 | 198724578 |
| 112 | AGAGGCTGAGGTGAAAAGATTGTTTGAGTCGAGTCACATGATCAAGCGCT CATTTCTGTT (SEQ ID NO: 470) | 1 | 198666125 | 198666156 | 198775795 | 198775826 |
| 113 | GAGGAGAGAAAGAAGACAAAGAAGCACTCGATCTGCCCTGCGGCCCCAC CTGAGTGATT (SEQ ID NO: 471) | 11 | 64747174 | 64747205 | 64765556 | 64765587 |
| 114 | AATGGCATTCTCCATTTATTCGTATTTATCGAGACTTTCTATGAAAGCTT TTTTGATGTT (SEQ ID NO: 472) & (SEQ ID NO: 572) | 14 | 72144533 | 72144564 | 72213251 | 72213282 |
| 115 | GGCTGAAGAATGGAATTGAAGTAGAAAATCGATGATTATCAAGTATATAC CAAACATTAT (SEQ ID NO: 473) | 15 | 60902137 | 60902168 | 61019417 | 61019448 |
| 116 | CTTAATTTTTTTTCTTTGAATGCCTCTATCGACAGTCTTCTCTCTACTTT CTACAGTGAA (SEQ ID NO: 140) & (SEQ ID NO: 474) & (SEQ ID NO: 573) | 1 | 24920810 | 24920841 | 24976006 | 24976037 |
| 117 | GGTGGGAGGATCACTTGAGGTCAGAAGTTCGATCTCCTGACCTCAAGTGA TCCTCTAGCT (SEQ ID NO: 164) & (SEQ ID NO: 475) | 19 | 38410632 | 38410663 | 38495982 | 38496013 |
| 118 | ATGAAAGAAATACCAATATTTGTTTAATTCGAATCTCCAACACGTTATTT ACCACTGGGA (SEQ ID NO: 476) | 8 | 14631157 | 14631188 | 14664413 | 14664444 |
| 119 | TGGTGGCTGAGTCCTGGCACAGCCACTGTCGAAGCTGGGCCCCGCACCCC CCACACAAAC (SEQ ID NO: 477) | 17 | 49700402 | 49700433 | 49724264 | 49724295 |

| TABLE 30.D4 | | | | | | TABLE 30.D4-continued | | | | |
|---|---|---|---|---|---|---|---|---|---|---|
| 90 | 20 | 57527297 | 57531298 | 5.8E+07 | 57583773 | 102 | 4 | 101055418 | 101059419 | 1E+08 | 101251820 |
| 91 | 20 | 57527297 | 57531298 | 5.8E+07 | 57587522 | 103 | 1 | 173434536 | 173438537 | 1.7E+08 | 173479100 |
| 92 | X | 24443949 | 24447950 | 2.4E+07 | 24484153 | 104 | 1 | 173434536 | 173438537 | 1.7E+08 | 173481718 |
| 93 | X | 24443949 | 24447950 | 2.4E+07 | 24494441 | 105 | 1 | 173448762 | 173452763 | 1.7E+08 | 173481718 |
| 94 | 7 | 77800747 | 77804748 | 7.8E+07 | 77960112 | 106 | 10 | 6435234 | 6439235 | 6485595 | 6489596 |
| 95 | 7 | 77846910 | 77850911 | 7.8E+07 | 77960112 | 107 | 1 | 198595771 | 198599772 | 2E+08 | 198666156 |
| 96 | 18 | 42033052 | 42037053 | 4.2E+07 | 42072187 | 108 | 1 | 198631562 | 198635563 | 2E+08 | 198666156 |
| 97 | 18 | 42068186 | 42072187 | 4.2E+07 | 42094691 | 109 | 1 | 198662155 | 198666156 | 2E+08 | 198701387 |
| 98 | 5 | 68190387 | 68194388 | 6.8E+07 | 68241297 | 110 | 1 | 198662155 | 198666156 | 2E+08 | 198708778 |
| 99 | 5 | 68209335 | 68213336 | 6.8E+07 | 68241550 | 111 | 1 | 198662155 | 198666156 | 2E+08 | 198724578 |
| 100 | 3 | 111719030 | 111723031 | 1.1E+08 | 111813066 | 112 | 1 | 198662155 | 198666156 | 2E+08 | 198775826 |
| 101 | 4 | 23876180 | 23880181 | 2.4E+07 | 23932379 | 113 | 11 | 64747174 | 64751175 | 6.5E+07 | 64765587 |
| | | | | | | 114 | 14 | 72140563 | 72144564 | 7.2E+07 | 72217252 |
| | | | | | | 115 | 15 | 60902137 | 60906138 | 6.1E+07 | 61023418 |

TABLE 30.D4-continued

| | | | | | |
|---|---|---|---|---|---|
| 116 | 1 | 24920810 | 24924811 | 2.5E+07 | 24976037 |
| 117 | 19 | 38410632 | 38414633 | 3.8E+07 | 38499983 |

TABLE 30.D4-continued

| | | | | | |
|---|---|---|---|---|---|
| 118 | 8 | 14631157 | 14635158 | 1.5E+07 | 14664444 |
| 119 | 17 | 49700402 | 49704403 | 5E+07 | 49728265 |

TABLE 30.E1

| | | | | | | |
|---|---|---|---|---|---|---|
| 120 | SLC35D1_1_66998822_67004850_67070417_67074223_FR | SLC35D1 | 83 | 35 | 0.689428445 | 1 |
| 121 | SMAD7_18_48917335_48920290_48969505_48974578_RF | SMAD7 | 49 | 21 | 0.632626918 | 1 |
| 122 | STIM1_11_4071215_4074242_4084365_4091420_FR | STIM1 | 200 | 71 | 0.99529685 | 1 |
| 123 | STK39_2_167959346_167965882_168109573_168114525_FF | STK39 | 200 | 95 | 0.198157163 | 0.697548759 |
| 124 | STK39_2_168057412_168062336_168109573_168114525_FF | STK39 | 200 | 95 | 0.198157163 | 0.697548759 |
| 125 | STXBP4_17_55035186_55042800_55142272_55149288_FR | STXBP4 | 178 | 72 | 0.865724188 | 1 |
| 126 | SULF2_20_47663998_47665865_47797013_47801718_FR | SULF2 | 200 | 95 | 0.198157163 | 0.697548759 |
| 127 | SYK_9_90789107_90793598_90876350_90879196_RF | SYK | 189 | 111 | 4.46333E-05 | 0.001946506 |
| 128 | SYK_9_90816328_90822228_90832284_90836084_RR | SYK | 189 | 111 | 4.46333E-05 | 0.001946506 |
| 129 | SYK_9_90816328_90822228_90836573_90843345_FR | SYK | 189 | 111 | 4.46333E-05 | 0.001946506 |
| 130 | SYK_9_90816328_90822228_90836573_90843345_RR | SYK | 189 | 111 | 4.46333E-05 | 0.001946506 |
| 131 | SYK_9_90816328_90822228_90872966_90875740_RR | SYK | 189 | 111 | 4.46333E-05 | 0.001946506 |
| 132 | TBX21_17_47685438_47687129_47704291_47707744_FR | TBX21 | 2 | 0 | 1 | 1 |
| 133 | TGFB2_1_218317687_218325587_218386401_218389011_FR | TGFB2 | 132 | 81 | 5.75498E-05 | 0.002258828 |
| 134 | TGFBR2_3_30563062_30565548_30608158_30611268_FF | TGFBR2 | 200 | 116 | 6.4811E-05 | 0.002312575 |
| 135 | TGFBR2_3_30566144_30567439_30633318_30636860_RR | TGFBR2 | 200 | 116 | 6.4811E-05 | 0.002312575 |
| 136 | TGFBR2_3_30566144_30567439_30694718_30698514_RR | TGFBR2 | 200 | 116 | 6.4811E-05 | 0.002312575 |
| 137 | TGFBR2_3_30641481_30645057_30688470_30694718_FF | TGFBR2 | 200 | 116 | 6.4811E-05 | 0.002312575 |
| 138 | THADA_2_43260154_43263093_43324949_43335758_FF | THADA | 200 | 116 | 6.4811E-05 | 0.002312575 |
| 139 | THADA_2_43260154_43263093_43415062_43421910_FF | THADA | 200 | 116 | 6.4811E-05 | 0.002312575 |
| 140 | THNSL2_2_88139809_88146295_88161717_88164554_FF | THNSL2 | 29 | 22 | 0.000554527 | 0.010705579 |
| 141 | THNSL2_2_88139809_88146295_88161717_88164554_FR | THNSL2 | 29 | 22 | 0.000554527 | 0.010705579 |
| 142 | TLR2_4_153659613_153661830_153693586_153700349_RF | TLR2 | 35 | 27 | 7.79458E-05 | 0.002581174 |
| 143 | TNFRSF25_1_6481328_6484248_6494588_6498048_FR | TNFRSF25 | 23 | 9 | 0.758494992 | 1 |
| 144 | TTN_2_178554164_178555670_178788193_178796485_FR | TTN | 200 | 105 | 0.011714369 | 0.093834484 |
| 145 | UACA_15_70715123_70719636_70780754_70784668_RF | UACA | 171 | 86 | 0.066058747 | 0.322087682 |
| 146 | WASL_7_123664155_123666896_123763390_123768284_RF | WASL | 117 | 46 | 0.880312179 | 1 |
| 147 | ZEB1_10_31273317_31275631_31437913_31439545_RF | ZEB1 | 181 | 122 | 2.83212E-10 | 3.70535E-08 |
| 148 | ZEB1_10_31273317_31275631_31507470_31524442_FF | ZEB1 | 181 | 122 | 2.83212E-10 | 3.70535E-08 |
| 149 | ZEB1_10_31437913_31439545_31458964_31462037_FR | ZEB1 | 181 | 122 | 2.83212E-10 | 3.70535E-08 |

TABLE 30.E2

| | | | | | | | | | | | |
|---|---|---|---|---|---|---|---|---|---|---|---|
| 120 | 42.17 | 0.32021 | 0.32021 | 6.5647 | 2.8E-06 | 4E-05 | 4.60189 | 1.24851 | 1.24851 | 1 | E__Ctrl |
| 121 | 42.86 | 0.40277 | 0.40277 | 2.5496 | 0.01993 | 0.04923 | -4.03372 | 1.32205 | 1.32205 | 1 | Str__Ctrl |
| 122 | 35.5 | -0.38567 | -0.38567 | -6.19747 | 6.1E-06 | 7.2E-05 | 3.83751 | 0.76542 | -1.30647 | -1 | E__Trn |
| 123 | 47.5 | -0.38658 | -0.38658 | -6.41859 | 3.8E-06 | 5.1E-05 | 4.29985 | 0.76494 | -1.30729 | -1 | E__Trn |
| 124 | 47.5 | -0.38862 | -0.38862 | -6.08691 | 7.6E-06 | 8.6E-05 | 3.60402 | 0.76386 | -1.30914 | -1 | E__Trn |
| 125 | 40.45 | -0.39909 | -0.39909 | -8.20964 | 1.2E-07 | 4E-06 | 7.80127 | 0.75834 | -1.31868 | -1 | E__Trn |
| 126 | 47.5 | -0.41472 | -0.41472 | -4.62876 | 0.0002 | 0.00167 | 0.44251 | 0.75016 | -1.33304 | -1 | Str__Trn |
| 127 | 58.73 | -0.40056 | -0.40056 | -15.082 | 5.4E-12 | 5.3E-09 | 17.6554 | 0.75756 | -1.32002 | -1 | E__Trn |
| 128 | 58.73 | 0.45488 | 0.45488 | 6.89229 | 1.5E-06 | 2.5E-05 | 5.26872 | 1.37067 | 1.37067 | 1 | E__Ctrl |
| 129 | 58.73 | -0.41655 | -0.41655 | -6.92127 | 1.4E-06 | 2.3E-05 | 5.32701 | 0.74922 | -1.33473 | -1 | E__Trn |
| 130 | 58.73 | 0.43262 | 0.43262 | 6.95618 | 1.3E-06 | 2.2E-05 | 5.39709 | 1.34968 | 1.34968 | 1 | E__Ctrl |
| 131 | 58.73 | 0.49185 | 0.49185 | 7.3328 | 6.2E-07 | 1.3E-05 | 6.14231 | 1.40625 | 1.40625 | 1 | E__Ctrl |
| 132 | 0 | -0.40849 | -0.40849 | -1.91206 | 0.07163 | 0.12978 | -5.19571 | 0.75341 | -1.32729 | -1 | Str__Trn |
| 133 | 61.36 | -0.42784 | -0.42784 | -9.6312 | 1E-08 | 6.8E-07 | 10.2712 | 0.74338 | -1.34521 | -1 | E__Trn |
| 134 | 58 | -0.38523 | -0.38523 | -10.9424 | 1.3E-09 | 1.8E-07 | 12.3234 | 0.76566 | -1.30607 | -1 | E__Trn |
| 135 | 58 | 0.62646 | 0.62646 | 4.01916 | 0.00078 | 0.00449 | -0.90676 | 1.54377 | 1.54377 | 1 | Str__Ctrl |
| 136 | 58 | 0.71377 | 0.71377 | 5.02096 | 8.4E-05 | 0.00091 | 1.30298 | 1.64008 | 1.64008 | 1 | Str__Ctrl |
| 137 | 58 | -0.38301 | -0.38301 | -6.46184 | 3.5E-06 | 4.7E-05 | 4.38955 | 0.76684 | -1.30406 | -1 | E__Trn |
| 138 | 58 | -0.44624 | -0.44624 | -2.33673 | 0.03099 | 0.06849 | -4.44221 | 0.73395 | -1.36248 | -1 | Str__Trn |
| 139 | 58 | -0.49656 | -0.49656 | -2.6351 | 0.01664 | 0.04305 | -3.86485 | 0.7088 | -1.41084 | -1 | Str__Trn |
| 140 | 75.86 | 0.33309 | 0.33309 | 6.66784 | 2.3E-06 | 3.4E-05 | 4.81339 | 1.25971 | 1.25971 | 1 | E__Ctrl |
| 141 | 75.86 | 0.3483 | 0.3483 | 5.48285 | 2.8E-05 | 0.00023 | 2.30294 | 1.27306 | 1.27306 | 1 | E__Ctrl |
| 142 | 77.14 | 0.37061 | 0.37061 | 12.6902 | 1.6E-10 | 9.4E-08 | 14.3497 | 1.2929 | 1.2929 | 1 | Str__Ctrl |
| 143 | 39.13 | -0.421 | -0.421 | -2.51835 | 0.02128 | 0.05168 | -4.09478 | 0.74691 | -1.33885 | -1 | Str__Trn |
| 144 | 52.5 | 0.32765 | 0.32765 | 14.3916 | 1.2E-11 | 8.6E-09 | 16.8699 | 1.25496 | 1.25496 | 1 | E__Ctrl |
| 145 | 50.29 | -0.45244 | -0.45244 | -6.64511 | 2.4E-06 | 3.5E-05 | 4.76692 | 0.7308 | -1.36836 | -1 | E__Trn |
| 146 | 39.32 | -0.54064 | -0.54064 | -8.60372 | 5.8E-08 | 2.4E-06 | 8.51248 | 0.68746 | -1.45462 | -1 | E__Trn |
| 147 | 67.4 | 0.3798 | 0.3798 | 3.26917 | 0.00406 | 0.01232 | -2.63478 | 1.30116 | 1.30116 | 1 | E__Ctrl |
| 148 | 67.4 | 0.3414 | 0.3414 | 8.35815 | 9E-08 | 3.2E-06 | 8.07177 | 1.26699 | 1.26699 | 1 | E__Ctrl |
| 149 | 67.4 | 0.35465 | 0.35465 | 3.41727 | 0.00291 | 0.00948 | -2.31101 | 1.27867 | 1.27867 | 1 | E__Ctrl |

TABLE 30.E3

| | | | | | | |
|---|---|---|---|---|---|---|
| 120 | TAAATTTTTACTTGTATTTTTTTGCATTTCGAGTACTGTTTCCTTATTGG TCTTCTATAT (SEQ ID NO: 478) | 1 | 67004819 | 67004850 | 67070417 | 67070448 |
| 121 | TATGAATCCCTAAATGTCACACATCAAGTCGAATTATATAAGATACCCTG AAATTTAAGG (SEQ ID NO: 190) & (SEQ ID NO: 479) | 18 | 48917335 | 48917366 | 48974547 | 48974578 |
| 122 | CTTGTTATGATTTTAGTATGAGATAGTTTCGAGACAGAATTTATTTGTAA TTTTATCAAT (SEQ ID NO: 480) | 11 | 4074211 | 4074242 | 4084365 | 4084396 |
| 123 | TCTGCGCAAGTTTTAATTTTCTCTAAGGTCGATTTCCCCACCTTCCCAAC CTCCAAGGGT (SEQ ID NO: 481) | 2 | 167965851 | 167965882 | 168114494 | 168114525 |
| 124 | TAAAATATAAATGAAAGAAGTACCTCGTTCGATTTCCCCACCTTCCCAAC CTCCAAGGGT (SEQ ID NO: 482) | 2 | 168062305 | 168062336 | 168114494 | 168114525 |
| 125 | TTTCATTTAGTTAAAACCAGATACATAATCGAGAGCACAAAGGGGAATCC CAACAGACTC (SEQ ID NO: 483) | 17 | 55042769 | 55042800 | 55142272 | 55142303 |
| 126 | CCTCTCCCGCTCTCCACTCACCTCGTGGTCGAAGTGTTGTCCCTGGACTG GCAGCATCTG (SEQ ID NO: 484) | 20 | 47665834 | 47665865 | 47797013 | 47797044 |
| 127 | AAATTATGTTTCATGGAATGATCAGGAATCGAAACTCTCTCCAATGAAAC AATTCTTTGA (SEQ ID NO: 485) | 9 | 90789107 | 90789138 | 90879165 | 90879196 |
| 128 | ATGACTGTGGAAGGTTCTGATGTCTCTGTCGATGAAATGGAGAGAGGAGA AAGAAAGAA (SEQ ID NO: 191) & (SEQ ID NO: 486) | 9 | 90816328 | 90816359 | 90832284 | 90832315 |
| 129 | TTTTACTGTTTTTGTAAGAGATATGTTTTCGAGAGTTGCAAGTACCTGCC TAAATCACTG (SEQ ID NO: 487) | 9 | 90822197 | 90822228 | 90836573 | 90836604 |
| 130 | ATGACTGTGGAAGGTTCTGATGTCTCTGTCGAGAGTTGCAAGTACCTGCC TAAATCACTG (SEQ ID NO: 488) | 9 | 90816328 | 90816359 | 90836573 | 90836604 |
| 131 | ATGACTGTGGAAGGTTCTGATGTCTCTGTCGACATCATTTTTACAAATAA GACCAGATGT (SEQ ID NO: 192) & (SEQ ID NO: 489) | 9 | 90816328 | 90816359 | 90872966 | 90872997 |
| 132 | GAGAGAGCGCCTGACATATAGTAGACCTTCGAGGAGAGAGAAGGGGCTCA AGGCGCCCGA (SEQ ID NO: 490) | 17 | 47687098 | 47687129 | 47704291 | 47704322 |
| 133 | AATATTGCTACTGGAAAATCTGAATCTTTCGAAGAAAGCCCTTTGTAAGT TGTTTTCAAA (SEQ ID NO: 193) & (SEQ ID NO: 491) | 1 | 218325556 | 218325587 | 218386401 | |
| 134 | TTAATTTTCAAAAATTCATTTCCAACATTCGACCTCAGTTGCATTAGATA CAGTAGGATG (SEQ ID NO: 492) | 3 | 30565517 | 30565548 | 30611237 | 30611268 |
| 135 | AACTATGTGACTTTTAGCTATACGAGTTTCGATAAATCATGATCATGGTA ATAATAATTA (SEQ ID NO: 493) | 3 | 30566144 | 30566175 | 30633318 | 30633349 |
| 136 | AACTATGTGACTTTTAGCTATACGAGTTTCGACTGGGTTCTAAATAGTTA ATGTCATAGT (SEQ ID NO: 194) & (SEQ ID NO: 494) | 3 | 30566144 | 30566175 | 30694718 | 30694749 |
| 137 | TTTCCCTTTCCTTTAGACCATCTCTCTTTCGATAACTAAGAAGAAGCTAC AGAATCTCTC (SEQ ID NO: 495) | 3 | 30645026 | 30645057 | 30694687 | 30694718 |
| 138 | GTTTGTCCTTCTCCCACCCTACCCCAACTCGAATCATTGACCTAGAATTT TAGAACTGGA (SEQ ID NO: 496) | 2 | 43263062 | 43263093 | 43335477 | 43335508 |
| 139 | GTTTGTCCTTCTCCCACCCTACCCCAACTCGATCTCTCAAAGAAAGAAG TTGGGATGCC (SEQ ID NO: 497) | 2 | 43263062 | 43263093 | 43421879 | 43421910 |
| 140 | TATCAAGTTAAACATTCAGACGTCTAGGTCGAGTAGTATTTAGCTTTCTT CCTTTCTAAC (SEQ ID NO: 498) | 2 | 88146264 | 88146295 | 88164523 | 88164554 |
| 141 | TATCAAGTTAAACATTCAGACGTCTAGGTCGACTTGAAGTTCACCTAAAG TTTTCCAGTC (SEQ ID NO: 165) & (SEQ ID NO: 499) & (SEQ ID NO: 615) | 2 | 88146264 | 88146295 | 88161717 | 88161748 |
| 142 | TAAAACTATTTTAAATGTTTTTAAAGTATCGATGTGTACTTTGACATCTG TGATGATGAT (SEQ ID NO: 195) & (SEQ ID NO: 500) | 4 | 153659613 | 153659644 | 153700318 | 153700349 |
| 143 | GCACCCCACCCTGGATCCCTTGAAAGCCTCGACAATGTTATTCTTTGTTT CTCTTACCAA (SEQ ID NO: 501) | 1 | 6484217 | 6484248 | 6494588 | 6494619 |
| 144 | TTGGAATTATCAAGAAAGATAACTAAATTCGAAAAAGATGTATTTGTTTT TGTTTAATAG (SEQ ID NO: 502) | 2 | 178555639 | 178555670 | 178788193 | 178788224 |
| 145 | ATAGTATAGAATGACAGCATGCTGGTTATCGACAAGAGTTCTTAAAAAGC CTAAATGTCA (SEQ ID NO: 166) & (SEQ ID NO: 503) | 15 | 70715123 | 70715154 | 70784637 | 70784668 |

TABLE 30.E3-continued

| 146 | GCCATTATTAAAATAAAAACCAAACAATTCGATAAATGTGTATTGAAGTT TTTTCCCTTT (SEQ ID NO: 504) | 7 | 123664155 | 123664186 | 123768253 | 123768284 |
| 147 | GTGTTCTAGATGAGGGGAACAGTGGTGATCGAAGTATACTAACTGAAGGA GAATAAAAAA (SEQ ID NO: 505) | 10 | 31273317 | 31273348 | 31439514 | 31439545 |
| 148 | ATTCCACAAATATTTGTGAGCACCATCTTCGAGCTCATTAGTTCAAGACC AGCCTGGGCA (SEQ ID NO: 167) & (SEQ ID NO: 506) | 10 | 31275600 | 31275631 | 31524411 | 31524442 |
| 149 | GTGTTCTAGATGAGGGGAACAGTGGTGATCGAAAATGCATTTAATATACT TAACCTATCA (SEQ ID NO: 507) | 10 | 31439514 | 31439545 | 31458964 | 31458995 |

TABLE 30.E4 / TABLE 30.E4-continued

| 120 | 1 | 67000849 | 67004850 | 6.7E+07 | 67074418 |
| 121 | 18 | 48917335 | 48921336 | 4.9E+07 | 48974578 |
| 122 | 11 | 4070241 | 4074242 | 4084365 | 4088366 |
| 123 | 2 | 167961881 | 167965882 | 1.7E+08 | 168114525 |
| 124 | 2 | 168058335 | 168062336 | 1.7E+08 | 168114525 |
| 125 | 17 | 55038799 | 55042800 | 5.5E+07 | 55146273 |
| 126 | 20 | 47661864 | 47665865 | 4.8E+07 | 47801014 |
| 127 | 9 | 90789107 | 90793108 | 9.1E+07 | 90879196 |
| 128 | 9 | 90816328 | 90820329 | 9.1E+07 | 90836285 |
| 129 | 9 | 90818227 | 90822228 | 9.1E+07 | 90840574 |
| 130 | 9 | 90816328 | 90820329 | 9.1E+07 | 90840574 |
| 131 | 9 | 90816328 | 90820329 | 9.1E+07 | 90876967 |
| 132 | 17 | 47683128 | 47687129 | 4.8E+07 | 47708292 |
| 133 | 1 | 218321586 | 218325587 | 2.2E+08 | 218390402 |
| 134 | 3 | 30561547 | 30565548 | 3.1E+07 | 30611268 |
| 135 | 3 | 30566144 | 30570145 | 3.1E+07 | 30637319 |
| 136 | 3 | 30566144 | 30570145 | 3.1E+07 | 30698719 |
| 137 | 3 | 30641056 | 30645057 | 3.1E+07 | 30694718 |
| 138 | 2 | 43259092 | 43263093 | 4.3E+07 | 43335508 |
| 139 | 2 | 43259092 | 43263093 | 4.3E+07 | 43421910 |
| 140 | 2 | 88142294 | 88146295 | 8.8E+07 | 88164554 |
| 141 | 2 | 88142294 | 88146295 | 8.8E+07 | 88165718 |
| 142 | 4 | 153659613 | 153663614 | 1.5E+08 | 153700349 |
| 143 | 1 | 6480247 | 6484248 | 6494588 | 6498589 |
| 144 | 2 | 178551669 | 178555670 | 1.8E+08 | 178792194 |
| 145 | 15 | 70715123 | 70719124 | 7.1E+07 | 70784668 |
| 146 | 7 | 123664155 | 123668156 | 1.2E+08 | 123768284 |
| 147 | 10 | 31273317 | 31277318 | 3.1E+07 | 31439545 |
| 148 | 10 | 31271630 | 31275631 | 3.2E+07 | 31524442 |
| 149 | 10 | 31435544 | 31439545 | 3.1E+07 | 31462965 |

TABLE 30.F1

| 150 | ZEB1_10_31437913_31439545_31463562_31470397_FR | ZEB1 | 181 | 122 | 2.83212E-10 | 3.70535E-08 |
| 151 | ZFHX3_16_73147488_73153243_73182254_73184585_FF | ZFHX3 | 200 | 131 | 1.15564E-09 | 1.13397E-07 |
| 152 | ADRB3_8_37962724_37965269_37987735_37989039_FR | ADRB3 | 29 | 12 | 0.689607935 | 1 |
| 153 | ADRB3_8_37962724_37965269_38014799_38016599_FR | ADRB3 | 29 | 12 | 0.689607935 | 1 |
| 154 | AGT_1_230717799_230719628_230752057_230757333_RF | AGT | 47 | 33 | 0.000290665 | 0.006914309 |
| 155 | AGT_1_230724515_230729957_230752057_230757333_RF | AGT | 47 | 33 | 0.000290665 | 0.006914309 |
| 156 | BMPR1B_4_94967703_94973952_95026184_95035151_FR | BMPR1B | 200 | 87 | 0.614370341 | 1 |
| 157 | HTR2A_13_46860092_46866824_46904346_46907815_RF | HTR2A | 87 | 42 | 0.259371991 | 0.827670783 |
| 158 | PPARA_22_46101029_46102611_46241078_46244347_FR | PPARA | 47 | 28 | 0.025050129 | 0.159872776 |
| 159 | SOS1_2_38982199_38993639_39061418_39066028_FF | SOS1 | 200 | 83 | 0.805923582 | 1 |
| 160 | SVEP1_9_110493529_110499578_110527410_110532406_FR | SVEP1 | 189 | 101 | 0.006989682 | 0.066107233 |
| 161 | UBE3A_15_25355032_25368345_25399797_25404434_FF | UBE3A | 154 | 109 | 2.51446E-11 | 3.9477E-09 |
| 162 | UBE3A_15_25355032_25368345_25457129_25464700_FR | UBE3A | 154 | 109 | 2.51446E-11 | 3.9477E-09 |
| 163 | ACBD6_1_180431719_180434683_180541491_180549122_RR | ACBD6 | 200 | 111 | 0.00091339 | 0.014340227 |
| 164 | BMPR1B_4_94821712_94826817_94866803_94871889_FF | BMPR1B | 200 | 87 | 0.614370341 | 1 |
| 165 | HADHA_2_26188355_26191067_26247231_26249308_FR | HADHA | 47 | 27 | 0.047791071 | 0.253486424 |
| 166 | HADHA_2_26188355_26191067_26280650_26284864_FF | HADHA | 47 | 27 | 0.047791071 | 0.253486424 |
| 167 | MTFR1_8_65658401_65661888_65780891_65782535_RF | MTFR1 | 184 | 76 | 0.812499278 | 1 |
| 168 | MYBPC1_12_101567479_101571538_101655128_101656342_RF | MYBPC1 | 186 | 94 | 0.05009075 | 0.263900932 |
| 169 | MYH1_17_10502067_10505465_10533547_10534931_RF | MYH1 | 103 | 52 | 0.121185055 | 0.485358512 |
| 170 | MYL1_2_210288997_210291732_210359762_210362293_FF | MYL1 | 10 | 5 | 0.476822977 | 1 |
| 171 | MYOD1_11_17685862_17689487_17729653_17733608_FR | MYOD1 | 17 | 6 | 0.838751191 | 1 |
| 172 | NECTIN3_3_111028574_111034204_111209684_111210764_FR | NECTIN3 | 97 | 52 | 0.040549948 | 0.23579044 |
| 173 | PON1_7_95303795_95305644_95332254_95337348_RF | PON1 | 21 | 14 | 0.032634239 | 0.195038964 |
| 174 | ACACB_12_109146008_109150083_109236052_109237242_RR | ACACB | 191 | 87 | 0.388279548 | 1 |
| 175 | ACACB_12_109236052_109237242_109268078_109273323_RR | ACACB | 191 | 87 | 0.388279548 | 1 |
| 176 | COL1A2_7_94359704_94366215_94394399_94397338_RF | COL1A2 | 47 | 26 | 0.08460057 | 0.378025067 |
| 177 | COX6A1_12_120397017_120399520_120449180_120450939_RF | COX6A1 | 22 | 5 | 0.990048121 | 1 |
| 178 | GGPS1_1_235284158_235288561_235306299_235310474_FR | GGPS1 | 29 | 5 | 0.999501849 | 1 |
| 179 | GSN_9_121182946_121189020_121323589_121328431_FF | GSN | 200 | 80 | 0.902128149 | 1 |

TABLE 30.F2

| | | | | | | | | | | | |
|---|---|---|---|---|---|---|---|---|---|---|---|
| 150 | 67.4 | 0.32502 | 0.32502 | 3.52284 | 0.00229 | 0.00784 | −2.07823 | 1.25268 | 1.25268 | 1 | E__Ctrl |
| 151 | 65.5 | −0.43734 | −0.43734 | −7.5712 | 4.7E−07 | 2.3E−05 | 6.48808 | 0.7385 | −1.3541 | −1 | Str_Trn |
| 152 | 41.38 | −0.4318 | −0.4318 | −3.39512 | 0.00316 | 0.01261 | −2.27663 | 0.74134 | −1.34892 | −1 | Str_Trn |
| 153 | 41.38 | −0.32388 | −0.32388 | −4.68737 | 0.00016 | 0.00094 | 0.53671 | 0.79892 | −1.25169 | −1 | Str_Trn |
| 154 | 70.21 | −0.43415 | −0.43415 | −3.86294 | 0.00111 | 0.00583 | −1.25218 | 0.74013 | −1.35111 | −1 | Str_Trn |
| 155 | 70.21 | −0.463 | −0.463 | −4.19239 | 0.00053 | 0.00337 | −0.52301 | 0.72548 | −1.3784 | −1 | Str_Trn |
| 156 | 43.5 | −0.46141 | −0.46141 | −4.19386 | 0.00053 | 0.00336 | −0.51977 | 0.72628 | −1.37689 | −1 | Str_Trn |
| 157 | 48.28 | −0.45067 | −0.45067 | −8.32753 | 1.2E−07 | 9.1E−06 | 7.85656 | 0.73171 | −1.36667 | −1 | Str_Trn |
| 158 | 59.57 | −0.33358 | −0.33358 | −9.83579 | 7.2E−09 | 5.5E−07 | 10.6041 | 0.79356 | −1.26014 | −1 | Str_Trn |
| 159 | 41.5 | −0.31318 | −0.31318 | −6.096 | 7.5E−06 | 8.5E−05 | 3.62327 | 0.80487 | −1.24244 | −1 | Str_Trn |
| 160 | 53.44 | −0.42515 | −0.42515 | −9.26758 | 2.4E−08 | 2.8E−06 | 9.44872 | 0.74476 | −1.34271 | −1 | Str_Trn |
| 161 | 70.78 | −0.20195 | −0.20195 | −3.01457 | 0.00716 | 0.01948 | −3.18176 | 0.86938 | −1.15025 | −1 | Str_Trn |
| 162 | 70.78 | −0.24775 | −0.24775 | −2.82758 | 0.01079 | 0.02719 | −3.57372 | 0.84221 | −1.18735 | −1 | Str_Trn |
| 163 | 55.5 | −0.43863 | −0.43863 | −7.21561 | 7.7E−07 | 1.5E−05 | 5.91252 | 0.73784 | −1.35531 | −1 | Str_Trn |
| 164 | 43.5 | −0.40597 | −0.40597 | −5.58481 | 2.2E−05 | 0.00019 | 2.52537 | 0.75473 | −1.32498 | −1 | Str_Trn |
| 165 | 57.45 | −0.39201 | −0.39201 | −14.4017 | 1.9E−11 | 2.6E−08 | 16.364 | 0.76207 | −1.31222 | −1 | Str_Trn |
| 166 | 57.45 | −0.19239 | −0.19239 | −1.68433 | 0.10907 | 0.18026 | −5.55862 | 0.87515 | −1.14266 | −1 | Str_Trn |
| 167 | 41.3 | −0.37341 | −0.37341 | −11.7997 | 3.7E−10 | 7.6E−08 | 13.5612 | 0.77195 | −1.29541 | −1 | Str_Trn |
| 168 | 50.54 | −0.42597 | −0.42597 | −4.76806 | 0.00014 | 0.00081 | 0.71784 | 0.74434 | −1.34348 | −1 | Str_Trn |
| 169 | 50.49 | −0.43395 | −0.43395 | −7.77363 | 2.7E−07 | 6.9E−06 | 6.98965 | 0.74023 | −1.35093 | −1 | Str_Trn |
| 170 | 50 | −0.38919 | −0.38919 | −13.7412 | 2.7E−11 | 1.4E−08 | 16.0955 | 0.76356 | −1.30966 | −1 | Str_Trn |
| 171 | 35.29 | −0.4449 | −0.4449 | −11.7045 | 4.2E−10 | 8.2E−08 | 13.4275 | 0.73463 | −1.36122 | −1 | Str_Trn |
| 172 | 53.61 | −0.36776 | −0.36776 | −7.28424 | 6.8E−07 | 1.4E−05 | 6.04732 | 0.77498 | −1.29035 | −1 | Str_Trn |
| 173 | 66.67 | −0.39554 | −0.39554 | −9.56195 | 1.1E−08 | 7.4E−07 | 10.156 | 0.76021 | −1.31543 | −1 | Str_Trn |
| 174 | 45.55 | 0.3764 | 0.3764 | 5.78418 | 1.6E−05 | 0.00028 | 2.93947 | 1.29809 | 1.29809 | 1 | E__Ctrl |
| 175 | 45.55 | 0.36198 | 0.36198 | 6.81205 | 2E−06 | 6.7E−05 | 5.03386 | 1.28519 | 1.28519 | 1 | E__Ctrl |
| 176 | 55.32 | 0.2558 | 0.2558 | 5.00789 | 7.9E−05 | 0.00053 | 1.254 | 1.194 | 1.194 | 1 | E__Ctrl |
| 177 | 22.73 | 0.30181 | 0.30181 | 5.45361 | 3E−05 | 0.00024 | 2.23895 | 1.23269 | 1.23269 | 1 | E__Ctrl |
| 178 | 17.24 | 0.29388 | 0.29388 | 2.41607 | 0.02598 | 0.05481 | −4.39757 | 1.22593 | 1.22593 | 1 | E__Ctrl |
| 179 | 40 | 0.2534 | 0.2534 | 3.85238 | 0.00108 | 0.00427 | −1.34367 | 1.19202 | 1.19202 | 1 | E__Ctrl |

TABLE 30.F3

| | | | | | | |
|---|---|---|---|---|---|---|
| 150 | GTGTTCTAGATGAGGGGAACAGTGGTGATCGACTGTGAGGATGAACTAAA AGCAAACCAT (SEQ ID NO: 508) | 10 | 31439514 | 31439545 | 31463562 | 31463593 |
| 151 | CTCTCAACTTTGGATGTAAGAATCATCTTCGAGATTTTGACTCTCCACCT GCCCCACAGG (SEQ ID NO: 168) & (SEQ ID NO: 509) & (SEQ ID NO: 574) | 16 | 73153212 | 73153243 | 73184554 | 73184585 |
| 152 | CGGTCCCTCTGCCCCGGTTACCTACCCGTCGACATGACACTTGGGTGGGG ATACAGGGCC (SEQ ID NO: 169) & (SEQ ID NO: 510) | 8 | 37965238 | 37965269 | 37987735 | 37987766 |
| 153 | CGGTCCCTCTGCCCCGGTTACCTACCCGTCGAAGTGGAATGAAGGAGCTT CTAAGTCATA (SEQ ID NO: 511) | 8 | 37965238 | 37965269 | 38014799 | 38014830 |
| 154 | TCCCCCTCTTCCTCTGCCTCCCTTCCCCTCGATTTGTAAAATGGGCTCAT TAGGGAAAAG (SEQ ID NO: 512) | 1 | 230717799 | 230717830 | 230757302 | 230757333 |
| 155 | TCCCCCTCTTCCTCTGCCTCCCTTCCCCTCGAAAACTGATTAAAAAGAAT ATTGCTGGCT (SEQ ID NO: 170) & (SEQ ID NO: 513) & (SEQ ID NO: 576) | 1 | 230724515 | 230724546 | 230757302 | 230757333 |
| 156 | AATTACTAAGAAAAAAGTGGTTACAATGTCGAAGAACATAAATATTATGT GGAGACTTAT (SEQ ID NO: 514) | 4 | 94973921 | 94973952 | 95026184 | 95026215 |
| 157 | TCACTTTTATTTATCTTACTCACTTTTCTCGAGGAATTCTCAGAATTCTC CTCAACCCAC (SEQ ID NO: 171) & (SEQ ID NO: 515) | 13 | 46860092 | 46860123 | 46907784 | 46907815 |
| 158 | ACACCTCACCCACCCAGCTGGGCTGGCCTCGATGCCATTAAATCATCCCG TGACCTTCCT (SEQ ID NO: 141) & (SEQ ID NO: 516) | 22 | 46102580 | 46102611 | 46241078 | 46241109 |
| 159 | TTTCTTCCAACTGAGAGAATCTTAAAAATCGAAATTGGATAAGGAAAAAA GTGAAATGTG (SEQ ID NO: 172) & (SEQ ID NO: 517) | 2 | 38993608 | 38993639 | 39065997 | 39066028 |
| 160 | TTATGGCTTAGAAGTAGAAAGTCATAAATCGATTCCTAAAAATTAATGAG GTGAATAGTA (SEQ ID NO: 196) & (SEQ ID NO: 518) | 9 | 110499547 | 110499578 | 110527410 | 110527441 |
| 161 | GTTATCAATTTTACTTATAAGACCTATTTCGAGGTATTAAGGGTTGGAAT GAAAAATACA (SEQ ID NO: 519) | 15 | 25368314 | 25368345 | 25404403 | 25404434 |
| 162 | GTTATCAATTTTACTTATAAGACCTATTTCGATGCAAAAGACAACAAAGT AGGATTTTCA (SEQ ID NO: 520) | 15 | 25368314 | 25368345 | 25457129 | 25457160 |
| 163 | TTTTAGTTTTATTTATTTAGTTATCATCTCGAAAAACAAACAACAATAAC AGCAACCCTC (SEQ ID NO: 173) & (SEQ ID NO: 521) | 1 | 180431719 | 180431750 | 180541491 | 180541522 |

TABLE 30.F3-continued

| | | | | | | |
|---|---|---|---|---|---|---|
| 164 | TGAAATCAATAGTTTTATATTAGTCGTATCGAGCATTCTAGAATCAAACC TTGGGGTATT (SEQ ID NO: 522) | 4 | 94826786 | 94826817 | 94871858 | 94871889 |
| 165 | TACCTTCCAACAGGAAGTGCAAACTAATTCGATCCTACCCTACCCTACCC TGGAGTTTCC (SEQ ID NO: 523) | 2 | 26191036 | 26191067 | 26247231 | 26247262 |
| 166 | TACCTTCCAACAGGAAGTGCAAACTAATTCGAATAAGAACCTCGTTATTC ATGTTCCTCT (SEQ ID NO: 524) | 2 | 26191036 | 26191067 | 26284833 | 26284864 |
| 167 | TTTCTATGAAGAATGTTCAAGATGCAATTCGAGCTACATACTATTATATA TTTTCACAGT (SEQ ID NO: 197) & (SEQ ID NO: 525) | 8 | 65658401 | 65658432 | 65782504 | 65782535 |
| 168 | AAATAATAACAAATATGACAGATATTGATCGATGTCTTAACTTGCCACAG AGATATTTTC (SEQ ID NO: 526) | 12 | 101567479 | 101567510 | 101656311 | 101656342 |
| 169 | GCAAGACTTTGTCTCAAAACAAAGTGTTCGAAAAAGTCATCGTTTAAAA GGTAAAATGT (SEQ ID NO: 174) & (SEQ ID NO: 527) | 17 | 10502067 | 10502098 | 10534900 | 10534931 |
| 170 | AATTTCACATTGATACATTGATAGACATTCGAAATCATACACAGCATACT CTCAAACCAT (SEQ ID NO: 144) & (SEQ ID NO: 528) & (SEQ ID NO: 577) | 2 | 210291701 | 210291732 | 210362262 | 210362293 |
| 171 | TCCATTAGCTCTGCTTTCAAATACTATATCGATGTAGCTTATGTAAAATA AATGTATTAA (SEQ ID NO: 175) & (SEQ ID NO: 529) | 11 | 17689456 | 17689487 | 17729653 | 17729684 |
| 172 | TCAAAGTTACAGTTTATATAATTAGAAATCGATCTAACCTCAATTCCAGT CCCACAAATG (SEQ ID NO: 176) & (SEQ ID NO: 530) | 3 | 111034173 | 111034204 | 111209684 | 111209715 |
| 173 | TAGAATTATAATACATTCCAAGCTCTTTTCGAAAAATTCGCATTCCTTGG TCAAGAAAAC (SEQ ID NO: 531) | 7 | 95303795 | 95303826 | 95337317 | 95337348 |
| 174 | TCAAGAAAAAATAATAATAATTTTTTTTTCGAACTTATGGCTCAAGCGAT TCTCTTGCTT (SEQ ID NO: 177) & (SEQ ID NO: 532) | 12 | 109146008 | 109146039 | 109236052 | 109236083 |
| 175 | AAGCAAGAGAATCGCTTGAGCCATAAGTTCGATGCTGCTTTGGGAACTGA AGGTTTTTCT (SEQ ID NO: 178) & (SEQ ID NO: 533) & (SEQ ID NO: 620) | 12 | 109236052 | 109236083 | 109268078 | 109268109 |
| 176 | AACATACTTTCCTAAATTTTACCTTTTTTCGAGAAAACATGGACATAAAG ATGGCAACAA (SEQ ID NO: 534) | 7 | 94359704 | 94359735 | 94397307 | 94397338 |
| 177 | GGCAGGCAGATCACTTTAGGTCAGGAGTTCGAACTCCTGACTTCAAGTGA TTCGCCCACC (SEQ ID NO: 535) | 12 | 120397017 | 120397048 | 120450908 | 120450939 |
| 178 | ATCTTTCTACATCAGTAAACACAAACTGTCGAGACCATCCTGGCTAAGAC AGTGAAACCC (SEQ ID NO: 536) | 1 | 235288530 | 235288561 | 235306299 | 235306330 |
| 179 | CTCTATAAATTTACCAGAATATAAATTCTCGACTAAAAGTTCAGTTCTTC ATTCCCACTA (SEQ ID NO: 198) & (SEQ ID NO: 537) | 9 | 121188989 | 121189020 | 121328400 | 121328431 |

TABLE 30.F4

| | | | | | |
|---|---|---|---|---|---|
| 150 | 10 | 31435544 | 31439545 | 3.1E+07 | 31467563 |
| 151 | 16 | 73149242 | 73153243 | 7.3E+07 | 73184585 |
| 152 | 8 | 37961268 | 37965269 | 3.8E+07 | 37991736 |
| 153 | 8 | 37961268 | 37965269 | 3.8E+07 | 38018800 |
| 154 | 1 | 230717799 | 230721800 | 2.3E+08 | 230757333 |
| 155 | 1 | 230724515 | 230728516 | 2.3E+08 | 230757333 |
| 156 | 4 | 94969951 | 94973952 | 9.5E+07 | 95030185 |
| 157 | 13 | 46860092 | 46864093 | 4.7E+07 | 46907815 |
| 158 | 22 | 46098610 | 46102611 | 4.6E+07 | 46245079 |
| 159 | 2 | 38989638 | 38993639 | 3.9E+07 | 39066028 |
| 160 | 9 | 110495577 | 110499578 | 1.1E+08 | 110531411 |
| 161 | 15 | 25364344 | 25368345 | 2.5E+07 | 25404434 |
| 162 | 15 | 25364344 | 25368345 | 2.5E+07 | 25461130 |
| 163 | 1 | 180431719 | 180435720 | 1.8E+08 | 180545492 |
| 164 | 4 | 94822816 | 94826817 | 9.5E+07 | 94871889 |
| 165 | 2 | 26187066 | 26191067 | 2.6E+07 | 26251232 |

TABLE 30.F4-continued

| | | | | | |
|---|---|---|---|---|---|
| 166 | 2 | 26187066 | 26191067 | 2.6E+07 | 26284864 |
| 167 | 8 | 65658401 | 65662402 | 6.6E+07 | 65782535 |
| 168 | 12 | 101567479 | 101571480 | 1E+08 | 101656342 |
| 169 | 17 | 10502067 | 10506068 | 1.1E+07 | 10534931 |
| 170 | 2 | 210287731 | 210291732 | 2.1E+08 | 210362293 |
| 171 | 11 | 17685486 | 17689487 | 1.8E+07 | 17733654 |
| 172 | 3 | 111030203 | 111034204 | 1.1E+08 | 111213685 |
| 173 | 7 | 95303795 | 95307796 | 9.5E+07 | 95337348 |
| 174 | 12 | 109146008 | 109150009 | 1.1E+08 | 109240053 |
| 175 | 12 | 109236052 | 109240053 | 1.1E+08 | 109272079 |
| 176 | 7 | 94359704 | 94363705 | 9.4E+07 | 94397338 |
| 177 | 12 | 120397017 | 120401018 | 1.2E+08 | 120450939 |
| 178 | 1 | 235284560 | 235288561 | 2.4E+08 | 235310300 |
| 179 | 9 | 121185019 | 121189020 | 1.2E+08 | 121328431 |

TABLE 30.G1

| | | | | | |
|---|---|---|---|---|---|
| 180 | HTR2A__13__46847106__46857832__46938758__46942222__RF | HTR2A | 87 | 42 | 0.259371991 | 0.827670783 |
| 181 | HTR2A__13__46877712__46880636__46938758__46942222__FF | HTR2A | 87 | 42 | 0.259371991 | 0.827670783 |
| 182 | IGF1R__15__98652565__98657862__98731539__98737034__RF | IGF1R | 200 | 106 | 0.008018013 | 0.06952724 |
| 183 | MUSK__9__110648469__110652659__110747866__110751903__FR | MUSK | 154 | 75 | 0.152643976 | 0.578867253 |
| 184 | MYOT__5__137829466__137834410__137882068__137884626__RR | MYOT | 75 | 20 | 0.999459925 | 1 |

TABLE 30.G1-continued

| | | | | | |
|---|---|---|---|---|---|
| 185 | PPARA__22__46128634__46134707__46231440__46235124__FR | PPARA | 47 | 28 | 0.025050129 | 0.159872776 |
| 186 | PPP1R9A__7__94903925__94908776__94951930__94967018__RF | PPP1R9A | 200 | 113 | 0.000335824 | 0.007753573 |
| 187 | PPP1R9A__7__94951930__94967018__95061734__95065150__FR | PPP1R9A | 200 | 113 | 0.000335824 | 0.007753573 |
| 188 | PPP1R9A__7__94951930__94967018__95258927__95267729__FF | PPP1R9A | 200 | 113 | 0.000335824 | 0.007753573 |
| 189 | RB1__13__48378062__48381344__48486008__48495146__FF | RB1 | 189 | 84 | 0.509778071 | 1 |
| 190 | SLC25A13__7__96209525__96214524__96295606__96302029__FF | SLC25A13 | 200 | 105 | 0.011714369 | 0.093834484 |
| 191 | ACE2__X__15558483__15561359__15624288__15632375__RR | ACE2 | 34 | 23 | 0.005085953 | 0.051850296 |
| 192 | DNAH5__5__13907228__13913186__13947622__13950495__FR | DNAH5 | 200 | 106 | 0.008018013 | 0.06952724 |
| 193 | EMCN__4__100636305__100649860__100744427__100745788__RR | EMCN | 200 | 121 | 2.82028E-06 | 0.000158137 |
| 194 | ITGAV__2__186622411__186639782__186682119__186696186__RR | ITGAV | 38 | 16 | 0.665375941 | 1 |
| 195 | MSTN__2__190044593__190053476__190068550__190073029__FR | MSTN | 11 | 5 | 0.58381774 | 1 |
| 196 | PLCXD2__3__111633890__111638317__111672672__111677327__FR | PLCXD2 | 200 | 76 | 0.969310539 | 1 |
| 197 | SGCZ__8__14631157__14642508__14778176__14785491__FF | SGCZ | 200 | 131 | 1.15564E-09 | 1.13397E-07 |
| 198 | SLC25A13__7__96178122__96182739__96295606__96302029__RF | SLC25A13 | 200 | 105 | 0.011714369 | 0.093834484 |
| 199 | SOCS7__17__38347510__38348776__38360864__38363420__FR | SOCS7 | 47 | 25 | 0.139363472 | 0.533660124 |
| 200 | SRI__7__88199682__88203042__88229166__88237101__RF | SRI | 61 | 34 | 0.047542529 | 0.253486424 |
| 201 | STXBP4__17__55035186__55042800__55117598__55123347__RR | STXBP4 | 178 | 72 | 0.865724188 | 1 |
| 202 | SVEP1__9__110397951__110405969__110503630__110509758__FF | SVEP1 | 189 | 101 | 0.006989682 | 0.066107233 |

TABLE 30.G2

| | | | | | | | | | | | |
|---|---|---|---|---|---|---|---|---|---|---|---|
| 180 | 48.28 | 0.23347 | 0.23347 | 2.92357 | 0.00875 | 0.02288 | -3.37367 | 1.17566 | 1.17566 | 1 | E_Ctrl |
| 181 | 48.28 | 0.31362 | 0.31362 | 5.2027 | 5.2E-05 | 0.00037 | 1.68658 | 1.24282 | 1.24282 | 1 | E_Ctrl |
| 182 | 53 | 0.23289 | 0.23289 | 2.56313 | 0.01907 | 0.04289 | -4.11013 | 1.17519 | 1.17519 | 1 | E_Ctrl |
| 183 | 48.7 | 0.30041 | 0.30041 | 3.63015 | 0.00179 | 0.00643 | -1.84018 | 1.23149 | 1.23149 | 1 | E_Ctrl |
| 184 | 26.67 | 0.26883 | 0.26883 | 6.70047 | 2.2E-06 | 3.3E-05 | 4.88 | 1.20483 | 1.20483 | 1 | E_Ctrl |
| 185 | 59.57 | 0.29923 | 0.29923 | 2.46766 | 0.02333 | 0.05033 | -4.29772 | 1.23049 | 1.23049 | 1 | E_Ctrl |
| 186 | 56.5 | 0.29403 | 0.29403 | 4.70344 | 0.00016 | 0.00091 | 0.57281 | 1.22606 | 1.22606 | 1 | E_Ctrl |
| 187 | 56.5 | 0.28471 | 0.28471 | 4.35389 | 0.00035 | 0.00171 | -0.21427 | 1.21816 | 1.21816 | 1 | E_Ctrl |
| 188 | 56.5 | 0.2709 | 0.2709 | 3.54424 | 0.00218 | 0.00753 | -2.03086 | 1.20656 | 1.20656 | 1 | E_Ctrl |
| 189 | 44.44 | 0.30464 | 0.30464 | 6.97933 | 1.2E-06 | 2.2E-05 | 5.44345 | 1.23511 | 1.23511 | 1 | E_Ctrl |
| 190 | 52.5 | 0.31224 | 0.31224 | 5.62896 | 2E-05 | 0.00018 | 2.62135 | 1.24163 | 1.24163 | 1 | E_Ctrl |
| 191 | 67.65 | 0.32899 | 0.32899 | 9.15537 | 2.2E-08 | 1.2E-06 | 9.47318 | 1.25614 | 1.25614 | 1 | E_Ctrl |
| 192 | 53 | 0.3725 | 0.3725 | 11.9417 | 3E-10 | 6.9E-08 | 13.7588 | 1.2946 | 1.2946 | 1 | E_Ctrl |
| 193 | 60.5 | 0.31985 | 0.31985 | 5.68628 | 1.8E-05 | 0.00016 | 2.74564 | 1.2482 | 1.2482 | 1 | E_Ctrl |
| 194 | 42.11 | 0.35248 | 0.35248 | 2.33791 | 0.03054 | 0.06245 | -4.54674 | 1.27675 | 1.27675 | 1 | E_Ctrl |
| 195 | 45.45 | 0.22853 | 0.22853 | 2.5176 | 0.021 | 0.04632 | -4.20002 | 1.17164 | 1.17164 | 1 | E_Ctrl |
| 196 | 38 | 0.37187 | 0.37187 | 9.14346 | 2.3E-08 | 1.2E-06 | 9.45286 | 1.29403 | 1.29403 | 1 | E_Ctrl |
| 197 | 65.5 | 0.35186 | 0.35186 | 12.46 | 1.5E-10 | 4.6E-08 | 14.44629 | 1.2762 | 1.2762 | 1 | E_Ctrl |
| 198 | 52.5 | 0.3227 | 0.3227 | 8.1037 | 1.4E-07 | 4.6E-06 | 7.60648 | 1.25067 | 1.25067 | 1 | E_Ctrl |
| 199 | 53.19 | 0.32563 | 0.32563 | 8.97975 | 3E-08 | 1.5E-06 | 9.17168 | 1.25321 | 1.25321 | 1 | E_Ctrl |
| 200 | 55.74 | 0.3451 | 0.3451 | 6.86348 | 1.6E-06 | 2.6E-05 | 5.21065 | 1.27024 | 1.27024 | 1 | E_Ctrl |
| 201 | 40.45 | 0.34798 | 0.34798 | 7.97475 | 1.8E-07 | 5.4E-06 | 7.36728 | 1.27277 | 1.27277 | 1 | E_Ctrl |
| 202 | 53.44 | 0.32848 | 0.32848 | 4.83516 | 0.00012 | 0.00072 | 0.86819 | 1.25569 | 1.25569 | 1 | E_Ctrl |

TABLE 30.G3

| | | | | | | |
|---|---|---|---|---|---|---|
| 180 | CCAAAAGTAATGGCAACAAAAGTCAAAATCGATTCTTG GGAATTTCCCAAAATACTGAAA (SEQ ID NO: 538) | 13 | 46847106 | 46847137 | 46942191 | 46942222 |
| 181 | GGCAGGCGGATCTCCTGAGGTCAGGAGATCGATTTTGA CTTTTGTTGCCATTACTTTTGG (SEQ ID NO: 539) | 13 | 46880605 | 46880636 | 46942191 | 46942222 |
| 182 | CGTAGAACTAAGATGTATTCAAAGTCAGTCGAAAAAGA TTAGAAAAGTTCAACTCTAAGA (SEQ ID NO: 179) & (SEQ ID NO: 540) & (SEQ ID NO: 616) | 15 | 98652565 | 98652596 | 98737003 | 98737034 |
| 183 | ATCTTACAAAGAATAATTCTAAGAAAAGTCGAGCATTG GAGAAAATCTCCCTTTTCTTTT (SEQ ID NO: 199) & (SEQ ID NO: 541) | 9 | 110652628 | 110652659 | 110747866 | 110747897 |
| 184 | CAAAACAATGTGTTAACTTTTTTTTTTTCGATTGATG AAGGAAGATTCTGCAGAATGGA (SEQ ID NO: 542) & (SEQ ID NO: 575) | 5 | 137829466 | 137829497 | 137882068 | 137882099 |
| 185 | TGTTTTTATTTTCATGTTTTAATTTTGTTCGAACTCTT GACCTCAGGTAAACCACCCACC (SEQ ID NO: 200) & (SEQ ID NO: 543) | 22 | 46134676 | 46134707 | 46231440 | 46231471 |
| 186 | AGAACTGGTTATTGATCTATTCAGGGATTCGAAATAAT AGATTATGAATAAATTATTCTG (SEQ ID NO: 201) & (SEQ ID NO: 544) | 7 | 94903925 | 94903956 | 94966987 | 94967018 |

TABLE 30.G3-continued

| 187 | AGAACTGGTTATTGATCTATTCAGGGATTCGAATGAAT<br>GAATGAAAATAAAGAGCCATGG (SEQ ID NO: 545) | 7 | 94966987 | 94967018 | 95061734 | 95061765 |
|---|---|---|---|---|---|---|
| 188 | AGAACTGGTTATTGATCTATTCAGGGATTCGAAGGGTA<br>AATACTTAAGTCTTTAAATAAA (SEQ ID NO: 546) | 7 | 94966987 | 94967018 | 95267698 | 95267729 |
| 189 | TTAAAAGCCTTTGATTTTTACAAAGTGATCGAGTCAGT<br>TTCCTTTTGGTATAAGGATATC (SEQ ID NO: 547) | 13 | 48381313 | 48381344 | 48495115 | 48495146 |
| 190 | GGCAGGCGGATCATTTCAGGTCAGGAGTTCGACCTGAA<br>ATTTCCATACTAAATTTAAATA<br>(SEQ ID NO: 142) & (SEQ ID NO: 548) | 7 | 96214493 | 96214524 | 96301998 | 96302029 |
| 191 | AAATAAGAAGAAGAAAGGAAAAAAATCTTCGAAAGAGC<br>GTAAGATAGAGAATAATTATTT (SEQ ID NO: 549) | X | 15558483 | 15558514 | 15624288 | 15624319 |
| 192 | TTGTTTGTAAATTGTTTTTCTAAAATCTTCGAGAGCTG<br>GTTGAAAATTTTGCTCTCAATT (SEQ ID NO: 550) | 5 | 13913155 | 13913186 | 13947622 | 13947653 |
| 193 | GGTATTACCTTGATGGCCTTAAAGAAGATCGAGCCAGA<br>GGGCCTCTGTTCATGTTTGGGC<br>(SEQ ID NO: 183) & (SEQ ID NO: 551) | 4 | 100636305 | 100636336 | 100744427 | 100744458 |
| 194 | AGAAGACTCACCAAAATTTATCCTGTTTCGAACCTTA<br>TAATGGTGATAAATCATTAATG (SEQ ID NO: 552) | 2 | 186622411 | 186622442 | 186682119 | 186682150 |
| 195 | TTCCAAATACTTCCTCTGCAAAATGCCATCGAACTCCT<br>GGCCTCAAGTCATCCATCCGCC (SEQ ID NO: 553) | 2 | 190053445 | 190053476 | 190068550 | 190068581 |
| 196 | CTTTTTGAAGATTATAATCTATTAGTGATCGAGGCTTT<br>TTTGCTTTTTTTTTTTGAGAT<br>(SEQ ID NO: 202) & (SEQ ID NO: 554) | 3 | 111638286 | 111638317 | 111672672 | 111672703 |
| 197 | CTATATGTAAGTTACAATATGTAAGGTATCGATAGTCA<br>CTGAGACTAATTTAATGTTATA<br>(SEQ ID NO: 203) & (SEQ ID NO: 555) | 8 | 14642477 | 14642508 | 14785460 | 14785491 |
| 198 | TATTTAAATTTAGTATGGAAATTTCAGGTCGAAGGCAC<br>TGAATGTCAGAGCCAAGCTGTA (SEQ ID NO: 556) | 7 | 96178122 | 96178153 | 96301998 | 96302029 |
| 199 | AGGCAGGCAGATCAATGAGGTTGGGAGATCGACAAGTT<br>CAGTAATTCTGAGGTGAGTTTT<br>(SEQ ID NO: 180) & (SEQ ID NO: 557) | 17 | 38348745 | 38348776 | 38360864 | 38360895 |
| 200 | TGTAGGCAGATTACCTGAAGTTAGGAGTTCGATTAGGA<br>ATAACCTATCATTAGAGTTGTT<br>(SEQ ID NO: 204) & (SEQ ID NO: 558) &<br>(SEQ ID NO: 578) | 7 | 88199682 | 88199713 | 88237070 | 88237101 |
| 201 | GTTGTTATAACTATATCATGAGACTAAGTCGAAAAAAA<br>AAAACAATAATTTCAGCTGTAT<br>(SEQ ID NO: 181) & (SEQ ID NO: 559) | 17 | 55035186 | 55035217 | 55117598 | 55117629 |
| 202 | TATATTAGAAACATGTCTGAAAAAAGTATCGATAAATG<br>TATACGTTGATGTACATTGATA<br>(SEQ ID NO: 182) & (SEQ ID NO: 560) | 9 | 110405938 | 110405969 | 110509727 | 110509758 |

TABLE 30.G4

| 180 | 13 | 46847106 | 46851107 | 4.7E+07 | 46942222 |
|---|---|---|---|---|---|
| 181 | 13 | 46876635 | 46880636 | 4.7E+07 | 46942222 |
| 182 | 15 | 98652565 | 98656566 | 9.9E+07 | 98737034 |
| 183 | 9 | 110648658 | 110652659 | 1.1E+08 | 110751867 |
| 184 | 5 | 137829466 | 137833467 | 1.4E+08 | 137886069 |
| 185 | 22 | 46130706 | 46134707 | 4.6E+07 | 46235441 |
| 186 | 7 | 94903925 | 94907926 | 9.5E+07 | 94967018 |
| 187 | 7 | 94963017 | 94967018 | 9.5E+07 | 95065735 |
| 188 | 7 | 94963017 | 94967018 | 9.5E+07 | 95267729 |
| 189 | 13 | 48377343 | 48381344 | 4.8E+07 | 48495146 |
| 190 | 7 | 96210523 | 96214524 | 9.6E+07 | 96302029 |
| 191 | X | 15558483 | 15562484 | 1.6E+07 | 15628289 |
| 192 | 5 | 13909185 | 13913186 | 1.4E+07 | 13951623 |

TABLE 30.G4-continued

| 193 | 4 | 100636305 | 100640306 | 1E+08 | 100748428 |
|---|---|---|---|---|---|
| 194 | 2 | 186622411 | 186626412 | 1.9E+08 | 186686120 |
| 195 | 2 | 190049475 | 190053476 | 1.9E+08 | 190072551 |
| 196 | 3 | 111634316 | 111638317 | 1.1E+08 | 111676673 |
| 197 | 8 | 14638507 | 14642508 | 1.5E+07 | 14785491 |
| 198 | 7 | 96178122 | 96182123 | 9.6E+07 | 96302029 |
| 199 | 17 | 38344775 | 38348776 | 3.8E+07 | 38364865 |
| 200 | 7 | 88199682 | 88203683 | 8.8E+07 | 88237101 |
| 201 | 17 | 55035186 | 55039187 | 5.5E+07 | 55121599 |
| 202 | 9 | 110401968 | 110405969 | 1.1E+08 | 110509758 |

TABLE 31.a

| | Probe | GeneLocus | Probe__Count__Total | Probe__Count__Sig |
|---|---|---|---|---|
| 1 | C1GALT1__7__7113076__7114831__7258228__7260668__FF | C1GALT1 | 89 | 52 |
| 2 | DKK3__11__11956071__11968035__11984245__11993733__FR | DKK3 | 54 | 36 |
| 3 | FBXO32__8__123526212__123527874__123555254__123559065__FR | FBXO32 | 41 | 26 |
| 4 | GPC6__13__94054831__94060621__94121445__94133208__RF | GPC6 | 166 | 105 |
| 5 | GSN__9__121177548__121180410__121268506__121274144__FR | GSN | 156 | 76 |
| 6 | LMO4__1__87315524__87318670__87343110__87349940__FF | LMO4 | 105 | 75 |
| 7 | MAPK10__4__86572598__86581486__86617317__86621940__FF | MAPK10 | 172 | 107 |
| 8 | MBNL1__3__152229500__152234786__152281057__152285843__FR | MBNL1 | 145 | 85 |
| 9 | PCK1__20__57527297__57530814__57579772__57583521__RR | PCK1 | 36 | 26 |
| 10 | PIK3C3__18__42070009__42072187__42088671__42094691__FF | PIK3C3 | 141 | 89 |
| 11 | PTPRC__1__198595771__198598296__198659753__198666156__RF | PTPRC | 185 | 91 |
| 12 | RGS6__14__72139099__72144564__72213251__72222544__FR | RGS6 | 174 | 104 |
| 13 | RUNX3__1__24920810__24923822__24973522__24976037__RF | RUNX3 | 51 | 24 |
| 14 | ZFHX3__16__73147488__73153243__73182254__73184585__FF | ZFHX3 | 171 | 123 |
| 15 | MYOT__5__137829466__137834410__137882068__137884626__RR | MYOT | 35 | 20 |
| 16 | AGT__1__230724515__230729957__230752057__230757333__RF | AGT | 47 | 31 |
| 17 | MYL1__2__210288997__210291732__210359762__210362293__FF | MYL1 | 9 | 5 |
| 18 | SRI__7__88199682__88203042__88229166__88237101__RF | SRI | 57 | 30 |

20

TABLE 31.b

| | HyperG__Stats | FDR__HyperG | Percent__Sig | logFC | AveExpr |
|---|---|---|---|---|---|
| 1 | 0.485083555 | 1 | 58.43 | −0.555546218 | −0.555546218 |
| 2 | 0.113222201 | 0.567553327 | 66.67 | −0.452190179 | −0.452190179 |
| 3 | 0.279504208 | 0.898561555 | 63.41 | −0.428908404 | −0.428908404 |
| 4 | 0.081947099 | 0.503453115 | 63.25 | 0.528815395 | 0.528815395 |
| 5 | 0.990051008 | 1 | 48.72 | −0.435924362 | −0.435924362 |
| 6 | 0.002438643 | 0.079967184 | 71.43 | −0.425303631 | −0.425303631 |
| 7 | 0.127316337 | 0.601206787 | 62.21 | 0.369477889 | 0.369477889 |
| 8 | 0.440065203 | 1 | 58.62 | −0.423225201 | −0.423225201 |
| 9 | 0.052274012 | 0.438252195 | 72.22 | −0.454377101 | −0.454377101 |
| 10 | 0.108139211 | 0.559937306 | 63.12 | 0.349058418 | 0.349058418 |
| 11 | 0.991656906 | 1 | 49.19 | 0.342871898 | 0.342871898 |
| 12 | 0.312185766 | 0.950015156 | 59.77 | 0.373553959 | 0.373553959 |
| 13 | 0.95196413 | 1 | 47.06 | 0.364233402 | 0.364233402 |
| 14 | 7.53E−05 | 0.010367006 | 71.93 | −0.437339546 | −0.437339546 |
| 15 | 0.594268263 | 1 | 57.14 | 0.377641822 | 0.377641822 |
| 16 | 0.156967939 | 0.666487236 | 65.96 | −0.462997504 | −0.462997504 |
| 17 | 0.682316487 | 1 | 55.56 | −0.356584057 | −0.356584057 |
| 18 | 0.816232021 | 1 | 52.63 | 0.347423032 | 0.347423032 |

TABLE 31.c

| | t | P.Value | adj.P.Val | B |
|---|---|---|---|---|
| 1 | −11.0417245 | 0.00000000111 | 0.000000163 | 12.47094565 |
| 2 | −4.498338722 | 0.000266954 | 0.002046882 | 0.154483715 |
| 3 | −11.06651685 | 0.00000000106 | 0.000000159 | 12.50758304 |
| 4 | 2.192030297 | 0.041519144 | 0.085450094 | −4.70897528 |
| 5 | −4.024149814 | 0.000771506 | 0.004457333 | −0.895719572 |
| 6 | −4.334227249 | 0.000385015 | 0.002678159 | −0.20873374 |
| 7 | 10.62330419 | 0.0000000289295572819759 | 0.00000681985048919552 | 11.54687815 |
| 8 | −5.762419013 | 0.0000171628795759885 | 0.000292745 | 2.893666517 |
| 9 | −3.146677782 | 0.005488024 | 0.018949968 | −2.809655881 |
| 10 | 10.19574365 | 0.00000000406 | 0.000000379 | 11.17917387 |
| 11 | 12.24688433 | 0.000000000196 | 0.0000000539 | 14.17658691 |
| 12 | 9.049855001 | 0.000000034856893346579 | 0.0000036264507177386 | 9.09037332 |
| 13 | 10.30993314 | 0.0000000004646642800056321 | 0.00000961862645683259 | 11.08156058 |
| 14 | −7.571199723 | 0.000000474476333843650 | 0.0000231189585700664 | 6.488080595 |
| 15 | 10.49506981 | 0.0000000350762736065339 | 0.000000777454166573518 | 11.35784279 |
| 16 | −4.192393926 | 0.00052891 | 0.00336987 | −0.523006115 |
| 17 | −7.810248605 | 0.000000305171587917033 | 0.0000169792808595093 | 6.929231219 |
| 18 | 5.646538925 | 0.0000219157968101507 | 0.000348185 | 2.648883369 |

TABLE 31.d

| | FC | FC_1 | LS | Loop Detected |
|---|---|---|---|---|
| 1 | 0.680399404 | −1.469724979 | −1 | E_Trn |
| 2 | 0.730932365 | −1.36811564 | −1 | Str_Trn |
| 3 | 0.742823621 | −1.346214596 | −1 | E_Trn |
| 4 | 1.442744064 | 1.442744064 | 1 | Str_Ctrl |
| 5 | 0.739219971 | −1.352777305 | −1 | Str_Trn |
| 6 | 0.744681988 | −1.342855092 | −1 | Str_Trn |
| 7 | 1.291885213 | 1.291885213 | 1 | Str_Ctrl |
| 8 | 0.745755594 | −1.34092189 | −1 | Str_Trn |
| 9 | 0.729825214 | −1.370191083 | −1 | Str_Trn |
| 10 | 1.27372905 | 1.27372905 | 1 | E_Ctrl |

TABLE 31.d-continued

| | FC | FC_1 | LS | Loop Detected |
|---|---|---|---|---|
| 11 | 1.26827878 | 1.26827878 | 1 | E_Ctrl |
| 12 | 1.295540359 | 1.295540359 | 1 | Str_Ctrl |
| 13 | 1.287197476 | 1.287197476 | 1 | Str_Ctrl |
| 14 | 0.738495203 | −1.354104937 | −1 | Str_Trn |
| 15 | 1.299216466 | 1.299216466 | 1 | Str_Ctrl |
| 16 | 0.725477359 | −1.378402768 | −1 | Str_Trn |
| 17 | 0.781011633 | −1.280390659 | −1 | Str_Trn |
| 18 | 1.272286016 | 1.272286016 | 1 | Str_Ctrl |

TABLE 31.e

| Probe sequence | | Probe Location | |
|---|---|---|---|
| 60 mer | | Chr | Start1 |
| 1 AAATGTATAAGAACAGAAGAGAATTATCTCGACATGTCTGAAAAGTATTATCAGCCCTCT (SEQ ID NO: 145) & (SEQ ID NO: 372) & (SEQ ID NO: 561) | | 7 | 7114800 |
| 2 GACACCTCCTCTCCCTTCCCTCCCCTTCTCGAGTTATCAAAATATTTTGAGAGACAGTAT (SEQ ID NO: 129) & (SEQ ID NO: 390) & (SEQ ID NO: 562) & (SEQ ID NO: 617) | | 11 | 11968004 |
| 3 TGCAGAAAGTACTACAAAAAAAGAAGCTTCGAAAATGTTGGAGATGAGAGTTTCTTCACC (SEQ ID NO: 131) & (SEQ ID NO: 402) & (SEQ ID NO: 563) | | 8 | 123527843 |
| 4 AATTAGACAACGACTATATGACTCGTCTCGACTTTAAAGCAAGTACTTCTTGTATGCTC (SEQ ID NO: 188) & (SEQ ID NO: 408) & (SEQ ID NO: 564) | | 13 | 94054831 |
| 5 AAAAAGAGAAAAGCAGGTTAGCACATTGTCGACCCCGCCCCCGGGATGGGGGAACTGGCC (SEQ ID NO: 151) & (SEQ ID NO: 411) & (SEQ ID NO: 565) | | 9 | 121180379 |
| 6 CCCCTGGCTCACCTACACAAAATTGTGCTCGACTCTACTCTTAGCCCTGCTAAATAAGTA (SEQ ID NO: 155) & (SEQ ID NO: 426) & (SEQ ID NO: 566) | | 1 | 87318639 |
| 7 ATTATATTAGTGCTGTAATAAAATTAAGTCGACACATTTGATACTGCTTATTGGGTTATT (SEQ ID NO: 156) & (SEQ ID NO: 428) & (SEQ ID NO: 567) | | 4 | 86581455 |
| 8 TACCTTGAAAAGCTCTTCAGTATGATTATCGAGCTTTAGCCATTCTAGTAATTATTAAAA (SEQ ID NO: 157) & (SEQ ID NO: 430) & (SEQ ID NO: 568) | | 3 | 152234755 |
| 9 CCTCGTCGTCCCCTCTCTTCCTCGTTCCTCGAACATCTCCAAGTCAGATAATCATAACAA (SEQ ID NO: 134) & (SEQ ID NO: 448) & (SEQ ID NO: 569) | | 20 | 57527297 |
| 10 ATCTATTATAATGATGCAATATTGTTAATCGATTCAAAGATCAAATTAATTATTAAAGCT (SEQ ID NO: 135) & (SEQ ID NO: 455) & (SEQ ID NO: 570) | | 18 | 42072156 |
| 11 AGAGGCTGAGGTGAAAAGATTGTTTGAGTCGAAGATCATTGTCTCATTTTTTTACTTGTT (SEQ ID NO: 162) & (SEQ ID NO: 465) & (SEQ ID NO: 571) & (SEQ ID NO: 621) | | 1 | 198595771 |
| 12 AATGGCATTCTCCATTTATTCGTATTTATCGAGACTTTCTATGAAAGCTTTTTTGATGTT (SEQ ID NO: 472) & (SEQ ID NO: 572) | | 14 | 72144533 |
| 13 CTTAATTTTTTTTCTTTGAATGCCTCTATCGACAGTCTTCTCTCTACTTTCTACAGTGAA (SEQ ID NO: 140) & (SEQ ID NO: 474) & (SEQ ID NO: 573) | | 1 | 24920810 |
| 14 CTCTCAACTTTGGATGTAAGAATCATCTTCGAGATTTTGACTCTCCACCTGCCCCACAGG (SEQ ID NO: 168) & (SEQ ID NO: 509) & (SEQ ID NO: 574) | | 16 | 73153212 |
| 15 CAAAACAATGTGTTAACTTTTTTTTTTTCGATTGATGAAGGAAGATTCTGCAGAATGGA (SEQ ID NO: 542) & (SEQ ID NO: 575) | | 5 | 137829466 |
| 16 TCCCCCTCTTCCTCTGCCTCCCTTCCCCTCGAAAACTGATTAAAAAGAATATTGCTGGCT (SEQ ID NO: 170) & (SEQ ID NO: 513) & (SEQ ID NO: 576) | | 1 | 230724515 |
| 17 AATTTCACATTGATACATTGATAGACATTCGAAATCATACACAGCATACTCTCAAACCAT (SEQ ID NO: 144) & (SEQ ID NO: 528) & (SEQ ID NO: 577) | | 2 | 210291701 |
| 18 TGTAGGCAGATTACCTGAAGTTAGGAGTTCGATTAGGAATAACCTATCATTAGAGTTGTT (SEQ ID NO: 204) & (SEQ ID NO: 558) & (SEQ ID NO: 578) | | 7 | 88199682 |

TABLE 31.f

| | Probe Location | | | 4 kb Sequence Location | | | | |
|---|---|---|---|---|---|---|---|---|
| | End1 | Start2 | End2 | Chr | Start1 | End1 | Start2 | End2 |
| 1 | 7114831 | 7260637 | 7260668 | 7 | 7110830 | 7114831 | 7256667 | 7260668 |
| 2 | 11968035 | 11984245 | 11984276 | 11 | 11964034 | 11968035 | 11984245 | 11988246 |
| 3 | 123527874 | 123555254 | 123555285 | 8 | 123523873 | 123527874 | 123555254 | 123559255 |
| 4 | 94054862 | 94133177 | 94133208 | 13 | 94054831 | 94058832 | 94129207 | 94133208 |
| 5 | 121180410 | 121268506 | 121268537 | 9 | 121176409 | 121180410 | 121268506 | 121272507 |
| 6 | 87318670 | 87349909 | 87349940 | 1 | 87314669 | 87318670 | 87345939 | 87349940 |
| 7 | 86581486 | 86621909 | 86621940 | 4 | 86577485 | 86581486 | 86617939 | 86621940 |
| 8 | 152234786 | 152281057 | 152281088 | 3 | 152230785 | 152234786 | 152281057 | 152285058 |
| 9 | 57527328 | 57579772 | 57579803 | 20 | 57527297 | 57531298 | 57579772 | 57583773 |
| 10 | 42072187 | 42094660 | 42094691 | 18 | 42068186 | 42072187 | 42090690 | 42094691 |
| 11 | 198595802 | 198666125 | 198666156 | 1 | 198595771 | 198599772 | 198662155 | 198666156 |
| 12 | 72144564 | 72213251 | 72213282 | 14 | 72140563 | 72144564 | 72213251 | 72217252 |
| 13 | 24920841 | 24976006 | 24976037 | 1 | 24920810 | 24924811 | 24972036 | 24976037 |
| 14 | 73153243 | 73184554 | 73184585 | 16 | 73149242 | 73153243 | 73180584 | 73184585 |
| 15 | 137829497 | 137882068 | 137882099 | 5 | 137829466 | 137833467 | 137882068 | 137886069 |
| 16 | 230724546 | 230757302 | 230757333 | 1 | 230724515 | 230728516 | 230753332 | 230757333 |
| 17 | 210291732 | 210362262 | 210362293 | 2 | 210287731 | 210291732 | 210358292 | 210362293 |
| 18 | 88199713 | 88237070 | 88237101 | 7 | 88199682 | 88203683 | 88233100 | 88237101 |

TABLE 31.g

| | Probe | Inner_primers PCR-Primer1_ID |
|---|---|---|
| 1 | C1GALT1_7_7113076_7114831_7258228_7260668_FF | OBD142_025 |
| 2 | DKK3_11_11956071_11968035_11984245_11993733_FR | OBD142_061 |
| 3 | FBXO32_8_123526212_123527874_123555254_123559065_FR | OBD142_089 |
| 4 | GPC6_13_94054831_94060621_94121445_94133208_RF | OBD142_109 |
| 5 | GSN_9_121177548_121180410_121268506_121274144_FR | OBD142_117 |
| 6 | LMO4_1_87315524_87318670_87343110_87349940_FF | OBD142_145 |
| 7 | MAPK10_4_86572598_86581486_86617317_86621940_FF | OBD142_153 |
| 8 | MBNL1_3_152229500_152234786_152281057_152285843_FR | OBD142_157 |
| 9 | PCK1_20_57527297_57530814_57579772_57583521_RR | OBD142_189 |
| 10 | PIK3C3_18_42070009_42072187_42088671_42094691_FF | OBD142_213 |
| 11 | PTPRC_1_198595771_198598296_198659753_198666156_RF | OBD142_233 |
| 12 | RGS6_14_72139099_72144564_72213251_72222544_FR | OBD142_245 |
| 13 | RUNX3_1_24920810_24923822_24973522_24976037_RF | OBD142_253 |
| 14 | ZFHX3_16_73147488_73153243_73182254_73184585_FF | OBD142_325 |
| 15 | MYOT_5_137829466_137834410_137882068_137884626_RR | OBD142_341 |
| 16 | AGT_1_230724515_230729957_230752057_230757333_RF | OBD142_365 |
| 17 | MYL1_2_210288997_210291732_210359762_210362293_FF | OBD142_449 |
| 18 | SRI_7_88199682_88203042_88229166_88237101_RF | OBD142_509 |

TABLE 31.h

| | Inner_primers | | | Category High or |
|---|---|---|---|---|
| | PCR_Primer1 | PCR-Primer2_ID | PCR_Primer2 | Low Responder |
| 1 | CACCTCAAAAGACAACCCCAGACCCA (SEQ ID NO: 222) & (SEQ ID NO: 579) & (SEQ ID NO: 1596) | OBD142_027 | CCCTCACTTTCCTTCTACTCTTCAAG (SEQ ID NO: 299) & (SEQ ID NO: 597) & (SEQ ID NO: 1614) | High |
| 2 | GCTCCACATTTCCCAATCTAACCTGC (SEQ ID NO: 206) & (SEQ ID NO: 580) & (SEQ ID NO: 624) & (SEQ ID NO: 1597) | OBD142_063 | GTCAGAGTTGCCGATAGGTCTTGCTA (SEQ ID NO: 283) & (SEQ ID NO: 598) & (SEQ ID NO: 631) & (SEQ ID NO: 1615) | High |
| 3 | AATCTCTGTCCCCAACTGTATCTGGC (SEQ ID NO: 208) & (SEQ ID NO: 581) & (SEQ ID NO: 1598) | OBD142_091 | ACATCTATCTTGCCCCTCACTCAGGT (SEQ ID NO: 285) & (SEQ ID NO: 599) & (SEQ ID NO: 1616) | High |
| 4 | GAGTATTTACGATGGTCAGGTGCTGC (SEQ ID NO: 227) & | OBD142_111 | ATCCAAACACAGGACGAGAATAAAGC (SEQ ID NO: 342) & | High |

TABLE 31.h-continued

| | Inner_primers | | | Category High or |
|---|---|---|---|---|
| | PCR_Primer1 | PCR-Primer2_ID | PCR_Primer2 | Low Responder |
| | (SEQ ID NO: 265) & (SEQ ID NO: 582) & (SEQ ID NO: 1599) | | (SEQ ID NO: 600) & (SEQ ID NO: 1617) | |
| 5 | GACCTGTGGTTCTGACTGTCCAG (SEQ ID NO: 228) & (SEQ ID NO: 583) & (SEQ ID NO: 1600) | OBD142_119 | TATCGTCCAGGAGGCAAGGGTCC (SEQ ID NO: 305) & (SEQ ID NO: 307) & (SEQ ID NO: 601) & (SEQ ID NO: 1618) | High |
| 6 | GCAACCTGGTCTCCTACCTGCTTCTA (SEQ ID NO: 232) & (SEQ ID NO: 584) & (SEQ ID NO: 1601) | OBD142_147 | GATGAGGTAACCAAAGTTCAGGGAGA (SEQ ID NO: 309) & (SEQ ID NO: 602) & (SEQ ID NO: 1619) | High |
| 7 | TAGCAGACAATCAGAGGGTTTTGC (SEQ ID NO: 233) & (SEQ ID NO: 585) & (SEQ ID NO: 1602) | OBD142_155 | CTCTCTCCTCATCCTCCCTCCTAATA (SEQ ID NO: 310) & (SEQ ID NO: 603) & (SEQ ID NO: 1620) | High |
| 8 | GCTGGTAGTTGGCTTTTGGGAAGAAC (SEQ ID NO: 234) & (SEQ ID NO: 586) & (SEQ ID NO: 1603) | OBD142_159 | GGGAGCCAGAAAGATAGCAATGCCTA (SEQ ID NO: 311) & (SEQ ID NO: 604) & (SEQ ID NO: 1621) | High |
| 9 | TTCTCCCTCGGACGCTCATCCTC (SEQ ID NO: 211) & (SEQ ID NO: 587) & (SEQ ID NO: 1604) | OBD142_191 | GAGGAGGAGAAACTCAGAAGCCC (SEQ ID NO: 288) & (SEQ ID NO: 605) & (SEQ ID NO: 1622) | High |
| 10 | CTGGAACTTGTTTAGGCACTGAAGCA (SEQ ID NO: 212) & (SEQ ID NO: 588) & (SEQ ID NO: 1605) | OBD142_215 | GCACAAGACCTCACATTCTGATGGGC (SEQ ID NO: 289) & (SEQ ID NO: 606) & (SEQ ID NO: 1623) | High |
| 11 | GCAAAGGGCAGGTCATCATCATTCAA (SEQ ID NO: 239) & (SEQ ID NO: 589) & (SEQ ID NO: 628) & (SEQ ID NO: 1606) | OBD142_235 | CTCTCCTTTATCCCCTACCCTGCTCA (SEQ ID NO: 316) & (SEQ ID NO: 607) & (SEQ ID NO: 635) & (SEQ ID NO: 1624) | High |
| 12 | CCCCGATGAATGTTACCCTGTCCC (SEQ ID NO: 590) & (SEQ ID NO: 1607) | OBD142_247 | CAGAGAAAGGGAGTTTGGAGGGC (SEQ ID NO: 608) & (SEQ ID NO: 1625) | High |
| 13 | CTGAAATCCCATAGTGAGATGCCTTC (SEQ ID NO: 217) & (SEQ ID NO: 591) & (SEQ ID NO: 1608) | OBD142_255 | CCCCAAACTCCCAGACACATCAGAGA (SEQ ID NO: 294) & (SEQ ID NO: 609) & (SEQ ID NO: 1626) | High |
| 14 | CCTGGATGTTCATTCCCACCTGG (SEQ ID NO: 245) & (SEQ ID NO: 592) & (SEQ ID NO: 1609) | OBD142_327 | AGAGGGAAAGGCAGGTCGTGAGC (SEQ ID NO: 322) & (SEQ ID NO: 610) & (SEQ ID NO: 1627) | Low |
| 15 | GCAGATTCCACAGGGCTTAC (SEQ ID NO: 247) & (SEQ ID NO: 593) & (SEQ ID NO: 1610) | OBD142_343 | GCTGGTCTCAAACTCCTGGG (SEQ ID NO: 611) & (SEQ ID NO: 1628) | Low |
| 16 | ACCCAACCCTGCTATACAATTCCA (SEQ ID NO: 594) & (SEQ ID NO: 1611) | OBD142_367 | GGGCATCTTTCCTCTTATTCAAGGT (SEQ ID NO: 612) & (SEQ ID NO: 1629) | Low |
| 17 | ACAGTCAGTGATTGGCACAGAGTAA (SEQ ID NO: 276) & (SEQ ID NO: 595) & (SEQ ID NO: 1612) | OBD142_451 | AGGAAATAGCCCAAATGCAACTGAA (SEQ ID NO: 353) & (SEQ ID NO: 613) & (SEQ ID NO: 1630) | High |
| 18 | GAATGAAACTCTGAGGCCGG (SEQ ID NO: 257) & (SEQ ID NO: 596) & (SEQ ID NO: 1613) | OBD142_511 | CCCATTCGTCTCTCTGAGCTG (SEQ ID NO: 334) & (SEQ ID NO: 614) & (SEQ ID NO: 1631) | High |

TABLE 31.i

|  | Gene | Marker | GLMNET |
|---|---|---|---|
| 1 | C1GALT1 | OBD142__025.027 | 0.242638274 |
| 2 | DKK3 | OBD142__061.063 | 0.147262728 |
| 3 | FBXO32 | OBD142__089.091 | −0.087251896 |
| 4 | GPC6 | OBD142__109.111 | 0.233745002 |
| 5 | GSN | OBD142__117.119 | 0.294663423 |
| 6 | LMO4 | OBD142__145.147 | −0.118956396 |
| 7 | MAPK10 | OBD142__153.155 | −0.17796692 |
| 8 | MBNL1 | OBD142__157.159 | −0.161065194 |
| 9 | PCK1 | OBD142__189.191 | 0.196530289 |
| 10 | PIK3C3 | OBD142__213.215 | −0.083748281 |

TABLE 31.i-continued

|  | Gene | Marker | GLMNET |
|---|---|---|---|
| 11 | PTPRC | OBD142__233.235 | 0.30236596 |
| 12 | RGS6 | OBD142__245.247 | 0.078658478 |
| 13 | RUNX3 | OBD142__253.255 | 0.06399744 |
| 14 | ZFHX3 | OBD142__325.327 | 0.115886108 |
| 15 | MYOT | OBD142__341.343 | −0.049119122 |
| 16 | AGT | OBD142__365.367 | 0.199239865 |
| 17 | MYL1 | OBD142__449.451 | −0.16982619 |
| 18 | SRI | OBD142__509.511 | 0.129049402 |

TABLE 32.a

|  | Probe | GeneLocus | Probe__Count__Total | Probe__Count__Sig |
|---|---|---|---|---|
| 1 | THNSL2__2__88139809__88146295__88161717__88164554__FR | THNSL2 | 29 | 20 |
| 2 | IGF1R__15__98652565__98657862__98731539__98737034__RF | IGF1R | 177 | 96 |
| 3 | DKK3__11__11956071__11968035__11984245__11993733__FR | DKK3 | 54 | 36 |
| 4 | CBL__11__119249760__119252653__119294588__119299643__RF | CBL | 24 | 19 |
| 5 | EYA1__8__71216399__71218728__71261816__71267769__RR | EYA1 | 139 | 80 |
| 6 | ACACB__12__109236052__109237242__109268078__109273323__RR | ACACB | 133 | 81 |
| 7 | PTPRC__1__198595771__198598296__198659753__198666156__RF | PTPRC | 185 | 91 |

TABLE 32.b

|  | HyperG__Stats | FDR__HyperG | Percent__Sig | logFC | AveExpr | t |
|---|---|---|---|---|---|---|
| 1 | 0.147351557 | 0.651492557 | 68.97 | 0.348303621 | 0.348303621 | 5.482854907 |
| 2 | 0.840040511 | 1 | 54.24 | 0.376793177 | 0.376793177 | 3.580450098 |
| 3 | 0.113222201 | 0.567553327 | 66.67 | −0.452190179 | −0.452190179 | −4.498338722 |
| 4 | 0.023815147 | 0.261918121 | 79.17 | −0.426375519 | −0.426375519 | −4.618561579 |
| 5 | 0.544172978 | 1 | 57.55 | −0.420279402 | −0.420279402 | −6.888734462 |
| 6 | 0.250820309 | 0.854526334 | 60.9 | 0.361980641 | 0.361980641 | 6.812052569 |
| 7 | 0.991656906 | 1 | 49.19 | 0.342871898 | 0.342871898 | 12.24688433 |

TABLE 32.c

|  | P.Value | adj.P.Val | B | FC | FC__1 |
|---|---|---|---|---|---|
| 1 | 0.0000279 | 0.000231594 | 2.302943346 | 1.273062829 | 1.273062829 |
| 2 | 0.002089314 | 0.00927894 | −1.873258731 | 1.298452444 | 1.298452444 |
| 3 | 0.000266954 | 0.002046882 | 0.154483715 | 0.730932365 | −1.36811564 |
| 4 | 0.000204351 | 0.001696324 | 0.420007759 | 0.744128913 | −1.343853172 |
| 5 | 0.00000174500366992146 | 0.0000602085318700566 | 5.184417423 | 0.747279887 | −1.338186692 |
| 6 | 0.0000202795176244020 | 0.0000670770127555545 | 5.033860861 | 1.285189092 | 1.285189092 |
| 7 | 0.000000000196 | 0.0000000539 | 14.17658691 | 1.26827878 | 1.26827878 |

TABLE 32.d

|  | LS | Loop Detected | Probe sequence 60 mer |
|---|---|---|---|
| 1 | 1 | E_Ctrl | TATCAAGTTAAACATTCAGACGTCTAGGTCGACTTGAAGTTCACCTAAAGTTTTCCAGTC (SEQ ID NO: 165) & (SEQ ID NO: 499) & (SEQ ID NO: 615) |
| 2 | 1 | E_Ctrl | CGTAGAACTAAGATGTATTCAAAGTCAGTCGAAAAAGATTAGAAAAGTTCAACTCTAAGA (SEQ ID NO: 179) & (SEQ ID NO: 540) & (SEQ ID NO: 616) |
| 3 | -1 | Str_Trn | GACACCTCCTCTCCCTTCCCTCCCCTTCTCGAGTTATCAAAATATTTTGAGAGACAGTAT (SEQ ID NO: 129) & (SEQ ID NO: 390) & (SEQ ID NO: 562) & (SEQ ID NO: 617) |
| 4 | -1 | Str_Trn | ACCGCCTCACCTCAGCTCTCCAGTGAGATCGATCCTCCCACCTAAGCTTCCCAAGTTGCT (SEQ ID NO: 128) & (SEQ ID NO: 376) & (SEQ ID NO: 618) |
| 5 | -1 | Str_Trn | TGTCCTTTCAAGGAAGGATTAGCATCCTTCGAAAGACCTATCAGGATTTCATTTGTAATG (SEQ ID NO: 133) & (SEQ ID NO: 400) & (SEQ ID NO: 619) |

TABLE 32.d-continued

| | LS | Loop Detected | Probe sequence 60 mer |
|---|---|---|---|
| 6 | 1 | E_Ctrl | AAGCAAGAGAATCGCTTGAGCCATAAGTTCGATGCTGCTTTGGGAACTGAAGGTTTTTCT (SEQ ID NO: 178) & (SEQ ID NO: 533) & (SEQ ID NO: 620) |
| 7 | 1 | E_Ctrl | AGAGGCTGAGGTGAAAAGATTGTTTGAGTCGAAGATCATTGTCTCATTTTTTTACTTGTT (SEQ ID NO: 162) & (SEQ ID NO: 465) & (SEQ ID NO: 571) & (SEQ ID NO: 621) |

TABLE 32.e

| | | Probe Location | | | |
|---|---|---|---|---|---|
| | Chr | Start1 | End1 | Start2 | End2 |
| 1 | 2 | 88146264 | 88146295 | 88161717 | 88161748 |
| 2 | 15 | 98652565 | 98652596 | 98737003 | 98737034 |
| 3 | 11 | 11968004 | 11968035 | 11984245 | 11984276 |
| 4 | 11 | 119249760 | 119249791 | 119299612 | 119299643 |
| 5 | 8 | 71216399 | 71216430 | 71261816 | 71261847 |
| 6 | 12 | 109236052 | 109236083 | 109268078 | 109268109 |
| 7 | 1 | 198595771 | 198595802 | 198666125 | 198666156 |

TABLE 32.f

| | | 4 kb Sequence Location | | | |
|---|---|---|---|---|---|
| | Chr | Start1 | End1 | Start2 | End2 |
| 1 | 2 | 88142294 | 88146295 | 88161717 | 88165718 |
| 2 | 15 | 98652565 | 98656566 | 98733033 | 98737034 |
| 3 | 11 | 11964034 | 11968035 | 11984245 | 11988246 |
| 4 | 11 | 119249760 | 119253761 | 119295642 | 119299643 |
| 5 | 8 | 71216399 | 71220400 | 71261816 | 71265817 |
| 6 | 12 | 109236052 | 109240053 | 109268078 | 109272079 |
| 7 | 1 | 198595771 | 198599772 | 198662155 | 198666156 |

TABLE 32.g

| | Probe | Inner_primers PCR-Primer1_ID |
|---|---|---|
| 1 | THNSL2_2_88139809_88146295_88161717_88164554_FR | OBD142_297 |
| 2 | IGF1R_15_98652565_98657862_98731539_98737034_RF | OBD142_329 |
| 3 | DKK3_11_11956071_11968035_11984245_11993733_FR | OBD142_061 |
| 4 | CBL_11_119249760_119252653_119294588_119299643_RF | OBD142_029 |
| 5 | EYA1_8_71216399_71218728_71261816_71267769_RR | OBD142_081 |
| 6 | ACACB_12_109236052_109237242_109268078_109273323_RR | OBD142_469 |
| 7 | PTPRC_1_198595771_198598296_198659753_198666156_RF | OBD142_233 |

TABLE 32.h

| | Inner_primers | | | | Category |
|---|---|---|---|---|---|
| | PCR_Primer1 | PCR-Primer2_ID | PCR_Primer2 | | High or Low Responder |
| 1 | GTAACACAGGTAGGAAGGAGTGGAGC (SEQ ID NO: 242) & (SEQ ID NO: 622) | OBD142_299 | CACCATAAAATAGGGCAAGGTCAGCA (SEQ ID NO: 319) & (SEQ ID NO: 629) | | High |
| 2 | TACTCCTCGTTCCCTTTTCTCTC (SEQ ID NO: 246) & (SEQ ID NO: 623) | OBD142_331 | TGTGTGCTAGGCTGATATGGTTTG (SEQ ID NO: 323) & (SEQ ID NO: 630) | | High |
| 3 | GCTCCACATTTCCCAATCTAACCTGC (SEQ ID NO: 206) & (SEQ ID NO: 580) & (SEQ ID NO: 624) & (SEQ ID NO: 1597) | OBD142_063 | GTCAGAGTTGCCGATAGGTCTTGCTA (SEQ ID NO: 283) & (SEQ ID NO: 598) & (SEQ ID NO: 631) & (SEQ ID NO: 1615) | | High |
| 4 | ACTGAAGGTTCCCAAGTTCCCGAGAG (SEQ ID NO: 205) & (SEQ ID NO: 625) | OBD142_031 | TTAGTCTGTATGGTAGTGTGTGCCTG (SEQ ID NO: 282) & (SEQ ID NO: 632) | | High |
| 5 | GGCAAGTTTCCTGACCTCTCTGACAT (SEQ ID NO: 210) & (SEQ ID NO: 626) | OBD142_083 | GAAGGAGGGAGGTAGGAGAGTCATTA (SEQ ID NO: 287) & (SEQ ID NO: 633) | | High |
| 6 | AGGAATGGTTACTGCTCCTCTTTGT (SEQ ID NO: 278) & (SEQ ID NO: 627) | OBD142_471 | ATTGAATTCTCTCTGTGGCCTTTGC (SEQ ID NO: 634) | | High |
| 7 | GCAAAGGGCAGGTCATCATCATTCAA (SEQ ID NO: 239) & (SEQ ID NO: 589) & (SEQ ID NO: 628) & (SEQ ID NO: 1606) | OBD142_235 | CTCTCCTTTATCCCCTACCCTGCTCA (SEQ ID NO: 316) & (SEQ ID NO: 607) & (SEQ ID NO: 635) & (SEQ ID NO: 1624) | | High |

TABLE 32.i

| | Gene | Marker | GLMNET |
|---|---|---|---|
| 1 | THNSL2 | OBD142__297.299 | 0.379691192 |
| 2 | IGF1R | OBD142__329.331 | 0.248382918 |
| 3 | DKK3 | OBD142__061.063 | −0.259421345 |
| 4 | CBL | OBD142__029.031 | 0.125293919 |

TABLE 32.i-continued

| | Gene | Marker | GLMNET |
|---|---|---|---|
| 5 | EYA1 | OBD142__081.083 | −0.165674931 |
| 6 | ACACB | OBD142__469.471 | −0.229960031 |
| 7 | PTPRC | OBD142__233.235 | −0.066564639 |

TABLE 33.a1

| N | Probe | GeneLocus | Probe_Count_Total | Probe_Count_Sig |
|---|---|---|---|---|
| 1 | ABCC9__6__47915416__47925286__48134697__48137569__RF | ABCC9 | 1 | 53 |
| 2 | ACACA__11__36333514__36339214__36350786__36357493__RR | ACACA | 4 | 219 |
| 3 | ACACA__11__36333514__36339214__36436048__36448276__RR | ACACA | 4 | 219 |
| 4 | ACACA__11__36333514__36339214__36541652__36552356__RF | ACACA | 4 | 219 |
| 5 | ACACA__11__36436048__36448276__36626441__36631346__FF | ACACA | 4 | 219 |
| 6 | ACACB__8__11863063__11867350__11908667__11911946__RR | ACACB | 1 | 31 |
| 7 | ACBD6__5__17677182__17680294__17812085__17822701__FR | ACBD6 | 3 | 206 |
| 8 | ACBD6__5__17677182__17680294__17952666__17962707__FF | ACBD6 | 3 | 206 |
| 9 | ACBD6__5__17677182__17680294__17952666__17962707__FR | ACBD6 | 3 | 206 |
| 10 | AHCYL2__4__84035626__84046686__84262207__84266431__FR | AHCYL2 | 2 | 209 |
| 11 | AHCYL2__4__84081753__84093856__84262207__84266431__FR | AHCYL2 | 2 | 209 |
| 12 | ANGPTL1__5__13716369__13718618__13770118__13781369__FR | ANGPTL1 | 2 | 41 |
| 13 | ANGPTL1__5__13716369__13718618__13770118__13781369__RR | ANGPTL1 | 2 | 41 |
| 14 | APC__14__59179179__59182887__59237657__59248555__FF | APC | 2 | 76 |
| 15 | APC__14__59179179__59182887__59237657__59248555__FR | APC | 2 | 76 |
| 16 | APOA2__5__35820030__35830912__35848600__35852478__RF | APOA2 | 3 | 65 |
| 17 | APOA2__5__35820030__35830912__35866091__35873759__RR | APOA2 | 3 | 65 |
| 18 | APOA2__5__35848600__35852478__35900637__35912475__FR | APOA2 | 3 | 65 |
| 19 | BECN1__11__20175502__20184049__20243179__20248279__RF | BECN1 | 3 | 28 |
| 20 | BECN1__11__20175502__20184049__20320840__20322495__RF | BECN1 | 3 | 28 |
| 21 | BECN1__11__20243179__20248279__20281555__20289129__FR | BECN1 | 3 | 28 |
| 22 | BTN1A1__20__24591764__24605263__24706408__24710466__FR | BTN1A1 | 1 | 122 |
| 23 | BTNL2__20__32536895__32543196__32585002__32592656__RF | BTNL2 | 6 | 66 |
| 24 | BTNL2__20__32570542__32582104__32597196__32598340__RF | BTNL2 | 6 | 66 |
| 25 | BTNL2__20__32570542__32582104__32598340__32606017__RR | BTNL2 | 6 | 66 |
| 26 | BTNL2__20__32570542__32582104__32672903__32675921__RF | BTNL2 | 6 | 66 |
| 27 | BTNL2__20__32585002__32592656__32716550__32722709__FF | BTNL2 | 6 | 66 |
| 28 | BTNL2__20__32598340__32606017__32645786__32652591__RR | BTNL2 | 6 | 66 |
| 29 | CACNA1G__11__26122948__26135515__26185131__26187822__RF | CACNA1G | 2 | 33 |
| 30 | CACNA1G__11__26122948__26135515__26187822__26192201__RF | CACNA1G | 2 | 33 |
| 31 | CACNA2D3__16__33352821__33354631__33641948__33654248__RF | CACNA2D3 | 14 | 766 |
| 32 | CACNA2D3__16__33410233__33413906__33641948__33654248__RF | CACNA2D3 | 14 | 766 |
| 33 | CACNA2D3__16__33479236__33480664__33641948__33654248__RF | CACNA2D3 | 14 | 766 |
| 34 | CACNA2D3__16__33563090__33565331__33641948__33654248__RF | CACNA2D3 | 14 | 766 |
| 35 | CACNA2D3__16__33622760__33627636__33641948__33654248__RF | CACNA2D3 | 14 | 766 |
| 36 | CACNA2D3__16__33641948__33654248__33704852__33706847__FF | CACNA2D3 | 14 | 766 |
| 37 | CACNA2D3__16__33641948__33654248__33729470__33733482__FF | CACNA2D3 | 14 | 766 |
| 38 | CACNA2D3__16__33641948__33654248__33733482__33741095__FF | CACNA2D3 | 14 | 766 |
| 39 | CACNA2D3__16__33641948__33654248__33733482__33741095__FR | CACNA2D3 | 14 | 766 |
| 40 | CACNA2D3__16__33641948__33654248__33757281__33760491__FF | CACNA2D3 | 14 | 766 |
| 41 | CACNA2D3__16__33641948__33654248__33760582__33768051__FR | CACNA2D3 | 14 | 766 |
| 42 | CACNA2D3__16__33641948__33654248__33768286__33770169__FR | CACNA2D3 | 14 | 766 |
| 43 | CACNA2D3__16__33641948__33654248__33815034__33817501__FR | CACNA2D3 | 14 | 766 |
| 44 | CACNA2D3__16__33641948__33654248__33848517__33852225__FF | CACNA2D3 | 14 | 766 |
| 45 | CACNB2__29__17033576__17046068__17154781__17155878__RF | CACNB2 | 6 | 225 |
| 46 | CACNB2__29__17048693__17053442__17144042__17154089__RR | CACNB2 | 6 | 225 |
| 47 | CACNB2__29__17144042__17154089__17262741__17269092__RR | CACNB2 | 6 | 225 |
| 48 | CACNB2__29__17144042__17154089__17332733__17336468__RF | CACNB2 | 6 | 225 |
| 49 | CACNB2__29__17144042__17154089__17332733__17336468__RR | CACNB2 | 6 | 225 |
| 50 | CACNB2__29__17286082__17289972__17348926__17357613__RF | CACNB2 | 6 | 225 |
| 51 | CAMK2G__1__61385709__61392305__61537867__61544849__FF | CAMK2G | 4 | 87 |
| 52 | CAMK2G__1__61385709__61392305__61570715__61577474__FF | CAMK2G | 4 | 87 |
| 53 | CAMK2G__1__61385709__61392305__61570715__61577474__FR | CAMK2G | 4 | 87 |
| 54 | CAMK2G__1__61385709__61392305__61578119__61589600__FR | CAMK2G | 4 | 87 |
| 55 | CARD11__13__4269642__4272623__4440946__4446573__RR | CARD11 | 1 | 31 |
| 56 | CASP3__27__25376884__25380938__25471835__25478467__RR | CASP3 | 1 | 60 |
| 57 | CCNDBP1__1__145659771__145664399__145699582__145711153__RR | CCNDBP1 | 4 | 96 |
| 58 | CCNDBP1__1__145659771__145664399__145762480__145771097__RR | CCNDBP1 | 4 | 96 |
| 59 | CCNDBP1__1__145659771__145664399__145793388__145800297__RF | CCNDBP1 | 4 | 96 |
| 60 | CCNDBP1__1__145659771__145664399__145793388__145800297__RR | CCNDBP1 | 4 | 96 |
| 61 | CD19__13__19942675__19947695__20028912__20034792__RF | CD19 | 3 | 29 |
| 62 | CD19__13__20002320__20006400__20028912__20034792__RF | CD19 | 3 | 29 |
| 63 | CD19__13__20007058__20010478__20028912__20034792__RF | CD19 | 3 | 29 |
| 64 | CD2__5__52197323__52200100__52321910__52330791__FF | CD2 | 1 | 30 |

TABLE 33.a2

| N | HyperG_Stats | FDR_HyperG | Percent_Sig | logFC | AveExpr |
|---|---|---|---|---|---|
| 1 | 0.283590396 | 0.318114445 | 1.89 | 0.320518457 | 9.948416738 |
| 2 | 0.071740684 | 0.151713905 | 1.83 | −0.293607855 | 7.847234944 |
| 3 | 0.071740684 | 0.151713905 | 1.83 | −0.210300022 | 8.374350236 |
| 4 | 0.071740684 | 0.151713905 | 1.83 | 0.231385222 | 8.833918508 |
| 5 | 0.071740684 | 0.151713905 | 1.83 | −0.305200929 | 6.737863734 |
| 6 | 0.198752749 | 0.267074007 | 3.23 | −0.96134378 | 7.26378007 |
| 7 | 0.149176662 | 0.267074007 | 1.46 | −0.26093573 | 9.509514883 |
| 8 | 0.149176662 | 0.267074007 | 1.46 | −0.258481627 | 9.295947643 |
| 9 | 0.149176662 | 0.267074007 | 1.46 | −0.281768793 | 9.595365742 |
| 10 | 0.266652717 | 0.310300562 | 0.96 | −0.295771266 | 9.712393304 |
| 11 | 0.266652717 | 0.310300562 | 0.96 | −0.335883754 | 9.167228863 |
| 12 | 0.039967104 | 0.109696945 | 4.88 | 0.305246417 | 7.108599809 |
| 13 | 0.039967104 | 0.109696945 | 4.88 | 0.30390975 | 9.437958235 |
| 14 | 0.104263108 | 0.213491126 | 2.63 | −0.21158792 | 10.04027255 |
| 15 | 0.104263108 | 0.213491126 | 2.63 | −0.18597646 | 10.12135456 |
| 16 | 0.014396814 | 0.064041001 | 4.62 | −0.285169774 | 10.6370881 |
| 17 | 0.014396814 | 0.064041001 | 4.62 | −0.188307832 | 9.94119358 |
| 18 | 0.014396814 | 0.064041001 | 4.62 | −0.35682778 | 10.37459386 |
| 19 | 0.001460812 | 0.014841655 | 10.71 | −0.806200399 | 8.954094586 |
| 20 | 0.001460812 | 0.014841655 | 10.71 | −0.172300256 | 11.08935116 |
| 21 | 0.001460812 | 0.014841655 | 10.71 | −0.689404695 | 9.24381568 |
| 22 | 0.369972517 | 0.369972517 | 0.82 | −0.188359359 | 10.5379586 |
| 23 | 0.0000162598909570469 | 0.000524381 | 9.09 | −0.626172706 | 7.90082566 |
| 24 | 0.0000162598909570469 | 0.000524381 | 9.09 | −0.914586684 | 9.145982862 |
| 25 | 0.0000162598909570469 | 0.000524381 | 9.09 | −0.419132349 | 9.090576394 |
| 26 | 0.0000162598909570469 | 0.000524381 | 9.09 | −0.87421888 | 9.197203863 |
| 27 | 0.0000162598909570469 | 0.000524381 | 9.09 | −0.774602225 | 7.429403071 |
| 28 | 0.0000162598909570469 | 0.000524381 | 9.09 | −0.630265492 | 10.1595488 |
| 29 | 0.027478161 | 0.080560972 | 6.06 | −0.802327215 | 9.327353317 |
| 30 | 0.027478161 | 0.080560972 | 6.06 | −0.583404038 | 9.095292225 |
| 31 | 0.002885548 | 0.019591352 | 1.83 | 0.209398931 | 11.18280673 |
| 32 | 0.002885548 | 0.019591352 | 1.83 | 0.194627322 | 11.7177864 |
| 33 | 0.002885548 | 0.019591352 | 1.83 | 0.198440578 | 11.24724562 |
| 34 | 0.002885548 | 0.019591352 | 1.83 | 0.200166764 | 10.76693749 |
| 35 | 0.002885548 | 0.019591352 | 1.83 | 0.242678129 | 10.92474812 |
| 36 | 0.002885548 | 0.019591352 | 1.83 | 0.19266085 | 11.39119603 |
| 37 | 0.002885548 | 0.019591352 | 1.83 | 0.199552427 | 11.12621619 |
| 38 | 0.002885548 | 0.019591352 | 1.83 | 0.221089342 | 11.19545935 |
| 39 | 0.002885548 | 0.019591352 | 1.83 | 0.276958928 | 10.73545888 |
| 40 | 0.002885548 | 0.019591352 | 1.83 | 0.203939961 | 11.05986864 |
| 41 | 0.002885548 | 0.019591352 | 1.83 | 0.210750359 | 11.34843609 |
| 42 | 0.002885548 | 0.019591352 | 1.83 | 0.20067327 | 11.31423277 |
| 43 | 0.002885548 | 0.019591352 | 1.83 | 0.245046459 | 10.85328784 |
| 44 | 0.002885548 | 0.019591352 | 1.83 | 0.219462879 | 10.72704267 |
| 45 | 0.008301566 | 0.042836079 | 2.67 | −0.593545035 | 8.631773695 |
| 46 | 0.008301566 | 0.042836079 | 2.67 | −0.195749334 | 7.90944735 |
| 47 | 0.008301566 | 0.042836079 | 2.67 | −0.287774413 | 9.577708179 |
| 48 | 0.008301566 | 0.042836079 | 2.67 | −0.274080009 | 7.326771399 |
| 49 | 0.008301566 | 0.042836079 | 2.67 | −0.292274875 | 9.957522807 |
| 50 | 0.008301566 | 0.042836079 | 2.67 | 0.283385806 | 7.748329166 |
| 51 | 0.005032361 | 0.029507937 | 4.6 | −0.236733028 | 11.38171809 |
| 52 | 0.005032361 | 0.029507937 | 4.6 | −0.484010849 | 10.01269368 |
| 53 | 0.005032361 | 0.029507937 | 4.6 | −0.303821538 | 10.44275862 |
| 54 | 0.005032361 | 0.029507937 | 4.6 | −0.378665253 | 10.33209023 |
| 55 | 0.198752749 | 0.267074007 | 3.23 | −0.205289586 | 10.29956667 |
| 56 | 0.303088108 | 0.331342084 | 1.67 | −0.355934967 | 8.751256232 |
| 57 | 0.006979045 | 0.037512367 | 4.17 | −0.63182397 | 10.94820024 |
| 58 | 0.006979045 | 0.037512367 | 4.17 | −0.696810436 | 10.48066661 |
| 59 | 0.006979045 | 0.037512367 | 4.17 | −0.322489712 | 9.760585457 |
| 60 | 0.006979045 | 0.037512367 | 4.17 | −0.625156464 | 10.77930783 |
| 61 | 0.001616117 | 0.014841655 | 10.34 | −0.390037974 | 8.434827236 |
| 62 | 0.001616117 | 0.014841655 | 10.34 | −0.673915806 | 8.40536563 |
| 63 | 0.001616117 | 0.014841655 | 10.34 | −0.395313235 | 7.939097247 |
| 64 | 0.193928419 | 0.267074007 | 3.33 | −0.259547189 | 9.581323717 |

TABLE 33.a3

| N | t | P.Value | adj.P.Val | B | FC |
|---|---|---|---|---|---|
| 1 | 7.263712103 | 0.00000065853271237312 | 0.000395221 | 6.182644836 | 1.248779238 |
| 2 | −5.291321916 | 0.0000408766051478055 | 0.006156743 | 2.287156198 | 0.815859225 |
| 3 | −5.050567397 | 0.0000698310885505510 | 0.008902323 | 1.777241611 | 0.864357461 |
| 4 | 5.096854125 | 0.0000629720358323017 | 0.008441715 | 1.875717506 | 1.173961602 |
| 5 | −5.402991698 | 0.0000319491285625712 | 0.005171517 | 2.521615893 | 0.809329491 |
| 6 | −7.453856126 | 0.00000045445192305040 | 0.000311021 | 6.527700337 | 0.513578324 |

TABLE 33.a3-continued

| N | t | P.Value | adj.P.Val | B | FC |
|---|---|---|---|---|---|
| 7 | −5.529047183 | 0.0000242301608260188 | 0.004416684 | 2.784577889 | 0.834546458 |
| 8 | −5.399685477 | 0.0000321824586248703 | 0.005178058 | 2.514694153 | 0.835967276 |
| 9 | −6.654810658 | 0.00000223206986757685 | 0.000837241 | 5.040151004 | 0.822581886 |
| 10 | −6.241524808 | 0.00000525766136243176 | 0.001576825 | 4.232788024 | 0.814636711 |
| 11 | −6.320309917 | 0.00000445769617599177 | 0.001402377 | 4.388632115 | 0.792298649 |
| 12 | 5.609172308 | 0.0000203429879959953 | 0.0039672 | 2.950743157 | 1.235629669 |
| 13 | 7.008043044 | 0.0000109276077875550 | 0.000532857 | 5.709861189 | 1.23448538 |
| 14 | −5.526775502 | 0.0000243508405008230 | 0.004416684 | 2.779855512 | 0.863586191 |
| 15 | −5.184267596 | 0.0000518309913407067 | 0.007221168 | 2.06113207 | 0.879053904 |
| 16 | −5.131092219 | 0.0000583432064738677 | 0.007902668 | 1.948429433 | 0.820645031 |
| 17 | −5.090952536 | 0.0000638069334895659 | 0.008495251 | 1.863172915 | 0.877634514 |
| 18 | −5.320752831 | 0.0000383014725598130 | 0.005929129 | 2.34908169 | 0.780879703 |
| 19 | −10.73162962 | 0.000000000156642896568417 | 0.00000555512672284904 | 11.63110669 | 0.571886043 |
| 20 | −5.071479915 | 0.0000666425700694542 | 0.008670693 | 1.821758099 | 0.887426625 |
| 21 | −11.43551668 | 0.000000000543755314186107 | 0.0000026514868508001 | 12.53781121 | 0.620109675 |
| 22 | −5.281294908 | 0.0000417937674137867 | 0.006270673 | 2.266037132 | 0.877603169 |
| 23 | −6.43285853 | 0.00000352629587947274 | 0.001196181 | 4.609695945 | 0.647892918 |
| 24 | −5.936360791 | 0.0000100392087096020 | 0.002463079 | 3.620834864 | 0.53049583 |
| 25 | −6.27688641 | 0.00000488175309950516 | 0.001499505 | 4.302847451 | 0.747874268 |
| 26 | −5.895655257 | 0.0000109534936492495 | 0.002605462 | 3.538234643 | 0.545549164 |
| 27 | −5.294894055 | 0.0000405548509879891 | 0.006131956 | 2.294677302 | 0.584549772 |
| 28 | −5.091526221 | 0.0000637252817777454 | 0.008495251 | 1.864392502 | 0.646057513 |
| 29 | −10.17863513 | 0.000000000372947965181301 | 0.00000909293757607660 | 10.87544294 | 0.57342344 |
| 30 | −6.90646185 | 0.00000133961123275428 | 0.000598065 | 5.519220905 | 0.667387219 |
| 31 | 5.662783116 | 0.0000181042793666228 | 0.003741337 | 3.061481776 | 1.156206374 |
| 32 | 5.631236286 | 0.0000193891442127443 | 0.003919018 | 2.996361868 | 1.144428493 |
| 33 | 5.666098866 | 0.0000179743992793013 | 0.003741337 | 3.068319007 | 1.147457388 |
| 34 | 5.427843178 | 0.0000302497258239690 | 0.005000177 | 2.573603928 | 1.148831143 |
| 35 | 5.312745619 | 0.0000389852287177481 | 0.005987456 | 2.332243017 | 1.183187018 |
| 36 | 5.053579322 | 0.0000693624553048217 | 0.008871572 | 1.783655581 | 1.142869637 |
| 37 | 5.139332812 | 0.0000572818435901524 | 0.007813163 | 1.965913201 | 1.148342045 |
| 38 | 5.771451184 | 0.0000143085584536262 | 0.003153542 | 3.284832702 | 1.165613379 |
| 39 | 7.603984521 | 0.000000340247830958195 | 0.000270685 | 6.796180224 | 1.211638166 |
| 40 | 5.197633668 | 0.0000503139299503325 | 0.007169673 | 2.08941646 | 1.151839706 |
| 41 | 5.184590564 | 0.0000517937896507643 | 0.007221168 | 2.061815727 | 1.157289945 |
| 42 | 5.508845037 | 0.0000253252202636046 | 0.00443021 | 2.742560003 | 1.149234549 |
| 43 | 6.888512233 | 0.00000138890201289527 | 0.000606823 | 5.485369802 | 1.185130935 |
| 44 | 5.190118523 | 0.0000511612462532849 | 0.007206844 | 2.073515633 | 1.164300032 |
| 45 | −5.951345629 | 0.00000972270336819660 | 0.002446985 | 3.651185844 | 0.662712467 |
| 46 | −5.006721458 | 0.0000770300340578710 | 0.009606804 | 1.683777572 | 0.873119281 |
| 47 | −5.945124115 | 0.00000985284933645142 | 0.002463079 | 3.638588206 | 0.819164776 |
| 48 | −5.085844945 | 0.0000645386031849005 | 0.00853441 | 1.852313415 | 0.826977505 |
| 49 | −6.066098719 | 0.00000761463569393438 | 0.0020486 | 3.882591854 | 0.816613388 |
| 50 | 5.41620177 | 0.0000310339784093617 | 0.00506542 | 2.549259461 | 1.217047779 |
| 51 | −6.036325672 | 0.00000811181608888997 | 0.002138121 | 3.822727459 | 0.848664933 |
| 52 | −8.409111112 | 0.000000000758476579555309 | 0.000084511023122425 | 8.176782156 | 0.714987116 |
| 53 | −6.341938105 | 0.00000426082327745524 | 0.001351339 | 4.431257193 | 0.810103678 |
| 54 | −7.527123857 | 0.0000003944401825262223 | 0.000284947 | 6.659163938 | 0.76914886 |
| 55 | −6.66299269 | 0.00000219503072654509 | 0.000837079 | 5.055878269 | 0.867364567 |
| 56 | −5.372396859 | 0.0000341760619744322 | 0.005375839 | 2.457516974 | 0.781363101 |
| 57 | −12.0166013 | 0.0000000000235462982188889 | 0.00000183708218703771 | 13.24249697 | 0.645359984 |
| 58 | −12.8061782 | 0.00000000000793212810435301 | 0.000000960392461716811 | 14.14079379 | 0.616934642 |
| 59 | −7.657502685 | 0.00000307118694602961 | 0.000254909 | 6.891044499 | 0.799688634 |
| 60 | −12.70330829 | 0.0000000000091121484638 0425 | 0.000000960392461716811 | 14.02745955 | 0.648349459 |
| 61 | −5.835579933 | 0.0000124617597410427 | 0.002859607 | 3.415923184 | 0.763109518 |
| 62 | −9.840705036 | 0.0000000006442602671 07065 | 0.000013962551677693 | 10.39393487 | 0.626803089 |
| 63 | −5.795472953 | 0.0000135859288607979 | 0.00308132 | 3.334000537 | 0.760324279 |
| 64 | −5.940740709 | 0.00000994561781482989 | 0.002463079 | 3.629709305 | 0.835350065 |

TABLE 33.a4

| N | FC_1 | Loop LS Detected | Probe sequence 60 mer |
|---|---|---|---|
| 1 | 1.248779238 | 1 Sprinter | AAAAAGAAAGAGGGAAGAAGGAAAGAAGTCGATGAAACATGCAGTCAACTTGGGAGGCCC (SEQ ID NO: 636) |
| 2 | −1.225701652 | −1 Stayer | ATGAAGGTAATAGTACCTTACCTCGTAGTCGAAAAAAAAATTCCTCCCCATAAAGAGACC (SEQ ID NO: 637) |
| 3 | −1.156928753 | −1 Stayer | ATGAAGGTAATAGTACCTTACCTCGTAGTCGATTATCAGCCTTTTTCTTGAAGAACCTCC (SEQ ID NO: 638) |
| 4 | 1.173961602 | 1 Sprinter | AACACAGATGATCATCATAAGACGTAGGTCGACTACGAGGTAAGGTACTATTACCTTCAT (SEQ ID NO: 639) |

TABLE 33.a4-continued

| N | FC_1 | Loop LS | Detected | Probe sequence 60 mer |
|---|------|---------|----------|------------------------|
| 5 | -1.23559071 | -1 | Stayer | GATGCAAGTACTTCCTAATTTCTCTAAGTCGAATCAAACTTTAATTTTTAGAAATTCAAA (SEQ ID NO: 640) |
| 6 | -1.947122673 | -1 | Stayer | ATTTTCATAGCTATTGCATTTAACTCTTTCGAAATTGATTTTTTTTAAATAGATAAGCAA (SEQ ID NO: 641) |
| 7 | -1.198255639 | -1 | Stayer | ACCAGCAATATTTGTGAGAGTACCAGTTTCGAACTTGATTCACACTGTACTGTGAGCCAG (SEQ ID NO: 642) |
| 8 | -1.196219074 | -1 | Stayer | ACCAGCAATATTTGTGAGAGTACCAGTTTCGATTTTCTAGAGATGTCCAAGTGTACACTT (SEQ ID NO: 643) |
| 9 | -1.215684441 | -1 | Stayer | ACCAGCAATATTTGTGAGAGTACCAGTTTCGAGAGAGCTATTGTTTGATGCTGTGTATTC (SEQ ID NO: 644) |
| 10 | -1.227541046 | -1 | Stayer | TTGCAGTTTGAAGAGATCAGCATTGAAATCGACCCAGCTCAGAAGTACTTCCTGCTGCCC (SEQ ID NO: 645) |
| 11 | -1.262150329 | -1 | Stayer | TGGTATACTAATTTTACAGATAAAGAAATCGACCCAGCTCAGAAGTACTTCCTGCTGCCC (SEQ ID NO: 646) |
| 12 | 1.235629669 | 1 | Sprinter | CCCCAAAATCTTTTATTTCTGTAGAAAATCGACAAATGTAGGTAATAAAAAAACATATGA (SEQ ID NO: 647) |
| 13 | 1.23448538 | 1 | Sprinter | TGCAAGTAGAGGATTAGTAGCAGTTAAATCGACAAATGTAGGTAATAAAAAAACATATGA (SEQ ID NO: 648) |
| 14 | -1.157962008 | -1 | Stayer | ACAGCTCTAGGTTTCTTCAATACGTTTGTCGAAGGCATTCTTTGCAAAGACATTTTTATG (SEQ ID NO: 649) |
| 15 | -1.137586666 | -1 | Stayer | ACAGCTCTAGGTTTCTTCAATACGTTTGTCGAACCCTAGAAATTAAGCAAATTATAGATA (SEQ ID NO: 650) |
| 16 | -1.218553653 | -1 | Stayer | TGATGTTGGTATAGAGAGGGCCCAGCTCTCGACTTCAAGACCCACCGAAAGACTGGGACT (SEQ ID NO: 651) |
| 17 | -1.139426474 | -1 | Stayer | AGTCCCAGTCTTTCGGTGGGTCTTGAAGTCGACTACCACTAAGCTCTCACTACTAAGCTG (SEQ ID NO: 652) |
| 18 | -1.280606982 | -1 | Stayer | TGATGTTGGTATAGAGAGGGCCCAGCTCTCGAGGGGAATGAAAAATTAAAGGAACTGACC (SEQ ID NO: 653) |
| 19 | -1.748600115 | -1 | Stayer | ATCTGGTCTATGTCCAGGTACTCTCGGATCGAGGTTAAGAGCATAGACTTTGGAGTTTCA (SEQ ID NO: 654) |
| 20 | -1.126853727 | -1 | Stayer | TGAGATCAGAGAACAAATTGTCCGGGAGTCGAGGTTAAGAGCATAGACTTTGGAGTTTCA (SEQ ID NO: 655) |
| 21 | -1.61261796 | -1 | Stayer | ATCTGGTCTATGTCCAGGTACTCTCGGATCGAGTGCAGGTATGTGGAAACATGTTTAGTG (SEQ ID NO: 656) |
| 22 | -1.139467171 | -1 | Stayer | ACCTGAAGTCAGAGTATGTGTGACAGTTTCGACCACGGGAGGAAAAAAGCGGTCCAAGTA (SEQ ID NO: 657) |
| 23 | -1.543464933 | -1 | Stayer | TAGAATATGTAGAGATGTCTCCTTTCTATCGATGTGAGTATCAAGCAGTAACCTGAAAAA (SEQ ID NO: 658) |
| 24 | -1.885028954 | -1 | Stayer | TAGGCAGATAAGGACATATCTGTAATTCTCGAAACAACACCTGTTTATTTGTTTACAGTT (SEQ ID NO: 659) |
| 25 | -1.337123154 | -1 | Stayer | AACTGTAAACAAATAAACAGGTGTTGTTTCGACAGAAGCAGCACTATGATCTCTCACTGA (SEQ ID NO: 660) |
| 26 | -1.833015367 | -1 | Stayer | GGTATCAATTATAGCCGTCTACCTTGTGTCGAAACAACACCTGTTTATTTGTTTACAGTT (SEQ ID NO: 661) |
| 27 | -1.710718313 | -1 | Stayer | TAGAATATGTAGAGATGTCTCCTTTCTATCGACAACACTAGGTTATGGTGTGATAAGGAC (SEQ ID NO: 662) |
| 28 | -1.547849811 | -1 | Stayer | TCAGTGAGAGATCATAGTGCTGCTTCTGTCGAGTCAGACTATAGCGCTACAGGCAACATG (SEQ ID NO: 663) |
| 29 | -1.743911968 | -1 | Stayer | ATCCAGACACTCAAGGACTTCCAGTACATCGAATGGCCAAATAATATCCCATTGTATGAA (SEQ ID NO: 664) |
| 30 | -1.498380509 | -1 | Stayer | TCCTCCTTCACTAGCTCTTGGTGGTACCTCGAATGGCCAAATAATATCCCATTGTATGAA (SEQ ID NO: 665) |

TABLE 33.a4-continued

| N | FC_1 | Loop LS | Detected | Probe sequence 60 mer |
|---|---|---|---|---|
| 31 | 1.156206374 | 1 | Sprinter | TCCCTCACACACAAGTCATGCAGTTTTTTCGATTCAGCCAGGCTTAGCTTTTCCAGGGAA (SEQ ID NO: 666) |
| 32 | 1.144428493 | 1 | Sprinter | TCCCTCACACACAAGTCATGCAGTTTTTTCGAAGTCAGGGCTCAATGGGCCTTGGGGGGG (SEQ ID NO: 667) |
| 33 | 1.147457388 | 1 | Sprinter | TCCCTCACACACAAGTCATGCAGTTTTTTCGAAATTGTCGTTTAATTGCCTAACCTGCAC (SEQ ID NO: 668) |
| 34 | 1.148831143 | 1 | Sprinter | TCCCTCACACACAAGTCATGCAGTTTTTTCGACTTGGGTCTTAATTAGGATCTTTTATGC (SEQ ID NO: 669) |
| 35 | 1.183187018 | 1 | Sprinter | TCCCTCACACACAAGTCATGCAGTTTTTTCGAATCTCTAAGACTAAAATGAAATCCTGGA (SEQ ID NO: 670) |
| 36 | 1.142869637 | 1 | Sprinter | TCCCTCACACACAAGTCATGCAGTTTTTTCGATTTATTTACGTTGGTGGCCACTTGGACT (SEQ ID NO: 671) |
| 37 | 1.148342045 | 1 | Sprinter | TCCCTCACACACAAGTCATGCAGTTTTTTCGACCCCAACAAAAATGGAATAAAACCCACC (SEQ ID NO: 672) |
| 38 | 1.165613379 | 1 | Sprinter | TCCCTCACACACAAGTCATGCAGTTTTTTCGAAGCTTGTTAAGATCCAGTTTCTGGCCTC (SEQ ID NO: 673) |
| 39 | 1.211638166 | 1 | Sprinter | TCCCTCACACACAAGTCATGCAGTTTTTTCGAGTAAACTACATTTTACAGTGTGAAAAAT (SEQ ID NO: 674) |
| 40 | 1.151839706 | 1 | Sprinter | TCCCTCACACACAAGTCATGCAGTTTTTTCGAATGTCCCTTACTATTTATTCCCCCAAAT (SEQ ID NO: 675) |
| 41 | 1.157289945 | 1 | Sprinter | TCCCTCACACACAAGTCATGCAGTTTTTTCGAATCTGACTCCATCACTTGATCTTGGGCA (SEQ ID NO: 676) |
| 42 | 1.149234549 | 1 | Sprinter | TCCCTCACACACAAGTCATGCAGTTTTTTCGACAAACGTCACCTCTGATGGAGAATGCTG (SEQ ID NO: 677) |
| 43 | 1.185130935 | 1 | Sprinter | TCCCTCACACACAAGTCATGCAGTTTTTTCGATTGAAGAGTTAATGAAATAACCATAATT (SEQ ID NO: 678) |
| 44 | 1.164300032 | 1 | Sprinter | TCCCTCACACACAAGTCATGCAGTTTTTTCGAAAAGGCTGCATACTATATGATTCCGATT (SEQ ID NO: 679) |
| 45 | −1.508950035 | −1 | Stayer | TGCTATAGAGGCAGCTGTAAATATAAATTCGAAAGTGTAGATTCAGAGATATCACATGGT (SEQ ID NO: 680) |
| 46 | −1.145318884 | −1 | Stayer | GAAGGCAACCAGCTTGCCTTCTGAAGGATCGAGGGTACATAAGAGGAGTCTACACTATGA (SEQ ID NO: 681) |
| 47 | −1.220755615 | −1 | Stayer | TCATAGTGTAGACTCCTCTTATGTACCCTCGATGAGGTGGGTAGAATCTTCATTTTAATC (SEQ ID NO: 682) |
| 48 | −1.209222735 | −1 | Stayer | TTTTTTAAAATTAAAATCATTTTTTGACTCGAGGGTACATAAGAGGAGTCTACACTATGA (SEQ ID NO: 683) |
| 49 | −1.224569686 | −1 | Stayer | TCATAGTGTAGACTCCTCTTATGTACCCTCGACCTAGAGCTGTTCTCTGGATTCTCAGAA (SEQ ID NO: 684) |
| 50 | 1.217047779 | 1 | Sprinter | TAAGGAAATGTAAATGTAAAAGATGATTCGATTCCCTGATGTTGACACTTCAATTTCCA (SEQ ID NO: 685) |
| 51 | −1.178321338 | −1 | Stayer | CTGTACCCCATTTCTTCCCACGTATTCCTCGAGGAAGGTTAGCCCTGAGCTAACATCTGC (SEQ ID NO: 686) |
| 52 | −1.3986266 | −1 | Stayer | CTGTACCCCATTTCTTCCCACGTATTCCTCGAAACTAGGAAATTAACATTAGTATAGTAC (SEQ ID NO: 687) |
| 53 | −1.2344099 | −1 | Stayer | CTGTACCCCATTTCTTCCCACGTATTCCTCGAGCCCAACGTTTTTTATTGACAAGTAATT (SEQ ID NO: 688) |
| 54 | −1.300138442 | −1 | Stayer | CTGTACCCCATTTCTTCCCACGTATTCCTCGATGGTCAGAGAGTTCTGAGCATGTTTGCA (SEQ ID NO: 689) |
| 55 | −1.152917744 | −1 | Stayer | GATGGCCAATAAACACTTGAAAAGGTACTCGATTTGCCAATATTTTGCTGAGGATTTTTC (SEQ ID NO: 690) |
| 56 | −1.279814722 | −1 | Stayer | TCTTTATATTGAGGTTCTAGCTTGTGATTCGAGAAGGAGACCTTGGTTATTTATTCTTAC (SEQ ID NO: 691) |

TABLE 33.a4-continued

| N | FC_1 | LS | Loop Detected | Probe sequence 60 mer |
|---|------|-----|---------------|----------------------|
| 57 | -1.549522786 | -1 | Stayer | TGGTACTTACTCATTTGATATCTGCCCGTCGAATGCAAACTATGCCATTCTCCACTACAA (SEQ ID NO: 692) |
| 58 | -1.620917244 | -1 | Stayer | TGGTACTTACTCATTTGATATCTGCCCGTCGAAGACATGGATATATAAATATATGTTTTC (SEQ ID NO: 693) |
| 59 | -1.250486699 | -1 | Stayer | ATGCAAAAATTCTCAAAATTTTGGCAACTCGACGGGCAGATATCAAATGAGTAAGTACCA (SEQ ID NO: 694) |
| 60 | -1.542378091 | -1 | Stayer | TGGTACTTACTCATTTGATATCTGCCCGTCGATCTAAGCAGAAAACACGAAGAAACATAA (SEQ ID NO: 695) |
| 61 | -1.310427896 | -1 | Stayer | ATATTAACAGCAAACCCTTAGTGGGTACTCGAAGCTCCCTAAGATTAGGAACCTTGTCTT (SEQ ID NO: 696) |
| 62 | -1.595397371 | -1 | Stayer | ATATTAACAGCAAACCCTTAGTGGGTACTCGAGGGTACTGAGTTGCAGACAGGTTAATGG (SEQ ID NO: 697) |
| 63 | -1.315228289 | -1 | Stayer | ATATTAACAGCAAACCCTTAGTGGGTACTCGAAGAAAGTAAAACAAATGGAGAGAAGTGT (SEQ ID NO: 698) |
| 64 | -1.197102917 | -1 | Stayer | TCAAAGTCCCGTTCAACTGTACATTTCTTCGAGTTATATCAGCCACTAACTAACAAAAAT (SEQ ID NO: 699) |

TABLE 33.a5

| N | Probe Location | | | | 4 kb Sequence Location | | | |
|---|------|--------|------|--------|------|--------|------|--------|
| | Chr | Start1 | End1 | Start2 | End2 | Chr | Start1 | End1 | Start2 |
| 1 | 6 | 47915416 | 47915447 | 48137538 | 48137569 | 6 | 47915416 | 47919417 | 48133568 |
| 2 | 11 | 36333514 | 36333545 | 36350786 | 36350817 | 11 | 36333514 | 36337515 | 36350786 |
| 3 | 11 | 36333514 | 36333545 | 36436048 | 36436079 | 11 | 36333514 | 36337515 | 36436048 |
| 4 | 11 | 36333514 | 36333545 | 36552325 | 36552356 | 11 | 36333514 | 36337515 | 36548355 |
| 5 | 11 | 36448245 | 36448276 | 36631315 | 36631346 | 11 | 36444275 | 36448276 | 36627345 |
| 6 | 8 | 11863063 | 11863094 | 11908667 | 11908698 | 8 | 11863063 | 11867064 | 11908667 |
| 7 | 5 | 17680263 | 17680294 | 17812085 | 17812116 | 5 | 17676293 | 17680294 | 17812085 |
| 8 | 5 | 17680263 | 17680294 | 17962676 | 17962707 | 5 | 17676293 | 17680294 | 17958706 |
| 9 | 5 | 17680263 | 17680294 | 17952666 | 17952697 | 5 | 17676293 | 17680294 | 17952666 |
| 10 | 4 | 84046655 | 84046686 | 84262207 | 84262238 | 4 | 84042685 | 84046686 | 84262207 |
| 11 | 4 | 84093825 | 84093856 | 84262207 | 84262238 | 4 | 84089855 | 84093856 | 84262207 |
| 12 | 5 | 13718587 | 13718618 | 13770118 | 13770149 | 5 | 13714617 | 13718618 | 13770118 |
| 13 | 5 | 13716400 | 13716400 | 13770118 | 13770149 | 5 | 13716369 | 13720370 | 13770118 |
| 14 | 14 | 59182856 | 59182887 | 59248524 | 59248555 | 14 | 59178886 | 59182887 | 59244554 |
| 15 | 14 | 59182856 | 59182887 | 59237657 | 59237688 | 14 | 59178886 | 59182887 | 59237657 |
| 16 | 5 | 35820030 | 35820061 | 35852447 | 35852478 | 5 | 35820030 | 35824031 | 35848477 |
| 17 | 5 | 35820030 | 35820061 | 35866091 | 35866122 | 5 | 35820030 | 35824031 | 35866091 |
| 18 | 5 | 35852447 | 35852478 | 35900637 | 35900668 | 5 | 35848477 | 35852478 | 35900637 |
| 19 | 11 | 20175502 | 20175533 | 20248248 | 20248279 | 11 | 20175502 | 20179503 | 20244278 |
| 20 | 11 | 20175502 | 20175533 | 20322464 | 20322495 | 11 | 20175502 | 20179503 | 20318494 |
| 21 | 11 | 20248248 | 20248279 | 20281555 | 20281586 | 11 | 20244278 | 20248279 | 20281555 |
| 22 | 20 | 24605232 | 24605263 | 24706408 | 24706439 | 20 | 24601262 | 24605263 | 24706408 |
| 23 | 20 | 32536895 | 32536926 | 32592625 | 32592656 | 20 | 32536895 | 32540896 | 32588655 |
| 24 | 20 | 32570542 | 32570573 | 32598309 | 32598340 | 20 | 32570542 | 32574543 | 32594339 |
| 25 | 20 | 32570542 | 32570573 | 32598340 | 32598371 | 20 | 32570542 | 32574543 | 32598340 |
| 26 | 20 | 32570542 | 32570573 | 32675890 | 32675921 | 20 | 32570542 | 32574543 | 32671920 |
| 27 | 20 | 32592625 | 32592656 | 32722678 | 32722709 | 20 | 32588655 | 32592656 | 32718708 |
| 28 | 20 | 32598340 | 32598371 | 32645786 | 32645817 | 20 | 32598340 | 32602341 | 32645786 |
| 29 | 11 | 26122948 | 26122979 | 26187791 | 26187822 | 11 | 26122948 | 26126949 | 26183821 |
| 30 | 11 | 26122948 | 26122979 | 26192170 | 26192201 | 11 | 26122948 | 26126949 | 26188200 |
| 31 | 16 | 33352821 | 33352852 | 33654217 | 33654248 | 16 | 33352821 | 33356822 | 33650247 |
| 32 | 16 | 33410233 | 33410264 | 33654217 | 33654248 | 16 | 33410233 | 33414234 | 33650247 |
| 33 | 16 | 33479236 | 33479267 | 33654217 | 33654248 | 16 | 33479236 | 33483237 | 33650247 |
| 34 | 16 | 33563090 | 33563121 | 33654217 | 33654248 | 16 | 33563090 | 33567091 | 33650247 |
| 35 | 16 | 33622760 | 33622791 | 33654217 | 33654248 | 16 | 33622760 | 33626761 | 33650247 |
| 36 | 16 | 33654217 | 33654248 | 33706816 | 33706847 | 16 | 33650247 | 33654248 | 33702846 |
| 37 | 16 | 33654217 | 33654248 | 33733451 | 33733482 | 16 | 33650247 | 33654248 | 33729481 |
| 38 | 16 | 33654217 | 33654248 | 33741064 | 33741095 | 16 | 33650247 | 33654248 | 33737094 |
| 39 | 16 | 33654217 | 33654248 | 33733482 | 33733513 | 16 | 33650247 | 33654248 | 33733482 |
| 40 | 16 | 33654217 | 33654248 | 33760460 | 33760491 | 16 | 33650247 | 33654248 | 33756490 |
| 41 | 16 | 33654217 | 33654248 | 33760582 | 33760613 | 16 | 33650247 | 33654248 | 33760582 |
| 42 | 16 | 33654217 | 33654248 | 33768286 | 33768317 | 16 | 33650247 | 33654248 | 33768286 |
| 43 | 16 | 33654217 | 33654248 | 33815034 | 33815065 | 16 | 33650247 | 33654248 | 33815034 |

TABLE 33.a5-continued

| N | Chr | Start1 | End1 | Start2 | End2 | Chr | Start1 | End1 | Start2 |
|---|---|---|---|---|---|---|---|---|---|
| | | Probe Location | | | | | 4 kb Sequence Location | | |
| 44 | 16 | 33654217 | 33654248 | 33852194 | 33852225 | 16 | 33650247 | 33654248 | 33848224 |
| 45 | 29 | 17033576 | 17033607 | 17155847 | 17155878 | 29 | 17033576 | 17037577 | 17151877 |
| 46 | 29 | 17048693 | 17048724 | 17144042 | 17144073 | 29 | 17048693 | 17052694 | 17144042 |
| 47 | 29 | 17144042 | 17144073 | 17262741 | 17262772 | 29 | 17144042 | 17148043 | 17262741 |
| 48 | 29 | 17144042 | 17144073 | 17336437 | 17336468 | 29 | 17144042 | 17148043 | 17332467 |
| 49 | 29 | 17144042 | 17144073 | 17332733 | 17332764 | 29 | 17144042 | 17148043 | 17332733 |
| 50 | 29 | 17286082 | 17286113 | 17357582 | 17357613 | 29 | 17286082 | 17290083 | 17353612 |
| 51 | 1 | 61392274 | 61392305 | 61544818 | 61544849 | 1 | 61388304 | 61392305 | 61540848 |
| 52 | 1 | 61392274 | 61392305 | 61577443 | 61577474 | 1 | 61388304 | 61392305 | 61573473 |
| 53 | 1 | 61392274 | 61392305 | 61570715 | 61570746 | 1 | 61388304 | 61392305 | 61570715 |
| 54 | 1 | 61392274 | 61392305 | 61578119 | 61578150 | 1 | 61388304 | 61392305 | 61578119 |
| 55 | 13 | 4269642 | 4269673 | 4440946 | 4440977 | 13 | 4269642 | 4273643 | 4440946 |
| 56 | 27 | 25376884 | 25376915 | 25471835 | 25471866 | 27 | 25376884 | 25380885 | 25471835 |
| 57 | 1 | 145659771 | 145659802 | 145699582 | 145699613 | 1 | 145659771 | 145663772 | 145699582 |
| 58 | 1 | 145659771 | 145659802 | 145762480 | 145762511 | 1 | 145659771 | 145663772 | 145762480 |
| 59 | 1 | 145659771 | 145659802 | 145800266 | 145800297 | 1 | 145659771 | 145663772 | 145796296 |
| 60 | 1 | 145659771 | 145659802 | 145793388 | 145793419 | 1 | 145659771 | 145663772 | 145793388 |
| 61 | 13 | 19942675 | 19942706 | 20034761 | 20034792 | 13 | 19942675 | 19946676 | 20030791 |
| 62 | 13 | 20002320 | 20002351 | 20034761 | 20034792 | 13 | 20002320 | 20006321 | 20030791 |
| 63 | 13 | 20007058 | 20007089 | 20034761 | 20034792 | 13 | 20007058 | 20011059 | 20030791 |
| 64 | 5 | 52200069 | 52200100 | 52330760 | 52330791 | 5 | 52196099 | 52200100 | 52326790 |

TABLE 33.a6

| N | 4 kb Sequence Location End2 | Probe | Primer ID-1 |
|---|---|---|---|
| 1 | 48137569 | ABCC9__6__47915416__47925286__48134697__48137569__RF | OBD RD043.001 |
| 2 | 36354787 | ACACA__11__36333514__36339214__36350786__36357493__RR | OBD RD043.005 |
| 3 | 36440049 | ACACA__11__36333514__36339214__36436048__36448276__RR | OBD RD043.009 |
| 4 | 36552356 | ACACA__11__36333514__36339214__36541652__36552356__RF | OBD RD043.013 |
| 5 | 36631346 | ACACA__11__36436048__36448276__36626441__36631346__FF | OBD RD043.017 |
| 6 | 11912668 | ACACB__8__11863063__11867350__11908667__11911946__RR | OBD RD043.021 |
| 7 | 17816086 | ACBD6__5__17677182__17680294__17812085__17822701__RR | OBD RD043.025 |
| 8 | 17962707 | ACBD6__5__17677182__17680294__17952666__17962707__FF | OBD RD043.029 |
| 9 | 17956667 | ACBD6__5__17677182__17680294__17952666__17962707__FR | OBD RD043.033 |
| 10 | 84266208 | AHCYL2__4__84035626__84046686__84262207__84266431__FR | OBD RD043.037 |
| 11 | 84266208 | AHCYL2__4__84081753__84093856__84262207__84266431__FR | OBD RD043.041 |
| 12 | 13774119 | ANGPTL1__5__13716369__13718618__13770118__13781369__FR | OBD RD043.045 |
| 13 | 13774119 | ANGPTL1__5__13716369__13718618__13770118__13781369__RR | OBD RD043.049 |
| 14 | 59248555 | APC__14__59179179__59182887__59237657__59248555__FF | OBD RD043.053 |
| 15 | 59241658 | APC__14__59179179__59182887__59237657__59248555__FR | OBD RD043.057 |
| 16 | 35852478 | APOA2__5__35820030__35830912__35848600__35852478__RF | OBD RD043.061 |
| 17 | 35870092 | APOA2__5__35820030__35830912__35866091__35873759__RR | OBD RD043.065 |
| 18 | 35904638 | APOA2__5__35848600__35852478__35900637__35912475__FR | OBD RD043.069 |
| 19 | 20248279 | BECN1__11__20175502__20184049__20243179__20248279__RF | OBD RD043.073 |
| 20 | 20322495 | BECN1__11__20175502__20184049__20320840__20322495__RF | OBD RD043.077 |
| 21 | 20285556 | BECN1__11__20243179__20248279__20281555__20289129__FR | OBD RD043.081 |
| 22 | 24710409 | BTN1A1__20__24591764__24605263__24706408__24710466__F R | OBD RD043.085 |
| 23 | 32592656 | BTNL2__20__32536895__32543196__32585002__32592656__RF | OBD RD043.089 |
| 24 | 32598340 | BTNL2__20__32570542__32582104__32597196__32598340__RF | OBD RD043.093 |
| 25 | 32602341 | BTNL2__20__32570542__32582104__32598340__32606017__RR | OBD RD043.097 |
| 26 | 32675921 | BTNL2__20__32570542__32582104__32672903__32675921__RF | OBD RD043.101 |
| 27 | 32722709 | BTNL2__20__32585002__32592656__32716550__32722709__FF | OBD RD043.105 |
| 28 | 32649787 | BTNL2__20__32598340__32606017__32645786__32652591__RR | OBD RD043.109 |
| 29 | 26187822 | CACNA1G__11__26122948__26135515__26185131__26187822__RF | OBD RD043.113 |
| 30 | 26192201 | CACNA1G__11__26122948__26135515__26187822__26192201__RF | OBD RD043.117 |
| 31 | 33654248 | CACNA2D3__16__33352821__33354631__33641948__33654248__RF | OBD RD043.121 |
| 32 | 33654248 | CACNA2D3__16__33410233__33413906__33641948__33654248__RF | OBD RD043.125 |
| 33 | 33654248 | CACNA2D3__16__33479236__33480664__33641948__33654248__RF | OBD RD043.129 |
| 34 | 33654248 | CACNA2D3__16__33563090__33565331__33641948__33654248__RF | OBD RD043.133 |
| 35 | 33654248 | CACNA2D3__16__33622760__33627636__33641948__33654248__RF | OBD RD043.137 |
| 36 | 33706847 | CACNA2D3__16__33641948__33654248__33704852__33706847__FF | OBD RD043.141 |
| 37 | 33733482 | CACNA2D3__16__33641948__33654248__33729470__33733482__FF | OBD RD043.145 |
| 38 | 33741095 | CACNA2D3__16__33641948__33654248__33733482__33741095__FF | OBD RD043.149 |
| 39 | 33737483 | CACNA2D3__16__33641948__33654248__33733482__33741095__FR | OBD RD043.153 |
| 40 | 33760491 | CACNA2D3__16__33641948__33654248__33757281__33760491__FF | OBD RD043.157 |
| 41 | 33764583 | CACNA2D3__16__33641948__33654248__33760582__33768051__FR | OBD RD043.161 |
| 42 | 33772287 | CACNA2D3__16__33641948__33654248__33768286__33770169__FR | OBD RD043.165 |
| 43 | 33819035 | CACNA2D3__16__33641948__33654248__33815034__33817501__FR | OBD RD043.169 |
| 44 | 33852225 | CACNA2D3__16__33641948__33654248__33848517__33852225__FF | OBD RD043.173 |
| 45 | 17155878 | CACNB2__29__17033576__17046068__17154781__17155878__RF | OBD RD043.177 |

TABLE 33.a6-continued

| N | 4 kb Sequence Location End2 | Probe | Primer ID-1 |
|---|---|---|---|
| 46 | 17148043 | CACN_B2__29__17048693__17053442__17144042__17154089__RR | OBD RD043.181 |
| 47 | 17266742 | CACNB2__29__17144042__17154089__17262741__17269092__RR | OBD RD043.185 |
| 48 | 17336468 | CACNB2__29__17144042__17154089__17332733__17336468__RF | OBD RD043.189 |
| 49 | 17336734 | CACNB2__29__17144042__17154089__17332733__17336468__RR | OBD RD043.193 |
| 50 | 17357613 | CACNB2__29__17286082__17289972__17348926__17357613__RF | OBD RD043.197 |
| 51 | 61544849 | CAMK2G__1__61385709__61392305__61537867__61544849__FF | OBD RD043.201 |
| 52 | 61577474 | CAMK2G__1__61385709__61392305__61570715__61577474__FF | OBD RD043.205 |
| 53 | 61574716 | CAMK2G__1__61385709__61392305__61570715__61577474__FR | OBD RD043.209 |
| 54 | 61582120 | CAMK2G__1__61385709__61392305__61578119__61589600__FR | OBD RD043.213 |
| 55 | 4444947 | CARD11__13__4269642__4272623__4440946__4446573__RR | OBD RD043.217 |
| 56 | 25475836 | CASP3__27__25376884__25380938__25471835__25478467__RR | OBD RD043.221 |
| 57 | 145703583 | CCNDBP1__1__145659771__145664399__145699582__145711153__RR | OBD RD043.225 |
| 58 | 145766481 | CCNDBP1__1__145659771__145664399__145762480__145771097__RR | OBD RD043.229 |
| 59 | 145800297 | CCNDBP1__1__145659771__145664399__145793388__145800297__RF | OBD RD043.233 |
| 60 | 145797389 | CCNDBP1__1__145659771__145664399__145793388__145800297__RR | OBD RD043.237 |
| 61 | 20034792 | CD19__13__19942675__19947695__20028912__20034792__RF | OBD RD043.241 |
| 62 | 20034792 | CD19__13__20002320__20006400__20028912__20034792__RF | OBD RD043.245 |
| 63 | 20034792 | CD19__13__20007058__20010478__20028912__20034792__RF | OBD RD043.249 |
| 64 | 52330791 | CD2__5__52197323__52200100__52321910__52330791__FF | OBD RD043.253 |

TABLE 33.a7

| N | Primer Sequence | Primer ID-2 | Primer Sequence |
|---|---|---|---|
| 1 | CTGGGAATACTTATGATTTGGCGACC (SEQ ID NO: 700) | OBD RD043.003 | TCCTTGTGACCTATTGGACTGAGGGC (SEQ ID NO: 764) |
| 2 | GCAGATTAGAAAGGAGTCATCAGAAA (SEQ ID NO: 701) | OBD RD043.007 | CCTGATTCTAAACAGCATTCTGGGAG(SEQ ID NO: 765) |
| 3 | CCAACTCTGTCGCTTGTTACACTTAG (SEQ ID NO: 702) & (SEQ ID NO: 704) & (SEQ ID NO: 767) | OBD RD043.011 | ACTCTTTACCCTGTGGTGTGGACGGT (SEQ ID NO: 766) |
| 4 | CAGTTCACGGAAATGTCCCCAGAGCA (SEQ ID NO: 703) | OBD RD043.015 | CCAACTCTGTCGCTTGTTACACTTAG (SEQ ID NO: 702) & (SEQ ID NO: 704) & (SEQ ID NO: 767) |
| 5 | CCAACTCTGTCGCTTGTTACACTTAG (SEQ ID NO: 702) & (SEQ ID NO: 704) & (SEQ ID NO: 767) | OBD RD043.019 | GCACAACAATGGAGTGACCCACAGCA (SEQ ID NO: 768) |
| 6 | GGAGAGCCACCCTGGATACACAG (SEQ ID NO: 705) | OBD RD043.023 | CCGACAAAGGGCAGAGGTGAGAT (SEQ ID NO: 769) |
| 7 | CGGATTTTAGAGTTGATAAGCACACC (SEQ ID NO: 706) & (SEQ ID NO: 707) & (SEQ ID NO: 708) | OBD RD043.027 | CACCAGGTTTTCCCCTTCAGTGTGAC (SEQ ID NO: 770) |
| 8 | CGGATTTTAGAGTTGATAAGCACACC (SEQ ID NO: 706) & (SEQ ID NO: 707) & (SEQ ID NO: 708) | OBD RD043.031 | GACCGATTTGAGGTGCTTACGGATGG (SEQ ID NO: 771) |
| 9 | CGGATTTTAGAGTTGATAAGCACACC (SEQ ID NO: 706) & (SEQ ID NO: 707) & (SEQ ID NO: 708) | OBD RD043.035 | GCTGGGTCACCACGCATAGGATGA (SEQ ID NO: 772) |
| 10 | GCAGCAGAGTATCATTCTTGCCCTC (SEQ ID NO: 709) | OBD RD043.039 | AGGGCAGAGGGCTATGGGTGCTT (SEQ ID NO: 773) & (SEQ ID NO: 774) |
| 11 | CGTCTGAGGAAAGTGCCAGGAAAG (SEQ ID NO: 710) | OBD RD043.043 | AGGGCAGAGGGCTATGGGTGCTT (SEQ ID NO: 773) & (SEQ ID NO: 774) |
| 12 | TGCTAAACAACCACTGGACCACTGGG (SEQ ID NO: 711) | OBD RD043.047 | ATGGATGGCTCTGTCAACTTCTTCAG (SEQ ID NO: 775) & (SEQ ID NO: 776) |
| 13 | CGGGCAAAGGTCTAACAGAAGCAGGA (SEQ ID NO: 712) | OBD RD043.051 | ATGGATGGCTCTGTCAACTTCTTCAG (SEQ ID NO: 775) & (SEQ ID NO: 776) |
| 14 | CTCCTCTGGACTCCTATTTCTGGGCA (SEQ ID NO: 713) & (SEQ ID NO: 714) | OBD RD043.055 | CACTTGGAGCGGTTTTGTTCACACTT (SEQ ID NO: 777) |

TABLE 33.a7-continued

| N | Primer Sequence | Primer ID-2 | Primer Sequence |
|---|---|---|---|
| 15 | CTCCTCTGGACTCCTATTTCTGGGCA (SEQ ID NO: 713) & (SEQ ID NO: 714) | OBD RD043.059 | GATGGCAGCATAGTAACAGTTCTACA (SEQ ID NO: 778) |
| 16 | CACTTCCTTCAGAAAGCGGGTGCTCA (SEQ ID NO: 715) | OBD RD043.063 | GAACAACTGCTCCAACACAAACAAGC (SEQ ID NO: 779) |
| 17 | TGGGAGGAACCAGGTGGGTAACG (SEQ ID NO: 716) & (SEQ ID NO: 717) | OBD RD043.067 | TTCCCCTCCTCTCCATTGGGTCA (SEQ ID NO: 780) |
| 18 | TGGGAGGAACCAGGTGGGTAACG (SEQ ID NO: 716) & (SEQ ID NO: 717) | OBD RD043.071 | CTTCCTTCAGAAAGCGGGTGCTC (SEQ ID NO: 781) |
| 19 | GTCGCCAGGTTCCGTTCTTGGTG (SEQ ID NO: 718) | OBD RD043.075 | GACTGAGCATTATGGAGGCAGCC (SEQ ID NO: 782) |
| 20 | TGTGGGCTTGTTCTTACTTCCTGAAT (SEQ ID NO: 719) | OBD RD043.079 | TCCATCTTGGGTCCCTTCTCCATCCT (SEQ ID NO: 783) |
| 21 | AAGCAACAGTGGTGGAGGAGACC (SEQ ID NO: 720) | OBD RD043.083 | TTGGGTCCCTTCTCCATCCTGCC (SEQ ID NO: 784) |
| 22 | GGTTAGGGAGTGCTATGAGGGAG (SEQ ID NO: 721) | OBD RD043.087 | GCCCTCGGTGTAGTCCTTGCTGT (SEQ ID NO: 785) |
| 23 | TACACTTTGGGAGTTTGTCTTTGAAG (SEQ ID NO: 722) & (SEQ ID NO: 724) | OBD RD043.091 | ACTTGAAGACAGAACTGCTTTGACAA (SEQ ID NO: 786) |
| 24 | CACTATGGAAAACAGTATGGAGAT (SEQ ID NO: 723) | OBD RD043.095 | TCTGAGATGTCCTTCTTGATTCATA (SEQ ID NO: 787) |
| 25 | TACACTTTGGGAGTTTGTCTTTGAAG (SEQ ID NO: 722) & (SEQ ID NO: 724) | OBD RD043.099 | CACCTGCGTAGATTTGTGTAACCACG (SEQ ID NO: 788) |
| 26 | TCTGATAGGGCTTGTGATTTTATTT (SEQ ID NO: 725) | OBD RD043.103 | ACTATGGAAAACAGTATGGAGATTT (SEQ ID NO: 789) |
| 27 | GTCTTTCCCTATGTCAACCTTGTGT (SEQ ID NO: 726) | OBD RD043.107 | GCCACTATGGAAAACAGTATGGAGAT (SEQ ID NO: 790) |
| 28 | TCTTCACCTTAGTCTCCTTATCTCTA (SEQ ID NO: 727) | OBD RD043.111 | GGACTCAGGGCTCATCTCTCATTTGT (SEQ ID NO: 791) |
| 29 | CCACCAGTGCCACGAGAACCTCT (SEQ ID NO: 728) | OBD RD043.115 | CCCAAAGGTCCAGAGCGGAGAAA (SEQ ID NO: 792) |
| 30 | CAGGGCTGCTTGAATGGAAAGGG (SEQ ID NO: 729) | OBD RD043.119 | CAACCCAAAGGTCCAGAGCGGAG (SEQ ID NO: 793) |
| 31 | GGGCAGCCAGAAAGCACACAGTT (SEQ ID NO: 730) & (SEQ ID NO: 732) & (SEQ ID NO: 733) & (SEQ ID NO: 734) & (SEQ ID NO: 735) & (SEQ ID NO: 738) & (SEQ ID NO: 739) & (SEQ ID NO: 741) | OBD RD043.123 | CCCTTGTGACCTCCTACTCTGCC (SEQ ID NO: 794) |
| 32 | AACCCAATCCAGGCAAGCCACCC (SEQ ID NO: 731) & (SEQ ID NO: 740) | OBD RD043.127 | GCTGAAGTTGACCTTGTCTCCGC (SEQ ID NO: 795) |
| 33 | GGGCAGCCAGAAAGCACACAGTT (SEQ ID NO: 730) & (SEQ ID NO: 732) & (SEQ ID NO: 733) & (SEQ ID NO: 734) & (SEQ ID NO: 735) & (SEQ ID NO: 738) & (SEQ ID NO: 739) & (SEQ ID NO: 741) | OBD RD043.131 | ATTCGGTGGGTCTGGAGAGAGGC (SEQ ID NO: 796) |
| 34 | GGGCAGCCAGAAAGCACACAGTT (SEQ ID NO: 730) & (SEQ ID NO: 732) & (SEQ ID NO: 733) & (SEQ ID NO: 734) & (SEQ ID NO: 735) & (SEQ ID NO: 738) & (SEQ ID NO: 739) & (SEQ ID NO: 741) | OBD RD043.135 | GGGAGGAGAAGCAGAGCACACAG (SEQ ID NO: 797) |
| 35 | GGGCAGCCAGAAAGCACACAGTT (SEQ ID NO: 730) & (SEQ ID NO: 732) & (SEQ ID NO: 733) & (SEQ ID NO: 734) & (SEQ ID NO: 735) & (SEQ ID NO: 738) & (SEQ ID NO: 739) & (SEQ ID NO: 741) | OBD RD043.139 | GGAGGCTGATGTCTGTCCTTGGG (SEQ ID NO: 798) |

TABLE 33.a7-continued

| N | Primer Sequence | Primer ID-2 | Primer Sequence |
|---|---|---|---|
| 36 | GGGCAGCCAGAAAGCACACAGTT (SEQ ID NO: 730) & (SEQ ID NO: 732) & (SEQ ID NO: 733) & (SEQ ID NO: 734) & (SEQ ID NO: 735) & (SEQ ID NO: 738) & (SEQ ID NO: 739) & (SEQ ID NO: 741) | OBD RD043.143 | CCCGCTGCTCTCAACAGACACTG (SEQ ID NO: 799) |
| 37 | TCCATTTTCCCCATCTCTCACCCTCC (SEQ ID NO: 736) & (SEQ ID NO: 737) | OBD RD043.147 | ATGAGAACCAAGGTCAGGGAGGTAAA (SEQ ID NO: 800) |
| 38 | TCCATTTTCCCCATCTCTCACCCTCC (SEQ ID NO: 736) & (SEQ ID NO: 737) | OBD RD043.151 | CCCACTCTCTTTGAAGGAAATCACAT (SEQ ID NO: 801) |
| 39 | GGGCAGCCAGAAAGCACACAGTT (SEQ ID NO: 730) & (SEQ ID NO: 732) & (SEQ ID NO: 733) & (SEQ ID NO: 734) & (SEQ ID NO: 735) & (SEQ ID NO: 738) & (SEQ ID NO: 739) & (SEQ ID NO: 741) | OBD RD043.155 | CCTCCACCATTCTCCTCCAGTCC (SEQ ID NO: 802) |
| 40 | GGGCAGCCAGAAAGCACACAGTT (SEQ ID NO: 730) & (SEQ ID NO: 732) & (SEQ ID NO: 733) & (SEQ ID NO: 734) & (SEQ ID NO: 735) & (SEQ ID NO: 738) & (SEQ ID NO: 739) & (SEQ ID NO: 741) | OBD RD043.159 | GGCAGGGTCATTGTGATGGTCCG (SEQ ID NO: 803) |
| 41 | AACCCAATCCAGGCAAGCCACCC (SEQ ID NO: 731) & (SEQ ID NO: 740) | OBD RD043.163 | CCTCCTATCATCTCTCTCCCCAC (SEQ ID NO: 804) |
| 42 | GGGCAGCCAGAAAGCACACAGTT (SEQ ID NO: 730) & (SEQ ID NO: 732) & (SEQ ID NO: 733) & (SEQ ID NO: 734) & (SEQ ID NO: 735) & (SEQ ID NO: 738) & (SEQ ID NO: 739) & (SEQ ID NO: 741) | OBD RD043.167 | AGTCTCCCCTCCCACTGTTGGCA (SEQ ID NO: 805) |
| 43 | ATCCATTTTCCCCATCTCTCACCCTC (SEQ ID NO: 742) | OBD RD043.171 | CTTAGACTCCAGTGGCTGAATGTCCA (SEQ ID NO: 806) |
| 44 | GTTGGGCAGCCAGAAAGCACACAG (SEQ ID NO: 743) | OBD RD043.175 | GAACTTCTCGTGGGACACCCTCA (SEQ ID NO: 807) |
| 45 | GAGCAAAGTAGTCAGCCAGCCAGAAT (SEQ ID NO: 744) | OBD RD043.179 | GTTCTTTTCCTGGTAGGTCATCCTGT (SEQ ID NO: 808) |
| 46 | AAACCTGTGCGGGCTGTCTGACCA (SEQ ID NO: 745) | OBD RD043.183 | GCCTGAACCCACTTAGATAATGTGTG (SEQ ID NO: 747) & (SEQ ID NO: 809) |
| 47 | TCCCGCTCCCTGTTTTCCACCAT (SEQ ID NO: 746) & (SEQ ID NO: 812) | OBD RD043.187 | CACTGTGGCACTGGGAGGAAACG (SEQ ID NO: 810) |
| 48 | GCCTGAACCCACTTAGATAATGTGTG (SEQ ID NO: 747) & (SEQ ID NO: 809) | OBD RD043.191 | GTTCCTGTGGTTGGTTGGTTGGGATG (SEQ ID NO: 811) |
| 49 | CCTGGGTAGATGAGCCTGTAGCC (SEQ ID NO: 748) | OBD RD043.195 | TCCCGCTCCCTGTTTTCCACCAT (SEQ ID NO: 746) & (SEQ ID NO: 812) |
| 50 | CCCTCGCCTCCTATTCCTATGGC (SEQ ID NO: 749) | OBD RD043.199 | CCCATCCCTTTCAGCCTCACTCA (SEQ ID NO: 813) |
| 51 | CCACGCCATTTAGGACTCGGGTC (SEQ ID NO: 750) | OBD RD043.203 | GGGTCAGTCTTCCGCAGCACAAA (SEQ ID NO: 814) |
| 52 | TATGGGATTTCTTTGGTAGGGACG (SEQ ID NO: 751) | OBD RD043.207 | TCAGTCAATACATACAGTTCATACT (SEQ ID NO: 815) |
| 53 | GCCCAACCTCTGTGTTCCCATTC (SEQ ID NO: 752) & (SEQ ID NO: 753) | OBD RD043.211 | TCCACGGTTCAGGCATCCACTGG (SEQ ID NO: 816) |
| 54 | GCCCAACCTCTGTGTTCCCATTC (SEQ ID NO: 752) & (SEQ ID NO: 753) | OBD RD043.215 | CCCCGAAGGCAGGCTATGGAGAA (SEQ ID NO: 817) |
| 55 | GAACAGGTGGCTCACAAAGGAGGATA (SEQ ID NO: 754) | OBD RD043.219 | GACAAGGACAACACAAAGAAGGAAAA (SEQ ID NO: 818) |

TABLE 33.a7-continued

| N | Primer Sequence | Primer ID-2 | Primer Sequence |
|---|---|---|---|
| 56 | GCTCCAGTTTGCTGAACCAACCC (SEQ ID NO: 755) | OBD RD043.223 | AGAGCGTCCCTGGAAAGTGGCAG (SEQ ID NO: 819) |
| 57 | GGCACCCCTTATCAGAGACCAGC (SEQ ID NO: 756) & (SEQ ID NO: 757) & (SEQ ID NO: 759) | OBD RD043.227 | TTGGGCAGAGGAGAAGAGTGTGC (SEQ ID NO: 820) |
| 58 | GGCACCCCTTATCAGAGACCAGC (SEQ ID NO: 756) & (SEQ ID NO: 757) & (SEQ ID NO: 759) | OBD RD043.231 | GGCATCTCCTCTTCTGCTCACAC (SEQ ID NO: 821) |
| 59 | CCAAAACCTGACAAGCACAGCAT (SEQ ID NO: 758) | OBD RD043.235 | GAGACAGGTGGATGGCGATGGTA (SEQ ID NO: 822) |
| 60 | GGCACCCCTTATCAGAGACCAGC (SEQ ID NO: 756) & (SEQ ID NO: 757) & (SEQ ID NO: 759) | OBD RD043.239 | CCTCCATCTCTGCCACTCAGGAA (SEQ ID NO: 823) |
| 61 | GACCTTCATCCGAGCCTCCGTTT (SEQ ID NO: 760) & (SEQ ID NO: 762) | OBD RD043.243 | TGCCTCTCCTGCCTCTGTCTCAC (SEQ ID NO: 824) |
| 62 | GAGACCTTCATCCGAGCCTCCGT (SEQ ID NO: 761) | OBD RD043.247 | GGGCGAACAGCAAGAGACAAGCA (SEQ ID NO: 825) |
| 63 | GACCTTCATCCGAGCCTCCGTTT (SEQ ID NO: 760) & (SEQ ID NO: 762) | OBD RD043.251 | CCCTGGATGTGTGACCTTCGGCA (SEQ ID NO: 826) |
| 64 | ATCCAAACCATTGAAACCCTGGGC (SEQ ID NO: 763) | OBD RD043.255 | GATTGAGACTTGCGTTTTGAGGGC (SEQ ID NO: 827) |

TABLE 33.a8

| N | Probe | Marker |
|---|---|---|
| 1 | ABCC9 | OBD RD043.001.003 |
| 2 | ACACA | OBD RD043.005.007 |
| 3 | ACACA | OBD RD043.009.011 |
| 4 | ACACA | OBD RD043.013.015 |
| 5 | ACACA | OBD RD043.017.019 |
| 6 | ACACB | OBD RD043.021.023 |
| 7 | ACBD6 | OBD RD043.025.027 |
| 8 | ACBD6 | OBD RD043.029.031 |
| 9 | ACBD6 | OBD RD043.033.035 |
| 10 | AHCYL2 | OBD RD043.037.039 |
| 11 | AHCYL2 | OBD RD043.041.043 |
| 12 | ANGPTL1 | OBD RD043.045.047 |
| 13 | ANGPTL1 | OBD RD043.049.051 |
| 14 | APC | OBD RD043.053.055 |
| 15 | APC | OBD RD043.057.059 |
| 16 | APOA2 | OBD RD043.061.063 |
| 17 | APOA2 | OBD RD043.065.067 |
| 18 | APOA2 | OBD RD043.069.071 |
| 19 | BECN1 | OBD RD043.073.075 |
| 20 | BECN1 | OBD RD043.077.079 |
| 21 | BECN1 | OBD RD043.081.083 |
| 22 | BTN1A1 | OBD RD043.085.087 |
| 23 | BTNL2 | OBD RD043.089.091 |
| 24 | BTNL2 | OBD RD043.093.095 |
| 25 | BTNL2 | OBD RD043.097.099 |
| 26 | BTNL2 | OBD RD043.101.103 |
| 27 | BTNL2 | OBD RD043.105.107 |
| 28 | BTNL2 | OBD RD043.109.111 |
| 29 | CACNA1G | OBD RD043.113.115 |
| 30 | CACNA1G | OBD RD043.117.119 |
| 31 | CACNA2D3 | OBD RD043.121.123 |
| 32 | CACNA2D3 | OBD RD043.125.127 |
| 33 | CACNA2D3 | OBD RD043.129.131 |

TABLE 33.a8-continued

| N | Probe | Marker |
|---|---|---|
| 34 | CACNA2D3 | OBD RD043.133.135 |
| 35 | CACNA2D3 | OBD RD043.137.139 |
| 36 | CACNA2D3 | OBD RD043.141.143 |
| 37 | CACNA2D3 | OBD RD043.145.147 |
| 38 | CACNA2D3 | OBD RD043.149.151 |
| 39 | CACNA2D3 | OBD RD043.153.155 |
| 40 | CACNA2D3 | OBD RD043.157.159 |
| 41 | CACNA2D3 | OBD RD043.161.163 |
| 42 | CACNA2D3 | OBD RD043.165.167 |
| 43 | CACNA2D3 | OBD RD043.169.171 |
| 44 | CACNA2D3 | OBD RD043.173.175 |
| 45 | CACNB2 | OBD RD043.177.179 |
| 46 | CACNB2 | OBD RD043.181.183 |
| 47 | CACNB2 | OBD RD043.185.187 |
| 48 | CACNB2 | OBD RD043.189.191 |
| 49 | CACNB2 | OBD RD043.193.195 |
| 50 | CACNB2 | OBD RD043.197.199 |
| 51 | CAMK2G | OBD RD043.201.203 |
| 52 | CAMK2G | OBD RD043.205.207 |
| 53 | CAMK2G | OBD RD043.209.211 |
| 54 | CAMK2G | OBD RD043.213.215 |
| 55 | CARD11 | OBD RD043.217.219 |
| 56 | CASP3 | OBD RD043.221.223 |
| 57 | CCNDBP1 | OBD RD043.225.227 |
| 58 | CCNDBP1 | OBD RD043.229.231 |
| 59 | CCNDBP1 | OBD RD043.233.235 |
| 60 | CCNDBP1 | OBD RD043.237.239 |
| 61 | CD19 | OBD RD043.241.243 |
| 62 | CD19 | OBD RD043.245.247 |
| 63 | CD19 | OBD RD043.249.251 |
| 64 | CD2 | OBD RD043.253.255 |

TABLE 33.b1

| N | Probe | GeneLocus | Probe_Count_Total | Probe_Count_Sig |
|---|---|---|---|---|
| 65 | CD226_8_85390137_85395670_85431393_85435046_RR | CD226 | 1 | 31 |
| 66 | CD40_22_34955976_34961456_35003447_35009473_FF | CD40 | 1 | 30 |

TABLE 33.b1-continued

| N | Probe | GeneLocus | Probe__Count__Total | Probe__Count__Sig |
|---|-------|-----------|---------------------|-------------------|
| 67 | CD5__12__20785118__20787274__20916990__20922807__RF | CD5 | 2 | 31 |
| 68 | CD5__12__20843696__20847942__20916990__20922807__RF | CD5 | 2 | 31 |
| 69 | CDH1__3__18955128__18959809__19065895__19074313__FF | CDH1 | 1 | 28 |
| 70 | CERK__28__42579274__42585201__42607249__42612447__RR | CERK | 1 | 31 |
| 71 | CHL1__16__15145284__15151298__15196227__15203340__FF | CHL1 | 6 | 73 |
| 72 | CHL1__16__15145284__15151298__15255076__15264032__FF | CHL1 | 6 | 73 |
| 73 | CHL1__16__15145284__15151298__15255076__15264032__FR | CHL1 | 6 | 73 |
| 74 | CHL1__16__15145284__15151298__15301390__15310795__FR | CHL1 | 6 | 73 |
| 75 | CHL1__16__15145284__15151298__15326701__15332680__FF | CHL1 | 6 | 73 |
| 76 | CHL1__16__15165960__15173124__15233430__15239181__RF | CHL1 | 6 | 73 |
| 77 | CHRDL2__7__69179023__69184961__69220436__69225536__RF | CHRDL2 | 2 | 61 |
| 78 | CHRDL2__7__69220436__69225536__69328532__69336827__FR | CHRDL2 | 2 | 61 |
| 79 | CHST10__15__8874159__8888709__8973363__8982576__FR | CHST10 | 3 | 64 |
| 80 | CHST10__15__8874159__8888709__9029805__9032751__FF | CHST10 | 3 | 64 |
| 81 | CHST10__15__8936185__8939355__8973363__8982576__RR | CHST10 | 3 | 64 |
| 82 | COL15A1__25__5777848__5781338__5838527__5844153__RR | COL15A1 | 1 | 31 |
| 83 | COL18A1__26__40666594__40668538__40680588__40685271__RR | COL18A1 | 1 | 30 |
| 84 | COL4A4__6__15299757__15310450__15375645__15378009__RF | COL4A4 | 2 | 48 |
| 85 | COL4A4__6__15436171__15443495__15487479__15493934__FR | COL4A4 | 2 | 48 |
| 86 | CREBBP__13__38904201__38905631__39179236__39195594__RF | CREBBP | 7 | 139 |
| 87 | CREBBP__13__38931046__38933583__39179236__39195594__RF | CREBBP | 7 | 139 |
| 88 | CREBBP__13__38974958__38977634__39179236__39195594__RF | CREBBP | 7 | 139 |
| 89 | CREBBP__13__38981963__38985123__39179236__39195594__RF | CREBBP | 7 | 139 |
| 90 | CREBBP__13__38999154__39003472__39179236__39195594__RF | CREBBP | 7 | 139 |
| 91 | CREBBP__13__39073684__39080240__39179236__39195594__RF | CREBBP | 7 | 139 |
| 92 | CREBBP__13__39112330__39113797__39179236__39195594__RF | CREBBP | 7 | 139 |
| 93 | CRP__5__37768331__37775673__37803790__37809028__RF | CRP | 3 | 33 |
| 94 | CRP__5__37768331__37775673__37803790__37809028__RR | CRP | 3 | 33 |
| 95 | CRP__5__37768331__37775673__37834953__37842330__RR | CRP | 3 | 33 |
| 96 | CTLA4__18__78522827__78530189__78600391__78604267__FR | CTLA4 | 1 | 29 |
| 97 | DDIT3__6__75012399__75018811__75092742__75096887__RR | DDIT3 | 2 | 23 |
| 98 | DDIT3__6__75012399__75018811__75098342__75106967__RR | DDIT3 | 2 | 23 |
| 99 | DGKH__17__27888277__27893919__27983597__27991700__RR | DGKH | 4 | 168 |
| 100 | DGKH__17__27888277__27893919__28023161__28030553__RR | DGKH | 4 | 168 |
| 101 | DGKH__17__27888277__27893919__28087062__28095320__RR | DGKH | 4 | 168 |
| 102 | DGKH__17__27983597__27991700__28038960__28044643__FF | DGKH | 4 | 168 |
| 103 | DIAPH3__17__35244506__35247777__35523297__35543766__RR | DIAPH3 | 2 | 250 |
| 104 | DIAPH3__17__35550338__35555886__35584820__35594304__FR | DIAPH3 | 2 | 250 |
| 105 | DLK1__24__42596087__42597712__42651466__42656554__FF | DLK1 | 1 | 31 |
| 106 | DOK5__22__41633839__41639527__41876029__41882809__RF | DOK5 | 2 | 31 |
| 107 | DOK5__22__41845220__41849884__41876029__41882809__RF | DOK5 | 2 | 31 |
| 108 | ETS1__7__37223720__37228234__37244778__37252642__RR | ETS1 | 1 | 56 |
| 109 | GABPA__26__23335158__23338855__23360793__23370765__RR | GABPA | 1 | 91 |
| 110 | GJA5__5__48248931__48256193__48407852__48413621__RR | GJA5 | 5 | 88 |
| 111 | GJA5__5__48248931__48256193__48407852__48413621__RR | GJA5 | 5 | 88 |
| 112 | GJA5__5__48256193__48265184__48407852__48413621__FR | GJA5 | 5 | 88 |
| 113 | GJA5__5__48297725__48306379__48407852__48413621__FR | GJA5 | 5 | 88 |
| 114 | GJA5__5__48370294__48376643__48407852__48413621__RR | GJA5 | 5 | 88 |
| 115 | GPC5__17__62030628__62037968__62292109__62298602__FR | GPC5 | 2 | 249 |
| 116 | GPC5__17__62161244__62167825__62292109__62298602__FR | GPC5 | 2 | 249 |
| 117 | GRK5__1__13009800__13016170__13161461__13167914__FR | GRK5 | 3 | 31 |
| 118 | GRK5__1__13009800__13016170__13204085__13213606__FF | GRK5 | 3 | 31 |
| 119 | GRK5__1__13135627__13139975__13204085__13213606__FF | GRK5 | 3 | 31 |
| 120 | GSK3B__19__38827199__38835574__39055705__39060019__RR | GSK3B | 1 | 132 |
| 121 | HDAC3__14__35404443__35406152__35458546__35471150__RR | HDAC3 | 1 | 104 |
| 122 | HDAC5__11__19330735__19336727__19434549__19441692__RR | HDAC5 | 2 | 30 |
| 123 | HDAC5__11__19372111__19379011__19491838__19494990__FF | HDAC5 | 2 | 30 |
| 124 | HDAC9__4__51008167__51021720__51107519__51111219__RF | HDAC9 | 1 | 280 |
| 125 | HOXC6__6__70794688__70801196__70818032__70820676__RF | HOXC6 | 1 | 31 |
| 126 | HSDL2__25__17089584__17093930__17167460__17175476__FF | HSDL2 | 3 | 102 |
| 127 | HSDL2__25__17089584__17093930__17167460__17175476__FR | HSDL2 | 3 | 102 |
| 128 | HSDL2__25__17089584__17093930__17197980__17209878__FF | HSDL2 | 3 | 102 |

TABLE 33.b2

| N | HyperG__Stats | FDR__HyperG | Percent__Sig | logFC | AveExpr |
|---|---------------|-------------|--------------|-------|---------|
| 65 | 0.198752749 | 0.267074007 | 3.23 | 0.341840161 | 7.247636443 |
| 66 | 0.193928419 | 0.267074007 | 3.33 | −0.178317344 | 10.69384186 |
| 67 | 0.024599258 | 0.075554863 | 6.45 | −0.242153231 | 10.73889105 |
| 68 | 0.024599258 | 0.075554863 | 6.45 | −0.260248811 | 11.120971 |
| 69 | 0.183998999 | 0.267074007 | 3.57 | −0.282497053 | 11.11483854 |
| 70 | 0.198752749 | 0.267074007 | 3.23 | −0.448599336 | 8.889809603 |
| 71 | 0.0000287855939384343 | 0.000742668 | 8.22 | 0.462470187 | 8.5481053 |
| 72 | 0.0000287855939384343 | 0.000742668 | 8.22 | 0.410028111 | 8.628990709 |

TABLE 33.b2-continued

| N | HyperG_Stats | FDR_HyperG | Percent_Sig | logFC | AveExpr |
|---|---|---|---|---|---|
| 73 | 0.0000287855939384343 | 0.000742668 | 8.22 | 0.445873686 | 8.369941593 |
| 74 | 0.0000287855939384343 | 0.000742668 | 8.22 | 0.413519891 | 8.631292888 |
| 75 | 0.0000287855939384343 | 0.000742668 | 8.22 | 0.451423499 | 8.55317371 |
| 76 | 0.0000287855939384343 | 0.000742668 | 8.22 | −0.251896305 | 6.606225387 |
| 77 | 0.075709775 | 0.157525178 | 3.28 | 0.284071373 | 7.894826629 |
| 78 | 0.075709775 | 0.157525178 | 3.28 | 0.298147218 | 7.7720811 |
| 79 | 0.013845037 | 0.064041001 | 4.69 | −0.409059439 | 7.708930887 |
| 80 | 0.013845037 | 0.064041001 | 4.69 | −0.25346967 | 8.649906865 |
| 81 | 0.013845037 | 0.064041001 | 4.69 | 0.252289513 | 8.203650527 |
| 82 | 0.198752749 | 0.267074007 | 3.23 | −0.638663316 | 8.462246587 |
| 83 | 0.193928419 | 0.267074007 | 3.33 | −0.691447546 | 9.504132323 |
| 84 | 0.051914218 | 0.131312433 | 4.17 | 0.26396571 | 9.117422855 |
| 85 | 0.051914218 | 0.131312433 | 4.17 | 0.357277506 | 7.749299691 |
| 86 | 0.000137621 | 0.002219133 | 5.04 | −0.489675835 | 8.316954487 |
| 87 | 0.000137621 | 0.002219133 | 5.04 | −0.59449685 | 8.143398203 |
| 88 | 0.000137621 | 0.002219133 | 5.04 | −0.258158385 | 9.427438624 |
| 89 | 0.000137621 | 0.002219133 | 5.04 | −0.542091889 | 7.809236934 |
| 90 | 0.000137621 | 0.002219133 | 5.04 | −0.570549519 | 8.272773989 |
| 91 | 0.000137621 | 0.002219133 | 5.04 | −0.519347042 | 8.352346785 |
| 92 | 0.000137621 | 0.002219133 | 5.04 | −0.474046419 | 8.086674809 |
| 93 | 0.002335573 | 0.01673827 | 9.09 | 0.225177272 | 9.290490657 |
| 94 | 0.002335573 | 0.01673827 | 9.09 | 0.257141717 | 10.68770958 |
| 95 | 0.002335573 | 0.01673827 | 9.09 | 0.225607706 | 10.55701332 |
| 96 | 0.189010904 | 0.267074007 | 3.45 | 0.244602905 | 8.422577617 |
| 97 | 0.014290491 | 0.064041001 | 8.7 | 0.215926084 | 10.1135098 |
| 98 | 0.014290491 | 0.064041001 | 8.7 | 0.413805259 | 9.019249379 |
| 99 | 0.037378088 | 0.104821159 | 2.38 | 0.406030868 | 7.865506845 |
| 100 | 0.037378088 | 0.104821159 | 2.38 | 0.335540786 | 8.434376341 |
| 101 | 0.037378088 | 0.104821159 | 2.38 | 0.268362014 | 8.83590478 |
| 102 | 0.037378088 | 0.104821159 | 2.38 | −0.1949879 | 9.068498407 |
| 103 | 0.272436907 | 0.310300562 | 0.8 | 1.177347719 | 8.350585003 |
| 104 | 0.272436907 | 0.310300562 | 0.8 | 0.198636698 | 10.37949827 |
| 105 | 0.198752749 | 0.267074007 | 3.23 | −0.400257671 | 9.279193522 |
| 106 | 0.024599258 | 0.075554863 | 6.45 | −0.255902452 | 11.31369569 |
| 107 | 0.024599258 | 0.075554863 | 6.45 | −0.197532334 | 11.33660679 |
| 108 | 0.292341721 | 0.325104155 | 1.79 | −0.325806823 | 7.500438844 |
| 109 | 0.356204452 | 0.369972517 | 1.1 | −1.140777936 | 8.452195491 |
| 110 | 0.00071906 | 0.009275877 | 5.68 | −0.415749473 | 11.59733518 |
| 111 | 0.00071906 | 0.009275877 | 5.68 | −0.307210255 | 11.22897697 |
| 112 | 0.00071906 | 0.009275877 | 5.68 | −0.383777265 | 9.880520247 |
| 113 | 0.00071906 | 0.009275877 | 5.68 | −0.367375654 | 10.47600421 |
| 114 | 0.00071906 | 0.009275877 | 5.68 | −0.418188826 | 11.1638961 |
| 115 | 0.272492977 | 0.310300562 | 0.8 | 0.312761226 | 8.158780766 |
| 116 | 0.272492977 | 0.310300562 | 0.8 | 0.218475376 | 9.612836388 |
| 117 | 0.001955877 | 0.014841655 | 9.68 | −0.376092453 | 10.23852086 |
| 118 | 0.001955877 | 0.014841655 | 9.68 | −0.346076177 | 10.08178634 |
| 119 | 0.001955877 | 0.014841655 | 9.68 | −0.19700025 | 11.98270597 |
| 120 | 0.368643954 | 0.369972517 | 0.76 | 0.236007177 | 7.969612712 |
| 121 | 0.365777771 | 0.369972517 | 0.96 | −0.318530813 | 7.005872794 |
| 122 | 0.023201487 | 0.075554863 | 6.67 | −0.567555056 | 9.695872092 |
| 123 | 0.023201487 | 0.075554863 | 6.67 | −0.311003579 | 8.846166998 |
| 124 | 0.230471214 | 0.297307866 | 0.36 | 0.267534336 | 7.807343578 |
| 125 | 0.198752749 | 0.267074007 | 3.23 | −0.284488126 | 10.50098524 |
| 126 | 0.04181789 | 0.112385579 | 2.94 | 0.409504025 | 8.955642386 |
| 127 | 0.04181789 | 0.112385579 | 2.94 | 0.275378575 | 9.43472352 |
| 128 | 0.04181789 | 0.112385579 | 2.94 | 0.37672213 | 9.562492703 |

TABLE 33.b3

| N | t | P.Value | adj.P.Val | B | FC |
|---|---|---|---|---|---|
| 65 | 5.618655797 | 0.0000199272532249328 | 0.003966133 | 2.970358272 | 1.2673721 |
| 66 | −5.10596284 | 0.0000617052113463042 | 0.008329136 | 1.895072775 | 0.883733119 |
| 67 | −5.936420225 | 0.0000100379326708335 | 0.002463079 | 3.620955306 | 0.845482482 |
| 68 | −6.14157352 | 0.00000648983188875642 | 0.001782876 | 4.03379312 | 0.834943911 |
| 69 | −7.909652841 | 0.000000190517352509565 | 0.000176954 | 7.332040725 | 0.822166758 |
| 70 | −7.419021619 | 0.000000486229190399068 | 0.000327031 | 6.464905236 | 0.732753909 |
| 71 | 6.686410206 | 0.00000209248781498571 | 0.000822758 | 5.100834912 | 1.377899042 |
| 72 | 5.428175718 | 0.0000302276235200180 | 0.005000177 | 2.574299106 | 1.328711704 |
| 73 | 6.52733514 | 0.0000290021776169651 | 0.001037747 | 4.793822411 | 1.362138768 |
| 74 | 5.554618228 | 0.0000229132183097780 | 0.004269944 | 2.83769231 | 1.331931503 |
| 75 | 5.455049104 | 0.0000284949740889623 | 0.004832995 | 2.630436111 | 1.367388786 |
| 76 | −5.621056707 | 0.0000198233899082524 | 0.003965695 | 2.975322416 | 0.839791852 |
| 77 | 4.983263565 | 0.0000811872515612103 | 0.009898247 | 1.633703508 | 1.217626256 |
| 78 | 5.44278257 | 0.0000292728922433219 | 0.004943444 | 2.604822343 | 1.22956433 |

TABLE 33.b3-continued

| N | t | P.Value | adj.P.Val | B | FC |
|---|---|---|---|---|---|
| 79 | −5.983309313 | 0.00000908136757827868 | 0.002361761 | 3.715824347 | 0.753114204 |
| 80 | −5.190006848 | 0.0000511739465631575 | 0.007206844 | 2.073279303 | 0.838876496 |
| 81 | 5.71974371 | 0.0000160008558050293 | 0.003467741 | 3.178744012 | 1.191095848 |
| 82 | −6.403087538 | 0.00000375123437915977 | 0.001240133 | 4.551401529 | 0.642307783 |
| 83 | −10.26896099 | 0.0000000322944539582748 | 0.00000854970466866222 | 11.00157549 | 0.619232224 |
| 84 | 6.538599393 | 0.00000283363426460291 | 0.001033085 | 4.815686956 | 1.200774887 |
| 85 | 8.497455807 | 0.0000000646633050589555 | 0.000078597025797400 | 8.322263656 | 1.281006243 |
| 86 | −6.177261672 | 0.00000601894082752241 | 0.001701441 | 4.105008693 | 0.712185103 |
| 87 | −5.47299969 | 0.0000273945059932764 | 0.004693558 | 2.66788725 | 0.662275388 |
| 88 | −5.496015116 | 0.0000260468384551831 | 0.004515943 | 2.715850222 | 0.836154599 |
| 89 | −6.291593561 | 0.00000473366295565049 | 0.001465557 | 4.331932541 | 0.686774373 |
| 90 | −5.958739229 | 0.00000957033212471167 | 0.002438159 | 3.666149932 | 0.673360258 |
| 91 | −7.020935167 | 0.00000106498214760689 | 0.000532857 | 5.733942795 | 0.697687533 |
| 92 | −5.913971946 | 0.0000105319433085296 | 0.00255187 | 3.57543078 | 0.719942494 |
| 93 | 5.231815445 | 0.0000466369274249531 | 0.006813882 | 2.161666862 | 1.168920872 |
| 94 | 5.007912479 | 0.0000768248326803410 | 0.009606804 | 1.68631868 | 1.195108595 |
| 95 | 7.210365056 | 0.00000731398300322928 | 0.000419586 | 6.084829449 | 1.169269676 |
| 96 | 6.094643967 | 0.00000716734949527807 | 0.001955233 | 3.939871515 | 1.184766624 |
| 97 | 5.419049822 | 0.0000308369119963444 | 0.005054403 | 2.555318501 | 1.161449224 |
| 98 | 6.915832549 | 0.00000131460036416667 | 0.000596309 | 5.536873458 | 1.332194988 |
| 99 | 5.856598637 | 0.0000119111980213138 | 0.002765809 | 3.458771257 | 1.325035367 |
| 100 | 6.902941252 | 0.00000134913450281018 | 0.000598065 | 5.512585315 | 1.261850317 |
| 101 | 5.17067204 | 0.0000534219908481310 | 0.007416341 | 2.032343624 | 1.204439572 |
| 102 | −5.2490489 | 0.0000448882307553045 | 0.006607886 | 2.198047673 | 0.873580223 |
| 103 | 5.956066197 | 0.00000962513428218130 | 0.002438159 | 3.660740777 | 2.261606163 |
| 104 | 5.540348785 | 0.0000236388142881637 | 0.004367942 | 2.808062497 | 1.147613384 |
| 105 | −5.662792363 | 0.0000181039158418541 | 0.003741337 | 3.061500844 | 0.757722939 |
| 106 | −5.516430295 | 0.0000249082421012251 | 0.004416684 | 2.758342073 | 0.83746311 |
| 107 | −4.983217873 | 0.0000811955680862767 | 0.009898247 | 1.633605924 | 0.872040876 |
| 108 | −8.393742068 | 0.0000000779901777084671 | 0.000084511023122425 | 8.151353285 | 0.797852065 |
| 109 | −7.690570015 | 0.000000288337468652026 | 0.000248829 | 6.94943685 | 0.453514966 |
| 110 | −8.767490453 | 0.0000000399545356666192 | 0.000064942768181451 | 8.759712775 | 0.749629965 |
| 111 | −6.227343692 | 0.00000541666889080595 | 0.001588754 | 4.204641449 | 0.808203075 |
| 112 | −6.509359957 | 0.00000300983019700269 | 0.001051643 | 4.75889243 | 0.766428298 |
| 113 | −5.587701438 | 0.0000213173634345125 | 0.004137265 | 2.906293096 | 0.775191333 |
| 114 | −6.963670287 | 0.00000119423299606347 | 0.00057037 | 5.626780498 | 0.748363538 |
| 115 | 5.331375489 | 0.0000374132338335943 | 0.005860047 | 2.371409711 | 1.242082693 |
| 116 | 5.387261614 | 0.0000330749297047718 | 0.005266339 | 2.488673122 | 1.163503359 |
| 117 | −5.679474637 | 0.0000174600811226560 | 0.003701727 | 3.095886422 | 0.770521729 |
| 118 | −7.010703269 | 0.00000108696808120982 | 0.000532857 | 5.714832403 | 0.786720904 |
| 119 | −6.14332049 | 0.00000646592182931229 | 0.001782876 | 4.037283391 | 0.872362554 |
| 120 | 4.997714723 | 0.0000785999737756243 | 0.009703117 | 1.664557166 | 1.177728649 |
| 121 | −5.976961259 | 0.00000920518649817264 | 0.002378108 | 3.702998116 | 0.801886073 |
| 122 | −7.630840059 | 0.000000323183938483918 | 0.000262654 | 6.843838746 | 0.674759339 |
| 123 | −5.872236016 | 0.0000115178359047956 | 0.002706691 | 3.490611042 | 0.806080832 |
| 124 | 5.079901556 | 0.0000654007694396312 | 0.008590182 | 1.839673798 | 1.20374878 |
| 125 | −5.695385681 | 0.0000168678678005674 | 0.00361547 | 3.128649589 | 0.821032863 |
| 126 | 6.025225618 | 0.00000830560993803541 | 0.002174509 | 3.800377209 | 1.328229112 |
| 127 | 5.861408292 | 0.0000117887628752507 | 0.00275377 | 3.468567823 | 1.210311644 |
| 128 | 7.68141304 | 0.000000293415956096893 | 0.000248829 | 6.933283828 | 1.298388503 |

TABLE 33.b4

| N | FC_1 | LS | Loop Detected | Probe sequence 60 mer |
|---|---|---|---|---|
| 65 | 1.2673721 | 1 | Sprinter | ATTGAAATAAAAAAGTCAGTAGAAAAGATCGACAATAAAGACTATCAAGTATTGTACTAA (SEQ ID NO: 828) |
| 66 | −1.131563341 | −1 | Stayer | GCTGGGGCCATGTACATCCTGGGCACCATCGATAAGAAAACAAAATGCCTCAAAAGAAGT (SEQ ID NO: 829) |
| 67 | −1.182756616 | −1 | Stayer | GCCTTTCTCAAAACCCACTGTACACAGCTCGATTTTAATGGCTGCTTAATCTGAGTGGCT (SEQ ID NO: 830) |
| 68 | −1.197685243 | −1 | Stayer | GCCTTTCTCAAAACCCACTGTACACAGCTCGAGCCACCAGCTCATAAAGCCCCTGTGATC (SEQ ID NO: 831) |
| 69 | −1.216298263 | −1 | Stayer | TGAACAGTCAAGACTGGTGAGGAAGAATTCGAAGCCTATGCTGCCTTCCTGAAGCCTCCT (SEQ ID NO: 832) |
| 70 | −1.364714658 | 1 | Stayer | CGTGTACCTCACAGGGTTCTTCTAAAGATCGATGAGAACTTTTAAGATCTACTCTCTTAG (SEQ ID NO: 833) |

TABLE 33.b4-continued

| N | FC_1 | LS | Loop Detected | Probe sequence 60 mer |
|---|---|---|---|---|
| 71 | 1.377899042 | 1 | Sprinter | ATTTCTTGACAGCGTGAATTCTTTACCCTCGAGCTAAAAATTTCACAAATAAACTCATAA (SEQ ID NO: 834) |
| 72 | 1.328711704 | 1 | Sprinter | ATTTCTTGACAGCGTGAATTCTTTACCCTCGATTATCTACTTGCAGATAACCTTTTTTCC (SEQ ID NO: 835) |
| 73 | 1.362138768 | 1 | Sprinter | ATTTCTTGACAGCGTGAATTCTTTACCCTCGAGGTACATAGAAGTACTAAAATACACAAA (SEQ ID NO: 836) |
| 74 | 1.331931503 | 1 | Sprinter | ATTTCTTGACAGCGTGAATTCTTTACCCTCGAGAGAAGTCAGAAGAATCTCTGGTTACTT (SEQ ID NO: 837) |
| 75 | 1.367388786 | 1 | Sprinter | ATTTCTTGACAGCGTGAATTCTTTACCCTCGATGATATTTATCTGTGTCATTTTTAATAG (SEQ ID NO: 838) |
| 76 | -1.190771258 | -1 | Stayer | ATTCAAAAACACACAAGTACTATTAAATTCGAATCCTTGCAAAAATTTCTCTTTTGTTTA (SEQ ID NO: 839) |
| 77 | 1.217626256 | 1 | Sprinter | AAAAAAATCTGTTCAGCTAATTTCTAACTCGACAAAGCTCTGTATTCTTTTTTTTAATTG (SEQ ID NO: 840) |
| 78 | 1.22956433 | 1 | Sprinter | AAAAAAATCTGTTCAGCTAATTTCTAACTCGAATAAAGGATGGTTGGAAAAAAAATAAAT (SEQ ID NO: 841) |
| 79 | -1.327819863 | -1 | Stayer | TACAGCTCAGATCAAATTGTTCTCAGAATCGATTGTATCCTGTTGGTCTATACTTCTGTC (SEQ ID NO: 842) |
| 80 | -1.19207059 | -1 | Stayer | TACAGCTCAGATCAAATTGTTCTCAGAATCGAAATGCACCAAGAAAAAGACTGCTATGTA (SEQ ID NO: 843) |
| 81 | 1.191095848 | 1 | Sprinter | TTAAGCACTTAATTTTTTTTTCTTGTGTTCGATTGTATCCTGTTGGTCTATACTTCTGTC (SEQ ID NO: 844) |
| 82 | -1.556886007 | -1 | Stayer | TCTCTCTAGAGCTCCACGGAGTTCGCAGTCGACTAATAAAGTAGCATCAAAATATATAAG (SEQ ID NO: 845) |
| 83 | -1.614903039 | -1 | Stayer | CTGTGCGTATGTACAATTGTTTTAATCCTCGACAGACGCGGTACCCGACCAGGTTGTCAC (SEQ ID NO: 846) |
| 84 | 1.200774887 | 1 | Sprinter | AGTTATTGACTCAACAAACATTATTGACTCGATGTACACTCTGGCTAGACCAGGGCAGGA (SEQ ID NO: 847) |
| 85 | 1.281006243 | 1 | Sprinter | GAGATATATACAGCATTTTTTCAGAAAATCGAGAGCAAAGAGACACTGGTTGAAATGAGA (SEQ ID NO: 848) |
| 86 | -1.404129341 | -1 | Stayer | TAAAGAAACGTCTATGAAAATTCAAAACTCGAAACACAATAATATTTGTATTTGGCTGTT (SEQ ID NO: 849) |
| 87 | -1.509945889 | -1 | Stayer | TAAAGAAACGTCTATGAAAATTCAAAACTCGAAGATATAATTCCACTACTTTTGGCTTCT (SEQ ID NO: 850) |
| 88 | -1.195951086 | -1 | Stayer | TAAAGAAACGTCTATGAAAATTCAAAACTCGACAGCGCTAACAGCAACAAAAACAGTCAA (SEQ ID NO: 851) |
| 89 | -1.456082288 | -1 | Stayer | TAAAGAAACGTCTATGAAAATTCAAAACTCGAGTTGAGTTTGATGTTAATTTCGTAAAAT (SEQ ID NO: 852) |
| 90 | -1.48508913 | -1 | Stayer | TAAAGAAACGTCTATGAAAATTCAAAACTCGATTCTGTAAAATGAAAGCTTTTTCAGAG (SEQ ID NO: 853) |
| 91 | -1.433306392 | .1 | Stayer | TAAAGAAACGTCTATGAAAATTCAAAACTCGACAGTTATGTAAATCAAAGTATGAAGACA (SEQ ID NO: 854) |
| 92 | -1.388999827 | -1 | Stayer | TAAAGAAACGTCTATGAAAATTCAAAACTCGAGTCTTGAGTTTTAATGTAGATTAAGCCA (SEQ ID NO: 855) |
| 93 | 1.168920872 | 1 | Sprinter | CGGGCAAAAACTAGCTATTTAATATCTCTCGAGAGGGGCAGAATAAATGATCGCTAATGC (SEQ ID NO: 856) |
| 94 | 1.195108595 | 1 | Sprinter | GCATTAGCGATCATTTATTCTGCCCCTCTCGAAGACTCTGATGGTTTCTGGTTTGTTGAA (SEQ ID NO: 857) |
| 95 | 1.169269676 | 1 | Sprinter | GCATTAGCGATCATTTATTCTGCCCCTCTCGAGGTGGGGTTTTTCTTGCGCTTGCACTGT (SEQ ID NO: 858) |
| 96 | 1.184766624 | 1 | Sprinter | CTCCACTCATATGTGGAAATTAAACATGTCGATTCAGTTTTGATGGACGAGGTTCAGAGA (SEQ ID NO: 859) |

TABLE 33.b4-continued

| N | FC_1 | LS | Loop Detected | Probe sequence 60 mer |
|---|------|----|--------------|----------------------|
| 97 | 1.161449224 | 1 | Sprinter | TGTCTTCAATAAATTGTGTTGGGAAAATTCGAGTCCCTCCTACAACTCCACTTAATGGGG (SEQ ID NO: 860) |
| 98 | 1.332194988 | 1 | Sprinter | TGTCTTCAATAAATTGTGTTGGGAAAATTCGAAATGAGGGTTTCAATAGTTCAAAATTTT (SEQ ID NO: 861) |
| 99 | 1.325035367 | 1 | Sprinter | GAACGTGATGATGTAGTCTATACAGAAGTCGAAGTGAGACTTCTTCAAAAAAAGTTCACG (SEQ ID NO: 862) |
| 100 | 1.261850317 | 1 | Sprinter | GAACGTGATGATGTAGTCTATACAGAAGTCGAAGTTTCACACAATATTCTATTAACTCAC (SEQ ID NO: 863) |
| 101 | 1.204439572 | 1 | Sprinter | GAACGTGATGATGTAGTCTATACAGAAGTCGACTGAACACCACAATCCAACGGAAGTTCC (SEQ ID NO: 864) |
| 102 | -1.14471456 | -1 | Stayer | CAACGGCATGTTGGATGTACAAATGGGTTCGAATAGTTACCATCTGTAGTCTTGATCTCT (SEQ ID NO: 865) |
| 103 | 2.261606163 | 1 | Sprinter | AGAATTGGTAGGTATTGTAGTGATGTATTCGAAGATTGTTCATTATATCAAACCATGACA (SEQ ID NO: 866) |
| 104 | 1.147613384 | 1 | Sprinter | ACTGGAGACTAGGCAGAGGAAAAACCTTTCGAGACAATTTATGATCAGGAAAAATGGACC (SEQ ID NO: 867) |
| 105 | -1.319743601 | -1 | Stayer | AATATAGTACAGGAACATCTTAGATTCCTCGAGTTCACACAGCCAAGAATGATCCGATTT (SEQ ID NO: 868) |
| 106 | -1.194082447 | -1 | Stayer | GCTGCAGGAAGTGATGTCAAAAGGAGGGTCGAAAACTACCACATTTCCATTTCAGTTTAA (SEQ ID NO: 869) |
| 107 | -1.146735237 | -1 | Stayer | GCTGCAGGAAGTGATGTCAAAAGGAGGGTCGATCAGTGGTCAACCCTTGTAAGTTCATCA (SEQ ID NO: 870) |
| 108 | -1.253365184 | -1 | Stayer | TTCCTTCTCTGTACACAAAGAAGTGAACTCGACTGCATTAATTTTTCCTTTTGAAACAGT (SEQ ID NO: 871) |
| 109 | -2.204998899 | -1 | Stayer | GGGGCCAAGAGTAATGCTTCGTATATAGTCGAATTTCCACAAGTAATTTTGAATTTCAGG (SEQ ID NO: 872) |
| 110 | -1.333991499 | -1 | Stayer | GGTTAAGAGCAGAGCCTTTAAAATCAGATCGAGAGCCGCGAGTTATGAGCTCTCCGCCTT (SEQ ID NO: 873) |
| 111 | -1.237312788 | -1 | Stayer | AGAGTTTGGAGAAGGAAGTTGGTCTCCTTCGAGAGCCGCGAGTTATGAGCTCTCCGCCTT (SEQ ID NO: 874) |
| 112 | -1.304753494 | -1 | Stayer | ATGTATTTAAAAACATTTCTTGAAGGCCTCGAGAGCCGCGAGTTATGAGCTCTCCGCCTT (SEQ ID NO: 875) |
| 113 | -1.290004103 | -1 | Stayer | ACTTTTCATAGTTTCTCCTTCTAAACTCTCGAGAGCCGCGAGTTATGAGCTCTCCGCCTT (SEQ ID NO: 876) |
| 114 | -1.336248961 | -1 | Stayer | TTTAAGCTCTGAGTTAGTCTATTTTCTATCGAGAGCCGCGAGTTATGAGCTCTCCGCCTT (SEQ ID NO: 877) |
| 115 | 1.242082693 | 1 | Sprinter | AAAAGAAATTATAGAGTTAATTACCTCATCGATTTCTGTTTGGGATGTGACGTACAATTC (SEQ ID NO: 878) |
| 116 | 1.163503359 | 1 | Sprinter | TTGTATCATTAATTAGGGCTTTGAATGGTCGATTTCTGTTTGGGATGTGACGTACAATTC (SEQ ID NO: 879) |
| 117 | -1.297821933 | -1 | Stayer | TCATTCATGGGTGAGTTGGTACTTTTTCTCGATGCTCAAACAGTGTTTGCCAAGTGGATG (SEQ ID NO: 880) |
| 118 | -1.271098804 | -1 | Stayer | TCATTCATGGGTGAGTTGGTACTTTTTCTCGACCACCTGTATAGCTGTGAGGCCACTGGT (SEQ ID NO: 881) |
| 119 | -1.146312385 | 1 | Stayer | ATACCCACATTCTGACCCCCGAGTCAGCTCGACCACCTGTATAGCTGTGAGGCCACTGGT (SEQ ID NO: 882) |
| 120 | 1.177728649 | 1 | Sprinter | ACATCATTAGTCATTGTGGAAATACAAATCGAAGTGTTTTATTTTCAAGAGCAAAGGTTA (SEQ ID NO: 883) |
| 121 | -1.247059943 | 1 | Stayer | TGGGAGTACAGAGAAAATTCTATAAGATTCGAACATCCAGGGAATCCATATTTTCTTTTA (SEQ ID NO: 884) |

TABLE 33.b4-continued

| N | FC_1 | Loop LS Detected | Probe sequence 60 mer |
|---|---|---|---|
| 122 | -1.482009871 | -1 Stayer | TTCCGTGACTCAGAGCTGTTGGTACCTTTCGAGTGCATTGAATGAGATGTAAGTCATCAC (SEQ ID NO: 885) |
| 123 | -1.240570375 | 1 Stayer | TGGCCTCATAATTTTTCAATATGCTCAATCGATAATTTGCTGGAACAGCTCAGAGAACTC (SEQ ID NO: 886) |
| 124 | 1.20374878 | 1 Sprinter | CACAATGAAAATTTGAAAATATTTTGAGTCGAAAACAAAATATTGGTTTCACCTAAGATA (SEQ ID NO: 887) |
| 125 | -1.217978043 | -1 Stayer | CCGTTCACGGAAGAAGCGCAAGCCCTATTCGATCAGCTCTGGCGCCGTGGGGAGTGGAGC (SEQ ID NO: 888) |
| 126 | 1.328229112 | 1 Sprinter | ATGAGAGACTCCCATTAAAAATCGTGTCTCGATGATTTACAGGAAGGCATCAACTAAAAA (SEQ ID NO: 889) |
| 127 | 1.210311644 | 1 Sprinter | ATGAGAGACTCCCATTAAAAATCGTGTCTCGATGCAGAGCAGTGAATAATATGTGTGCAG (SEQ ID NO: 890) |
| 128 | 1.298388503 | 1 Sprinter | ATGAGAGACTCCCATTAAAAATCGTGTCTCGACACCAAGAACTGAACATCTATACTCTTC (SEQ ID NO: 891) |

TABLE 33.b5

| N | Probe Location | | | | 4 kb Sequence Location | | | |
|---|---|---|---|---|---|---|---|---|
| | Chr | Start1 | End1 | Start2 | End2 | Chr | Start1 | End1 | Start2 |
| 65 | 8 | 85390137 | 85390168 | 85431393 | 85431424 | 8 | 85390137 | 85394138 | 85431393 |
| 66 | 22 | 34961425 | 34961456 | 35009442 | 35009473 | 22 | 34957455 | 34961456 | 35005472 |
| 67 | 12 | 20785118 | 20785149 | 20922776 | 20922807 | 12 | 20785118 | 20789119 | 20918806 |
| 68 | 12 | 20843696 | 20843727 | 20922776 | 20922807 | 12 | 20843696 | 20847697 | 20918806 |
| 69 | 3 | 18959778 | 18959809 | 19074282 | 19074313 | 3 | 18959778 | 18959809 | 19070312 |
| 70 | 28 | 42579274 | 42579305 | 42607249 | 42607280 | 28 | 42579274 | 42583275 | 42607249 |
| 71 | 16 | 15151267 | 15151298 | 15203309 | 15203340 | 16 | 15147297 | 15151298 | 15199339 |
| 72 | 16 | 15151267 | 15151298 | 15264001 | 15264032 | 16 | 15147297 | 15151298 | 15260031 |
| 73 | 16 | 15151267 | 15151298 | 15255076 | 15255107 | 16 | 15147297 | 15151298 | 15255076 |
| 74 | 16 | 15151267 | 15151298 | 15301390 | 15301421 | 16 | 15147297 | 15151298 | 15301390 |
| 75 | 16 | 15151267 | 15151298 | 15332649 | 15332680 | 16 | 15147297 | 15151298 | 15328679 |
| 76 | 16 | 15165960 | 15165991 | 15239150 | 15239181 | 16 | 15165960 | 15169961 | 15235180 |
| 77 | 7 | 69179023 | 69179054 | 69225505 | 69225536 | 7 | 69179023 | 69183024 | 69221535 |
| 78 | 7 | 69225505 | 69225536 | 69328532 | 69328563 | 7 | 69221535 | 69225536 | 69328532 |
| 79 | 15 | 8888678 | 8888709 | 8973363 | 8973394 | 15 | 8884708 | 8888709 | 8973363 |
| 80 | 15 | 8888678 | 8888709 | 9032720 | 9032751 | 15 | 8884708 | 8888709 | 9028750 |
| 81 | 15 | 8936185 | 8936216 | 8973363 | 8973394 | 15 | 8936185 | 8940186 | 8973363 |
| 82 | 25 | 5777848 | 5777879 | 5838527 | 5838558 | 25 | 5777848 | 5781849 | 5838527 |
| 83 | 26 | 40666594 | 40666625 | 40680588 | 40680619 | 26 | 40666594 | 40670595 | 40680588 |
| 84 | 6 | 15299757 | 15299788 | 15377978 | 15378009 | 6 | 15299757 | 15303758 | 15374008 |
| 85 | 6 | 15443464 | 15443495 | 15487479 | 15487510 | 6 | 15439494 | 15443495 | 15487479 |
| 86 | 13 | 38904201 | 38904232 | 39195563 | 39195594 | 13 | 38904201 | 38908202 | 39191593 |
| 87 | 13 | 38931046 | 38931077 | 39195563 | 39195594 | 13 | 38931046 | 38935047 | 39191593 |
| 88 | 13 | 38974958 | 38974989 | 39195563 | 39195594 | 13 | 38974958 | 38978959 | 39191593 |
| 89 | 13 | 38981963 | 38981994 | 39195563 | 39195594 | 13 | 38981963 | 38985964 | 39191593 |
| 90 | 13 | 38999154 | 38999185 | 39195563 | 39195594 | 13 | 38999154 | 39003155 | 39191593 |
| 91 | 13 | 39073684 | 39073715 | 39195563 | 39195594 | 13 | 39073684 | 39077685 | 39191593 |
| 92 | 13 | 39112330 | 39112361 | 39195563 | 39195594 | 13 | 39112330 | 39116331 | 39191593 |
| 93 | 5 | 37768331 | 37768362 | 37808997 | 37809028 | 5 | 37768331 | 37772332 | 37805027 |
| 94 | 5 | 37768331 | 37768362 | 37803790 | 37803821 | 5 | 37768331 | 37772332 | 37803790 |
| 95 | 5 | 37768331 | 37768362 | 37834953 | 37834984 | 5 | 37768331 | 37772332 | 37834953 |
| 96 | 18 | 78530158 | 78530189 | 78600391 | 78600422 | 18 | 78526188 | 78530189 | 78600391 |
| 97 | 6 | 75012399 | 75012430 | 75092742 | 75092773 | 6 | 75012399 | 75016400 | 75092742 |
| 98 | 6 | 75012399 | 75012430 | 75098342 | 75098373 | 6 | 75012399 | 75016400 | 75098342 |
| 99 | 17 | 27888277 | 27888308 | 27983597 | 27983628 | 17 | 27888277 | 27892278 | 27983597 |
| 100 | 17 | 27888277 | 27888308 | 28023161 | 28023192 | 17 | 27888277 | 27892278 | 28023161 |
| 101 | 17 | 27888277 | 27888308 | 28087062 | 28087093 | 17 | 27888277 | 27892278 | 28087062 |
| 102 | 17 | 27991669 | 27991700 | 28044612 | 28044643 | 17 | 27987670 | 27991700 | 28040642 |
| 103 | 17 | 35244506 | 35244537 | 35523297 | 35523328 | 17 | 35244506 | 35248507 | 35523297 |
| 104 | 17 | 35555855 | 35555886 | 35584820 | 35584851 | 17 | 35551885 | 35555886 | 35584820 |
| 105 | 24 | 42597681 | 42597712 | 42656523 | 42656554 | 24 | 42593711 | 42597712 | 42652553 |
| 106 | 22 | 41633839 | 41633870 | 41882778 | 41882809 | 22 | 41633839 | 41637840 | 41878808 |
| 107 | 22 | 41845220 | 41845251 | 41882778 | 41882809 | 22 | 41845220 | 41849221 | 41878808 |
| 108 | 7 | 37223720 | 37223751 | 37244778 | 37244809 | 7 | 37223720 | 37227721 | 37244778 |
| 109 | 26 | 23335158 | 23335189 | 23360793 | 23360824 | 26 | 23335158 | 23339159 | 23360793 |
| 110 | 5 | 48256162 | 48256193 | 48407852 | 48407883 | 5 | 48252192 | 48256193 | 48407852 |
| 111 | 5 | 48248931 | 48248962 | 48407852 | 48407883 | 5 | 48248931 | 48252932 | 48407852 |

TABLE 33.b5-continued

| | Probe Location | | | | 4 kb Sequence Location | | | |
|---|---|---|---|---|---|---|---|---|
| N | Chr | Start1 | End1 | Start2 | End2 | Chr | Start1 | End1 | Start2 |
| 112 | 5 | 48265153 | 48265184 | 48407852 | 48407883 | 5 | 48261183 | 48265184 | 48407852 |
| 113 | 5 | 48306348 | 48306379 | 48407852 | 48407883 | 5 | 48302378 | 48306379 | 48407852 |
| 114 | 5 | 48370294 | 48370325 | 48407852 | 48407883 | 5 | 48370294 | 48374295 | 48407852 |
| 115 | 17 | 62037937 | 62037968 | 62292109 | 62292140 | 17 | 62033967 | 62037968 | 62292109 |
| 116 | 17 | 62167794 | 62167825 | 62292109 | 62292140 | 17 | 62163824 | 62167825 | 62292109 |
| 117 | 1 | 13016139 | 13016170 | 13161461 | 13161492 | 1 | 13012169 | 13016170 | 13161461 |
| 118 | 1 | 13016139 | 13016170 | 13213575 | 13213606 | 1 | 13012169 | 13016170 | 13209605 |
| 119 | 1 | 13139944 | 13139975 | 13213575 | 13213606 | 1 | 13135974 | 13139975 | 13209605 |
| 120 | 19 | 38827199 | 38827230 | 39055705 | 39055736 | 19 | 38827199 | 38831200 | 39055705 |
| 121 | 14 | 35404443 | 35404474 | 35458546 | 35458577 | 14 | 35404443 | 35408444 | 35458546 |
| 122 | 11 | 19330735 | 19330766 | 19434549 | 19434580 | 11 | 19330735 | 19334736 | 19434549 |
| 123 | 11 | 19378980 | 19379011 | 19494959 | 19494990 | 11 | 19375010 | 19379011 | 19490989 |
| 124 | 4 | 51008167 | 51008198 | 51111188 | 51111219 | 4 | 51008167 | 51012168 | 51107218 |
| 125 | 6 | 70794688 | 70794719 | 70820645 | 70820676 | 6 | 70794688 | 70798689 | 70816675 |
| 126 | 25 | 17093899 | 17093930 | 17175445 | 17175476 | 25 | 17089929 | 17093930 | 17171475 |
| 127 | 25 | 17093899 | 17093930 | 17167460 | 17167491 | 25 | 17089929 | 17093930 | 17167460 |
| 128 | 25 | 17093899 | 17093930 | 17209847 | 17209878 | 25 | 17089929 | 17093930 | 17205877 |

TABLE 33.b6

| N | 4 kb Sequence Location End2 | Probe | Primer ID-1 |
|---|---|---|---|
| 65 | 85435394 | CD226__8__85390137__85395670__85431393__85435046__RR | OBD RD043.257 |
| 66 | 35009473 | CD40__22__34955976__34961456__35003447__35009473__FF | OBD RD043.261 |
| 67 | 20922807 | CD5__12__20785118__20787274__20916990__20922807__RF | OBD RD043.265 |
| 68 | 20922807 | CD5__12__20843696__20847942__20916990__20922807__RF | OBD RD043.269 |
| 69 | 19074313 | CDH1__3__18955128__18959809__19065895__19074313__FF | OBD RD043.273 |
| 70 | 42611250 | CERK__28__42579274__42585201__42607249__42612447__RR | OBD RD043.277 |
| 71 | 15203340 | CHL1__16__15145284__15151298__15196227__15203340__FF | OBD RD043.281 |
| 72 | 15264032 | CHL1__16__15145284__15151298__15255076__15264032__FF | OBD RD043.285 |
| 73 | 15259077 | CHL1__16__15145284__15151298__15255076__15264032__FR | OBD RD043.289 |
| 74 | 15305391 | CHL1__16__15145284__15151298__15301390__15310795__FR | OBD RD043.293 |
| 75 | 15332680 | CHL1__16__15145284__15151298__15326701__15332680__FF | OBD RD043.297 |
| 76 | 15239181 | CHL1__16__15165960__15173124__15233430__15239181__RF | OBD RD043.301 |
| 77 | 69225536 | CHRDL2__7__69179023__69184961__69220436__69225536__RF | OBD RD043.305 |
| 78 | 69332533 | CHRDL2__7__69220436__69225536__69328532__69336827__FR | OBD RD043.309 |
| 79 | 8977364 | CHST10__15__8874159__8888709__8973363__8982576__FR | OBD RD043.313 |
| 80 | 9032751 | CHST10__15__8874159__8888709__9029805__9032751__FF | OBD RD043.317 |
| 81 | 8977364 | CHST10__15__8936185__8939355__8973363__8982576__RR | OBD RD043.321 |
| 82 | 5842528 | COL15A1__25__5777848__5781338__5838527__5844153__RR | OBD RD043.325 |
| 83 | 40684589 | COL18A1__26__40666594__40668538__40680588__40685271__RR | OBD RD043.329 |
| 84 | 15378009 | COL4A4__6__15299757__15310450__15375645__15378009__RF | OBD RD043.333 |
| 85 | 15491480 | COL4A4__6__15436171__15443495__15487479__15493934__FR | OBD RD043.337 |
| 86 | 39195594 | CREBBP__13__38904201__38905631__39179236__39195594__RF | OBD RD043.341 |
| 87 | 39195594 | CREBBP__13__38931046__38933583__39179236__39195594__RF | OBD RD043.345 |
| 88 | 39195594 | CREBBP__13__38974958__38977634__39179236__39195594__RF | OBD RD043.349 |
| 89 | 39195594 | CREBBP__13__38981963__38985123__39179236__39195594__RF | OBD RD043.353 |
| 90 | 39195594 | CREBBP__13__38999154__39003472__39179236__39195594__RF | OBD RD043.357 |
| 91 | 39195594 | CREBBP__13__39073684__39080240__39179236__39195594__RF | OBD RD043.361 |
| 92 | 39195594 | CREBBP__13__39112330__39113797__39179236__39195594__RF | OBD RD043.365 |
| 93 | 37809028 | CRP__5__37768331__37775673__37803790__37809028__RF | OBD RD043.369 |
| 94 | 37807791 | CRP__5__37768331__37775673__37803790__37809028__RR | OBD RD043.373 |
| 95 | 37838954 | CRP__5__37768331__37775673__37834953__37842330__RR | OBD RD043.377 |
| 96 | 78604392 | CTLA4__18__78522827__78530189__78600391__78604267__FR | OBD RD043.381 |
| 97 | 75096743 | DDIT3__6__75012399__75018811__75092742__75096887__RR | OBD RD043.385 |
| 98 | 75102343 | DDIT3__6__75012399__75018811__75098342__75106967__RR | OBD RD043.389 |
| 99 | 27987598 | DGKH__17__27888277__27893919__27983597__27991700__RR | OBD RD043.393 |
| 100 | 28027162 | DGKH__17__27888277__27893919__28023161__28030553__RR | OBD RD043.397 |
| 101 | 28091063 | DGKH__17__27888277__27893919__28087062__28095320__RR | OBD RD043.401 |
| 102 | 28044643 | DGKH__17__27983597__27991700__28038960__28044643__FF | OBD RD043.405 |
| 103 | 35527298 | DIAPH3__17__35244506__35247777__35523297__35543766__RR | OBD RD043.409 |
| 104 | 35588821 | DIAPH3__17__35550338__35555886__35584820__35594304__FR | OBD RD043.413 |
| 105 | 42656554 | DLK1__24__42596087__42597712__42651466__42656554__FF | OBD RD043.417 |
| 106 | 41882809 | DOK5__22__41633839__41639527__41876029__41882809__RF | OBD RD043.421 |
| 107 | 41882809 | DOK5__22__41845220__41849884__41876029__41882809__RF | OBD RD043.425 |
| 108 | 37248779 | ETS1__7__37223720__37228234__37244778__37252642__RR | OBD RD043.429 |
| 109 | 23364794 | GABPA__26__23335158__23338855__23360793__23370765__RR | OBD RD043.433 |
| 110 | 48411853 | GJA5__5__48248931__48256193__48407852__48413621__FR | OBD RD043.437 |
| 111 | 48411853 | GJA5__5__48248931__48256193__48407852__48413621__RR | OBD RD043.441 |
| 112 | 48411853 | GJA5__5__48256193__48265184__48407852__48413621__FR | OBD RD043.445 |
| 113 | 48411853 | GJA5__5__48297725__48306379__48407852__48413621__FR | OBD RD043.449 |

TABLE 33.b6-continued

| N | 4 kb Sequence Location End2 | Probe | Primer ID-1 |
|---|---|---|---|
| 114 | 48411853 | GJA5__5__48370294__48376643__48407852__48413621__RR | OBD RD043.453 |
| 115 | 62296110 | GPC5__17__62030628__62037968__62292109__62298602__FR | OBD RD043.457 |
| 116 | 62296110 | GPC5__17__62161244__62167825__62292109__62298602__FR | OBD RD043.461 |
| 117 | 13165462 | GRK5__1__13009800__13016170__13161461__13167914__FR | OBD RD043.465 |
| 118 | 13213606 | GRK5__1__13009800__13016170__13204085__13213606__FF | OBD RD043.469 |
| 119 | 13213606 | GRK5__1__13135627__13139975__13204085__13213606__FF | OBD RD043.473 |
| 120 | 39059706 | GSK3B__19__38827199__38835574__39055705__39060019__RR | OBD RD043.477 |
| 121 | 35462547 | HDAC3__14__35404443__35406152__35458546__35471150__RR | OBD RD043.481 |
| 122 | 19438550 | HDAC5__11__19330735__19336727__19434549__19441692__RR | OBD RD043.485 |
| 123 | 19494990 | HDAC5__11__19372111__19379011__19491838__19494990__FF | OBD RD043.489 |
| 124 | 51111219 | HDAC9__4__51008167__51021720__51107519__51111219__RF | OBD RD043.493 |
| 125 | 70820676 | HOXC6__6__70794688__70801196__70818032__70820676__RF | OBD RD043.497 |
| 126 | 17175476 | HSDL2__25__17089584__17093930__17167460__17175476__FF | OBD RD043.501 |
| 127 | 17171461 | HSDL2__25__17089584__17093930__17167460__17175476__FR | OBD RD043.505 |
| 128 | 17209878 | HSDL2__25__17089584__17093930__17197980__17209878__FF | OBD RD043.509 |

TABLE 33.b7

| N | Primer Sequence | Primer ID-2 | Primer Sequence |
|---|---|---|---|
| 65 | GTCAATGGAAGGAGGGAAATAATA (SEQ ID NO: 892) | OBD RD043.259 | TCTCAACAGAGGAGTAAGATGTAT (SEQ ID NO: 956) |
| 66 | CCTCGGACCTCTCTCGCTGATAC (SEQ ID NO: 893) | OBD RD043.263 | GCCGTCAGTATTGTTTGGCTGGC (SEQ ID NO: 957) |
| 67 | AGAACTGCTGGCAAGGGAGACAG (SEQ ID NO: 894) | OBD RD043.267 | ACACAGAGAGAGCCCCTCAGAGC (SEQ ID NO: 958) |
| 68 | AACTGCTGGCAAGGGAGACAGGG (SEQ ID NO: 895) | OBD RD043.271 | GACAAGGGAAGGACCGAAAAGCC (SEQ ID NO: 959) |
| 69 | AGCCTGAAGTGGGAACCAACCCC (SEQ ID NO: 896) | OBD RD043.275 | GACAAGGTGGAAAGGTAGGCACG (SEQ ID NO: 960) |
| 70 | ACTGTAAACCTGGGAACAACACCA (SEQ ID NO: 897) | OBD RD043.279 | AATAAGTCCTCGGGATGTAATGTA (SEQ ID NO: 961) |
| 71 | GGATGACCCTAACATTTCAGCAAACA (SEQ ID NO: 898) | OBD RD043.283 | CCTACAATCACCACAGGACCTCTCCA (SEQ ID NO: 962) |
| 72 | CTTTGCTCTTAGACCCTCCTTCCACA (SEQ ID NO: 899) & (SEQ ID NO: 900) | OBD RD043.287 | GGATAGGAACAAAGCAAGAATGATGT (SEQ ID NO: 963) |
| 73 | CTTTGCTCTTAGACCCTCCTTCCACA (SEQ ID NO: 899) & (SEQ ID NO: 900) | OBD RD043.291 | GAAGATAGTGGAATGCTTTTGGTGAC (SEQ ID NO: 964) |
| 74 | TGACCCTAACATTTCAGCAAACATTG (SEQ ID NO: 901) | OBD RD043.295 | CACTAACAGAGCATTTTCTTCAAGGA (SEQ ID NO: 965) |
| 75 | TGAAGGCAGGCTTTGTTCTATTTT (SEQ ID NO: 902) | OBD RD043.299 | TGAAGAATAAAACCCAGACCAAAA (SEQ ID NO: 966) |
| 76 | TTTGCTCTTAGACCCTCCTTCCACAT (SEQ ID NO: 903) | OBD RD043.303 | GCCGACCTTCTGAGATACTAACGGTG (SEQ ID NO: 967) |
| 77 | CTGTAGGTTCAACTTCTTATCAGTGC (SEQ ID NO: 904) | OBD RD043.307 | CAGTTGTTAGCCCAGGTGCCAAT (SEQ ID NO: 968) |
| 78 | CCCCTGTAGGTTCAACTTCTTATCAG (SEQ ID NO: 905) | OBD RD043.311 | CCGTTTCCTACCAGTGTGACTACCAG (SEQ ID NO: 969) |
| 79 | GTGAGCACAGAGTGAGAGAATCATCT (SEQ ID NO: 906) & (SEQ ID NO: 907) | OBD RD043.315 | GCAGTCCCTATGAGAAACCCAGC (SEQ ID NO: 970) & (SEQ ID NO: 972) |
| 80 | GTGAGCACAGAGTGAGAGAATCATCT (SEQ ID NO: 906) & (SEQ ID NO: 907) | OBD RD043.319 | CAAATCTGGTGATAAATCCGCATCCA (SEQ ID NO: 971) |
| 81 | AGGGAGGCTCACGCTGGCAGTAA (SEQ ID NO: 908) | OBD RD043.323 | GCAGTCCCTATGAGAAACCCAGC (SEQ ID NO: 970) & (SEQ ID NO: 972) |
| 82 | GTCAGCAACCATCATTATTTCCTA (SEQ ID NO: 909) | OBD RD043.327 | TGTTACTCCGATACTGCTTTCTTA (SEQ ID NO: 973) |

TABLE 33.b7-continued

| N | Primer Sequence | Primer ID-2 | Primer Sequence |
|---|---|---|---|
| 83 | GACTCCGCTGGCTCATCTCCTTC (SEQ ID NO: 910) | OBD RD043.331 | GGACTTGCCCTCGGTGTTTTGTG (SEQ ID NO: 974) |
| 84 | GGCATACTGTCGTGTCTCAGGAG (SEQ ID NO: 911) | OBD RD043.335 | CCTCCTCTCCCTTCTGCCATCAG (SEQ ID NO: 975) |
| 85 | CACTCGTGGCATTGAAACCAAAGTCT (SEQ ID NO: 912) | OBD RD043.339 | AGTCTGTCTTCACTAACGATGGC (SEQ ID NO: 976) |
| 86 | CTGACCTGCTCCCCAGTGAAACT (SEQ ID NO: 913) & (SEQ ID NO: 914) & (SEQ ID NO: 915) & (SEQ ID NO: 916) & (SEQ ID NO: 917) & (SEQ ID NO: 919) | OBD RD043.343 | TCCCTTTTCCTGCCTCCCTCCCC (SEQ ID NO: 977) |
| 87 | CTGACCTGCTCCCCAGTGAAACT (SEQ ID NO: 913) & (SEQ ID NO: 914) & (SEQ ID NO: 915) & (SEQ ID NO: 916) & (SEQ ID NO: 917) & (SEQ ID NO: 919) | OBD RD043.347 | GACAGTGGTCTCCTTCTTACCTG (SEQ ID NO: 978) |
| 88 | CTGACCTGCTCCCCAGTGAAACT (SEQ ID NO: 913) & (SEQ ID NO: 914) & (SEQ ID NO: 915) & (SEQ ID NO: 916) & (SEQ ID NO: 917) & (SEQ ID NO: 919) | OBD RD043.351 | CAGGGACAATCACTTCTAAACACTAA (SEQ ID NO: 979) |
| 89 | CTGACCTGCTCCCCAGTGAAACT (SEQ ID NO: 913) & (SEQ ID NO: 914) & (SEQ ID NO: 915) & (SEQ ID NO: 916) & (SEQ ID NO: 917) & (SEQ ID NO: 919) | OBD RD043.355 | GTTTTGTTGACTTCTCACCAGCAAGA (SEQ ID NO: 980) |
| 90 | CTGACCTGCTCCCCAGTGAAACT (SEQ ID NO: 913) & (SEQ ID NO: 914) & (SEQ ID NO: 915) & (SEQ ID NO: 916) & (SEQ ID NO: 917) & (SEQ ID NO: 919) | OBD RD043.359 | ATCCACACAGAAGTTAGGGCTGC (SEQ ID NO: 981) |
| 91 | ATGCTGACCTGCTCCCCAGTGAA (SEQ ID NO: 918) | OBD RD043.363 | AGGAAGAGCAGCACCAGGCACCT (SEQ ID NO: 982) |
| 92 | CTGACCTGCTCCCCAGTGAAACT (SEQ ID NO: 913) & (SEQ ID NO: 914) & (SEQ ID NO: 915) & (SEQ ID NO: 916) & (SEQ ID NO: 917) & (SEQ ID NO: 919) | OBD RD043.367 | CCACATTTCTCACTTCAGGTAAGC (SEQ ID NO: 983) |
| 93 | GGAGAAAGCAACCAATGAACGGAAGA (SEQ ID NO: 920) | OBD RD043.371 | GATTTCCCTCTGTCCTGCCTCAATGC (SEQ ID NO: 984) |
| 94 | TTCCCTCTGTCCTGCCTCAATGC (SEQ ID NO: 921) | OBD RD043.375 | CAAGCGGAGAGAGACGACACTGC (SEQ ID NO: 985) |
| 95 | GTGCGGTCACAAGAATCTCTAATACG (SEQ ID NO: 922) | OBD RD043.379 | CTTTCCGCACCCTCTGAACTTTTGGG (SEQ ID NO: 986) |
| 96 | GTGAAATAAGCCAGATAGAGAAAGAC (SEQ ID NO: 923) | OBD RD043.383 | GAGCGAAAGAACGGATGAAGCATTTT (SEQ ID NO: 987) |
| 97 | TAGAGAGCCCAGAAATAAATCCAT (SEQ ID NO: 924) | OBD RD043.387 | CAGGACCATCAAGATAAATGAATA (SEQ ID NO: 988) |
| 98 | GAATAGAGAGCCCAGAAATAAATCCA (SEQ ID NO: 925) | OBD RD043.391 | TGGAGGAAGGGAGCCAGGACCCC (SEQ ID NO: 989) |
| 99 | GCGACACCTCCTCTGTTGCCAAG (SEQ ID NO: 926) | OBD RD043.395 | GCACCACTGGCAGAGTTTACGGT (SEQ ID NO: 990) |
| 100 | TACAGAGAACAGATTGGTGGTCAC (SEQ ID NO: 927) & (SEQ ID NO: 928) & (SEQ ID NO: 929) | OBD RD043.399 | CTGGAGAAAAGGAGTATGGAGAAT (SEQ ID NO: 991) |
| 101 | TACAGAGAACAGATTGGTGGTCAC (SEQ ID NO: 927) & (SEQ ID NO: 928) & (SEQ ID NO: 929) | OBD RD043.403 | AAGGCTTTTATGTGAACAGAGATA (SEQ ID NO: 992) |
| 102 | TACAGAGAACAGATTGGTGGTCAC (SEQ ID NO: 927) & (SEQ ID NO: 928) & (SEQ ID NO: 929) | OBD RD043.407 | GAAATAAAGTCAATCTTCCTGAAAA (SEQ ID NO: 993) |
| 103 | CACTGCCACAAAAGCCGCTCTGG (SEQ ID NO: 930) | OBD RD043.411 | CACTGACTACACGGAAGATGGCG (SEQ ID NO: 994) |
| 104 | GAAAGATGCCCAGTCTGTGTCGGAGA (SEQ ID NO: 931) | OBD RD043.415 | TTTTGACCAGCAGATAGTGTCGTGTC (SEQ ID NO: 995) |
| 105 | TGGAGTAAGACGCCGAAAACACT (SEQ ID NO: 932 | OBD RD043.419 | GGGCACTCTGGATTGAGACAGTA (SEQ ID NO: 996) |
| 106 | AGGAGTCCCTGCCCTCGGAATCT (SEQ ID NO: 933) & (SEQ ID NO: 934) | OBD RD043.423 | GCTTCCCAGAACCCAAATCTCCC (SEQ ID NO: 997) |

TABLE 33.b7-continued

| N | Primer Sequence | Primer ID-2 | Primer Sequence |
|---|-----------------|-------------|-----------------|
| 107 | AGGAGTCCCTGCCCTCGGAATCT (SEQ ID NO: 933) & (SEQ ID NO: 934) | OBD RD043.427 | CTTCCGATGGACGAATCTCAGGC (SEQ ID NO: 998) |
| 108 | GCAGGGAGTCAGTCATTTTGTTTCTC (SEQ ID NO: 935) | OBD RD043.431 | CCCTCCAATGAAAGTAGTCTGCCTGC (SEQ ID NO: 999) |
| 109 | TTATCTTCTTTACCTACATTCCAGGG (SEQ ID NO: 936) | OBD RD043.435 | TGGGCACAAAGGGTGAAGTGGTG (SEQ ID NO: 1000) |
| 110 | ACTTACAAACCCAATCACTACATA (SEQ ID NO: 937) | OBD RD043.439 | GGAAGACCAGAGAACAGAACTGAT (SEQ ID NO: 1001) & (SEQ ID NO: 1002) & (SEQ ID NO: 1003) & (SEQ ID NO: 1004) & (SEQ ID NO: 1005) |
| 111 | AATCTATTCCCACTCACCTCTGG (SEQ ID NO: 938) | OBD RD043.443 | GGAAGACCAGAGAACAGAACTGAT (SEQ ID NO: 1001) & (SEQ ID NO: 1002) & (SEQ ID NO: 1003) & (SEQ ID NO: 1004) & (SEQ ID NO: 1005) |
| 112 | GAATAGGTCCTTTTGTTTTGTTTT (SEQ ID NO: 939) | OBD RD043.447 | GGAAGACCAGAGAACAGAACTGAT (SEQ ID NO: 1001) & (SEQ ID NO: 1002) & (SEQ ID NO: 1003) & (SEQ ID NO: 1004) & (SEQ ID NO: 1005) |
| 113 | ACGGAAGCAGAATGGAGAGTGGG (SEQ ID NO: 940) | OBD RD043.451 | GGAAGACCAGAGAACAGAACTGAT (SEQ ID NO: 1001) & (SEQ ID NO: 1002) & (SEQ ID NO: 1003) & (SEQ ID NO: 1004) & (SEQ ID NO: 1005) |
| 114 | CCCAAGTGCTGCTTCTATTTCCT (SEQ ID NO: 941) | OBD RD043.455 | GGAAGACCAGAGAACAGAACTGAT (SEQ ID NO: 1001) & (SEQ ID NO: 1002) & (SEQ ID NO: 1003) & (SEQ ID NO: 1004) & (SEQ ID NO: 1005) |
| 115 | TCCCAGATTCTACCCTTGACCCTCAT (SEQ ID NO: 942) | OBD RD043.459 | GACCTCAACAGAAAGTCCTCAACAGG (SEQ ID NO: 1006) |
| 116 | GGATGAGTTCTAAATGAATAATGA (SEQ ID NO: 943) | OBD RD043.463 | CCTCAACAGAAAGTCCTCAACAGG (SEQ ID NO: 1007) |
| 117 | ATTGAGTGGCTGGCGGTCACGGT (SEQ ID NO: 944) | OBD RD043.467 | GGTCCTGCTCTATCTTTCCCCTC (SEQ ID NO: 1008) |
| 118 | TTATTGAGTGGCTGGCGGTCACG (SEQ ID NO: 945) | OBD RD043.471 | AGGGCTTCAGCAGGCAGAGGGAT (SEQ ID NO: 1009) |
| 119 | GGTGGCAAAAGCCCCAAGAGAATGAG (SEQ ID NO: 946) | OBD RD043.475 | GGTAACTTGAAATAAGCCACAGAGGG (SEQ ID NO: 1010) |
| 120 | GGCAAAGGACTTGAAAAGACATTT (SEQ ID NO: 947) | OBD RD043.479 | TTGAAGTTTACCAGGAGAGGAAAA (SEQ ID NO: 1011) |
| 121 | GAGGATTGGCAGCAGATGTTAGC (SEQ ID NO: 948) | OBD RD043.483 | GGAGATGAAAGACAATGGATGAGATA (SEQ ID NO: 1012) |
| 122 | CCCTACCAGGCTCAGATGGGATT (SEQ ID NO: 949) | OBD RD043.487 | CCTGCCTCCCCTCACAACACACA (SEQ ID NO: 1013) |
| 123 | CCCAGGACCCAGGTTTTCTTACC (SEQ ID NO: 950) | OBD RD043.491 | CTCGCCCTGTGTAGCACCTCTCT (SEQ ID NO: 1014) |
| 124 | TGTGCCCATCTTCCTCTACTTTAT (SEQ ID NO: 951) | OBD RD043.495 | TCCAACATTGCTTTACTCTTATGA (SEQ ID NO: 1015) |
| 125 | CCCTACTGGTTCATCTCCACCCA (SEQ ID NO: 952) | OBD RD043.499 | GCCGCTTCCACCCAGGACAGTAA (SEQ ID NO: 1016) |
| 126 | CCCCTCTCCAGCAGTTTTGAGTAATA (SEQ ID NO: 953) | OBD RD043.503 | CTGACACTGAGCACAGGGTTTGGAAG (SEQ ID NO: 1017) |

TABLE 33.b7-continued

| N | Primer Sequence | Primer ID-2 | Primer Sequence |
|---|---|---|---|
| 127 | GCCCCTCTCCAGCAGTTTTGAGTAAT (SEQ ID NO: 954) | OBD RD043.507 | GAGAGAAGCCACCAAGATAAGTCCAC (SEQ ID NO: 1018) |
| 128 | CCCTCTCCAGCAGTTTTGAGTAA (SEQ ID NO: 955) | OBD RD043.511 | CTTTGTTTACCTGGCATCTTGAGTCA (SEQ ID NO: 1019) |

TABLE 33.b8

| N | Probe | Marker |
|---|---|---|
| 65 | CD226 | OBD RD043.257.259 |
| 66 | CD40 | OBD RD043.261.263 |
| 67 | CD5 | OBD RD043.265.267 |
| 68 | CD5 | OBD RD043.269.271 |
| 69 | CDH1 | OBD RD043.273.275 |
| 70 | CERK | OBD RD043.277.279 |
| 71 | CHL1 | OBD RD043.281.283 |
| 72 | CHL1 | OBD RD043.285.287 |
| 73 | CHL1 | OBD RD043.289.291 |
| 74 | CHL1 | OBD RD043.293.295 |
| 75 | CHL1 | OBD RD043.297.299 |
| 76 | CHL1 | OBD RD043.301.303 |
| 77 | CHRDL2 | OBD RD043.305.307 |
| 78 | CHRDL2 | OBD RD043.309.311 |
| 79 | CHST10 | OBD RD043.313.315 |
| 80 | CHST10 | OBD RD043.317.319 |
| 81 | CHST10 | OBD RD043.321.323 |
| 82 | COL15A1 | OBD RD043.325.327 |
| 83 | COL18A1 | OBD RD043.329.331 |
| 84 | COL4A4 | OBD RD043.333.335 |
| 85 | COL4A4 | OBD RD043.337.339 |
| 86 | CREBBP | OBD RD043.341.343 |
| 87 | CREBBP | OBD RD043.345.347 |
| 88 | CREBBP | OBD RD043.349.351 |
| 89 | CREBBP | OBD RD043.353.355 |
| 90 | CREBBP | OBD RD043.357.359 |
| 91 | CREBBP | OBD RD043.361.363 |
| 92 | CREBBP | OBD RD043.365.367 |
| 93 | CRP | OBD RD043.369.371 |
| 94 | CRP | OBD RD043.373.375 |
| 95 | CRP | OBD RD043.377.379 |
| 96 | CTLA4 | OBD RD043.381.383 |
| 97 | DDIT3 | OBD RD043.385.387 |

TABLE 33.b8-continued

| N | Probe | Marker |
|---|---|---|
| 98 | DDIT3 | OBD RD043.389.391 |
| 99 | DGKH | OBD RD043.393.395 |
| 100 | DGKH | OBD RD043.397.399 |
| 101 | DGKH | OBD RD043.401.403 |
| 102 | DGKH | OBD RD043.405.407 |
| 103 | DIAPH3 | OBD RD043.409.411 |
| 104 | DIAPH3 | OBD RD043.413.415 |
| 105 | DLK1 | OBD RD043.417.419 |
| 106 | DOK5 | OBD RD043.421.423 |
| 107 | DOK5 | OBD RD043.425.427 |
| 108 | ETS1 | OBD RD043.429.431 |
| 109 | GABPA | OBD RD043.433.435 |
| 110 | GJA5 | OBD RD043.437.439 |
| 111 | GJA5 | OBD RD043.441.443 |
| 112 | GJA5 | OBD RD043.445.447 |
| 113 | GJA5 | OBD RD043.449.451 |
| 114 | GJA5 | OBD RD043.453.455 |
| 115 | GPC5 | OBD RD043.457.459 |
| 116 | GPC5 | OBD RD043.461.463 |
| 117 | GRK5 | OBD RD043.465.467 |
| 118 | GRK5 | OBD RD043.469.471 |
| 119 | GRK5 | OBD RD043.473.475 |
| 120 | GSK3B | OBD RD043.477.479 |
| 121 | HDAC3 | OBD RD043.481.483 |
| 122 | HDAC5 | OBD RD043.485.487 |
| 123 | HDAC5 | OBD RD043.489.491 |
| 124 | HDAC9 | OBD RD043.493.495 |
| 125 | HOXC6 | OBD RD043.497.499 |
| 126 | HSDL2 | OBD RD043.501.503 |
| 127 | HSDL2 | OBD RD043.505.507 |
| 128 | HSDL2 | OBD RD043.509.511 |

TABLE 33.c1

| N | Probe | GeneLocus | Probe_Count_Total | Probe_Count_Sig |
|---|---|---|---|---|
| 129 | IGF1_28_26127450_26135782_26165074_26175137_FF | IGF1 | 1 | 83 |
| 130 | IL17F_20_49908438_49915179_49992351_49998114_RR | IL17F | 1 | 23 |
| 131 | IL1R1_15_7480700_7491275_7547275_7554471_FR | IL1R1 | 1 | 34 |
| 132 | IL1RAP_19_27981648_27987302_28153765_28161424_FR | IL1RAP | 3 | 212 |
| 133 | IL1RAP_19_28069654_28081538_28153765_28161424_FR | IL1RAP | 3 | 212 |
| 134 | IL1RAP_19_28153765_28161424_28173183_28182762_RR | IL1RAP | 3 | 212 |
| 135 | IL21R_13_20649899_20654880_20738447_20749797_FF | IL21R | 1 | 43 |
| 136 | IL6ST_21_16316515_16320787_16507936_16519953_RF | IL6ST | 5 | 74 |
| 137 | IL6ST_21_16361905_16367133_16507936_16519953_RF | IL6ST | 5 | 74 |
| 138 | IL6ST_21_16380568_16382969_16507936_16519953_FF | IL6ST | 5 | 74 |
| 139 | IL6ST_21_16389402_16396020_16507936_16519953_RF | IL6ST | 5 | 74 |
| 140 | IL6ST_21_16427757_16430421_16507936_16519953_FF | IL6ST | 5 | 74 |
| 141 | IPMK_1_47907514_47915619_47934069_47940539_RF | IPMK | 1 | 49 |
| 142 | KCND3_5_56337143_56347199_56370847_56374140_RF | KCND3 | 2 | 315 |
| 143 | KCND3_5_56337143_56347199_56514669_56519275_RF | KCND3 | 2 | 315 |
| 144 | KCNE2_26_30910971_30912196_30981829_30991799_FF | KCNE2 | 2 | 53 |
| 145 | KCNE2_26_30910971_30912196_30981829_30991799_FR | KCNE2 | 2 | 53 |
| 146 | KCNH2_4_102471847_102478321_102526070_102533652_RF | KCNH2 | 1 | 31 |
| 147 | KCNJ2_11_10875120_10880378_10941535_10945829_RF | KCNJ2 | 2 | 24 |
| 148 | KCNJ2_11_10907501_10914338_10941535_10945829_RF | KCNJ2 | 2 | 24 |
| 149 | KDM1A_2_31709535_31721093_31731426_31738065_RR | KDM1A | 8 | 105 |
| 150 | KDM1A_2_31709535_31721093_31749361_31751529_RR | KDM1A | 8 | 105 |
| 151 | KDM1A_2_31709535_31721093_31757482_31759922_RR | KDM1A | 8 | 105 |
| 152 | KDM1A_2_31709535_31721093_31759922_31772142_RR | KDM1A | 8 | 105 |
| 153 | KDM1A_2_31709535_31721093_31779719_31783168_RR | KDM1A | 8 | 105 |
| 154 | KDM1A_2_31709535_31721093_31795486_31798526_RR | KDM1A | 8 | 105 |

TABLE 33.c1-continued

| N | Probe | GeneLocus | Probe__Count__Total | Probe__Count__Sig |
|---|---|---|---|---|
| 155 | KDM1A__2__31709535__31721093__31816722__31820715__RR | KDM1A | 8 | 105 |
| 156 | KDM1A__2__31709535__31721093__31841824__31843977__RR | KDM1A | 8 | 105 |
| 157 | LAMA2__10__75419882__75421720__75481925__75491582__FF | LAMA2 | 33 | 325 |
| 158 | LAMA2__10__75419882__75421720__75481925__75491582__FR | LAMA2 | 33 | 325 |
| 159 | LAMA2__10__75419882__75421720__75481925__75491582__RR | LAMA2 | 33 | 325 |
| 160 | LAMA2__10__75433825__75441819__75481925__75491582__RR | LAMA2 | 33 | 325 |
| 161 | LAMA2__10__75481925__75491582__75503397__75505438__RF | LAMA2 | 33 | 325 |
| 162 | LAMA2__10__75481925__75491582__75503397__75505438__RR | LAMA2 | 33 | 325 |
| 163 | LAMA2__10__75481925__75491582__75510267__75513025__RR | LAMA2 | 33 | 325 |
| 164 | LAMA2__10__75481925__75491582__75515462__75518504__RF | LAMA2 | 33 | 325 |
| 165 | LAMA2__10__75481925__75491582__75515462__75518504__RR | LAMA2 | 33 | 325 |
| 166 | LAMA2__10__75481925__75491582__75537867__75543336__RR | LAMA2 | 33 | 325 |
| 167 | LAMA2__10__75481925__75491582__75558780__75560310__RR | LAMA2 | 33 | 325 |
| 168 | LAMA2__10__75481925__75491582__75583879__75585705__RF | LAMA2 | 33 | 325 |
| 169 | LAMA2__10__75481925__75491582__75583879__75585705__RR | LAMA2 | 33 | 325 |
| 170 | LAMA2__10__75481925__75491582__75598703__75603065__RR | LAMA2 | 33 | 325 |
| 171 | LAMA2__10__75481925__75491582__75630159__75632019__RR | LAMA2 | 33 | 325 |
| 172 | LAMA2__10__75481925__75491582__75657275__75659989__RF | LAMA2 | 33 | 325 |
| 173 | LAMA2__10__75481925__75491582__75657275__75659989__RR | LAMA2 | 33 | 325 |
| 174 | LAMA2__10__75481925__75491582__75673465__75680786__RF | LAMA2 | 33 | 325 |
| 175 | LAMA2__10__75481925__75491582__75673465__75680786__RR | LAMA2 | 33 | 325 |
| 176 | LAMA2__10__75481925__75491582__75689296__75698651__RF | LAMA2 | 33 | 325 |
| 177 | LAMA2__10__75481925__75491582__75689296__75698651__RR | LAMA2 | 33 | 325 |
| 178 | LAMA2__10__75481925__75491582__75699217__75700676__RR | LAMA2 | 33 | 325 |
| 179 | LAMA2__10__75481925__75491582__75710114__75711790__RF | LAMA2 | 33 | 325 |
| 180 | LAMA2__10__75481925__75491582__75710114__75711790__RR | LAMA2 | 33 | 325 |
| 181 | LAMA2__10__75481925__75491582__75727142__75730779__RR | LAMA2 | 33 | 325 |
| 182 | LAMA2__10__75481925__75491582__75731193__75737098__RF | LAMA2 | 33 | 325 |
| 183 | LAMA2__10__75481925__75491582__75731193__75737098__RR | LAMA2 | 33 | 325 |
| 184 | LAMA2__10__75481925__75491582__75761081__75765848__RR | LAMA2 | 33 | 325 |
| 185 | LAMA2__10__75481925__75491582__75767487__75769615__RF | LAMA2 | 33 | 325 |
| 186 | LAMA2__10__75481925__75491582__75772669__75776905__RR | LAMA2 | 33 | 325 |
| 187 | LAMA2__10__75481925__75491582__75789669__75791964__RF | LAMA2 | 33 | 325 |
| 188 | LAMA2__10__75985731__76002512__76077151__76079817__FF | LAMA2 | 33 | 325 |
| 189 | LAMA2__10__75985731__76002512__76077151__76079817__RF | LAMA2 | 33 | 325 |
| 190 | LDB2__3__106480842__106484500__106716847__106728445__RR | LDB2 | 2 | 196 |
| 191 | LDB2__3__106716847__106728445__106944178__106947885__RF | LDB2 | 2 | 196 |
| 192 | LEPR__5__95193431__95200537__95211956__95218723__RR | LEPR | 1 | 31 |

TABLE 33.c2

| N | HyperG__Stats | FDR__HyperG |
|---|---|---|
| 129 | 0.346998557 | 0.36994061 |
| 130 | 0.157480479 | 0.267074007 |
| 131 | 0.212678487 | 0.282840462 |
| 132 | 0.154850013 | 0.267074007 |
| 133 | 0.154850013 | 0.267074007 |
| 134 | 0.154850013 | 0.267074007 |
| 135 | 0.249797286 | 0.310300562 |
| 136 | 0.00033129 | 0.004748485 |
| 137 | 0.00033129 | 0.004748485 |
| 138 | 0.00033129 | 0.004748485 |
| 139 | 0.00033129 | 0.004748485 |
| 140 | 0.00033129 | 0.004748485 |
| 141 | 0.270953196 | 0.310300562 |
| 142 | 0.253289491 | 0.310300562 |
| 143 | 0.253289491 | 0.310300562 |
| 144 | 0.060873696 | 0.137915817 |
| 145 | 0.060873696 | 0.137915817 |
| 146 | 0.198752749 | 0.267074007 |
| 147 | 0.015462469 | 0.066488616 |
| 148 | 0.015462469 | 0.066488616 |
| 149 | 0.00000240079898941557 | 0.000103234 |
| 150 | 0.00000240079898941557 | 0.000103234 |
| 151 | 0.00000240079898941557 | 0.000103234 |
| 152 | 0.00000240079898941557 | 0.000103234 |
| 153 | 0.00000240079898941557 | 0.000103234 |
| 154 | 0.00000240079898941557 | 0.000103234 |
| 155 | 0.00000240079898941557 | 0.000103234 |
| 156 | 0.00000240079898941557 | 0.000103234 |
| 157 | 0.0000000000000000000000000050961641335098 | 0.0000000000000000000000000657405173222766 |
| 158 | 0.0000000000000000000000000050961641335098 | 0.0000000000000000000000000657405173222766 |
| 159 | 0.0000000000000000000000000050961641335098 | 0.0000000000000000000000000657405173222766 |
| 160 | 0.0000000000000000000000000050961641335098 | 0.0000000000000000000000000657405173222766 |

TABLE 33.c2-continued

| N | HyperG_Stats | FDR_HyperG |
|---|---|---|
| 161 | 0.00000000000000000000000000509616413350981 | 0.00000000000000000000000000657405173222766 |
| 162 | 0.00000000000000000000000000509616413350981 | 0.00000000000000000000000000657405173222766 |
| 163 | 0.00000000000000000000000000509616413350981 | 0.00000000000000000000000000657405173222766 |
| 164 | 0.00000000000000000000000000509616413350981 | 0.00000000000000000000000000657405173222766 |
| 165 | 0.00000000000000000000000000509616413350981 | 0.00000000000000000000000000657405173222766 |
| 166 | 0.00000000000000000000000000509616413350981 | 0.00000000000000000000000000657405173222766 |
| 167 | 0.00000000000000000000000000509616413350981 | 0.00000000000000000000000000657405173222766 |
| 168 | 0.00000000000000000000000000509616413350981 | 0.00000000000000000000000000657405173222766 |
| 169 | 0.00000000000000000000000000509616413350981 | 0.00000000000000000000000000657405173222766 |
| 170 | 0.00000000000000000000000000509616413350981 | 0.00000000000000000000000000657405173222766 |
| 171 | 0.00000000000000000000000000509616413350981 | 0.00000000000000000000000000657405173222766 |
| 172 | 0.00000000000000000000000000509616413350981 | 0.00000000000000000000000000657405173222766 |
| 173 | 0.00000000000000000000000000509616413350981 | 0.00000000000000000000000000657405173222766 |
| 174 | 0.00000000000000000000000000509616413350981 | 0.00000000000000000000000000657405173222766 |
| 175 | 0.00000000000000000000000000509616413350981 | 0.00000000000000000000000000657405173222766 |
| 176 | 0.00000000000000000000000000509616413350981 | 0.00000000000000000000000000657405173222766 |
| 177 | 0.00000000000000000000000000509616413350981 | 0.00000000000000000000000000657405173222766 |
| 178 | 0.00000000000000000000000000509616413350981 | 0.00000000000000000000000000657405173222766 |
| 179 | 0.00000000000000000000000000509616413350981 | 0.00000000000000000000000000657405173222766 |
| 180 | 0.00000000000000000000000000509616413350981 | 0.00000000000000000000000000657405173222766 |
| 181 | 0.00000000000000000000000000509616413350981 | 0.00000000000000000000000000657405173222766 |
| 182 | 0.00000000000000000000000000509616413350981 | 0.00000000000000000000000000657405173222766 |
| 183 | 0.00000000000000000000000000509616413350981 | 0.00000000000000000000000000657405173222766 |
| 184 | 0.00000000000000000000000000509616413350981 | 0.00000000000000000000000000657405173222766 |
| 185 | 0.00000000000000000000000000509616413350981 | 0.00000000000000000000000000657405173222766 |
| 186 | 0.00000000000000000000000000509616413350981 | 0.00000000000000000000000000657405173222766 |
| 187 | 0.00000000000000000000000000509616413350981 | 0.00000000000000000000000000657405173222766 |
| 188 | 0.00000000000000000000000000509616413350981 | 0.00000000000000000000000000657405173222766 |
| 189 | 0.00000000000000000000000000509616413350981 | 0.00000000000000000000000000657405173222766 |
| 190 | 0.260903936 | 0.310300562 |
| 191 | 0.260903936 | 0.310300562 |
| 192 | 0.198752749 | 0.267074007 |

TABLE 33.c3

| N | Percent_Sig | logFC | AveExpr | t | P.Value |
|---|---|---|---|---|---|
| 129 | 1.2 | −0.25974584 | 9.184771261 | −5.05789465 | 0.0000686965968072954 |
| 130 | 4.35 | −0.42286988 | 9.795885578 | −8.986284737 | 0.000000027231627824 2442 |
| 131 | 2.94 | −0.285238748 | 8.475210157 | −5.003309015 | 0.0000776210585910804 |
| 132 | 1.42 | −0.233297428 | 7.917147257 | −5.063868868 | 0.0000677854972204880 |
| 133 | 1.42 | −0.261678217 | 7.906642716 | −7.35841864 | 0.00000547113238929680 |
| 134 | 1.42 | −0.247346127 | 10.12235567 | −6.078434637 | 0.00000741791913423433 |
| 135 | 2.33 | −0.504771054 | 9.843131031 | −10.25775021 | 0.0000000328750499948560 |
| 136 | 6.76 | −0.416415403 | 12.34496702 | −5.613648976 | 0.0000201456451707163 |
| 137 | 6.76 | −0.426151333 | 12.51889676 | −5.249917488 | 0.0000448018862245979 |
| 138 | 6.76 | −0.23353917 | 12.44377995 | −5.538440914 | 0.0000237375958014509 |
| 139 | 6.76 | −0.411700512 | 12.62002559 | −5.185430873 | 0.0000516971247274845 |
| 140 | 6.76 | −0.223557802 | 11.04467508 | −5.194995118 | 0.0000506097781533960 |
| 141 | 2.04 | 0.248972748 | 9.763034476 | 5.472372277 | 0.0000274322269039290 |
| 142 | 0.63 | −0.826874049 | 9.755934263 | −11.64073761 | 0.0000000000403131843228993 |
| 143 | 0.63 | −0.188752779 | 9.124965652 | −5.134174071 | 0.0000579439468653047 |
| 144 | 3.77 | −0.263863415 | 9.389840285 | −5.665269959 | 0.0000180067783076360 |
| 145 | 3.77 | −0.277105906 | 9.211949107 | −5.081146529 | 0.0000652192037780800 |
| 146 | 3.23 | −0.350022028 | 11.18568763 | −6.168156484 | 0.00000613563582584375 |
| 147 | 8.33 | 0.694351653 | 8.391007916 | 7.96791572 | 0.00000170820887322144 |
| 148 | 8.33 | 0.461719332 | 8.783986871 | 6.236727656 | 0.00000531090520632885 |
| 149 | 7.62 | −0.734667206 | 8.882775953 | −7.565318365 | 0.00000366470308028 7362 |
| 150 | 7.62 | −0.260872283 | 10.51288503 | −6.881875363 | 0.00000140759853742685 |
| 151 | 7.62 | −0.302726916 | 10.11606951 | −5.433872607 | 0.0000298515328569823 |
| 152 | 7.62 | −0.53472543 | 9.308125792 | −11.46362698 | 0.0000000000521792977583466 |
| 153 | 7.62 | −0.364206415 | 9.729541969 | −6.308264284 | 0.00000457138115916845 |
| 154 | 7.62 | −0.460314357 | 9.475119298 | −7.40716807 | 0.00000497560114213970 |
| 155 | 7.62 | −0.621721431 | 8.876491488 | −7.539008509 | 0.00000385508372459963 |
| 156 | 7.62 | −0.47363865 | 9.446359898 | −7.234458458 | 0.000000697508104712342 |
| 157 | 10.15 | −0.501711845 | 10.09895493 | −8.589317091 | 0.00000054837363418 2702 |
| 158 | 10.15 | −0.428220161 | 13.02189528 | −7.167747421 | 0.00000795580379158680 |
| 159 | 10.15 | −0.339941253 | 12.88803216 | −5.561186413 | 0.0000225869301073419 |
| 160 | 10.15 | −0.228417033 | 13.56928534 | −5.920840322 | 0.0000103781975494252 |
| 161 | 10.15 | −0.30207162 | 13.37620496 | −5.439499489 | 0.0000294847593610427 |
| 162 | 10.15 | −0.39204058 | 13.89495223 | −5.801140554 | 0.0000134209610425670 |
| 163 | 10.15 | −0.343069197 | 13.96715152 | −6.417777669 | 0.00000363844975130824 |
| 164 | 10.15 | −0.354475767 | 13.22017743 | −5.259160113 | 0.0000438935269293937 |
| 165 | 10.15 | −0.446958091 | 13.8037429 | −5.840868856 | 0.0000123208089585518 |
| 166 | 10.15 | −0.379960986 | 13.89492979 | −6.236715524 | 0.00000531104056573792 |

TABLE 33.c3-continued

| N | Percent_Sig | logFC | AveExpr | t | P.Value |
|---|---|---|---|---|---|
| 167 | 10.15 | −0.449915255 | 13.94340659 | −9.137780656 | 0.000000209555895296964 |
| 168 | 10.15 | −0.356701022 | 12.87002792 | −5.553163982 | 0.0000229861111463834 |
| 169 | 10.15 | −0.428629599 | 13.82169896 | −6.617643858 | 0.00000240861706096913 |
| 170 | 10.15 | −0.419629634 | 13.93664391 | −8.158999079 | 0.000000119804038144258 |
| 171 | 10.15 | −0.430573855 | 13.96364886 | −8.446068963 | 0.0000000709422502038841 |
| 172 | 10.15 | −0.256004051 | 13.24896441 | −5.56584902 | 0.0000223581954829190 |
| 173 | 10.15 | −0.41467922 | 14.1640228 | −7.07939174 | 0.000000947891998878803 |
| 174 | 10.15 | −0.331716046 | 12.41203838 | −4.98917938 | 0.0000801177911327344 |
| 175 | 10.15 | −0.393636052 | 13.86311599 | −5.696573254 | 0.0000168245001760445 |
| 176 | 10.15 | −0.33697792 | 12.45047432 | −5.039670375 | 0.0000715536819400699 |
| 177 | 10.15 | −0.43042349 | 13.94505376 | −5.895952776 | 0.0000109465097531085 |
| 178 | 10.15 | −0.417317056 | 13.83868121 | −7.743329932 | 0.00000260799615293896 |
| 179 | 10.15 | −0.349687395 | 12.88984807 | −6.592764316 | 0.0000253479528084738 |
| 180 | 10.15 | −0.401014761 | 13.96210217 | −5.511317857 | 0.0000251885049881526 |
| 181 | 10.15 | −0.376700577 | 13.82296798 | −7.462445086 | 0.00000446952562820082 |
| 182 | 10.15 | −0.361735429 | 12.82385418 | −5.647753484 | 0.0000187051686375902 |
| 183 | 10.15 | −0.384425532 | 13.87283328 | −5.612599396 | 0.0000201917366403219 |
| 184 | 10.15 | −0.481052786 | 13.9255892 | −9.4062159 | 0.0000000132641985345548 |
| 185 | 10.15 | −0.302151184 | 13.18318606 | −5.156392006 | 0.0000551467689003870 |
| 186 | 10.15 | −0.362843331 | 14.28924283 | −6.234521481 | 0.00000533557766392404 |
| 187 | 10.15 | −0.346934118 | 12.83387771 | −5.572053104 | 0.0000220575120754949 |
| 188 | 10.15 | −0.387765562 | 8.971457443 | −8.562458613 | 0.0000000575383157451633 |
| 189 | 10.15 | −0.346223991 | 10.11461327 | −6.659629102 | 0.00000221017993365992 |
| 190 | 1.02 | −0.479413897 | 9.999705501 | −7.255881323 | 0.00000668739609939400 |
| 191 | 1.02 | −0.24620165 | 9.243513309 | −5.088361737 | 0.0000641770071013719 |
| 192 | 3.23 | 0.414997972 | 6.542688969 | 7.586596983 | 0.000000351791539018826 |

TABLE 33.c4

| N | adj.P.Val | B | FC | FC_1 | LS | Loop Detected |
|---|---|---|---|---|---|---|
| 129 | 0.00881531 | 1.792843727 | 0.83523505 | −1.197267763 | −1 | Stayer |
| 130 | 0.000048275438684640 | 9.106256241 | 0.745939288 | −1.340591675 | −1 | Stayer |
| 131 | 0.00961269 | 1.676496246 | 0.820605797 | −1.218611912 | −1 | Stayer |
| 132 | 0.008756001 | 1.805561135 | 0.850688333 | −1.17551865 | −1 | Stayer |
| 133 | 0.00033823 | 6.355209789 | 0.834117067 | −1.198872484 | −1 | Stayer |
| 134 | 0.002009535 | 3.907359412 | 0.842444688 | −1.18702155 | −1 | Stayer |
| 135 | 0.00000854970466866222 | 10.98597877 | 0.704772211 | −1.418898169 | −1 | Stayer |
| 136 | 0.0039679 | 2.96000383 | 0.749284025 | −1.334607395 | −1 | Stayer |
| 137 | 0.006607886 | 2.199880493 | 0.744244555 | −1.343644361 | −1 | Stayer |
| 138 | 0.004367942 | 2.804099038 | 0.8505458 | −1.17571564 | −1 | Stayer |
| 139 | 0.007221168 | 2.063594435 | 0.751736775 | −1.330252866 | −1 | Stayer |
| 140 | 0.007179227 | 2.083834368 | 0.856450753 | −1.167609458 | −1 | Stayer |
| 141 | 0.004693558 | 2.666578884 | 1.188360657 | 1.188360657 | 1 | Sprinter |
| 142 | 0.0000262102886739384 | 12.79107546 | 0.563749421 | −1.773837743 | −1 | Stayer |
| 143 | 0.00875935 | 1.954968861 | 0.877363882 | −1.139777943 | −1 | Stayer |
| 144 | 0.003741337 | 3.066609893 | 0.832854617 | −1.200689748 | −1 | Stayer |
| 145 | 0.008590182 | 1.842321715 | 0.825244826 | −1.211761611 | −1 | Stayer |
| 146 | 0.001721951 | 4.086856496 | 0.784572118 | −1.274580088 | −1 | Stayer |
| 147 | 0.00016253 | 7.432545616 | 1.61815707 | 1.61815707 | 1 | Sprinter |
| 148 | 0.001576825 | 4.223269904 | 1.377182098 | 1.377182098 | 1 | Sprinter |
| 149 | 0.000274925 | 6.727366085 | 0.600956635 | −1.664013578 | −1 | Stayer |
| 150 | 0.000606823 | 5.472840867 | 0.834583161 | −1.198202944 | −1 | Stayer |
| 151 | 0.004995541 | 2.58620654 | 0.810718564 | −1.233473667 | −1 | Stayer |
| 152 | 0.00000265148685080001 | 12.57279103 | 0.690290038 | −1.448666422 | −1 | Stayer |
| 153 | 0.001426637 | 4.364862947 | 0.776896105 | −1.287173398 | −1 | Stayer |
| 154 | 0.00032898 | 6.443494308 | 0.726827869 | −1.375841575 | −1 | Stayer |
| 155 | 0.000283749 | 6.680410031 | 0.649895007 | −1.538710083 | −1 | Stayer |
| 156 | 0.000406116 | 6.129060869 | 0.720146011 | −1.388607289 | −1 | Stayer |
| 157 | 0.000076400198105240 | 8.472295113 | 0.706268254 | −1.415892608 | −1 | Stayer |
| 158 | 0.000449791 | 6.006370737 | 0.743178071 | −1.345572533 | −1 | Stayer |
| 159 | 0.004245102 | 2.851322566 | 0.790073483 | −1.265705053 | −1 | Stayer |
| 160 | 0.002530334 | 3.5893669 | 0.853570941 | −1.171548787 | −1 | Stayer |
| 161 | 0.004957761 | 2.597963987 | 0.81108689 | −1.23291353 | −1 | Stayer |
| 162 | 0.003061706 | 3.345590015 | 0.76205098 | −1.312248165 | −1 | Stayer |
| 163 | 0.001213128 | 4.580182501 | 0.788362361 | −1.268452237 | −1 | Stayer |
| 164 | 0.006535445 | 2.219378577 | 0.782153803 | −1.27852092 | −1 | Stayer |
| 165 | 0.002843993 | 3.426710531 | 0.733587982 | −1.363163008 | −1 | Stayer |
| 166 | 0.001576825 | 4.223245828 | 0.768458371 | −1.301306665 | −1 | Stayer |
| 167 | 0.000038927502264450 | 9.342123058 | 0.73208585 | −1.365960017 | −1 | Stayer |
| 168 | 0.004269944 | 2.834673761 | 0.780948316 | −1.28049447 | −1 | Stayer |
| 169 | 0.000894859 | 4.968583134 | 0.742967187 | −1.345954461 | −1 | Stayer |
| 170 | 0.000119835 | 7.758516636 | 0.747616527 | −1.337584128 | −1 | Stayer |
| 171 | 0.000081395799425103 | 8.23778519 | 0.741966597 | −1.347769567 | −1 | Stayer |
| 172 | 0.004245102 | 2.860995205 | 0.837404136 | −1.19416654 | −1 | Stayer |

TABLE 33.c4-continued

| N | adj.P.Val | B | FC | FC_1 | LS | Loop Detected |
|---|---|---|---|---|---|---|
| 173 | 0.000513573 | 5.842814484 | 0.750186279 | −1.333002254 | −1 | Stayer |
| 174 | 0.009828286 | 1.64633615 | 0.794590778 | −1.258509447 | −1 | Stayer |
| 175 | 0.00361547 | 3.131093689 | 0.761208696 | −1.313700179 | −1 | Stayer |
| 176 | 0.009092212 | 1.754029209 | 0.791697982 | −1.26310793 | −1 | Stayer |
| 177 | 0.002605462 | 3.538839183 | 0.742043933 | −1.347629103 | −1 | Stayer |
| 178 | 0.0002366 | 7.042253477 | 0.748815885 | −1.335441756 | −1 | Stayer |
| 179 | 0.000932852 | 4.920559418 | 0.784754121 | −1.274284484 | −1 | Stayer |
| 180 | 0.00443021 | 2.747705761 | 0.757325409 | −1.320436351 | −1 | Stayer |
| 181 | 0.000311021 | 6.543154484 | 0.770197007 | −1.298369106 | −1 | Stayer |
| 182 | 0.003840466 | 3.030472673 | 0.77822788 | −1.284970669 | −1 | Stayer |
| 183 | 0.0039679 | 2.957832836 | 0.766083985 | −1.305339909 | −1 | Stayer |
| 184 | 0.000025871819241649 | 9.751972552 | 0.716454611 | −1.395761832 | −1 | Stayer |
| 185 | 0.007628636 | 2.002085961 | 0.81104216 | −1.232981526 | −1 | Stayer |
| 186 | 0.001576825 | 4.21889148 | 0.777630478 | −1.285957827 | −1 | Stayer |
| 187 | 0.004238737 | 2.873861568 | 0.786253196 | −1.271854925 | −1 | Stayer |
| 188 | 0.000077398955076511 | 8.4285593 | 0.764312451 | −1.308365444 | −1 | Stayer |
| 189 | 0.000837079 | 5.049414099 | 0.786640303 | −1.271229043 | −1 | Stayer |
| 190 | 0.000395266 | 6.168314166 | 0.717268959 | −1.394177159 | −1 | Stayer |
| 191 | 0.008515459 | 1.857664798 | 0.843113258 | −1.18608027 | −1 | Stayer |
| 192 | 0.000270685 | 6.765264284 | 1.333296803 | 1.333296803 | 1 | Sprinter |

TABLE 33.c5

| | Probe sequence | Probe Location | |
|---|---|---|---|
| N | 60 mer | Chr | Start1 |
| 129 | TTCCTTCATCATTTGTTATTTCCTCTGTTCGAATAGGGCTGAACCAATGGCCATACACAC (SEQ ID NO: 1020) | 28 | 26135751 |
| 130 | GAGGCCCATTGCAGGTACTTGGGCTGCATCGATTATCCCACTACACAGGATTTATATAAG (SEQ ID NO: 1021) | 20 | 49908438 |
| 131 | CCAGACTGAATTTTGTACAGAGTACACCTCGAAGTAATCTGACTTTAAAATGGTTCTTTT (SEQ ID NO: 1022) | 15 | 7491244 |
| 132 | TGGTAAGTGTATTATATAAGAAAAAAACTCGATCCTCTAATCCTGAATACCAGGTTGGGC (SEQ ID NO: 1023) | 19 | 27987271 |
| 133 | TTGCATTCATTCTTTTGCAGAAACATACTCGATCCTCTAATCCTGAATACCAGGTTGGGC (SEQ ID NO: 1024) | 19 | 28081507 |
| 134 | GCCCAACCTGGTATTCAGGATTAGAGGATCGAGAAGCCAGGCATGAATTCTGGTGTTTGC (SEQ ID NO: 1025) | 19 | 28153765 |
| 135 | CTCGTCAGTACTCTCAGTGTTTCCTCATTCGATCACTTTGGACATTTTAACAGCACTAAG (SEQ ID NO: 1026) | 13 | 20654849 |
| 136 | TCTTGCCCGAAGGCAGAGAGCTCAGAACTCGAAGTGAGCAGGATTTATTGAATAACAGAA (SEQ ID NO: 1027) | 21 | 16316515 |
| 137 | TCTTGCCCGAAGGCAGAGAGCTCAGAACTCGAACACTCTTGTTCTGCTTCCTCATCACTT (SEQ ID NO: 1028) | 21 | 16361905 |
| 138 | TTGCTTGGGTTTATGATTTTGTGCGGGGTCGAGTTCTGAGCTCTCTGCCTTCGGGCAAGA (SEQ ID NO: 1029) | 21 | 16382938 |
| 139 | TCTTGCCCGAAGGCAGAGAGCTCAGAACTCGAGCTGCTGCAGTCATTTTGTCACCATACA (SEQ ID NO: 1030) | 21 | 16389402 |
| 140 | CTGTCTAGTATCTTAAAATTGACATGGATCGAGTTCTGAGCTCTCTGCCTTCGGGCAAGA (SEQ ID NO: 1031) | 21 | 16430390 |
| 141 | AGTCTATCCAATTACAGTAATTTAAGCTTCGAGAGCCTGTGGTCTAAGAAAGAGTGAGAG (SEQ ID NO: 1032) | 1 | 47907514 |
| 142 | CCTTAGTACCTGCTTAGTACCCGCTTTGTCGAAGCAAAAGCAATTACCACCCCCAGCTTT (SEQ ID NO: 1033) | 5 | 56337143 |
| 143 | TAAAAACACATTTACAGTGCCACTGTACTCGAAGCAAAAGCAATTACCACCCCCAGCTTT (SEQ ID NO: 1034) | 5 | 56337143 |
| 144 | GACCTCCCTTACAGTACCTGCAGACTTGTCGATGAACTCCCACTCCAGTGGTGAGAAACC (SEQ ID NO: 1035) | 26 | 30912165 |

TABLE 33.c5-continued

| | Probe sequence | Probe Location | |
|---|---|---|---|
| N | 60 mer | Chr | Start1 |
| 145 | GACCTCCCTTACAGTACCTGCAGACTTGTCGAGTTCCCATATGGGCAGTATGTAGGGCAC<br>(SEQ ID NO: 1036) | 26 | 30912165 |
| 146 | TAATTCTCTGTAGTGAATCCCTTCCTGATCGAGGGGGCATCACAGAGTCAAAGGCAGCGA<br>(SEQ ID NO: 1037) | 4 | 102471847 |
| 147 | GGAATATAATCTAACACCGTGTAACCATTCGACTCCAAATAAACTGAATACAGAAAGTTT<br>(SEQ ID NO: 1038) | 11 | 10875120 |
| 148 | GGAATATAATCTAACACCGTGTAACCATTCGAAAATTTTGAAACAATTCCTCTGCCATTT<br>(SEQ ID NO: 1039) | 11 | 10907501 |
| 149 | GGTACTAGATGACGTAGTCCGATAAGATTCGATTTCCCCATCTGTAAAATGTTTTCTTTG<br>(SEQ ID NO: 1040) | 2 | 31709535 |
| 150 | GGTACTAGATGACGTAGTCCGATAAGATTCGACACAAATCCCCCTGCTACTGTTTAATTC<br>(SEQ ID NO: 1041) | 2 | 31709535 |
| 151 | GGTACTAGATGACGTAGTCCGATAAGATTCGAAAAGTTCTGCCAGTCCTCCACTTACAGC<br>(SEQ ID NO: 1042) | 2 | 31709535 |
| 152 | GGTACTAGATGACGTAGTCCGATAAGATTCGAAACCCGAAATAAAATTCTTACCCTGGCT<br>(SEQ ID NO: 1043) | 2 | 31709535 |
| 153 | GGTACTAGATGACGTAGTCCGATAAGATTCGAGTTCCAATTCCTTAGCCTGGTAACCAAG<br>(SEQ ID NO: 1044) | 2 | 31709535 |
| 154 | GGTACTAGATGACGTAGTCCGATAAGATTCGACAACATTCTGGTGTGACTGTGAATGAGC<br>(SEQ ID NO: 1045) | 2 | 31709535 |
| 155 | GGTACTAGATGACGTAGTCCGATAAGATTCGACTCTGCAGAGTTCTCACTACTCCGCTTG<br>(SEQ ID NO: 1046) | 2 | 31709535 |
| 156 | GGTACTAGATGACGTAGTCCGATAAGATTCGATTGGTTTGGCTGTTCTTGATCCGTTTAC<br>(SEQ ID NO: 1047) | 2 | 31709535 |
| 157 | AAACTGCCTCATAGGTTTCTTGTGAGGATCGAAAAAGATGCTTGATATGATTTCACTCTT<br>(SEQ ID NO: 1048) | 10 | 75421689 |
| 158 | AAACTGCCTCATAGGTTTCTTGTGAGGATCGATGATGTTAGTGGTTGTAGTGGCTCTTTG<br>(SEQ ID NO: 1049) | 10 | 75421689 |
| 159 | GCAATGTGCTATACTGCAGATTCTAAACTCGATGATGTTAGTGGTTGTAGTGGCTCTTTG<br>(SEQ ID NO: 1050) | 10 | 75419882 |
| 160 | CTAGAGCTCTGGAGGCCCTGCTGACGGCTCGATGATGTTAGTGGTTGTAGTGGCTCTTTG<br>(SEQ ID NO: 1051) | 10 | 75433825 |
| 161 | AAGACTAATTCTGGGCTGTGCCAATTGGTCGATGATGTTAGTGGTTGTAGTGGCTCTTTG<br>(SEQ ID NO: 1052) | 10 | 75481925 |
| 162 | CAAAGAGCCACTACAACCACTAACATCATCGAATTTTTGGAAGGCTTGTTATTTGGAAGA<br>(SEQ ID NO: 1053) | 10 | 75481925 |
| 163 | CAAAGAGCCACTACAACCACTAACATCATCGAAAAGTTGCAATCATGCTTAATACATAAT<br>(SEQ ID NO: 1054) | 10 | 75481925 |
| 164 | CAAGAGAAGACAACATTTATCTGTTATGTCGATGATGTTAGTGGTTGTAGTGGCTCTTTG<br>(SEQ ID NO: 1055) | 10 | 75481925 |
| 165 | CAAAGAGCCACTACAACCACTAACATCATCGAGAGAAGCATTTTCCTTTGTTTCTATCTC<br>(SEQ ID NO: 1056) | 10 | 75481925 |
| 166 | CAAAGAGCCACTACAACCACTAACATCATCGATGCTTCTGTGGGATAAAAAGTGTAGTTC<br>(SEQ ID NO: 1057) | 10 | 75481925 |
| 167 | CAAAGAGCCACTACAACCACTAACATCATCGATAGGAGGCAACTATTAAGAAAGGGCTTT<br>(SEQ ID NO: 1058) | 10 | 75481925 |
| 168 | TGATACTTTAAAAAATTTTTTTAAATGATCGATGATGTTAGTGGTTGTAGTGGCTCTTTG<br>(SEQ ID NO: 1059) | 10 | 75481925 |
| 169 | CAAAGAGCCACTACAACCACTAACATCATCGAAGTGTTTAGTGAGAGAATCTTTTTTCTT<br>(SEQ ID NO: 1060) | 10 | 75481925 |

TABLE 33.c5-continued

| | Probe sequence | Probe Location | |
|---|---|---|---|
| N | 60 mer | Chr | Start1 |
| 170 | CAAAGAGCCACTACAACCACTAACATCATCGATGTGGAGAATAGCCCATCTTGCTCATTT (SEQ ID NO: 1061) | 10 | 75481925 |
| 171 | CAAAGAGCCACTACAACCACTAACATCATCGAAGGTAGAGAGAGAATGCTCTGGGGATGA (SEQ ID NO: 1062) | 10 | 75481925 |
| 172 | TTTTAGAGCCTGCCCTCTGTACTCCAAATCGATGATGTTAGTGGTTGTAGTGGCTCTTTG (SEQ ID NO: 1063) | 10 | 75481925 |
| 173 | CAAAGAGCCACTACAACCACTAACATCATCGACAAAAAGAAAAATCAGCCTCATAATGCA (SEQ ID NO: 1064) | 10 | 75481925 |
| 174 | TGCATTTGTCAAAATTAAGAAATTAACATCGATGATGTTAGTGGTTGTAGTGGCTCTTTG (SEQ ID NO: 1065) | 10 | 75481925 |
| 175 | CAAAGAGCCACTACAACCACTAACATCATCGAATGCCCCCATTTGAAAAGAGTTATAATA (SEQ ID NO: 1066) | 10 | 75481925 |
| 176 | TTAACTATCCCAAATTCCATTCTCTTTCTCGATGATGTTAGTGGTTGTAGTGGCTCTTTG (SEQ ID NO: 1067) | 10 | 75481925 |
| 177 | CAAAGAGCCACTACAACCACTAACATCATCGATTTCAAAGCACTTGTCATACACTCTTTC (SEQ ID NO: 1068) | 10 | 75481925 |
| 178 | CAAAGAGCCACTACAACCACTAACATCATCGAGGAAATGAGTATCCTCAAGAGTCTACAC (SEQ ID NO: 1069) | 10 | 75481925 |
| 179 | GCTCCAAGACAGGACATGGAGGTGTTCATCGATGATGTTAGTGGTTGTAGTGGCTCTTTG (SEQ ID NO: 1070) | 10 | 75481925 |
| 180 | CAAAGAGCCACTACAACCACTAACATCATCGAAAATTTCCGAGACTTCGTTGGCTTTGTT (SEQ ID NO: 1071) | 10 | 75481925 |
| 181 | CAAAGAGCCACTACAACCACTAACATCATCGATAAATCTGTTAAAAATGAGCAAAGATCA (SEQ ID NO: 1072) | 10 | 75481925 |
| 182 | CTTGACAAGTTCAATCTAAACAAATATATCGATGATGTTAGTGGTTGTAGTGGCTCTTTG (SEQ ID NO: 1073) | 10 | 75481925 |
| 183 | CAAAGAGCCACTACAACCACTAACATCATCGATTTTAAAGAGAAACATGGTATTTCACCC (SEQ ID NO: 1074) | 10 | 75481925 |
| 184 | CAAAGAGCCACTACAACCACTAACATCATCGAATCAGAGCCTTTGCCAGAATCTGACAGA (SEQ ID NO: 1075) | 10 | 75481925 |
| 185 | GTCTTCACATTGCTTCCAACAGTAGTCGTCGATGATGTTAGTGGTTGTAGTGGCTCTTTG (SEQ ID NO: 1076) | 10 | 75481925 |
| 186 | CAAAGAGCCACTACAACCACTAACATCATCGACCCCACAAGGCTTAGCAGGGACAAGGTT (SEQ ID NO: 1077) | 10 | 75481925 |
| 187 | CCCCTCTTTGAACTCTTCGTTGGAAGTTTCGATGATGTTAGTGGTTGTAGTGGCTCTTTG (SEQ ID NO: 1078) | 10 | 75481925 |
| 188 | AGAGAATAGTGTGAGAAATGGTCATCTTTCGAGGAATGAGATGGTCGGTACATGAGAACA (SEQ ID NO: 1079) | 10 | 76002481 |
| 189 | TGTTCTCATGTACCGACCATCTCATTCCTCGAGTGAGGCTGTTTTATTTGCTTGGTGCAC (SEQ ID NO: 1080) | 10 | 75985731 |
| 190 | GCGCCATGTTAACCGTCAAACGGGTACCTCGATGCTGGTAGATAGGGGAATGGTTCCTGG (SEQ ID NO: 1081) | 3 | 106480842 |
| 191 | CTATGTAATCACAGCTTGATGTTCCAATTCGATGCTGGTAGATAGGGGAATGGTTCCTGG (SEQ ID NO: 1082) | 3 | 106716847 |
| 192 | AACTACATTAATTAAGAACTTCTGTTCATCGATTTCAGTTTTGAAACTGTAAGAGTAATT (SEQ ID NO: 1083) | 5 | 95193431 |

TABLE 33.c6

| | Probe Location | | | 4 kb Sequence Location | | | |
|---|---|---|---|---|---|---|---|
| N | End1 | Start2 | End2 | Chr | Start1 | End1 | Start2 | End2 |
| 129 | 26135782 | 26175106 | 26175137 | 28 | 26131781 | 26135782 | 26171136 | 26175137 |
| 130 | 49908469 | 49992351 | 49992382 | 20 | 49908438 | 49912439 | 49992351 | 49996352 |
| 131 | 7491275 | 7547275 | 7547306 | 15 | 7487274 | 7491275 | 7547275 | 7551276 |
| 132 | 27987302 | 28153765 | 28153796 | 19 | 27983301 | 27987302 | 28153765 | 28157766 |
| 133 | 28081538 | 28153765 | 28153796 | 19 | 28077537 | 28081538 | 28153765 | 28157766 |
| 134 | 28153796 | 28173183 | 28173214 | 19 | 28153765 | 28157766 | 28173183 | 28177184 |
| 135 | 20654880 | 20749766 | 20749797 | 13 | 20650879 | 20654880 | 20745796 | 20749797 |
| 136 | 16316546 | 16519922 | 16519953 | 21 | 16316515 | 16320516 | 16515952 | 16519953 |
| 137 | 16361936 | 16519922 | 16519953 | 21 | 16361905 | 16365906 | 16515952 | 16519953 |
| 138 | 16382969 | 16519922 | 16519953 | 21 | 16378968 | 16382969 | 16515952 | 16519953 |
| 139 | 16389433 | 16519922 | 16519953 | 21 | 16389402 | 16393403 | 16515952 | 16519953 |
| 140 | 16430421 | 16519922 | 16519953 | 21 | 16426420 | 16430421 | 16515952 | 16519953 |
| 141 | 47907545 | 47940508 | 47940539 | 1 | 47907514 | 47911515 | 47936538 | 47940539 |
| 142 | 56337174 | 56374109 | 56374140 | 5 | 56337143 | 56341144 | 56370139 | 56374140 |
| 143 | 56337174 | 56519244 | 56519275 | 5 | 56337143 | 56341144 | 56515274 | 56519275 |
| 144 | 30912196 | 30991768 | 30991799 | 26 | 30908195 | 30912196 | 30987798 | 30991799 |
| 145 | 30912196 | 30981829 | 30981860 | 26 | 30908195 | 30912196 | 30981829 | 30985830 |
| 146 | 102471878 | 102533621 | 102533652 | 4 | 102471847 | 102475848 | 102529651 | 102533652 |
| 147 | 10875151 | 10945798 | 10945829 | 11 | 10875120 | 10879121 | 10941828 | 10945829 |
| 148 | 10907532 | 10945798 | 10945829 | 11 | 10907501 | 10911502 | 10941828 | 10945829 |
| 149 | 31709566 | 31731426 | 31731457 | 2 | 31709535 | 31713536 | 31731426 | 31735427 |
| 150 | 31709566 | 31749361 | 31749392 | 2 | 31709535 | 31713536 | 31749361 | 31753362 |
| 151 | 31709566 | 31757482 | 31757513 | 2 | 31709535 | 31713536 | 31757482 | 31761483 |
| 152 | 31709566 | 31759922 | 31759953 | 2 | 31709535 | 31713536 | 31759922 | 31763923 |
| 153 | 31709566 | 31779719 | 31779750 | 2 | 31709535 | 31713536 | 31779719 | 31783720 |
| 154 | 31709566 | 31795486 | 31795517 | 2 | 31709535 | 31713536 | 31795486 | 31799487 |
| 155 | 31709566 | 31816722 | 31816753 | 2 | 31709535 | 31713536 | 31816722 | 31820723 |
| 156 | 31709566 | 31841824 | 31841855 | 2 | 31709535 | 31713536 | 31841824 | 31845825 |
| 157 | 75421720 | 75491551 | 75491582 | 10 | 75417719 | 75421720 | 75487581 | 75491582 |
| 158 | 75421720 | 75481925 | 75481956 | 10 | 75417719 | 75421720 | 75481925 | 75485926 |
| 159 | 75419913 | 75481925 | 75481956 | 10 | 75419882 | 75423883 | 75481925 | 75485926 |
| 160 | 75433856 | 75481925 | 75481956 | 10 | 75433825 | 75437826 | 75481925 | 75485926 |
| 161 | 75481956 | 75505407 | 75505438 | 10 | 75481925 | 75485926 | 75501437 | 75505438 |
| 162 | 75481956 | 75503397 | 75503428 | 10 | 75481925 | 75485926 | 75503397 | 75507398 |
| 163 | 75481956 | 75510267 | 75510298 | 10 | 75481925 | 75485926 | 75510267 | 75514268 |
| 164 | 75481956 | 75518473 | 75518504 | 10 | 75481925 | 75485926 | 75514503 | 75518504 |
| 165 | 75481956 | 75515462 | 75515493 | 10 | 75481925 | 75485926 | 75515462 | 75519463 |
| 166 | 75481956 | 75537867 | 75537898 | 10 | 75481925 | 75485926 | 75537867 | 75541868 |
| 167 | 75481956 | 75558780 | 75558811 | 10 | 75481925 | 75485926 | 75558780 | 75562781 |
| 168 | 75481956 | 75585674 | 75585705 | 10 | 75481925 | 75485926 | 75581704 | 75585705 |
| 169 | 75481956 | 75583879 | 75583910 | 10 | 75481925 | 75485926 | 75583879 | 75587880 |
| 170 | 75481956 | 75598703 | 75598734 | 10 | 75481925 | 75485926 | 75598703 | 75602704 |
| 171 | 75481956 | 75630159 | 75630190 | 10 | 75481925 | 75485926 | 75630159 | 75634160 |
| 172 | 75481956 | 75659958 | 75659989 | 10 | 75481925 | 75485926 | 75655988 | 75659989 |
| 173 | 75481956 | 75657275 | 75657306 | 10 | 75481925 | 75485926 | 75657275 | 75661276 |
| 174 | 75481956 | 75680755 | 75680786 | 10 | 75481925 | 75485926 | 75676785 | 75680786 |
| 175 | 75481956 | 75673465 | 75673496 | 10 | 75481925 | 75485926 | 75673465 | 75677466 |
| 176 | 75481956 | 75698620 | 75698651 | 10 | 75481925 | 75485926 | 75694650 | 75698651 |
| 177 | 75481956 | 75689296 | 75689327 | 10 | 75481925 | 75485926 | 75689296 | 75693297 |
| 178 | 75481956 | 75699217 | 75699248 | 10 | 75481925 | 75485926 | 75699217 | 75703218 |
| 179 | 75481956 | 75711759 | 75711790 | 10 | 75481925 | 75485926 | 75707789 | 75711790 |
| 180 | 75481956 | 75710114 | 75710145 | 10 | 75481925 | 75485926 | 75710114 | 75714115 |
| 181 | 75481956 | 75727142 | 75727173 | 10 | 75481925 | 75485926 | 75727142 | 75731143 |
| 182 | 75481956 | 75737067 | 75737098 | 10 | 75481925 | 75485926 | 75733097 | 75737098 |
| 183 | 75481956 | 75731193 | 75731224 | 10 | 75481925 | 75485926 | 75731193 | 75735194 |
| 184 | 75481956 | 75761081 | 75761112 | 10 | 75481925 | 75485926 | 75761081 | 75765082 |
| 185 | 75481956 | 75769584 | 75769615 | 10 | 75481925 | 75485926 | 75765614 | 75769615 |
| 186 | 75481956 | 75772669 | 75772700 | 10 | 75481925 | 75485926 | 75772669 | 75776670 |
| 187 | 75481956 | 75791933 | 75791964 | 10 | 75481925 | 75485926 | 75787963 | 75791964 |
| 188 | 76002512 | 76079786 | 76079817 | 10 | 75998511 | 76002512 | 76075816 | 76079817 |
| 189 | 75985762 | 76079786 | 76079817 | 10 | 75985731 | 75989732 | 76075816 | 76079817 |
| 190 | 106480873 | 106716847 | 106716878 | 3 | 106480842 | 106484843 | 106716847 | 106720848 |
| 191 | 106716878 | 106947854 | 106947885 | 3 | 106716847 | 106720848 | 106943884 | 106947885 |
| 192 | 95193462 | 95211956 | 95211987 | 5 | 95193431 | 95197432 | 95211956 | 95215957 |

TABLE 33.c7

| N | Probe | Primer ID-1 | Primer Sequence |
|---|---|---|---|
| 129 | IGF1_28_26127450_26135782_26165074_26175137_FF | OBD RD043.513 | ACTTGTAGGTGAGAAAGAAATAGC (SEQ ID NO: 1084) |

TABLE 33.c7-continued

| N | Probe | Primer ID-1 | Primer Sequence |
|---|---|---|---|
| 130 | IL17F_20_49908438_49915179_49992351_49998114_RR | OBD RD043.517 | CCTGTCTCACCATCTTCTTTTGCCTG (SEQ ID NO: 1085) |
| 131 | IL1R1_15_7480700_7491275_7547275_7554471_FR | OBD RD043.521 | CCAACTGAACAAGTGAACGCTGCCAG (SEQ ID NO: 1086) |
| 132 | IL1RAP_19_27981648_27987302_28153765_28161424_FR | OBD RD043.525 | AAATCGGTGAAGAAATGTAGAAAA (SEQ ID NO: 1087) |
| 133 | IL1RAP_19_28069654_28081538_28153765_28161424_FR | OBD RD043.529 | ATTTCCCCTTGTAGGCTGGTGGC (SEQ ID NO: 1088) |
| 134 | IL1RAP_19_28153765_28161424_28173183_28182762_RR | OBD RD043.533 | TATGCCAGGGAGGTAGAGCAGCC (SEQ ID NO: 1089) & (SEQ ID NO: 1152) |
| 135 | IL21R_13_20649899_20654880_20738447_20749797_FF | OBD RD043.537 | GACCTTGTTTTGTTCCCGTGACAGCA (SEQ ID NO: 1090) |
| 136 | IL6ST_21_16316515_16320787_16507936_16519953_RF | OBD RD043.541 | GCAAAGAGCAATGAGATGTCTATGAT (SEQ ID NO: 1091) |
| 137 | IL6ST_21_16361905_16367133_16507936_16519953_RF | OBD RD043.545 | AGCCTCTCCCTCCCAGCAAAGCG (SEQ ID NO: 1092) & (SEQ ID NO: 1093) & (SEQ ID NO: 1094) & (SEQ ID NO: 1155) & (SEQ ID NO: 1159) |
| 138 | IL6ST_21_16380568_16382969_16507936_16519953_FF | OBD RD043.549 | AGCCTCTCCCTCCCAGCAAAGCG (SEQ ID NO: 1092) & (SEQ ID NO: 1093) & (SEQ ID NO: 1094) & (SEQ ID NO: 1155) & (SEQ ID NO: 1159) |
| 139 | IL6ST_21_16389402_16396020_16507936_16519953_RF | OBD RD043.553 | AGCCTCTCCCTCCCAGCAAAGCG (SEQ ID NO: 1092) & (SEQ ID NO: 1093) & (SEQ ID NO: 1094) & (SEQ ID NO: 1155) & (SEQ ID NO: 1159) |
| 140 | IL6ST_21_16427757_16430421_16507936_16519953_FF | OBD RD043.557 | TATCAGTCAGCAACTCAGAGGAAC (SEQ ID NO: 1095) |
| 141 | IPMK_1_47907514_47915619_47934069_47940539_RF | OBD RD043.561 | AGCCAGAGCCTTGCTGTAGTCAG (SEQ ID NO: 1096) |
| 142 | KCND3_5_56337143_56347199_56370847_56374140_RF | OBD RD043.565 | TGTCCTCCTTTTGCCCCTCCCCT (SEQ ID NO: 1097) |
| 143 | KCND3_5_56337143_56347199_56514669_56519275_RF | OBD RD043.569 | GCCCTCTGCTTAGTAACCCCTCC (SEQ ID NO: 1098) |
| 144 | KCNE2_26_30910971_30912196_30981829_30991799_FF | OBD RD043.573 | CCAAAACCCCACCCACGCTGAGC (SEQ ID NO: 1099) |
| 145 | KCNE2_26_30910971_30912196_30981829_30991799_FR | OBD RD043.577 | TCCAAAACCCCACCCACGCTGAG (SEQ ID NO: 1100) |
| 146 | KCNH2_4_102471847_102478321_102526070_102533652_RF | OBD RD043.581 | GAGGTCACAGTTCCCTTGTTGGC (SEQ ID NO: 1101) |
| 147 | KCNJ2_11_10875120_10880378_10941535_10945829_RF | OBD RD043.585 | GGAGGAGTAAATGAATGTTTGTTT (SEQ ID NO: 1102) |
| 148 | KCNJ2_11_10907501_10914338_10941535_10945829_RF | OBD RD043.589 | CGTAATGAAGCAGACTTTTGGTCAGG (SEQ ID NO: 1103) |
| 149 | KDM1A_2_31709535_31721093_31731426_31738065_RR | OBD RD043.593 | CCAGCAGATGACAGCAGCAATAAGGG (SEQ ID NO: 1104) |
| 150 | KDM1A_2_31709535_31721093_31749361_31751529_RR | OBD RD043.597 | CGCCAGCAGATGACAGCAGCAAT (SEQ ID NO: 1105) & (SEQ ID NO: 1106) & (SEQ ID NO: 1107) & (SEQ ID NO: 1108) & (SEQ ID NO: 1110) |

TABLE 33.c7-continued

| N | Probe | Primer ID-1 | Primer Sequence |
|---|---|---|---|
| 151 | KDM1A_2_31709535_31721093_31757482_31759922_RR | OBD RD043.601 | CGCCAGCAGATGACAGCAGCAAT (SEQ ID NO: 1105) & (SEQ ID NO: 1106) & (SEQ ID NO: 1107) & (SEQ ID NO: 1108) & (SEQ ID NO: 1110) |
| 152 | KDM1A_2_31709535_31721093_31759922_31772142_RR | OBD RD043.605 | CGCCAGCAGATGACAGCAGCAAT (SEQ ID NO: 1105) & (SEQ ID NO: 1106) & (SEQ ID NO: 1107) & (SEQ ID NO: 1108) & (SEQ ID NO: 1110) |
| 153 | KDM1A_2_31709535_31721093_31779719_31783168_RR | OBD RD043.609 | CGCCAGCAGATGACAGCAGCAAT (SEQ ID NO: 1105) & (SEQ ID NO: 1106) & (SEQ ID NO: 1107) & (SEQ ID NO: 1108) & (SEQ ID NO: 1110) |
| 154 | KDM1A_2_31709535_31721093_31795486_31798526_RR | OBD RD043.613 | GCACCTGACAGCAGCACAGACTG (SEQ ID NO: 1109) & (SEQ ID NO: 1111) |
| 155 | KDM1A_2_31709535_31721093_31816722_31820715_RR | OBD RD043.617 | CGCCAGCAGATGACAGCAGCAAT (SEQ ID NO: 1105) & (SEQ ID NO: 1106) & (SEQ ID NO: 1107) & (SEQ ID NO: 1108) & (SEQ ID NO: 1110) |
| 156 | KDM1A_2_31709535_31721093_31841824_31843977_RR | OBD RD043.621 | GCACCTGACAGCAGCACAGACTG (SEQ ID NO: 1109) & (SEQ ID NO: 1111) |
| 157 | LAMA2_10_75419882_75421720_75481925_75491582_FF | OBD RD043.625 | GGATGTTCCAGCCTGAGTTCCTC (SEQ ID NO: 1112) |
| 158 | LAMA2_10_75419882_75421720_75481925_75491582_FR | OBD RD043.629 | GCTCGCCGTAGCATTCCTCACAC (SEQ ID NO: 1113) & (SEQ ID NO: 1119) & (SEQ ID NO: 1138) & (SEQ ID NO: 1176) & (SEQ ID NO: 1189) & (SEQ ID NO: 1192) & (SEQ ID NO: 1193) & (SEQ ID NO: 1198) |
| 159 | LAMA2_10_75419882_75421720_75481925_75491582_RR | OBD RD043.633 | CAACCTATTGCCGATGCCCTCAAACT (SEQ ID NO: 1114) & (SEQ ID NO: 1123) & (SEQ ID NO: 1203) & (SEQ ID NO: 1207) |
| 160 | LAMA2_10_75433825_75441819_75481925_75491582_RR | OBD RD043.637 | CCTACTACAACCTATTGCCGATGCCC (SEQ ID NO: 1115) & (SEQ ID NO: 1130) & (SEQ ID NO: 1135) & (SEQ ID NO: 1140) & (SEQ ID NO: 1144) & (SEQ ID NO: 1184) & (SEQ ID NO: 1196) & (SEQ ID NO: 1200) & (SEQ ID NO: 1201) |
| 161 | LAMA2_10_75481925_75491582_75503397_75505438_RF | OBD RD043.641 | GCCGATGCCCTCAAACTATTTATCAA (SEQ ID NO: 1116) |
| 162 | LAMA2_10_75481925_75491582_75503397_75505438_RR | OBD RD043.645 | GCAAAGGACCCAACATCGTAGGC (SEQ ID NO: 1117) & (SEQ ID NO: 1118) & (SEQ ID NO: 1122) & (SEQ ID NO: 1131) & (SEQ ID NO: 1133) |
| 163 | LAMA2_10_75481925_75491582_75510267_75513025_RR | OBD RD043.649 | GCAAAGGACCCAACATCGTAGGC (SEQ ID NO: 1117) & (SEQ ID NO: 1118) & (SEQ ID NO: 1122) & (SEQ ID NO: 1131) & (SEQ ID NO: 1133) |
| 164 | LAMA2_10_75481925_75491582_75515462_75518504_RF | OBD RD043.653 | GCTCGCCGTAGCATTCCTCACAC (SEQ ID NO: 1113) & (SEQ ID NO: 1119) & (SEQ ID NO: 1138) & (SEQ ID NO: 1176) & (SEQ ID NO: 1189) & (SEQ ID NO: 1192) & (SEQ ID NO: 1193) & (SEQ ID NO: 1198) |

TABLE 33.c7-continued

| N | Probe | Primer ID-1 | Primer Sequence |
|---|---|---|---|
| 165 | LAMA2_10_75481925_75491582_75515462_75518504_RR | OBD RD043.657 | TGTGATTGATAGGACTGCTTTGAGGC (SEQ ID NO: 1120) |
| 166 | LAMA2_10_75481925_75491582_75537867_75543336_RR | OBD RD043.661 | TTGTGTTTGAGTCTGGCTTGTCTAAT (SEQ ID NO: 1121) |
| 167 | LAMA2_10_75481925_75491582_75558780_75560310_RR | OBD RD043.665 | GCAAAGGACCCAACATCGTAGGC (SEQ ID NO: 1117) & (SEQ ID NO: 1118) & (SEQ ID NO: 1122) & (SEQ ID NO: 1131) & (SEQ ID NO: 1133) |
| 168 | LAMA2_10_75481925_75491582_75583879_75585705_RF | OBD RD043.669 | CAACCTATTGCCGATGCCCTCAAACT (SEQ ID NO: 1114) & (SEQ ID NO: 1123) & (SEQ ID NO: 1203) & (SEQ ID NO: 1207) |
| 169 | LAMA2_10_75481925_75491582_75583879_75585705_RR | OBD RD043.673 | CTACAACCTATTGCCGATGCCCTC (SEQ ID NO: 1124) |
| 170 | LAMA2_10_75481925_75491582_75598703_75603065_RR | OBD RD043.677 | GGCTTAGGGCATTGGTTAGGAGC (SEQ ID NO: 1125) |
| 171 | LAMA2_10_75481925_75491582_75630159_75632019_RR | OBD RD043.681 | TCTCTCTGTTTCTCAGTTCTATCGC (SEQ ID NO: 1126) |
| 172 | LAMA2_10_75481925_75491582_75657275_75659989_RF | OBD RD043.685 | ATCATTGAAGTTAGAAAAGGTCTT (SEQ ID NO: 1127) |
| 173 | LAMA2_10_75481925_75491582_75657275_75659989_RR | OBD RD043.689 | GCAAAGGAATGCCAACTGCCAGC (SEQ ID NO: 1128) |
| 174 | LAMA2_10_75481925_75491582_75673465_75680786_RF | OBD RD043.693 | CCTTTACCCAACTCCCACTGAGG (SEQ ID NO: 1129) |
| 175 | LAMA2_10_75481925_75491582_75673465_75680786_RR | OBD RD043.697 | CCTACTACAACCTATTGCCGATGCCC (SEQ ID NO: 1115) & (SEQ ID NO: 1130) & (SEQ ID NO: 1135) & (SEQ ID NO: 1140) & (SEQ ID NO: 1144) & (SEQ ID NO: 1184) & (SEQ ID NO: 1196) & (SEQ ID NO: 1200) & (SEQ ID NO: 1201) |
| 176 | LAMA2_10_75481925_75491582_75689296_75698651_RF | OBD RD043.701 | GCAAAGGACCCAACATCGTAGGC (SEQ ID NO: 1117) & (SEQ ID NO: 1118) & (SEQ ID NO: 1122) & (SEQ ID NO: 1131) & (SEQ ID NO: 1133) |
| 177 | LAMA2_10_75481925_75491582_75689296_75698651_RR | OBD RD043.705 | CTGATTTGTGGGCATCGTCTACAGTT (SEQ ID NO: 1132) |
| 178 | LAMA2_10_75481925_75491582_75699217_75700676_RR | OBD RD043.709 | GCAAAGGACCCAACATCGTAGGC (SEQ ID NO: 1117) & (SEQ ID NO: 1118) & (SEQ ID NO: 1122) & (SEQ ID NO: 1131) & (SEQ ID NO: 1133) |
| 179 | LAMA2_10_75481925_75491582_75710114_75711790_RF | OBD RD043.713 | CGAGGGAGAGAGTAAAGCCAACC (SEQ ID NO: 1134) |
| 180 | LAMA2_10_75481925_75491582_75710114_75711790_RR | OBD RD043.717 | CCTACTACAACCTATTGCCGATGCCC (SEQ ID NO: 1115) & (SEQ ID NO: 1130) & (SEQ ID NO: 1135) & (SEQ ID NO: 1140) & (SEQ ID NO: 1144) & (SEQ ID NO: 1184) & (SEQ ID NO: 1196) & (SEQ ID NO: 1200) & (SEQ ID NO: 1201) |
| 181 | LAMA2_10_75481925_75491582_75727142_75730779_RR | OBD RD043.721 | TCAGGTAGCACTCTTATCTTTCCAGA (SEQ ID NO: 1136) |
| 182 | LAMA2_10_75481925_75491582_75731193_75737098_RF | OBD RD043.725 | TAGGGAGTTGGCACTGGCACTTTT (SEQ ID NO: 1137) |

TABLE 33.c7-continued

| N | Probe | Primer ID-1 | Primer Sequence |
|---|-------|-------------|-----------------|
| 183 | LAMA2_10_75481925_75491582_75731193_75737098_RR | OBD RD043.729 | GCTCGCCGTAGCATTCCTCACAC (SEQ ID NO: 1113) & (SEQ ID NO: 1119) & (SEQ ID NO: 1138) & (SEQ ID NO: 1176) & (SEQ ID NO: 1189) & (SEQ ID NO: 1192) & (SEQ ID NO: 1193) & (SEQ ID NO: 1198) |
| 184 | LAMA2_10_75481925_75491582_75761081_75765848_RR | OBD RD043.733 | CAGGAAGACTTTATTATGGAATGCGT (SEQ ID NO: 1139) |
| 185 | LAMA2_10_75481925_75491582_75767487_75769615_RF | OBD RD043.737 | CCTACTACAACCTATTGCCGATGCCC (SEQ ID NO: 1115) & (SEQ ID NO: 1130) & (SEQ ID NO: 1135) & (SEQ ID NO: 1140) & (SEQ ID NO: 1144) & (SEQ ID NO: 1184) & (SEQ ID NO: 1196) & (SEQ ID NO: 1200) & (SEQ ID NO: 1201) |
| 186 | LAMA2_10_75481925_75491582_75772669_75776905_RR | OBD RD043.741 | CTTGAAACCTGACAAAGATACCAGC (SEQ ID NO: 1141) |
| 187 | LAMA2_10_75481925_75491582_75789669_75791964_RF | OBD RD043.745 | TTCCATTCCAAGATTGATGAAAAT (SEQ ID NO: 1142) |
| 188 | LAMA2_10_75985731_76002512_76077151_76079817_FF | OBD RD043.749 | GCAGACACAAGCAAGTAAATAGACAA (SEQ ID NO: 1143) |
| 189 | LAMA2_10_75985731_76002512_76077151_76079817_RF | OBD RD043.753 | CCTACTACAACCTATTGCCGATGCCC (SEQ ID NO: 1115) & (SEQ ID NO: 1130) & (SEQ ID NO: 1135) & (SEQ ID NO: 1140) & (SEQ ID NO: 1144) & (SEQ ID NO: 1184) & (SEQ ID NO: 1196) & (SEQ ID NO: 1200) & (SEQ ID NO: 1201) |
| 190 | LDB2_3_106480842_106484500_106716847_106728445_RR | OBD RD043.757 | CACAGAATAGTCTCCCAAATAGTTTATG (SEQ ID NO: 1145) |
| 191 | LDB2_3_106716847_106728445_106944178_106947885_RF | OBD RD043.761 | AGTGAAGGAGGAGAGTCATCTGCT (SEQ ID NO: 1146) |
| 192 | LEPR_5_95193431_95200537_95211956_95218723_RR | OBD RD043.765 | GAGCCAAACCATAAAGAGAAAGACTG (SEQ ID NO: 1147) |

TABLE 33.c7

| N | Primer ID-2 | Primer Sequence | Probe | Marker |
|---|-------------|-----------------|-------|--------|
| 129 | OBD RD043.515 | TCCATAAACAGGTGAGGAAGACAC (SEQ ID NO: 1148) | IGF1 | OBD RD043.513.515 |
| 130 | OBD RD043.519 | TTAGTCTCTTTCTTCAGATGGCTATC (SEQ ID NO: 1149) | IL17F | OBD RD043.517.519 |
| 131 | OBD RD043.523 | ACAACGAGGACTCAGATTTCTCAGAG (SEQ ID NO: 1150) | IL1R1 | OBD RD043.521.523 |
| 132 | OBD RD043.527 | GCAAGTTAGTGGTTGAGATTGGAT (SEQ ID NO: 1151) | IL1RAP | OBD RD043.525.527 |
| 133 | OBD RD043.531 | TATGCCAGGGAGGTAGAGCAGCC (SEQ ID NO: 1089) & (SEQ ID NO: 1152) | IL1RAP | OBD RD043.529.531 |
| 134 | OBD RD043.535 | GCTTGACTTGCTCTGGGAGGAGA (SEQ ID NO: 1153) | IL1RAP | OBD RD043.533.535 |
| 135 | OBD RD043.539 | CTAATAAACTCAGCGAGGCAGCAGGA (SEQ ID NO: 1154) | IL21R | OBD RD043.537.539 |
| 136 | OBD RD043.543 | AGCCTCTCCCTCCCAGCAAAGCG (SEQ ID NO: 1092) & (SEQ ID NO: 1093) & (SEQ ID NO: 1094) & (SEQ ID NO: 1155) & (SEQ ID NO: 1159) | IL6ST | OBD RD043.541.543 |

TABLE 33.c7-continued

| N | Primer ID-2 | Primer Sequence | Probe | Marker |
|---|---|---|---|---|
| 137 | OBD RD043.547 | GCCTCAGAAAGAGTTGTAGTTATTGT (SEQ ID NO: 1156) | IL6ST | OBD RD043.545.547 |
| 138 | OBD RD043.551 | CAGTTTTGTAGAGCACCTGATTAGAA (SEQ ID NO: 1157) | IL6ST | OBD RD043.549.551 |
| 139 | OBD RD043.555 | GGGCTCTACTCAGTGATTGCCTG (SEQ ID NO: 1158) | IL6ST | OBD RD043.553.555 |
| 140 | OBD RD043.559 | AGCCTCTCCCTCCCAGCAAAGCG (SEQ ID NO: 1092) & (SEQ ID NO: 1093) & (SEQ ID NO: 1094) & (SEQ ID NO: 1155) & (SEQ ID NO: 1159) | IL6ST | OBD RD043.557.559 |
| 141 | OBD RD043.563 | GCCATCAGTGACCAAGGCACCTC (SEQ ID NO: 1160) | IPMK | OBD RD043.561.563 |
| 142 | OBD RD043.567 | ATCAGAGGGTGGTTATGTCGGGC (SEQ ID NO: 1161) & (SEQ ID NO: 1162) | KCND3 | OBD RD043.565.567 |
| 143 | OBD RD043.571 | ATCAGAGGGTGGTTATGTCGGGC (SEQ ID NO: 1161) & (SEQ ID NO: 1162) | KCND3 | OBD RD043.569.571 |
| 144 | OBD RD043.575 | GGGTCAGGTTGGTGAGAGAAGGG (SEQ ID NO: 1163) | KCNE2 | OBD RD043.573.575 |
| 145 | OBD RD043.579 | ATGGATGGTGGATGGTGGGAACC (SEQ ID NO: 1164) | KCNE2 | OBD RD043.577.579 |
| 146 | OBD RD043.583 | TTCCACCCCGTCCCCATCTTCAC (SEQ ID NO: 1165) | KCNH2 | OBD RD043.581.583 |
| 147 | OBD RD043.587 | AAGAGTAATCTGCTTGGTAAATAG (SEQ ID NO: 1166) | KCNJ2 | OBD RD043.585.587 |
| 148 | OBD RD043.591 | CTACTTGAAGAAATAAGCCTTGCTGC (SEQ ID NO: 1167) | KCNJ2 | OBD RD043.589.591 |
| 149 | OBD RD043.595 | CCACTTTATGAAGCAAATGGACAAGC (SEQ ID NO: 1168) | KDM1A | OBD RD043.593.595 |
| 150 | OBD RD043.599 | CCCTTCTCTCTGTTGCTGCCGTG (SEQ ID NO: 1169) | KDM1A | OBD RD043.597.599 |
| 151 | OBD RD043.603 | GCTCGCAGGTGCTGGGAATACAG (SEQ ID NO: 1170) | KDM1A | OBD RD043.601.603 |
| 152 | OBD RD043.607 | TGGTGTCTCAGGCTTGGCAGCAG (SEQ ID NO: 1171) | KDM1A | OBD RD043.605.607 |
| 153 | OBD RD043.611 | GAGAGAGCCCAGGTTAGACAGCG (SEQ ID NO: 1172) | KDM1A | OBD RD043.609.611 |
| 154 | OBD RD043.615 | AAACAAAGCCAGGGAGGAGGACG (SEQ ID NO: 1173) | KDM1A | OBD RD043.613.615 |
| 155 | OBD RD043.619 | GCCAGAAAGGAAGGTGGGAGCCT (SEQ ID NO: 1174) | KDM1A | OBD RD043.617.619 |
| 156 | OBD RD043.623 | CCACTACTCTCATAGGGAGGGAG (SEQ ID NO: 1175) | KDM1A | OBD RD043.621.623 |
| 157 | OBD RD043.627 | GCTCGCCGTAGCATTCCTCACAC (SEQ ID NO: 1113) & (SEQ ID NO: 1119) & (SEQ ID NO: 1138) & (SEQ ID NO: 1176) & (SEQ ID NO: 1189) & (SEQ ID NO: 1192) & (SEQ ID NO: 1193) & (SEQ ID NO: 1198) | LAMA2 | OBD RD043.625.627 |
| 158 | OBD RD043.631 | GGCTTCAACCGTCTCCAAGGCTT (SEQ ID NO: 1177) | LAMA2 | OBD RD043.629.631 |

TABLE 33.c7-continued

| N | Primer ID-2 | Primer Sequence | Probe | Marker |
|---|---|---|---|---|
| 159 | OBD RD043.635 | TTCTGTAGAGCCTCACCAACACTGTG (SEQ ID NO: 1178) | LAMA2 | OBD RD043.633.635 |
| 160 | OBD RD043.639 | CGACTTCTCGGTTGTTTAGCATCACA (SEQ ID NO: 1179) | LAMA2 | OBD RD043.637.639 |
| 161 | OBD RD043.643 | CGTGACAGCAGTTTTATTGTTTGGG (SEQ ID NO: 1180) | LAMA2 | OBD RD043.641.643 |
| 162 | OBD RD043.647 | GGACCCGAGCACCACTCTTGAGA (SEQ ID NO: 1181) | LAMA2 | OBD RD043.645.647 |
| 163 | OBD RD043.651 | TCCCAGAACAGCCAGCACAGCAG (SEQ ID NO: 1182) | LAMA2 | OBD RD043.649.651 |
| 164 | OBD RD043.655 | GTGACTGCCAGGTTTGCCACCAA (SEQ ID NO: 1183) | LAMA2 | OBD RD043.653.655 |
| 165 | OBD RD043.659 | CCTACTACAACCTATTGCCGATGCCC (SEQ ID NO: 1115) & (SEQ ID NO: 1130) & (SEQ ID NO: 1135) & (SEQ ID NO: 1140) & (SEQ ID NO: 1144) & (SEQ ID NO: 1184) & (SEQ ID NO: 1196) & (SEQ ID NO: 1200) & (SEQ ID NO: 1201) | LAMA2 | OBD RD043.657.659 |
| 166 | OBD RD043.663 | CGATGCCCTCAAACTATTTATCAAAG (SEQ ID NO: 1185) | LAMA2 | OBD RD043.661.663 |
| 167 | OBD RD043.667 | GACCACACACCAGGAGGCTGATG (SEQ ID NO: 1186) | LAMA2 | OBD RD043.665.667 |
| 168 | OBD RD043.671 | CCACTATTTCCACACCACACAGTCTG (SEQ ID NO: 1187) | LAMA2 | OBD RD043.669.671 |
| 169 | OBD RD043.675 | TGGCACTCCTCCTCGTCATCAGG (SEQ ID NO: 1188) | LAMA2 | OBD RD043.673.675 |
| 170 | OBD RD043.679 | GCTCGCCGTAGCATTCCTCACAC (SEQ ID NO: 1113) & (SEQ ID NO: 1119) & (SEQ ID NO: 1138) & (SEQ ID NO: 1176) & (SEQ ID NO: 1189) & (SEQ ID NO: 1192) & (SEQ ID NO: 1193) & (SEQ ID NO: 1198) | LAMA2 | OBD RD043.677.679 |
| 171 | OBD RD043.683 | ACATAAAGAACACTCTATCCAAAA (SEQ ID NO: 1190) | LAMA2 | OBD RD043.681.683 |
| 172 | OBD RD043.687 | TTCGCAAAGGACCCAACATCGTAG (SEQ ID NO: 1191) | LAMA2 | OBD RD043.685.687 |
| 173 | OBD RD043.691 | GCTCGCCGTAGCATTCCTCACAC (SEQ ID NO: 1113) & (SEQ ID NO: 1119) & (SEQ ID NO: 1138) & (SEQ ID NO: 1176) & (SEQ ID NO: 1189) & (SEQ ID NO: 1192) & (SEQ ID NO: 1193) & (SEQ ID NO: 1198) | LAMA2 | OBD RD043.689.691 |
| 174 | OBD RD043.695 | GCTCGCCGTAGCATTCCTCACAC (SEQ ID NO: 1113) & (SEQ ID NO: 1119) & (SEQ ID NO: 1138) & (SEQ ID NO: 1176) & (SEQ ID NO: 1189) & (SEQ ID NO: 1192) & (SEQ ID NO: 1193) & (SEQ ID NO: 1198) | LAMA2 | OBD RD043.693.695 |
| 175 | OBD RD043.699 | TCGCTGAGGAGCATCCAACTTGATTA (SEQ ID NO: 1194) | LAMA2 | OBD RD043.697.699 |
| 176 | OBD RD043.703 | CTGTCAACGGGATGTGAGGTCAGC (SEQ ID NO: 1195) | LAMA2 | OBD RD043.701.703 |
| 177 | OBD RD043.707 | CCTACTACAACCTATTGCCGATGCCC (SEQ ID NO: 1115) & (SEQ ID NO: 1130) & (SEQ ID NO: 1135) & (SEQ ID | LAMA2 | OBD RD043.705.707 |

TABLE 33.c7-continued

| N | Primer ID-2 | Primer Sequence | Probe | Marker |
|---|---|---|---|---|
| | | NO: 1140) & (SEQ ID NO: 1144) & (SEQ ID NO: 1184) & (SEQ ID NO: 1196) & (SEQ ID NO: 1200) & (SEQ ID NO: 1201) | | |
| 178 | OBD RD043.711 | CTCAGCAGGAAATCGCCCTCCAG (SEQ ID NO: 1197) | LAMA2 | OBD RD043.709.711 |
| 179 | OBD RD043.715 | GCTCGCCGTAGCATTCCTCACAC (SEQ ID NO: 1113) & (SEQ ID NO: 1119) & (SEQ ID NO: 1138) & (SEQ ID NO: 1176) & (SEQ ID NO: 1189) & (SEQ ID NO: 1192) & (SEQ ID NO: 1193) & (SEQ ID NO: 1198) | LAMA2 | OBD RD043.713.715 |
| 180 | OBD RD043.719 | GCTCCAACACAACCCAGTTATTTCTG (SEQ ID NO: 1199) | LAMA2 | OBD RD043.717.719 |
| 181 | OBD RD043.723 | CCTACTACAACCTATTGCCGATGCCC (SEQ ID NO: 1115) & (SEQ ID NO: 1130) & (SEQ ID NO: 1135) & (SEQ ID NO: 1140) & (SEQ ID NO: 1144) & (SEQ ID NO: 1184) & (SEQ ID NO: 1196) & (SEQ ID NO: 1200) & (SEQ ID NO: 1201) | LAMA2 | OBD RD043.721.723 |
| 182 | OBD RD043.727 | CCTACTACAACCTATTGCCGATGCCC (SEQ ID NO: 1115) & (SEQ ID NO: 1130) & (SEQ ID NO: 1135) & (SEQ ID NO: 1140) & (SEQ ID NO: 1144) & (SEQ ID NO: 1184) & (SEQ ID NO: 1196) & (SEQ ID NO: 1200) & (SEQ ID NO: 1201) | LAMA2 | OBD RD043.725.727 |
| 183 | OBD RD043.731 | GACCCAAAGCAGAGAGGCAACTG (SEQ ID NO: 1202) | LAMA2 | OBD RD043.729.731 |
| 184 | OBD RD043.735 | CAACCTATTGCCGATGCCCTCAAACT (SEQ ID NO: 1114) & (SEQ ID NO: 1123) & (SEQ ID NO: 1203) & (SEQ ID NO: 1207) | LAMA2 | OBD RD043.733.735 |
| 185 | OBD RD043.739 | TAGGGAACCGACTGAATCTGATACAG (SEQ ID NO: 1204) | LAMA2 | OBD RD043.737.739 |
| 186 | OBD RD043.743 | CAATACTTTAGAGTCACATCTCGTGC (SEQ ID NO: 1205) | LAMA2 | OBD RD043.741.743 |
| 187 | OBD RD043.747 | GTGTGTAAGTTCTAAGTGTTTATTA (SEQ ID NO: 1206) | LAMA2 | OBD RD043.745.747 |
| 188 | OBD RD043.751 | CAACCTATTGCCGATGCCCTCAAACT (SEQ ID NO: 1114) & (SEQ ID NO: 1123) & (SEQ ID NO: 1203) & (SEQ ID NO: 1207) | LAMA2 | OBD RD043.749.751 |
| 189 | OBD RD043.755 | CAACCCAAAGCAATCCAGCAAAGCAT (SEQ ID NO: 1208) | LAMA2 | OBD RD043.753.755 |
| 190 | OBD RD043.759 | GATGTTTCTTATTTTGAGTTTTCCCAGG (SEQ ID NO: 1209) | LDB2 | OBD RD043.757.759 |
| 191 | OBD RD043.763 | GTCATCATTTATGTGGAAGGAATA (SEQ ID NO: 1210) | LDB2 | OBD RD043.761.763 |
| 192 | OBD RD043.767 | AACCCTGTCATAAGTTGAAGAAGAGC (SEQ ID NO: 1211) | LEPR | OBD RD043.765.767 |

TABLE 33.d1

| N | Probe | GeneLocus | Probe_Count_Total | Probe_Count_Sig |
|---|---|---|---|---|
| 193 | LMO7_17_48756745_48760926_48985578_48994371_FR | LMO7 | 1 | 47 |
| 194 | LY6D_9_81540380_81548206_81579682_81590550_FR | LY6D | 2 | 31 |
| 195 | LY6D_9_81540380_81548206_81579682_81590550_RR | LY6D | 2 | 31 |
| 196 | MAP3K4_31_2786762_2795002_2851292_2856203_FR | MAP3K4 | 1 | 31 |
| 197 | MAP3K9_24_16803396_16807626_16910389_16918093_RF | MAP3K9 | 1 | 29 |
| 198 | MAPK1_8_3352241_3355955_3404723_3412822_RR | MAPK1 | 3 | 31 |
| 199 | MAPK1_8_3435741_3439526_3469888_3479148_FF | MAPK1 | 3 | 31 |
| 200 | MAPK1_8_3435741_3439526_3469888_3479148_FR | MAPK1 | 3 | 31 |
| 201 | MAPK3_13_19583177_19588616_19608792_19619090_FF | MAPK3 | 1 | 31 |
| 202 | MAPK9_14_2229196_2237168_2274036_2279957_RR | MAPK9 | 2 | 38 |
| 203 | MAPK9_14_2229196_2237168_2401910_2410518_RR | MAPK9 | 2 | 38 |
| 204 | MDH1_15_37903511_37909683_38029907_38037711_RR | MDH1 | 2 | 125 |
| 205 | MDH1_15_37903511_37909683_38069969_38081007_RR | MDH1 | 2 | 125 |
| 206 | MDM4_5_1002213_1010298_1034976_1038480_FF | MDM4 | 1 | 31 |
| 207 | MED25_10_19508221_19515457_19591613_19593754_RF | MED25 | 1 | 30 |
| 208 | MEF2A_1_104992073_105002150_105161756_105164976_RF | MEF2A | 1 | 181 |
| 209 | MIPEP_17_4332285_4337643_4521242_4528379_FF | MIPEP | 3 | 131 |
| 210 | MIPEP_17_4413535_4418797_4506914_4517925_FF | MIPEP | 3 | 131 |
| 211 | MIPEP_17_4413535_4418797_4521242_4528379_FF | MIPEP | 3 | 131 |
| 212 | MMP1_7_12601995_12610418_12711728_12717668_RF | MMP1 | 2 | 33 |
| 213 | MMP1_7_12711728_12717668_12737470_12745025_FR | MMP1 | 2 | 33 |
| 214 | MS4A2_12_19894956_19896244_19962410_19974828_RF | MS4A2 | 2 | 112 |
| 215 | MS4A2_12_19992086_20002065_20049543_20053548_RF | MS4A2 | 2 | 112 |
| 216 | MSI2_11_31942510_31947907_32032038_32042221_RR | MSI2 | 3 | 204 |
| 217 | MSI2_11_31953015_31955643_32032038_32042221_RF | MSI2 | 3 | 204 |
| 218 | MSI2_11_31953015_31955643_32032038_32042221_RR | MSI2 | 3 | 204 |
| 219 | MSTN_18_66448734_66450075_66490497_66500489_RF | MSTN | 1 | 50 |
| 220 | MTHFR_2_39760745_39767847_39804925_39808549_FR | MTHFR | 3 | 29 |
| 221 | MTHFR_2_39760745_39767847_39835824_39839260_FF | MTHFR | 3 | 29 |
| 222 | MTHFR_2_39760745_39767847_39835824_39839260_FR | MTHFR | 3 | 29 |
| 223 | MTMR3_8_6868138_6874813_6923181_6926871_RR | MTMR3 | 1 | 31 |
| 224 | MYBPC2_10_20037236_20038811_20080873_20084086_RF | MYBPC2 | 1 | 31 |
| 225 | MYH1_11_52882980_52886797_52907287_52915321_RF | MYH1 | 1 | 50 |
| 226 | MYL1_6_1098854_1104299_989242_996235_RR | MYL1 | 1 | 44 |
| 227 | MYL4_11_17193641_17194702_17358881_17368963_RF | MYL4 | 6 | 34 |
| 228 | MYL4_11_17206623_17211708_17358881_17368963_RF | MYL4 | 6 | 34 |
| 229 | MYL4_11_17246461_17251113_17358881_17368963_RF | MYL4 | 6 | 34 |
| 230 | MYL4_11_17257199_17259878_17358881_17368963_RF | MYL4 | 6 | 34 |
| 231 | MYL4_11_17267739_17271299_17358881_17368963_RF | MYL4 | 6 | 34 |
| 232 | MYL4_11_17290815_17294484_17358881_17368963_RF | MYL4 | 6 | 34 |
| 233 | MYOZ1_1_61314759_61323626_61385709_61392305_FF | MYOZ1 | 3 | 109 |
| 234 | MYOZ1_1_61323626_61338801_61385709_61392305_FF | MYOZ1 | 3 | 109 |
| 235 | MYOZ1_1_61350438_61357018_61385709_61392305_RF | MYOZ1 | 3 | 109 |
| 236 | NDN_1_109635329_109640204_109733366_109741347_RF | NDN | 3 | 31 |
| 237 | NDN_1_109711483_109720818_109733366_109741347_RF | NDN | 3 | 31 |
| 238 | NDN_1_109733366_109741347_109779877_109789352_FR | NDN | 3 | 31 |
| 239 | NDUFA8_25_25717207_25721463_25884535_25891335_FR | NDUFA8 | 1 | 31 |
| 240 | NEUROD2_11_22762666_22765277_22824653_22836914_FR | NEUROD2 | 1 | 35 |
| 241 | NFIB_23_34300375_34312881_34537544_34541097_RF | NFIB | 2 | 195 |
| 242 | NFIB_23_34364872_34370510_34413070_34423547_FR | NFIB | 2 | 195 |
| 243 | NPPA_2_39707018_39708108_39760745_39767847_RF | NPPA | 4 | 31 |
| 244 | NPPA_2_39714609_39718671_39760745_39767847_FF | NPPA | 4 | 31 |
| 245 | NPPA_2_39714609_39718671_39760745_39767847_RF | NPPA | 4 | 31 |
| 246 | NPPA_2_39741527_39742701_39760745_39767847_RF | NPPA | 4 | 31 |
| 247 | PALLD_2_66194319_66195345_66291709_66310979_FF | PALLD | 5 | 288 |
| 248 | PALLD_2_66194319_66195345_66291709_66310979_FR | PALLD | 5 | 288 |
| 249 | PALLD_2_66212034_66222303_66449615_66454401_FF | PALLD | 5 | 288 |
| 250 | PALLD_2_66291709_66310979_66324859_66327343_FR | PALLD | 5 | 288 |
| 251 | PALLD_2_66291709_66310979_66449615_66454401_RF | PALLD | 5 | 288 |
| 252 | PCBP4_16_35681721_35687901_35707118_35711409_FF | PCBP4 | 2 | 31 |
| 253 | PCBP4_16_35681721_35687901_35729420_35734814_FF | PCBP4 | 2 | 31 |
| 254 | PHOSPHO1_11_25089999_25092180_25214955_25221072_RR | PHOSPHO1 | 2 | 30 |
| 255 | PHOSPHO1_11_25177016_25183355_25214955_25221072_RR | PHOSPHO1 | 2 | 30 |
| 256 | PIK3R1_21_5606382_5618174_5697527_5698879_RF | PIK3R1 | 1 | 44 |

TABLE 33.d2

| N | HyperG_Stats | FDR_HyperG | Percent_Sig | logFC | AveExpr |
|---|---|---|---|---|---|
| 193 | 0.264202412 | 0.310300562 | 2.13 | 0.308955 | 8.756434343 |
| 194 | 0.024599258 | 0.075554863 | 6.45 | −0.510502405 | 10.21074765 |
| 195 | 0.024599258 | 0.075554863 | 6.45 | −0.475839307 | 10.73785324 |
| 196 | 0.198752749 | 0.267074007 | 3.23 | −0.262976484 | 8.919564336 |
| 197 | 0.189010904 | 0.267074007 | 3.45 | −0.180023399 | 10.17483943 |
| 198 | 0.001955877 | 0.014841655 | 9.68 | −0.189403578 | 11.32640428 |

TABLE 33.d2-continued

| N | HyperG_Stats | FDR_HyperG | Percent_Sig | logFC | AveExpr |
|---|---|---|---|---|---|
| 199 | 0.001955877 | 0.014841655 | 9.68 | −0.357643779 | 9.43283737 |
| 200 | 0.001955877 | 0.014841655 | 9.68 | −0.455473419 | 9.347542263 |
| 201 | 0.198752749 | 0.267074007 | 3.23 | −0.414926364 | 10.40126841 |
| 202 | 0.035117143 | 0.100669145 | 5.26 | −0.304638764 | 10.45869573 |
| 203 | 0.035117143 | 0.100669145 | 5.26 | −0.350361266 | 10.09820875 |
| 204 | 0.189650589 | 0.267074007 | 1.6 | −0.39554798 | 7.948266107 |
| 205 | 0.189650589 | 0.267074007 | 1.6 | −0.352490885 | 8.366984869 |
| 206 | 0.198752749 | 0.267074007 | 3.23 | −0.184406239 | 9.603449014 |
| 207 | 0.193928419 | 0.267074007 | 3.33 | −1.002322155 | 9.303488712 |
| 208 | 0.337499771 | 0.365861096 | 0.55 | −0.268195094 | 9.66649256 |
| 209 | 0.070335458 | 0.151221234 | 2.29 | 0.181091948 | 9.982716815 |
| 210 | 0.070335458 | 0.151221234 | 2.29 | −0.243481105 | 10.43396472 |
| 211 | 0.070335458 | 0.151221234 | 2.29 | −0.262461763 | 10.1207347 |
| 212 | 0.027478161 | 0.080560972 | 6.06 | −0.363422404 | 9.195426411 |
| 213 | 0.027478161 | 0.080560972 | 6.06 | −0.344950706 | 9.351822484 |
| 214 | 0.169245181 | 0.267074007 | 1.79 | −0.432136877 | 12.0727133 |
| 215 | 0.169245181 | 0.267074007 | 1.79 | −0.227521522 | 9.522194245 |
| 216 | 0.147248814 | 0.267074007 | 1.47 | 0.571287251 | 9.737071247 |
| 217 | 0.147248814 | 0.267074007 | 1.47 | −0.250081475 | 9.240013839 |
| 218 | 0.147248814 | 0.267074007 | 1.47 | −0.454717411 | 10.26002015 |
| 219 | 0.274219102 | 0.310300562 | 2 | 0.301875352 | 8.089384778 |
| 220 | 0.001616117 | 0.014841655 | 10.34 | −0.275284765 | 10.54722144 |
| 221 | 0.001616117 | 0.014841655 | 10.34 | −0.290761819 | 10.35745977 |
| 222 | 0.001616117 | 0.014841655 | 10.34 | −0.323026508 | 10.39283037 |
| 223 | 0.198752749 | 0.267074007 | 3.23 | −0.306058656 | 10.27824044 |
| 224 | 0.198752749 | 0.267074007 | 3.23 | 0.218360553 | 10.39432728 |
| 225 | 0.274219102 | 0.310300562 | 2 | −0.340884422 | 11.66695629 |
| 226 | 0.253514025 | 0.310300562 | 2.27 | −0.590441109 | 8.581505532 |
| 227 | 0.00000311818145952167 | 0.0000201122704139147 | 17.65 | 0.269287734 | 9.380557343 |
| 228 | 0.00000311818145952167 | 0.0000201122704139147 | 17.65 | 0.204015501 | 9.601273444 |
| 229 | 0.00000311818145952167 | 0.0000201122704139147 | 17.65 | 0.256704897 | 9.061911736 |
| 230 | 0.00000311818145952167 | 0.0000201122704139147 | 17.65 | 0.183545822 | 10.10564073 |
| 231 | 0.00000311818145952167 | 0.0000201122704139147 | 17.65 | 0.205055848 | 10.06240784 |
| 232 | 0.00000311818145952167 | 0.0000201122704139147 | 17.65 | 0.220380659 | 9.12627111 |
| 233 | 0.048283923 | 0.124572522 | 2.75 | −0.212727454 | 10.43860627 |
| 234 | 0.048283923 | 0.124572522 | 2.75 | −0.281776187 | 9.409288269 |
| 235 | 0.048283923 | 0.124572522 | 2.75 | −0.492368455 | 10.04957678 |
| 236 | 0.001955877 | 0.014841655 | 9.68 | −0.340662221 | 9.476696148 |
| 237 | 0.001955877 | 0.014841655 | 9.68 | −0.43400853 | 9.302335644 |
| 238 | 0.001955877 | 0.014841655 | 9.68 | −0.3910292 | 9.299496898 |
| 239 | 0.198752749 | 0.267074007 | 3.23 | 0.253713189 | 8.751509754 |
| 240 | 0.217141868 | 0.285829602 | 2.86 | −0.204232609 | 12.1874556 |
| 241 | 0.260374827 | 0.310300562 | 1.03 | 0.324297214 | 8.32941724 |
| 242 | 0.260374827 | 0.310300562 | 1.03 | −0.228545891 | 7.918191482 |
| 243 | 0.000112254 | 0.002068688 | 12.9 | −0.235040273 | 10.43931511 |
| 244 | 0.000112254 | 0.002068688 | 12.9 | −0.298128772 | 9.961402566 |
| 245 | 0.000112254 | 0.002068688 | 12.9 | −0.196073384 | 11.28835418 |
| 246 | 0.000112254 | 0.002068688 | 12.9 | −0.358964974 | 10.23538918 |
| 247 | 0.057376468 | 0.137915817 | 1.74 | −0.331113386 | 8.504927574 |
| 248 | 0.057376468 | 0.137915817 | 1.74 | −0.333004015 | 8.42257663 |
| 249 | 0.057376468 | 0.137915817 | 1.74 | 0.337185069 | 9.542961911 |
| 250 | 0.057376468 | 0.137915817 | 1.74 | −0.19420402 | 10.03309215 |
| 251 | 0.057376468 | 0.137915817 | 1.74 | 0.285252571 | 10.1390655 |
| 252 | 0.024599258 | 0.075554863 | 6.45 | −0.606928989 | 7.90009089 |
| 253 | 0.024599258 | 0.075554863 | 6.45 | −0.5741059 | 7.791564161 |
| 254 | 0.023201487 | 0.075554863 | 6.67 | −0.435541833 | 8.652187929 |
| 255 | 0.023201487 | 0.075554863 | 6.67 | −0.452293144 | 9.746122909 |
| 256 | 0.253514025 | 0.310300562 | 2.27 | −0.222099166 | 10.2584473 |

TABLE 33.d3

| N | t | P.Value | adj.P.Val | B | FC |
|---|---|---|---|---|---|
| 193 | 5.578062929 | 0.0000217701905479979 | 0.004204233 | 2.8863206 | 1.238810056 |
| 194 | −8.542517182 | 0.00000000596329188972969 | 0.000077542672206118 | 8.396017365 | 0.701977938 |
| 195 | −5.419897283 | 0.0000307827940531150 | 0.005054403 | 2.556989182 | 0.719048353 |
| 196 | −5.295421974 | 0.0000405075194431574 | 0.006131956 | 2.295788713 | 0.833366791 |
| 197 | −5.303171478 | 0.0000398191777050705 | 0.006067758 | 2.312100067 | 0.88268868 |
| 198 | −5.26401715 | 0.0000434237366404068 | 0.006490268 | 2.229621301 | 0.876968192 |
| 199 | −7.362483567 | 0.000000542792493499413 | 0.00033823 | 6.362585392 | 0.780438157 |
| 200 | −6.920589559 | 0.00000130208881243147 | 0.000596309 | 5.545829579 | 0.729270823 |
| 201 | −6.507834204 | 0.00000301932875673387 | 0.001051643 | 4.755925321 | 0.750057777 |
| 202 | −5.2522991 | 0.0000445660037600909 | 0.006607886 | 2.204905558 | 0.809644918 |
| 203 | −6.955664773 | 0.00000121355337901372 | 0.00057037 | 5.611759271 | 0.784387655 |
| 204 | −5.962344466 | 0.00000949692524861803 | 0.002437336 | 3.673443959 | 0.760200574 |

TABLE 33.d3-continued

| N | t | P.Value | adj.P.Val | B | FC |
|---|---|---|---|---|---|
| 205 | −6.959876235 | 0.00000120334955772376 | 0.00057037 | 5.619662717 | 0.783230643 |
| 206 | −5.197233953 | 0.0000503586344752859 | 0.007169673 | 2.088570872 | 0.880011182 |
| 207 | −11.12974035 | 0.0000000000855760191439498 | 0.00000370924500756165 | 12.15128673 | 0.49919585 |
| 208 | −6.217777769 | 0.00000552671615692750 | 0.001607736 | 4.185638781 | 0.830357728 |
| 209 | 5.017111985 | 0.0000752584737618864 | 0.009531926 | 1.705942088 | 1.133741668 |
| 210 | −6.41916147 | 0.0000362800718522512 | 0.001213128 | 4.582892014 | 0.844704648 |
| 211 | −6.682538446 | 0.00000210909449126610 | 0.000822758 | 5.093407671 | 0.833664171 |
| 212 | −5.560509533 | 0.0000226203345689378 | 0.004245102 | 2.849918149 | 0.777318413 |
| 213 | −5.730820553 | 0.0000156218240048023 | 0.003423637 | 3.201499442 | 0.787334878 |
| 214 | −5.520053358 | 0.0000247115601581872 | 0.004416684 | 2.76587789 | 0.741163183 |
| 215 | −6.250406563 | 0.00000516052782800820 | 0.001572751 | 4.250401752 | 0.854100935 |
| 216 | 10.84451596 | 0.0000000001131747089617564 | 0.00000513945396598118 | 11.78059039 | 1.485848734 |
| 217 | −5.219666256 | 0.0000479113597540456 | 0.006948038 | 2.136000723 | 0.840848928 |
| 218 | −7.685287888 | 0.000000291255727507992 | 0.000248829 | 6.940120692 | 0.72965308 |
| 219 | 6.038727238 | 0.00000807050267149696 | 0.002138121 | 3.82756083 | 1.232745812 |
| 220 | −5.887655696 | 0.0000111429983778881 | 0.002634475 | 3.521975599 | 0.826287206 |
| 221 | −5.456068621 | 0.0000284312776732711 | 0.004832995 | 2.632564179 | 0.817470277 |
| 222 | −6.439861138 | 0.00000347543587764876 | 0.00118927 | 4.623388743 | 0.799391142 |
| 223 | −7.58351219 | 0.000000353881586378611 | 0.000270685 | 6.759774473 | 0.808848462 |
| 224 | 5.073968482 | 0.0000662731427137706 | 0.008670693 | 1.827052816 | 1.16341076 |
| 225 | −8.114538033 | 0.00000130057060380918 | 0.000126838 | 7.683168577 | 0.789557138 |
| 226 | −8.247664393 | 0.000000101785970767585 | 0.000104491 | 7.907878402 | 0.664139813 |
| 227 | 5.610514627 | 0.0000202836082244147 | 0.0039673 | 2.953520209 | 1.205212661 |
| 228 | 5.212827288 | 0.0000486443312060846 | 0.007002271 | 2.121546166 | 1.151900019 |
| 229 | 5.148455682 | 0.0000561297752836139 | 0.007709938 | 1.985261129 | 1.194746794 |
| 230 | 5.217277153 | 0.0000481661245096288 | 0.006959113 | 2.130951759 | 1.135671685 |
| 231 | 5.625048666 | 0.0000196519236843458 | 0.003951657 | 2.983574644 | 1.152730969 |
| 232 | 5.403530817 | 0.0000319112455916194 | 0.005171517 | 2.522744449 | 1.165040945 |
| 233 | −5.566335209 | 0.0000223344813272804 | 0.004245102 | 2.862003659 | 0.862904344 |
| 234 | −5.636876017 | 0.0000191527686471659 | 0.003891404 | 3.008012687 | 0.82257767 |
| 235 | −7.033201866 | 0.00000103922865236368 | 0.000532857 | 5.756832398 | 0.710857134 |
| 236 | −6.838387929 | 0.00000153671624367046 | 0.000651601 | 5.390579615 | 0.789678753 |
| 237 | −8.482004556 | 0.0000000664881274369185 | 0.000078597025797400 | 8.296903933 | 0.740202273 |
| 238 | −8.714888103 | 0.0000000438512643767021 | 0.000068425512933406 | 8.675347723 | 0.762585392 |
| 239 | 5.20108882 | 0.0000499291851743305 | 0.0071608 | 2.09672508 | 1.192271822 |
| 240 | −5.785373903 | 0.0000138850583130889 | 0.00313096 | 3.313338935 | 0.868000266 |
| 241 | 5.491634267 | 0.0000262980290948125 | 0.004539319 | 2.706725558 | 1.252054372 |
| 242 | −5.2300823 | 0.0000468165952760807 | 0.00681461 | 2.158006387 | 0.853494705 |
| 243 | −5.382789941 | 0.0000334023098752759 | 0.005277635 | 2.479303216 | 0.84966128 |
| 244 | −5.150382787 | 0.0000558894507041173 | 0.007704055 | 1.98934712 | 0.813306601 |
| 245 | −5.523154669 | 0.0000245444648394958 | 0.004416684 | 2.772327241 | 0.872923188 |
| 246 | −6.676552256 | 0.00000213503855287626 | 0.000824632 | 5.081919838 | 0.779723773 |
| 247 | −5.77339837 | 0.0000142485411810267 | 0.003153542 | 3.288821006 | 0.794922773 |
| 248 | −6.210571382 | 0.0000561113691758904 | 0.001609489 | 4.171314668 | 0.793881722 |
| 249 | 6.879077809 | 0.00000141555716527236 | 0.000606823 | 5.467557689 | 1.263289306 |
| 250 | −5.639859813 | 0.0000190289062701250 | 0.00388648 | 3.01417515 | 0.874055006 |
| 251 | 5.102219822 | 0.0000622226113504969 | 0.008370014 | 1.887120126 | 1.218623588 |
| 252 | −4.99093597 | 0.0000798300028297843 | 0.009820552 | 1.65008659 | 0.65659288 |
| 253 | −5.313651741 | 0.0000389072312178752 | 0.005987456 | 2.334148884 | 0.671702405 |
| 254 | −10.36202183 | 0.00000000278690058103200 | 0.0000083628455127737 | 11.13041085 | 0.739416 |
| 255 | −9.587137852 | 0.0000000097931846734589 | 0.000020106954426927 | 10.02246539 | 0.7308802 |
| 256 | −5.143048179 | 0.0000568097724220449 | 0.007775962 | 1.973793794 | 0.857317105 |

TABLE 33.d4

| N | FC_1 | LS | Loop Detected | Probe sequence 60 mer |
|---|---|---|---|---|
| 193 | 1.238810056 | 1 | Sprinter | AATATTTCTTTAAGACTAATTGTTCTACTCGAGGCATTAAATACTTTCCCTCTAGCCAGC (SEQ ID NO: 1212) |
| 194 | −1.424546194 | −1 | Stayer | CAGAATCTCTCTGCTTAATGGGCCCATATCGACAGCTTAACGGATTTTCACAGAGTACAC (SEQ ID NO: 1213) |
| 195 | −1.390727058 | −1 | Stayer | CATTGGAGTGGAATAGAGAGCTTATAAATCGACAGCTTAACGGATTTTCACAGAGTACAC (SEQ ID NO: 1214) |
| 196 | −1.199951823 | −1 | Stayer | GACCCTATGCTCCTTTCCTGGAACATCATCGAGATGTATGACAACAAATGCCAGTATTTA (SEQ ID NO: 1215) |
| 197 | −1.132902259 | −1 | Stayer | TAACCAAACCATAGTGTGAAAACAGCTTTCGATATGTAATTTTATTAAGAATATTATTTT (SEQ ID NO: 1216) |
| 198 | −1.140292212 | −1 | Stayer | GAATGGGTACTCTGCTGGAAAGTTGATTTCGAGGTGAAAGCCGAGGGAAGTGAGTAGCCA (SEQ ID NO: 1217) |

TABLE 33.d4-continued

| N | FC_1 | LS | Loop Detected | Probe sequence 60 mer |
|---|------|----|----|----|
| 199 | -1.281331507 | -1 | Stayer | TTGGGTACTAGAACCCTTACAGCTCCTTTCGATAAGAATGCCAGGATCTTTTGCTGGGGA (SEQ ID NO: 1218) |
| 200 | -1.3712327 | -1 | Stayer | TTGGGTACTAGAACCCTTACAGCTCCTTTCGACAAATCTATGATATCAAGAATAACTAAC (SEQ ID NO: 1219) |
| 201 | -1.333230627 | -1 | Stayer | TAACATGCTCAGTAAATGCTACCTGTGGTCGAGCTTTTCTTATCCATGCTTCAGGGGTGA (SEQ ID NO: 1220) |
| 202 | -1.23510934 | -1 | Stayer | ATCCCTGTACTCCTGTGACCAGGGCACGTCGAGCTTTCAACTGAAACTTAGGATTTTGGA (SEQ ID NO: 1221) |
| 203 | -1.27487983 | -1 | Stayer | ATCCCTGTACTCCTGTGACCAGGGCACGTCGATTAATATAATACATCACATTAACAGAAT (SEQ ID NO: 1222) |
| 204 | -1.315442311 | -1 | Stayer | CAAAAAATGCACTCTTTCAAAGAATCTCTCGAAAAGCAAGATCCTTCTTTTAATGGAATT (SEQ ID NO: 1223) |
| 205 | -1.276763121 | -1 | Stayer | CAAAAAATGCACTCTTTCAAAGAATCTCTCGATTCAGTGTGATTGGAATCATGGAAGGAG (SEQ ID NO: 1224) |
| 206 | -1.136349196 | -1 | Stayer | TTAAACAACAAAACCCAACAGAGGAAATTCGACACTTACCACAATGAGGTGGATGCCTTC (SEQ ID NO: 1225) |
| 207 | -2.003221783 | -1 | Stayer | GTCACTGCCTTCAAACCTTATGGTACGATCGAGAAGCTAAAACAAGTATAAATATATATG (SEQ ID NO: 1226) |
| 208 | -1.204300227 | -1 | Stayer | CTGCTGTTTACTCAATATCATGACAATTTCGACTGGTAAATATGGTAACCCCAAAGCAAT (SEQ ID NO: 1227) |
| 209 | 1.133741668 | 1 | Sprinter | TTGTCACAGTGTAGTGAGGAGATAAATATCGAAGAGGATAAACTGGTCCCTGCACAGTCT (SEQ ID NO: 1228) |
| 210 | -1.183845741 | -1 | Stayer | GTTACAACCCCTGACATGAAAAAGGTACTCGATGCTGGGTTTGAGTAACGCTGGAGCTGC (SEQ ID NO: 1229) |
| 211 | -1.199523783 | -1 | Stayer | GTTACAACCCCTGACATGAAAAAGGTACTCGAAGAGGATAAACTGGTCCCTGCACAGTCT (SEQ ID NO: 1230) |
| 212 | -1.286474093 | -1 | Stayer | ACAGTAAAGGTGTTTTGGACTTATTGGCTCGATGTTAAAGAATAGTTCTATTCTACTTTG (SEQ ID NO: 1231) |
| 213 | -1.270107585 | -1 | Stayer | ACAGTAAAGGTGTTTTGGACTTATTGGCTCGAAATATATTATGATGTACCTCTGAAAAAA (SEQ ID NO: 1232) |
| 214 | -1.349230538 | -1 | Stayer | TGTGTTTTACTTTTAATGGAGTTGCTGTTCGAGAGTGGTGTGTTAGCTCTCCGCCTTGGG (SEQ ID NO: 1233) |
| 215 | -1.170821807 | -1 | Stayer | TAAGTCTCTTCTGAAAAAAAATAGCAGGTCGAATCCAATCACATTTGCGAATGCCCTTCA (SEQ ID NO: 1234) |
| 216 | 1.485848734 | 1 | Sprinter | ATTGTGCGCAAAGGAAATTATTCTAAGATCGAACACTGTTCAGCTCTTTTGTCTGGTGAT (SEQ ID NO: 1235) |
| 217 | -1.189274276 | -1 | Stayer | AACCAGACTGATGTTAACATCGCCACGTTCGAGTACCTGTGCTCAGCAACAAGATGGCTT (SEQ ID NO: 1236) |
| 218 | -1.370514328 | -1 | Stayer | AAGCCATCTTGTTGCTGAGCACAGGTACTCGAACACTGTTCAGCTCTTTTGTCTGGTGAT (SEQ ID NO: 1237) |
| 219 | 1.232745812 | 1 | Sprinter | AAATCAGAGAGACACTCTCTGGATGGTCTCGAACACTAGATCTTTGAGTCTAGTCTCTTT (SEQ ID NO: 1238) |
| 220 | -1.210232946 | -1 | Stayer | GAGTCTCTAGGTACCTGTCCGCTTCAGGTCGAGCATCTGGACTAATTTGTCCCGAGCTGC (SEQ ID NO: 1239) |
| 221 | -1.223286066 | -1 | Stayer | GAGTCTCTAGGTACCTGTCCGCTTCAGGTCGATAGAAATGAAGAGCTCAGCTGGGTGGCT (SEQ ID NO: 1240) |
| 222 | -1.250952065 | -1 | Stayer | GAGTCTCTAGGTACCTGTCCGCTTCAGGTCGATTTGGAGATGGTTGTACAATGCTATAAA (SEQ ID NO: 1241) |
| 223 | -1.236325525 | -1 | Stayer | AGGAAATGAACATCTAAATTCAAGAAGCTCGACAGTACTAGAAACCAACCCCTTCTCCCC (SEQ ID NO: 1242) |
| 224 | 1.16341076 | 1 | Sprinter | CTATTTCATGCTACGCCCTTGGGCTTTATCGAGAGTCTGCTGAATTTGTCTGCCACCTCT (SEQ ID NO: 1243) |

TABLE 33.d4-continued

| N | FC_1 | LS | Loop Detected | Probe sequence 60 mer |
|---|------|----|----|----|
| 225 | -1.266532784 | -1 | Stayer | TAATTAAAATTTGATAATAAAGGCCTACTCGATGCCCTCCTTCTTGTACTCCTCCTGCTC (SEQ ID NO: 1244) |
| 226 | -1.505707053 | -1 | Stayer | CCTCCAGGAATTCTGTTAAGATGTATTTTCGAGTTAGAAAATTCCCCTCTATTTGTAGTT (SEQ ID NO: 1245) |
| 227 | 1.205212661 | 1 | Sprinter | ATAAAAAGCAAATAAGTGCTAGTGTTACTCGAAAAGTTGGCAGGTCTTAATCTACTGGAT (SEQ ID NO: 1246) |
| 228 | 1.151900019 | 1 | Sprinter | ATAAAAAGCAAATAAGTGCTAGTGTTACTCGAGGCTTACATTTCATCTGGGAAGTTTTTC (SEQ ID NO: 1247) |
| 229 | 1.194746794 | 1 | Sprinter | ATAAAAAGCAAATAAGTGCTAGTGTTACTCGAATACCACGTTTACTCAGACAAGAGAAAC (SEQ ID NO: 1248) |
| 230 | 1.135671685 | 1 | Sprinter | ATAAAAAGCAAATAAGTGCTAGTGTTACTCGAGCCTGTTGGGCGTGAGATAATCACCTTC (SEQ ID NO: 1249) |
| 231 | 1.152730969 | 1 | Sprinter | ATAAAAAGCAAATAAGTGCTAGTGTTACTCGAGCCTCCAGAACTCTGAGGAATAAATGTC (SEQ ID NO: 1250) |
| 232 | 1.165040945 | 1 | Sprinter | ATAAAAAGCAAATAAGTGCTAGTGTTACTCGAATTTCGTTTCTGCTAGTGCTTTAGCACA (SEQ ID NO: 1251) |
| 233 | -1.158877003 | -1 | Stayer | ATGTCCAGAGAATGGAAACAAACCTGACTCGAGGAATACGTGGGAAGAAATGGGGTACAG (SEQ ID NO: 1252) |
| 234 | -1.215690672 | -1 | Stayer | AATAACCAACATAACTAGAAAATTCTCCTCGAGGAATACGTGGGAAGAAATGGGGTACAG (SEQ ID NO: 1253) |
| 235 | -1.40675243 | -1 | Stayer | CTGTACCCCATTTCTTCCCACGTATTCCTCGAGAGCTATATCAAAAAGATTTTGGTATTT (SEQ ID NO: 1254) |
| 236 | -1.266337731 | -1 | Stayer | GACAGGGGTCTAGAATCATAGATTTCCCTCGATCTTGAGGTTGACAGTTACCACAATTAT (SEQ ID NO: 1255) |
| 237 | -1.350982072 | -1 | Stayer | GACAGGGGTCTAGAATCATAGATTTCCCTCGAATATGTAGTTGAGTCAGATCTGGGATTT (SEQ ID NO: 1256) |
| 238 | -1.311328555 | -1 | Stayer | GACAGGGGTCTAGAATCATAGATTTCCCTCGATACCCCAGTTTTCTTTTTGATCCCTTCA (SEQ ID NO: 1257) |
| 239 | 1.192271822 | 1 | Sprinter | GCTTCCAGAAATGAGAGCAGACTTCAAGTCGATATTTTGAATAAGGCTTACAGCAAGGGT (SEQ ID NO: 1258) |
| 240 | -1.152073379 | -1 | Stayer | GGTGTGTAGGCACAGGGGTTGGATCTCTTCGATTTTTATGGGTATCTCACTCTACAATTT (SEQ ID NO: 1259) |
| 241 | 1.252054372 | 1 | Sprinter | ACATGCTCAGAAATAAAAACATTAATTTTCGACAAATACTGTAGGATTTCAAGGGAAGAA (SEQ ID NO: 1260) |
| 242 | -1.171653431 | -1 | Stayer | TTAAAGCTATAGTGAATGAAGCAATATATCGAGTTGTCTTCTAAAAGACAGTCTAATAAT (SEQ ID NO: 1261) |
| 243 | -1.176939591 | -1 | Stayer | GAGTCTCTAGGTACCTGTCCGCTTCAGGTCGAGCTGTCAAGGGGCAAAAAAAAAAAAAAA (SEQ ID NO: 1262) |
| 244 | -1.229548609 | -1 | Stayer | AGGGCACTGCCCTTGATCAGGTAAATGTTCGACCTGAAGCGGACAGGTACCTAGAGACTC (SEQ ID NO: 1263) |
| 245 | -1.145576167 | 1 | Stayer | GAGTCTCTAGGTACCTGTCCGCTTCAGGTCGATGGTCGGCACATTTTCGTAGCCACCCTG (SEQ ID NO: 1264) |
| 246 | -1.282505466 | -1 | Stayer | GAGTCTCTAGGTACCTGTCCGCTTCAGGTCGAAATTAACAGACACATCTGTGTCTGCTCT (SEQ ID NO: 1265) |
| 247 | -1.257983837 | -1 | Stayer | GCGAGGTCATGAATGTACAAGTATAATGTCGAGTATAAGTTAAACGTGATTAAATGTAAG (SEQ ID NO: 1266) |
| 248 | -1.259633485 | -1 | Stayer | GCGAGGTCATGAATGTACAAGTATAATGTCGATTAAAATATTTTACTTTTCCTTAATTAC (SEQ ID NO: 1267) |
| 249 | 1.263289306 | 1 | Sprinter | ATGGGTATTGCTTTATGCCTGCTGTGTTTCGAATTGAATGGAGACGCCTTTTGGTAGGAT (SEQ ID NO: 1268) |
| 250 | -1.144092755 | -1 | Stayer | CTTACATTTAATCACGTTTAACTTATACTCGAGGTGCTCATCCCGAGGTACTTAGCGCCT (SEQ ID NO: 1269) |

TABLE 33.d4-continued

| N | FC_1 | LS | Loop Detected | Probe sequence 60 mer |
|---|---|---|---|---|
| 251 | 1.218623588 | 1 | Sprinter | ATCCTACCAAAAGGCGTCTCCATTCAATTCGATTAAAATATTTTACTTTTCCTTAATTAC (SEQ ID NO: 1270) |
| 252 | -1.523013774 | -1 | Stayer | CAACGACACAAAGGTGTACACACAAACATCGATTTTTGCTAAGATGGTTGCAAATGATAG (SEQ ID NO: 1271) |
| 253 | -1.488754532 | -1 | Stayer | CAACGACACAAAGGTGTACACACAAACATCGAAAGAAAGATTTCTTTAGACTCTTAAGAT (SEQ ID NO: 1272) |
| 254 | -1.352418666 | -1 | Stayer | CAGCTGTACATTTTTAGTTGTGCGCACTTCGACGAGTCAAAACCGACGGAAGTCAGGCAG (SEQ ID NO: 1273) |
| 255 | -1.368213286 | -1 | Stayer | AATCTCACTAGAAGGTACAGGTGTCAAGTCGACGAGTCAAAACCGACGGAAGTCAGGCAG (SEQ ID NO: 1274) |
| 256 | -1.166429544 | -1 | Stayer | CTCAGGTTAAGTCCCCCTGTACCTGCTGTCGAGACAGACGTGTGCCTTCTTGAAAAAGCC (SEQ ID NO: 1275) |

TABLE 33.d5

| N | Probe Location | | | | | 4 kb Sequence Location | | | |
|---|---|---|---|---|---|---|---|---|---|
| | Chr | Start1 | End1 | Start2 | End2 | Chr | Start1 | End1 | Start2 |
| 193 | 17 | 48760895 | 48760926 | 48985578 | 48985609 | 17 | 48756925 | 48760926 | 48985578 |
| 194 | 9 | 81548175 | 81548206 | 81579682 | 81579713 | 9 | 81544205 | 81548206 | 81579682 |
| 195 | 9 | 81540380 | 81540411 | 81579682 | 81579713 | 9 | 81540380 | 81544381 | 81579682 |
| 196 | 31 | 2794971 | 2795002 | 2851292 | 2851323 | 31 | 2791001 | 2795002 | 2851292 |
| 197 | 24 | 16803396 | 16803427 | 16918062 | 16918093 | 24 | 16803396 | 16807397 | 16914092 |
| 198 | 8 | 3352241 | 3352272 | 3404723 | 3404754 | 8 | 3352241 | 3356242 | 3404723 |
| 199 | 8 | 3439495 | 3439526 | 3479117 | 3479148 | 8 | 3435525 | 3439526 | 3475147 |
| 200 | 8 | 3439495 | 3439526 | 3469888 | 3469919 | 8 | 3435525 | 3439526 | 3469888 |
| 201 | 13 | 19588585 | 19588616 | 19619059 | 19619090 | 13 | 19584615 | 19588616 | 19615089 |
| 202 | 14 | 2229196 | 2229227 | 2274036 | 2274067 | 14 | 2229196 | 2233197 | 2274036 |
| 203 | 14 | 2229196 | 2229227 | 2401910 | 2401941 | 14 | 2229196 | 2233197 | 2401910 |
| 204 | 15 | 37903511 | 37903542 | 38029907 | 38029938 | 15 | 37903511 | 37907512 | 38029907 |
| 205 | 15 | 37903511 | 37903542 | 38069969 | 38070000 | 15 | 37903511 | 37907512 | 38069969 |
| 206 | 5 | 1010267 | 1010298 | 1038449 | 1038480 | 5 | 1006297 | 1010298 | 1034479 |
| 207 | 10 | 19508221 | 19508252 | 19593723 | 19593754 | 10 | 19508221 | 19512222 | 19589753 |
| 208 | 1 | 104992073 | 104992104 | 105164945 | 105164976 | 1 | 104992073 | 104996074 | 105160975 |
| 209 | 17 | 4337612 | 4337643 | 4528348 | 4528379 | 17 | 4333642 | 4337643 | 4524378 |
| 210 | 17 | 4418766 | 4418797 | 4517894 | 4517925 | 17 | 4414796 | 4418797 | 4513924 |
| 211 | 17 | 4418766 | 4418797 | 4528348 | 4528379 | 17 | 4414796 | 4418797 | 4524378 |
| 212 | 7 | 12601995 | 12602026 | 12717637 | 12717668 | 7 | 12601995 | 12605996 | 12713667 |
| 213 | 7 | 12717637 | 12717668 | 12737470 | 12737501 | 7 | 12713667 | 12717668 | 12737470 |
| 214 | 12 | 19894956 | 19894987 | 19974797 | 19974828 | 12 | 19894956 | 19898957 | 19970827 |
| 215 | 12 | 19992086 | 19992117 | 20053517 | 20053548 | 12 | 19992086 | 19996087 | 20049547 |
| 216 | 11 | 31942510 | 31942541 | 32032038 | 32032069 | 11 | 31942510 | 31946511 | 32032038 |
| 217 | 11 | 31953015 | 31953046 | 32042190 | 32042221 | 11 | 31953015 | 31957016 | 32038220 |
| 218 | 11 | 31953015 | 31953046 | 32032038 | 32032069 | 11 | 31953015 | 31957016 | 32032038 |
| 219 | 18 | 66450044 | 66450075 | 66500458 | 66500489 | 18 | 66446074 | 66450075 | 66496488 |
| 220 | 2 | 39767816 | 39767847 | 39804925 | 39804956 | 2 | 39763846 | 39767847 | 39804925 |
| 221 | 2 | 39767816 | 39767847 | 39839229 | 39839260 | 2 | 39763846 | 39767847 | 39835259 |
| 222 | 2 | 39767816 | 39767847 | 39835824 | 39835855 | 2 | 39763846 | 39767847 | 39835824 |
| 223 | 8 | 6868138 | 6868169 | 6923181 | 6923212 | 8 | 6868138 | 6872139 | 6923181 |
| 224 | 10 | 20037236 | 20037267 | 20084055 | 20084086 | 10 | 20037236 | 20041237 | 20080085 |
| 225 | 11 | 52882980 | 52883011 | 52915290 | 52915321 | 11 | 52882980 | 52886981 | 52911320 |
| 226 | 6 | 1098854 | 1098885 | 989242 | 989273 | 6 | 1098854 | 1102855 | 989242 |
| 227 | 11 | 17193641 | 17193672 | 17368932 | 17368963 | 11 | 17193641 | 17197642 | 17364962 |
| 228 | 11 | 17206623 | 17206654 | 17368932 | 17368963 | 11 | 17206623 | 17210624 | 17364962 |
| 229 | 11 | 17246461 | 17246492 | 17368932 | 17368963 | 11 | 17246461 | 17250462 | 17364962 |
| 230 | 11 | 17257199 | 17257230 | 17368932 | 17368963 | 11 | 17257199 | 17261200 | 17364962 |
| 231 | 11 | 17267739 | 17267770 | 17368932 | 17368963 | 11 | 17267739 | 17271740 | 17364962 |
| 232 | 11 | 17290815 | 17290846 | 17368932 | 17368963 | 11 | 17290815 | 17294816 | 17364962 |
| 233 | 1 | 61323595 | 61323626 | 61392274 | 61392305 | 1 | 61319625 | 61323626 | 61388304 |
| 234 | 1 | 61338770 | 61338801 | 61392274 | 61392305 | 1 | 61334800 | 61338801 | 61388304 |
| 235 | 1 | 61350438 | 61350469 | 61392274 | 61392305 | 1 | 61350438 | 61354439 | 61388304 |
| 236 | 1 | 109635329 | 109635360 | 109741316 | 109741347 | 1 | 109635329 | 109639330 | 109737346 |
| 237 | 1 | 109711483 | 109711514 | 109741316 | 109741347 | 1 | 109711483 | 109715484 | 109737346 |
| 238 | 1 | 109741316 | 109741347 | 109779877 | 109779908 | 1 | 109737346 | 109741347 | 109779877 |
| 239 | 25 | 25721432 | 25721463 | 25884535 | 25884566 | 25 | 25717462 | 25721463 | 25884535 |
| 240 | 11 | 22765246 | 22765277 | 22824653 | 22824684 | 11 | 22761276 | 22765277 | 22824653 |
| 241 | 23 | 34300375 | 34300406 | 34541066 | 34541097 | 23 | 34300375 | 34304376 | 34537096 |

TABLE 33.d5-continued

| | | Probe Location | | | | 4 kb Sequence Location | | |
|---|---|---|---|---|---|---|---|---|
| N | Chr | Start1 | End1 | Start2 | End2 | Chr | Start1 | End1 | Start2 |
| 242 | 23 | 34370479 | 34370510 | 34413070 | 34413101 | 23 | 34366509 | 34370510 | 34413070 |
| 243 | 2 | 39707018 | 39707049 | 39767816 | 39767847 | 2 | 39707018 | 39711019 | 39763846 |
| 244 | 2 | 39718640 | 39718671 | 39767816 | 39767847 | 2 | 39714670 | 39718671 | 39763846 |
| 245 | 2 | 39714609 | 39714640 | 39767816 | 39767847 | 2 | 39714609 | 39718610 | 39763846 |
| 246 | 2 | 39741527 | 39741558 | 39767816 | 39767847 | 2 | 39741527 | 39745528 | 39763846 |
| 247 | 2 | 66195314 | 66195345 | 66310948 | 66310979 | 2 | 66191344 | 66195345 | 66306978 |
| 248 | 2 | 66195314 | 66195345 | 66291709 | 66291740 | 2 | 66191344 | 66195345 | 66291709 |
| 249 | 2 | 66222272 | 66222303 | 66454370 | 66454401 | 2 | 66218302 | 66222303 | 66450400 |
| 250 | 2 | 66310948 | 66310979 | 66324859 | 66324890 | 2 | 66306978 | 66310979 | 66324859 |
| 251 | 2 | 66291709 | 66291740 | 66454370 | 66454401 | 2 | 66291709 | 66295710 | 66450400 |
| 252 | 16 | 35687870 | 35687901 | 35711378 | 35711409 | 16 | 35683900 | 35687901 | 35707408 |
| 253 | 16 | 35687870 | 35687901 | 35734783 | 35734814 | 16 | 35683900 | 35687901 | 35730813 |
| 254 | 11 | 25089999 | 25090030 | 25214955 | 25214986 | 11 | 25089999 | 25094000 | 25214955 |
| 255 | 11 | 25177016 | 25177047 | 25214955 | 25214986 | 11 | 25177016 | 25181017 | 25214955 |
| 256 | 21 | 5606382 | 5606413 | 5698848 | 5698879 | 21 | 5606382 | 5610383 | 5694878 |

TABLE 33.d6

| N | 4 kb Sequence Location End2 | Probe | Primer ID-1 |
|---|---|---|---|
| 193 | 48989579 | LMO7_17_48756745_48760926_48985578_48994371_FR | OBD RD043.769 |
| 194 | 81583683 | LY6D_9_81540380_81548206_81579682_81590550_FR | OBD RD043.773 |
| 195 | 81583683 | LY6D_9_81540380_81548206_81579682_81590550_RR | OBD RD043.777 |
| 196 | 2855293 | MAP3K4_31_2786762_2795002_2851292_2856203_FR | OBD RD043.781 |
| 197 | 16918093 | MAP3K9_24_16803396_16807626_16910389_16918093_RF | OBD RD043.785 |
| 198 | 3408724 | MAPK1_8_3352241_3355955_3404723_3412822_RR | OBD RD043.789 |
| 199 | 3479148 | MAPK1_8_3435741_3439526_3469888_3479148_FF | OBD RD043.793 |
| 200 | 3473889 | MAPK1_8_3435741_3439526_3469888_3479148_FR | OBD RD043.797 |
| 201 | 19619090 | MAPK3_13_19583177_19588616_19608792_19619090_FF | OBD RD043.801 |
| 202 | 2278037 | MAPK9_14_2229196_2237168_2274036_2279957_RR | OBD RD043.805 |
| 203 | 2405911 | MAPK9_14_2229196_2237168_2401910_2410518_RR | OBD RD043.809 |
| 204 | 38033908 | MDH1_15_37903511_37909683_38029907_38037711_RR | OBD RD043.813 |
| 205 | 38073970 | MDH1_15_37903511_37909683_38069969_38081007_RR | OBD RD043.817 |
| 206 | 1038480 | MDM4_5_1002213_1010298_1034976_1038480_FF | OBD RD043.821 |
| 207 | 19593754 | MED25_10_19508221_19515457_19591613_19593754_RF | OBD RD043.825 |
| 208 | 105164976 | MEF2A_1_104992073_105002150_105161756_105164976_RF | OBD RD043.829 |
| 209 | 4528379 | MIPEP_17_4332285_4337643_4521242_4528379_FF | OBD RD043.833 |
| 210 | 4517925 | MIPEP_17_4413535_4418797_4506914_4517925_FF | OBD RD043.837 |
| 211 | 4528379 | MIPEP_17_4413535_4418797_4521242_4528379_FF | OBD RD043.841 |
| 212 | 12717668 | MMP1_7_12601995_12610418_12711728_12717668_RF | OBD RD043.845 |
| 213 | 12741471 | MMP1_7_12711728_12717668_12737470_12745025_FR | OBD RD043.849 |
| 214 | 19974828 | MS4A2_12_19894956_19896244_19962410_19974828_RF | OBD RD043.853 |
| 215 | 20053548 | MS4A2_12_19992086_20002065_20049543_20053548_RF | OBD RD043.857 |
| 216 | 32036039 | MSI2_11_31942510_31947907_32032038_32042221_RR | OBD RD043.861 |
| 217 | 32042221 | MSI2_11_31953015_31955643_32032038_32042221_RF | OBD RD043.865 |
| 218 | 32036039 | MSI2_11_31953015_31955643_32032038_32042221_RR | OBD RD043.869 |
| 219 | 66500489 | MSTN_18_66448734_66450075_66490497_66500489_FF | OBD RD043.873 |
| 220 | 39808926 | MTHFR_2_39760745_39767847_39804925_39808549_FR | OBD RD043.877 |
| 221 | 39839260 | MTHFR_2_39760745_39767847_39835824_39839260_FF | OBD RD043.881 |
| 222 | 39839825 | MTHFR_2_39760745_39767847_39835824_39839260_FR | OBD RD043.885 |
| 223 | 6927182 | MTMR3_8_6868138_6874813_6923181_6926871_RR | OBD RD043.889 |
| 224 | 20084086 | MYBPC2_10_20037236_20038811_20080873_20084086_RF | OBD RD043.893 |
| 225 | 52915321 | MYH1_11_52882980_52886797_52907287_52915321_RF | OBD RD043.897 |
| 226 | 993243 | MYL1_6_1098854_1104299_989242_996235_RR | OBD RD043.901 |
| 227 | 17368963 | MYL4_11_17193641_17194702_17358881_17368963_RF | OBD RD043.905 |
| 228 | 17368963 | MYL4_11_17206623_17211708_17358881_17368963_RF | OBD RD043.909 |
| 229 | 17368963 | MYL4_11_17246461_17251113_17358881_17368963_RF | OBD RD043.913 |
| 230 | 17368963 | MYL4_11_17257199_17259878_17358881_17368963_RF | OBD RD043.917 |
| 231 | 17368963 | MYL4_11_17267739_17271299_17358881_17368963_RF | OBD RD043.921 |
| 232 | 17368963 | MYL4_11_17290815_17294484_17358881_17368963_RF | OBD RD043.925 |
| 233 | 61392305 | MYOZ1_1_61314759_61323626_61385709_61392305_FF | OBD RD043.929 |
| 234 | 61392305 | MYOZ1_1_61323626_61338801_61385709_61392305_FF | OBD RD043.933 |
| 235 | 61392305 | MYOZ1_1_61350438_61357018_61385709_61392305_RF | OBD RD043.937 |
| 236 | 109741347 | NDN_1_109635329_109640204_109733366_109741347_RF | OBD RD043.941 |
| 237 | 109741347 | NDN_1_109711483_109720818_109733366_109741347_RF | OBD RD043.945 |
| 238 | 109783878 | NDN_1_109733366_109741347_109779877_109789352_FR | OBD RD043.949 |
| 239 | 25888536 | NDUFA8_25_25717207_25721463_25884535_25891335_FR | OBD RD043.953 |
| 240 | 22828654 | NEUROD2_11_22762666_22765277_22824653_22836914_FR | OBD RD043.957 |
| 241 | 34541097 | NFIB_23_34300375_34312881_34537544_34541097_RF | OBD RD043.961 |
| 242 | 34417071 | NFIB_23_34364872_34370510_34413070_34423547_FR | OBD RD043.965 |
| 243 | 39767847 | NPPA_2_39707018_39708108_39760745_39767847_RF | OBD RD043.969 |

TABLE 33.d6-continued

| N | 4 kb Sequence Location End2 | Probe | Primer ID-1 |
|---|---|---|---|
| 244 | 39767847 | NPPA__2__39714609__39718671__39760745__39767847__FF | OBD RD043.973 |
| 245 | 39767847 | NPPA__2__39714609__39718671__39760745__39767847__RF | OBD RD043.977 |
| 246 | 39767847 | NPPA__2__39741527__39742701__39760745__39767847__RF | OBD RD043.981 |
| 247 | 66310979 | PALLD__2__66194319__66195345__66291709__66310979__FF | OBD RD043.985 |
| 248 | 66295710 | PALLD__2__66194319__66195345__66291709__66310979__FR | OBD RD043.989 |
| 249 | 66454401 | PALLD__2__66212034__66222303__66449615__66454401__FF | OBD RD043.993 |
| 250 | 66328860 | PALLD__2__66291709__66310979__66324859__66327343__FR | OBD RD043.997 |
| 251 | 66454401 | PALLD__2__66291709__66310979__66449615__66454401__RF | OBD RD043.1001 |
| 252 | 35711409 | PCBP4__16__35681721__35687901__35707118__35711409__FF | OBD RD043.1005 |
| 253 | 35734814 | PCBP4__16__35681721__35687901__35729420__35734814__FF | OBD RD043.1009 |
| 254 | 25218956 | PHOSPHO1__11__25089999__25092180__25214955__25221072__RR | OBD RD043.1013 |
| 255 | 25218956 | PHOSPHO1__11__25177016__25183355__25214955__25221072__RR | OBD RD043.1017 |
| 256 | 5698879 | PIK3Rl__21__5606382__5618174__5697527__5698879__RF | OBD RD043.1021 |

TABLE 33.d7

| N | Primer Sequence | Primer ID-2 | Primer Sequence |
|---|---|---|---|
| 193 | TTTTGTGTCCTAATGGAAGGCTGTGC (SEQ ID NO: 1276) | OBD RD043.771 | CCCGAGTGCTCAGATTCTTGCTGG (SEQ ID NO: 1340) |
| 194 | GGCACTTCTGGTGTTTCAGCCTC (SEQ ID NO: 1277) | OBD RD043.775 | CGGACGCTGGTTCCATAGTCGTG (SEQ ID NO: 1341) & (SEQ ID NO: 1342) |
| 195 | CAGTGCGGTATCGGTGAAGGGAA (SEQ ID NO: 1278) | OBD RD043.779 | CGGACGCTGGTTCCATAGTCGTG (SEQ ID NO: 1341) & (SEQ ID NO: 1342) |
| 196 | CCTGCCACATCCGCTCTTGGTTG (SEQ ID NO: 1279) | OBD RD043.783 | ACGAGCATTTATTGGGCACGGGC (SEQ ID NO: 1343) |
| 197 | CGTCTCCCCATTGTAAGGTAAACTCC (SEQ ID NO: 1280) | OBD RD043.787 | TGAAAGCAAAGCACTTGGAAAGCATA (SEQ ID NO: 1344) |
| 198 | GTTGTGTGGAAACCTCTTCTGCCCCA (SEQ ID NO: 1281) | OBD RD043.791 | GTAGATTTTGGACCTCGTGTCTCAGA (SEQ ID NO: 1345) |
| 199 | TGGTGTTGTGTGGAAACCTCTTCTGC (SEQ ID NO: 1282) | OBD RD043.795 | ATGTGGCTATCCAACTATCCCAGCAC (SEQ ID NO: 1346) |
| 200 | CCCTTTTCATCAATGTTCGGGTG (SEQ ID NO: 1283) | OBD RD043.799 | CCTGGGCGTCCTCAGACTGTCCG (SEQ ID NO: 1347) |
| 201 | CCGTGCCTTGGTTCTCTCTTCTG (SEQ ID NO: 1284) | OBD RD043.803 | GCGGTGTTGTGGGCATCAAGGTG (SEQ ID NO: 1348) |
| 202 | GGCTGACTGAAGATACTTTGGCAT (SEQ ID NO: 1285) | OBD RD043.807 | TTTTATCCTTGAAGCGTATTGAAT (SEQ ID NO: 1349) |
| 203 | CCTGGCTGACTGAAGATACTTTGGCA (SEQ ID NO: 1286) | OBD RD043.811 | TAAGAGTTGGGAAGTGGTCAAGC (SEQ ID NO: 1350) |
| 204 | TACCCATAAATGTGTTTGCTGTTCAC (SEQ ID NO: 1287) & (SEQ ID NO: 1288) | OBD RD043.815 | CGGCAAGGGAGTAAACATCAGAGCAA (SEQ ID NO: 1351) |
| 205 | TACCCATAAATGTGTTTGCTGTTCAC (SEQ ID NO: 1287) & (SEQ ID NO: 1288) | OBD RD043.819 | CCCTTTGTCTCCTGAGCATCTGGTTT (SEQ ID NO: 1352) |
| 206 | GACACTTGGAGCCTGTTGTTTCT (SEQ ID NO: 1289) | OBD RD043.823 | ACTCACATCAGTCAGCAGGAAGG (SEQ ID NO: 1353) |
| 207 | GAGTTGTAGTCCCCTGCCCACCT (SEQ ID NO: 1290) | OBD RD043.827 | CGTGTATTCTGCTGTTTCCAGGTGG (SEQ ID NO: 1354) |
| 208 | CACCACGCAGCAGCCCGAAACAT (SEQ ID NO: 1291) | OBD RD043.831 | GGGCAAGGAAACAGAGCCGTGTA (SEQ ID NO: 1355) |
| 209 | GGGAACTAACCCCACGACAAGAC (SEQ ID NO: 1292) & (SEQ ID NO: 1294) | OBD RD043.835 | GAGTCTCCCAGTCTCAGCCCATC (SEQ ID NO: 1356) & (SEQ ID NO: 1357) |
| 210 | GACTCCCACGGATAAGATGCTCC (SEQ ID NO: 1293) | OBD RD043.839 | GAGTCTCCCAGTCTCAGCCCATC (SEQ ID NO: 1356) & (SEQ ID NO: 1357) |

TABLE 33.d7-continued

| N | Primer Sequence | Primer ID-2 | Primer Sequence |
|---|---|---|---|
| 211 | GGGAACTAACCCCACGACAAGAC (SEQ ID NO: 1292) & (SEQ ID NO: 1294) | OBD RD043.843 | GGCTCAGGGTTAGGTCAGGAGTC (SEQ ID NO: 1358) |
| 212 | GGATTTCCTATGGCAGCCTCCTTGGA (SEQ ID NO: 1295) & (SEQ ID NO: 1296) | OBD RD043.847 | CCCTTCTAACCACACACAAGTCCTTT (SEQ ID NO: 1359) |
| 213 | GGATTTCCTATGGCAGCCTCCTTGGA (SEQ ID NO: 1295) & (SEQ ID NO: 1296) | OBD RD043.851 | TACATTCAGGAGGACTGGAGACG (SEQ ID NO: 1360) |
| 214 | GCTTTCCCTATTTGATTTCAGAAG (SEQ ID NO: 1297) | OBD RD043.855 | TAGGCAGGAACACTGTCTACTACA (SEQ ID NO: 1361) |
| 215 | GGGCTGTAACTGACCAGAATCTTTGA (SEQ ID NO: 1298) | OBD RD043.859 | TTACACCCTTCGGAGGCACTGGAACA (SEQ ID NO: 1362) |
| 216 | CAAGGGTGGTGTGACAGGAAGTC (SEQ ID NO: 1299) | OBD RD043.863 | GCGAGCCATCGGGAAAGAGCATC (SEQ ID NO: 1363) |
| 217 | TCAAGTCAGTGCCAGTCAAGGGC (SEQ ID NO: 1300) | OBD RD043.867 | CTCCCCACCCAAGCCAAACAGGT (SEQ ID NO: 1364) & (SEQ ID NO: 1365) |
| 218 | CTTTGTGGTTCATCCTCAGCCCC (SEQ ID NO: 1301) | OBD RD043.871 | CTCCCCACCCAAGCCAAACAGGT (SEQ ID NO: 1364) & (SEQ ID NO: 1365) |
| 219 | GGATAGTCTGTGGCAGGCTGGCTTTT (SEQ ID NO: 1302) | OBD RD043.875 | TTCTCTGCTCCTTCCTTTCCAAACTG (SEQ ID NO: 1366) |
| 220 | TGGCTACGGCTGTGAGAGATGGA (SEQ ID NO: 1303) & (SEQ ID NO: 1327) & (SEQ ID NO: 1329) | OBD RD043.879 | AGAGGAGGAAATGGCAGGCAGCC (SEQ ID NO: 1367) |
| 221 | TCACCCAAACCGTAGAGACAGGAGTG (SEQ ID NO: 1304) | OBD RD043.883 | TATCCCTAAATGTCCCTTTTCACAGC (SEQ ID NO: 1368) |
| 222 | GTGGCTACGGCTGTGAGAGATGG (SEQ ID NO: 1305) & (SEQ ID NO: 1326) | OBD RD043.887 | CCTGCGTTTCTCCAAGGATGGTC (SEQ ID NO: 1369) |
| 223 | GGAACACCAATAAGTGGGCTAATACA (SEQ ID NO: 1306) | OBD RD043.891 | CCCTGTGGCAAGTGATGGCAGTAGAA (SEQ ID NO: 1370) |
| 224 | GGGCAGAGAAAAGAGTCACTGTG (SEQ ID NO: 1307) | OBD RD043.895 | TTCTGTGGTCCCTCCGCCTCCGC (SEQ ID NO: 1371) |
| 225 | CAGGGACTCCAGAATAACTGACCC (SEQ ID NO: 1308) | OBD RD043.899 | GCAGTTCAACAGCCTGGAGCAGC (SEQ ID NO: 1372) |
| 226 | CTCAAACACTCCCAGCGTTGGCA (SEQ ID NO: 1309) | OBD RD043.903 | GCCCTAACCTCTCCCCTTCACCA (SEQ ID NO: 1373) |
| 227 | GACTGTAAAGATGAAAGAAGATTC (SEQ ID NO: 1310) & (SEQ ID NO: 1312) & (SEQ ID NO: 1315) | OBD RD043.907 | AGAAGAGACTTACTGTGCTATTTT (SEQ ID NO: 1374) |
| 228 | CAAAAGTCTGCCAAGTTATTCCTGGG (SEQ ID NO: 1311) & (SEQ ID NO: 1313) & (SEQ ID NO: 1314) | OBD RD043.911 | TCAGACTCTAACCCACCTGTTCTTGG (SEQ ID NO: 1375) |
| 229 | GACTGTAAAGATGAAAGAAGATTC (SEQ ID NO: 1310) & (SEQ ID NO: 1312) & (SEQ ID NO: 1315) | OBD RD043.915 | CTTGGTTTCCTTTGCCTTCCAGAA (SEQ ID NO: 1376) |
| 230 | CAAAAGTCTGCCAAGTTATTCCTGGG (SEQ ID NO: 1311) & (SEQ ID NO: 1313) & (SEQ ID NO: 1314) | OBD RD043.919 | GGCTCTCACTCTTTCTCCTCAGCAGA (SEQ ID NO: 1377) |
| 231 | CAAAAGTCTGCCAAGTTATTCCTGGG (SEQ ID NO: 1311) & (SEQ ID NO: 1313) & (SEQ ID NO: 1314) | OBD RD043.923 | GGCAGGATGGCATTCCACCTTATGTC (SEQ ID NO: 1378) |
| 232 | GACTGTAAAGATGAAAGAAGATTC (SEQ ID NO: 1310) & (SEQ ID NO: 1312) & (SEQ ID NO: 1315) | OBD RD043.927 | GGTTGCTGTGACAAAATGCCATAG (SEQ ID NO: 1379) |
| 233 | GCTATTGTAAAGAGGCTATGCCAACT (SEQ ID NO: 1316) | OBD RD043.931 | CATTCAACATACCCTCCTCCTCGCTG (SEQ ID NO: 1380) |
| 234 | CCATTCAACATACCCTCCTCCTCGC (SEQ ID NO: 1317) | OBD RD043.935 | GGACATTATTCTCCAGGAAAGACCT (SEQ ID NO: 1381) |

TABLE 33.d7-continued

| N | Primer Sequence | Primer ID-2 | Primer Sequence |
|---|---|---|---|
| 235 | CATAAAGTAGAGGAGGACTGGTC (SEQ ID NO: 1318) | OBD RD043.939 | TCCCATTCAACATACCCTCCTCC (SEQ ID NO: 1382) |
| 236 | GCCCTCTTGGGACTGAACTCTCT (SEQ ID NO: 1319) | OBD RD043.943 | CGCCCCAACCTTGCTGGACATTG (SEQ ID NO: 1383) |
| 237 | CAGCCCTCTTGGGACTGAACTCTCTA (SEQ ID NO: 1320) & (SEQ ID NO: 1321) | OBD RD043.947 | CAGAAGAACTCCTGAAACGCCAAGAA (SEQ ID NO: 1384) |
| 238 | CAGCCCTCTTGGGACTGAACTCTCTA (SEQ ID NO: 1320) & (SEQ ID NO: 1321) | OBD RD043.951 | GCCAACACTGTGGAACTGAATCTAAG (SEQ ID NO: 1385) |
| 239 | TCATAGGCAATAGATTTCCTGGGAGC (SEQ ID NO: 1322) | OBD RD043.955 | CAGCCGACAGTAGCCCTTAGATTGCT (SEQ ID NO: 1386) |
| 240 | GACAGCCAGACTGATGGGTGAGG (SEQ ID NO: 1323) | OBD RD043.959 | CCACTCCCTTCCCATTCCTCCTT (SEQ ID NO: 1387) |
| 241 | CACTCGGCAGATGGCGTGGCATA (SEQ ID NO: 1324) | OBD RD043.963 | TCTCTGCCCGTGACTTTGCTCCT (SEQ ID NO: 1388) |
| 242 | ATGTAACTGCCTACGAACCCTCCAGG (SEQ ID NO: 1325) | OBD RD043.967 | AGATTAGGGTTGCTGAGTGGGTCAAT (SEQ ID NO: 1389) |
| 243 | GTGGCTACGGCTGTGAGAGATGG (SEQ ID NO: 1305) & (SEQ ID NO: 1326) | OBD RD043.971 | CAGGAACCTCTAATCCACGCCCT (SEQ ID NO: 1390) |
| 244 | TGGCTACGGCTGTGAGAGATGGA (SEQ ID NO: 1303) & (SEQ ID NO: 1327) & (SEQ ID NO: 1329) | OBD RD043.975 | TTCCAGGACAACCGCATCCAGGG (SEQ ID NO: 1391) |
| 245 | GACCACCCCGCCCAGGCTGACCT (SEQ ID NO: 1328) | OBD RD043.979 | ACGGCTGTGAGAGATGGAGAGTC (SEQ ID NO: 1392) |
| 246 | TGGCTACGGCTGTGAGAGATGGA (SEQ ID NO: 1303) & (SEQ ID NO: 1327) & (SEQ ID NO: 1329) | OBD RD043.983 | AGGTGGCTTCCTGTGGGCTGAGA (SEQ ID NO: 1393) |
| 247 | GAGGAAGATTGGCAACAGATGCTA (SEQ ID NO: 1330) | OBD RD043.987 | CCTCTATGTTTTCTCGTTCTTTTA (SEQ ID NO: 1394) |
| 248 | CCCACACACCACACCACTCATCA (SEQ ID NO: 1331) | OBD RD043.991 | AGGCAGTCCACAAAGCCAGCGTG (SEQ ID NO: 1395) |
| 249 | GGCTTCTGGCACTTACTGAATGGCTT (SEQ ID NO: 1332) | OBD RD043.995 | AGGTGGAAATGTAAGGCTGAGTAGGC (SEQ ID NO: 1396) |
| 250 | GAAAGAGAAATACACTCAACAGAGA (SEQ ID NO: 1333) | OBD RD043.999 | TCCTCTATGTTTTCTCGTTCTTTTA (SEQ ID NO: 1397) |
| 251 | TCCAGAGGGCTGAAGACTTGAGAAAG (SEQ ID NO: 1334) | OBD RD043.1003 | GGGACTCATAGGGAGACACATTA (SEQ ID NO: 1398) |
| 252 | TAGGTCCTTGGCATACGCATTGA (SEQ ID NO: 1335) | OBD RD043.1007 | CTAAATAAAAGAGCACTACTGCCAGA (SEQ ID NO: 1399) |
| 253 | GAGTCTACGCTACAGATACAAGGG (SEQ ID NO: 1336) | OBD RD043.1011 | AGAATCCACAAATCCATACTGATA (SEQ ID NO: 1400) |
| 254 | ATGGTCTGTGCCCCTGGTGCCTA (SEQ ID NO: 1337) | OBD RD043.1015 | ATTGGGCAGGAGGTGAGGAACTG (SEQ ID NO: 1401) |
| 255 | CACCTCACATTCTAACATCTCAGTCT (SEQ ID NO: 1338) | OBD RD043.1019 | TTGATGCTCTGGATTGGGCAGGAGGT (SEQ ID NO: 1402) |
| 256 | CCAGACAGGAGGAGAGAACAGATTTC (SEQ ID NO: 1339) | OBD RD043.1023 | GTTTTGTTCCCAAGTGCCTCTGACAG (SEQ ID NO: 1403) |

60

TABLE 33.d8

| N | Probe | Marker |
|---|---|---|
| 193 | LMO7 | OBD RD043.769.771 |
| 194 | LY6D | OBD RD043.773.775 |

TABLE 33.d8-continued

| N | Probe | Marker |
|---|---|---|
| 195 | LY6D | OBD RD043.777.779 |
| 196 | MAP3K4 | OBD RD043.781.783 |

65

TABLE 33.d8-continued

| N | Probe | Marker |
|---|---|---|
| 197 | MAP3K9 | OBD RD043.785.787 |
| 198 | MAPK1 | OBD RD043.789.791 |
| 199 | MAPK1 | OBD RD043.793.795 |
| 200 | MAPK1 | OBD RD043.797.799 |
| 201 | MAPK3 | OBD RD043.801.803 |
| 202 | MAPK9 | OBD RD043.805.807 |
| 203 | MAPK9 | OBD RD043.809.811 |
| 204 | MDH1 | OBD RD043.813.815 |
| 205 | MDH1 | OBD RD043.817.819 |
| 206 | MDM4 | OBD RD043.821.823 |
| 207 | MED25 | OBD RD043.825.827 |
| 208 | MEF2A | OBD RD043.829.831 |
| 209 | MIPEP | OBD RD043.833.835 |
| 210 | MIPEP | OBD RD043.837.839 |
| 211 | MIPEP | OBD RD043.841.843 |
| 212 | MMP1 | OBD RD043.845.847 |
| 213 | MMP1 | OBD RD043.849.851 |
| 214 | MS4A2 | OBD RD043.853.855 |
| 215 | MS4A2 | OBD RD043.857.859 |
| 216 | MSI2 | OBD RD043.861.863 |
| 217 | MSI2 | OBD RD043.865.867 |
| 218 | MSI2 | OBD RD043.869.871 |
| 219 | MSTN | OBD RD043.873.875 |
| 220 | MTHFR | OBD RD043.877.879 |
| 221 | MTHFR | OBD RD043.881.883 |
| 222 | MTHFR | OBD RD043.885.887 |
| 223 | MTMR3 | OBD RD043.889.891 |
| 224 | MYBPC2 | OBD RD043.893.895 |
| 225 | MYH1 | OBD RD043.897.899 |
| 226 | MYL1 | OBD RD043.901.903 |
| 227 | MYL4 | OBD RD043.905.907 |

TABLE 33.d8-continued

| N | Probe | Marker |
|---|---|---|
| 228 | MYL4 | OBD RD043.909.911 |
| 229 | MYL4 | OBD RD043.913.915 |
| 230 | MYL4 | OBD RD043.917.919 |
| 231 | MYL4 | OBD RD043.921.923 |
| 232 | MYL4 | OBD RD043.925.927 |
| 233 | MYOZ1 | OBD RD043.929.931 |
| 234 | MYOZ1 | OBD RD043.933.935 |
| 235 | MYOZ1 | OBD RD043.937.939 |
| 236 | NDN | OBD RD043.941.943 |
| 237 | NDN | OBD RD043.945.947 |
| 238 | NDN | OBD RD043.949.951 |
| 239 | NDUFA8 | OBD RD043.953.955 |
| 240 | NEUROD2 | OBD RD043.957.959 |
| 241 | NFIB | OBD RD043.961.963 |
| 242 | NFIB | OBD RD043.965.967 |
| 243 | NPPA | OBD RD043.969.971 |
| 244 | NPPA | OBD RD043.973.975 |
| 245 | NPPA | OBD RD043.977.979 |
| 246 | NPPA | OBD RD043.981.983 |
| 247 | PALLD | OBD RD043.985.987 |
| 248 | PALLD | OBD RD043.989.991 |
| 249 | PALLD | OBD RD043.993.995 |
| 250 | PALLD | OBD RD043.997.999 |
| 251 | PALLD | OBD RD043.1001.1003 |
| 252 | PCBP4 | OBD RD043.1005.1007 |
| 253 | PCBP4 | OBD RD043.1009.1011 |
| 254 | PHOSPHO1 | OBD RD043.1013.1015 |
| 255 | PHOSPHO1 | OBD RD043.1017.1019 |
| 256 | PIK3R1 | OBD RD043.1021.1023 |

TABLE 33.e1

| N | Probe | GeneLocus | Probe_Count_Total | Probe_Count_Sig |
|---|---|---|---|---|
| 257 | PLXDC1_11_23117935_23125158_23188757_23196195_RR | PLXDC1 | 1 | 27 |
| 258 | PRKAG2_4_103028895_103043216_103233754_103234780_RF | PRKAG2 | 2 | 177 |
| 259 | PRKAG2_4_103028895_103043216_103342192_103345172_RR | PRKAG2 | 2 | 177 |
| 260 | PRKCA_11_13786370_13794644_13849517_13854647_RF | PRKCA | 1 | 60 |
| 261 | PRKCB_13_23475428_23483033_23690253_23695272_RF | PRKCB | 2 | 19 |
| 262 | PRKCB_13_23532412_23540462_23690253_23695272_RF | PRKCB | 2 | 19 |
| 263 | RAB33B_2_91817483_91819013_91968018_91981648_FF | RAB33B | 2 | 45 |
| 264 | RAB33B_2_91817483_91819013_91968018_91981648_RR | RAB33B | 2 | 45 |
| 265 | RAG2_12_2995445_3004477_3070874_3072970_RF | RAG2 | 3 | 49 |
| 266 | RAG2_12_2995445_3004477_3070874_3072970_RR | RAG2 | 3 | 49 |
| 267 | RAG2_12_2995445_3004477_3124836_3128121_RF | RAG2 | 3 | 49 |
| 268 | RASSF5_5_2727413_2732312_2768970_2779500_FF | RASSF5 | 3 | 31 |
| 269 | RASSF5_5_2727413_2732312_2857276_2865680_FF | RASSF5 | 3 | 31 |
| 270 | RASSF5_5_2752106_2755183_2768970_2779500_FF | RASSF5 | 3 | 31 |
| 271 | RBPJL_22_34286715_34290143_34327562_34334894_FR | RBPJL | 2 | 28 |
| 272 | RBPJL_22_34286715_34290143_34327562_34334894_RR | RBPJL | 2 | 28 |
| 273 | SCN10A_16_46394076_46405616_46559136_46563398_RF | SCN10A | 3 | 120 |
| 274 | SCN10A_16_46394076_46405616_46644599_46646012_RF | SCN10A | 3 | 120 |
| 275 | SCN10A_16_46542432_46554053_46644599_46646012_RF | SCN10A | 3 | 120 |
| 276 | SCN2B_7_25981242_25985420_26023779_26030228_FF | SCN2B | 2 | 31 |
| 277 | SCN2B_7_25981242_25985420_26102356_26109968_FF | SCN2B | 2 | 31 |
| 278 | SCN4B_7_25954012_25959734_25981242_25985420_RF | SCN4B | 1 | 31 |
| 279 | SCN5A_16_46559136_46563398_46724067_46732988_FF | SCN5A | 2 | 30 |
| 280 | SCN5A_16_46559136_46563398_46724067_46732988_FR | SCN5A | 2 | 30 |
| 281 | SELL_5_6104471_6117065_6186372_6188629_FR | SELL | 1 | 111 |
| 282 | SEPT7_4_65366992_65373527_65534812_65540822_RF | SEPT7 | 1 | 127 |
| 283 | SGCA_11_25806231_25808754_26000893_26002740_RF | SGCA | 2 | 13 |
| 284 | SGCA_11_25806231_25808754_26000893_26002740_RR | SGCA | 2 | 13 |
| 285 | SIK2_7_20268830_20278159_20296076_20300289_FR | SIK2 | 4 | 204 |
| 286 | SIK2_7_20268830_20278159_20375473_20380173_FF | SIK2 | 4 | 204 |
| 287 | SIK2_7_20268830_20278159_20391427_20402715_FR | SIK2 | 4 | 204 |
| 288 | SIK2_7_20268830_20278159_20407650_20411122_FR | SIK2 | 4 | 204 |
| 289 | SNAP29_8_3045435_3054804_3164300_3172603_FF | SNAP29 | 2 | 50 |
| 290 | SNAP29_8_3117316_3123446_3164300_3172603_FF | SNAP29 | 2 | 50 |
| 291 | SPRED1_1_149873033_149876737_150087432_150097168_RF | SPRED1 | 8 | 166 |
| 292 | SPRED1_1_149873033_149876737_150099832_150110035_RF | SPRED1 | 8 | 166 |
| 293 | SPRED1_1_149910043_149913663_150087432_150097168_RF | SPRED1 | 8 | 166 |
| 294 | SPRED1_1_149910043_149913663_150099832_150110035_RF | SPRED1 | 8 | 166 |
| 295 | SPRED1_1_149923380_149924915_150099832_150110035_RF | SPRED1 | 8 | 166 |
| 296 | SPRED1_1_150016977_150019540_150099832_150110035_RF | SPRED1 | 8 | 166 |

TABLE 33.e1-continued

| N | Probe | GeneLocus | Probe__Count__Total | Probe__Count__Sig |
|---|---|---|---|---|
| 297 | SPRED1__1__150032266__150036031__150087432__150097168__RF | SPRED1 | 8 | 166 |
| 298 | SPRED1__1__150068252__150074099__150099832__150110035__RF | SPRED1 | 8 | 166 |
| 299 | SRC__22__27681702__27686300__27826003__27831147__FR | SRC | 1 | 28 |
| 300 | SRF__20__42097551__42100241__42177997__42186255__FR | SRF | 1 | 31 |
| 301 | STAT1__18__67266270__67281181__67315145__67320245__RF | STAT1 | 3 | 37 |
| 302 | STAT1__18__67266270__67281181__67340514__67345500__RF | STAT1 | 3 | 37 |
| 303 | STAT1__18__67266270__67281181__67404406__67407824__RR | STAT1 | 3 | 37 |
| 304 | STAT3__11__20601546__20610244__20625038__20630547__FF | STAT3 | 2 | 28 |
| 305 | STAT3__11__20601546__20610244__20625038__20630547__RF | STAT3 | 2 | 28 |
| 306 | STAT5A__11__20625038__20630547__20748936__20755885__FF | STAT5A | 1 | 30 |
| 307 | STXBP4__11__29798087__29803880__29820062__29826392__RF | STXBP4 | 2 | 58 |
| 308 | STXBP4__11__29820062__29826392__29856303__29862822__FR | STXBP4 | 2 | 58 |
| 309 | TGFBR1__25__5777848__5781338__5953575__5963779__RF | TGFBR1 | 2 | 29 |
| 310 | TGFBR1__25__5838527__5844153__5953575__5963779__RF | TGFBR1 | 2 | 29 |
| 311 | TMEM156__3__88174369__88185533__88338789__88351273__FF | TMEM156 | 1 | 90 |
| 312 | TOB1__11__26381091__26387145__26421158__26424834__RR | TOB1 | 2 | 31 |
| 313 | TOB1__11__26381091__26387145__26552180__26554959__RR | TOB1 | 2 | 31 |
| 314 | TSPAN3__1__117377450__117387477__117527452__117533304__RF | TSPAN3 | 2 | 53 |
| 315 | TSPAN3__1__117501086__117515708__117527452__117533304__RF | TSPAN3 | 2 | 53 |
| 316 | TSPAN5__3__40723323__40732311__40838443__40842795__RF | TSPAN5 | 1 | 176 |
| 317 | VAV1__7__4248599__4253460__4432636__4444354__FF | VAV1 | 1 | 38 |
| 318 | VEGFC__27__31943096__31950700__31994751__32003367__RR | VEGFC | 2 | 54 |
| 319 | VEGFC__27__31943096__31950700__32006848__32015827__RR | VEGFC | 2 | 54 |
| 320 | ZFHX3__3__20954370__20958861__21248124__21260027__FF | ZFHX3 | 1 | 141 |

TABLE 33.e2

| N | HyperG_Stats | FDR_HyperG | Percent_Sig | logFC | AveExpr |
|---|---|---|---|---|---|
| 257 | 0.178891485 | 0.267074007 | 3.7 | −0.498546573 | 8.334899675 |
| 258 | 0.248623084 | 0.310300562 | 1.13 | −0.938829032 | 8.830030136 |
| 259 | 0.248623084 | 0.310300562 | 1.13 | −0.409357346 | 9.945611435 |
| 260 | 0.303088108 | 0.331342084 | 1.67 | −0.32685719 | 9.445425416 |
| 261 | 0.009980432 | 0.049518297 | 10.53 | −0.470343416 | 9.5078615 |
| 262 | 0.009980432 | 0.049518297 | 10.53 | −0.310412046 | 10.44482443 |
| 263 | 0.046697041 | 0.122937109 | 4.44 | −0.192180899 | 10.74179204 |
| 264 | 0.046697041 | 0.122937109 | 4.44 | −0.354237277 | 9.242623502 |
| 265 | 0.006920652 | 0.037512367 | 6.12 | 0.358172408 | 9.004366375 |
| 266 | 0.006920652 | 0.037512367 | 6.12 | 0.207569755 | 9.114059545 |
| 267 | 0.006920652 | 0.037512367 | 6.12 | 0.274277591 | 8.211642632 |
| 268 | 0.001955877 | 0.014841655 | 9.68 | −0.380422279 | 10.05354755 |
| 269 | 0.001955877 | 0.014841655 | 9.68 | −0.379141769 | 10.15172147 |
| 270 | 0.001955877 | 0.014841655 | 9.68 | −0.321187765 | 8.346983577 |
| 271 | 0.020494302 | 0.075554863 | 7.14 | −0.418632216 | 9.712363657 |
| 272 | 0.020494302 | 0.075554863 | 7.14 | 0.256227174 | 9.629544001 |
| 273 | 0.059031661 | 0.137915817 | 2.5 | −0.303249497 | 9.538210055 |
| 274 | 0.059031661 | 0.137915817 | 2.5 | −0.392996971 | 10.12637726 |
| 275 | 0.059031661 | 0.137915817 | 2.5 | −0.517204321 | 9.549017556 |
| 276 | 0.024599258 | 0.075554863 | 6.45 | −0.330982641 | 8.754115738 |
| 277 | 0.024599258 | 0.075554863 | 6.45 | −0.600780426 | 8.122591447 |
| 278 | 0.198752749 | 0.267074007 | 3.23 | −0.513873909 | 8.171494225 |
| 279 | 0.023201487 | 0.075554863 | 6.67 | −0.275782912 | 9.599314892 |
| 280 | 0.023201487 | 0.075554863 | 6.67 | −0.332593132 | 9.221879302 |
| 281 | 0.368532709 | 0.369972517 | 0.9 | −0.192237265 | 11.73871812 |
| 282 | 0.369595168 | 0.369972517 | 0.79 | 0.236701745 | 11.5277415 |
| 283 | 0.004781729 | 0.029373479 | 15.38 | −0.299567355 | 9.597332982 |
| 284 | 0.004781729 | 0.029373479 | 15.38 | −0.395116377 | 8.436344868 |
| 285 | 0.060939547 | 0.137915817 | 1.96 | −0.250370376 | 8.821107854 |
| 286 | 0.060939547 | 0.137915817 | 1.96 | −0.205233587 | 8.887500946 |
| 287 | 0.060939547 | 0.137915817 | 1.96 | −0.328539529 | 8.245361941 |
| 288 | 0.060939547 | 0.137915817 | 1.96 | −0.366691703 | 8.419551683 |
| 289 | 0.055461917 | 0.137588217 | 4 | −0.245937866 | 10.96109836 |
| 290 | 0.055461917 | 0.137588217 | 4 | −0.261369209 | 11.03851689 |
| 291 | 0.0000634628527405492 | 0.001364451 | 4.82 | 0.626539336 | 8.460307208 |
| 292 | 0.0000634628527405492 | 0.001364451 | 4.82 | 0.45135055 | 7.830572417 |
| 293 | 0.0000634628527405492 | 0.001364451 | 4.82 | 0.514959643 | 8.178202101 |
| 294 | 0.0000634628527405492 | 0.001364451 | 4.82 | 0.330234467 | 7.825606038 |
| 295 | 0.0000634628527405492 | 0.001364451 | 4.82 | 0.347918733 | 8.022790865 |
| 296 | 0.0000634628527405492 | 0.001364451 | 4.82 | 0.265700639 | 8.225367878 |
| 297 | 0.0000634628527405492 | 0.001364451 | 4.82 | 0.418287098 | 8.296113768 |
| 298 | 0.0000634628527405492 | 0.001364451 | 4.82 | 0.292449794 | 7.689848783 |
| 299 | 0.183998999 | 0.267074007 | 3.57 | −0.257211227 | 8.96771926 |
| 300 | 0.198752749 | 0.267074007 | 3.23 | −0.289791551 | 11.53768831 |
| 301 | 0.003219239 | 0.020764093 | 8.11 | 0.950923864 | 8.127367441 |
| 302 | 0.003219239 | 0.020764093 | 8.11 | 0.339957139 | 10.88074422 |

TABLE 33.e2-continued

| N | HyperG_Stats | FDR_HyperG | Percent_Sig | logFC | AveExpr |
|---|---|---|---|---|---|
| 303 | 0.003219239 | 0.020764093 | 8.11 | 0.422734986 | 8.738942644 |
| 304 | 0.020494302 | 0.075554863 | 7.14 | −0.34818003 | 9.404675926 |
| 305 | 0.020494302 | 0.075554863 | 7.14 | −0.308351369 | 10.09067586 |
| 306 | 0.193928419 | 0.267074007 | 3.33 | −0.327160983 | 10.04088364 |
| 307 | 0.070089709 | 0.151221234 | 3.45 | 0.301994949 | 8.888178828 |
| 308 | 0.070089709 | 0.151221234 | 3.45 | 0.297112393 | 8.516631477 |
| 309 | 0.02183283 | 0.075554863 | 6.9 | −0.462921799 | 9.298865314 |
| 310 | 0.02183283 | 0.075554863 | 6.9 | −0.502142385 | 8.308741006 |
| 311 | 0.355201455 | 0.369972517 | 1.11 | −0.25947705 | 8.734272977 |
| 312 | 0.024599258 | 0.075554863 | 6.45 | −0.67235893 | 8.052267141 |
| 313 | 0.024599258 | 0.075554863 | 6.45 | −0.658106699 | 8.007819166 |
| 314 | 0.060873696 | 0.137915817 | 3.77 | −0.576817806 | 8.097751634 |
| 315 | 0.060873696 | 0.137915817 | 3.77 | −0.568732319 | 8.537384311 |
| 316 | 0.341994894 | 0.367644511 | 0.57 | −0.456101192 | 9.282066601 |
| 317 | 0.23001238 | 0.297307866 | 2.63 | −0.183925655 | 10.27585426 |
| 318 | 0.062698978 | 0.139451175 | 3.7 | −0.51992089 | 8.803285229 |
| 319 | 0.062698978 | 0.139451175 | 3.7 | −0.570858041 | 8.216821116 |
| 320 | 0.365633172 | 0.369972517 | 0.71 | −0.359210093 | 10.90927278 |

TABLE 33.e3

| N | t | P.Value | adj.P.Val | B | FC |
|---|---|---|---|---|---|
| 257 | −8.679819127 | 0.0000000466671136396821 | 0.000070018619349385 | 8.618875681 | 0.707819507 |
| 258 | −12.72862254 | 0.0000000000880568203541454 | 0.000000960392461716811 | 14.05544918 | 0.521656113 |
| 259 | −7.136605672 | 0.000000846145358915483 | 0.000471545 | 5.94886147 | 0.752958707 |
| 260 | −7.042847832 | 0.00000101943002074247 | 0.00053024 | 5.774815448 | 0.797271393 |
| 261 | −7.060938638 | 0.00000098334286615856 | 0.000518381 | 5.808503626 | 0.721792764 |
| 262 | −6.523007013 | 0.00000292622869023077 | 0.001037747 | 4.785416246 | 0.806411408 |
| 263 | −6.177861318 | 0.00000601133616970513 | 0.001701441 | 4.106203741 | 0.875281571 |
| 264 | −6.685600302 | 0.00000209595044430101 | 0.000822758 | 5.09928145 | 0.782283111 |
| 265 | 5.396796706 | 0.0000323877534937054 | 0.005178058 | 2.508645352 | 1.281801096 |
| 266 | 5.003725624 | 0.0000775486565602272 | 0.00961269 | 1.677385244 | 1.154741363 |
| 267 | 6.369772263 | 0.00000402056197173788 | 0.001307018 | 4.48601267 | 1.209388354 |
| 268 | −5.516753496 | 0.0000248906319064535 | 0.004416684 | 2.75901438 | 0.768212701 |
| 269 | −5.382597738 | 0.0000334164554567416 | 0.005277635 | 2.478900424 | 0.768894855 |
| 270 | −5.006426169 | 0.0000770809956858349 | 0.009606804 | 1.683147538 | 0.800410631 |
| 271 | −5.662219604 | 0.0000181264479152015 | 0.003741337 | 3.060319651 | 0.748133575 |
| 272 | 5.012432569 | 0.0000760511136821973 | 0.009570174 | 1.695961392 | 1.194351241 |
| 273 | −6.533997102 | 0.00000286064608645947 | 0.001033276 | 4.806755937 | 0.810424954 |
| 274 | −6.783534136 | 0.00000171722954949946 | 0.0007607 | 5.286406035 | 0.761545969 |
| 275 | −7.367545782 | 0.000000537461051340749 | 0.00033823 | 6.371766941 | 0.698724522 |
| 276 | −5.071224906 | 0.0000666805443887129 | 0.008670693 | 1.821215505 | 0.794994816 |
| 277 | −6.716956804 | 0.00000196610975254916 | 0.0007907 | 5.159353307 | 0.659397158 |
| 278 | −6.486863965 | 0.00000315305553468220 | 0.001088502 | 4.715109769 | 0.700339367 |
| 279 | −6.351012197 | 0.00000418091312232632 | 0.00133884 | 4.449120217 | 0.826001948 |
| 280 | −6.052890375 | 0.00000783121810960962 | 0.002092437 | 3.856049162 | 0.794107853 |
| 281 | −5.560217945 | 0.0000226347401909662 | 0.004245102 | 2.849313135 | 0.875247375 |
| 282 | 5.779181792 | 0.0000140717989649137 | 0.003153542 | 3.300663941 | 1.178295788 |
| 283 | −7.386976626 | 0.000000517495203192340 | 0.000336458 | 6.406972586 | 0.812496017 |
| 284 | −6.766116831 | 0.00000177901940080403 | 0.000730522 | 5.253232767 | 0.760428033 |
| 285 | −7.016707493 | 0.00000107401014567895 | 0.000532857 | 5.726048608 | 0.840680564 |
| 286 | −5.060793325 | 0.0000682529865421064 | 0.00878729 | 1.799014592 | 0.867398235 |
| 287 | −5.72356327 | 0.0000158691029014987 | 0.003458401 | 3.186592403 | 0.79634223 |
| 288 | −7.062768364 | 0.00000097976728195195514 | 0.000518381 | 5.81190808 | 0.775558922 |
| 289 | −5.519623473 | 0.0000247348136116668 | 0.004416684 | 2.764983829 | 0.843267427 |
| 290 | −5.324822449 | 0.0000379586640410418 | 0.005899472 | 2.357637174 | 0.834295744 |
| 291 | 8.610941071 | 0.0000052587433889362 | 0.000076226614059348 | 8.507428978 | 1.543857222 |
| 292 | 8.317816898 | 0.0000000895362606598224 | 0.000094400257522694 | 8.025208094 | 1.367319647 |
| 293 | 5.398124663 | 0.0000322932145065220 | 0.005178058 | 2.51142608 | 1.428954167 |
| 294 | 5.241619663 | 0.0000456337287914882 | 0.006692375 | 2.18236792 | 1.257217681 |
| 295 | 5.310396024 | 0.0000391882227946439 | 0.00599503 | 2.327300642 | 1.272723241 |
| 296 | 5.519453444 | 0.0000247440170633763 | 0.004416684 | 2.764630201 | 1.202219761 |
| 297 | 7.351175156 | 0.000000554901072898733 | 0.00033823 | 6.342060509 | 1.336339985 |
| 298 | 5.014061752 | 0.0000757741890045537 | 0.009566185 | 1.699436487 | 1.224718167 |
| 299 | −6.350304057 | 0.00000418709338863960 | 0.00133884 | 4.447726623 | 0.836703731 |
| 300 | −5.771975103 | 0.0000142923844781131 | 0.003153542 | 3.285905862 | 0.818020242 |
| 301 | 6.786415088 | 0.00000170722463564491 | 0.00071265 | 5.291888693 | 1.933110174 |
| 302 | 5.902616329 | 0.0000107912833479968 | 0.002598568 | 3.552375976 | 1.265718991 |
| 303 | 5.329665604 | 0.0000375547764940088 | 0.005860047 | 2.367816494 | 1.340466334 |
| 304 | −5.50999994 | 0.0000252612746619697 | 0.00443021 | 2.744963363 | 0.785574481 |
| 305 | −6.758325987 | 0.0000180739710817034 | 0.000734443 | 5.238379279 | 0.807564071 |
| 306 | −6.387863787 | 0.00000387192196030923 | 0.001269275 | 4.521541626 | 0.797103527 |
| 307 | 7.516520233 | 0.000000402590246451762 | 0.000285546 | 6.640189451 | 1.232848009 |
| 308 | 6.214597334 | 0.00000556381172965962 | 0.001607736 | 4.179317957 | 1.228682697 |

TABLE 33.e3-continued

| N | t | P.Value | adj.P.Val | B | FC |
|---|---|---|---|---|---|
| 309 | −5.501989713 | 0.0000257082159965563 | 0.004477132 | 2.728290772 | 0.725515429 |
| 310 | −5.432137617 | 0.0000299655620481664 | 0.004995541 | 2.58258052 | 0.706057515 |
| 311 | −5.691989465 | 0.0000169925238007217 | 0.003622286 | 3.121658976 | 0.835390678 |
| 312 | −8.960872932 | 0.0000000284628323441866 | 0.000048275438684640 | 9.066366288 | 0.627479865 |
| 313 | −8.504782119 | 0.0000000638163252172577 | 0.000078597025797400 | 8.334275623 | 0.633709391 |
| 314 | −9.911052133 | 0.0000000000574350539340819 | 0.000013179655611580 | 10.49543486 | 0.670440958 |
| 315 | −12.64601994 | 0.00000000000984765405503011 | 0.000000960392461716811 | 13.96387344 | 0.674208949 |
| 316 | −7.115525574 | 0.000000882250643786341 | 0.000484741 | 5.909847949 | 0.728953558 |
| 317 | −5.065028806 | 0.0000676100320214694 | 0.008756001 | 1.80802993 | 0.880304376 |
| 318 | −6.932852329 | 0.00000127040040821895 | 0.00058998 | 5.568900951 | 0.697410075 |
| 319 | −6.149465237 | 0.00000638253863761245 | 0.001778449 | 4.049556555 | 0.673216275 |
| 320 | −10.65803034 | 0.0000000001175481548070441 | 0.00000570461265852324 | 11.5327881 | 0.779591306 |

TABLE 33.e4

| N | FC_1 | LS | Loop Detected | Probe sequence 60 mer |
|---|---|---|---|---|
| 257 | -1.412789547 | -1 | Stayer | AGTATTTGTATTTATTCTGGGAGTTTCATCGAACTGGCTTCATGCCAGATGCTGGAATTG (SEQ ID NO: 1404) |
| 258 | -1.91697169 | -1 | Stayer | AAGTTAGTACTGCATTGTTAGTCAAGTGTCGAAATTGCTATGTATACCAAAGATTAAGGC (SEQ ID NO: 1405) |
| 259 | -1.328094078 | -1 | Stayer | GCCTTAATCTTTGGTATACATAGCAATTTCGACCCACACAGCTCAAGAAGCTAATGCGCA (SEQ ID NO: 1406) |
| 260 | -1.254278039 | -1 | Stayer | GTACAATATAGAGACATCATTCTCGTTATCGATTGGCGCACAAGTGCCAGGGACACCTGC (SEQ ID NO: 1407) |
| 261 | -1.385439215 | -1 | Stayer | GGAAGAGGAAAAGAGAACTTAAAGAAGATCGAGAGAAAAGAAGGACAGACGAGGCTTCCA (SEQ ID NO: 1408) |
| 262 | -1.240061822 | -1 | Stayer | GGAAGAGGAAAAGAGAACTTAAAGAAGATCGACGGCAGCATAGCCTCTGAGCTGGACAGG (SEQ ID NO: 1409) |
| 263 | -1.142489494 | -1 | Stayer | TACAGGTGCCGTGTACCACTTTGATAAGTCGAACATTTGTTATTTTTTGTCTTGGTAATT (SEQ ID NO: 1410) |
| 264 | -1.278309587 | -1 | Stayer | AAAACTTTCATCGCAAATGTACTAGCTGTCGAAAACAGCACAGCTTTTTGAGCCAGAAAA (SEQ ID NO: 1411) |
| 265 | 1.281801096 | 1 | Sprinter | GTGCTTCTTTAAGATACCAGATAATTGATCGATACGACAGAACCTAGAAAAAGTTCCGAG (SEQ ID NO: 1412) |
| 266 | 1.154741363 | 1 | Sprinter | CTCGGAACTTTTTCTAGGTTCTGTCGTATCGATTCAATTCGTATATCTCCCTCTTTCTCA (SEQ ID NO: 1413) |
| 267 | 1.209388354 | 1 | Sprinter | GGTCTACCCGTGCGTGTTAACGCCGGGGTCGATACGACAGAACCTAGAAAAAGTTCCGAG (SEQ ID NO: 1414) |
| 268 | -1.301722815 | -1 | Stayer | CGGCAGAGCTCACTGCAGTCAATTGGAATCGAACACTATGATAATTCTTTCCCAGATTCA (SEQ ID NO: 1415) |
| 269 | -1.300567943 | -1 | Stayer | CGGCAGAGCTCACTGCAGTCAATTGGAATCGAGTTTATGCCTATCATAGGACTTGAACAG (SEQ ID NO: 1416) |
| 270 | -1.249358718 | -1 | Stayer | TCTTCATTTATTTAGTGCTCACAAAAACTCGAACACTATGATAATTCTTTCCCAGATTCA (SEQ ID NO: 1417) |
| 271 | -1.3366597 | -1 | Stayer | GGGCGTATTGCTATGGTTATGCCCCAGCTCGATTGTCTTATTTTTATTTATTTCTATCAC (SEQ ID NO: 1418) |
| 272 | 1.194351241 | 1 | Sprinter | CTTTTTTACAAATCCTAAAGGATGCCCCTCGATTGTCTTATTTTTATTTATTTCTATCAC (SEQ ID NO: 1419) |
| 273 | -1.233920543 | -1 | Stayer | ACCAGTGTCATCAGTACCCTAGAGGGCTTCGATGTTGTCTGCCTTTTTAATTTTTAACCA (SEQ ID NO: 1420) |
| 274 | -1.313118369 | -1 | Stayer | CCTTTGAGTCTCTGGTCAAGATTCTGGCTCGATGTTGTCTGCCTTTTTAATTTTTAACCA (SEQ ID NO: 1421) |
| 275 | -1.431179196 | -1 | Stayer | CCTTTGAGTCTCTGGTCAAGATTCTGGCTCGAAGATTAGAAATATTTGGATATATTTCTA (SEQ ID NO: 1422) |

TABLE 33.e4-continued

| N | FC_1 | LS | Loop Detected | Probe sequence 60 mer |
|---|------|-----|---------------|-----------------------|
| 276 | -1.257869837 | -1 | Stayer | GTGCGCTGCGCAGCTTAAACAGCAGAATTCGATGATTCTTGCCCGAGTCATATTTCACTA (SEQ ID NO: 1423) |
| 277 | -1.516536715 | -1 | Stayer | GTGCGCTGCGCAGCTTAAACAGCAGAATTCGATCTTAAATTTATTGTATTTTGTTTGCAT (SEQ ID NO: 1424) |
| 278 | -1.427879178 | -1 | Stayer | GTGCGCTGCGCAGCTTAAACAGCAGAATTCGACAAGGATCAGATATCATTAAGTCAAGTT (SEQ ID NO: 1425) |
| 279 | -1.210650898 | -1 | Stayer | ACCAGTGTCATCAGTACCCTAGAGGGCTTCGAATGTTGAAACATACTCTCCAGTGTGATG (SEQ ID NO: 1426) |
| 280 | -1.25927479 | -1 | Stayer | ACCAGTGTCATCAGTACCCTAGAGGGCTTCGAAACAAATGCTTTATATACTTACATCATC (SEQ ID NO: 1427) |
| 281 | -1.142534132 | -1 | Stayer | AGTATTGGGAAGGAGTCACGGTCAGTAATCGAGAGCAGCATGTTAGCTCTCCGCCTTCGG (SEQ ID NO: 1428) |
| 282 | 1.178295788 | 1 | Sprinter | CCCCTGCCTTACTCCCAGGGGCCGCCATTCGATGGGGGCACCGGGCAAGTCACTCACCCT (SEQ ID NO: 1429) |
| 283 | -1.230775265 | 1 | Stayer | AAGGGGAAAAAATAAAAATAGAAGACCATCGAATCCGGTACTTTCTGGCCTTCCAAAAG (SEQ ID NO: 1430) |
| 284 | -1.315048836 | -1 | Stayer | CTTTTTGGAAGGCCAGAAAGTACCGGATTCGACCGTGGTGTATAATCCTTTTAATATACT (SEQ ID NO: 1431) |
| 285 | -1.189512454 | -1 | Stayer | ATAAGTTTGTTCTGTAACCGTAATTAAGTCGAAGGATGTTGGTCCTAGACCCATCCAAAC (SEQ ID NO: 1432) |
| 286 | -1.152872993 | -1 | Stayer | ATAAGTTTGTTCTGTAACCGTAATTAAGTCGAATAGCCCACGTTCAAGTGGAGAGGAATT (SEQ ID NO: 1433) |
| 287 | -1.255741517 | -1 | Stayer | ATAAGTTTGTTCTGTAACCGTAATTAAGTCGACAAATTCTATCAACTGATGAATTTATAA (SEQ ID NO: 1434) |
| 288 | -1.289392684 | -1 | Stayer | ATAAGTTTGTTCTGTAACCGTAATTAAGTCGAAGCTAAAAATATGCTTTAGTTTAAAATT (SEQ ID NO: 1435) |
| 289 | -1.185863426 | -1 | Stayer | GCAAAGAAATATCTTTTATTTGCAAAATTCGAGATCTGGGGGTACTGGGTGGACTCTGGG (SEQ ID NO: 1436) |
| 290 | -1.198615727 | -1 | Stayer | ACAAAGATTCTGTGGTTCCTTACCTTCTTCGAGATCTGGGGGTACTGGGTGGACTCTGGG (SEQ ID NO: 1437) |
| 291 | 1.543857222 | 1 | Sprinter | GTTTGAAGTTTTGATTATTGCATGTAATTCGACTCTAGAAAAGTCTTTGAAAGATAAAAG (SEQ ID NO: 1438) |
| 292 | 1.367319647 | 1 | Sprinter | TCAGTTATGGACATGTCTTGAAGTTAAATCGACTCTAGAAAAGTCTTTGAAAGATAAAAG (SEQ ID NO: 1439) |
| 293 | 1.428954167 | 1 | Sprinter | GTTTGAAGTTTTGATTATTGCATGTAATTCGATCAAACATTATTCTGGATGTTTAAGTGA (SEQ ID NO: 1440) |
| 294 | 1.257217681 | 1 | Sprinter | TCAGTTATGGACATGTCTTGAAGTTAAATCGATCAAACATTATTCTGGATGTTTAAGTGA (SEQ ID NO: 1441) |
| 295 | 1.272723241 | 1 | Sprinter | TCAGTTATGGACATGTCTTGAAGTTAAATCGAATACACAGGGTGTGAGATTAAGAGAAGA (SEQ ID NO: 1442) |
| 296 | 1.202219761 | 1 | Sprinter | TCAGTTATGGACATGTCTTGAAGTTAAATCGAGAAATGTGACGCAATAAATTTCCGTTGT (SEQ ID NO: 1443) |
| 297 | 1.336339985 | 1 | Sprinter | GTTTGAAGTTTTGATTATTGCATGTAATTCGAAAGCCCAGGTTGTCACTGGGCTTCTGAC (SEQ ID NO: 1444) |
| 298 | 1.224718167 | 1 | Sprinter | TCAGTTATGGACATGTCTTGAAGTTAAATCGAATATTACCTAAATTTTATCTATATAGAA (SEQ ID NO: 1445) |
| 299 | -1.195166178 | -1 | Stayer | GGGAGCTAAAAGTACAATTTTTAAAGAGTCGATCCGTCACGTAGCAATATCAGCTGTGCG (SEQ ID NO: 1446) |
| 300 | -1.222463636 | -1 | Stayer | TGCCAGTGTACCCAATAGGTACGGCCCGTCGAGTCACCCCAGTTCTGAGTCACCCCACTT (SEQ ID NO: 1447) |
| 301 | 1.933110174 | 1 | Sprinter | AAAACCCAAGTAAATGTCCTTGATTATTTCGAGGGTTTTTTTTTTTTTTAATTGGTTTTA (SEQ ID NO: 1448) |

TABLE 33.e4-continued

| N | FC_1 | LS | Loop Detected | Probe sequence 60 mer |
|---|---|---|---|---|
| 302 | 1.265718991 | 1 | Sprinter | TAAAACCCAAAGACTTCAGCTTTCCCTCTCGAGGGTTTTTTTTTTTTTAATTGGTTTTA (SEQ ID NO: 1449) |
| 303 | 1.340466334 | 1 | Sprinter | TAAAACCAATTAAAAAAAAAAAAAAACCCTCGAGTCTCTTAACCAATTACATGTGTGTTGG (SEQ ID NO: 1450) |
| 304 | -1.272953774 | 1 | Stayer | ATGGCCCAATGGAATCAGCTGCAGCAGCTCGATGACCTGCACTAGGTACCGCAATGACCT (SEQ ID NO: 1451) |
| 305 | -1.238291841 | -1 | Stayer | AGGTCATTGCGGTACCTAGTGCAGGTCATCGAGCCTGATTGTAATTTATAGACTGAACAG (SEQ ID NO: 1452) |
| 306 | -1.254542185 | -1 | Stayer | AGGTCATTGCGGTACCTAGTGCAGGTCATCGAGCATGCGCTGCTTGAGCGTCCGCGGCAG (SEQ ID NO: 1453) |
| 307 | 1.232848009 | 1 | Sprinter | ATTGCTTAAAAGTAAAAGTGCCATTGAGTCGAAAAACTTTTGAGGCATCCACTGAAAAGC (SEQ ID NO: 1454) |
| 308 | 1.228682697 | 1 | Sprinter | ATTGCTTAAAAGTAAAAGTGCCATTGAGTCGAATATTAATGTTTTCCAACAACAGATTTA (SEQ ID NO: 1455) |
| 309 | -1.378330439 | -1 | Stayer | AGCTGATTTTACTCTTGGATTTATTTCATCGACTGCGAACTCCGTGGAGCTCTAGAGAGA (SEQ ID NO: 1456) |
| 310 | -1.416315213 | -1 | Stayer | AGCTGATTTTACTCTTGGATTTATTTCATCGACTAATAAAGTAGCATCAAAATATATAAG (SEQ ID NO: 1457) |
| 311 | -1.19704472 | -1 | Stayer | GGTTCACAATGTAGCTATTTCCAAGCGATCGATTCAGTTCCACCTAAGTTCTTACTGATA (SEQ ID NO: 1458) |
| 312 | -1.593676636 | -1 | Stayer | TCATCCATGGAATGTAATGACTATGAGATCGAATTAATACCTTTTGAAAAAAACTTAGCA (SEQ ID NO: 1459) |
| 313 | -1.578010384 | -1 | Stayer | TCATCCATGGAATGTAATGACTATGAGATCGACTCTATGCTCCAGTCATTTAAAAATAGT (SEQ ID NO: 1460) |
| 314 | -1.491555651 | -1 | Stayer | TAGTGACTTTCCCCAAAATAAAGTACATTCGATATTTGGCCAGATTTCCTGGCTAAAGTT (SEQ ID NO: 1461) |
| 315 | -1.483219708 | -1 | Stayer | TAGTGACTTTCCCCAAAATAAAGTACATTCGAGATTTTCCTGACAAGGTACCACCCAAGC (SEQ ID NO: 1462) |
| 316 | -1.371829506 | -1 | Stayer | ATATTTGTACTGGCAAACTGTTCTTTACTCGATACAGTCAGCTCCCTGTACACTCAGGAA (SEQ ID NO: 1463) |
| 317 | -1.135970725 | -1 | Stayer | ATGGAGTACCTGAGAAGGTGATGTTAGCTCGAAAAAAATATCTGCCAAGAGTGTGGTACTT (SEQ ID NO: 1464) |
| 318 | -1.433876619 | -1 | Stayer | GCTCAATGAAAGGGTTCCAAATCATTGATCGATCACTGACACTGCTCACTGTGATCTCTT (SEQ ID NO: 1465) |
| 319 | -1.485406752 | -1 | Stayer | GCTCAATGAAAGGGTTCCAAATCATTGATCGATTTGGACCTTGAGTGCGCAGTGTCTGTG (SEQ ID NO: 1466) |
| 320 | -1.282723386 | -1 | Stayer | ATTATGATTGTGGCAATGCTTCGGAAGGTCGAAACCACCCTTTAAAAAAACATTTTTTTA (SEQ ID NO: 1467) |

TABLE 33.e5

| | Probe Location | | | | 4 kb Sequence Location | | | |
|---|---|---|---|---|---|---|---|---|
| N | Chr | Start1 | End1 | Start2 | End2 | Chr | Start1 | End1 | Start2 |
| 257 | 11 | 23117935 | 23117966 | 23188757 | 23188788 | 11 | 23117935 | 23121936 | 23188757 |
| 258 | 4 | 103028895 | 103028926 | 103234749 | 103234780 | 4 | 103028895 | 103032896 | 103230779 |
| 259 | 4 | 103028895 | 103028926 | 103342192 | 103342223 | 4 | 103028895 | 103032896 | 103342192 |
| 260 | 11 | 13786370 | 13786401 | 13854616 | 13854647 | 11 | 13786370 | 13790371 | 13850646 |
| 261 | 13 | 23475428 | 23475459 | 23695241 | 23695272 | 13 | 23475428 | 23479429 | 23691271 |
| 262 | 13 | 23532412 | 23532443 | 23695241 | 23695272 | 13 | 23532412 | 23536413 | 23691271 |
| 263 | 2 | 91818982 | 91819013 | 91981617 | 91981648 | 2 | 91815012 | 91819013 | 91977647 |
| 264 | 2 | 91817483 | 91817514 | 91968018 | 91968049 | 2 | 91817483 | 91821484 | 91968018 |
| 265 | 12 | 2995445 | 2995476 | 3072939 | 3072970 | 12 | 2995445 | 2999446 | 3068969 |
| 266 | 12 | 2995445 | 2995476 | 3070874 | 3070905 | 12 | 2995445 | 2999446 | 3070874 |

TABLE 33.e5-continued

| N | Probe Location | | | | | 4 kb Sequence Location | | | |
|---|---|---|---|---|---|---|---|---|---|
| | Chr | Start1 | End1 | Start2 | End2 | Chr | Start1 | End1 | Start2 |
| 267 | 12 | 2995445 | 2995476 | 3128090 | 3128121 | 12 | 2995445 | 2999446 | 3124120 |
| 268 | 5 | 2732281 | 2732312 | 2779469 | 2779500 | 5 | 2728311 | 2732312 | 2775499 |
| 269 | 5 | 2732281 | 2732312 | 2865649 | 2865680 | 5 | 2728311 | 2732312 | 2861679 |
| 270 | 5 | 2755152 | 2755183 | 2779469 | 2779500 | 5 | 2751182 | 2755183 | 2775499 |
| 271 | 22 | 34290112 | 34290143 | 34327562 | 34327593 | 22 | 34286142 | 34290143 | 34327562 |
| 272 | 22 | 34286715 | 34286746 | 34327562 | 34327593 | 22 | 34286715 | 34290716 | 34327562 |
| 273 | 16 | 46394076 | 46394107 | 46563367 | 46563398 | 16 | 46394076 | 46398077 | 46559397 |
| 274 | 16 | 46394076 | 46394107 | 46645981 | 46646012 | 16 | 46394076 | 46398077 | 46642011 |
| 275 | 16 | 46542432 | 46542463 | 46645981 | 46646012 | 16 | 46542432 | 46546433 | 46642011 |
| 276 | 7 | 25985389 | 25985420 | 26030197 | 26030228 | 7 | 25981419 | 25985420 | 26026227 |
| 277 | 7 | 25985389 | 25985420 | 26109937 | 26109968 | 7 | 25981419 | 25985420 | 26105967 |
| 278 | 7 | 25954012 | 25954043 | 25985389 | 25985420 | 7 | 25954012 | 25958013 | 25981419 |
| 279 | 16 | 46563367 | 46563398 | 46732957 | 46732988 | 16 | 46559397 | 46563398 | 46728987 |
| 280 | 16 | 46563367 | 46563398 | 46724067 | 46724098 | 16 | 46559397 | 46563398 | 46724067 |
| 281 | 5 | 6117034 | 6117065 | 6186372 | 6186403 | 5 | 6113064 | 6117065 | 6186372 |
| 282 | 4 | 65366992 | 65367023 | 65540791 | 65540822 | 4 | 65366992 | 65370993 | 65536821 |
| 283 | 11 | 25806231 | 25806262 | 26002709 | 26002740 | 11 | 25806231 | 25810232 | 25998739 |
| 284 | 11 | 25806231 | 25806262 | 26000893 | 26000924 | 11 | 25806231 | 25810232 | 26000893 |
| 285 | 7 | 20278128 | 20278159 | 20296076 | 20296107 | 7 | 20274158 | 20278159 | 20296076 |
| 286 | 7 | 20278128 | 20278159 | 20380142 | 20380173 | 7 | 20274158 | 20278159 | 20376172 |
| 287 | 7 | 20278128 | 20278159 | 20391427 | 20391458 | 7 | 20274158 | 20278159 | 20391427 |
| 288 | 7 | 20278128 | 20278159 | 20407650 | 20407681 | 7 | 20274158 | 20278159 | 20407650 |
| 289 | 8 | 3054773 | 3054804 | 3172572 | 3172603 | 8 | 3050803 | 3054804 | 3168602 |
| 290 | 8 | 3123415 | 3123446 | 3172572 | 3172603 | 8 | 3119445 | 3123446 | 3168602 |
| 291 | 1 | 149873033 | 149873064 | 150097137 | 150097168 | 1 | 149873033 | 149877034 | 150093167 |
| 292 | 1 | 149873033 | 149873064 | 150110004 | 150110035 | 1 | 149873033 | 149877034 | 150106034 |
| 293 | 1 | 149910043 | 149910074 | 150097137 | 150097168 | 1 | 149910043 | 149914044 | 150093167 |
| 294 | 1 | 149910043 | 149910074 | 150110004 | 150110035 | 1 | 149910043 | 149914044 | 150106034 |
| 295 | 1 | 149923380 | 149923411 | 150110004 | 150110035 | 1 | 149923380 | 149927381 | 150106034 |
| 296 | 1 | 150016977 | 150017008 | 150110004 | 150110035 | 1 | 150016977 | 150020978 | 150106034 |
| 297 | 1 | 150032266 | 150032297 | 150097137 | 150097168 | 1 | 150032266 | 150036267 | 150093167 |
| 298 | 1 | 150068252 | 150068283 | 150110004 | 150110035 | 1 | 150068252 | 150072253 | 150106034 |
| 299 | 22 | 27686269 | 27686300 | 27826003 | 27826034 | 22 | 27682299 | 27686300 | 27826003 |
| 300 | 20 | 42100210 | 42100241 | 42177997 | 42178028 | 20 | 42096240 | 42100241 | 42177997 |
| 301 | 18 | 67266270 | 67266301 | 67320214 | 67320245 | 18 | 67266270 | 67270271 | 67316244 |
| 302 | 18 | 67266270 | 67266301 | 67345469 | 67345500 | 18 | 67266270 | 67270271 | 67341499 |
| 303 | 18 | 67266270 | 67266301 | 67404406 | 67404437 | 18 | 67266270 | 67270271 | 67404406 |
| 304 | 11 | 20610213 | 20610244 | 20630516 | 20630547 | 11 | 20606243 | 20610244 | 20626546 |
| 305 | 11 | 20601546 | 20601577 | 20630516 | 20630547 | 11 | 20601546 | 20605547 | 20626546 |
| 306 | 11 | 20630516 | 20630547 | 20755854 | 20755885 | 11 | 20626546 | 20630547 | 20751884 |
| 307 | 11 | 29798087 | 29798118 | 29826361 | 29826392 | 11 | 29798087 | 29802088 | 29822391 |
| 308 | 11 | 29826361 | 29826392 | 29856303 | 29856334 | 11 | 29822391 | 29826392 | 29856303 |
| 309 | 25 | 5777848 | 5777879 | 5963748 | 5963779 | 25 | 5777848 | 5781849 | 5959778 |
| 310 | 25 | 5838527 | 5838558 | 5963748 | 5963779 | 25 | 5838527 | 5842528 | 5959778 |
| 311 | 3 | 88185502 | 88185533 | 88351242 | 88351273 | 3 | 88181532 | 88185533 | 88347272 |
| 312 | 11 | 26381091 | 26381122 | 26421158 | 26421189 | 11 | 26381091 | 26385092 | 26421158 |
| 313 | 11 | 26381091 | 26381122 | 26552180 | 26552211 | 11 | 26381091 | 26385092 | 26552180 |
| 314 | 1 | 117377450 | 117377481 | 117533273 | 117533304 | 1 | 117377450 | 117381451 | 117529303 |
| 315 | 1 | 117501086 | 117501117 | 117533273 | 117533304 | 1 | 117501086 | 117505087 | 117529303 |
| 316 | 3 | 40723323 | 40723354 | 40842764 | 40842795 | 3 | 40723323 | 40727324 | 40838794 |
| 317 | 7 | 4253429 | 4253460 | 4444323 | 4444354 | 7 | 4249459 | 4253460 | 4440353 |
| 318 | 27 | 31943096 | 31943127 | 31994751 | 31994782 | 27 | 31943096 | 31947097 | 31994751 |
| 319 | 27 | 31943096 | 31943127 | 32006848 | 32006879 | 27 | 31943096 | 31947097 | 32006848 |
| 320 | 3 | 20958830 | 20958861 | 21259996 | 21260027 | 3 | 20954860 | 20958861 | 21256026 |

TABLE 33.e6

| N | 4 kb Sequence Location End2 | Probe | Primer ID-1 |
|---|---|---|---|
| 257 | 23192758 | PLXDC1__11__23117935__23125158__23188757__23196195__RR | OBD RD043.1025 |
| 258 | 103234780 | PRKAG2__4__103028895__103043216__103233754__103234780__RF | OBD RD043.1029 |
| 259 | 103346193 | PRKAG2__4__103028895__103043216__103342192__103345172__RR | OBD RD043.1033 |
| 260 | 13854647 | PRKCA__11__13786370__13794644__13849517__13854647__RF | OBD RD043.1037 |
| 261 | 23695272 | PRKCB__13__23475428__23483033__23690253__23695272__RF | OBD RD043.1041 |
| 262 | 23695272 | PRKCB__13__23532412__23540462__23690253__23695272__RF | OBD RD043.1045 |
| 263 | 91981648 | RAB33B__2__91817483__91819013__91968018__91981648__FF | OBD RD043.1049 |
| 264 | 91972019 | RAB33B__2__91817483__91819013__91968018__91981648__RR | OBD RD043.1053 |
| 265 | 3072970 | RAG2__12__2995445__3004477__3070874__3072970__RF | OBD RD043.1057 |
| 266 | 3074875 | RAG2__12__2995445__3004477__3070874__3072970__RR | OBD RD043.1061 |
| 267 | 3128121 | RAG2__12__2995445__3004477__3124836__3128121__RF | OBD RD043.1065 |
| 268 | 2779500 | RASSF5__5__2727413__2732312__2768970__2779500__FF | OBD RD043.1069 |

TABLE 33.e6-continued

| N | 4 kb Sequence Location End2 | Probe | Primer ID-1 |
|---|---|---|---|
| 269 | 2865680 | RASSF5__5__2727413__2732312__2857276__2865680__FF | OBD RD043.1073 |
| 270 | 2779500 | RASSF5__5__2752106__2755183__2768970__2779500__FF | OBD RD043.1077 |
| 271 | 34331563 | RBPJL__22__34286715__34290143__34327562__34334894__FR | OBD RD043.1081 |
| 272 | 34331563 | RBPJL__22__34286715__34290143__34327562__34334894__RR | OBD RD043.1085 |
| 273 | 46563398 | SCN10A__16__46394076__46405616__46559136__46563398__RF | OBD RD043.1089 |
| 274 | 46646012 | SCN10A__16__46394076__46405616__46644599__46646012__RF | OBD RD043.1093 |
| 275 | 46646012 | SCN10A__16__46542432__46554053__46644599__46646012__RF | OBD RD043.1097 |
| 276 | 26030228 | SCN2B__7__25981242__25985420__26023779__26030228__FF | OBD RD043.1101 |
| 277 | 26109968 | SCN2B__7__25981242__25985420__26102356__26109968__FF | OBD RD043.1105 |
| 278 | 25985420 | SCN4B__7__25954012__25959734__25981242__25985420__RF | OBD RD043.1109 |
| 279 | 46732988 | SCN5A__16__46559136__46563398__46724067__46732988__FF | OBD RD043.1113 |
| 280 | 46728068 | SCN5A__16__46559136__46563398__46724067__46732988__FR | OBD RD043.1117 |
| 281 | 6190373 | SELL__5__6104471__6117065__6186372__6188629__FR | OBD RD043.1121 |
| 282 | 65540822 | SEPT7__4__65366992__65373527__65534812__65540822__RF | OBD RD043.1125 |
| 283 | 26002740 | SGCA__11__25806231__25808754__26000893__26002740__RF | OBD RD043.1129 |
| 284 | 26004894 | SGCA__11__25806231__25808754__26000893__26002740__RR | OBD RD043.1133 |
| 285 | 20300077 | SIK2__7__20268830__20278159__20296076__20300289__FR | OBD RD043.1137 |
| 286 | 20380173 | SIK2__7__20268830__20278159__20375473__20380173__FF | OBD RD043.1141 |
| 287 | 20395428 | SIK2__7__20268830__20278159__20391427__20402715__FR | OBD RD043.1145 |
| 288 | 20411651 | SIK2__7__20268830__20278159__20407650__20411122__FR | OBD RD043.1149 |
| 289 | 3172603 | SNAP29__8__3045435__3054804__3164300__3172603__FF | OBD RD043.1153 |
| 290 | 3172603 | SNAP29__8__3117316__3123446__3164300__3172603__FF | OBD RD043.1157 |
| 291 | 150097168 | SPRED1__1__149873033__149876737__150087432__150097168__RF | OBD RD043.1161 |
| 292 | 150110035 | SPRED1__1__149873033__149876737__150099832__150110035__RF | OBD RD043.1165 |
| 293 | 150097168 | SPRED1__1__149910043__149913663__150087432__150097168__RF | OBD RD043.1169 |
| 294 | 150110035 | SPRED1__1__149910043__149913663__150099832__150110035__RF | OBD RD043.1173 |
| 295 | 150110035 | SPRED1__1__149923380__149924915__150099832__150110035__RF | OBD RD043.1177 |
| 296 | 150110035 | SPRED1__1__150016977__150019540__150099832__150110035__RF | OBD RD043.1181 |
| 297 | 150097168 | SPRED1__1__150032266__150036031__150087432__150097168__RF | OBD RD043.1185 |
| 298 | 150110035 | SPRED1__1__150068252__150074099__150099832__150110035__RF | OBD RD043.1189 |
| 299 | 27830004 | SRC__22__27681702__27686300__27826003__27831147__FR | OBD RD043.1193 |
| 300 | 42181998 | SRF__20__42097551__42100241__42177997__42186255__FR | OBD RD043.1197 |
| 301 | 67320245 | STAT1__18__67266270__67281181__67315145__67320245__RF | OBD RD043.1201 |
| 302 | 67345500 | STAT1__18__67266270__67281181__67340514__67345500__RF | OBD RD043.1205 |
| 303 | 67408407 | STAT1__18__67266270__67281181__67404406__67407824__RR | OBD RD043.1209 |
| 304 | 20630547 | STAT3__11__20601546__20610244__20625038__20630547__FF | OBD RD043.1213 |
| 305 | 20630547 | STAT3__11__20601546__20610244__20625038__20630547__RF | OBD RD043.1217 |
| 306 | 20755885 | STAT5A__11__20625038__20630547__20748936__20755885__FF | OBD RD043.1221 |
| 307 | 29826392 | STXBP4__11__29798087__29803880__29820062__29826392__RF | OBD RD043.1225 |
| 308 | 29860304 | STXBP4__11__29820062__29826392__29856303__29862822__FR | OBD RD043.1229 |
| 309 | 5963779 | TGFBR1__25__5777848__5781338__5953575__5963779__RF | OBD RD043.1233 |
| 310 | 5963779 | TGFBR1__25__5838527__5844153__5953575__5963779__RF | OBD RD043.1237 |
| 311 | 88351273 | TMEM156__3__88174369__88185533__88338789__88351273__FF | OBD RD043.1241 |
| 312 | 26425159 | TOB1__11__26381091__26387145__26421158__26424834__RR | OBD RD043.1245 |
| 313 | 26556181 | TOB1__11__26381091__26387145__26552180__26554959__RR | OBD RD043.1249 |
| 314 | 117533304 | TSPAN3__1__117377450__117387477__117527452__117533304__RF | OBD RD043.1253 |
| 315 | 117533304 | TSPAN3__1__117501086__117515708__117527452__117533304__RF | OBD RD043.1257 |
| 316 | 40842795 | TSPAN5__3__40723323__40732311__40838443__40842795__RF | OBD RD043.1261 |
| 317 | 4444354 | VAV1__7__4248599__4253460__4432636__4444354__FF | OBD RD043.1265 |
| 318 | 31998752 | VEGFC__27__31943096__31950700__31994751__32003367__RR | OBD RD043.1269 |
| 319 | 32010849 | VEGFC__27__31943096__31950700__32006848__32015827__RR | OBD RD043.1273 |
| 320 | 21260027 | ZFHX3__3__20954370__20958861__21248124__21260027__FF | OBD RD043.1277 |

TABLE 33.e7

| N | Primer Sequence | Primer ID-2 | Primer Sequence |
|---|---|---|---|
| 257 | AAGCCACATCCTTCCCACCCAGC (SEQ ID NO: 1468) | OBD RD043.1027 | GGAGAGCAAGGTCCTGGGAGTTA (SEQ ID NO: 1532) |
| 258 | GGAAGAGTCCTGACGACATCCTG (SEQ ID NO: 1469) & (SEQ ID NO: 1534) | OBD RD043.1031 | GAAGAAATGGTAGTGCCCGCCCC (SEQ ID NO: 1533) |
| 259 | GGGCTGCGGATGCTGTTCCTTGA (SEQ ID NO: 1470) | OBD RD043.1035 | GGAAGAGTCCTGACGACATCCTG (SEQ ID NO: 1469) & (SEQ ID NO: 1534) |
| 260 | GTCAACATTTCACTCCGTCGGGC (SEQ ID NO: 1471) | OBD RD043.1039 | GGCGAGGCTCTCTCATCTCTCTC (SEQ ID NO: 1535) |
| 261 | CGCCTCAGCGACACAGAGAACAA (SEQ ID NO: 1472) & (SEQ ID NO: 1473) | OBD RD043.1043 | CCGTCATAGTTCCCGTCCTGAGG (SEQ ID NO: 1536) |

TABLE 33.e7-continued

| N | Primer Sequence | Primer ID-2 | Primer Sequence |
|---|---|---|---|
| 262 | CGCCTCAGCGACACAGAGAACAA (SEQ ID NO: 1472) & (SEQ ID NO: 1473) | OBD RD043.1047 | CTGGAGACACGCTGAGGATTGGC (SEQ ID NO: 1537) |
| 263 | AATGCCCTTCCCTAACTCTGAACG (SEQ ID NO: 1474) | OBD RD043.1051 | AAACTACAATGAGATAACCACCCT (SEQ ID NO: 1538) |
| 264 | CCAAACTTTTCTGTGGAATACACG (SEQ ID NO: 1475) | OBD RD043.1055 | CATAATGAGACTAAATAACTTGTCC (SEQ ID NO: 1539) |
| 265 | CCTGAGCGAGGTCACACTGTTCA (SEQ ID NO: 1476) | OBD RD043.1059 | TCCAGAGTGCTTCCTGCCCCAAG (SEQ ID NO: 1540) & (SEQ ID NO: 1541) |
| 266 | TGAGAGCCGCTGGTGTAGATACG (SEQ ID NO: 1477) | OBD RD043.1063 | TCCAGAGTGCTTCCTGCCCCAAG (SEQ ID NO: 1540) & (SEQ ID NO: 1541) |
| 267 | GGTGGTGGCTACCCTGAAACTCATTG (SEQ ID NO: 1478) | OBD RD043.1067 | TAACAGGTGTGTGTGTAAGAGAGGGA (SEQ ID NO: 1542) |
| 268 | TCCCCTCTCTGGTGCTCCTGACA (SEQ ID NO: 1479) & (SEQ ID NO: 1480) | OBD RD043.1071 | ACCCCAGGTTCACGAAAGTCAGG (SEQ ID NO: 1543) |
| 269 | TCCCCTCTCTGGTGCTCCTGACA (SEQ ID NO: 1479) & (SEQ ID NO: 1480) | OBD RD043.1075 | AAGGCAGGGAGAGCCAGAGAAGA (SEQ ID NO: 1544) |
| 270 | ACCTTCTGAGCACCTCCCACAGC (SEQ ID NO: 1481) | OBD RD043.1079 | GTTTATGTCTTGTTTCTCCTGGACG (SEQ ID NO: 1545) |
| 271 | CTCTGAGTTGCTTACTGCCTCCTGC (SEQ ID NO: 1482) | OBD RD043.1083 | CCATTCTGGAAACAATCTGGCAGTA (SEQ ID NO: 1546) & (SEQ ID NO: 1547) |
| 272 | GACAACATACACCTCTCAGACGATGC (SEQ ID NO: 1483) | OBD RD043.1087 | CCATTCTGGAAACAATCTGGCAGTA (SEQ ID NO: 1546) & (SEQ ID NO: 1547) |
| 273 | TAGTTTTAGGGCTGGGCACACAGGA (SEQ ID NO: 1484) | OBD RD043.1091 | AAAGACAGTAGACACTTCACCAATGA (SEQ ID NO: 1548) |
| 274 | AAGGTGGAGGGTTCAGATGGGCTCAT (SEQ ID NO: 1485) | OBD RD043.1095 | AGACTGGCAGGAAATAAACCAAGTTG (SEQ ID NO: 1549) |
| 275 | TCAACAATGCTAAATCACCAAGGG (SEQ ID NO: 1486) | OBD RD043.1099 | AGACAGTAGACACTTCACCAATGA (SEQ ID NO: 1550) |
| 276 | TAAGACACAACCCCTGCCACGGG (SEQ ID NO: 1487) & (SEQ ID NO: 1488) | OBD RD043.1103 | CCAGGTAACAGGATGGCTCAAGG (SEQ ID NO: 1551) |
| 277 | TAAGACACAACCCCTGCCACGGG (SEQ ID NO: 1487) & (SEQ ID NO: 1488) | OBD RD043.1107 | CTCTGTGGTGTCATTGCCCCTTC (SEQ ID NO: 1552) |
| 278 | AGAAGAGTAAGACACAACCCCTGCCA (SEQ ID NO: 1489) | OBD RD043.1111 | TGGTCCTGAGACGACTACCTTGAAGT (SEQ ID NO: 1553) |
| 279 | TAGTTTTAGGGCTGGGCACACAGGAG (SEQ ID NO: 1490) | OBD RD043.1115 | CTTTAGAGCATACAGTAAGCCAATGG (SEQ ID NO: 1554) |
| 280 | ATGAGAAGGGCAGGACAGGGCTG (SEQ ID NO: 1491) | OBD RD043.1119 | CCACCTTTCCGCAGTATCCTCAC (SEQ ID NO: 1555) |
| 281 | GTGATAAGATGGAAGCCAAGACAAAA (SEQ ID NO: 1492) | OBD RD043.1123 | GGACGCAGCCATCTTGCCCCGAA (SEQ ID NO: 1556) |
| 282 | TTCCTCTTACCGTCTCTTGCGAT (SEQ ID NO: 1493) | OBD RD043.1127 | GTAGAAGTGGGGTTTTAGAGAGGGT (SEQ ID NO: 1557) |
| 283 | GCAAGGTTAGTGAGTGGCGAGGT (SEQ ID NO: 1494) | OBD RD043.1131 | TGGCTGGACCTGCCTCTCCTTTC (SEQ ID NO: 1495) & (SEQ ID NO: 1558) |
| 284 | TGGCTGGACCTGCCTCTCCTTTC (SEQ ID NO: 1495) & (SEQ ID NO: 1558) | OBD RD043.1135 | CAGACCAGCAGCCCTTATGGACA (SEQ ID NO: 1559) |
| 285 | GCAAAATGGGCAGGAAGGACATACAA (SEQ ID NO: 1496) & (SEQ ID NO: 1498) | OBD RD043.1139 | GGTTTAGAGGTCCTGATTTGTTCTCC (SEQ ID NO: 1560) |
| 286 | AATGGGCAGGAAGGACATACAAAATA (SEQ ID NO: 1497) | OBD RD043.1143 | TGACACTTCTCCCATCAAGAGGG (SEQ ID NO: 1561) |
| 287 | GCAAAATGGGCAGGAAGGACATACAA (SEQ ID NO: 1496) & (SEQ ID NO: 1498) | OBD RD043.1147 | CTTGCCCTTGTGGATAGAGAGTAGGC (SEQ ID NO: 1562) |

TABLE 33.e7-continued

| N | Primer Sequence | Primer ID-2 | Primer Sequence |
|---|---|---|---|
| 288 | TGGGCAGGAAGGACATACAAAATA (SEQ NO: 1499) | OBD RD043.1151 | GGGAGATTGGCAACAGATGTAAGC (SEQ ID NO: 1563) |
| 289 | TGTGGAAACAGGAAGGGCACGAC (SEQ ID NO: 1500) | OBD RD043.1155 | TCCACCGCATCAGCACCTTCCCA (SEQ NO: 1564) & (SEQ ID NO: 1565) |
| 290 | CAGAAGCAACACTTAGGCACCCAG (SEQ ID NO: 1501) | OBD RD043.1159 | TCCACCGCATCAGCACCTTCCCA (SEQ ID NO: 1564) & (SEQ ID NO: 1565) |
| 291 | CGCTTTCCTGACCTCCTACCCATCAA (SEQ ID NO: 1502) | OBD RD043.1163 | TTTTCATACTTTCCTCTCCTTGCCCC (SEQ ID NO: 1566) & (SEQ ID NO: 1568) |
| 292 | GACAGCCCATAGGTTAGGGACACC (SEQ ID NO: 1503) & (SEQ ID NO: 1506) & (SEQ ID NO: 1508) | OBD RD043.1167 | GCTTCCGCCTCCAAATGGCATCT (SEQ ID NO: 1567) |
| 293 | GACAGCCCATAGGTTAGGGACACCAA (SEQ ID NO: 1504) | OBD RD043.1171 | TTTTCATACTTTCCTCTCCTTGCCCC (SEQ ID NO: 1566) & (SEQ ID NO: 1568) |
| 294 | CCGCTTTCCTGACCTCCTACCCA (SEQ ID NO: 1505) | OBD RD043.1175 | GAGTTCCTTCTTGCTCACGGGTG (SEQ ID NO: 1569) & (SEQ ID NO: 1570) |
| 295 | GACAGCCCATAGGTTAGGGACACC (SEQ ID NO: 1503) & (SEQ ID NO: 1506) & (SEQ ID NO: 1508) | OBD RD043.1179 | GAGTTCCTTCTTGCTCACGGGTG (SEQ ID NO: 1569) & (SEQ ID NO: 1570) |
| 296 | GTTAGGGACACCAAATAGTATGCT (SEQ ID NO: 1507) | OBD RD043.1183 | TTGAAAGAAATGCCAACAAATGAT (SEQ ID NO: 1571) |
| 297 | GACAGCCCATAGGTTAGGGACACC (SEQ ID NO: 1503) & (SEQ ID NO: 1506) & (SEQ ID NO: 1508) | OBD RD043.1187 | GGGCAGAAGTTGAAGCCATCCTG (SEQ ID NO: 1572) |
| 298 | GCTTTCCTGACCTCCTACCCATC (SEQ ID NO: 1509) | OBD RD043.1191 | CCCTCTCACATCCCTTGCCCTGT (SEQ ID NO: 1573) |
| 299 | ATCATCCATCCTCACTTGGGCACA (SEQ ID NO: 1510) | OBD RD043.1195 | CTTTTGTTAGACAGAAGTTATCAAT (SEQ ID NO: 1574) |
| 300 | TCAAAGCCCAGAATCTCCAGCAT (SEQ ID NO: 1511) | OBD RD043.1199 | TACGGGATGAAGTCTGGAGGCAT (SEQ ID NO: 1575) |
| 301 | GCACTAAGAATCAAAGTCGCCTTCCA (SEQ ID NO: 1512) | OBD RD043.1203 | CCCAAAAGGCTTCTGACCAACACCTC (SEQ ID NO: 1576) |
| 302 | AAGGCTTCTGACCAACACCTCTGAGA (SEQ ID NO: 1513) | OBD RD043.1207 | GAGAATAAATAGGTGATGTGGGAGGC (SEQ ID NO: 1577) |
| 303 | AGGCTGCTGAAGTCCCCGTAGGG (SEQ ID NO: 1514) | OBD RD043.1211 | CAAACTCAAGACCTCACATTGTCAGG (SEQ ID NO: 1578) |
| 304 | CCAAGGTGAGTGCCCATCCTCTG (SEQ ID NO: 1515) & (SEQ ID NO: 1517) & (SEQ ID NO: 1580) | OBD RD043.1215 | GGTTTGGTGACTTGCTGAAGGGC (SEQ ID NO: 1579) |
| 305 | TACAGTTGGGACCCCTGATTCCG (SEQ ID NO: 1516) | OBD RD043.1219 | CCAAGGTGAGTGCCCATCCTCTG (SEQ ID NO: 1515) & (SEQ ID NO: 1517) & (SEQ ID NO: 1580) |
| 306 | CCAAGGTGAGTGCCCATCCTCTG (SEQ ID NO: 1515) & (SEQ ID NO: 1517) & (SEQ ID NO: 1580) | OBD RD043.1223 | AGGACCTCAAGGACTTCATCCGC (SEQ ID NO: 1581) |
| 307 | GACTGACCTATGTTGGGAAAAGCAAA (SEQ ID NO: 1518) | OBD RD043.1227 | CTAAACAGCATAATACTACTTGCCTC (SEQ ID NO: 1582) |
| 308 | ATGTATGTTTATGTATGACTTCCT (SEQ ID NO: 1519) | OBD RD043.1231 | GAATAAAGTAATGTAACAGGAAGA (SEQ ID NO: 1583) |
| 309 | TTTTGCTTGGCTTGCTTCCTTTGGA (SEQ ID NO: 1520) | OBD RD043.1235 | ATGTTACTCCGATACTGCTTTCTT (SEQ ID NO: 1584) |
| 310 | GGTTTTCAGCAGATTCTTCCTTGAGG (SEQ ID NO: 1521) | OBD RD043.1239 | AGCGGAAGTGCCCCTGCTTTGGTTTA (SEQ ID NO: 1585) |
| 311 | GAACTGCCTACTGCTATGTGAGGATG (SEQ ID NO: 1522) | OBD RD043.1243 | GGATGTGTCCAATAACTGGTGGCTGT (SEQ ID NO: 1586) |

TABLE 33.e7-continued

| N | Primer Sequence | Primer ID-2 | Primer Sequence |
|---|---|---|---|
| 312 | GGGTGAGGAAGGGACACAGGCAT (SEQ NO: 1523) & (SEQ ID NO: 1524) | OBD RD043.1247 | GAGAGGGAAGGAGGAAACGAAGC (SEQ ID NO: 1587) |
| 313 | GGGTGAGGAAGGGACACAGGCAT (SEQ NO: 1523) & (SEQ ID NO: 1524) | OBD RD043.1251 | CTATGTGCTGTGCCAGAGATGGG (SEQ ID NO: 1588) |
| 314 | GAAGTTAGTCCTCACTCTCCTCCC (SEQ ID NO: 1525) | OBD RD043.1255 | TCTCCGCCTTGCCAACCCCATCA(SEQ ID NO: 1589) |
| 315 | AAGTTAGTCCTCACTCTCCTCCCA (SEQ ID NO: 1526) | OBD RD043.1259 | AAAGTGAGACATTTTAGTGCTCCG (SEQ ID NO: 1590) |
| 316 | CTGCCAATGGAGCAAGAACTTCAAAA (SEQ ID NO: 1527) | OBD RD043.1263 | ACAGAACCCGAACAGTCAGACGCTCT (SEQ ID NO: 1591) |
| 317 | GCACCTATTGCCTGTCAAGCCTC (SEQ ID NO: 1528) | OBD RD043.1267 | TGGCACCACATCACTCCTGCTGC (SEQ ID NO: 1592) |
| 318 | CGGCTATGTCACTCACTACCTGG (SEQ ID NO: 1529) | OBD RD043.1271 | CACTCCACCCTGGCGTGTTTTCC (SEQ ID NO: 1593) |
| 319 | CACCTACGGTCTGATGGTATGTTA (SEQ ID NO: 1530) | OBD RD043.1275 | TTTCAGGGCAGAATAAAGATACAT (SEQ ID NO: 1594) |
| 320 | GACACAAATACCAAGGAGAGAAAGGC (SEQ ID NO: 1531) | OBD RD043.1279 | CAGAACCTGACTATGTAGGCACGCTG (SEQ ID NO: 1595) |

TABLE 33.e8

| N | Probe | Marker |
|---|---|---|
| 257 | PLXDC1 | OBD RD043.1025.1027 |
| 258 | PRKAG2 | OBD RD043.1029.1031 |
| 259 | PRKAG2 | OBD RD043.1033.1035 |
| 260 | PRKCA | OBD RD043.1037.1039 |
| 261 | PRKCB | OBD RD043.1041.1043 |
| 262 | PRKCB | OBD RD043.1045.1047 |
| 263 | RAB33B | OBD RD043.1049.1051 |
| 264 | RAB33B | OBD RD043.1053.1055 |
| 265 | RAG2 | OBD RD043.1057.1059 |
| 266 | RAG2 | OBD RD043.1061.1063 |
| 267 | RAG2 | OBD RD043.1065.1067 |
| 268 | RASSF5 | OBD RD043.1069.1071 |
| 269 | RASSF5 | OBD RD043.1073.1075 |
| 270 | RASSF5 | OBD RD043.1077.1079 |
| 271 | RBPJL | OBD RD043.1081.1083 |
| 272 | RBPJL | OBD RD043.1085.1087 |
| 273 | SCN10A | OBD RD043.1089.1091 |
| 274 | SCN10A | OBD RD043.1093.1095 |
| 275 | SCN10A | OBD RD043.1097.1099 |
| 276 | SCN2B | OBD RD043.1101.1103 |
| 277 | SCN2B | OBD RD043.1105.1107 |
| 278 | SCN4B | OBD RD043.1109.1111 |
| 279 | SCN5A | OBD RD043.1113.1115 |
| 280 | SCN5A | OBD RD043.1117.1119 |
| 281 | SELL | OBD RD043.1121.1123 |
| 282 | SEPT7 | OBD RD043.1125.1127 |
| 283 | SGCA | OBD RD043.1129.1131 |
| 284 | SGCA | OBD RD043.1133.1135 |
| 285 | SIK2 | OBD RD043.1137.1139 |
| 286 | SIK2 | OBD RD043.1141.1143 |
| 287 | SIK2 | OBD RD043.1145.1147 |
| 288 | SIK2 | OBD RD043.1149.1151 |
| 289 | SNAP29 | OBD RD043.1153.1155 |

TABLE 33.e8-continued

| N | Probe | Marker |
|---|---|---|
| 290 | SNAP29 | OBD RD043.1157.1159 |
| 291 | SPRED1 | OBD RD043.1161.1163 |
| 292 | SPRED1 | OBD RD043.1165.1167 |
| 293 | SPRED1 | OBD RD043.1169.1171 |
| 294 | SPRED1 | OBD RD043.1173.1175 |
| 295 | SPRED1 | OBD RD043.1177.1179 |
| 296 | SPRED1 | OBD RD043.1181.1183 |
| 297 | SPRED1 | OBD RD043.1185.1187 |
| 298 | SPRED1 | OBD RD043.1189.1191 |
| 299 | SRC | OBD RD043.1193.1195 |
| 300 | SRF | OBD RD043.1197.1199 |
| 301 | STAT1 | OBD RD043.1201.1203 |
| 302 | STAT1 | OBD RD043.1205.1207 |
| 303 | STAT1 | OBD RD043.1209.1211 |
| 304 | STAT3 | OBD RD043.1213.1215 |
| 305 | STAT3 | OBD RD043.1217.1219 |
| 306 | STAT5A | OBD RD043.1221.1223 |
| 307 | STXBP4 | OBD RD043.1225.1227 |
| 308 | STXBP4 | OBD RD043.1229.1231 |
| 309 | TGFBR1 | OBD RD043.1233.1235 |
| 310 | TGFBR1 | OBD RD043.1237.1239 |
| 311 | TMEM156 | OBD RD043.1241.1243 |
| 312 | TOB1 | OBD RD043.1245.1247 |
| 313 | TOB1 | OBD RD043.1249.1251 |
| 314 | TSPAN3 | OBD RD043.1253.1255 |
| 315 | TSPAN3 | OBD RD043.1257.1259 |
| 316 | TSPAN5 | OBD RD043.1261.1263 |
| 317 | VAV1 | OBD RD043.1265.1267 |
| 318 | VEGFC | OBD RD043.1269.1271 |
| 319 | VEGFC | OBD RD043.1273.1275 |
| 320 | ZFHX3 | OBD RD043.1277.1279 |

TABLE 34.a

| N | Marker with Dilution | Marker | Freq | Rank Sum | Rank Mean | Rank Median |
|---|---|---|---|---|---|---|
| 1 | OBD142__437.439__1.2x | OBD142__437.439 | 1000 | 198 | 1.98 | 2 |
| 2 | OBD142__025.027__1x | OBD142__025.027 | 1000 | 1224.5 | 12.245 | 8.5 |
| 3 | OBD142__417.419__1x | OBD142__417.419 | 1000 | 1369 | 13.69 | 13 |
| 4 | OBD142__517.519__1.2x | OBD142__517.519 | 1000 | 1251.5 | 12.515 | 13 |

TABLE 34.a-continued

| N | Marker with Dilution | Marker | Freq | Rank Sum | Rank Mean | Rank Median |
|---|---|---|---|---|---|---|
| 5 | OBD142__065.067__1x | OBD142__065.067 | 971 | 3903 | 39.03 | 35.5 |
| 6 | OBD142__513.515__1.2x | OBD142__513.515 | 971 | 3903 | 39.03 | 35.5 |
| 7 | OBD142__017.019__1x | OBD142__017.019 | 977 | 4446 | 44.46 | 40 |
| 8 | OBD142__029.031__1x | OBD142__029.031 | 972 | 4681.5 | 46.815 | 40.5 |
| 9 | OBD142__069.071__1.2x | OBD142__069.071 | 972 | 5103.5 | 51.035 | 40 |
| 10 | OBD142__085.087__1.2x | OBD142__085.087 | 972 | 4667 | 46.67 | 41 |
| 11 | OBD142__093.095__1x | OBD142__093.095 | 1000 | 3945 | 39.45 | 40 |
| 12 | OBD142__117.119__1.2x | OBD142__117.119 | 1000 | 4206.5 | 42.065 | 38.5 |
| 13 | OBD142__125.127__1.2x | OBD142__125.127 | 977 | 4446 | 44.46 | 40 |
| 14 | OBD142__157.159__1.4x | OBD142__157.159 | 1000 | 3707.5 | 37.075 | 38 |
| 15 | OBD142__233.235__1.4x | OBD142__233.235 | 1000 | 3707.5 | 37.075 | 38 |
| 16 | OBD142__285.287__1.4x | OBD142__285.287 | 975 | 4749 | 47.49 | 37.75 |
| 17 | OBD142__325.327__1.4x | OBD142__325.327 | 1000 | 4206.5 | 42.065 | 38.5 |
| 18 | OBD142__449.451__1x | OBD142__449.451 | 1000 | 3738 | 37.38 | 38.25 |
| 19 | OBD142__461.463__1.4x | OBD142__461.463 | 972 | 4667 | 46.67 | 41 |
| 20 | OBD142__469.471__1x | OBD142__469.471 | 975 | 4749 | 47.49 | 37.75 |
| 21 | OBD142__133.135__1x | OBD142__133.135 | 504 | 14009 | 140.09 | 86.5 |
| 22 | OBD142__181.183__1.4x | OBD142__181.183 | 504 | 14009 | 140.09 | 86.5 |
| 23 | OBD142__397.399__1x | OBD142__397.399 | 504 | 14009 | 140.09 | 86.5 |
| 24 | OBD142__253.255__1.2x | OBD142__253.255 | 867 | 7643 | 76.43 | 109.25 |
| 25 | OBD142__181.183__1.4x | OBD142__181.183 | 504 | 14009 | 140.09 | 86.5 |
| 26 | OBD142__037.039__1x | OBD142__037.039 | 779 | 8626.5 | 86.265 | 113 |
| 27 | OBD142__353.355__1x | OBD142__353.355 | 699 | 8585.5 | 85.855 | 113 |
| 28 | OBD142__005.007__1x | OBD142__005.007 | 527 | 12594.5 | 125.945 | 76.5 |
| 29 | OBD142__009.011__1.4x | OBD142__009.011 | 737 | 9784 | 97.84 | 44.5 |
| 30 | OBD142__025.027__1.2x | OBD142__025.027 | 1000 | 11604 | 116.04 | 42 |
| 31 | OBD142__029.031__1.4x | OBD142__029.031 | 1000 | 2760.5 | 27.605 | 38 |
| 32 | OBD142__041.043__1.2x | OBD142__041.043 | 737 | 9784 | 97.84 | 44.5 |
| 33 | OBD142__045.047__1x | OBD142__045.047 | 525 | 13251.5 | 132.515 | 77.5 |
| 34 | OBD142__057.059__1.8x | OBD142__057.059 | 715 | 11959.5 | 119.595 | 51.5 |
| 35 | OBD142__061.063__1.4x | OBD142__061.063 | 814 | 10698.5 | 106.985 | 44.5 |
| 36 | OBD142__065.067__1.2x | OBD142__065.067 | 1000 | 859.5 | 8.595 | 9.5 |
| 37 | OBD142__069.071__1.2x | OBD142__069.071 | 967 | 10625.5 | 106.255 | 43 |
| 38 | OBD142__081.083__1.4x | OBD142__081.083 | 1000 | 2686 | 26.86 | 34 |
| 39 | OBD142__097.099__1.8x | OBD142__097.099 | 1000 | 11838 | 118.38 | 51.5 |
| 40 | OBD142__101.103__1x | OBD142__101.103 | 1000 | 5050 | 50.5 | 70 |
| 41 | OBD142__109.111__1.2x | OBD142__109.111 | 1000 | 11604 | 116.04 | 42 |
| 42 | OBD142__121.123__1.8x | OBD142__121.123 | 814 | 10698.5 | 106.985 | 44.5 |
| 43 | OBD142__133.135__1.8x | OBD142__133.135 | 737 | 9784 | 97.84 | 44.5 |
| 44 | OBD142__137.139__1.2x | OBD142__137.139 | 1000 | 3052 | 30.52 | 39 |
| 45 | OBD142__141.143__1.4x | OBD142__141.143 | 737 | 9784 | 97.84 | 44.5 |
| 46 | OBD142__145.147__1.4x | OBD142__145.147 | 523 | 12431.5 | 124.315 | 81.5 |
| 47 | OBD142__153.155__1.4x | OBD142__153.155 | 1000 | 914 | 9.14 | 10 |
| 48 | OBD142__157.159__1.4x | OBD142__157.159 | 514 | 13293.5 | 132.935 | 83.5 |
| 49 | OBD142__165.167__1x | OBD142__165.167 | 1000 | 4818.5 | 48.185 | 69.5 |
| 50 | OBD142__185.187__1.4x | OBD142__185.187 | 1000 | 3161 | 31.61 | 39 |
| 51 | OBD142__189.191__1x | OBD142__189.191 | 1000 | 2760.5 | 27.605 | 38 |
| 52 | OBD142__197.199__1.4x | OBD142__197.199 | 1000 | 2795 | 27.95 | 38 |
| 53 | OBD142__201.203__1.4x | OBD142__201.203 | 1000 | 2903.5 | 29.035 | 38.5 |
| 54 | OBD142__213.215__1.4x | OBD142__213.215 | 151 | 19515.5 | 195.155 | 212 |
| 55 | OBD142__233.235__1.2x | OBD142__233.235 | 505 | 12737 | 127.37 | 81.5 |
| 56 | OBD142__241.243__1x | OBD142__241.243 | 1000 | 2820.5 | 28.205 | 38 |
| 57 | OBD142__253.255__1.2x | OBD142__253.255 | 1000 | 5334.5 | 53.345 | 70 |
| 58 | OBD142__257.259__1.2x | OBD142__257.259 | 1000 | 11995.5 | 119.955 | 51.5 |
| 59 | OBD142__261.263__1x | OBD142__261.263 | 1000 | 5144 | 51.44 | 69.5 |
| 60 | OBD142__265.267__1.4x | OBD142__265.267 | 967 | 9975.5 | 99.755 | 41.5 |
| 61 | OBD142__273.275__1.4x | OBD142__273.275 | 962 | 12527 | 125.27 | 51.5 |
| 62 | OBD142__277.279__1.2x | OBD142__277.279 | 1000 | 3060 | 30.6 | 38.5 |
| 63 | OBD142__297.299__1.2x | OBD142__297.299 | 1000 | 847.5 | 8.475 | 9.5 |
| 64 | OBD142__309.311__1.4x | OBD142__309.311 | 806 | 9550 | 95.5 | 42 |
| 65 | OBD142__313.315__1x | OBD142__313.315 | 1000 | 2760.5 | 27.605 | 38 |
| 66 | OBD142__321.323__1.2x | OBD142__321.323 | 1000 | 11995.5 | 119.955 | 51.5 |
| 67 | OBD142__325.327__1.2x | OBD142__325.327 | 1000 | 4958.5 | 49.585 | 69.5 |
| 68 | OBD142__329.331__1.4x | OBD142__329.331 | 1000 | 2795 | 27.95 | 38 |
| 69 | OBD142__337.339__1x | OBD142__337.339 | 817 | 10759.5 | 107.595 | 43 |
| 70 | OBD142__357.359__1.4x | OBD142__357.359 | 962 | 12527 | 125.27 | 51.5 |
| 71 | OBD142__361.363__1.2x | OBD142__361.363 | 932 | 11406.5 | 114.065 | 43 |
| 72 | OBD142__373.375__1x | OBD142__373.375 | 1000 | 2903.5 | 29.035 | 38.5 |
| 73 | OBD142__393.395__1.2x | OBD142__393.395 | 1000 | 921.5 | 9.215 | 10.5 |
| 74 | OBD142__401.403__1x | OBD142__401.403 | 1000 | 2820.5 | 28.205 | 38 |
| 75 | OBD142__405.407__1x | OBD142__405.407 | 537 | 11739.5 | 117.395 | 73.5 |
| 76 | OBD142__413.415__1.2x | OBD142__413.415 | 638 | 10473 | 104.73 | 45.5 |
| 77 | OBD142__433.435__1x | OBD142__433.435 | 1000 | 2969.5 | 29.695 | 39 |
| 78 | OBD142__437.439__1x | OBD142__437.439 | 1000 | 5144 | 51.44 | 69.5 |
| 79 | OBD142__445.447__1.2x | OBD142__445.447 | 752 | 10351.5 | 103.515 | 45 |
| 80 | OBD142__457.459__1x | OBD142__457.459 | 1000 | 3016 | 30.16 | 38.5 |
| 81 | OBD142__469.471__1.2x | OBD142__469.471 | 1000 | 2829 | 28.29 | 38.5 |

TABLE 34.a-continued

| N | Marker with Dilution | Marker | Freq | Rank Sum | Rank Mean | Rank Median |
|---|---|---|---|---|---|---|
| 82 | OBD142__477.479__1.2x | OBD142__477.479 | 752 | 10351.5 | 103.515 | 45 |
| 83 | OBD142__489.491__1x | OBD142__489.491 | 937 | 9975.5 | 99.755 | 41.5 |
| 84 | OBD142__501.503__1x | OBD142__501.503 | 537 | 11739.5 | 117.395 | 73.5 |
| 85 | OBD142__509.511__1.8x | OBD142__509.511 | 970 | 11725.5 | 117.255 | 43.25 |
| 86 | OBD142__517.519__1x | OBD142__517.519 | 1000 | 914 | 9.14 | 10 |

TABLE 34.b

| N | Mean p value | Median p value | Classification |
|---|---|---|---|
| 1 | 0.01576 | 0.01562 | Present in Strength Training |
| 2 | 0.08678 | 0.09375 | Present in Strength Training |
| 3 | 0.09328 | 0.125 | Present in Strength Training |
| 4 | 0.09312 | 0.125 | Present in Strength Training |
| 5 | 0.20758 | 0.13696 | Present in Strength Training |
| 6 | 0.20758 | 0.13696 | Present in Strength Training |
| 7 | 0.23382 | 0.28125 | Present in Strength Training |
| 8 | 0.23992 | 0.28125 | Present in Strength Training |
| 9 | 0.26566 | 0.28125 | Present in Strength Training |
| 10 | 0.24252 | 0.28125 | Present in Strength Training |
| 11 | 0.22246 | 0.28125 | Present in Strength Training |
| 12 | 0.23621 | 0.28125 | Present in Strength Training |
| 13 | 0.23382 | 0.28125 | Present in Strength Training |
| 14 | 0.22324 | 0.28125 | Present in Strength Training |
| 15 | 0.22324 | 0.28125 | Present in Strength Training |
| 16 | 0.24953 | 0.28125 | Present in Strength Training |
| 17 | 0.23621 | 0.28125 | Present in Strength Training |
| 18 | 0.21652 | 0.28125 | Present in Strength Training |
| 19 | 0.24252 | 0.28125 | Present in Strength Training |
| 20 | 0.24953 | 0.28125 | Present in Strength Training |
| 21 | 0.60112 | 0.34375 | Present in Strength Training |
| 22 | 0.60112 | 0.34375 | Present in Strength Training |
| 23 | 0.60112 | 0.34375 | Present in Strength Training |
| 24 | 0.62216 | 0.34375 | Present in Strength Training |
| 25 | 0.60112 | 0.34375 | Present in Strength Training |
| 26 | 0.35984 | 0.45312 | Present in Strength Training |
| 27 | 0.35078 | 0.45312 | Present in Strength Training |
| 28 | 0.57 | 0.28906 | Present in Endurance Training |
| 29 | 0.4475 | 0.1875 | Present in Endurance Training |
| 30 | 0.53687 | 0.1875 | Present in Endurance Training |
| 31 | 0.13594 | 0.1875 | Present in Endurance Training |
| 32 | 0.4475 | 0.1875 | Present in Endurance Training |
| 33 | 0.60297 | 0.28906 | Present in Endurance Training |
| 34 | 0.55312 | 0.1875 | Present in Endurance Training |
| 35 | 0.49625 | 0.1875 | Present in Endurance Training |
| 36 | 0.05469 | 0.07031 | Present in Endurance Training |
| 37 | 0.48812 | 0.1875 | Present in Endurance Training |
| 38 | 0.13008 | 0.1875 | Present in Endurance Training |
| 39 | 0.545 | 0.1875 | Present in Endurance Training |
| 40 | 0.21125 | 0.28906 | Present in Endurance Training |
| 41 | 0.53687 | 0.1875 | Present in Endurance Training |
| 42 | 0.49625 | 0.1875 | Present in Endurance Training |
| 43 | 0.4475 | 0.1875 | Present in Endurance Training |
| 44 | 0.14414 | 0.1875 | Present in Endurance Training |
| 45 | 0.4475 | 0.1875 | Present in Endurance Training |
| 46 | 0.56711 | 0.28906 | Present in Endurance Training |
| 47 | 0.05781 | 0.07031 | Present in Endurance Training |
| 48 | 0.6025 | 0.28906 | Present in Endurance Training |
| 49 | 0.20031 | 0.28906 | Present in Endurance Training |
| 50 | 0.15117 | 0.1875 | Present in Endurance Training |
| 51 | 0.13594 | 0.1875 | Present in Endurance Training |
| 52 | 0.13711 | 0.1875 | Present in Endurance Training |
| 53 | 0.1418 | 0.1875 | Present in Endurance Training |
| 54 | 0.90047 | 1 | Present in Endurance Training |
| 55 | 0.57758 | 0.28906 | Present in Endurance Training |
| 56 | 0.13828 | 0.1875 | Present in Endurance Training |
| 57 | 0.22125 | 0.28906 | Present in Endurance Training |
| 58 | 0.55312 | 0.1875 | Present in Endurance Training |
| 59 | 0.21031 | 0.28906 | Present in Endurance Training |
| 60 | 0.46375 | 0.1875 | Present in Endurance Training |
| 61 | 0.58562 | 0.1875 | Present in Endurance Training |
| 62 | 0.14766 | 0.1875 | Present in Endurance Training |
| 63 | 0.05531 | 0.07031 | Present in Endurance Training |
| 64 | 0.43937 | 0.1875 | Present in Endurance Training |

TABLE 34.b-continued

| N | Mean p value | Median p value | Classification |
|---|---|---|---|
| 65 | 0.13594 | 0.1875 | Present in Endurance Training |
| 66 | 0.55312 | 0.1875 | Present in Endurance Training |
| 67 | 0.20344 | 0.28906 | Present in Endurance Training |
| 68 | 0.13711 | 0.1875 | Present in Endurance Training |
| 69 | 0.49625 | 0.1875 | Present in Endurance Training |
| 70 | 0.58562 | 0.1875 | Present in Endurance Training |
| 71 | 0.52875 | 0.1875 | Present in Endurance Training |
| 72 | 0.1418 | 0.1875 | Present in Endurance Training |
| 73 | 0.05781 | 0.07031 | Present in Endurance Training |
| 74 | 0.13828 | 0.1875 | Present in Endurance Training |
| 75 | 0.5257 | 0.28906 | Present in Endurance Training |
| 76 | 0.48812 | 0.1875 | Present in Endurance Training |
| 77 | 0.14297 | 0.1875 | Present in Endurance Training |
| 78 | 0.21031 | 0.28906 | Present in Endurance Training |
| 79 | 0.48 | 0.1875 | Present in Endurance Training |
| 80 | 0.14414 | 0.1875 | Present in Endurance Training |
| 81 | 0.13594 | 0.1875 | Present in Endurance Training |
| 82 | 0.48 | 0.1875 | Present in Endurance Training |
| 83 | 0.46375 | 0.1875 | Present in Endurance Training |
| 84 | 0.5257 | 0.28906 | Present in Endurance Training |
| 85 | 0.545 | 0.1875 | Present in Endurance Training |
| 86 | 0.05781 | 0.07031 | Present in Endurance Training |

TABLE 35

| N | Equine Marker | Exact__Boschloo__p.value |
|---|---|---|
| 1 | OBD154__001/OBD154__003__1:2x | 0.597203758 |
| 2 | OBD154__009/OBD154__011__1:2x | 0.180069259 |
| 3 | OBD154__013/OBD154__015__1x | 0.050106528 |
| 4 | OBD154__033/OBD154__035__1:4x | 0.283703806 |
| 5 | OBD154__037/OBD154__039__1:8x | 0.523402567 |
| 6 | OBD154__041/OBD154__043__1x | 0.64299739 |
| 7 | OBD154__045/OBD154__047__1x | 0.180069259 |
| 8 | OBD154__049/OBD154__051__1:4x | 0.11992508 |
| 9 | OBD154__053/OBD154__055__1:2x | 0.597203758 |
| 10 | OBD154__057/OBD154__059__1:2x | 0.663949317 |
| 11 | OBD154__061/OBD154__063__1x | 0.663949317 |
| 12 | OBD154__069/OBD154__071__1x | 0.23718116 |
| 13 | OBD154__073/OBD154__075__1x | 0.125083174 |
| 14 | OBD154__077/OBD154__079__1x | 0.422463565 |
| 15 | OBD154__085/OBD154__087__1:2x | 0.038860637 |
| 16 | OBD154__093/OBD154__095__1:2x | 0.075142123 |
| 17 | OBD154__097/OBD154__099__1x | 0.523402567 |
| 18 | OBD154__105/OBD154__107__1:2x | 0.210490032 |
| 19 | OBD154__109/OBD154__111__1:2x | 0.387940572 |
| 20 | OBD154__113/OBD154__115__1:4x | 0.523402567 |
| 21 | OBD154__117/OBD154__119__1x | 0.659282164 |
| 22 | OBD154__121/OBD154__123__1x | 0.659282164 |
| 23 | OBD154__125/OBD154__127__1:2x | 0.006313179 |
| 24 | OBD154__133/OBD154__135__1:2x | 0.32961205 |
| 25 | OBD154__137/OBD154__139__1x | 0.663949317 |
| 26 | OBD154__141/OBD154__143__1x | 0.180069259 |
| 27 | OBD154__149/OBD154__151__1:2x | 0.678620772 |
| 28 | OBD154__153/OBD154__155__1:8x | 0.523402567 |
| 29 | OBD154__157/OBD154__159__1:2x | 0.038860637 |
| 30 | OBD154__161/OBD154__163__1:2x | 0.422463565 |
| 31 | OBD154__165/OBD154__167__1x | 0.180069259 |
| 32 | OBD154__169/OBD154__171__1:4x | 0.283703806 |
| 33 | OBD154__177/OBD154__179__1x | 0.23718116 |
| 34 | OBD154__185/OBD154__187__1x | 0.64299739 |
| 35 | OBD154__201/OBD154__203__1x | 0.11992508 |

TABLE 35-continued

| N | Equine Marker | Exact_Boschloo_p.value |
|---|---|---|
| 36 | OBD154_205/OBD154_207_1:2x | 0.125083174 |
| 37 | OBD154_209/OBD154_211_1:2x | 0.253032887 |
| 38 | OBD154_213/OBD154_215_1:2x | 0.180069259 |
| 39 | OBD154_217/OBD154_219_1x | 0.387940572 |
| 40 | OBD154_229/OBD154_231_1x | 0.054191604 |
| 41 | OBD154_237/OBD154_239_1x | 0.23718116 |
| 42 | OBD154_245/OBD154_247_1x | 0.050106528 |

TABLE 36

Top Human Markers (from I to IIIB)

| N | Marker for Human | Training | Odds Ratio | Combined | Cardio | Strength |
|---|---|---|---|---|---|---|
| 1 | OBD142_029.031_1x | Any | 7.2 | 0.01668097 | 0.066688 | 0.01613009 |
| 2 | OBD142_061.063_1.8x | Any | 8.2 | 0.01851064 | 0.11741215 | 0.10680154 |
| 3 | OBD142_069.071_1.2x | Any | 8 | 0.00255609 | 0.066688 | 0.05766889 |
| 4 | OBD142_089.091_1x | Any | 2.9 | 0.12375267 | 0.40122897 | 0.18059725 |
| 5 | OBD142_137.139_1.2x | Any | 8 | 0.06270144 | 0.11741215 | 0.18262433 |
| 6 | OBD142_081.083_1.4x | Endurance | 6 | 0.13923948 | 0.070484 | 0.7999889 |
| 7 | OBD142_189.191_1x | Endurance | 4.5 | 0.11969458 | 0.11741215 | 0.84528948 |
| 8 | OBD142_213.215_1.4x | Endurance | 2.25 | 1 | 0.69409048 | 0.13523206 |
| 9 | OBD142_017.019_1.2x | Strength | 4 | 0.72495046 | 0.54542431 | 0.28124028 |
| 10 | OBD142_037.039_1x | Strength | 12 | 0.15251771 | 1 | 0.02525659 |
| 11 | OBD142_065.067_1x | Strength | 5 | 0.13191103 | 0.54542431 | 0.05766889 |
| 12 | OBD142_133.135_1x | Strength | 4 | 0.46156086 | 1 | 0.01613009 |
| 13 | OBD142_253.255_1.2x | Strength | 12 | 0.44960749 | 0.61010368 | 0.02421162 |
| 14 | OBD142_353.355_1x | Strength | 9 | 0.11969458 | 1 | 0.01615402 |
| 15 | OBD142_477.479_1x | Strength | 9 | 0.42751765 | 1 | 0.02525659 |
| 16 | OBD142_181.183_1.4x | Strength | 2 | 0.75595814 | 0.74070856 | 0.17780781 |
| 17 | OBD142_397.399_1x | Strength | 2 | 0.15163712 | 0.66842823 | 0.09667637 |

Table 37 is shown below. Some parts of the table have been left out which relate to information shown in other tables.

TABLE 37.A1

| | probe | GeneLocus | Loop detected |
|---|---|---|---|
| 1 | ACACB_12_109146008_109150083_109185066_109187324_RR | ACACB | E_Trn |
| 2 | ACBD6_1_180269638_180272765_180371571_180375410_RR | ACBD6 | E_Trn |
| 3 | ACBD6_1_180337907_180340909_180371571_180375410_FR | ACBD6 | E_Trn |
| 4 | ADRB3_8_37962724_37965269_37984580_37986052_FF | ADRB3 | Str_Trn |
| 5 | ADRB3_8_37962724_37965269_37996522_37999233_FR | ADRB3 | Str_Trn |
| 6 | ALDH1A2_15_58053198_58062371_58157807_58162832_RR | ALDH1A2 | Str_Trn |
| 7 | ALDH1A2_15_58053198_58062371_58229591_58234474_RF | ALDH1A2 | E_Trn |
| 8 | ANO2_12_5767708_5775129_5922387_5930466_RR | ANO2 | Str_Trn |
| 9 | ANO2_12_5872622_5877860_5922387_5930466_RR | ANO2 | Str_Trn |
| 10 | B3GAT1_11_134376219_134382136_134419343_134423366_FF | B3GAT1 | Str_Trn |
| 11 | B3GAT2_6_70837358_70839856_70855194_70857991_FR | B3GAT2 | E_Trn |
| 12 | B3GAT2_6_70837358_70839856_70933019_70941366_FF | B3GAT2 | Str_Ctrl |
| 13 | BMP7_20_57274840_57277666_57290751_57294583_RF | BMP7 | E_Ctrl |
| 14 | C1GALT1_7_7113076_7114831_7258228_7260668_FF | C1GALT1 | E_Trn |
| 15 | CALCR_7_93553156_93563952_93593898_93597071_RF | CALCR | E_Ctrl |
| 16 | CARD11_7_2966372_2970772_3066095_3073017_RR | CARD11 | E_Trn |
| 17 | CASP9_1_15526774_15533191_15569002_15572579_FR | CASP9 | E_Trn |
| 18 | CBL_11_119249760_119252653_119294588_119299643_RF | CBL | E_Trn |
| 19 | CD36_7_80539507_80544315_80603212_80611693_FR | CD36 | E_Ctrl |
| 20 | CD36_7_80539507_80544315_80679651_80687690_FR | CD36 | Str_Ctrl |
| 21 | COL13A1_10_69769669_69775141_69840301_69843474_RF | COL13A1 | E_Trn |
| 22 | COL25A1_4_109024771_109031337_109090838_109104305_RR | COL25A1 | E_Ctrl |
| 23 | COL25A1_4_109090838_109104305_109307411_109309712_RF | COL25A1 | E_Ctrl |
| 24 | COL4A2_13_110272408_110277108_110487749_110493325_FR | COL4A2 | E_Trn |
| 25 | COL5A1_9_134738485_134741113_134811418_134816113_RR | COL5A1 | Str_Trn |
| 26 | CYGB_17_76511049_76513649_76555120_76557454_RF | CYGB | Str_Trn |
| 27 | CYGB_17_76533052_76534398_76555120_76557454_RF | CYGB | Str_Trn |
| 28 | CYGB_17_76555120_76557454_76593886_76595265_FF | CYGB | Str_Trn |
| 29 | CYGB_17_76555120_76557454_76593886_76595265_FR | CYGB | Str_Trn |

TABLE 37.B1

| | | | |
|---|---|---|---|
| 30 | DGKH__13__42011104__42015078__42235825__42240914__RR | DGKH | E_Trn |
| 31 | DIAPH3__13__59818047__59823591__59854837__59860534__RR | DIAPH3 | E_Ctrl |
| 32 | DKK3__11__11956071__11968035__11984245__11993733__FR | DKK3 | Str_Trn |
| 33 | DKK3__11__11956071__11968035__12010923__12019458__FF | DKK3 | Str_Trn |
| 34 | DKK3__11__11956071__11968035__12010923__12019458__FR | DKK3 | Str_Trn |
| 35 | DKK3__11__11956071__11968035__12048403__12051930__FR | DKK3 | Str_Trn |
| 36 | DLK1__14__100687837__100692867__100749541__100751577__RF | DLK1 | Str_Trn |
| 37 | DOK5__20__54466479__54470848__54572383__54577350__RF | DOK5 | E_Ctrl |
| 38 | EGR3__8__22681793__22682820__22737091__22739184__FF | EGR3 | E_Trn |
| 39 | EHD1__11__64868178__64874017__64914431__64916090__RF | EHD1 | E_Trn |
| 40 | EMCN__4__100525710__100532027__100732651__100738720__RR | EMCN | Str_Ctrl |
| 41 | ETS1__11__128476761__128480323__128561632__128566579__RR | ETS1 | E_Trn |
| 42 | EYA1__8__71216399__71218728__71261816__71267769__RR | EYA1 | E_Trn |
| 43 | FBLN2__3__13512352__13515076__13582406__13590343__RF | FBLN2 | E_Trn |
| 44 | FBXO32__8__123526212__123527874__123555254__123559065__FR | FBXO32 | E_Trn |
| 45 | FOXO1__13__40524349__40526124__40688580__40690771__RR | FOXO1 | Str_Ctrl |
| 46 | FOXO3__6__108603215__108604436__108629992__108635481__FR | FOXO3 | E_Trn_ |
| 47 | FTO__16__53844989__53854574__54045378__54052319__RF | FTO | E_Trn |
| 48 | GPC5__13__91724432__91728749__91910388__91925040__FR | GPC5 | E_Trn |
| 49 | GPC5__13__91794062__91815301__91953115__91957441__RR | GPC5 | E_Trn |
| 50 | GPC6__13__94054831__94060621__94121445__94133208__RF | GPC6 | Str_Ctrl |
| 51 | GPC6__13__94121445__94133208__94296633__94304225__FF | GPC6 | Str_Ctrl |
| 52 | GRB10__7__50706363__50709345__50775503__50780905__RF | GRB10 | E_Trn |
| 53 | GSN__9__121177548__121180410__121268506__121274144__FR | GSN | E_Trn |
| 54 | GSN__9__121182946__121189020__121239116__121243347__FF | GSN | Str_Ctrl |
| 55 | GSN__9__121227501__121232628__121268506__121274144__FR | GSN | E_Trn |
| 56 | GSN__9__121239116__121243347__121268506__121274144__FR | GSN | E_Trn |
| 57 | GSN__9__121253564__121256485__121268506__121274144__RR | GSN | Str_Trn |
| 58 | HDAC9__7__18055950__18064786__18135886__18142010__RF | HDAC9 | E_Ctrl |
| 59 | HOXC6__12__53956382__53960014__53992251__53994278__FF | HOXC6 | Str_Trn |

TABLE 37.C1

| | | | |
|---|---|---|---|
| 60 | IGF1R__15__98659065__98662585__98893484__98899517__FR | IGF1R | E_Trn |
| 61 | IL1RAP__3__190465562__190469171__190489665__190498302__RF | IL1RAP | E_Trn |
| 62 | IL1RAP__3__190489665__190498302__190560851__190563356__FR | IL1RAP | E_Ctrl |
| 63 | KDM1A__1__23064655__23070269__23096951__23098159__FR | KDM1A | Str_Ctrl |
| 64 | LAMA2__6__128920996__128927003__129105731__129113111__FF | LAMA2 | E_Trn |
| 65 | LAMA2__6__129342029__129351351__129383008__129389769__FR | LAMA2 | E_Trn |
| 66 | LCK__1__32214585__32217213__32237144__32241139__RF | LCK | E_Ctrl |
| 67 | LDB2__4__16489298__16494220__16535160__16542582__RR | LDB2 | E_Ctrl |
| 68 | LMO4__1__87315524__87318670__87343110__87349940__FF | LMO4 | E_Trn |
| 69 | LMO4__1__87315524__87318670__87355277__87360229__FR | LMO4 | Str_Trn |
| 70 | MAPK10__4__86572598__86581486__86617317__86621940__FF | MAPK10 | E_Trn_ |
| 71 | MBNL1__3__152229500__152234786__152252961__152257281__FR | MBNL1 | E_Trn |
| 72 | MBNL1__3__152229500__152234786__152281057__152285843__FR | MBNL1 | Str_Trn |
| 73 | MYBPC1__12__101527342__101530065__101646571__101655128__RF | MYBPC1 | Str_Ctrl |
| 74 | MYH1__17__10491098__10496051__10520297__10523271__RR | MYH1 | Str_Trn |
| 75 | MYH1__17__10523271__10524567__10560779__10565755__FF | MYH1 | E_Ctrl |
| 76 | MYO18B__22__26004818__26009467__26030914__26037279__FF | MYO18B | E_Trn |
| 77 | NCAM1__11__113019160__113028536__113163748__113168132__FR | NCAM1 | E_Trn |
| 78 | NECTIN2__19__44815042__44816736__44827160__44828776__RR | NECTIN2 | E_Ctrl |
| 79 | NFKB1__4__102504137__102509238__102557818__102560252__FF | NFKB1 | Str_Ctrl |
| 80 | NFKB1__4__102557818__102560252__102627099__102634363__FR | NFKB1 | E_Trn |
| 81 | NFKB1__4__102599188__102601960__102627099__102634363__FR | NFKB1 | E_Trn |
| 82 | NR4A1__12__51995149__51997631__52041793__52046779__RR | NR4A1 | Str_Trn |
| 83 | NRXN1__2__50580957__50583587__50867546__50884047__RF | NRXN1 | E_Ctrl |
| 84 | NTRK2__9__84804816__84814325__84917519__84924935__FR | NTRK2 | E_Ctrl |
| 85 | NTRK2__9__84804816__84814325__84934592__84942655__FR | NTRK2 | E_Ctrl |
| 86 | PAG1__8__81007411__81018107__81069439__81070856__FR | PAG1 | E_Trn |
| 87 | PAG1__8__81007411__81018107__81126745__81129448__FR | PAG1 | E_Trn |
| 88 | PCK1__20__57527297__57530814__57551578__57557205__RR | PCK1 | E_Trn |
| 89 | PCK1__20__57527297__57530814__57570220__57572870__RR | PCK1 | E_Trn |

TABLE 37.E1

| | | | |
|---|---|---|---|
| 90 | PCK1__20__57527297__57530814__57579772__57583521__RR | PCK1 | E_Trn |
| 91 | PCK1__20__57527297__57530814__57583521__57585923__RR | PCK1 | Str_Trn |
| 92 | PDK3__X__24441637__24447950__24480152__24481252__FR | PDK3 | E_Trn |
| 93 | PDK3__X__24441637__24447950__24490440__24491541__FR | PDK3 | E_Trn |
| 94 | PHTF2__7__77800747__77805972__77956111__77960107__RR | PHTF2 | E_Trn |
| 95 | PHTF2__7__77846910__77851576__77956111__77960107__RR | PHTF2 | Str_Ctrl |
| 96 | PIK3C3__18__42033052__42039159__42070009__42072187__RF | PIK3C3 | Str_Ctrl |
| 97 | PIK3C3__18__42070009__42072187__42088671__42094691__FF | PIK3C3 | E_Ctrl |
| 98 | PIK3R1__5__68187850__68194388__68237549__68241297__FF | PIK3R1 | E_Trn |

TABLE 37.E1-continued

| | | | |
|---|---|---|---|
| 99 | PIK3R1_5_68203536_68213336_68237549_68241297_FR | PIK3R1 | E_Trn |
| 100 | PLCXD2_3_111719030_111722119_111809065_111815838_RR | PLCXD2 | E_Ctrl |
| 101 | PPARGC1A_4_23871872_23880181_23925180_23932379_FF | PPARGC1A | E_Ctrl |
| 102 | PPP3CA_4_101055418_101067369_101247819_101259416_RR | PPP3CA | E_Trn |
| 103 | PRDX6_1_173434669_173438537_173475099_173476805_FR | PRDX6 | E_Trn |
| 104 | PRDX6_1_173434669_173438537_173477717_173485417_FR | PRDX6 | E_Trn |
| 105 | PRDX6_1_173450908_173452763_173477717_173485417_FR | PRDX6 | Str_Trn |
| 106 | PRKCCL10_6432893_6439235_6488207_6489596_FF | PRKCQ | E_Trn |
| 107 | PTPRC_1_198595771_198598296_198659753_198666156_RF | PTPRC | E_Ctrl |
| 108 | PTPRC_1_198631562_198634915_198659753_198666156_RF | PTPRC | E_Ctrl |
| 109 | PTPRC_1_198659753_198666156_198697386_198704777_FR | PTPRC | E_Ctrl |
| 110 | PTPRC_1_198659753_198666156_198704777_198709653_FR | PTPRC | E_Ctrl |
| 111 | PTPRC_1_198659753_198666156_198721093_198724578_FR | PTPRC | E_Ctrl |
| 112 | PTPRC_1_198659753_198666156_198768850_198775826_FF | PTPRC | E_Ctrl |
| 113 | PYGM_11_64747174_64749438_64762879_64765587_RF | PYGM | E_Trn |
| 114 | RGS6_14_72139099_72144564_72213251_72222544_FR | RGS6 | Str_Ctrl |
| 115 | RORA_15_60902137_60909221_61019417_61030714_RR | RORA | E_Trn |
| 116 | RUNX3_1_24920810_24923822_24973522_24976037_RF | RUNX3 | Str_Ctrl |
| 117 | RYR1_19_38410632_38413089_38495982_38499305_RR | RYR1 | Str_Ctrl |
| 118 | SGCZ_8_14631157_14642508_14656955_14664444_RF | SGCZ | E_Trn |
| 119 | SLC35B1_17_49700402_49702340_49724264_49725934_RR | SLC35B1 | Str_Trn |
| 120 | SLC35D1_1_66998822_67004850_67070417_67074223_FR | SLC35D1 | E_Ctrl |
| 121 | SMAD7_18_48917335_48920290_48969505_48974578_RF | SMAD7 | Str_Ctrl |
| 122 | STIM1_11_4071215_4074242_4084365_4091420_FR | STIM1 | E_Trn |
| 123 | STK39_2_167959346_167965882_168109573_168114525_FF | STK39 | E_Trn |
| 124 | STK39_2_168057412_168062336_168109573_168114525_FF | STK39 | E_Trn |
| 125 | STXBP4_17_55035186_55042800_55142272_55149288_FR | STXBP4 | E_Trn |
| 126 | SULF2_20_47663998_47665865_47797013_47801718_FR | SULF2 | Str_Trn |
| 127 | SYK_9_90789107_90793598_90876350_90879196_RF | SYK | E_Trn |
| 128 | SYK_9_90816328_90822228_90832284_90836084_RR | SYK | E_Ctrl |
| 129 | SYK_9_90816328_90822228_90836573_90843345_FR | SYK | E_Trn |
| 130 | SYK_9_90816328_90822228_90836573_90843345_RR | SYK | E_Ctrl |
| 131 | SYK_9_90816328_90822228_90872966_90875740_RR | SYK | E_Ctrl |
| 132 | TBX21_17_47685438_47687129_47704291_47707744_FR | TBX21 | Str_Trn |
| 133 | TGFB2_1_218317687_218325587_218386401_218389011_FR | TGFB2 | E_Trn |
| 134 | TGFBR2_3_30563062_30565548_30608158_30611268_FF | TGFBR2 | E_Trn |
| 135 | TGFBR2_3_30566144_30567439_30633318_30636860_RR | TGFBR2 | Str_Ctrl |
| 136 | TGFBR2_3_30566144_30567439_30694718_30698514_RR | TGFBR2 | Str_Ctrl |
| 137 | TGFBR2_3_30641481_30645057_30688470_30694718_FF | TGFBR2 | E_Trn |
| 138 | THADA_2_43260154_43263093_43324949_43335508_FF | THADA | Str_Trn |
| 139 | THADA_2_43260154_43263093_43415062_43421910_FF | THADA | Str_Trn |
| 140 | THNSL2_2_88139809_88146295_88161717_88164554_FF | THNSL2 | E_Ctrl |
| 141 | THNSL2_2_88139809_88146295_88161717_88164554_FR | THNSL2 | E_Ctrl |
| 142 | TLR2_4_153659613_153661830_153693586_153700349_RF | TLR2 | Str_Ctrl |
| 143 | TNFRSF25_1_6481328_6484248_6494588_6498048_FR | TNFRSF25 | Str_Trn |
| 144 | TTN_2_178554164_178555670_178788193_178796485_FR | TTN | E_Ctrl |
| 145 | UACA_15_70715123_70719636_70780754_70784668_RF | UACA | E_Trn |
| 146 | WASL_7_123664155_123666896_123763390_123768284_RF | WASL | E_Trn |
| 147 | ZEB1_10_31273317_31275631_31437913_31439545_RF | ZEB1 | E_Ctrl |
| 148 | ZEB1_10_31273317_31275631_31507470_31524442_FF | ZEB1 | E_Ctrl |
| 149 | ZEB1_10_31437913_31439545_31458964_31462037_FR | ZEB1 | E_Ctrl |
| 150 | ZEB1_10_31437913_31439545_31463562_31470397_FR | ZEB1 | E_Ctrl |
| 151 | ZFHX3_16_73147488_73153243_73182254_73184585_FF | ZFHX3 | Str_Trn |
| 152 | ADRB3_8_37962724_37965269_37987735_37989039_FR | ADRB3 | Str_Trn |
| 153 | ADRB3_8_37962724_37965269_38014799_38016599_FR | ADRB3 | Str_Trn |
| 154 | AGT_1_230717799_230719628_230752057_230757333_RF | AGT | Str_Trn |
| 155 | AGT_1_230724515_230729957_230752057_230757333_RF | AGT | Str_Trn |
| 156 | BMPR1B_4_94967703_94973952_95026184_95035151_FR | BMPR1B | Str_Trn |
| 157 | HTR2A_13_46860092_46866824_46904346_46907815_RF | HTR2A | Str_Trn |
| 158 | PPARA_22_46101029_46102611_46241078_46244347_FR | PPARA | E_Trn |
| 159 | SOS1_2_38982199_38993639_39061418_39066028_FF | SOS1 | Str_Trn |
| 160 | SVEP1_9_110493529_110499578_110527410_110532406_FR | SVEP1 | Str_Trn |
| 161 | UBE3A_15_25355032_25368345_25399797_25404434_FF | UBE3A | Str_Trn |
| 162 | UBE3A_15_25355032_25368345_25457129_25464700_FR | UBE3A | Str_Trn |
| 163 | ACBD6_1_180431719_180434683_180541491_180549122_RR | ACBD6 | E_Trn |
| 164 | BMPR1B_4_94821712_94826817_94866803_94871889_FF | BMPR1B | Str_Trn |
| 165 | HADHA_2_26188355_26191067_26247231_26249308_FR | HADHA | Str_Trn |
| 166 | HADHA_2_26188355_26191067_26280650_26284864_FF | HADHA | Str_Trn |
| 167 | MTFR1_8_65658401_65661888_65780891_65782535_RF | MTFR1 | E_Trn |
| 168 | MYBPC1_12_101567479_101571538_101655128_101656342_RF | MYBPC1 | Str_Trn |
| 169 | MYH1_17_10502067_10505465_10533547_10534931_RF | MYH1 | Str_Trn |
| 170 | MYL1_2_210288997_210291732_210359762_210362293_FF | MYL1 | E_Trn |
| 171 | MYOD1_11_17685862_17689487_17729653_17733608_FR | MYOD1 | E_Trn |
| 172 | NECTIN3_3_111028574_111034204_111209684_111210764_FR | NECTIN3 | Str_Trn |
| 173 | PON1_7_95303795_95305644_95332254_95337348_RF | PON1 | Str_Trn |
| 174 | ACACB_12_109146008_109150083_109236052_109237242_RR | ACACB | E_Ctrl |
| 175 | ACACB_12_109236052_109237242_109268078_109273323_RR | ACACB | E_Ctrl |

TABLE 37.E1-continued

| | | | |
|---|---|---|---|
| 176 | COL1A2__7__94359704__94366215__94394399__94397338__RF | COL1A2 | E__Ctrl |
| 177 | COX6A1__12__120397017__120399520__120449180__120450939__RF | COX6A1 | E__Ctrl |
| 178 | GGPS1__1__235284158__235288561__235306299__235310474__FR | GGPS1 | E__Ctrl |
| 179 | GSN__9__121182946__121189020__121323589__121328431__FF | GSN | Str__Trn__ |

TABLE 37.F2

| | | | |
|---|---|---|---|
| 180 | HTR2A__13__46847106__46857832__46938758__46942222__RF | HTR2A | E__Ctrl |
| 181 | HTR2A__13__46877712__46880636__46938758__46942222__FF | HTR2A | E__Ctrl |
| 182 | IGF1R__15__98652565__98657862__98731539__98737034__RF | IGF1R | Str__Trn |
| 183 | MUSK__9__110648469__110652659__110747866__110751903__FR | MUSK | Str__Trn__ |
| 184 | MYOT__5__137829466__137834410__137882068__137884626__RR | MYOT | E__Ctrl |
| 185 | PPARA__22__46128634__46134707__46231440__46235124__FR | PPARA | Str__Trn |
| 186 | PPP1R9A__7__94903925__94908776__94951930__94967018__RF | PPP1R9A | E__Ctrl |
| 187 | PPP1R9A__7__94951930__94967018__95061734__95065150__FR | PPP1R9A | E__Ctrl |
| 188 | PPP1R9A__7__94951930__94967018__95258927__95267729__FF | PPP1R9A | E__Ctrl |
| 189 | RB1__13__48378062__48381344__48486008__48495146__FF | RB1 | E__Ctrl |
| 190 | SLC25A13__7__96209525__96214524__96295606__96302029__FF | SLC25A13 | E__Ctrl |
| 191 | ACE2__X__15558483__15561359__15624288__15632375__RR | ACE2 | E__Ctrl |
| 192 | DNAH5__5__13907228__13913186__13947622__13950495__FR | DNAH5 | E__Ctrl |
| 193 | EMCN__4__100636305__100649860__100744427__100745788__RR | EMCN | E__Ctrl |
| 194 | ITGAV__2__186622411__186639782__186682119__186696186__RR | ITGAV | E__Ctrl |
| 195 | MSTN__2__190044593__190053476__190068550__190073029__FR | MSTN | E__Ctrl |
| 196 | PLCXD2__3__111633890__111638317__111672672__111677327__FR | PLCXD2 | E__Ctrl |
| 197 | SGCZ__8__14631157__14642508__14778176__14785491__FF | SGCZ | E__Ctrl |
| 198 | SLC25A13__7__96178122__96182739__96295606__96302029__RF | SLC25A13 | E__Ctrl |
| 199 | SOCS7__17__38347510__38348776__38360864__38363420__FR | SOCS7 | E__Ctrl |
| 200 | SRI__7__88199682__88203042__88229166__88237101__RF | SRI | E__Ctrl |
| 201 | STXBP4__17__55035186__55042800__55117598__55123347__RR | STXBP4 | E__Ctrl |
| 202 | SVEP1__9__110397951__110405969__110503630__110509758__FF | SVEP1 | E__Ctrl |

Table 38 is below. Some parts of the table have been left out which relates to information in other tables.

TABLE 38.a

| | Probe | GeneLocus | Loop Detected |
|---|---|---|---|
| 1 | C1GALT1__7__7113076__7114831__7258228__7260668__FF | C1GALT1 | E__Trn |
| 2 | DKK3__11__11956071__11968035__11984245__11993733__FR | DKK3 | Str__Trn |
| 3 | FBXO32__8__123526212__123527874__123555254__123559065__FR | FBXO32 | E__Trn |
| 4 | GPC6__13__94054831__94060621__94121445__94133208__RF | GPC6 | Str__Ctrl |
| 5 | GSN__9__121177548__121180410__121268506__121274144__FR | GSN | E__Trn |
| 6 | LMO4__1__87315524__87318670__87343110__87349940__FF | LMO4 | E__Trn |
| 7 | MAPK10__4__86572598__86581486__86617317__86621940__FF | MAPK10 | E__Trn |
| 8 | MBNL1__3__152229500__152234786__152281057__152285843__FR | MBNL1 | Str__Trn |
| 9 | PCK1__20__57527297__57530814__57579772__57583521__RR | PCK1 | E__Trn |
| 10 | PIK3C3__18__42070009__42072187__42088671__42094691__FF | PIK3C3 | E__Ctrl |
| 11 | PTPRC__1__198595771__198598296__198659753__198666156__RF | PTPRC | E__Ctrl |
| 12 | RGS6__14__72139099__72144564__72213251__72222544__FR | RGS6 | Str__Ctrl |
| 13 | RUNX3__1__24920810__24923822__24973522__24976037__RF | RUNX3 | Str__Ctrl |
| 14 | ZFHX3__16__73147488__73153243__73182254__73184585__FF | ZFHX3 | Str__Trn |
| 15 | MYOT__5__137829466__137834410__137882068__137884626__RR | MYOT | Str__Ctrl |
| 16 | AGT__1__230724515__230729957__230752057__230757333__RF | AGT | Str__Trn |
| 17 | MYL1__2__210288997__210291732__210359762__210362293__FF | MYL1 | E__Trn |
| 18 | SRI__7__88199682__88203042__88229166__88237101__RF | SRI | E__Ctrl |

TABLE 38.g

| | Probe | Inner__primers PCR-Primer1__ID |
|---|---|---|
| 1 | C1GALT1__7__7113076__7114831__7258228__7260668__FF | OBD142__025 |
| 2 | DKK3__11__11956071__11968035__11984245__11993733__FR | OBD142__061 |
| 3 | FBXO32__8__123526212__123527874__123555254__123559065__FR | OBD142__089 |
| 4 | GPC6__13__94054831__94060621__94121445__94133208__RF | OBD142__109 |
| 5 | GSN__9__121177548__121180410__121268506__121274144__FR | OBD142__117 |
| 6 | LMO4__1__87315524__87318670__87343110__87349940__FF | OBD142__145 |

TABLE 38.g-continued

| Probe | Inner_primers PCR-Primer1_ID |
|---|---|
| 7 MAPK10_4_86572598_86581486_86617317_86621940_FF | OBD142_153 |
| 8 MBNL1_3_152229500_152234786_152281057_152285843_FR | OBD142_157 |
| 9 PCK1_20_57527297_57530814_57579772_57583521_RR | OBD142_189 |
| 10 PIK3C3_18_42070009_42072187_42088671_42094691_FF | OBD142_213 |
| 11 PTPRC_1_198595771_198598296_198659753_198666156_RF | OBD142_233 |
| 12 RGS6_14_72139099_72144564_72213251_72222544_FR | OBD142_245 |
| 13 RUNX3_1_24920810_24923822_24973522_24976037_RF | OBD142_253 |
| 14 ZFHX3_16_73147488_73153243_73182254_73184585_FF | OBD142_325 |
| 15 MYOT_5_137829466_137834410_137882068_137884626_RR | OBD142_341 |
| 16 AGT_1_230724515_230729957_230752057_230757333_RF | OBD142_365 |
| 17 MYL1_2_210288997_210291732_210359762_210362293_FF | OBD142_449 |
| 18 SRI_7_88199682_88203042_88229166_88237101_RF | OBD142_509 |

TABLE 38.h

| | Inner_primers | | | Category High or |
|---|---|---|---|---|
| | PCR_Primer1 | PCR-Primer2_ID | PCR_Primer2 | Low Responder |
| 1 | CACCTCAAAAGACAACCCCAGACCCA (SEQ ID NO: 222) & (SEQ ID NO: 579) & (SEQ ID NO: 1596) | OBD142_027 | CCCTCACTTTCCTTCTACTCTTCAAG (SEQ ID NO: 299) & (SEQ ID NO: 597) & (SEQ ID NO: 1614) | Presence in strength high responder |
| 2 | GCTCCACATTTCCCAATCTAACCTGC (SEQ ID NO: 206) & (SEQ ID NO: 580) & (SEQ ID NO: 624) & (SEQ ID NO: 1597) | OBD142_063 | GTCAGAGTTGCCGATAGGTCTTGCTA (SEQ ID NO: 283) & (SEQ ID NO: 598) & (SEQ ID NO: 631) & (SEQ ID NO: 1615) | Presence in strength high responder |
| 3 | AATCTCTGTCCCCAACTGTATCTGGC (SEQ ID NO: 208) & (SEQ ID NO: 581) & (SEQ ID NO: 1598) | OBD142_091 | ACATCTATCTTGCCCCTCACTCAGGT (SEQ ID NO: 285) & (SEQ ID NO: 599) & (SEQ ID NO: 1616) | Presence in strength high responder |
| 4 | GAGTATTTACGATGGTCAGGTGCTGC (SEQ ID NO: 227) & (SEQ ID NO: 265) & (SEQ ID NO: 582) & (SEQ ID NO: 1599) | OBD142_111 | ATCCAAACACAGGACGAGAATAAAGC (SEQ ID NO: 342) & (SEQ ID NO: 600) & (SEQ ID NO: 1617) | Presence in strength high responder |
| 5 | GACCTGTGGTTCTGACTGTCCAG (SEQ ID NO: 228) & (SEQ ID NO: 583) & (SEQ ID NO: 1600) | OBD142_119 | TATCGTCCAGGAGGCAAGGGTCC (SEQ ID NO: 305) & (SEQ ID NO: 307) & (SEQ ID NO: 601) & (SEQ ID NO: 1618) | Presence in strength high responder |
| 6 | GCAACCTGGTCTCCTACCTGCTTCTA (SEQ ID NO: 232) & (SEQ ID NO: 584) & (SEQ ID NO: 1601) | OBD142_147 | GATGAGGTAACCAAAGTTCAGGGAGA (SEQ ID NO: 309) & (SEQ ID NO: 602) & (SEQ ID NO: 1619) | Presence in strength high responder |
| 7 | TAGCAGACAATCAGAGGGTTTTGC (SEQ ID NO: 233) & (SEQ ID NO: 585) & (SEQ ID NO: 1602) | OBD142_155 | CTCTCTCCTCATCCTCCCTCCTAATA (SEQ ID NO: 310) & (SEQ ID NO: 603) & (SEQ ID NO: 1620) | Presence in strength high responder |
| 8 | GCTGGTAGTTGGCTTTTGGGAAGAAC (SEQ ID NO: 234) & (SEQ ID NO: 586) & (SEQ ID NO: 1603) | OBD142_159 | GGGAGCCAGAAAGATAGCAATGCCTA (SEQ ID NO: 311) & (SEQ ID NO: 604) & (SEQ ID NO: 1621) | Presence in strength high responder |
| 9 | TTCTCCCTCGGACGCTCATCCTC (SEQ ID NO: 211) & (SEQ ID NO: 587) & (SEQ ID NO: 1604) | OBD142_191 | GAGGAGGAGAAACTCAGAAGCCC (SEQ ID NO: 288) & (SEQ ID NO: 605) & (SEQ ID NO: 1622) | Presence in strength high responder |
| 10 | CTGGAACTTGTTTAGGCACTGAAGCA (SEQ ID NO: 212) & (SEQ ID NO: 588) & (SEQ ID NO: 1605) | OBD142_215 | GCACAAGACCTCACATTCTGATGGGC (SEQ ID NO: 289) & (SEQ ID NO: 606) & (SEQ ID NO: 1623) | Presence in strength high responder |

TABLE 38.h-continued

| | | Inner_primers | | | Category High or |
|---|---|---|---|---|---|
| | PCR_Primer1 | PCR-Primer2_ID | PCR_Primer2 | | Low Responder |
| 11 | GCAAAGGGCAGGTCATCATCATTCAA (SEQ ID NO: 239) & (SEQ ID NO: 589) & (SEQ ID NO: 628) & (SEQ ID NO: 1606) & (SEQ ID NO: 1606) | OBD142_235 | CTCTCCTTTATCCCCTACCCTGCTCA (SEQ ID NO: 316) & (SEQ ID NO: 607) & (SEQ ID NO: 635) & (SEQ ID NO: 1624) | | Presence in strength high responder |
| 12 | CCCCGATGAATGTTACCCTGTCCC (SEQ ID NO: 590) & (SEQ ID NO: 1607) | OBD142_247 | CAGAGAAAGGGAGTTTGGAGGGC (SEQ ID NO: 608) & (SEQ ID NO: 1625) | | Presence in strength high responder |
| 13 | CTGAAATCCCATAGTGAGATGCCTTC (SEQ ID NO: 217) & (SEQ ID NO: 591) & (SEQ ID NO: 1608) | OBD142_255 | CCCCAAACTCCCAGACACATCAGAGA (SEQ ID NO: 294) & (SEQ ID NO: 609) & (SEQ ID NO: 1626) | | Presence in strength high responder |
| 14 | CCTGGATGTTCATTCCCACCTGG (SEQ ID NO: 245) & (SEQ ID NO: 592) & (SEQ ID NO: 1609) | OBD142_327 | AGAGGGAAAGGCAGGTCGTGAGC (SEQ ID NO: 322) & (SEQ ID NO: 610) & (SEQ ID NO: 1627) | | Presence in strength high responder |
| 15 | GCAGATTCCACAGGGCTTAC (SEQ ID NO: 247) & (SEQ ID NO: 593) & (SEQ ID NO: 1610) | OBD142_343 | GCTGGTCTCAAACTCCTGGG (SEQ ID NO: 611) & (SEQ ID NO: 1628) | | Presence in strength high responder |
| 16 | ACCCAACCCTGCTATACAATTCCA (SEQ ID NO: 594) & (SEQ ID NO: 1611) | OBD142_367 | GGGCATCTTTCCTCTTATTCAAGGT (SEQ ID NO: 612) & (SEQ ID NO: 1629) | | Presence in strength high responder |
| 17 | ACAGTCAGTGATTGGCACAGAGTAA (SEQ ID NO: 276) & (SEQ ID NO: 595) & (SEQ ID NO: 1612) | OBD142_451 | AGGAAATAGCCCAAATGCAACTGAA (SEQ ID NO: 353) & (SEQ ID NO: 613) & (SEQ ID NO: 1630) | | Presence in strength high responder |
| 18 | GAATGAAACTCTGAGGCCGG (SEQ ID NO: 257) & (SEQ ID NO: 596) & (SEQ ID NO: 1613) | OBD142_511 | CCCATTCGTCTCTCTGAGCTG (SEQ ID NO: 334) & (SEQ ID NO: 614) & (SEQ ID NO: 1631) | | Presence in strength high responder |

TABLE 39.a

| | Probe | GeneLocus | |
|---|---|---|---|
| 1 | THNSL2__2__88139809__88146295__88161717__88164554__FR | THNSL2 | E_Ctrl |
| 2 | IGF1R__15__98652565__98657862__98731539__98737034__RF | IGF1R | Str_Ctrl |
| 3 | DKK3__11__11956071__11968035__11984245__11993733__FR | DKK3 | Str_Trn |
| 4 | CBL__11__119249760__119252653__119294588__119299643__RF | CBL | E_Trn |
| 5 | EYA1__8__71216399__71218728__71261816__71267769__RR | EYA1 | Str_Trn |
| 6 | ACACB__12__109236052__109237242__109268078__109273323__RR | ACACB | E_Ctrl |
| 7 | PTPRC__1__198595771__198598296__198659753__198666156__RF | PTPRC | E_Ctrl |

TABLE 40

| | Gene |
|---|---|
| CV Only | |
| OBD142__513.515 | SRI |
| Shared | |
| OBD142__261.263 | SMAD7 |
| OBD142__313.315 | WASL |
| OBD142__021.023 | B3GAT2 |

TABLE 40-continued

| | Gene |
|---|---|
| Strength Only | |
| OBD142__473.475 | RB1 |
| OBD142__389.391 | MTFR1 |
| OBD142__301.303 | TLR2 |
| OBD142__169.171 | NFKB1 |
| OBD142__173.175 | NTRK2 |
| OBD142__489.491 | ITGAV |
| OBD142__457.459 | PPARA |

| No. | Probe | Loci | |
|---|---|---|---|
| 1 | CBL__11__119249760__119252653__119294588__119299643__RF | CBL | Present in Endurance |
| 2 | DKK3__11__11956071__11968035__11984245__11993733__FR | DKK3 | Present in Strength |
| 3 | DKK3__11__11956071__11968035__12048403__12051930__FR | DKK3 | Present in Strength |
| 4 | FBXO32__8__123526212__123527874__123555254__123559065__FR | FBXO32 | Present in Endurance |
| 5 | KDM1A__1__23064655__23070269__23096951__23098159__FR | KDM1A | Present in Strength |
| 6 | EYA1__8__71216399__71218728__71261816__71267769__RR | EYA1 | Present in Strength |
| 7 | PCK1__20__57527297__57530814__57579772__57583521__RR | PCK1 | Present in Endurance |
| 8 | PIK3C3__18__42070009__42072187__42088671__42094691__FF | PIK3C3 | Present in Endurance |
| 9 | ALDH1A2__15__58053198__58062371__58157807__58162832__RR | ALDH1A2 | Present in Strength |
| 10 | CD36__7__80539507__80544315__80679651__80687690__FR | CD36 | Present in Strength |
| 11 | DKK3__11__11956071__11968035__12010923__12019458__FF | DKK3 | Present in Strength |
| 12 | IL1RAP__3__190489665__190498302__190560851__190563356__FR | IL1RAP | Present in Endurance |
| 13 | RUNX3__1__24920810__24923822__24973522__24976037__RF | RUNX3 | Present in Strength |
| 14 | PPARA__22__46101029__46102611__46241078__46244347__FR | PPARA | Present in Endurance |
| 15 | SLC25A13__7__96209525__96214524__96295606__96302029__FF | SLC25A13 | Present in Endurance |
| 16 | PCK1__20__57527297__57530814__57551578__57557205__RR | PCK1 | Present in Endurance |
| 17 | MYL1__2__210288997__210291732__210359762__210362293__FF | MYL1 | Present in Endurance |
| 18 | C1GALT1__7__7113076__7114831__7258228__7260668__FF | C1GALT1 | Present in Endurance |
| 19 | COL25A1__4__109024771__109031337__109090838__109104305__RR | COL25A1 | Present in Endurance |
| 20 | COL5A1__9__134738485__134741113__134811418__134816113__RR | COL5A1 | Present in Strength |
| 21 | DIAPH3__13__59818047__59823591__59854837__59860534__RR | DIAPH3 | Present in Endurance |
| 22 | FBLN2__3__13512352__13515076__13582406__13590343__RF | FBLN2 | Present in Endurance |
| 23 | GPC6__13__94121445__94133208__94296633__94304225__FF | GPC6 | Present in Strength |
| 24 | GSN__9__121177548__121180410__121268506__121274144__FR | GSN | Present in Endurance |
| 25 | GSN__9__121227501__121232628__121268506__121274144__FR | GSN | Present in Endurance |
| 26 | GSN__9__121239116__121243347__121268506__121274144__FR | GSN | Present in Endurance |
| 27 | LCK__1__32214585__32217213__32237144__32241139__RF | LCK | Present in Endurance |
| 28 | LMO4__1__87315524__87318670__87343110__87349940__FF | LMO4 | Present in Endurance |
| 29 | MAPK10__4__86572598__86581486__86617317__86621940__FF | MAPK10 | Present in Endurance |
| 30 | MBNL1__3__152229500__152234786__152281057__152285843__FR | MBNL1 | Present in Strength |
| 31 | NCAM1__11__113019160__113028536__113163748__113168132__FR | NCAM1 | Present in Endurance |
| 32 | PCK1__20__57527297__57530814__57570220__57572870__RR | PCK1 | Present in Endurance |
| 33 | PDK3__X__24441637__24447950__24480152__24481252__FR | PDK3 | Present in Endurance |
| 34 | PDK3__X__24441637__24447950__24490440__24491541__FR | PDK3 | Present in Endurance |
| 35 | PTPRC__1__198595771__198598296__198659753__198666156__RF | PTPRC | Present in Endurance |
| 36 | PTPRC__1__198659753__198666156__198721093__198724578__FF | PTPRC | Present in Endurance |
| 37 | RYR1__19__38410632__38413089__38495982__38499305__RR | RYR1 | Present in Strength |
| 38 | THNSL2__2__88139809__88146295__88161717__88164554__FR | THNSL2 | Present in Endurance |
| 39 | UACA__15__70715123__70719636__70780754__70784668__RF | UACA | Present in Endurance |

-continued

| No. | Probe | Loci | |
|---|---|---|---|
| 40 | ZEB1__10__31273317__31275631__31507470__31524442__FF | ZEB1 | Present in Endurance |
| 41 | ZFHX3__16__73147488__73153243__73182254__73184585__FF | ZFHX3 | Present in Strength |
| 42 | ADRB3__8__37962724__37965269__37987735__37989039__FR | ADRB3 | Present in Strength |
| 43 | AGT__1__230724515__230729957__230752057__230757333__RF | AGT | Present in Strength |
| 44 | HTR2A__13__46860092__46866824__46904346__46907815__RF | HTR2A | Present in Strength |
| 45 | SOS1__2__38982199__38993639__39061418__39066028__FF | SOS1 | Present in Strength |
| 46 | ACBD6__1__180431719__180434683__180541491__180549122__RR | ACBD6 | Present in Endurance |
| 47 | MYH1__17__10502067__10505465__10533547__10534931__RF | MYH1 | Present in Endurance |
| 48 | MYOD1__11__17685862__17689487__17729653__17733608__FR | MYOD1 | Present in Endurance |
| 49 | NECTIN3__3__111028574__111034204__111209684__111210764__FR | NECTIN3 | Present in Endurance |
| 50 | ACACB__12__109146008__109150083__109236052__109237242__RR | ACACB | Present in Endurance |
| 51 | ACACB__12__109236052__109237242__109268078__109273323__RR | ACACB | Present in Endurance |
| 52 | IGF1R__15__98652565__98657862__98731539__98737034__RF | IGF1R | Present in Strength |
| 53 | SOCS7__17__38347510__38348776__38360864__38363420__FR | SOCS7 | Present in Endurance |
| 54 | STXBP4__17__55035186__55042800__55117598__55123347__RR | STXBP4 | Present in Endurance |
| 55 | SVEP1__9__110397951__110405969__110503630__110509758__FF | SVEP1 | Present in Endurance |
| 56 | EMCN__4__100636305__100649860__100744427__100745788__RR | EMCN | Present in Endurance |
| 57 | ACACB__12__109146008__109150083__109185066__109187324__RR | ACACB | Present in Endurance |
| 58 | FOXO1__13__40524349__40526124__40688580__40690771__RR | FOXO1 | Present in Strength |
| 59 | FOXO3__6__108603215__108604436__108629992__108635481__FR | FOXO3 | Present in Endurance |
| 60 | FTO__16__53844989__53854574__54045378__54052319__RF | FTO | Present in Endurance |
| 61 | GPC6__13__94054831__94060621__94121445__94133208__RF | GPC6 | Present in Strength |
| 62 | PPP3CA__4__101055418__101067369__101247819__101259416__RR | PPP3CA | Present in Endurance |
| 63 | SMAD7__18__48917335__48920290__48969505__48974578__RF | SMAD7 | Present in Strength |
| 64 | SYK__9__90816328__90822228__90832284__90836084__RR | SYK | Present in Endurance |
| 65 | SYK__9__90816328__90822228__90872966__90875740__RR | SYK | Present in Endurance |
| 66 | TGFB2__1__218317687__218325587__218386401__218389011__FR | TGFB2 | Present in Endurance |
| 67 | TGFBR2__3__30566144__30567439__30694718__30698514__RR | TGFBR2 | Present in Strength |
| 68 | TLR2__4__153659613__153661830__153693586__153700349__RF | TLR2 | Present in Strength |
| 69 | SVEP1__9__110493529__110499578__110527410__110532406__FR | SVEP1 | Present in Strength |
| 70 | MTFR1__8__65658401__65661888__65780891__65782535__RF | MTFR1 | Present in Endurance |
| 71 | GSN__9__121182946__121189020__121323589__121328431__FF | GSN | Present in Strength |
| 72 | MUSK__9__110648469__110652659__110747866__110751903__FR | MUSK | Present in Strength |
| 73 | PPARA__22__46128634__46134707__46231440__46235124__FR | PPARA | Present in Strength |
| 74 | PPP1R9A__7__94903925__94908776__94951930__94967018__RF | PPP1R9A | Present in Endurance |
| 75 | PLCXD2__3__111633890__111638317__111672672__111677327__FR | PLCXD2 | Present in Endurance |
| 76 | SGCZ__8__14631157__14642508__14778176__14785491__FF | SGCZ | Present in Endurance |
| 77 | SRI__7__88199682__88203042__88229166__88237101__RF | SRI | Present in Endurance |

Table 41 shows markers identified in the human study, which are preferably used to type humans.

---

The invention claimed is:

1. A process for detecting a chromosome state in a human individual comprising determining whether a chromosome interactions relating to that chromosome state is present or absent in the individual, wherein said chromosome interactions relates to endurance or strength in an individual; wherein the process comprises detecting the presence or absence of:

at least 10 of the 77 chromosome interactions shown in Table 25 which are present in the genes shown in Table 25.h, wherein each chromosome interaction is detected by a method comprising the steps of:

(i) cross-linking of chromosome regions of the individual, wherein the chromosome regions have come together in a chromosome interaction, (ii) subjecting the cross-linked regions to cleavage;

(iii) ligating the cross-linked cleaved DNA ends to form ligated nucleic acids, and (iv) detecting the presence or absence of a ligated nucleic acid corresponding to each chromosome interaction by a probe that has at least 70% identity to any of the specific probe sequences set forth in SEQ ID NOS: 128 to 204.

2. A process according to claim 1 wherein:

the process is carried out to select an individual suitable for a sport.

3. A process according to claim 1 in which the presence or absence of each chromosome interactions is detected:

in a sample from an individual.

4. A process according to claim 1:

which is carried out to identify an individual that is suited to endurance training or

which is carried out to identify an individual that is suited to strength training.

5. A process according to claim 1 which is carried out to select an individual for racing.

6. A process according to claim 1, wherein detecting the presence or absence of each ligated nucleic acid by quantitative PCR (qPCR) which uses primers capable of amplifying the ligated nucleic acid and the probe which binds the ligation site during the PCR reaction, wherein said probe comprises:

a fluorophore covalently attached to the 5' end of the oligonucleotide, and/or a quencher covalently attached to the 3' end of the oligonucleotide.

\* \* \* \* \*